United States Patent
Itoh et al.

[11] Patent Number: 5,932,737
[45] Date of Patent: Aug. 3, 1999

[54] PEPTIDE COMPOUNDS FOR TREATMENT OF NO-MEDIATED DISEASES

[75] Inventors: Yoshikuni Itoh, Tsukuba; Toshiro Iwamoto, Tsuchiura; Takumi Yatabe, Tsukuba; Hitoshi Hamashima, Tsukuba; Takayuki Inoue, Tsukuba; Seiji Hashimoto, Tsukuba; Teruo Oku, Tsukuba, all of Japan

[73] Assignee: Fujisawa Pharmaceutical Co., Ltd., Osaka, Japan

[21] Appl. No.: 08/849,076

[22] PCT Filed: Nov. 29, 1995

[86] PCT No.: PCT/JP95/02428

§ 371 Date: May 30, 1997

§ 102(e) Date: May 30, 1997

[87] PCT Pub. No.: WO96/16981

PCT Pub. Date: Jun. 6, 1996

[30] Foreign Application Priority Data

| Dec. 2, 1994 | [GB] | United Kingdom | 9424408 |
| Mar. 10, 1995 | [GB] | United Kingdom | 9504891 |
| May 18, 1995 | [GB] | United Kingdom | 9510042 |

[51] Int. Cl.$^6$ .......... A61K 31/44; C07D 407/14
[52] U.S. Cl. .......... 546/256; 514/333
[58] Field of Search .......... 546/256; 514/333

[56] References Cited

FOREIGN PATENT DOCUMENTS

| A 394989 | 10/1990 | European Pat. Off. |
| A 0 446 699 | 9/1991 | European Pat. Off. |
| WO A 92 22569 | 12/1992 | European Pat. Off. |
| A 0 525 420 | 2/1993 | European Pat. Off. |

OTHER PUBLICATIONS

D. Hagiwara et al, "3tudies on Neurokinin Antagonist, 3, Design and Structure–Activity Relationships or New Branched Tripeptides Nalpha, (Substituted L–aspartyl, L–ornithyl, or L–lysyl)–N–(phenylmethyl–L–phenyla-laninamides as Substance P Antagonists", J. Med.Chem. vol. 36 1993, pp. 2266–2278 (XP002006315).

D. Hagiwara et al: "Studies on Neurokinin Antagonists. 4", (see Table 1), J. Med. Chem, vol. 37, Jun. 21, 1991, pp. 2090 99, (XP002006316).

*Primary Examiner*—Robert W. Ramsuer
*Attorney, Agent, or Firm*—Oblon, Spivak, McClelland, Maier & Neustadt, P.C.

[57] ABSTRACT

New peptide compounds of the formula:
1. A compound of the formula:

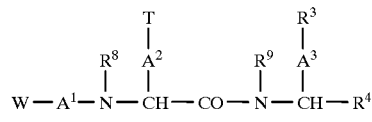

14 Claims, No Drawings

PEPTIDE COMPOUNDS FOR TREATMENT OF NO-MEDIATED DISEASES

This continuation is a 371 of PCT/JP95/02428 filed Nov. 20, 1995.

TECHNICAL FIELD

This invention relates to new peptide compounds and pharmaceutically acceptable salt thereof which are useful as a medicament.

BACKGROUND ART

Some peptide compounds have been known as described, for example, in EP 0 394 989 A2.

DISCLOSURE OF INVENTION

This invention relates to new peptide compounds.

One object of this invention is to provide the new and useful peptide compounds and pharmaceutically acceptable salts thereof which possess a strong inhibitory activity on the production of nitric oxide (NO).

Another object of this invention is to provide process for preparation of the peptide compounds and salts thereof.

A further object o this invention is to provide a pharmaceutical composition comprising said peptide compounds or a pharmaceutically acceptable salt thereof.

Still further object of this invention is to provide a use of said peptide compounds or a pharmaceutically acceptable salt thereof as a medicament for prophylactic and therapeutic treatment of NO-mediated diseases such as adult respiratory distress syndrome, cardiovascular ischemia, myocarditis, heart failure, synovitis, shock (e.g., septic shock, etc.), diabetes (e.g. insulin-dependent diabetes mellitus, etc.), diabetic nephropathy, diabetic retinopathy, diabetic neuropathy, glomerulonephritis, peptic ulcer, inflammatory bowel disease (e.g., ulcerative colitis, chronic colitis, etc.), cerebral infarction, cerebral ischemia, migraine, rheumatoid arthritis, gout, neuritis, postherpetic neuralgia, osteoarthritis, osteoporosis, systemic lupus erythematosis, rejection by organ transplantation, asthma, metastasis, Alzheimer's disease, arthritis, CNS disorders, and the like in human being and animals.

The object peptide compounds of the present invention are novel and can be represented by the following general formula (I)

$$\text{W}-\text{A}^1-\overset{\overset{\text{T}}{|}}{\underset{\underset{\text{R}^8}{|}}{\text{N}}}-\overset{\overset{\text{A}^2}{|}}{\text{CH}}-\text{CO}-\overset{\overset{\text{R}^3}{|}}{\underset{\underset{\text{R}^9}{|}}{\text{N}}}-\overset{\overset{\text{A}^3}{|}}{\text{CH}}-\text{R}^4 \quad (I)$$

wherein

W is lower alkyl, aryl which may have suitable substituent(s), fluorenyl which may have suitable substituent(s), heteromonocyclic group which may have suitable substituent(s), or a group of the formula:

[in which $R^1$ is hydrogen, halogen, lower alkyl, nitro, di(lower)alkylamino, amino, protected amino, hydroxyamino or lower alkoxy, Q is CH or N, L is a bivalent radical selected from (in which Y is CH or N, Z is NH, O or S, and --- is a single bond or a double bond) and (in which M is CH or N, and J is CH or N)], $A^1$ is lower alkylene, —NHCO—, $$-\overset{\overset{\text{V}}{\|}}{\text{C}}-$$

(in which V is O or S), or —$SO_2$—,

T is hydrogen, aryl which may have suitable substituent(s), heterocyclic group, hydroxy, acyloxy, ar(lower)alkoxy, sulfooxy, mercapto, lower alkylthio, mono(or di or tri)ar(lower)alkylthio, acylthio, amino, protected amino, guanidino, acylguanidino or a group of the formula:

$$\overset{\overset{\text{R}^2}{|}}{\underset{|}{\text{C}}}=\text{O}$$

(in which $R^2$ is hydroxy, ar(lower)alkoxy, morpholinyl, piperazinyl which may have suitable substituents), piperidyl which may have suitable substituent(s), pyrrolidinyl, thiomorpholinyl, homopiperazinyl which may have suitable substituent(s), piperazinlo which may have suitable substituent(s), piperidyloxy which may have suitable substituent(s), or amino having one or two suitable substituent(s), $A^2$ is lower alkylene, $R^8$ is hydrogen or lower alkyl, or $R^8$ and a group of the formula: —$A^2$—T are linked together to form

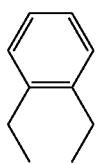

$R^3$ is hydrogen, aryl which may have suitable substituent(s), hydroxy, protected hydroxy, cyclo(lower)alkyl, lower alkylthio, or heterocyclic group which may have suitable substituent(s), $A^3$ is bond or lower alkylene, $R^9$ is hydrogen or lower alkyl, or $R^9$ and a group of the formula: —$A^3$—$R^3$ are linked together to form

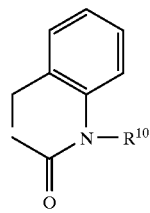

and $R^4$ is carboxy, protected carboxy, heterocycliccarbonyl which may have suitable substituent(s), or a group of the formula:

$$-CO-N\begin{matrix}R^5\\R^6\end{matrix}$$

(in which $R^5$ is hydrogen or lower alkyl, and $R^6$ is hydrogen, aryl, ar(lower)alkyl which may have suitable substituent(s), [di(lower)alkylamino](lower)alkyl, or heterocyclic(lower)alkyl which may have suitable substituent(s)), or $R^4$ and a group of the formula: —$A^3$—$R^3$ are linked together to form

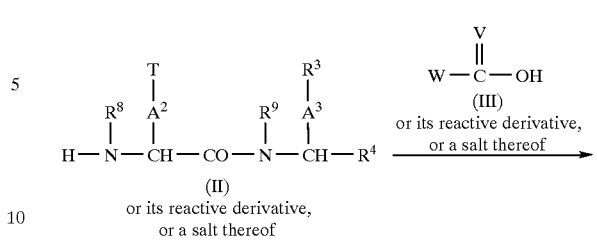

(in which $R^{10}$ is ar(lower)alkyl), with proviso that when M is CH, and J is CH, then Q is N.

The main object compound (I) of the present invention can be prepared by the following processes.

Process (1)

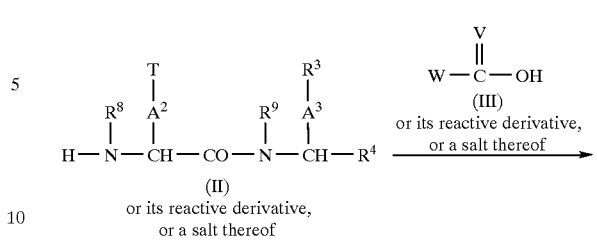

Process (2)

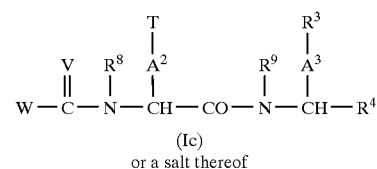

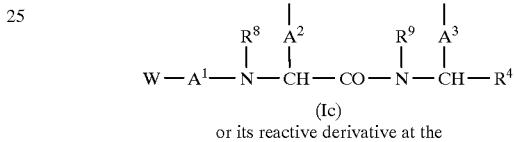

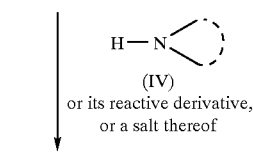

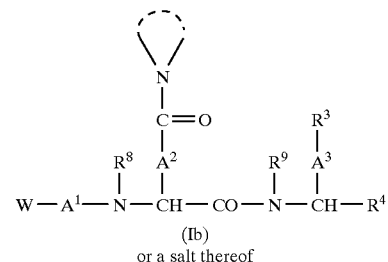

Process (3)

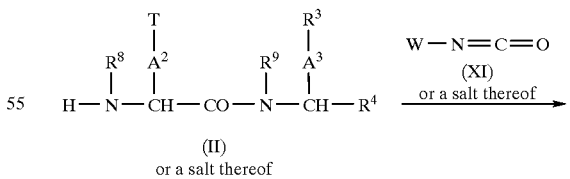

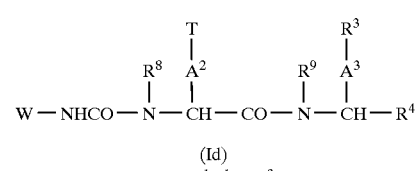

Process (4)

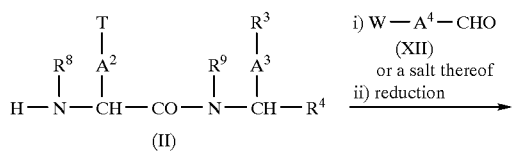

(II) or a salt thereof i) W—A⁴—CHO
(XII)
or a salt thereof
ii) reduction

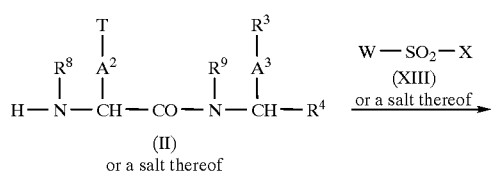

(Ie) or a salt thereof

Process (5)

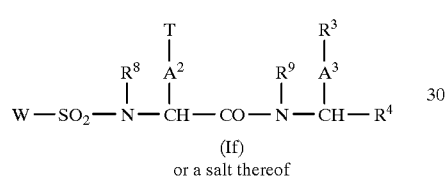

(II) or a salt thereof

W—SO₂—X
(XIII)
or a salt thereof

W—SO₂—N(R⁸)—CH(A²-T)—CO—N(R⁹)—CH(A³-R³)—R⁴

(If) or a salt thereof wherein
W, T, $A^1$, $A^2$, $A^3$, V, $R^3$, $R^4$, $R^8$ and $R^9$ are each as defined above, and
$A^4$ is bond or $C_1$–$C_5$ alkylene,
X is a leaving group, is morpholino, piperazino which may have suitable substituent(s), piperidino which may have suitable substituent s), pyrrolidino, thiomorpholino, homopiperazino which may have suitable substituent(s), piperazinio which may have suitable substituent(s) or amino having one or two suitable substituent(s).

The other compound (I) of the present invention can be prepared by the following examples or by a conventional method.

The starting compound can be prepared by the following processes.

Process (A)

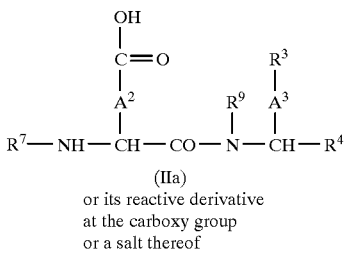

(IIa)
or its reactive derivative
at the carboxy group
or a salt thereof

H—N⟨
(IV)
or its reactive derivative,
or a salt thereof

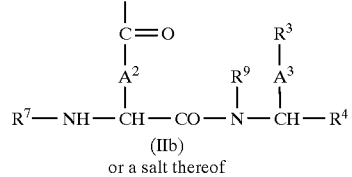

(IIb)
or a salt thereof

Process (B)

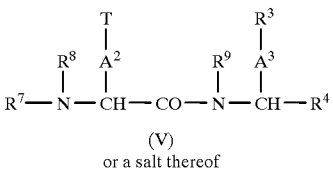

(V)
or a salt thereof

Elimination reaction of the amino protective group

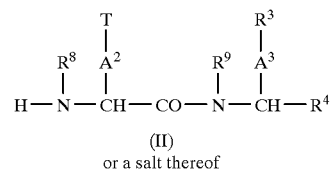

(II)
or a salt thereof

Process (C)

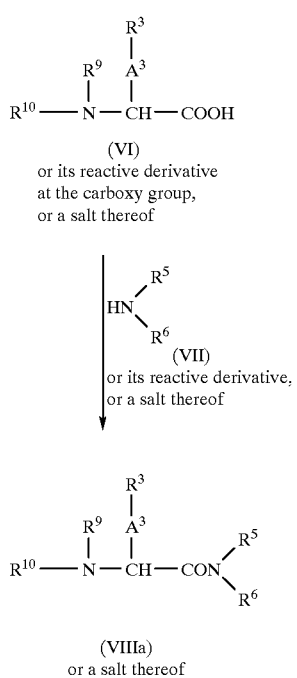

Process (D)

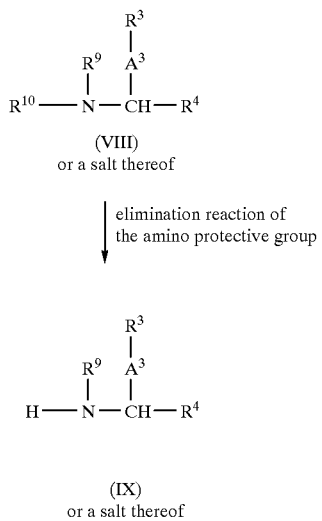

Process (E)

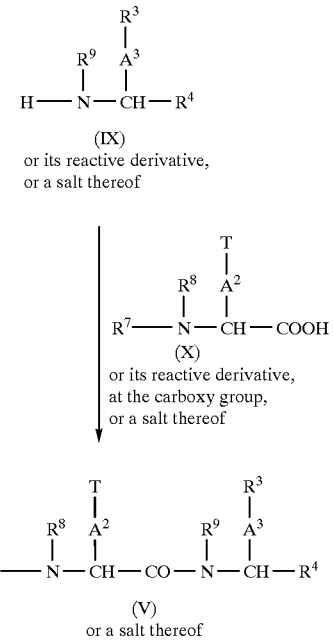

wherein $R^3$, $R^4$, $R^5$, $R^6$, R8, $R^9$, T, $A^2$, $A^3$

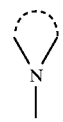

and are each as defined above,
$R^7$ and $R^{10}$ are each amino protective group.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); a salt with a basic or acidic amino acid (e.g., arginine, aspartic acid, glutamic acid, etc.).

In the above and subseuent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "ar(lower)alkyl", "heterocyclic(lower)ialkyl", "di(lower)alkylamino", "lower alkylthio", "mono(or di or tri)ar(lower)alkylthio" and "[di(lower)alkylamino](lower)-alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$–$C_4$ alkyl.

Suitable "lower alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkoxy" and "lower alkoxy moiety" in the term "ar(lower)alkoxy" may include methoxy, ethoxy, propoxy, isopropoxy, butoxy, isobutoxy, t-butoxy, pentyloxy, t-pentyloxy, hexyloxy and the like.

Suitable "cyclo(lower)alkyl" may include cyclopropyl, cyclobutyl, cyclopentyl, cyclohexyl, cyclohentyl and the like.

Suitable "cyclo(lower)alkenyl" may include cyclohexenyl, cyclohexadienyl and the like.

Suitable "aryl" and "aryl moiety" in the terms "ar(lower)alkoxy" and "ark(lower)alkyl" may include phenyl, naphthyl and the like.

Suitable "halogen" may include fluorine, bromine, chlorine and iodine.

Suitable "leaving group" may include acid residue, lower alkoxy as exemplified above, and the like.

Suitable "acid residue" may include halogen as exemplified above, acyloxy and the like.

Suitable "lower alkylene" may include straight or branched one such as methylene, ethylene, trimethylene, tetramethylene, pentamethylene, hexamethylene, methylmethylene, 1-(or 2-)methyltrimethylene, ethylethylene, propylene, and the like, in which more preferable example may be $C_1$–$C_4$ alkylene and the most preferable one may be methylene.

Suitable "$C_1$–$C_5$ alkylene" may include straight or branched one such as methylene, ethylene, trimethylene, tetramethylene, pentamethylene, methylmethylene, 1-(or 2-)-methyltrimethylene, ethylethylene, propylene, and the like.

Suitable "protected carboxy" may include commonly protected carboxy, and the like.

Suitable "commonly protected carboxy" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono(or di or tri)halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)-[methoxycarbonyloxy]ethyl ester, 1-(or 2-)[ethoxycarbonyloxy]ethyl ester, 1-(or 2-)[propoxycarbonyloxy]ethyl ester, 1-(or 2-)[isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower)alkyi ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester; (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; mono(or di or tri)aryl(lower)alkyl ester, for example, mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkylsilyl ester; lower alkylthioester (e.g., methylthioester, ethylthioester, etc.) and the like.

Suitable "hydroxy protective group" in the term "protected hydroxy" may include acyl, mono(or di or tri)phenyl (lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "amino protective group" may include acyl or a conventional protective group such as mono(or di or tri) aryl-(lower)alkyl, for example, mono (or di or tri)phenyl (lower)-alkyl (e.g., benzyl, trityl, etc.) or the like.

Suitable "protected amino" may include acylamino or an amino group substituted by a conventional protecting group such as mono(or di or tri)aryl(lower)alkyl, for example, mono(or di or tri)phenyl(lower)alkyl (e.g., benzyl, trityl, etc.) or the like.

Suitable "acyl" and "acyl moiety" in the terms "acylamino", "acyloxy", "acylthio" and "acylguanidino" may include carbamoyl, aliphatic acyl group and acyl group containing an aromatic ring, which is referred to as aromatic acyl, or heterocyclic ring, whIch is referred to as heterocyclic acyl.

Suitable example of said acyl may be illustrated as follows:

Carbamoyl; Thiocarbamoyl;

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.);

cyclo(lower)alkylcarbonyl (e.g., cyclopentylcarbonyl, cyclohexylcarbonyl, etc.); or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacety, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.];

ar(lower)alkoxycarbonyl [e.g., phenyl(lower) alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.); or the like;

Heterocyclic acyl such as heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like;

in which suitable "heterocyclic moiety" in the terms "heterocycliccarbonyl", "heterocyclic(lower)alkanoyl", heterocyclic(lower)alkenoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1, 2,4-triazolyl, 1H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl (e.g. 1H-benzimidazolyl, etc.), quinolyl, isoquinolyl, tetrahydroisoquinolyl (e.g. 1,2,3,4-tetrahydroisoquinolyl, etc.) indazolyl, benzotriazolyl, quinazolinyl, quinoxalinyl, phthalazinyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2, 3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiomorpholinyl, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above, lower alkoxy as exemplified above, lower alkylthio wherein lower alkyl moiety is as exemplified above, lower alkylamino wherein lower alkyl moiety is as exemplified above, di(lower)alkylamino wherein lower alkyl moiety is as exemplified above, cyclo(lower)alkyl as exemplified above, cyclo(lower)alkenyl as exemplified above, halogen as exemplified above, aryl as exemplified above, amino, protected amino as exemplified above, hydroxy, protected hydroxy as exemplified above, cyano, nitro, carboxy, protected carboxy as exemplified above, sulfo, sulfamoyl, imino, oxo, amino(lower)alkyl wherein lower alkyl moiety is as exemplified above, carbamoyloxy, mono(or di or tri)halo(lower)alkyl wherein halogen moiety and lower alkyl moiety are each as exemplified above, hydroxy(lower)alkyl wherein lower alkyl moiety is as exemplified above, or the like.

Suitable "heterocyclic group" and "heterocyclic moiety" in the terms "heterocycliccarbonyl" and "heterocyclic (lower)alkyl" can be referred to the ones as exemplified above.

Suitable "commonly protected amino" may include amino substituted with a common N-protective group such as substituted or unsubstituted lower alkanoyl (e.g., formyl, acetyl, propionyl, trifluoroacetyl, etc.), phthaloyl, lower alkoxycarbonyl (e.g., tert-butoxycarbonyl, tert-amyloxycarbonyl, etc.), substituted or unsubstituted ar(lower)alkanoyl (e.g., benzyloxycarbonyl, p-nitrobenzyloxycarbonyl, etc.), carbamoyl, substituted carbamoyl [e.g., mono or di(lower alkyl)carbamoyl (e.g., methylcarbamoyl, dimethylcarbamoyl, etc.), arylcarbamoyl (e.g., phenylcarbamoyl, etc.), etc.], substituted or unsubstituted arylsulfonyl (e.g., phenylsulfonyl, tosyl, etc.), nitrophenylsulfenyl, ar(lower)alkyl (e.g., trityl or benzyl, etc.), or the like.

Suitable "heteromonocyclic group" may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H, tetrazolyl, 2H-tetrazolyl, etc.), etc.;

saturated 3 to 8-membered (more preferably 5 or 6-membered) heteromonocyclic group containing 1 to 4 nitrogen atom(s), for example pyrrolidinyl, imidazolidinyl, piperidyl, piperazinyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyi, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heterorionocyclic group containing 1 to 2 sulfur atom(s), for example, thienyl, dihydrodithiinyl, dihydrodithionyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.; and the like.

Suitable "substituent" in the terms "aryl which may have suitable substituent(s)", "fluorenyl which may have suitable substituent(s)", "piperidyl which may have suitable substituent(s)", "piperazanyl which may have suitable substituent(s)", "piperazinio which may have suitable substituent(s)", "homopiperazinyl which may have suitable substituent(s)", "piperidyloxy which may have suitable substituentfs)", "amino having one or two suitable substituent(s)", "heterocyclic group which may have suitable substituent(s)", "ar(lower)alkyl which may have suitable substituent(s)", "heterocycliccarbonyl which may have suitable substituent(s)", "heterocyclic(lower)alkyl which may have suitable substituent(s)", "heteromonocyclic group which may have suitable substituent(s)", "piperaziro which may have suitable substituent(s)", "piperidino which may have suitable substituent(s)" and "homopiperidino which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo (lower) alkyl as exemplilied above, cyclo (lower) alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino (lower)alkyl wherein protected amino moiety and lower alkyl moiety are each as exemplified above, acyl as exemplified above, cyano, sulfo, oxo, sulfamoyl, carbamoyloxy, mercapto, lower alkylthio wherein lower alkyl moiety is as exemplified above, hydroxy, protected hydroxy as exemplified above, heterocyclic group which may have lower alkyl wherein heterocyclic moiety and lower alkyl moiety are each as exemplified above, imino, [di(lower)alkylamino] (lower)alkyl wherein lower alkyl moiety is as exemplified above, [di(lower)alkylamino](lower)alkoxy wherein lower alkyl moiety and lower alkoxy moiety are each as exemplified above, mono(or di or tri)(protected hydroxy)(lower) alkyl wherein protected hydroxy moiety and lower alkyl moiety are each as exemplified above, mono(or di or tri) (hydroxy)(lower)alkyl wherein lower alkyl moiety is as exemplified above, methylenedioxy and the like.

The processes for preparing the object and starting compounds are explained in detail in the following.

Process (1)

The compound (Ic) or a salt thereof can be prepared by reacting the compound (II) or its reactive derivative or a salt thereof with the compound (III) or its reactive derivative at the carboxy group, or a salt thereof.

Suitable reactive derivative of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N, O-bis (trimethylsilyl)acetamide, N-trimethylsilylacetamide or the like; a derivative formed by the reaction of the compound (II) with phosphorus trichloride or phosgene, and the like.

Suitable reactive derivative of the compound (III) may include an acid halide, an acid anhydride, an activated ester, and the like. The suitable example may be an acid chloride;

acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonlc acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl $[(CH_3)_2^+ N=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamlne, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (III) is used in free acid form or its salt form in the reaction, the reaction is preferable carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl) carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may be also be carried out in the presence of an organic or inorganic base such as an alkali metal bicarbonate, tri (lower)alkylamine, pyridine, N-(lower)-alkylmorphorine, N,N-di(lower)alkylbenzylamine, or the like.

The reaction temperature is not critical, and the reaction is usually carried out under cooling to heating.

Process (2)

The compound (Ib) or a salt thereof can be prepared by reacting the compound (Ia) or its reactive derivative at the carboxy group, or a salt thereof with the compound (IV) or its reactive derivative, or a salt thereof.

This reaction can be carried out in a similar manner to that of the aforementioned Process (1), and therefore the reagents to be used and the reaction conditions (e.g., solvent, reaction temperature, etc.) can be referred to those of the Process (I).

Process (3)

The compound (Id) or a salt thereof can be prepared by reacting the compound (II) or a salt thereof with the compound (XI) or a salt thereof.

The reaction can be carried out in the manner disclosed in Example 12 or similar manners thereto.

Process (4)

The compound (Ie) or a salt thereof can be prepared by reacting the compound (II) or a salt thereof with the compound (XII) and then by subjecting the resultant compound to reduction reaction.

The reaction can be carried out in the manner disclosed in Example 13 or similar manners thereto.

Process (5)

The compound (If) or a salt thereof can be prepared by reacting the compound (II) or a salt thereof with the compound (XIII) or a salt thereof.

The reaction can be carried out in the manner disclosed in Example 39 or similar manners thereto.

Process (A)

The compound (IIb) or a salt thereof can be prepared by reacting the compound (IIa) or its reactive derivative at the carboxy group, or a salt thereof with the compound (IV) or its reactive derivative, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

Process (B)

The compound (II) or a salt thereof can be prepared by subjecting the compound (V) or a salt thereof to elimination reaction of the amino protective group.

Suitable method of this elimination reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]-non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.]. This reaction is usually carried out in no solvent.

The reaction may be carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

The reaction temperature is not critical and the reaction is usually carried out under cooling to warming.

(ii) For reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

Additionally, in case that the above-mentioned acids to be used in chemical reduction are in liquid, they can also be used as a solvent.

The reaction temperature of this reduction is not critical and the reaction is usually carried out under cooling to warming.

Process C

The compound (VIIIa) or a salt thereof can be prepared by reacting the compound (VI) or its reactive derivative at the carboxy group, or a salt thereof with the compound (VII) or its reactive derivative, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

Process (D)

The compound (IX) or a salt thereof can be prepared by subjecting the compound (VIII) or a salt thereof to elimination reaction of the amino protective group.

This reaction can be carried out in a similar manner to that of the aforementioned Process (B), and therefore the reagents to be used and the reaction conditions (e.g., solvent, reaction temperature, etc.) can be referred to those of the Process (B).

Process (E)

The compound (V) or a salt thereof can be prepared by reacting the compound (IX) or its reactive derivative, or a salt thereof with the compound (X) or its reactive derivative at the carboxy group, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

Suitable salts of the object, starting compounds and their reactive derivatives in Processes (1)-(5) and (A)-(E) can be referred to the ones as exemplified for the compound (I).

The compounds obtained by the above processes can be isolated and purified by a conventional method such as pulverization, recrystallization, column chromatography, reprecipitation, or the like.

It is to be noted that the compound (I) and the other compounds may include one or more stereoisomer(s) such as optical isomer(s) and geometrical isomer(s) due to asymmetric carbon atom(s) and double bond(s), and all of such isomers and mixture thereof are included within the scope of this invention.

The object compounds (I) and pharmaceutically acceptable salts thereof possess a strong inhibitory activity on the production of nitric oxide (NO).

Accordingly, the object compounds (I) and pharmaceutically acceptable salts thereof are expected to possess a nitric oxide synthase (NOS)-inhibitory activity or a NOS-production inhibitory activity.

Accordingly, they are useful for prevention and/or treatment of NO-mediated diseases such as adult respiratory distress syndrome, cardiovascular ischemia, myocarditis, heart failure, synovitis, shock (e.g., septic shock, etc.), diabetes (e.g., insulin-dependent diabetes mellitus, etc.), diabetic nephropathy, diabetic retinopathy, diabetic neuropathy, glomerulonephritis, peptic ulcer, inflammatory bowel disease (e.g., ulcerative colitis, chronic colitis, etc.), cerebral infarction, cerebral ischemia, migraine, rheumatoid arthritis, gout, neuritis, postherpetic neuralgia, osteoarthritis, osteoporosis, systemic lupus erythematosis, rejection by organ transplantation, asthma, metastasis, Alzheimer's disease, arthritis, CNS disorders, and the like.

In order to illustrate the usefulness of the object compound (I), the pharmacological test data of the representative compound of the compound (I) are shown in the following.

Test Compounds

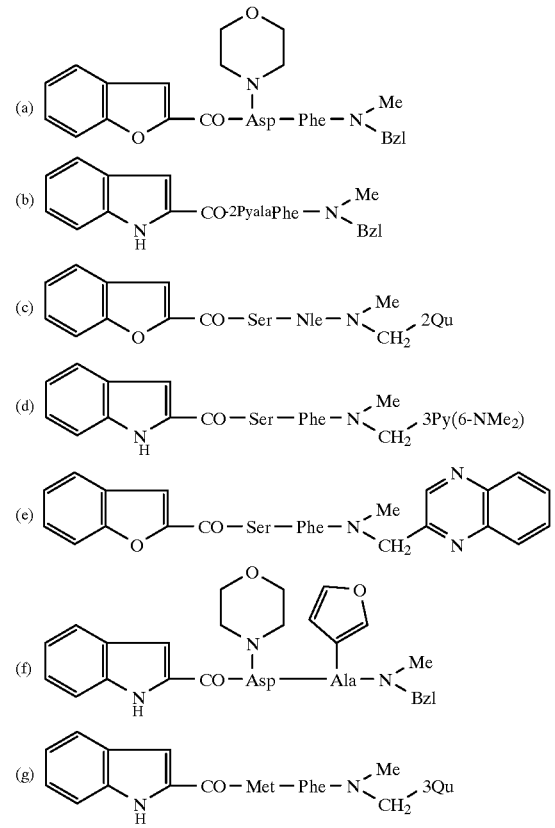

Test: Assay for Inhibitory activity on the production of Nitric Oxide

The murine macrophage cell line RAW264.7 (American Type Culture Collection, No. TIB71) were used in this study. RAW264.7 cells were grown on F75 plastic culture flasks at 37° C., 5% in Dulbecco's modified Eagles medium (DMEM) supplement with L-glutamine, penicillin, streptomycin and 10% heat-inactivated fetal bovine serum. They were removed from culture flasks by rubber cell scraper and were centrifuged and resuspended in DMEM without phenol red. They were plated in 96-well microliter plates ($10^5$ cells per well) and allowed to adhere for 2 hours. The test samples were added and preincubated for 1 hour. Thereafter the cells were activated by both of lipopolysaccharide (LPS) (1 μg/ml) and interferon γ (INF γ) (3 u/ml) for 18–24 hours and were mixed with an equal volume of Griess reagent (1% sulfanilamide/0.1% N-naphthylethylenediamine dihydrochloride/2.5% $H_3PO_4$) and incubated at room temperature for 10 minutes. The absorbance was read at 570 nm using microplatereader and $NO_2$ was measured using $NaNO_2$ as a standard.

Test result

| Test Compounds ($10^{-5}$M) | inhibition (%) |
|---|---|
| (a) | 100 |
| (b) | 100 |
| (c) | 100 |
| (d) | 100 |
| (e) | 100 |
| (f) | 100 |
| (g) | 100 |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, intravenous drip, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

W is lower alkyl, 1,2-methylenedioxyphenyl, phenyl, naphthyl, fluorenyl which may have oxo, pyrrolyl, pyridyl, furyl, which may have phenyl, thienyl or a group of the formula:

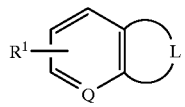

[in which $R^1$ is hydrogen, halogen, lower alkyl, nitro, di(lower)alkylamino, amino, hydroxyamino or lower alkoxy,
Q is CH or N, L is a bivalent radical selected from

(in which Y is CH or N,
Z is NH, O or S, and
--- is a single bond or a double bond) and

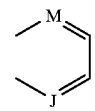

(in which M is CH or N, and J is CH or N)],
$A^1$ is lower alkylene (more preferably $C_1$–$C_4$ alkylene; more preferably methylene), —NHCO—,

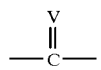

(in which V is O or S), or —$SO_2$—,
T is hydrogen, phenyl or naphthyl, each of which may have 1 to 3 (more preferably one or two; most preferably one) substituent(s) selected from the group consisting of hydroxy, protected hydroxy (more preferably acyloxy), halogen, lower alkoxy and lower alkyl; imidazolyl; pyridyl; indolyl; thienyl; furyl; hydroxy; lower alkanoyloxy; heterocycliccarbonyloxy(more preferably pyridylcarbonyloxy); heterocyclic(lower)alkanoyloxy (more preferably pyridyl(lower)alkanoyloxy or piperidyl(lower)alkanoyloxy); [di(lower)alkylamino] (lower)alkanoyloxy; ar(lower)alkoxy (more preferably phenyl(lower)alkoxy); sulfooxy; mercapto; lower alkylthio; mono(or di or tri)phenyl(lower)alkylthio; [di (lower)-alkylamino](lower)alkanoylthio; amino; acylamino [more preferably aroylamino (more preferably benzoylamino), lower alkanoylamino or ar(lower) alkoxycarbonylamino (more preferably phenyl(lower) alkoxycarbonylamino)]; guanidino or guanidino having phenylsulfonyl substituted with 3 lower alkyl and lower alkoxy; or a group of the formula:

(in which
$R^2$ is hydroxy, phenyl(lower)alkoxy (more preferably benzyloxy); morpholinyl; piperazinyl which may have 1 to 3 (more preferably one or two; most preferably one) suitable substituent(s) (more preferably substituent selected from the group consisting of lower alkyl, carboxy, protected carboxy (more preferably esterified carboxy; most preferably lower alkoxycarbonyl), carboxy(lower)alkyl, protected carboxy(lower)alkyl (more preferably esterified carboxy(lower)alkyl; most preferably lower alkoxycarbonyl(lower)alkyl), heterocyclic group (more preferably pyridyl or pyrimidinyl), cyclo (lower)alkyl, aryl (more preferably phenyl), hydroxy (lower)alkyl, protected hydroxy(lower)alkyl (more preferably acyloxy(lower)alkyl), di(lower)alkylamino(lower)alkyl and acyl (more preferably lower alkanoyl or lower alkoxycarbonyl); piperidyl which may have 1 to 3 (more preferably one or two; most preferably one) suitable substituent(s) (more preferably heterocyclic group; most preferably piperidyl); pyrrolidinyl; thiomorpholinyl; homopiperazinyl which may have 1 to 3 (more preferably one or two; most preferably one) suitable substituent(s) (more preferably lower alkyl); piperazinio which may have two or three (more preferably two) suitable substituent (more preferably-lower alkyl); piperidyloxy which may have 1 to 3 (more preferably one or two; most preferably one) suitable substituent(s) (more preferably lower alkyl); or amino having one or two substituent(s) selected from the group consisting of lower alkyl, ar(lower)alkyl (more preferably phenyl(lower)alkyl), cyclo(lower)alkyl, heterocyclic group (more preferably morpholinyl or pyrazolyl), mono (or di or tri)hydroxy(lower)alkyl (more preferably di(or tri)hydroxyklower)alkyl), mono(or di or tri)(protected hydroxy)(lower)alkyl (more preferably di(or tri)acyloxy(lower)alkyl) and [di(lower)alkylamino](lower)alkyl [more preferably mono(or di)(lower)alkylamino, cyclo(lower)alkylamino, phenyl(lower)alkylamino, morpholinylamino, pyrazolylamino, [di(lower)alkylamino](lower)alkylamino, amino having lower alkyl and [di(lower)alkylamino](lower)alkyl, di(or tri)hydroxy(lower)alkylamino];

$A^2$ is lower alkylene (more preferably $C_1$–$C_2$ alkylene), $R^8$ is hydrogen or lower alkyl, or $R^8$ and a group of the formula: —$A^2$—T are linked together to form a group of the formula:

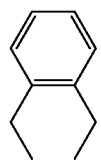

$R^3$ is hydrogen; phenyl which may have 1 to 3 (more preferably one or two; most preferably one) suitable substituent(s) [more preferably substituent selected from the group consisting of hydroxy, protected hydroxy (more preferably phenyl(lower)alkoxy), lower alkoxy and halogen]; hydroxy; protected hydroxy (more preferably acyloxy); cyclo(lower)alkyl; lower alkylthio; pyridyl; imidazolyl which may have acyl (more preferably tolylsulfonyl); thienyl; or furyl;

$A^3$ is bond or lower alkylene, $R^9$ is hydrogen or lower alkyl, or $R^9$ and a group of the formula: —$A^3$—$R^3$ are linked together to form a group of the formula:

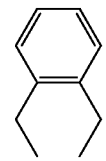

$R^4$ is carboxy, esterified carboxy (more preferably lower alkoxycarbonyl), piperazinylcarbonyl which may have lower alkyl, tetrahydroquinolylcarbonyl, or a group of the formula:

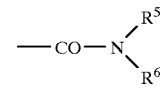

(in which
$R^5$ is hydrogen or lower alkyl, and
$R^6$ is hydrogen; phenyl; phenyl(lower)alkyl which may have 1 to 3 (more preferably one or two; most preferably one) suitable substituent(s) (more preferably substituent selected from the group consisting of lower alkyl, lower alkoxy, carboxy, protected carboxy (more preferably esterified carboxy; most preferably lower alkoxycarbonyl), mono(or di or tri)halo(lower)alkyl (more preferably trihalo(lower)alkyl), di(lower)alkylamino, [di(lower)alkylamino](lower)alkyl, [di(lower)alkylamino](lower)alkoxy, halogen and heterocyclic group (more preferably triazolyl, piperazinyl, pyrazolyl or imidazolyl) which may have lower alkyl); [di(lower)alkylamino](lower)alkyl; pyridyl(lower)alkyl which may have 1 to 3 (more preferably one or two; most preferably one) suitable substituent(s) (more preferably substituent selected from the group consisting of lower alkyl, lower alkoxy, halogen, di(lower)alkylamino, protected amino (more preferably acylamino; lower alkanoylamino), heterocyclic group (more preferably pyridyl) and lower alkylthio), quinolyl(lower)alkyl, quinoxalinyl(lower)alkyl, pyrimidinyl(lower)alkyl, pyrazinyl(lower)alkyl, pyrazolyl(lower)alkyl or benzimidazolyl(lower)alkyl), or $R^4$ and a group of the formula: —$A^3$—$R^3$ are linked together to form

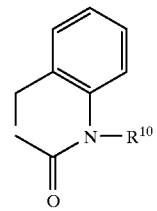

(in which $R^{10}$ is phenyl(lower)alkyl),
with proviso that
when M is CH, and J is CH, then Q is N.

More preferred embodiment(s) of the object compound (I) are represented by the following formulae (A)–(D).

(A)

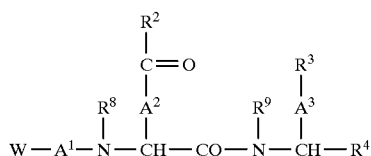

wherein
W is lower alkyl, 1,2-methylenedioxyphenyl, phenyl, naphthyl, fluorenyl which may have oxo, pyrrolyl, pyridyl, furyl which may have phenyl, thienyl or a group of the formula:

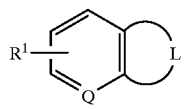

[in which $R^1$ is hydrogen, halogen, lower alkyl, nitro, di(lower)alkylamino, amino, hydroxyamino or lower alkoxy,
Q is CH or N,
L is a bivalent radical selected from

(in which Y is CH or N,
Z is NH, O or S, and
--- is a single bond or a double bond) and

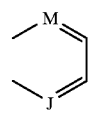

(in which M is CH or N, and
J is CH or N)],
$A^1$ is lower alkylene (more preferably $C_1$–$C_4$ alkylene; more preferably methylene), —NHCO—,

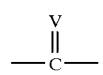

(in which V is O or S), or —$SO_2$—,
$R^2$ is morpholinyl,
$A^2$ is lower alkylene (more preferably $C_1$–$C_2$ alkylene),
$R^8$ is hydrogen or lower alkyl,
$R^3$ is hydrogen; phenyl which may have 1 to 3 (more preferably one or two; most preferably one) suitable substituent(s) [more preferably substituent selected from the group consisting of hydroxy, protected hydroxy (more preferably phenyl(lower)alkoxy), lower alkoxy and halogen]; hydroxy; protected hydroxy (more preferably acyloxy); cyclo(lower)alkyl; lower alkylthio; pyridyl; imidazolyl which may have acyl (more preferably tolylsulfonyl); thienyl; or furyl;
$A^3$ is bond or lower alkylene, $R^9$ is hydrogen or lower alkyl, or
$R^9$ and a group of the formula: —$A^3$—$R^3$ are linked together to form a group of the formula:

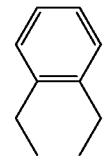

$R^4$ is carboxy, esterified carboxy (more preferably lower alkoxycarbonyl), piperazinylcarbonyl which may have lower alkyl, tetrahydroquinolylcarbonyl, or a group of the formula:

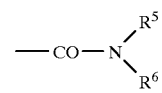

(in which
$R^5$ is hydrogen or lower alkyl, and
$R^6$ is hydrogen; phenyl; pyridyl(lower)alkyl substituted with 1 to 3 (more preferably one or two; most preferably one) suitable substituent(s) (more preferably substituent selected from the group consisting of lower alkyl, lower alkoxy, halogen, di(lower)alkylamino, protected amino (more preferably acylamino; lower alkanoylamino), heterocyclic group (more preferably pyridyl) and lower alkylthio), quinolyl(lower)alkyl, quinoxalinyl(lower)alkyl, pyrimidinyl(lower)alkyl, pyrazinyl(lower)alkyl, pyrazolyl (lower)alkyl or benzimidazolyl(lower)alkyl), or
$R^4$ and a group of the formula: —$A^3$—$R^3$ are linked together to form

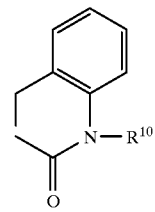

(in which $R^{10}$ is phenyl(lower)alkyl), with proviso that when M is CH, and J is CH, then Q is N.

(B)

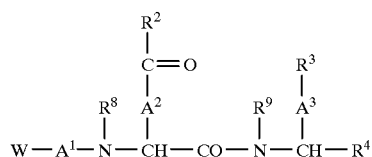

wherein
W is lower alkyl, 1,2-methylenedioxyphenyl, phenyl, naphthyl, fluorenyl which may have oxo, pyrrolyl, pyridyl, furyl which may have phenyl, thienyl or a group of the formula:

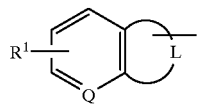

[in which R¹ is hydrogen, halogen, lower alkyl, nitro, di(lower)alkylamino, amino, hydroxyamino or lower alkoxy,
Q is CH or N,
L is a bivalent radical selected from

(in which Y is CH or N,
Z is NH, O or S, and
--- is a single bond or a double bond) and

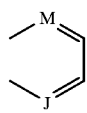

(in which M is CH or N, and
J is CH or N)],
A¹ is lower alkylene (more preferably $C_1$–$C_4$ alkylene; more preferably methylene), —NHCO—,

(in which V is O or S), or —$SO_2$—,
R² is lower alkylpiperazinyl,
A² is lower alkylene (more preferably $C_1$–$C_2$ alkylene),
R⁸ is hydrogen or lower alkyl,
R³ is hydrogen; phenyl which may have 1 to 3 (more preferably one or two; most preferably one) suitable substituent(s) [more preferably substituent selected from the group consisting of hydroxy, protected hydroxy (more preferably phenyl(lower)alkoxy), lower alkoxy and halogen]; hydroxy; protected hydroxy (more preferably acyloxy); cyclo(lower)alkyl; lower alkylthio; pyridyl; imidazolyl which may have acyl (more preferably tolylsulfonyl); thienyl; or furyl;
A³ is bond or lower alkylene,
R⁹ is hydrogen or lower alkyl, or
R⁹ and a group of the formula: —A³—R³ are linked together to form a group of the formula:

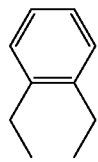

R⁴ is carboxy, esterified carboxy (more preferably lower alkoxycarbonyl), piperazinylcarbonyl which may have lower alkyl, tetrahydroquinolylcarbonyl, or a group of the formula:

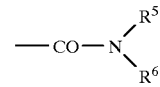

(in which
R⁵ is hydrogen or lower alkyl, and
R⁶ is hydrogen; phenyl; phenyl(lower)alkyl which may have 1 to 3 (more preferably one or two; most preferably one) suitable substituent(s) (more preferably substituent selected from the group consisting of lower alkyl, lower alkoxy, carboxy, protected carboxy (more preferably esterified carboxy; most preferably lower alkoxycarbonyl), mono(or di or tri)halo(lower)alkyl (more preferably trihalo(lower) alkyl), di(lower)alkylamino, [di(lower)alkylamino] (lower)alkyl, [di(lower)-alkylamino](lower)alkoxy, halogen and heterocyclic group (more preferably triazolyl, piperazinyl, pyrazolyl or imidazolyl) which may have lower alkyl); [di(lower)alkylamino] (lower)alkyl; pyridyl(lower)alkyl which may have 1 to 3 (more preferably one or two; most preferably one) suitable substituent(s) (more preferably substituent selected from the group consisting of lower alkyl, lower alkoxy, halogen, di(lower)alkylamino, protected amino (more preferably acylamino; lower alkanoylamino), heterocyclic group (more preferably pyridyl) and lower alkylthio), quinolyl(lower) alkyl, quinoxalinyl(lower)alkyl, pyrimidinyl(lower) alkyl, pyrazinyl(lower)alkyl, pyrazolyl(lower)alkyl or benzimidazolyl(lower)alkyl), or
R⁴ and a group of the formula: —A³—R³ are linked together to form

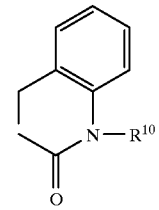

(in which R¹⁰ is phenyl(lower)alkyl),
with proviso that
when M is CH, and J is CH, then Q is N.

(C)

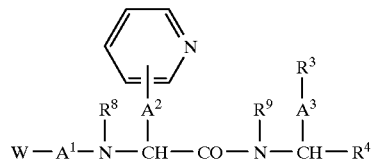

wherein
W is lower alkyl, 1,2-methylenedioxyphenyl, phenyl, naphthyl, fluorenyl which may have oxo, pyrrolyl, pyridyl, furyl which may have phenyl, thienyl or a group of the formula:

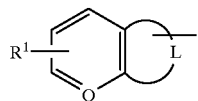

[in which R¹ is hydrogen, halogen, lower alkyl, nitro, di(lower)alkylamino, amino, hydroxyamino or lower alkoxy, Q is CH or N, L is a bivalent radical selected from

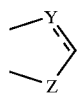

(in which Y is CH or N, Z is NH, O or S, and --- is a single bond or a double bond) and

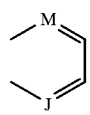

(in which M is CH or N, and J is CH or N)],

A¹ is lower alkylene (more preferably $C_1$–$C_4$ alkylene; more preferably methylene), —NHCO—,

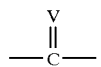

(in which V is O or S), or —$SO_2$—,

A² is lower alkylene (more preferably $C_1$–$C_2$ alkylene),

R⁸ is hydrogen or lower alkyl,

R³ is hydrogen; phenyl which may have 1 to 3 (more preferably one or two; most preferably one) suitable substituent(s) [more preferably substituent selected from the group consisting of hydroxy, protected hydroxy (more preferably phenyl(lower)alkoxy), lower alkoxy and halogen]; hydroxy; protected hydroxy (more preferably acyloxy); cyclo(lower)alkyl; lower alkylthio; pyridyl; imidazolyl which may have acyl (more preferably tolylsulfonyl); thienyl; or furyl;

A³ is bond or lower alkylene,

R⁹ is hydrogen or lower alkyl, or

R⁹ and a group of the formula: —A³—R³ are linked together to form a group of the formula:

R⁴ is carboxy, esterified carboxy (more preferably lower alkoxycarbonyl), piperazinylcarbonyl which may have lower alkyl, tetrahydroquinolylcarbonyl, or a group of the formula:

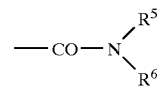

(in which

R⁵ is hydrogen or lower alkyl, and

R⁶ is hydrogen; phenyl; phenyl(lower)alkyl which may have 1 to 3 (more preferably one or two; most preferably one) suitable substituent(s) (more preferably substituent selected from the group consisting of lower alkyl, lower alkoxy, carboxy, protected carboxy (more preferably esterified carboxy; most preferably lower alkoxycarbonyl), mono(or di or tri)halo(lower)alkyl (more preferably trihalo(lower)alkyl), di(lower)alkylamino, [di(lower)alkylamino](lower)alkyl, [di(lower)alkylamino](lower)alkoxy, halogen and heterocyclic group (more preferably triazolyl, piperazinyl, pyrazolyl or imidazolyl) which may have lower alkyl); [di(lower) alkylamino](lower)alkyl; pyridyl(lower)alkyl which may have 1 to 3 (more preferably one or two; most preferably one) suitable substituent(s) (more preferably substituent selected from the group consisting of lower alkyl, lower alkoxy, halogen, di(lower)alkylamino, protected amino (more preferably acylamino; lower alkanoylamino), heterocyclic group (more preferably pyridyl) and lower alkylthio), quinolyl(lower)alkyl, quinoxalinyl(lower)alkyl, pyrimidinyl(lower)alkyl, pyrazinyl(lower)alkyl, pyrazolyl(lower)alkyl or benzimidazolyl(lower)alkyl), or R⁴ and a group of the formula: —A³—R³ are linked together to form

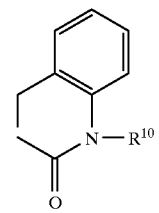

(in which R¹⁰ is phenyl(lower)alkyl), with proviso that when M is CH, and J is CH, then Q is N.

(D)

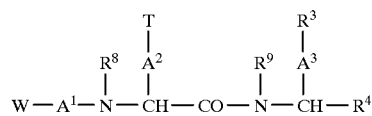

wherein

W is lower alkyl, 1,2-methylenedioxyphenyl, phenyl, naphthyl, fluorenyl which may have oxo, pyrrolyl, pyridyl, furyl which may have phenyl, thienyl or a group of the formula:

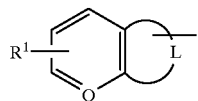

[in which $R^1$ is hydrogen, halogen, lower alkyl, nitro, di(lower)alkylamino, amino, hydroxyamino or lower alkoxy,
Q is CH or N,
L is a bivalent radical selected from

(in which Y is CH or N,
Z is NH, O or S, and
--- is a single bond or a double bond) and

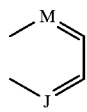

(in which M is CH or N, and J is CH or N)],
$A^1$ is lower alkylene (more preferably $C_1$-$C_4$ alkylene; more preferably methylene), —NHCO—,

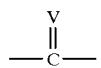

(in which V is O or S), or —$SO_2$—,
T is hydroxy or lower alkylthio,
$A^2$ is lower alkylene (more preferably $C_1$-$C_2$ alkylene),
$R^8$ is hydrogen or lower alkyl,
$R^3$ is hydrogen; phenyl which may have 1 to 3 (more preferably one or two; most preferably one) suitable substituent(s) [more preferably substituent selected from the group consisting of hydroxy, protected hydroxy (more preferably phenyl(lower)alkoxy), lower alkoxy and halogen]; hydroxy; protected hydroxy (more preferably acyloxy); cyclo(lower)alkyl; lower alkylthio; pyridyl; imidazolyl which may have acyl (more preferably tolylsulfonyl); thienyl; or furyl;
$A^3$ is bond or lower alkylene,
$R^9$ is hydrogen or lower alkyl, or
$R^9$ and a group of the formula: —$A^3$—$R^3$ are linked together to form a group of the formula:

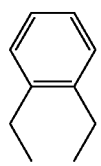

$R^4$ is carboxy, esterified carboxy (more preferably lower alkoxycarbonyl), piperazinylcarbonyl which may have lower alkyl, tetrahydroquinolylcarbonyl, or a group of the formula:

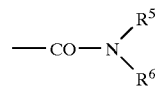

(in which
$R^5$ is hydrogen or lower alkyl, and
$R^6$ is hydrogen; phenyl; [di(lower)alkylamino](lower)alkyl; pyridyl(lower)alkyl substituted with 1 to 3 (more preferably one or two; most preferably one) suitable substituent(s) (more preferably substituent selected from the group consisting of lower alkyl, lower alkoxy, halogen, di(lower)alkylamino, protected amino (more preferably acylamino; lower alkanoylamino), heterocyclic group (more preferably pyridyl) and lower alkylthio), quinolyl(lower)alkyl, quinoxalinyl(lower)alkyl, pyrimidinyl(lower)alkyl, pyrazinyl(lower)alkyl, pyrazolyl(lower)alkyl or benzimidazolyl(lower)alkyl), or $R^4$ and a group of the formula: —$A^3$—$R^3$ are linked together to form

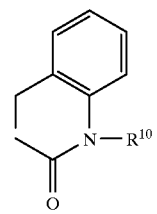

(in which $R^{10}$ is phenyl(lower)alkyl),
with proviso that
when M is CH, and J is CH, then Q is N.

The following Preparations and Examples are given for the purpose of illustrating the present invention in detail.

In the following Examples and Preparations, there are employed the other abbreviations in addition to the abbreviations adopted by the IUPAC-IUB (Commission on Biological Nomenclature).

The abbreviations used are as follows.

| | |
|---|---|
| Ac | acetyl |
| 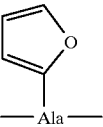 | 3-cyclohexyl-L-alanine |
| 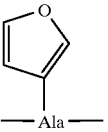 | 3-(2-furyl)-L-alanine |
| | 3-(3-furyl)-L-alanine |

-continued

| | |
|---|---|
| 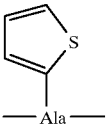 | 3-(2-thienyl)-L-alanine |
| Arg | L-arginine |
| Asp | L-aspartic acid |
| D-Asp | D-aspartic acid |
| Boc | t-butoxycarbonyl |
| Bz | benzoyl |
| Bzl | benzyl |
| Bzl(4-COOH) | 4-carboxybenzyl |
| Bzl(4-COOMe) | 4-methoxycarbonylbenzyl |
| Bzl(4-OH) | 4-hydroxybenzyl |
| Bzl(4-NMe₂) | 4-dimethylaminobenzyl |
| Bzl(4-CH₂NMe₂) | 4-(dimethylaminomethyl)benzyl |
| Bzl(4-Cl) | 4-chlorobenzyl |
| Bzl(4-Br) | 4-bromobenzyl |
| Bzl(4-F) | 4-fluorobenzyl |
| Bzl(4-OMe) | 4-methoxybenzyl |
| Bzl(2-Me) | 2-methylbenzyl |
| Bzl(3-Me) | 3-methylbenzyl |
| Bzl(4-Me) | 4-methylbenzyl |
| Bzl(4-CF₃) | 4-trifluoromethylbenzyl |
| Bzl(4-O—(CH₂)₂—NMe₂) | 4-(2-dimethylaminoethoxy)benzyl |
| 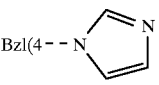 | 4-(1-1H-imidazolyl)benzyl |
| 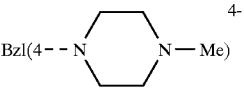 | 4-(1-methylpiperazin-4-yl)benzyl |
| 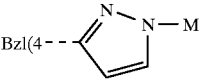 | 4-(1-methylpyrazol-3-yl)benzyl |
| 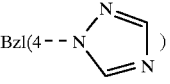 | 4-(1-1H-triazolyl)benzyl |
| Cys | L-cysteine |
| Et | ethyl |
| Glu | L-glutamic acid |
| Gly | glycine |
| His | L-histidine |
| Leu | L-leucine |
| Lys | L-lysine |
| Me | methyl |
| MePhe | N-methyl-L-phenylalanine |
| Met | L-methionine |
| 1Nal | 3-(1-naphthyl)-L-alanine |
| 2Nal | 3-(2-naphthyl)-L-alanine |
| 1Naph | 1-naphthyl |
| 2Naph | 2-naphthyl |
| Nle | L-norleucine |
| Nva | L-norvaline |
| Orn | L-ornithine |
| ⁿPr | n-propyl |
| Phe | L-phenylalanine |
| D-Phe | D-phenylalanine |
| Phe(4-Cl) | 3-(4-chlorophenyl)-L-alanine |
| Phe(4-Me) | 3-(4-methylphenyl)-L-alanine |
| Phg | (S)-2-phenylglycine |
| 4Pm | 4-Pyrimidinyl |
| 2Pyala | 3-(2-pyridyl)-L-alanine |
| 3Pyala | 3-(3-pyridyl)-L-alanine |
| 4Pyala | 3-(4-pyridyl)-L-alanine |
| 2Py | 2-pyridyl |
| 3Py | 3-pyridyl |
| 4Py | 4-pyridyl |
| 3Py(6-NHAc) | (6-acetylaminopyridin-3-yl) |
| 3Py(5-Br) | (5-bromopyridin-3-yl) |
| 3Py(6-Cl) | (6-chloropyridin-3-yl) |
| 3Py(6-NMe₂) | (6-dimethylaminopyridin-3-yl) |
| 3Py(6-OEt) | (6-ethoxypyridin-3-yl) |
| 3Py(4-OMe) | (4-methoxypyridin-3-yl) |
| 3Py(5-OMe) | (5-methoxypyridin-3-yl) |
| 3Py(6-OMe) | (6-methoxypyridin-3-yl) |
| 3Py(6-Me) | (6-methoxypyridin-3-yl) |
| 3Py(6-SMe) | (6-methylthiopyridin-3-yl) |
| 3Py(6-n-Pr) | (6-n-propylpyridin-3-yl) |
| 3Py(6-2Py) | [6-(2-pyridyl)pyridin-3-yl] |
| 3Py(6-3Py) | [6-(3-pyridyl)pyridin-3-yl] |
| 2Qu | 2-quinolyl |
| 3Qu | 3-quinolyl |
| 6Qu | 6-quinolyl |
| 7Qu | 7-quinolyl |
| Ser | L-serine |
| Thr | L-trheonine |
| Tos | p-toluenesulfonyl |
| Trt | trityl |
| Tyr | L-tyrosine |
| Val | L-valine |
| Z | benzyloxycarbonyl |
| Z(2-Cl) | 2-chlorobenzyloxycarbonyl |

The Starting Compounds used and the Object Compounds obtained in the following Prenarations and Examples are given in the Table as below, in which the formulae of the Starting Compounds are in the upper and the formulae of the Object Compounds are in the lower, respectively.

TABLE

| Preparation No. | Formula |
|---|---|
| 1 | 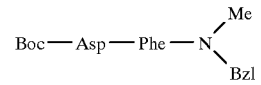 |

TABLE-continued
| Preparation No. | Formula |
|---|---|
| | 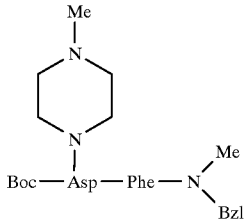 Boc—Asp—Phe—N(Me)(Bzl), with 4-methylpiperazin-1-yl on Asp |
| 2 | 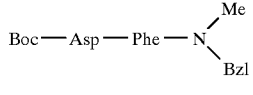 Boc—Asp—Phe—N(Me)(Bzl), with morpholin-4-yl on Asp |
| 3 | 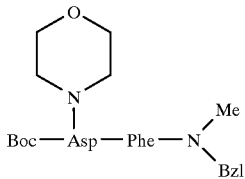 Boc—Asp—Phe—N(Me)(Bzl), with 4-methylpiperazin-1-yl on Asp |
| | 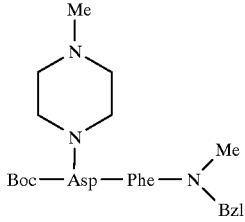 H—Asp—Phe—N(Me)(Bzl), with 4-methylpiperazin-1-yl on Asp |
| 4 | 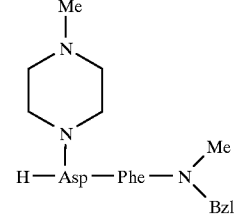 Boc—Asp—2Pyala—N(Me)(Bzl), with 4-methylpiperazin-1-yl on Asp |
| | 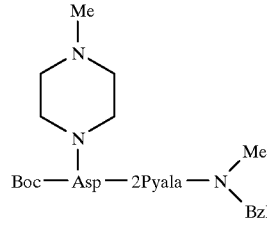 H—Asp—2Pyala—N(Me)(Bzl) · 3HCl, with 4-methylpiperazin-1-yl on Asp |

TABLE-continued
| Preparation No. | Formula |
| --- | --- |
| 5-(1) | 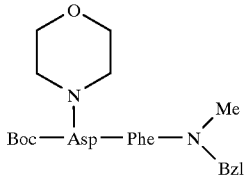 |
| | 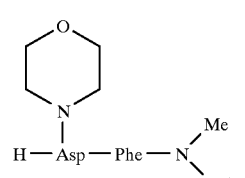 |
| 5-(2) | 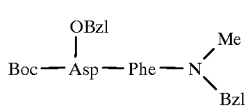 |
| | 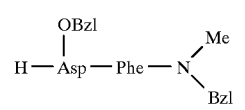 |
| 5-(3) | 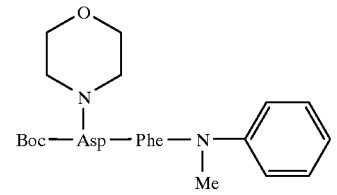 |
| | 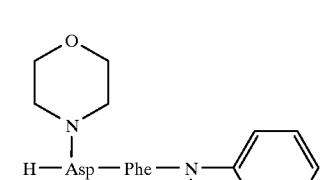 |
| 5-(4) | 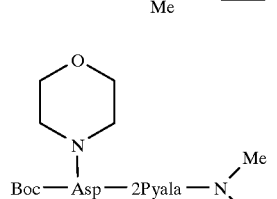 |
| | 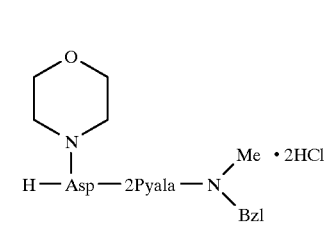 |

TABLE-continued

| Preparation No. | Formula |
|---|---|
| 5-(5) | Boc—Asp(N-morpholino)—Phe—N(Me)—(CH₂)₂N(Me)₂ |
| | H—Asp(N-morpholino)—Phe—N(Me)—(CH₂)₂N(Me)₂ •2HCl |
| 5-(6) | Boc—Asp(N-morpholino)—Phe—(4-methylpiperazin-1-yl) |
| | H—Asp(N-morpholino)—Phe—(4-methylpiperazin-1-yl) |
| 5-(7) | Boc—Asp(OBzl)—Phe—OEt |
| | H—Asp(OBzl)—Phe—OEt •HCl |
| 6 | Boc—Asp—OBzl |
| | Boc—Asp(4-methylpiperazin-1-yl)—OBzl |
| 7 | Boc—Asp—OMe |

TABLE-continued

| Preparation No. | Formula |
|---|---|
| 8 | Boc—Asp(morpholine)—OMe<br><br>Boc—Phe—N(4-methylpiperazine) |
| 9-(1) | H—Phe—N(4-methylpiperazine)<br><br>Boc—2Pyala—N(Me)(Bzl) |
| 9-(2) | H—2Pyala—N(Me)(Bzl) · 2HCl<br><br>Boc—Phe—N(Me)—(CH$_2$)$_2$N(Me)$_2$ |
| 10 | H—Phe—N(Me)—(CH$_2$)$_2$N(Me)$_2$<br><br>Boc—Asp(4-methylpiperazine)—OBzl |
| 11 | Boc—Asp(4-methylpiperazine)—OH<br><br>Z—Phe—OH |
| 12-(1) | Z—Phe—N(Me)(Ph)<br><br>Boc—2Pyala—OH |

TABLE-continued

| Preparation No. | Formula |
|---|---|
| | Boc—2Pyala—N(Me)(Bzl) |
| 12-(2) | Boc—Phe—OH |
| | Boc—Phe—N(Me)—(CH$_2$)$_2$N(Me)$_2$ |
| 12-(3) | Boc—Phe—OH |
| | Boc—Phe—N(piperazine)N—CH$_3$ |
| 12-(4) | Boc—Asp—OH (morpholine) |
| | Boc—Asp—NH(CH$_2$)$_2$—Ph (morpholine) |
| 13 | Boc—Asp—OMe (morpholine) |
| | Boc—Asp—OH (morpholine) |
| 14-(1) | Boc—Asp—OH (N-Me piperazine) |

TABLE-continued

| Preparation No. | Formula |
|---|---|
| | Boc—Asp(4-methylpiperazin-1-yl)—2Pyala—N(Me)(Bzl) |
| 14-(2) | Boc—Asp(morpholino)—OH |
| | Boc—Asp(morpholino)—2Pyala—N(Me)(Bzl) |
| 14-(3) | Boc—Asp(morpholino)—OH |
| | Boc—Asp(morpholino)—Phe—N(Me)(Ph) |
| 14-(4) | Boc—Asp(morpholino)—OH |
| | Boc—Asp(morpholino)—Phe—N(Me)—(CH$_2$)$_2$N(Me)$_2$ |

TABLE-continued

| Preparation No. | Formula |
|---|---|
| 14-(5) | Boc—Asp(morpholine)—OH |
| | Boc—Asp(morpholine)—Phe—N(4-methylpiperazine) |
| 14-(6) | Boc—Asp(OBzl)—OH |
| | Boc—Asp(OBzl)—Phe—OEt |
| 15 | indole-2-COOH |
| | indole-2-CO—Asp(morpholine)—OMe |
| 16 | indole-2-CO—Asp(morpholine)—OMe |
| | indole-2-CO—Asp(morpholine)—OH |
| 17 | Z—Phe—N(Me)(Ph) |

TABLE-continued

| Preparation No. | Formula |
| --- | --- |
| | H—Phe—N(Me)(phenyl) |
| 18-(1) | Boc—Asp(morpholine)—NH(CH₂)₂—phenyl |
| | H—Asp(morpholine)—NH(CH₂)₂—phenyl ·HCl |
| 18-(2) | Boc—Asp(morpholine)—OMe |
| | H—Asp(morpholine)—OMe ·HCl |
| 19 | indole-2-COOH |
| | indole-2-CO—Asp(morpholine)—NH—(CH₂)₂—phenyl |
| 20 | H—Phe—N(Me)(Bzl) |
| | morpholine-N—CH₂CH₂CONH—Phe—N(Me)(Bzl) |

TABLE-continued
| Preparation No. | Formula |
|---|---|
| 21 | 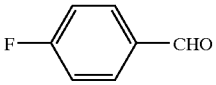 |
| 22 | 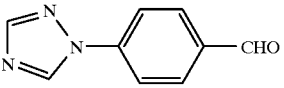 |
| 23 | 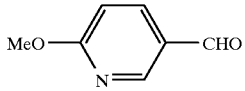 |
| 24 | 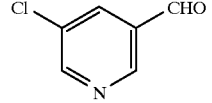 |
| 25 | 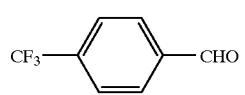 |
| 26 | 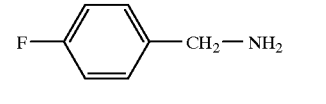 |

TABLE-continued

| Preparation No. | Formula |
|---|---|
| 27 | MeOOC—C₆H₄—CH₂—NH₂ ·HCl |
| | MeOOC—C₆H₄—CH₂—NH—Boc |
| 28 | F—C₆H₄—CH₂—NH—Boc |
| | F—C₆H₄—CH₂—N(Boc)(Me) |
| 29 | MeOOC—C₆H₄—CH₂—NH—Boc |
| | MeOOC—C₆H₄—CH₂—N(Boc)(Me) |
| 30 | HOOC—C₆H₄—CH₂—NH₂ |
| | MeOOC—C₆H₄—CH₂—NH₂ ·HCl |
| 31 | H₂N—CH₂—C₆H₄—COOH |
| | Me₂N—CH₂—C₆H₄—COOH |
| 32 | Me₂N—CH₂—C₆H₄—COOH |
| | Me₂N—CH₂—C₆H₄—CONH—Me |

TABLE-continued

| Preparation No. | Formula |
|---|---|
| 33 | Me₂N—CH₂—C₆H₄—CONH—Me |
| | Me₂N—CH₂—C₆H₄—CH₂—NH—Me |
| 34 | Boc—Asp—OBzl |
| | [piperazine with CH₂—COOEt on N1 and Boc—Asp—OBzl on N4] |
| 35 | [piperazine with CH₂—COOEt on N1 and Boc—Asp—OBzl on N4] |
| | [piperazine with CH₂—COOEt on N1 and Boc—Asp—OH on N4] |
| 36 | MeOOC—C₆H₄—CH₂—N(Boc)(Me) |
| | Boc—Phe—CON(Me)(Bzl(4-COOMe)) |
| 37 | F—C₆H₄—CH₂—N(Boc)(Me) |
| | Boc—Phe—CON(Me)(Bzl(4-F)) |
| 38 | Boc—His(τ-Tos)—OH |

TABLE-continued

| Preparation No. | Formula |
|---|---|
| | Boc—His(τ-Tos)—N(Me)(Bzl) |
| 39-(1) | Boc—Phe—OH |
| | Boc—Phg—N(Me)(Bzl) |
| 39-(2) | Z—Phe—OH |
| | Z—Phe—NH—Bzl |
| 39-(3) | Boc—Gly—OH |
| | Boc—Gly—N(Me)(Bzl) |
| 39-(4) | Boc—Phe—OH |
| | Boc—Phe—N(Me)(Bzl(4-OMe)) |
| 39-(5) | Boc—Tyr(Bzl)—OH |
| | Boc—Tyr(Bzl)—N(Me)(Bzl) |
| 39-(6) | Boc—Phe—OH |
| | Boc—Phe—N(Me)((CH$_2$)$_2$-Ph) |
| 39-(7) | Boc—Phe—OH |
| | Boc—Phe—N(Me)(CH$_2$-2Naph) |
| 39-(8) | Boc—Phe—OH |

TABLE-continued

| Preparation No. | Formula |
|---|---|
| 39-(9) | Boc—Phe—N(Me)(CH₂—1Naph)<br>Boc—Phe—OH |
| 39-(10) | Boc—Phe—N(Me)(Bzl(4-NMe₂))<br>Boc—Phe—OH |
| 39-(11) | Boc—Phe—N(Me)(Bzl(4-CH₂NMe₂))<br>Boc—Phe—OH |
| 39-12) | Boc—Phe—N(1,2,3,4-tetrahydroisoquinolin-2-yl)<br>Boc—Phe—OH |
| 39-(13) | Boc—Phe—N(Me)(Bzl(4-Cl))<br>Boc—Phe—OH |
| 39-(14) | Boc—Phe—N(Me)(Bzl(4-Br))<br>Boc—Phe—OH |
| 39-(15) | Boc—Phe—N(Me)(CH₂—3Py(6-OMe))<br>Boc—Phe—OH |
| 39-(16) | Boc—Phe—N(Et)(Bzl)<br>Boc—Phe—OH |
| | Boc—Phe—N(Me)(CH₂—3Py(6-Cl)) |

TABLE-continued

| Preparation No. | Formula |
|---|---|
| 39-(17) | Boc—Phe—OH <br><br> Boc—Phe—N(Me)(CH₂—3Py(6-Me)) |
| 39-(18) | Boc—Phe—OH <br><br> Boc—Phe—N(Me)(Bzl(4--N-1,2,4-triazole)) |
| 39-(19) | Boc—Phe—OH <br><br> Boc—Phe—N(Me)(CH₂—3Py(5-Cl)) |
| 39-(20) | Boc—Phe—OH <br><br> Boc—Phe—N(Me)(CH₂—2Py) |
| 39-(21) | Boc—Phe—OH <br><br> Boc—Phe—N(Me)(CH₂—4Py) |
| 39-(22) | Boc—Phe—OH <br><br> Boc—Phe—N(Me)(CH₂—3Py) |
| 39-(23) | Boc—Phe—OH <br><br> Boc—Phe—N(Me)(Bzl(4-OMe)) |
| 39-(24) | Boc—Phe—OH <br><br> Boc—Phe—N(Me)(Bzl(4-Me)) |

TABLE-continued

| Preparation No. | Formula |
|---|---|
| 39-(25) | Boc—Ser—OH |
| | Boc—Ser—N(Me)(Bzl) |
| 39-(26) | Boc—Leu—OH |
| | Boc—Leu—N(Me)(Bzl) |
| 39-(27) | Boc—Phe—OH |
| | Boc—Phe—N(Me)(Bzl(4-CF$_3$)) |
| 39-(28) | Boc-D-Phe—OH |
| | Boc-D-Phe—N(Me)(Bzl) |
| 40 | Boc—Phe—N(Me)(Bzl(4-OMe)) |
| | H—Phe—N(Me)(Bzl(4-OH)) |
| 41 | Boc—His(τ-Tos)—N(Me)(Bzl) |
| | H—His(τ-Tos)—N(Me)(Bzl) |
| 42-(1) | Boc—Phg—N(Me)(Bzl) |
| | H—Phg—N(Me)(Bzl) |

TABLE-continued

| Preparation No. | Formula |
|---|---|
| 42-(2) | Boc—Phe—N(Me)(Bzl(4-NMe₂)) |
| | H—Phe—N(Me)(Bzl(4-NMe₂)) |
| 42-(3) | Boc—Phe—N(Me)(Bzl(4-CH₂NMe₂)) |
| | H—Phe—N(Me)(Bzl(4-CH₂NMe₂)) |
| 42-(4) | Boc—Phe—N(1,2,3,4-tetrahydroisoquinolin-2-yl) |
| | H—Phe—N(1,2,3,4-tetrahydroisoquinolin-2-yl) |
| 42-(5) | Boc—Phe—N(Me)(Bzl(4-Cl)) |
| | H—Phe—N(Me)(Bzl(4-Cl)) |
| 42-(6) | Boc—Phe—N(Me)(Bzl(4-Br)) |
| | H—Phe—N(Me)(Bzl(4-Br)) |
| 42-(7) | Boc—Phe—N(Me)(Bzl(4-F)) |
| | H—Phe—N(Me)(Bzl(4-F)) |

TABLE-continued

| Preparation No. | Formula |
|---|---|
| 42-(8) | Boc—Phe—N(Me)(CH₂—3Py(6-OMe)) |
| | H—Phe—N(Me)(CH₂—3Py(6-OMe)) |
| 42-(9) | Boc—Phe—N(Et)(Bzl) |
| | H—Phe—N(Et)(Bzl) |
| 42-(10) | Boc—Phe—N(Me)(CH₂—3Py(6-Cl)) |
| | H—Phe—N(Me)(CH₂—3Py(6-Cl)) |
| 42-(11) | Boc—Phe—N(Me)(CH₂—3Py(6-Me)) |
| | H—Phe—N(Me)(CH₂—3Py(6-Me)) |
| 42-(12) | Boc—Phe—N(Me)(Bzl(4——1,2,4-triazol-1-yl)) |
| | H—Phe—N(Me)(Bzl(4——1,2,4-triazol-1-yl)) |
| 42-(13) | Boc—Phe—N(Me)(CH₂—3Py(5-Cl)) |
| | H—Phe—N(Me)(CH₂—3Py(5-Cl)) |

TABLE-continued

| Preparation No. | Formula |
|---|---|
| 42-(14) | Boc—Phe—N(Me)(CH₂—3Py) |
| | H—Phe—N(Me)(CH₂—3Py) |
| 42-(15) | Boc—Phe—N(Me)(Bzl(4-OMe)) |
| | H—Phe—N(Me)(Bzl(4-Me)) |
| 42-(16) | Boc—Phe—N(Me)(Bzl(4-Me)) |
| | H—Phe—N(Me)(Bzl(4-Me)) |
| 42-(17) | Boc—Ser—N(Me)(Bzl) |
| | HCl·H—Ser—N(Me)(Bzl) |
| 42-(18) | Boc—Leu—N(Me)(Bzl) |
| | HCl·H—Leu—N(Me)(Bzl) |
| 42-(19) | Boc—Phe—N(Me)(Bzl(4-CF₃)) |
| | HCl·H—Phe—N(Me)(Bzl(4-CF₃)) |
| 42-(20) | Boc-D-Phe—N(Me)(Bzl) |

| Preparation No. | Formula |
|---|---|
| | HCl·H-D-Phe—N(Me)(Bzl) |
| 43-(1) | Boc-D-Asp(OBzl)-D-Phe—N(Me)(Bzl) |
| | Boc-D-Asp-D-Phe—N(Me)(Bzl) |
| 43-(2) | Boc-D-Asp(OBzl)—Phe—N(Me)(Bzl) |
| | Boc-D-Asp—Phe—N(Me)(Bzl) |
| 44 | Boc—Asp—Phe—N(Me)(Bzl) |
| 45-(1) | Boc—Asp(4-ethylpiperazin-1-yl)—Phe—N(Me)(Bzl)<br>Boc-D-Asp-D-Phe—N(Me)(Bzl) |
| 45-(2) | Boc-D-Asp(4-methylpiperazin-1-yl)-D-Phe—N(Me)(Bzl)<br>Boc-D-Asp—Phe—N(Me)(Bzl) |

TABLE-continued
| Preparation No. | Formula |
|---|---|
| 45-(3) | 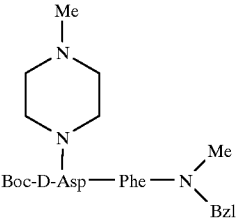 |
| 46-(1) | 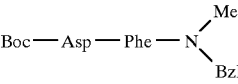<br>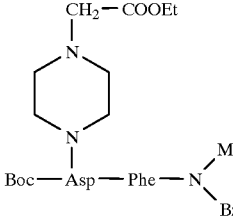 |
| 46-(2) | 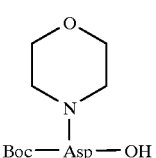<br>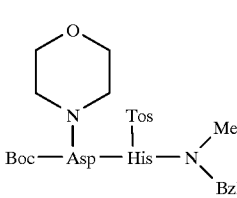 |

TABLE-continued

| Preparation No. | Formula |
|---|---|
| 46-(3) | Boc—Asp(morpholine)—OH |
|  | Boc—Asp(morpholine)—Phe—N(Me)Bzl(4-OH) |
| 46-(4) | Boc—Asp(4-Me-piperazine)—OH |
|  | Boc—Asp(4-Me-piperazine)—Phe—N(Me)Bzl(4-NMe₂) |
| 46-(5) | Boc—Asp(4-Me-piperazine)—OH |
|  | Boc—Asp(4-Me-piperazine)—Phe—N(Me)Bzl(4-CH₂NMe₂) |

TABLE-continued
| Preparation No. | Formula |
|---|---|
| 46-(6) | 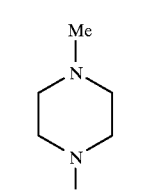 |
| | 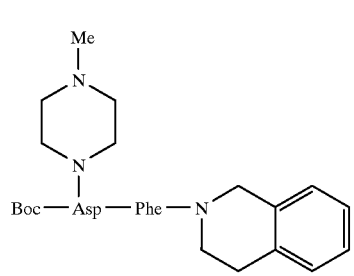 |
| 46-(7) | 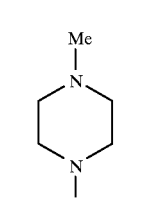 |
| | 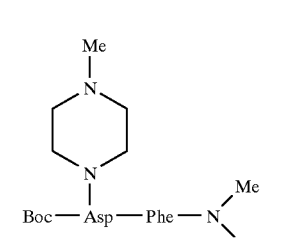 |
| 46-(8) | 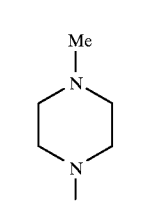 |
| | 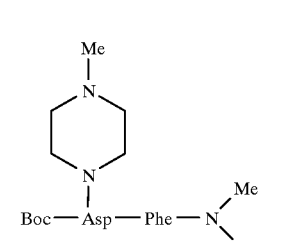 |

TABLE-continued

| Preparation No. | Formula |
|---|---|
| 46-(9) | ![structure] Me-N(piperazine)N-Asp(Boc)-OH |
| | Boc-Asp(piperazine-N-Me)-Phe-N(Me)(Bzl(4-F)) |
| 46-(10) | Me-N(piperazine)N-Asp(Boc)-OH |
| | Boc-Asp(piperazine-N-Me)-Phe-N(Me)(CH₂—3Py(6-OMe)) |
| 46-(11) | Me-N(piperazine)N-Asp(Boc)-OH |
| | Boc-Asp(piperazine-N-Me)-Phe-N(Et)(Bzl) |

TABLE-continued
| Preparation No. | Formula |
|---|---|
| 46-(12) | 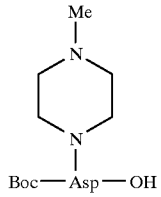 |
| 46-(13) | 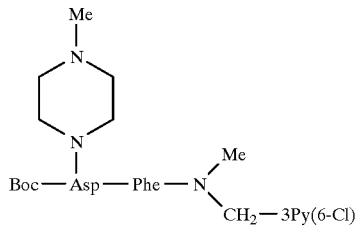 |
| 46-(14) | 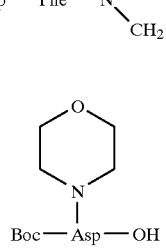 |

TABLE-continued
| Preparation No. | Formula |
|---|---|
| 46-(15) | 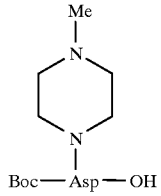 |
| 46-(16) | 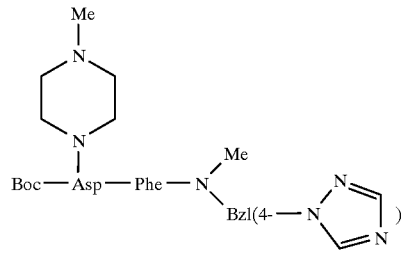 |
| 46-(17) | 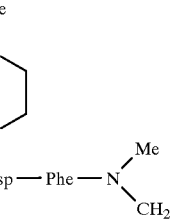 |
| 46-(18) | 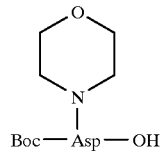 |

TABLE-continued
| Preparation No. | Formula |
|---|---|
| | 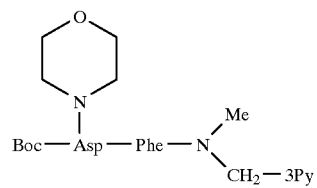 |
| 46-(19) | 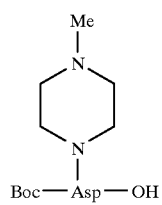 |
| | 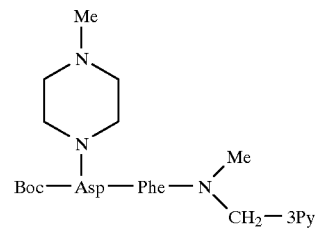 |
| 46-(20) | 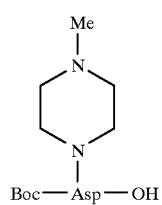 |
| | 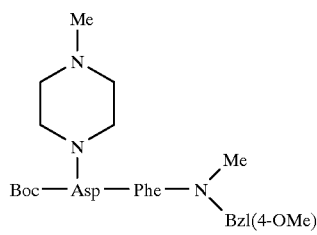 |
| 46-(21) | 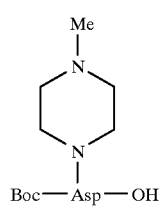 |

TABLE-continued

| Preparation No. | Formula |
|---|---|
| | Boc—Asp—Phe—N(Me)(Bzl(4-Me)), Asp side chain: 4-methylpiperazin-1-yl amide |
| 46-(22) | Boc—Asp—OH, Asp side chain: 4-methylpiperazin-1-yl amide |
| | Boc—Asp—Ser—N(Me)(Bzl), Asp side chain: 4-methylpiperazin-1-yl amide |
| 46-(23) | Boc—Asp—OH, Asp side chain: 4-methylpiperazin-1-yl amide |
| | Boc—Asp—Leu—N(Me)(Bzl), Asp side chain: 4-methylpiperazin-1-yl amide |
| 46-(24) | Boc—Asp—OH, Asp side chain: 4-methylpiperazin-1-yl amide |

TABLE-continued

| Preparation No. | Formula |
|---|---|
| | Boc—Asp(N-methylpiperazinyl)—Phe—N(Me)(Bzl(4-CF₃)) |
| 46-(25) | Boc—Asp(N-methylpiperazinyl)—OH |
| | Boc—Asp(N-methylpiperazinyl)-D-Phe—N(Me)(Bzl) |
| 46-(26) | Boc-D-Asp(OBzl)—OH |
| | Boc-D-Asp(OBzl)-D-Phe—N(Me)(Bzl) |
| 46-(27) | Boc-D-Asp(OBzl)—OH |
| | Boc-D-Asp(OBzl)—Phe—N(Me)(Bzl) |
| 47 | Z—Phe—NH—Bzl |
| Compound A | Boc—Asp(morpholinyl)—OH |

TABLE-continued

| Preparation No. | Formula |
|---|---|
| | Boc—Asp(morpholino)—Phe—NH—Bzl |
| 48 | Z—Phe—NH₂ |
| | Boc—Asp(morpholino)—Phe—NH₂ |
| 49 | Boc—Phe—N(Me)(Bzl(4-OMe)) |
| | Compound A |
| | Boc—Asp(morpholino)—OH |
| | Boc—Asp(morpholino)—Phe—N(Me)(Bzl(4-OMe)) |
| 50-(1) | Boc—Gly—N(Me)(Bzl) |
| | Boc—Asp(morpholino)—Gly—N(Me)(Bzl) |
| 50-(2) | Boc—Phg—N(Me)(Bzl) |

TABLE-continued
| Preparation No. | Formula |
|---|---|
| | Boc—Asp(morpholine)—Phg—N(Me)(Bzl) |
| 50-(3) | Boc—Tyr(Bzl)—N(Me)(Bzl) |
| | Boc—Asp(morpholine)—Tyr(Bzl)—N(Me)(Bzl) |
| 50-(4) | Boc—Tyr(Bzl)—N(Me)(Bzl) |
| | Boc—Asp(4-methylpiperazine)—Tyr(Bzl)—N(Me)(Bzl) |
| 50-(5) | Boc—Tyr—N(Me)(Bzl) |
| | Boc—Asp(morpholine)—Tyr—N(Me)(Bzl) |
| 50-(6) | Bos—Phe—N(Me)(CH₂)₂—Ph |
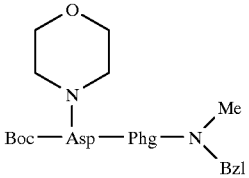
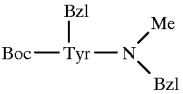
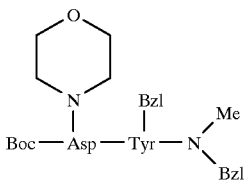
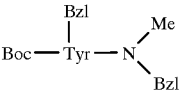
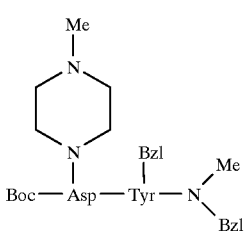
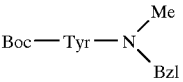
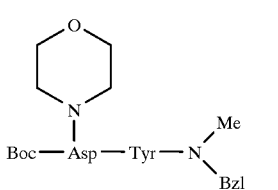
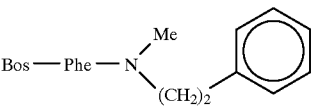

TABLE-continued

| Preparation No. | Formula |
|---|---|
| | Boc—Asp(morpholino)—Phe—N(Me)(CH₂)₂Ph |
| 50-(7) | Boc—Phe—N(Me)Bzl(4-COOMe) |
| | Boc—Asp(morpholino)—Phe—N(Me)Bzl(4-COOMe) |
| 50-(8) | Boc—Phe—N(Me)CH₂-2Naph |
| | Boc—Asp(morpholino)—Phe—N(Me)CH₂-2Naph |
| 50-(9) | Boc—Phe—N(Me)CH₂-1Naph |
| | Boc—Asp(morpholino)—Phe—N(Me)CH₂-1Naph |
| 50-(10) | Boc—Phe—N(Me)CH₂-2Py |
| | Boc—Asp(morpholino)—Phe—N(Me)CH₂-2Py |

TABLE-continued

| Preparation No. | Formula |
|---|---|
| 50-(11) | Boc—Phe—N(Me)(CH2-4Py) |
| | Boc—Asp(morpholino)—Phe—N(Me)(CH2-4Py) |
| 50-(12) | Boc—Phe—N(Me)(Bzl(4-COOMe)) |
| | Boc—Asp(4-Me-piperazino)—Phe—N(Me)(Bzl(4-COOMe)) |
| 50-(13) | Boc—Phe—N(Me)(Bzl(4-COOMe)) |
| | Boc—Asp(4-(CH2COOEt)-piperazino)—Phe—N(Me)(Bzl(4-COOMe)) |
| 50-(14) | Boc—Phe—N(Me)(Bzl(4-NMe2)) |
| | Boc—Asp(morpholino)—Phe—N(Me)(Bzl(4-NMe2)) |

TABLE-continued

| Preparation No. | Formula |
|---|---|
| 51-(1) | Boc—Asp(4-Me-piperazin-1-yl)—Phg—N(Me)(Bzl) |
|  | H—Asp(4-Me-piperazin-1-yl)—Phg—N(Me)(Bzl) |
| 51-(2) | Boc—Asp(4-Me-piperazin-1-yl)—Phe—N(Me)(Bzl(4-NMe₂)) |
|  | H—Asp(4-Me-piperazin-1-yl)—Phe—N(Me)(Bzl(4-NMe₂)) |
| 51-(3) | Boc—Asp(4-Me-piperazin-1-yl)—Phe—N(Me)(Bzl(4-CH₂NMe₂)) |
|  | H—Asp(4-Me-piperazin-1-yl)—Phe—N(Me)(Bzl(4-CH₂NMe₂)) |

TABLE-continued
| Preparation No. | Formula |
|---|---|
| 51-(4) | 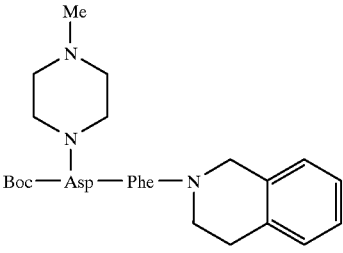 |
| 51-(5) | 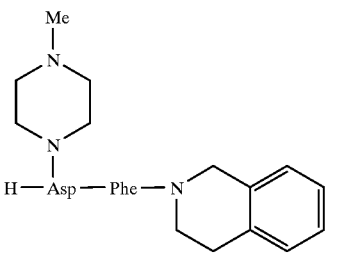 |
| 51-(6) | 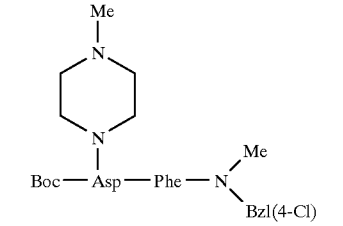 |

TABLE-continued
| Preparation No. | Formula |
| --- | --- |
| 51-(7) | 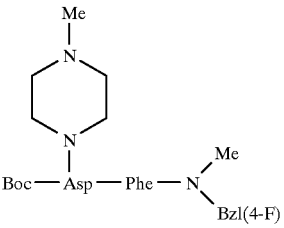 |
| | 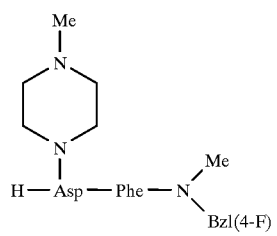 |
| 51-(8) | 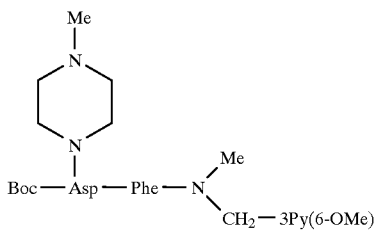 |
| | 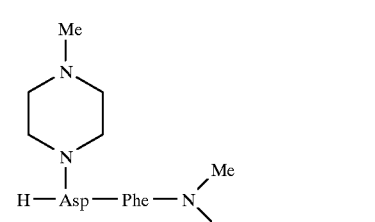 |
| 51-(9) | 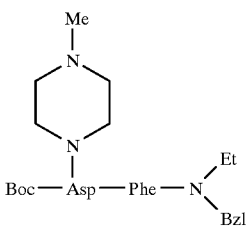 |
| | 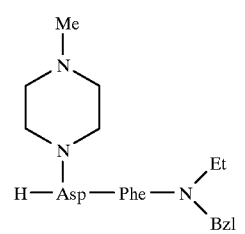 |

TABLE-continued
| Preparation No. | Formula |
|---|---|
| 51-(10) | 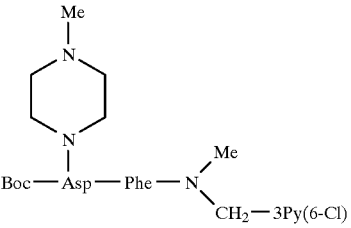 |
| | 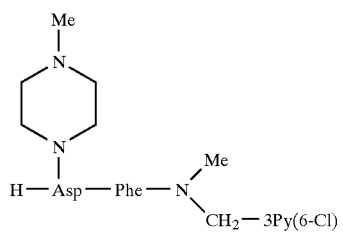 |
| 51-(11) | 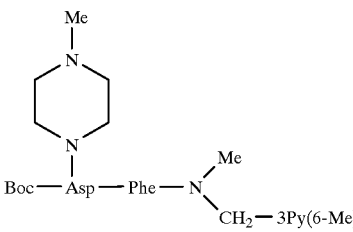 |
| | 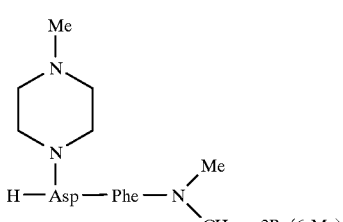 |
| 51-(12) | 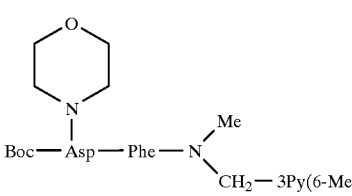 |
| | 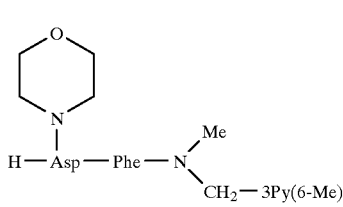 |

TABLE-continued
| Preparation No. | Formula |
|---|---|
| 51-(13) | 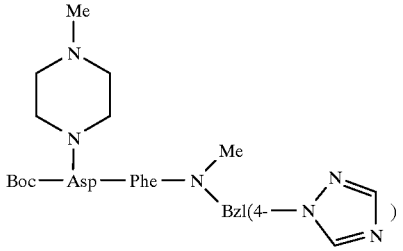 |
| 51-(14) | 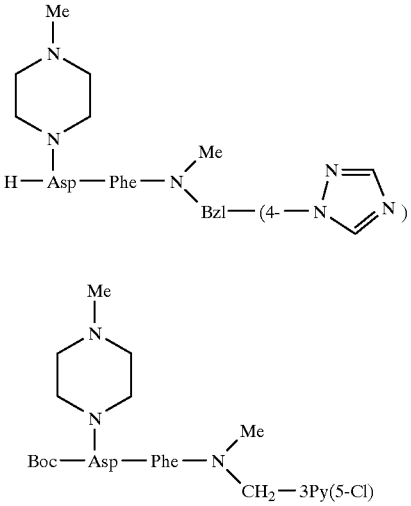 |
| 51-(15) | 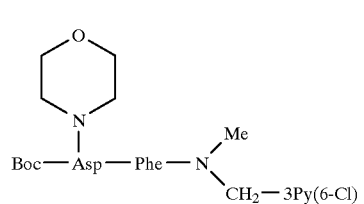 |

TABLE-continued
| Preparation No. | Formula |
|---|---|
| 51-(16) | 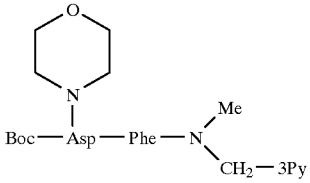 |
| 51-(17) | 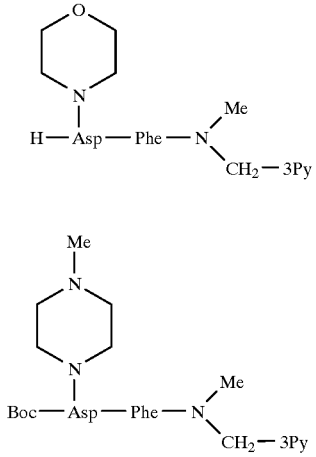 |
| 51-(18) | 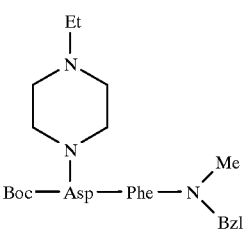 |

TABLE-continued
| Preparation No. | Formula |
|---|---|
| 51-(19) | 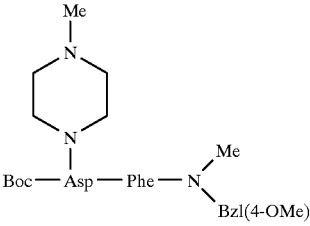 |
| | 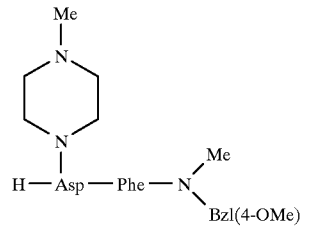 |
| 51-(20) | 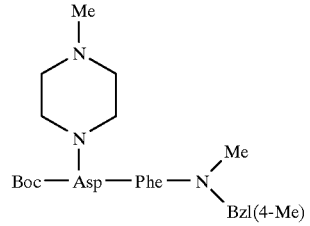 |
| | 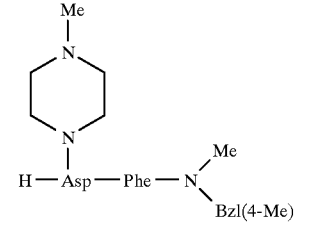 |
| 51-(21) | 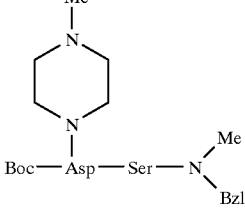 |
| | 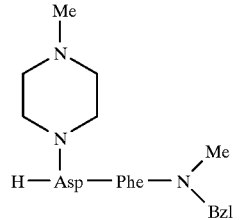 |

TABLE-continued
| Preparation No. | Formula |
|---|---|
| 51-(22) | 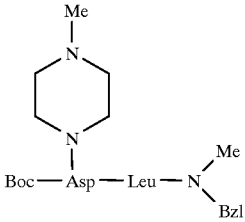 |
| 51-(23) | 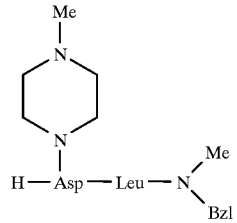 |
| 51-(24) | 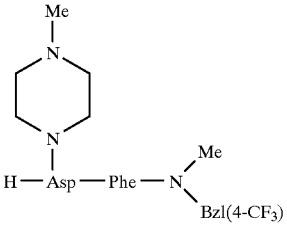 |

TABLE-continued

| Preparation No. | Formula |
| --- | --- |
| 51-(25) | Boc-D-Asp-D-Phe-N(Me)(Bzl), with 4-methylpiperazinyl on Asp side chain |
|  | H-D-Asp-D-Phe-N(Me)(Bzl), with 4-methylpiperazinyl on Asp side chain |
| 51-(26) | Boc-D-Asp—Phe—N(Me)(Bzl), with 4-methylpiperazinyl on Asp side chain |
|  | H-D-Asp—Phe—N(Me)(Bzl), with 4-methylpiperazinyl on Asp side chain |
| 51-(27) | Boc—Asp—Phe—N(Me)(Bzl), with piperazinyl-CH₂—COOEt on Asp side chain |
|  | H—Asp—Phe—N(Me)(Bzl), with piperazinyl-CH₂—COOEt on Asp side chain |

TABLE-continued

| Preparation No. | Formula |
|---|---|
| 51-(28) | Boc—Asp(piperazine-N-Me)—Phe—N(Me)Bzl(4-COOMe) |
| | H—Asp(piperazine-N-Me)—Phe—N(Me)Bzl(4-COOMe) |
| 51-(29) | Boc—Asp(piperazine-N-CH₂-COOEt)—Phe—N(Me)Bzl(4-COOMe) |
| | H—Asp(piperazine-N-CH₂-COOEt)—Phe—N(Me)Bzl(4-COOMe) |
| 52 | Boc—Phe—OH |
| | Boc—Phe—N(Me)(CH₂-3Py) |
| 53-(1) | Boc—Phe—OH |
| | Boc—Phe—N(Me)(CH₂-3Py(6-Cl)) |
| 53-(2) | Boc—Phe—OH |
| | Boc—Phe—N(Me)(CH₂-4Py) |

TABLE-continued

| Preparation No. | Formula |
|---|---|
| 54 | Boc—Phe—N(CH₂-3Py)(Me) |
| | H—Phe—N(CH₂-3Py)(Me) |
| 55 | Boc—Phe—N(CH₂-3Py(6-Cl))(Me) |
| | H—Phe—N(CH₂-3Py(6-Cl))(Me) |
| 56 | H—Phe—N(CH₂-3Py)(Me) |
| | Boc—2Pyala—Phe—N(CH₂-3Py)(Me) |
| 57-(1) | H—Phe—N(Bzl)(Me) · HCl |
| | Boc—Trp—Phe—N(Bzl)(Me) |
| 57-(2) | H—Phe—N(Bzl)(Me) · HCl |
| | Boc—His—Phe—N(Bzl)(Me) |
| 57-(3) | H—Phe—N(CH₂-3Py(6-Cl))(Me) |
| | Boc—2Pyala—Phe—N(CH₂-3Py(6-Cl))(Me) |
| 57-(4) | H—Phe—N(CH₂-4Py)(Me) |

TABLE-continued

| Preparation No. | Formula |
|---|---|
| | Boc—2Pyala—Phe—N(CH₂-4Py)(Me) |
| 57-(5) | H—Phe—N(Bzl)(Me) · HCl |
| 58-(1) | Boc—2Pyala—Phe—N(Bzl)(Me) |
| | Boc—2Pyala—Phe—N(CH₂-4Py)(Me) |
| 58-(2) | H—2Pyala—Phe—N(CH₂-4Py)(Me) |
| | Boc—2Pyala—Phe—N(Bzl)(Me) |
| 58-(3) | H—2Pyala—Phe—N(Bzl)(Me) |
| | Boc—2Pyala—Phe—N(CH₂-3Py(6-Cl))(Me) |
| 58-(4) | H—2Pyala—Phe—N(CH₂-3Py(6-Cl))(Me) |
| | Boc—His—Phe—N(Bzl)(Me) |
| 58-(5) | H—His—Phe—N(Bzl)(Me) |
| | Boc—Trp—Phe—N(Bzl)(Me) |
| 58-(6) | H—Trp—Phe—N(Bzl)(Me) |
| | Boc—2Pyala—Phe—N(CH₂-3Py)(Me) |

TABLE-continued

| Preparation No. | Formula |
|---|---|
| | H—2Pyala—Phe—N(Me)(CH₂-3Py) |
| 59 | H—Phe—N(Me)(Bzl) |
| | Boc—Cys(Trt)—Phe—N(Me)(Bzl) |
| 60-(1) | H—Phe—N(Me)(CH₂-3Py(6-Cl)) |
| | Boc—Ser—Phe—N(Me)(CH₂-3Py(6-Cl)) |
| 60-(2) | H—Phe—N(Me)(Bzl) |
| | Boc—Cys(Trt)—Phe—N(Me)(Bzl) |
| 60-(3) | H—Phe—N(Me)(CH₂-3Qu) |
| | Boc—Ser—Phe—N(Me)(CH₂-3Qu) |
| 60-(4) | HCl·H—Phe—N(Me)(Bzl) |
| | Boc—Phe—Phe—N(Me)(Bzl) |
| 60-(5) | H—Phe—N(Me)(CH₂-4Py) |
| | Boc—Ser—Phe—N(Me)(CH₂-4Py) |

TABLE-continued

| Preparation No. | Formula |
|---|---|
| 60-(6) | H—Phe—N(Me)(CH$_2$3Py) |
| | Boc—Ser—Phe—N(Me)(CH$_2$3Py) |
| 60-(7) | HCl·H—Phe—N(Me)(Bzl) |
| | Boc—Ser(Bzl)—Phe—N(Me)(Bzl) |
| 60-(8) | HCl·H—Phe—N(Me)(Bzl) |
| | Boc—Leu—Phe—N(Me)(Bzl) |
| 60-(9) | 2HCl·H—2Pyala—N(Me)(Bzl) |
| | Boc—Ser(Bzl)—2Pyala—N(Me)(Bzl) |
| 60-(10) | H—Phe—N(Me)(Bzl) |
| | Boc—Met—Phe—N(Me)(Bzl) |
| 60-(11) | H—Phe—N(Me)(Bzl) |
| | Boc—Tyr—Phe—N(Me)(Bzl) |
| 60-(12) | H—Phe—N(Me)(CH$_2$3Py(6-Me)) |

TABLE-continued

| Preparation No. | Formula |
|---|---|
| | Boc—Ser—Phe—N(Me)(CH₂-3Py(6-Me)) |
| 60-(13) | H—Phe—N(Me)(Bzl) |
| | Boc—Thr—Phe—N(Me)(Bzl) |
| 60-(14) | H—Phe—N(Me)(Bzl) |
| | Boc—2Nal—Phe—N(Me)(Bzl) |
| 60-(15) | H—Phe—N(Me)(CH₂-3Py(6-Me)) |
| | Boc—His—Phe—N(Me)(CH₂-3Py(6-Me)) |
| 60-(16) | H—Phe—N(Me)(Bzl) |
| | Boc—MePhe—Phe—N(Me)(Bzl) |
| 60-(17) | H—Phe—N(Me)(CH₂-3Qu) |
| | Boc—2Pyala—Phe—N(Me)(CH₂-3Qu) |
| 60-(18) | H—Phe—N(Me)(CH₂-quinoxalinyl) |
| | Boc—Ser—Phe—N(Me)(CH₂-quinoxalinyl) |

TABLE-continued

| Preparation No. | Formula |
|---|---|
| 60-(19) | H—Phe—N(Me)(CH₂-quinoxalin-2-yl) |
|  | Boc—2Pyala—Phe—N(Me)(CH₂-quinoxalin-2-yl) |
| 60-(20) | H—Phe—N(Me)(CH₂-quinoxalin-2-yl) |
|  | Boc—His—Phe—N(Me)(CH₂-quinoxalin-2-yl) |
| 60-(21) | H—Phe—N(Me)(CH₂-3Py(6-2Py)) |
|  | Boc—Ser—Phe—N(Me)(CH₂-3Py(6-2Py)) |
| 60-(22) | H—Phe—N(Me)(CH₂-3Py(6-3Py)) |
|  | Boc—2Pyala—Phe—N(Me)(CH₂-3Py(6-3Py)) |
| 60-(23) | H—Phe—N(Me)(CH₂-3Py(6-3Py)) |
|  | Boc—Ser—Phe—N(Me)(CH₂-3Py(6-3Py)) |
| 60-(24) | HCl·H—Phe—N(Me)(Bzl) |

TABLE-continued

| Preparation No. | Formula |
|---|---|
| | Boc—Arg(SO₂-C₆(Me)₃(OMe))—Phe—N(Me)(Bzl) |
| 60-(25) | H—Phe—N(Me)(CH₂-3Py) |
| | Boc—Phe—Phe—N(Me)(CH₂-3Py) |
| 60-(26) | H—Phe—N(Me)(CH₂-3Py) |
| | Boc—4Pyala—Phe—N(Me)(CH₂-3Py) |
| 60-(27) | H—Phe—N(Me)(Bzl(4--1,2,4-triazol-1-yl)) |
| | Boc—Ser—Phe—N(Me)(Bzl(4--1,2,4-triazol-1-yl)) |
| 60-(28) | H—Phe—N(Me)(CH₂-3Py(6-Me)) |
| | Boc—Met—Phe—N(Me)(CH₂-3Py(6-Me)) |
| 60-(29) | H—Phe—N(Me)(CH₂-3Py) |
| | Boc—Met—Phe—N(Me)(CH₂-3Py) |

TABLE-continued

| Preparation No. | Formula |
|---|---|
| 60-(30) | H—Phe—N(Me)(CH₂-3Qu) |
| | Boc—Met—Phe—N(Me)(CH₂-3Qu) |
| 60-(31) | H—Phe—N(Me)(CH₂-quinoxalin-2-yl) |
| | Boc—Met—Phe—N(Me)(CH₂-quinoxalin-2-yl) |
| 60-(32) | H—Phe—N(Me)(CH₂-3Py(6-3Py)) |
| | Boc—Met—Phe—N(Me)(CH₂-3Py(6-3Py)) |
| 60-(33) | H—Phe—N(Me)(Bzl) |
| | Boc—Ala—Phe—N(Me)(Bzl) [with thienyl substituent on Ala] |
| 60-(34) | H—Phe—N(Me)(CH₂-3Py(6-NMe₂)) |
| | Boc—Ser—Phe—N(Me)(CH₂-3Py(6-NMe₂)) |
| 60-(35) | H—Phe—N(Me)(CH₂-3Qu) |
| | Boc—Ser(Bzl)—Phe—N(Me)(CH₂-3Qu) |

TABLE-continued

| Preparation No. | Formula |
|---|---|
| 60-(36) | H—Phe—N(Me)(Bzl) |
| | Boc—Ala(3-furyl)—Phe—N(Me)(Bzl) |
| 60-(37) | H—Phe—N(Me)(Bzl) |
| | Boc—Ala(2-furyl)—Phe—N(Me)(Bzl) |
| 60-(38) | H—Phe—N(Me)(CH₂-3Py(6-OMe)) |
| | Boc—Ser—Phe—N(Me)(CH₂-3Py(6-OMe)) |
| 60-(39) | H—Phe—N(Me)(CH₂-3Qu) |
| | Boc—His—Phe—N(Me)(CH₂-3Qu) |
| 60-(40) | H—Phe—N(Me)(CH₂-3Py(6-3Py)) |
| | Boc—His—Phe—N(Me)(CH₂-3Py(6-3Py)) |
| 60-(41) | H—Phe—N(Me)(Bzl) |
| | Boc—Tyr(Me)—Phe—N(Me)(Bzl) |

TABLE-continued

| Preparation No. | Formula |
|---|---|
| 60-(42) | H—Phe—N(Me)(CH₂-quinoxalin-6-yl) |
| | Boc—2Pyala—Phe—N(Me)(CH₂-quinoxalin-6-yl) |
| 60-(43) | H—Phe—N(Me)(Bzl) |
| | Boc—1Nal—Phe—N(Me)(Bzl) |
| 60-(44) | H—Phe—N(Me)(CH₂-3Py) |
| | Boc—His—Phe—N(Me)(CH₂-3Py) |
| 60-(45) | H—Phe—N(Me)(CH₂-3Py(6-Me)) |
| | Boc—2Pyala—Phe—N(Me)(CH₂-3Py(6-Me)) |
| 60-(46) | H—Phe—N(Me)(Bzl) |
| | Boc—3Pyala—Phe—N(Me)(Bzl) |
| 60-(47) | H—Phe—N(Me)(Bzl) |
| | Boc—Phe(4-Cl)—Phe—N(Me)(Bzl) |

TABLE-continued

| Preparation No. | Formula |
|---|---|
| 60-(48) | H—Phe—N(Me)(Bzl) |
| | [1,2,3,4-tetrahydroisoquinoline-3-CO—Phe—N(Me)(Bzl), N-Boc] |
| 61-(1) | Boc—Cys(Me)—Phe—N(Me)(Bzl) |
| | H—Cys(Me)—Phe—N(Me)(Bzl) |
| 61-(2) | Boc—Ser—Phe—N(Me)(CH$_2$-3Py(6-Cl)) |
| | H—Ser—Phe—N(Me)(CH$_2$-3Py(6-Cl)) |
| 61-(3) | Boc—Cys(Trt)—Phe—N(Me)(Bzl) |
| | H—Cys(Trt)—Phe—N(Me)(Bzl) |
| 61-(4) | Boc—Ser—Phe—N(Me)(CH$_2$-3Qu) |
| | H—Ser—Phe—N(Me)(CH$_2$-3Qu) |
| 61-(5) | Boc—Ser(Bzl)—Phe—N(Me)(Bzl) |

TABLE-continued

| Preparation No. | Formula |
|---|---|
|  | HCl·H—Ser(Bzl)—Phe—N(Me)(Bzl) |
| 61-(6) | Boc—Leu—Phe—N(Me)(Bzl) |
|  | HCl·H—Leu—Phe—N(Me)(Bzl) |
| 61-(7) | Boc—Ser(Bzl)—2Pyala—N(Me)(Bzl) |
|  | 2HCl·H—Ser(Bzl)—2Pyala—N(Me)(Bzl) |
| 61-(8) | Boc—Ser—Phe—N(Me)(CH$_2$-4Py) |
|  | H—Ser—Phe—N(Me)(CH$_2$-4Py) |
| 61-(9) | Boc—Phe—Phe—N(Me)(Bzl) |
|  | H—Phe—Phe—N(Me)(Bzl) |
| 61-(10) | Boc—Ser—Phe—N(Me)(CH$_2$-3Py) |
|  | 2HCl·H—Ser—Phe—N(Me)(CH$_2$-3Py) |
| 61-(11) | Boc—Met—Phe—N(Me)(Bzl) |
|  | H—Met—Phe—N(Me)(Bzl) |

TABLE-continued

| Preparation No. | Formula |
|---|---|
| 61-(12) | Boc—Ser—Phe—N(Me)(Bzl) |
| | H—Ser—Phe—N(Me)(Bzl) |
| 61-(13) | Boc—Ser—Phe—N(Me)(CH₂-3Py(6-Me)) |
| | H—Ser—Phe—N(Me)(CH₂-3Py(6-Me)) |
| 61-(14) | Boc—Thr—Phe—N(Me)(Bzl) |
| | H—Thr—Phe—N(Me)(Bzl) |
| 61-(15) | Boc—2Nal—Phe—N(Me)(Bzl) |
| | H—2Nal—Phe—N(Me)(Bzl) |
| 61-(16) | Boc—His—Phe—N(Me)(CH₂-3Py(6-Me)) |
| | H—His—Phe—N(Me)(CH₂-3Py(6-Me)) |
| 61-(17) | Boc—MePhe—Phe—N(Me)(Bzl) |
| | H—MePhe—Phe—N(Me)(Bzl) |
| 61-(18) | Boc—2Pyala—Phe—N(Me)(CH₂-3Qu) |

TABLE-continued

| Preparation No. | Formula |
|---|---|
| 61-(19) | H—2Pyala—Phe—N(Me)(CH₂-3Qu) |
| 61-(20) | Boc—Ser—Phe—N(Me)(CH₂-quinoxalin-2-yl) |
| 61-(21) | H—Ser—Phe—N(Me)(CH₂-quinoxalin-2-yl) |
| | Boc—2Pyala—Phe—N(Me)(CH₂-quinoxalin-2-yl) |
| | H—2Pyala—Phe—N(Me)(CH₂-quinoxalin-2-yl) |
| 61-(22) | Boc—His—Phe—N(Me)(CH₂-quinoxalin-2-yl) |
| | H—His—Phe—N(Me)(CH₂-quinoxalin-2-yl) |
| 61-(23) | Boc—Ser—Phe—N(Me)(CH₂-3Py(6-2Py)) |
| | H—Ser—Phe—N(Me)(CH₂-3Py(6-2Py)) |
| | Boc—2Pyala—Phe—N(Me)(CH₂-3Py(6-3Py)) |
| | H—2Pyala—Phe—N(Me)(CH₂-3Py(6-3Py)) |
| 61-(24) | Boc—Ser—Phe—N(Me)(CH₂-3Py(6-3Py)) |

TABLE-continued
| Preparation No. | Formula |
|---|---|
| | 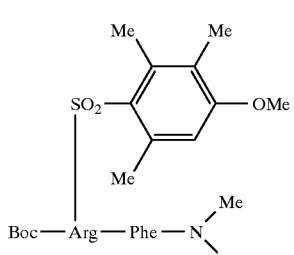 |
| 61-(25) | |
| 61-(26) | |
| 61-(27) | |
| 61-(28) | |
| 61-(29) | |

TABLE-continued

| Preparation No. | Formula |
| --- | --- |
| | H—Met—Phe—N(Me)(CH₂-3Py(6-Me)) |
| 61-(30) | Boc—Met—Phe—N(Me)(CH₂-3Py) |
| | H—Met—Phe—N(Me)(CH₂-3Py) |
| 61-(31) | Boc—Met—Phe—N(Me)(CH₂-3Qu) |
| | H—Met—Phe—N(Me)(CH₂-3Qu) |
| 61-(32) | Boc—Met—Phe—N(Me)(CH₂-quinoxalinyl) |
| | H—Met—Phe—N(Me)(CH₂-quinoxalinyl) |
| 61-(33) | Boc—Met—Phe—N(Me)(CH₂-3Py(6-3Py)) |
| | H—Met—Phe—N(Me)(CH₂-3Py(6-3Py)) |
| 61-(34) | Boc—Ala(thienyl)—Phe—N(Me)(Bzl) |
| | H—Ala(thienyl)—Phe—N(Me)(Bzl) |

TABLE-continued

| Preparation No. | Formula |
| --- | --- |
| 61-(35) | Boc—Ser—Phe—N(Me)(CH₂-3Py(6-NMe₂)) |
| | H—Ser—Phe—N(Me)(CH₂-3Py(6-NMe₂)) |
| 61-(36) | Boc—Ser(Bzl)—Phe—N(Me)(CH₂-3Qu) |
| | H—Ser(Bzl)—Phe—N(Me)(CH₂-3Qu) |
| 61-(37) | Boc—Ala(3-furyl)—Phe—N(Me)(Bzl) |
| | H—Ala(3-furyl)—Phe—N(Me)(Bzl) |
| 61-(38) | Boc—Ala(2-furyl)—Phe—N(Me)(Bzl) |
| | H—Ala(2-furyl)—Phe—N(Me)(Bzl) |
| 61-(39) | Boc—Ser—Phe—N(Me)(CH₂-3Py(6-OMe)) |
| | H—Ser—Phe—N(Me)(CH₂-3Py(6-OMe)) |

TABLE-continued

| Preparation No. | Formula |
|---|---|
| 61-(40) | Boc—His—Phe—N(Me)(CH₂-3Qu) |
|  | H—His—Phe—N(Me)(CH₂-3Qu) |
| 61-(41) | Boc—His—Phe—N(Me)(CH₂-3Py(6-3Py)) |
|  | H—His—Phe—N(Me)(CH₂-3Py(6-3Py)) |
| 61-(42) | Boc—Tyr(Me)—Phe—N(Me)(Bzl) |
|  | H—Tyr(Me)—Phe—N(Me)(Bzl) |
| 61-(43) | Boc—2Pyala—Phe—N(Me)(CH₂-quinoxalinyl) |
|  | H—2Pyala—Phe—N(Me)(CH₂-quinoxalinyl) |
| 61-(44) | Boc—1Nal—Phe—N(Me)(Bzl) |
|  | H—1Nal—Phe—N(Me)(Bzl) |
| 61-(45) | Boc—His—Phe—N(Me)(CH₂-3Py) |
|  | H—His—Phe—N(Me)(CH₂-3Py) |

TABLE-continued

| Preparation No. | Formula |
|---|---|
| 61-(46) | Boc—2Pyala—Phe—N(Me)(CH₂-3Py(6-Me)) |
| | H—2Pyala—Phe—N(Me)(CH₂-3Py(6-Me)) |
| 61-(47) | Boc—3Pyala—Phe—N(Me)(Bzl) |
| | H—3Pyala—Phe—N(Me)(Bzl) |
| 61-(48) | Boc—Phe(4-Cl)—Phe—N(Me)(Bzl) |
| | H—Phe(4-Cl)—Phe—N(Me)(Bzl) |
| 61-(49) | N-Boc tetrahydroisoquinoline-3-CO—Phe—N(Me)(Bzl) |
| | N-H tetrahydroisoquinoline-3-CO—Phe—N(Me)(Bzl) |
| 62-(1) | H—Cys(Me)—OH |
| | Boc—Cys(Me)—OH |
| 62-(2) | H₂N—Bzl(2-Me) |
| | Boc—NH—Bzl(2-Me) |

TABLE-continued

| Preparation No. | Formula |
|---|---|
| 62-(3) | H₂N—Bzl(3-Me) |
| | Boc—NH—Bzl(3-Me) |
| 63-(1) | Boc—2Nal—OH |
| | Boc—2Nal—N(Me)(Bzl) |
| 63-(2) | Boc—MePhe—OH |
| | Boc—MePhe—N(Me)(Bzl) |
| 63-(3) | Boc—Tyr(Me)—OH |
| | Boc—Tyr(Me)—N(Me)(Bzl) |
| 63-(4) | Boc—Phe—OH |
| | Boc—Phe—N(Me)(Bzl(3-Me)) |
| 63-(5) | Boc—Phe—OH |
| | Boc—Phe—N(Me)(Bzl(2-Me)) |
| 63-(6) | Boc—Phe—OH |
| | Boc—Phe—N(Me)(CH₂-4Pm) |
| 63-(7) | Boc—Phe—OH |
| | Boc—Phe—N(Me)(CH₂-quinoxalin-2-yl) |
| 63-(8) | Boc—Phe—OH |

TABLE-continued

| Preparation No. | Formula |
|---|---|
| | Boc—Phe—N(Me)(CH₂-2Qu) |
| 63-(9) | Boc—Phe—OH |
| | Boc—Phe—N(Me)(CH₂-7Qu) |
| 63-(10) | Boc—Phe—OH |
| | Boc—Phe—N(Me)(CH₂-pyrazinyl) |
| 63-(11) | Boc—Phe—OH |
| | Boc—Phe—N(Me)(CH₂-3Py(6-3Py)) |
| 63-(12) | Boc—Phe—OH |
| | Boc—Phe—N(Me)(CH₂-3Py(6-2Py)) |
| 63-(13) | Boc—Val—OH |
| | Boc—Val—N(Me)(Bzl) |
| 63-(14) | Boc—Ala(cHex)—OH |
| | Boc—Ala(cHex)—N(Me)(Bzl) |
| 63-(15) | Boc—Phe—OH |
| | Boc—Phe—N(Me)(Bzl(4-N-piperazine-N-Me)) |

TABLE-continued

| Preparation No. | Formula |
|---|---|
| 63-(16) | Boc—4Pyala—OH |
| | Boc—4Pyala—N(Me)(Bzl) |
| 63-(17) | Boc—Phe—OH |
| | Boc—Phe—N(Me)(CH₂-3Qu) |
| 63-(18) | Boc—Phe—OH |
| | Boc—Phe—N(Me)(CH₂-6Qu) |
| 63-(19) | Boc—Phe—OH |
| | Boc—Phe—N(Me)(CH₂-3Py(6-NHAc)) |
| 63-(20) | Boc—Phe—OH |
| | Boc—Phe—N(Me)(Bzl(4--pyrazol-N-Me)) |
| 63-(21) | Boc—Phe—OH |
| | Boc—Phe—N(Me)(CH₂-3Py(6-NMe₂)) |
| 63-(22) | Boc—Phe—OH |
| | Boc—Phe—N(Me)(Bzl(4--imidazole)) |
| 63-(23) | Boc—Phe—OH |

| Preparation No. | Formula |
|---|---|
| | Boc—Phe—N(Me)—CH₂—[2-Me-1-Me-benzimidazol-5-yl] |
| 63-(24) | Boc—Ala(3-furyl)—OH |
| | Boc—Ala(3-furyl)—N(Me)(Bzl) |
| 63-(25) | Boc—Phe—OH |
| | Boc—Phe—N(Me)—CH₂—[1-Me-pyrazol-4-yl] |
| 63-(26) | Boc—Phe(4-Cl)—OH |
| | Boc—Phe(4-Cl)—N(Me)(Bzl) |
| 63-(27) | Boc—Ala(2-furyl)—OH |
| | Boc—Ala(2-furyl)—N(Me)(Bzl) |
| 63-(28) | Boc—Phe—OH |
| | Boc—Phe—N(Me)—CH₂—[quinoxalin-6-yl] |
| 63-(29) | Boc—1Nal—OH |

TABLE-continued

| Preparation No. | Formula |
|---|---|
| | Boc—1Nal—N(Me)(Bzl) |
| 64-(5) | Boc—Phe—N(Me)(Bzl(2-Me)) |
| | H—Phe—N(Me)(Bzl(2-Me)) |
| 64-(6) | Boc—Phe—N(Me)(CH₂-4Pm) |
| | H—Phe—N(Me)(CH₂-4Pm) |
| 64-(7) | Boc—Phe—N(Me)(CH₂-quinoxalinyl) |
| | H—Phe—N(Me)(CH₂-quinoxalinyl) |
| 64-(8) | Boc—Phe—N(Me)(CH₂-2Qu) |
| | H—Phe—N(Me)(CH₂-2Qu) |
| 64-(9) | Boc—Phe—N(Me)(CH₂-7Qu) |
| | H—Phe—N(Me)(CH₂-7Qu) |
| 64-(10) | Boc—Phe—N(Me)(CH₂-pyrazinyl) |

TABLE-continued
| Preparation No. | Formula |
|---|---|
| | 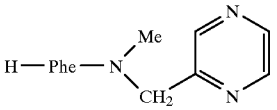 |
| 64-(11) | 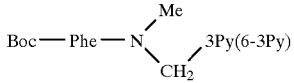 |
| 64-(12) | 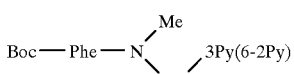 |
| 64-(13) | 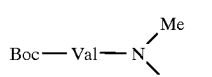 |
| 64-(14) | 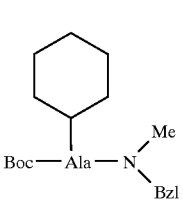 |
| 64-(15) | 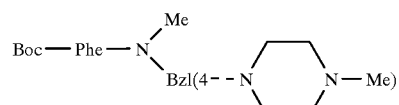 |
| | 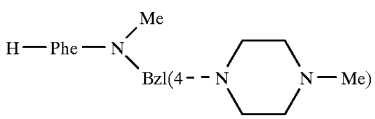 |

TABLE-continued

| Preparation No. | Formula |
|---|---|
| 64-(16) | Boc—4Pyala—N(Me)(Bzl) |
|  | H—4Pyala—N(Me)(Bzl) |
| 64-(17) | Boc—Phe—N(Me)(CH₂-3Qu) |
|  | H—Phe—N(Me)(CH₂-3Qu) |
| 64-(18) | Boc—Phe—N(Me)(CH₂-6Qu) |
|  | H—Phe—N(Me)(CH₂-6Qu) |
| 64-(19) | Boc—Phe—N(Me)(CH₂-3Py(6-NHAc)) |
|  | H—Phe—N(Me)(CH₂-3Py(6-NHAc)) |
| 64-(20) | Boc—Ala(2-thienyl)—N(Me)(Bzl) |
|  | H—Ala(2-thienyl)—N(Me)(Bzl) |
| 64-(21) | Boc—Phe—N(Me)(Bzl(4-(1-methylpyrazol-3-yl))) |

TABLE-continued

| Preparation No. | Formula |
|---|---|
|  | H—Phe—N(Me)(Bzl(4--[1-methylpyrazol-3-yl])) |
| 64-(22) | Boc—Phe—N(Me)(CH₂-3Py(6-NMe₂)) |
|  | H—Phe—N(Me)(CH₂-3Py(6-NMe₂)) |
| 64-(23) | Boc—Phe—N(Me)(Bzl(4--[imidazol-1-yl])) |
|  | H—Phe—N(Me)(Bzl(4--[imidazol-1-yl])) |
| 64-(24) | Boc—Phe—N(Me)(CH₂-[1,2-dimethylbenzimidazol-5-yl]) |
|  | H—Phe—N(Me)(CH₂-[1,2-dimethylbenzimidazol-5-yl]) |
| 64-(25) | Boc—Ala(3-furyl)—N(Me)(Bzl) |
|  | H—Ala(3-furyl)—N(Me)(Bzl) |
| 64-(26) | Boc—Phe—N(Me)(CH₂-[1-methylpyrazol-3-yl]) |

TABLE-continued

| Preparation No. | Formula |
|---|---|
| | H—Phe—N(Me)—CH₂-(1-methylpyrazol-4-yl) |
| 64-(27) | Boc—Phe(4-Cl)—N(Me)(Bzl) |
| | H—Phe(4-Cl)—N(Me)(Bzl) |
| 64-(28) | Boc—Ala(2-furyl)—N(Me)(Bzl) |
| | H—Ala(2-furyl)—N(Me)(Bzl) |
| 64-(29) | Boc—Phe—N(Me)—CH₂-(quinoxalin-2-yl) |
| | H—Phe—N(Me)—CH₂-(quinoxalin-2-yl) |
| 64-(30) | Boc—1Nal—N(Me)(Bzl) |
| | H—1Nal—N(Me)(Bzl) |
| 64-(31) | Boc—3Pyala—N(Me)(Bzl) |
| | H—3Pyala—N(Me)(Bzl) |

TABLE-continued

| Preparation No. | Formula |
|---|---|
| 64-(32) | Boc—Nle—N(Me)(Bzl) |
| | H—Nle—N(Me)(Bzl) |
| 65-(1) | H—2Nal—N(Me)(Bzl) |
| | Boc—Asp(morpholino)—2Nal—N(Me)(Bzl) |
| 65-(2) | H—MePhe—N(Me)(Bzl) |
| | Boc—Asp(morpholino)—MePhe—N(Me)(Bzl) |
| 65-(3) | H—Tyr(Me)—N(Me)(Bzl) |
| | Boc—Asp(morpholino)—Tyr(Me)—N(Me)(Bzl) |
| 65-(4) | H—Phe—N(Me)(CH$_2$-3Py(6-Me)) |
| | Boc—Asp(NMe$_2$)—Phe—N(Me)(CH$_2$-3Py(6-Me)) |

TABLE-continued

| Preparation No. | Formula |
|---|---|
| 65-(5) | H—Phe—N(Me)(Bzl(3-Me)) |
| | Boc—Asp(4-Me-piperazinyl)—Phe—N(Me)(Bzl(3-Me)) |
| 65-(6) | H—Phe—N(Me)(Bzl(2-Me)) |
| | Boc—Asp(4-Me-piperazinyl)—Phe—N(Me)(Bzl(2-Me)) |
| 65-(7) | H—Phe—N(Me)(CH₂-4Pm) |
| | Boc—Asp(morpholino)—Phe—N(Me)(CH₂-4Pm) |
| 65-(8) | H—Phe—N(Me)(CH₂-quinoxalin-2-yl) |
| | Boc—Asp(morpholino)—Phe—N(Me)(CH₂-quinoxalin-2-yl) |
| 65-(9) | H—Phe—N(Me)(CH₂-2Qu) |

TABLE-continued
| Preparation No. | Formula |
|---|---|
| 65-(10) | 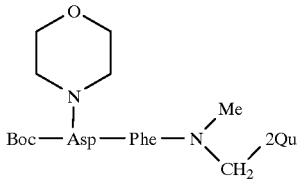 |
| 65-(11) | 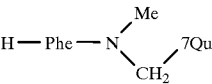 |
| 65-(12) | 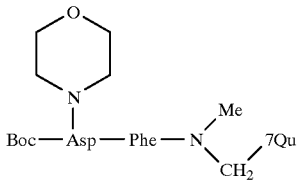 |
| 65-(13) | 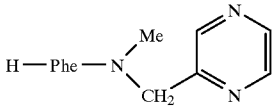 |

TABLE-continued
| Preparation No. | Formula |
|---|---|
| 65-(14) | 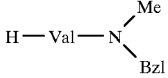 |
| | 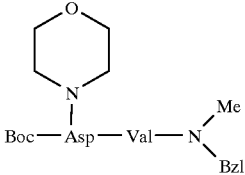 |
| 65-(15) | 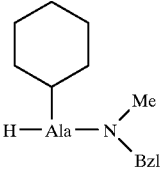 |
| | 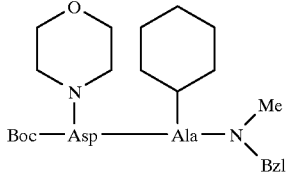 |
| 65-(16) | 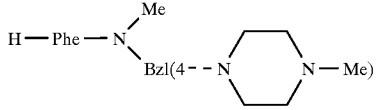 |
| | 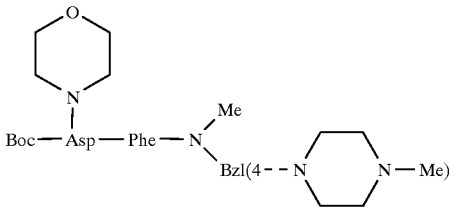 |
| 65-(17) | 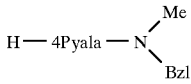 |
| | 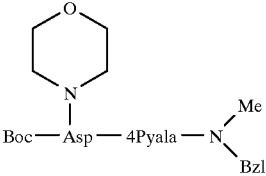 |

TABLE-continued

| Preparation No. | Formula |
|---|---|
| 65-(18) | H—Phe—N(Me)—Bzl(4--N-imidazole) |
| | Boc—Asp(morpholine)—Phe—N(Me)—Bzl(4--N-imidazole) |
| 65-(19) | H—Phe—N(Me)(CH₂-3Qu) |
| | Boc—Asp(morpholine)—Phe—N(Me)(CH₂-3Qu) |
| 65-(20) | H—Phe—N(Me)(CH₂-6Qu) |
| | Boc—Asp(morpholine)—Phe—N(Me)(CH₂-6Qu) |
| 65-(21) | H—Phe—N(Me)(CH₂-3Py(6-NHAc)) |
| | Boc—Asp(morpholine)—Phe—N(Me)(CH₂-3Py(6-NHAc)) |
| 65-(22) | H—Phe—N(Me)(Bzl) |

TABLE-continued
| Preparation No. | Formula |
|---|---|
| | Boc—Glu(Bzl)—Phe—N(Me)(Bzl) |
| 65-(23) | 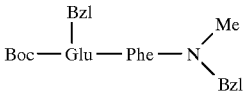 |
| | 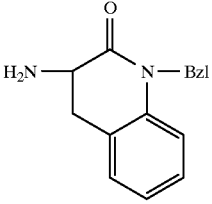 |
| 65-(24) | 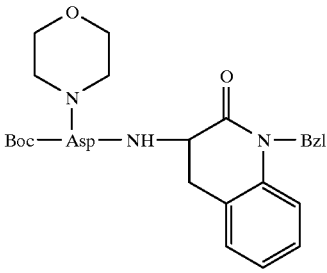 |
| | 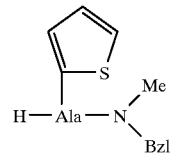 |
| 65-(25) | 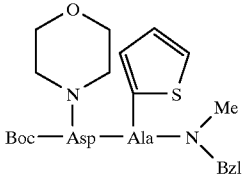 |
| | 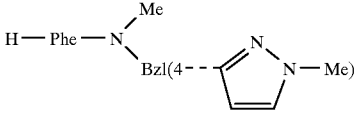 |
| 65-(26) | 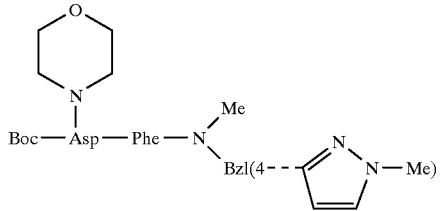 |

TABLE-continued
| Preparation No. | Formula |
|---|---|
| | 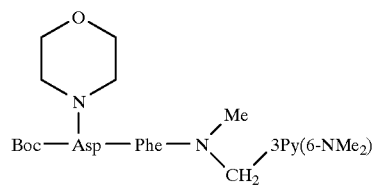 |
| 65-(27) | 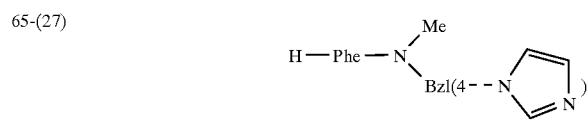 |
| | 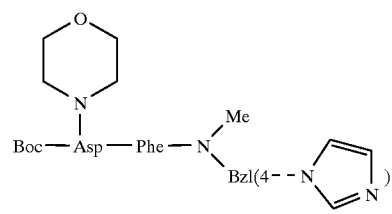 |
| 65-(28) | 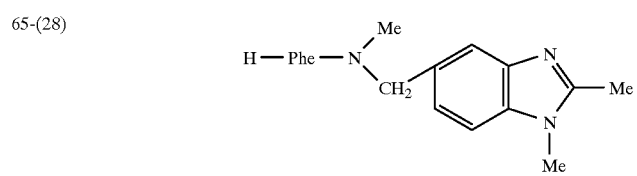 |
| | 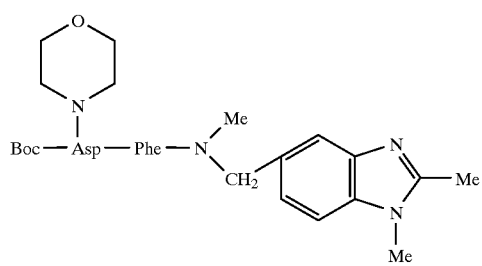 |
| 65-(29) |  |
| | 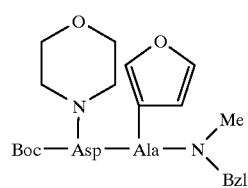 |

TABLE-continued
| Preparation No. | Formula |
|---|---|
| 65-(30) | 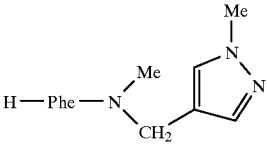 |
| | 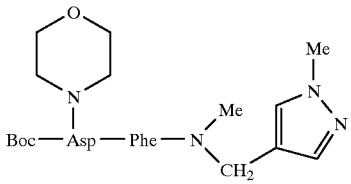 |
| 65-(31) | 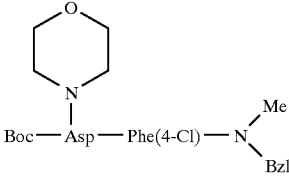 |
| | 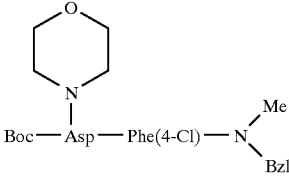 |
| 65-(32) |  |
| |  |
| 65-(33) | 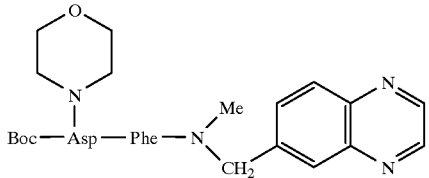 |
| | 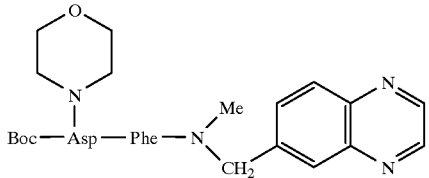 |

TABLE-continued

| Preparation No. | Formula |
|---|---|
| 65-(34) | H—1Nal—N(Me)(Bzl) |
| | Boc—Asp(morpholino)—1Nal—N(Me)(Bzl) |
| 65-(35) | H—3Pyala—N(Me)(Bzl) |
| | Boc—Asp(morpholino)—3Pyala—N(Me)(Bzl) |
| 65-(36) | H—Phe—N(Me)(CH$_2$-3Py(6-OMe)) |
| | Boc—Asp(morpholino)—Phe—N(Me)(CH$_2$-3Py(6-OMe)) |
| 65-(37) | H—Nle—N(Me)(Bzl) |
| | Boc—Asp(morpholino)—Nle—N(Me)(Bzl) |
| 66-(1) | Boc—Asp(morpholino)—2Nal—N(Me)(Bzl) |

TABLE-continued

| Preparation No. | Formula |
|---|---|
| | Morpholine-N-Asp(H)—2Nal—N(Me)(Bzl) |
| 66-(2) | Morpholine-N-Asp(Boc)—MePhe—N(Me)(Bzl) |
| | Morpholine-N-Asp(H)—MePhe—N(Me)(Bzl) |
| 66-(3) | Morpholine-N-Asp(Boc)—Tyr(Me)—N(Me)(Bzl) |
| | Morpholine-N-Asp(H)—Tyr(Me)—N(Me)(Bzl) |
| 66-(4) | Boc—Asp(NMe$_2$)—Phe—N(Me)(CH$_2$-3Py(6-Me)) |
| | H—Asp(NMe$_2$)—Phe—N(Me)(CH$_2$-3Py(6-Me)) |
| 66-(5) | 4-Me-piperazine-N-Asp(Boc)—Phe—N(Me)(Bzl(3-Me)) |

TABLE-continued

| Preparation No. | Formula |
|---|---|
| | 4-methylpiperazine-N-CO-Asp(H)-Phe-N(Me)-Bzl(3-Me) |
| 66-(6) | 4-methylpiperazine-N-CO-Asp(Boc)-Phe-N(Me)-Bzl(2-Me) |
| | 4-methylpiperazine-N-CO-Asp(H)-Phe-N(Me)-Bzl(2-Me) |
| 66-(7) | morpholine-N-CO-Asp(Boc)-Phe-N(Me)-CH$_2$-4Pm |
| | morpholine-N-CO-Asp(H)-Phe-N(Me)-CH$_2$-4Pm |
| 66-(8) | morpholine-N-CO-Asp(Boc)-Phe-N(Me)-CH$_2$-quinoxaline |

TABLE-continued
| Preparation No. | Formula |
|---|---|
| | 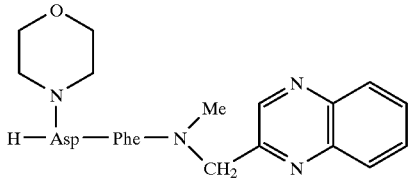 |
| 66-(9) | 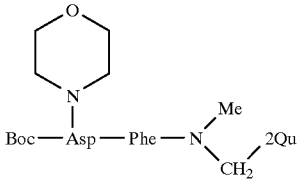 |
| | 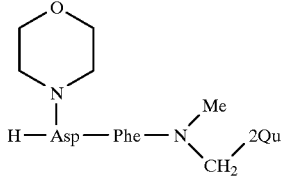 |
| 66-(10) | 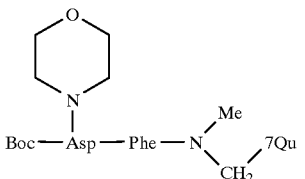 |
| | 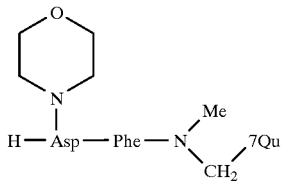 |
| 66-(11) | 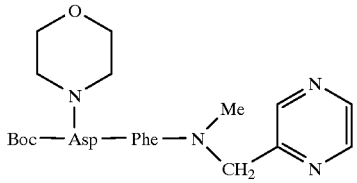 |
| | 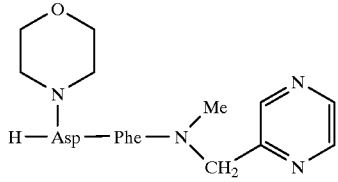 |

TABLE-continued

| Preparation No. | Formula |
|---|---|
| 66-(12) | Boc—Asp(morpholine)—Phe—N(Me)(CH₂-3Py(6-3Py)) |
| | H—Asp(morpholine)—Phe—N(Me)(CH₂-3Py(6-3Py)) |
| 66-(13) | Boc—Asp(morpholine)—Phe—N(Me)(CH₂-3Py(6-2Py)) |
| | H—Asp(morpholine)—Phe—N(Me)(CH₂-3Py(6-2Py)) |
| 66-(14) | Boc—Asp(morpholine)—Val—N(Me)(Bzl) |
| | H—Asp(morpholine)—Val—N(Me)(Bzl) |
| 66-(15) | Boc—Asp(morpholine)—Ala(cHex)—N(Me)(Bzl) |

TABLE-continued
| Preparation No. | Formula |
|---|---|
| | 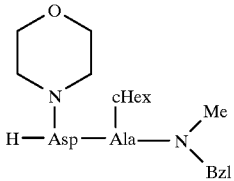 H—Asp—Ala(cHex)—N(Me)(Bzl), Asp-N-morpholino |
| 66-(16) | 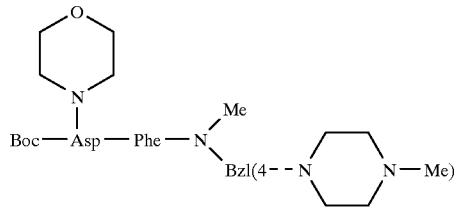 Boc—Asp—Phe—N(Me)(Bzl(4--N N—Me)), Asp-N-morpholino |
| | 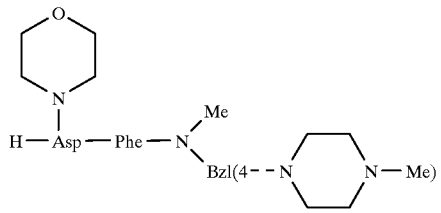 H—Asp—Phe—N(Me)(Bzl(4--N N—Me)), Asp-N-morpholino |
| 66-(17) | 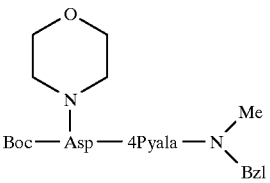 Boc—Asp—4Pyala—N(Me)(Bzl), Asp-N-morpholino |
| | 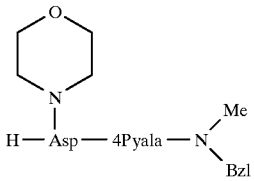 H—Asp—4Pyala—N(Me)(Bzl), Asp-N-morpholino |
| 66-(18) | 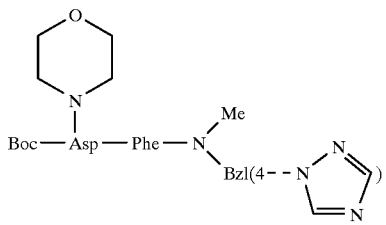 Boc—Asp—Phe—N(Me)(Bzl(4--1,2,4-triazol-1-yl)), Asp-N-morpholino |

TABLE-continued

| Preparation No. | Formula |
|---|---|
| | H—Asp—Phe—N(Me)(Bzl(4—1,2,4-triazol-N)), Asp-N-morpholino |
| 66-(19) | Boc—Asp—Phe—N(Me)(CH₂-3Qu), Asp-N-morpholino |
| | H—Asp—Phe—N(Me)(CH₂-3Qu), Asp-N-morpholino |
| 66-(20) | Boc—Asp—Phe—N(Me)(CH₂-6Qu), Asp-N-morpholino |
| | H—Asp—Phe—N(Me)(CH₂-6Qu), Asp-N-morpholino |
| 66-(21) | Boc—Asp—Phe—N(Me)(CH₂-3Py(6-NHAc)), Asp-N-morpholino |
| | H—Asp—Phe—N(Me)(CH₂-3Py(6-NHAc)), Asp-N-morpholino |

TABLE-continued
| Preparation No. | Formula |
|---|---|
| 66-(22) | 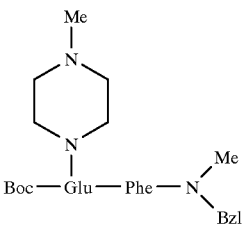 |
| 66-(23) | 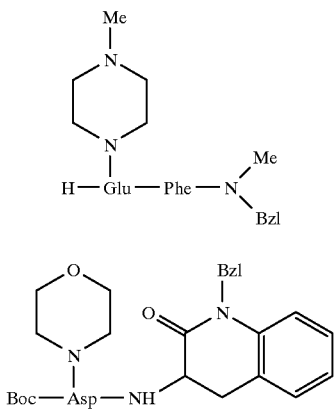 |
| 66-(24) | 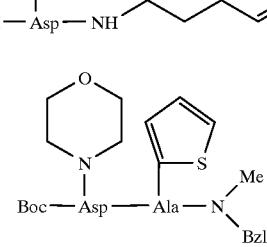 |
| 66-(25) | 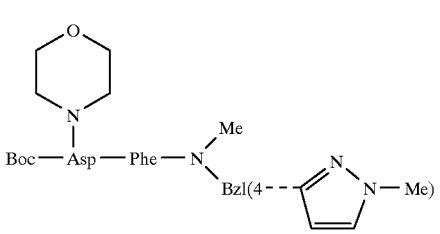 |

TABLE-continued
| Preparation No. | Formula |
|---|---|
|  | 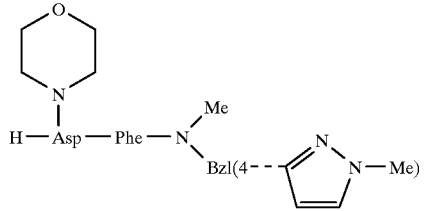 |
| 66-(26) | 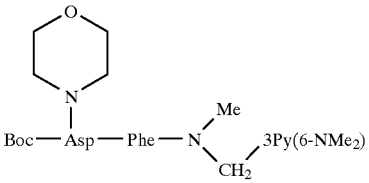 |
|  | 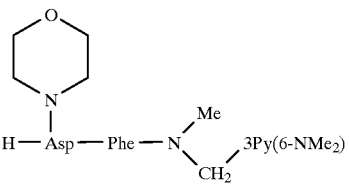 |
| 66-(27) | 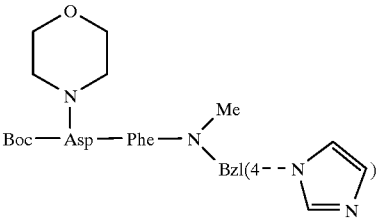 |
|  | 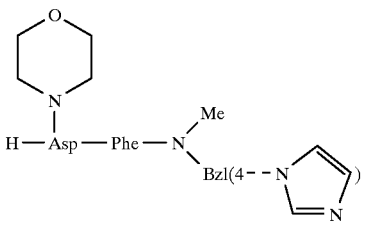 |
| 66-(28) | 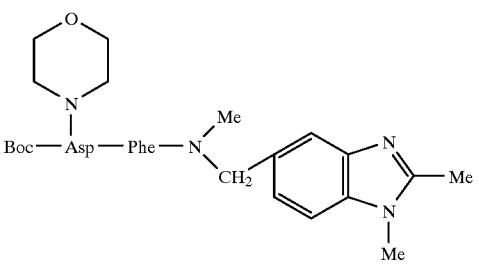 |

TABLE-continued

| Preparation No. | Formula |
|---|---|
| | H—Asp—Phe—N(Me)(CH₂-[1,2-dimethylbenzimidazol-5-yl]) with morpholine on Asp |
| 66-(29) | Boc—Asp—Ala—N(Me)(Bzl) with morpholine on Asp and furan on Ala |
| | H—Asp—Ala—N(Me)(Bzl) with morpholine on Asp |
| 66-(30) | Boc—Asp—Phe—N(Me)(CH₂-[1-methylpyrazol-4-yl]) with morpholine on Asp |
| | H—Asp—Phe—N(Me)(CH₂-[1-methylpyrazol-4-yl]) with morpholine on Asp |
| 66-(31) | Boc—Asp—Phe(4-Cl)—N(Me)(Bzl) with morpholine on Asp |
| | H—Asp—Phe(4-Cl)—N(Me)(Bzl) with morpholine on Asp |

TABLE-continued
| Preparation No. | Formula |
|---|---|
| 66-(32) | 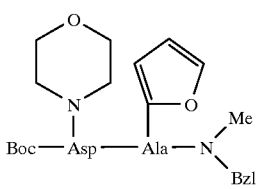 |
| 66-(33) | 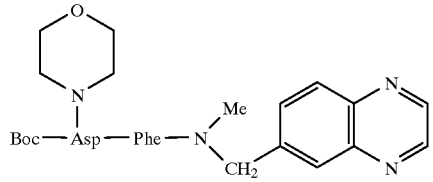 |
| 66-(34) | 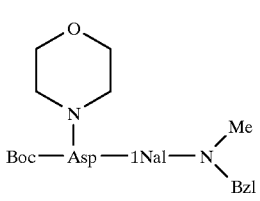 |
| 66-(35) | 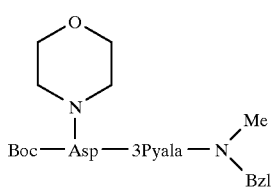 |

TABLE-continued

| Preparation No. | Formula |
|---|---|
| | morpholine-N-CO-Asp(H)-3Pyala-N(Me)(Bzl) |
| 66-(36) | morpholine-N-CO-Asp(Boc)-Phe-N(Me)(CH₂-3Py(6-OMe)) |
| | morpholine-N-CO-Asp(H)-Phe-N(Me)(CH₂-3Py(6-OMe)) |
| 66-(37) | morpholine-N-CO-Asp(Boc)-Nle-N(Me)(Bzl) |
| | morpholine-N-CO-Asp(H)-Nle-N(Me)(Bzl) |
| 67 | quinoline-3-CHO |
| | quinoline-3-CH₂-NH-Me |
| 68 | 5-formyl-2-(NHAc)-pyridine |

TABLE-continued

| Preparation No. | Formula |
| --- | --- |
| | Me—NH—CH₂-[5-(6-NHAc)pyridine] |
| 69-(1) | Me-N(piperazine)N-[4-CHO-phenyl] |
| | Me-N(piperazine)N-[4-(CH₂—NH—Me)-phenyl] |
| 69-(2) | HCO-[6-quinoline] |
| | Me—NH—CH₂-[6-quinoline] |
| 69-(3) | [2,2'-bipyridine]-5-CHO |
| | [2,2'-bipyridine]-5-CH₂—NH—Me |
| 69-(4) | [3,2'-bipyridine]-5-CHO |
| | [3,2'-bipyridine]-5-CH₂—NH—Me |
| 69-(5) | pyrazine-2-CHO |
| | pyrazine-2-CH₂—NH—Me |
| 69-(6) | [7-quinoline]-CHO |

TABLE-continued
| Preparation No. | Formula |
|---|---|
|  | 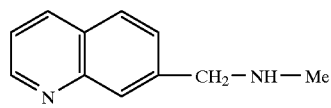 |
| 69-(7) | 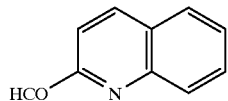 |
|  | 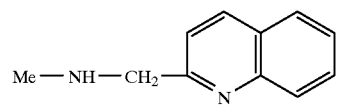 |
| 69-(8) | 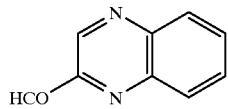 |
|  | 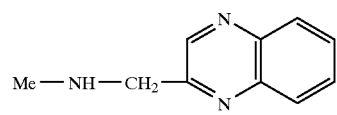 |
| 69-(9) | 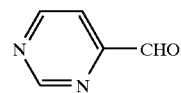 |
|  | 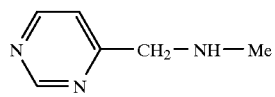 |
| 69-(10) | 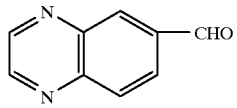 |
|  | 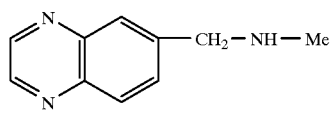 |
| 69-(11) | 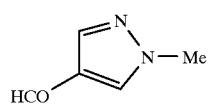 |
|  | 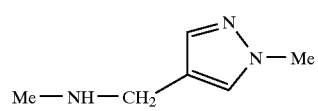 |

| Preparation No. | Formula |
|---|---|
| 69-(12) | HCO-[5-formyl-1,2-dimethylbenzimidazole]<br><br>Me—NH—CH₂-[1,2-dimethylbenzimidazol-5-yl] |
| 69-(13) | HCO-[4-(1-imidazolyl)phenyl]<br><br>Me—NH—CH₂-[4-(1-imidazolyl)phenyl] |
| 69-(14) | HCO-[6-(dimethylamino)pyridin-3-yl]<br><br>Me—NH—CH₂-[4-(dimethylamino)phenyl]-NMe₂ |
| 69-(15) | [1-methyl-1H-pyrazol-3-yl]-C₆H₄-CHO<br><br>[1-methyl-1H-pyrazol-3-yl]-C₆H₄-CH₂—NH—Me |
| 70 | 7-methylquinoline<br><br>quinoline-7-carbaldehyde |

TABLE-continued

| Preparation No. | Formula |
|---|---|
| 71-(1) | 2-methylquinoline<br>2-formylquinoline (HCO-quinoline) |
| 71-(2) | 2-methylquinoxaline<br>2-formylquinoxaline (HCO-quinoxaline) |
| 71-(3) | 4-methylpyrimidine<br>pyrimidine-4-carbaldehyde (CHO) |
| 71-(4) | 6-methylquinoxaline<br>quinoxaline-6-carbaldehyde (CHO) |
| 72 | 5-(hydroxymethyl)-2,2'-bipyridine (CH₂—OH)<br>2,2'-bipyridine-5-carbaldehyde (CHO) |
| 73-(1) | 2-(hydroxymethyl)pyrazine (CH₂OH) |

TABLE-continued

| Preparation No. | Formula |
|---|---|
| | pyrazine-2-CHO |
| 73-(2) | 3,2'-bipyridine-5'-CH₂OH |
| | 3,2'-bipyridine-5'-CHO |
| 74 | 2,2'-bipyridine-5'-CO₂Et |
| | 2,2'-bipyridine-5'-CH₂—OH |
| 75-(1) | 3,2'-bipyridine-5'-CO₂Et |
| | 3,2'-bipyridine-5'-CH₂—OH |
| 75-(2) | pyrazine-2-CO₂Me |
| | pyrazine-2-CH₂—OH |
| 76 | quinoline-6-COOH |
| | quinoline-6-C(O)-N(Me)(OMe) |

TABLE-continued

| Preparation No. | Formula |
|---|---|
| 77 | Me-N(OMe)-CO-[quinolin-6-yl] |
|  | HCO-[quinolin-6-yl] |
| 78 | F-C6H4-CHO (4-fluorobenzaldehyde) |
|  | Me-N(piperazine)N-C6H4-CHO (4-(4-methylpiperazin-1-yl)benzaldehyde) |
| 79-(1) | Boc-NH-CH2-[2-methylphenyl] |
|  | Boc-N(Me)-CH2-[2-methylphenyl] |
| 79-(2) | Boc-NH-CH2-[3-methylphenyl] |
|  | Boc-N(Me)-CH2-[3-methylphenyl] |
| 80-(1) | Boc-N(Me)-CH2-[2-methylphenyl] |
|  | H-N(Me)-CH2-[2-methylphenyl] |

TABLE-continued

| Preparation No. | Formula |
|---|---|
| 80-(2) | Boc—N(Me)—CH₂—(3-methylphenyl) |
| | H—N(Me)—CH₂—(3-methylphenyl) |
| 81 | Boc—Asp—OBzl |
| | Boc—Asp(NMe₂)—OBzl |
| 82 | Boc—Asp(NMe₂)—OBzl |
| | Boc—Asp(NMe₂)—OH |
| 83 | Boc—Asp(Bzl)—Phe—N(Me)(Bzl) |
| | Boc—Asp—Phe—N(Me)(Bzl) |
| 84 | Boc—Asp—Phe—N(Me)(Bzl) |
| | Boc—Asp(4-methylpiperazin-1-yl)—Phe—N(Me)(Bzl) |
| 85 | Boc—Glu(Bzl)—Phe—N(Me)(Bzl) |

TABLE-continued
| Preparation No. | Formula |
|---|---|
| | 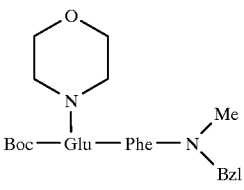 |
| 86 | 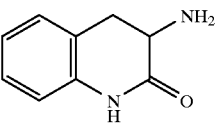 |
| | 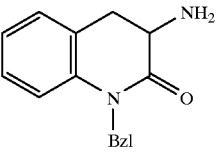 |
| 87 | 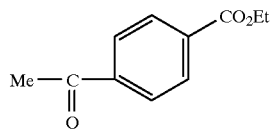 |
| | 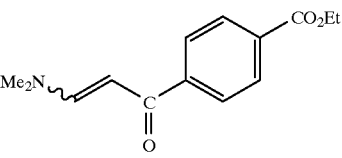 |
| 88 | 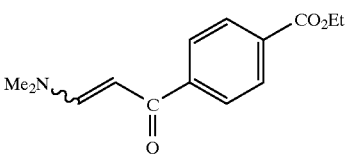 |
| | Object Compound A<br>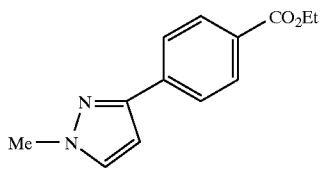<br>Object Compound B<br>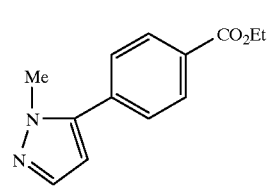 |

TABLE-continued
| Preparation No. | Formula |
|---|---|
| 89 | 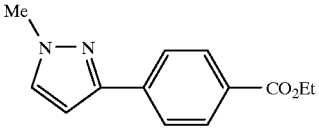 |
|  | 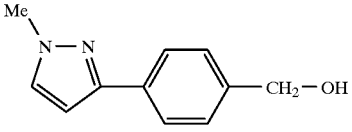 |
| 90 | 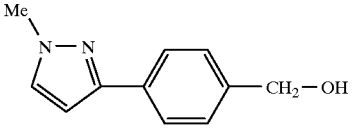 |
|  | 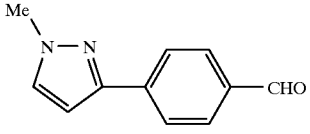 |
| 91 | 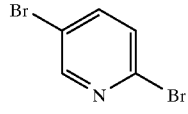 |
|  | 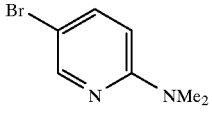 |
| 92 | 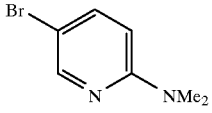 |
|  | 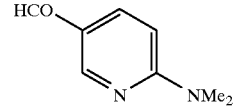 |
| 93 | 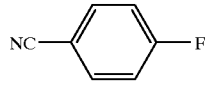 |
|  | 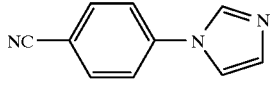 |

TABLE-continued

| Preparation No. | Formula |
|---|---|
| 94 | 4-(1H-imidazol-1-yl)benzonitrile (NC-C6H4-N-imidazole) |
|  | 4-(1H-imidazol-1-yl)benzaldehyde (HCO-C6H4-N-imidazole) |
| 95 | Ethyl 3-nitro-4-acetamidobenzoate (EtO2C-C6H3(NO2)-NHAc) |
|  | Ethyl 4-(N-methyl-N-acetylamino)-3-nitrobenzoate (EtO2C-C6H3(NO2)-N(Me)Ac) |
| 96 | Ethyl 4-(N-methyl-N-acetylamino)-3-nitrobenzoate (EtO2C-C6H3(NO2)-N(Me)Ac) |
|  | Ethyl 1,2-dimethyl-1H-benzimidazole-5-carboxylate |
| 97 | Ethyl 1,2-dimethyl-1H-benzimidazole-5-carboxylate |
|  | (1,2-dimethyl-1H-benzimidazol-5-yl)methanol (HO-CH2-benzimidazole-Me,Me) |
| 98 | (1,2-dimethyl-1H-benzimidazol-5-yl)methanol (HO-CH2-benzimidazole-Me,Me) |

TABLE-continued

| Preparation No. | Formula |
| --- | --- |
|  | [structure: 1-methyl-2-methyl-5-formyloxy-benzimidazole, HCO-O on benzimidazole with N-Me and 2-Me] |
| 99-(1) | HCl·H—Phe—N(Me)(Bzl) |
| 99-(2) | Boc—Phe(4-Me)—Phe—N(Me)(Bzl) |
|  | [structure: tetrahydroisoquinoline-3-carboxamide with NH, CON(Me)(Bzl)] |
| 99-(3) | Boc—Phe—N[tetrahydroisoquinoline]—CON(Me)(Bzl) |
|  | H—Nle—N(Me)(CH₂-3Qu) |
| 99-(4) | Boc—Ser—Nle—N(Me)(CH₂-3Qu) |
|  | H—Nle—N(Me)(CH₂-3Qu) |
|  | Boc—2Pyala—Nle—N(Me)(CH₂-3Qu) |
| 99-(5) | H—Phe—N(Me)(CH₂-3Py(6-OMe)) |
|  | Boc—Met—Phe—N(Me)(CH₂-3Py(6-OMe)) |

| Preparation No. | Formula |
|---|---|
| 99-(6) | H—Nle—N(Me)(CH₂-3Qu) |
| | Boc—Met—Nle—N(Me)(CH₂-3Qu) |
| 99-(7) | H—Nle—N(Me)(CH₂-3Qu) |
| | Boc—His—Nle—N(Me)(CH₂-3Qu) |
| 99-(8) | H—Phe—N(Me)(CH₂-3Py(6-OEt)) |
| | Boc—Asp(N-methylpiperazinyl)—Phe—N(Me)(CH₂-3Py(6-OEt)) |
| 99-(9) | H—Phe(4-Me)—N(Me)(Bzl) |
| | Boc—Asp(morpholinyl)—Phe(4-Me)—N(Me)(Bzl) |
| 99-(10) | H—Nva—N(Me)(Bzl) |
| | Boc—Asp(morpholinyl)—Nva—N(Me)(Bzl) |

TABLE-continued

| Preparation No. | Formula |
|---|---|
| 99-(11) | H—Phe—N(Me)(CH₂-3Py(6-SMe)) |
| | Boc—Asp(N-methylpiperazine)—Phe—N(Me)(CH₂-3Py(6-SMe)) |
| 99-(12) | H—Nle—N(Me)(CH₂-3Qu) |
| | Boc—Asp(morpholino)—Nle—N(Me)(CH₂-3Qu) |
| 99-(13) | H—Phe—N(Me)(CH₂-3Py(6-OⁿPr)) |
| | Boc—Asp(N-methylpiperazine)—Phe—N(Me)(CH₂-3Py(6-OⁿPr)) |
| 99-(14) | H—Phe—N(Me)(CH₂-3Py(6-OMe)) |
| | Boc—Asp(morpholino)—Phe—N(Me)(CH₂-3Py(6-OMe)) |
| 100-(1) | Boc—Phe(4-Me)—Phe—N(Me)(Bzl) |

TABLE-continued

| Preparation No. | Formula |
|---|---|
| | H—Phe(4-Me)—Phe—N(Me)(Bzl) |
| 100-(2) | Boc—Phe—N[tetrahydroisoquinoline-3-carbonyl]—N(Me)(Bzl) |
| | H—Phe—N[tetrahydroisoquinoline-3-carbonyl]—N(Me)(Bzl) |
| 100-(3) | Boc—Ser—Nle—N(Me)(CH₂-3Qu) |
| | H—Ser—Nle—N(Me)(CH₂-3Qu) |
| 100-(4) | Boc—2Pyala—Nle—N(Me)(CH₂-3Qu) |
| | H—2Pyala—Nle—N(Me)(CH₂-3Qu) |
| 100-(5) | Boc—Met—Phe—N(Me)(CH₂-3Py(6-OMe)) |
| | H—Met—Phe—N(Me)(CH₂-3Py(6-OMe)) |
| 100-(6) | Boc—Met—Nle—N(Me)(CH₂-3Qu) |
| | H—Met—Nle—N(Me)(CH₂-3Qu) |
| 100-(7) | Boc—His—Nle—N(Me)(CH₂-3Qu) |

TABLE-continued

| Preparation No. | Formula |
|---|---|
| | H—His—Nle—N(Me)(CH₂-3Qu) |
| 100-(8) | Boc—Asp(N-methylpiperazide)—Phe—N(Me)(CH₂-3Py(6-OEt)) |
| | H—Asp(N-methylpiperazide)—Phe—N(Me)(CH₂-3Py(6-OEt)) |
| 100-(9) | Boc—Asp(morpholide)—Phe(4-Me)—N(Me)(Bzl) |
| | H—Asp(morpholide)—Phe(4-Me)—N(Me)(Bzl) |
| 100-(10) | Boc—Asp(morpholide)—Nva—N(Me)(Bzl) |
| | H—Asp(morpholide)—Nva—N(Me)(Bzl) |

TABLE-continued
| Preparation No. | Formula |
|---|---|
| 100-(11) | 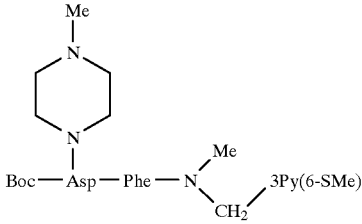 |
| 100-(12) | 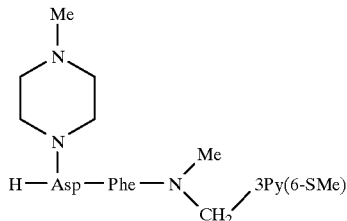 |
| 100-(13) | 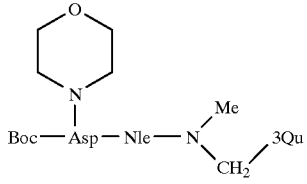 |
| 100-(14) | 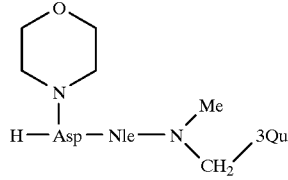 |

TABLE-continued
| Preparation No. | Formula |
|---|---|
| | 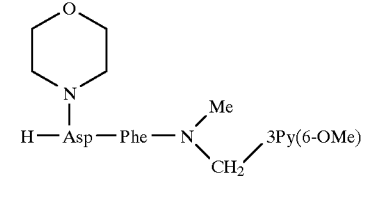 |
| 101-(1) | Boc—Phe—OH |
| | 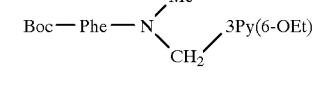 |
| 101-(2) | Boc—Phe(4-Me)—OH |
| | 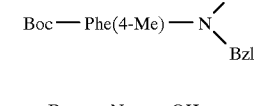 |
| 101-(3) | Boc—Nva—OH |
| | 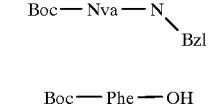 |
| 101-(4) | Boc—Phe—OH |
| | 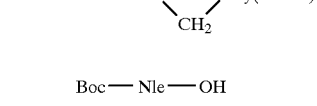 |
| 101-(5) | Boc—Nle—OH |
| | 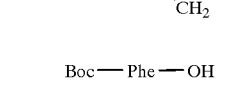 |
| 101-(6) | Boc—Phe—OH |
| | 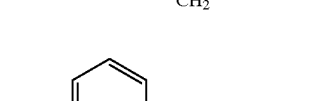 |
| 101-(7) | 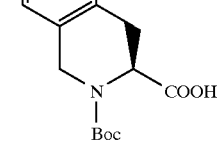 |

TABLE-continued

| Preparation No. | Formula |
|---|---|
| | [structure: tetrahydroisoquinoline with N-Boc and CON(Me)Bzl substituent] |
| 102-(1) | Boc—Phe—N(Me)(CH₂-3Py(6-OEt)) |
| | H—Phe—N(Me)(CH₂-3Py(6-OEt)) |
| 102-(2) | Boc—Phe(4-Me)—N(Me)(Bzl) |
| | H—Phe(4-Me)—N(Me)(Bzl) |
| 102-(3) | Boc—Nva—N(Me)(Bzl) |
| | H—Nva—N(Me)(Bzl) |
| 102-(4) | Boc—Phe—N(Me)(CH₂-3Py(6-SMe)) |
| | H—Phe—N(Me)(CH₂-3Py(6-SMe)) |
| 102-(5) | Boc—Nle—N(Me)(CH₂-3Qu) |
| | H—Nle—N(Me)(CH₂-3Qu) |
| 102-(6) | Boc—Phe—N(Me)(CH₂-3Py(6-OⁿPr)) |
| | H—Phe—N(Me)(CH₂-3Py(6-OⁿPr)) |

TABLE-continued

| Preparation No. | Formula |
|---|---|
| 102-(7) | 1,2,3,4-tetrahydroisoquinoline-3-carboxylic acid N-methyl-N-benzyl amide, N-Boc |
| | 1,2,3,4-tetrahydroisoquinoline-3-carboxylic acid N-methyl-N-benzyl amide, NH |
| 103-(1) | 6-EtO-pyridine-3-CHO |
| | 6-EtO-pyridine-3-CH$_2$—NHMe |
| 103-(2) | 6-MeS-pyridine-3-CHO |
| | 6-MeS-pyridine-3-CH$_2$—NHMe |
| 103-(3) | 6-$^n$Pro-pyridine-3-CHO |
| | 6-$^n$Pro-pyridine-3-CH$_2$—NHMe |
| 104-(1) | Boc—Nle—OH |
| | Boc—Nle—N(Me)(CH$_2$-3Py(6-3Py)) |
| 104-(2) | Boc—Nle—OH |
| | Boc—Nle—N(Me)(CH$_2$-3Py(6-Me)) |

TABLE-continued

| Preparation No. | Formula |
|---|---|
| 104-(3) | Boc—Phe—OH |
| | Boc—Phe—N(Me)(CH₂)3Py(5-OMe) |
| 104-(4) | Boc—Phe—OH |
| | Boc—Phe—N(Me)(CH₂)3Py(4-OMe) |
| 104-(5) | Boc—Phe—OH |
| | Boc—Phe—N(Me)(CH₂)3Py(5-Br) |
| 105-(1) | Boc—Nle—N(Me)(CH₂)3Py(6-3Py) |
| | H—Nle—N(Me)(CH₂)3Py(6-3Py) |
| 105-(2) | Boc—Nle—N(Me)(CH₂)3Py(6-Me) |
| | H—Nle—N(Me)(CH₂)3Py(6-Me) |
| 105-(3) | Boc—Phe—N(Me)(CH₂)3Py(5-OMe) |
| | H—Phe—N(Me)(CH₂)3Py(5-OMe) |
| 105-(4) | Boc—Phe—N(Me)(CH₂)3Py(4-OMe) |
| | H—Phe—N(Me)(CH₂)3Py(4-OMe) |
| 105-(5) | Boc—Phe—N(Me)(CH₂)3Py(5-Br) |

TABLE-continued

| Preparation No. | Formula |
| --- | --- |
| | H—Phe—N(Me)(CH₂-3Py(5-Br)) |
| 106-(1) | H—Nle—N(Me)(CH₂-3Py(6-3Py)) |
| | Boc—Asp(morpholino)—Nle—N(Me)(CH₂-3Py(6-3Py)) |
| 106-(2) | H—Nle—N(Me)(CH₂-3Py(6-3Py)) |
| | Boc—2Pyala—Nle—N(Me)(CH₂-3Py(6-3Py)) |
| 106-(3) | H—Nle—N(Me)(CH₂-3Py(6-3Py)) |
| | Boc—Met—Nle—N(Me)(CH₂-3Py(6-3Py)) |
| 106-(4) | H—Nle—N(Me)(CH₂-3Py(6-Me)) |
| | Boc—Asp(morpholino)—Nle—N(Me)(CH₂-3Py(6-Me)) |
| 106-(5) | H—Nle—N(Me)(CH₂-3Py(6-Me)) |
| | Boc—2-Pyala—Nle—N(Me)(CH₂-3Py(6-Me)) |
| 106-(6) | H—Nle—N(Me)(CH₂-3Py(6-Me)) |

TABLE-continued

| Preparation No. | Formula |
|---|---|
| | Boc—Met—Nle—N(Me)(CH₂-3Py(6-Me)) |
| 106-(7) | H—Nle—N(Me)(CH₂-3Py(6-Me)) |
| | Boc—Ser—Nle—N(Me)(CH₂-3Py(6-Me)) |
| 106-(8) | H—Phe—N(Me)(CH₂-3Py(5-OMe)) |
| | Boc—Asp(N-methylpiperazinyl)—Phe—N(Me)(CH₂-3Py(5-OMe)) |
| 106-(9) | H—Phe—N(Me)(CH₂-3Py(4-OMe)) |
| | Boc—Asp(N-methylpiperazinyl)—Phe—N(Me)(CH₂-3Py(4-OMe)) |
| 106-(10) | H—Phe—N(Me)(CH₂-3Py(5-Br)) |
| | Boc—Asp(N-methylpiperazinyl)—Phe—N(Me)(CH₂-3Py(5-Br)) |
| 107-(1) | Boc—Asp(morpholinyl)—Nle—N(Me)(CH₂-3Py(6-3Py)) |

TABLE-continued

| Preparation No. | Formula |
|---|---|
| | morpholine-N-Asp(H)—Nle—N(Me)(CH₂-3Py(6-3Py)) |
| 107-(2) | Boc—2Pyala—Nle—N(Me)(CH₂-3Py(6-3Py)) |
| | H—2Pyala—Nle—N(Me)(CH₂-3Py(6-3Py)) |
| 107-(3) | Boc—Met—Nle—N(Me)(CH₂-3Py(6-3Py)) |
| | H—Met—Nle—N(Me)(CH₂-3Py(6-3Py)) |
| 107-(4) | morpholine-N-Asp(Boc)—Nle—N(Me)(CH₂-3Py(6-Me)) |
| | morpholine-N-Asp(H)—Nle—N(Me)(CH₂-3Py(6-Me)) |
| 107-(5) | Boc—2Pyala—Nle—N(Me)(CH₂-3Py(6-Me)) |
| | H—2Pyala—Nle—N(Me)(CH₂-3Py(6-Me)) |
| 107-(6) | Boc—Met—Nle—N(Me)(CH₂-3Py(6-Me)) |
| | H—Met—Nle—N(Me)(CH₂-3Py(6-Me)) |

TABLE-continued

| Preparation No. | Formula |
|---|---|
| 107-(7) | Boc—Ser—Nle—N(Me)(CH₂-3Py(6-Me)) |
| | H—Ser—Nle—N(Me)(CH₂-3Py(6-Me)) |
| 107-(8) | (4-Me-piperazin-1-yl)-Boc—Asp—Phe—N(Me)(CH₂-3Py(5-OMe)) |
| | (4-Me-piperazin-1-yl)-H—Asp—Phe—N(Me)(CH₂-3Py(5-OMe)) |
| 107-(9) | (4-Me-piperazin-1-yl)-Boc—Asp—Phe—N(Me)(CH₂-3Py(4-OMe)) |
| | (4-Me-piperazin-1-yl)-H—Asp—Phe—N(Me)(CH₂-3Py(4-OMe)) |
| 107-(10) | (4-Me-piperazin-1-yl)-Boc—Asp—Phe—N(Me)(CH₂-3Py(5-Br)) |

TABLE-continued
| Preparation No. | Formula |
|---|---|
| | 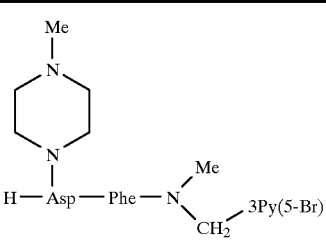 H—Asp—Phe—N(Me)(CH$_2$3Py(5-Br)) with N-methylpiperazine |
| 108 | 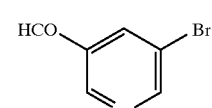 3-formyl-5-bromopyridine 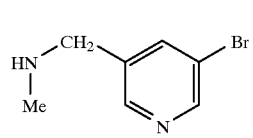 HN(Me)CH$_2$-(5-bromopyridin-3-yl) |
| 109 | 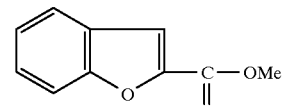 methyl benzofuran-2-carboxylate 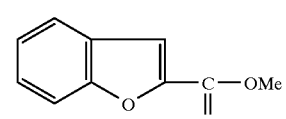 methyl benzofuran-2-carbothioate |
| 110 | Boc—Met—OH 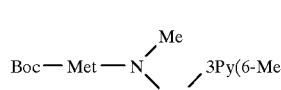 Boc—Met—N(Me)(CH$_2$3Py(6-Me)) |
| 111 | 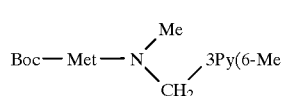 Boc—Met—N(Me)(CH$_2$3Py(6-Me)) 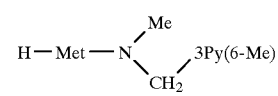 H—Met—N(Me)(CH$_2$3Py(6-Me)) |
| 112-(1) | 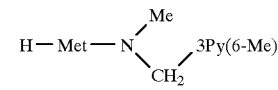 H—Met—N(Me)(CH$_2$3Py(6-Me)) 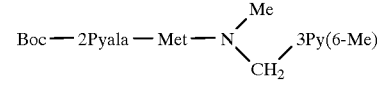 Boc—2Pyala—Met—N(Me)(CH$_2$3Py(6-Me)) |
| 112-(2) | 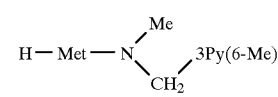 H—Met—N(Me)(CH$_2$3Py(6-Me)) |

TABLE-continued

| Preparation No. | Formula |
| --- | --- |
|  | Boc—Ser—Met—N(Me)(CH₂-3Py(6-Me)) |
| 112-(3) | H—Met—N(Me)(CH₂-3Py(6-Me)) |
|  | Boc—Asp(morpholino)—Met—N(Me)(CH₂-3Py(6-Me)) |
| 112-(4) | H—Met—N(Me)(CH₂-3Py(6-Me)) |
|  | Boc—Met—Met—N(Me)(CH₂-3Py(6-Me)) |
| 113-(1) | Boc—2Pyala—Met—N(Me)(CH₂-3Py(6-Me)) |
|  | H—2Pyala—Met—N(Me)(CH₂-3Py(6-Me)) |
| 113-(2) | Boc—Ser—Met—N(Me)(CH₂-3Py(6-Me)) |
|  | H—Ser—Met—N(Me)(CH₂-3Py(6-Me)) |
| 113-(3) | Boc—Asp(morpholino)—Met—N(Me)(CH₂-3Py(6-Me)) |
|  | H—Asp(morpholino)—Met—N(Me)(CH₂-3Py(6-Me)) |

TABLE-continued

| Preparation No. | Formula |
|---|---|
| 113-(4) | Boc—Met—Met—N(Me)(CH₂-3Py(6-Me)) |
| | H—Met—Met—N(Me)(CH₂-3Py(6-Me)) |
| 114-(1) | 4-OMe-pyridine-3-CHO |
| | 4-OMe-pyridine-3-CH₂—NHMe |
| 114-(12) | 5-MeO-pyridine-3-CHO |
| | 5-MeO-pyridine-3-CH₂—NHMe |

| Example No. | Formula |
|---|---|
| 1 | H—Asp(4-methylpiperazin-1-yl)—Phe—N(Me)(Bzl) |
| | Benzofuran-2-CO—Asp(4-methylpiperazin-1-yl)—Phe—N(Me)(Bzl) |

-continued
| Example No. | Formula |
|---|---|
| 2-(1) | 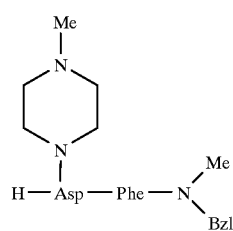 |
| | 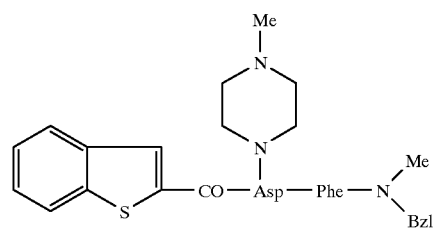 |
| 2-(2) | 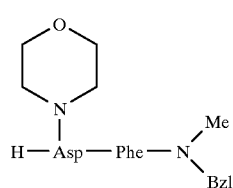 |
| |  |
| 2-(3) | 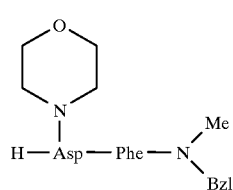 |
| | 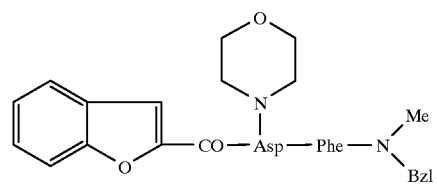 |
| 2-(4) | 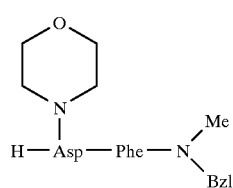 |

| Example No. | Formula |
|---|---|
| | 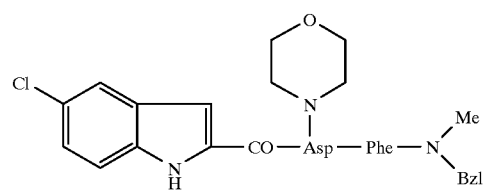 |
| 2-(5) | 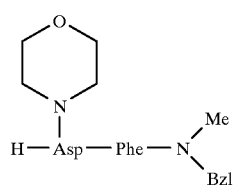 |
| | 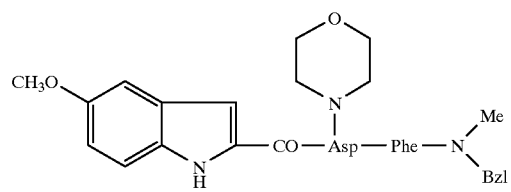 |
| 2-(6) | 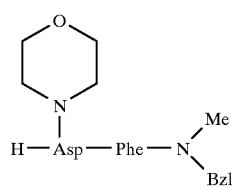 |
| | 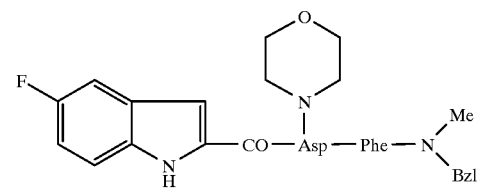 |
| 2-(7) | 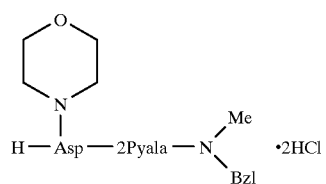 |
| | 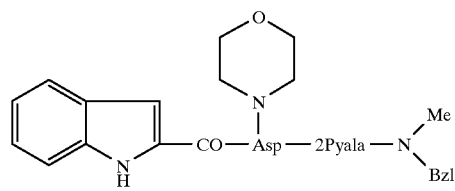 |

| Example No. | Formula |
|---|---|
| 2-(8) | 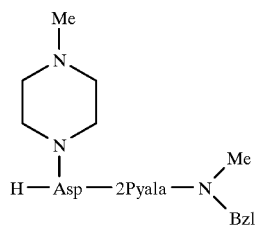 |
| | 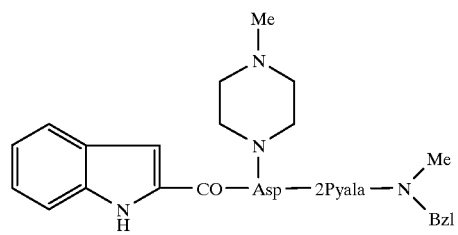 |
| 2-(9) | 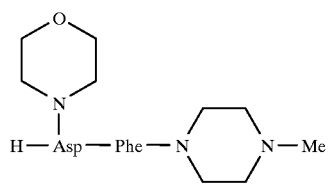 |
| | 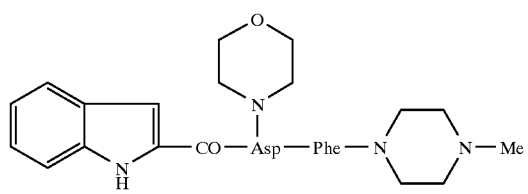 |
| 2-(10) | 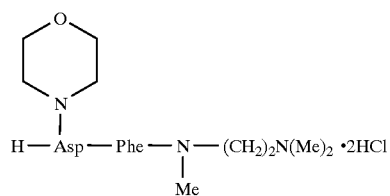 |
| | 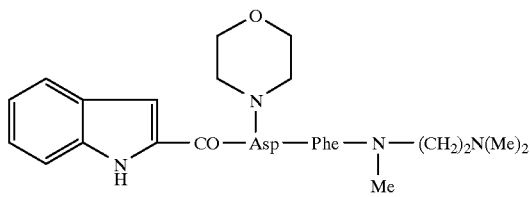 |
| 2-(11) | 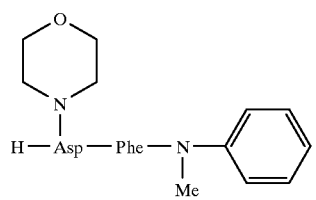 |

-continued
| Example No. | Formula |
|---|---|
| | 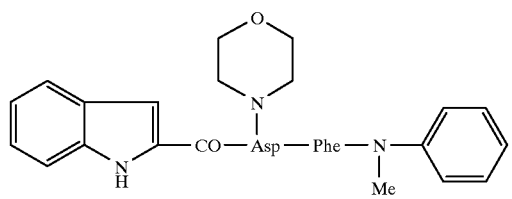 |
| 2-(12) | 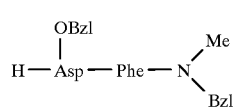 |
| | 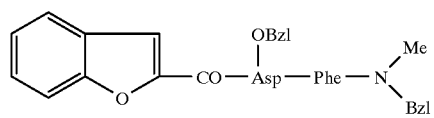 |
| 2-(13) | 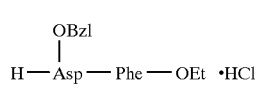 |
| | 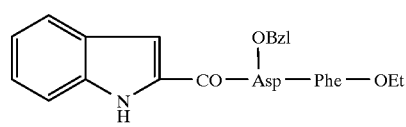 |
| 3 | 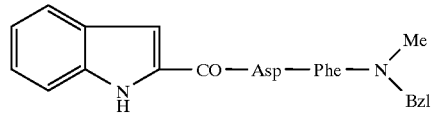 |
| | 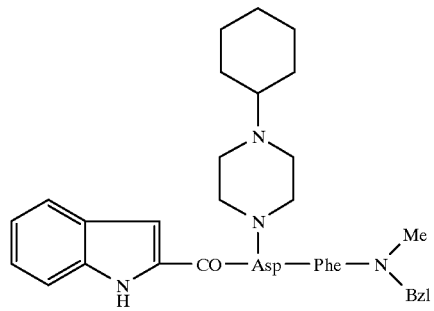 |
| 4-(1) | 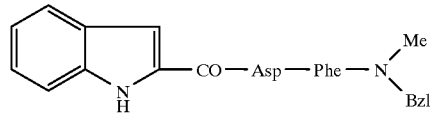 |
| | 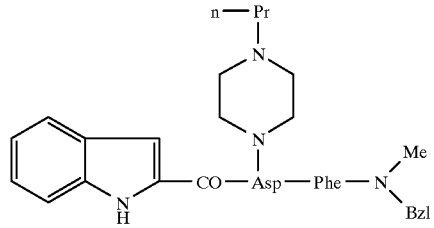 |

| Example No. | Formula |
|---|---|
| 4-(2) | 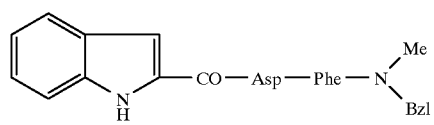 |
| | 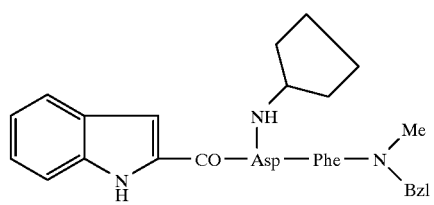 |
| 4-(3) | 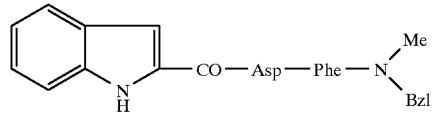 |
| | 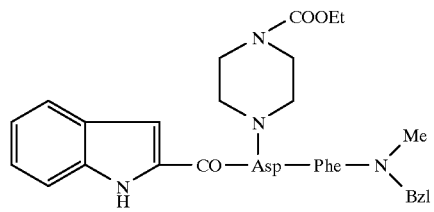 |
| 4-(4) | 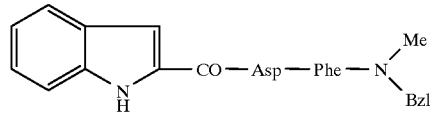 |
| | 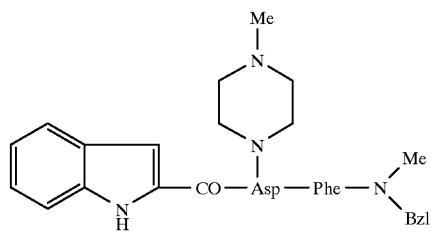 |
| 4-(5) | 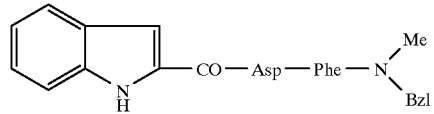 |
| | 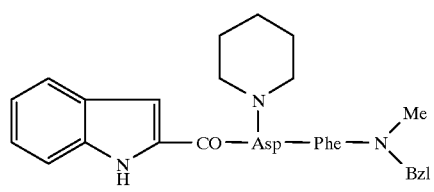 |
| 4-(6) | 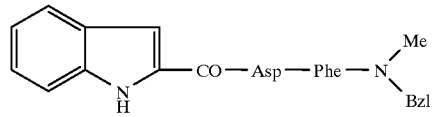 |

| Example No. | Formula |
|---|---|
| 4-(7) | 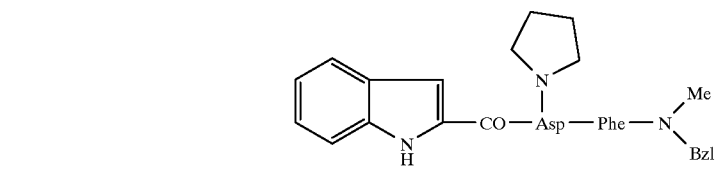<br>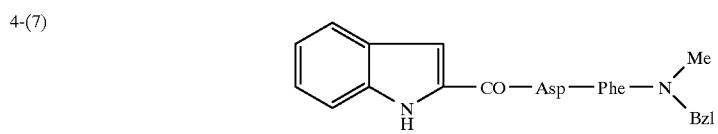 |
| 4-(8) | 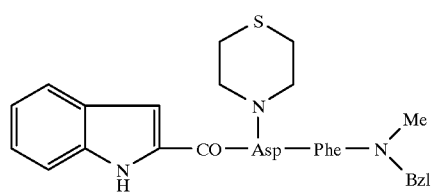<br>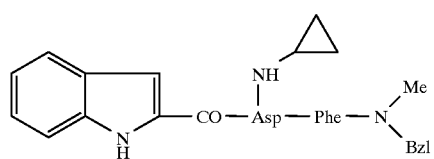 |
| 4-(9) | 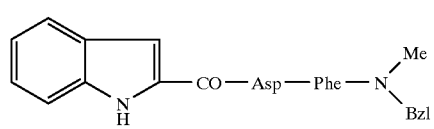<br>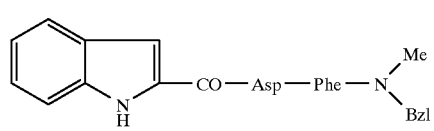 |
| 4-(10) | 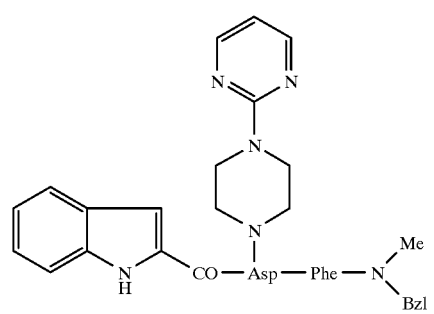 |

| Example No. | Formula |
|---|---|
| 4-(11) | 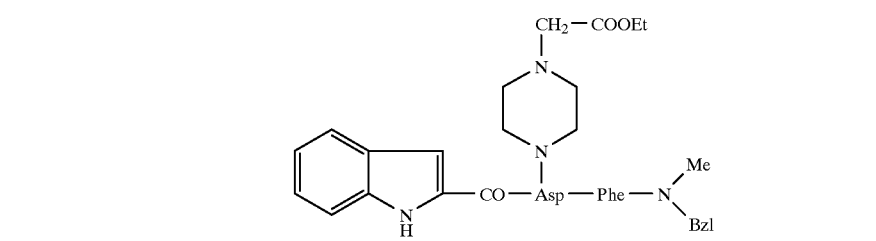<br>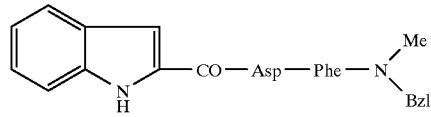 |
| 4-(12) | 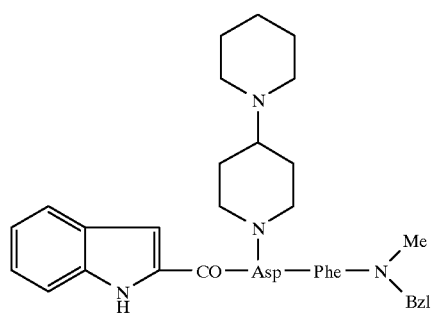<br>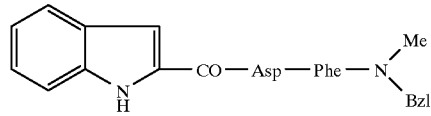 |
| 4-(13) | 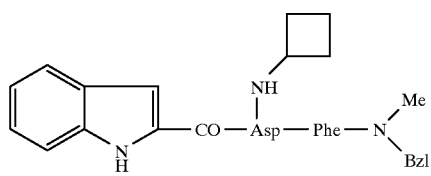<br>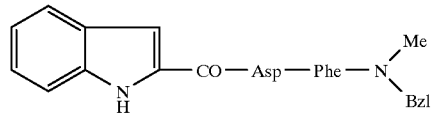 |
| 4-(14) | 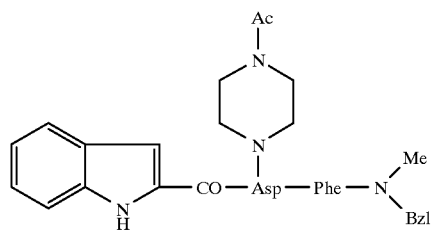<br>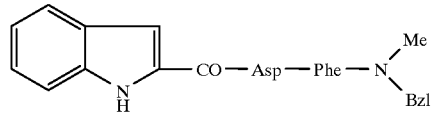 |

-continued
| Example No. | Formula |
|---|---|
| | 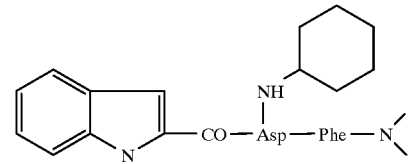 |
| 4-(15) | 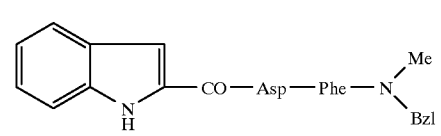 |
| | 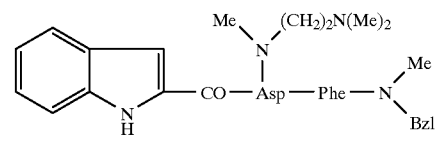 |
| 4-(16) | 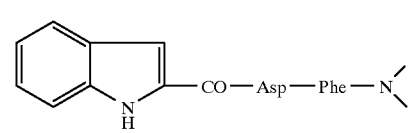 |
| | 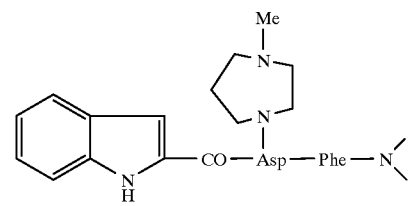 |
| 4-(17) | 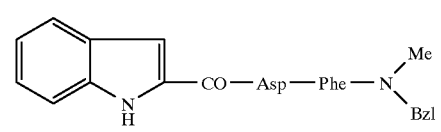 |
| | 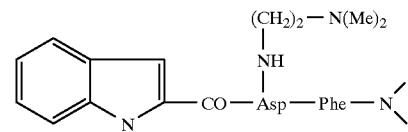 |
| 4-(18) | 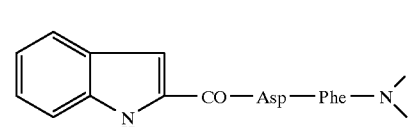 |
| | 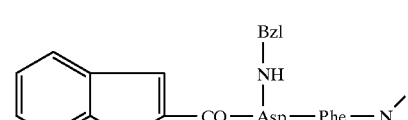 |
| 4-(19) | 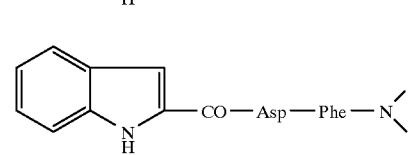 |

| Example No. | Formula |
|---|---|
| | 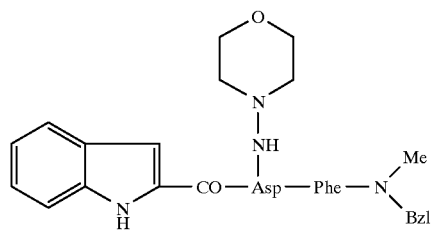 |
| 4-(20) | 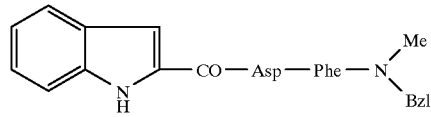 |
| | 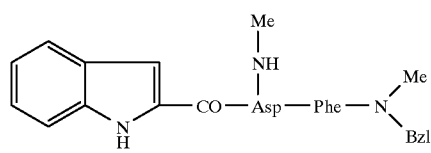 |
| 4-(21) | 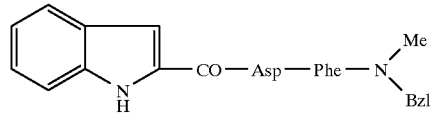 |
| | 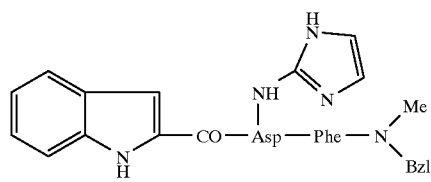 |
| 4-(22) | 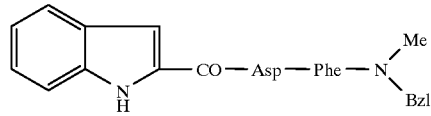 |
| | 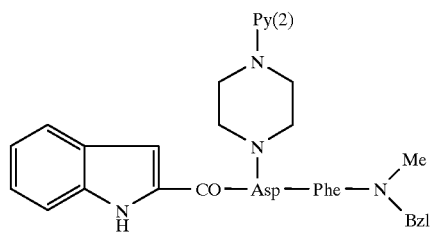 |
| 4-(23) | 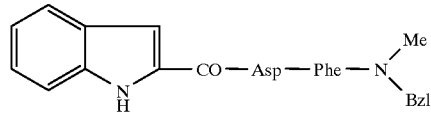 |

-continued
| Example No. | Formula |
|---|---|
| | 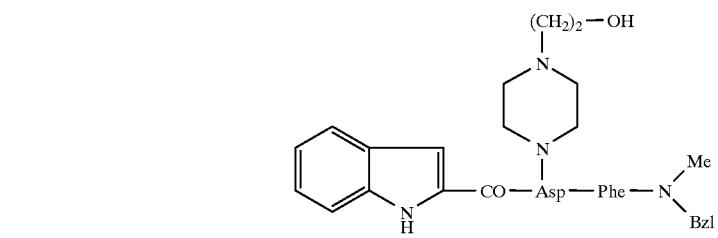 |
| 4-(24) | 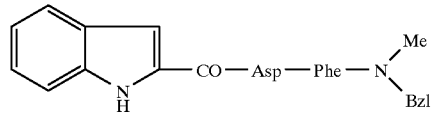 |
| | 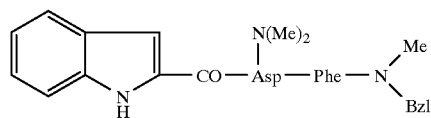 |
| 4-(25) | 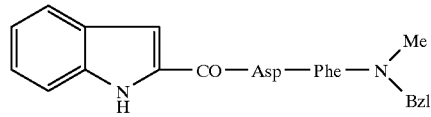 |
| | 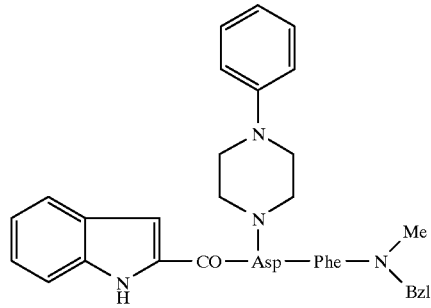 |
| 4-(26) | 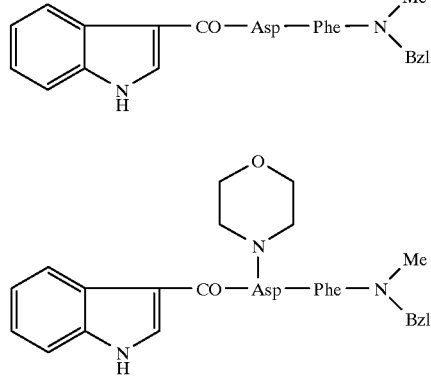 |
| 4-(27) | 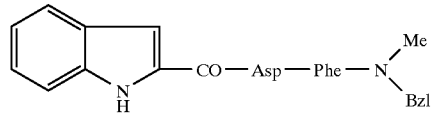 |

| Example No. | Formula |
|---|---|
| | 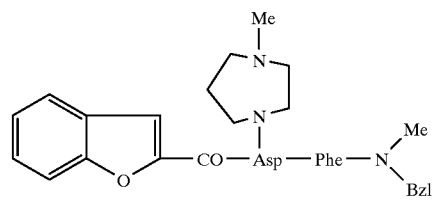 |
| 4-(28) | 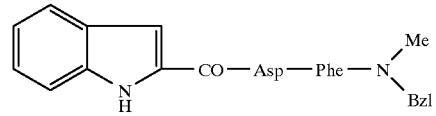 |
| | 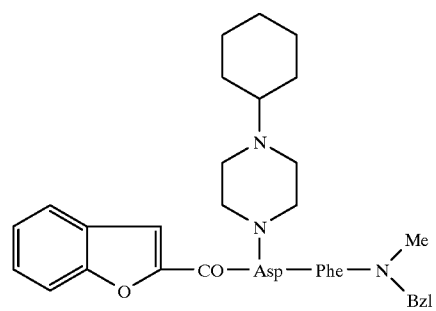 |
| 4-(29) | 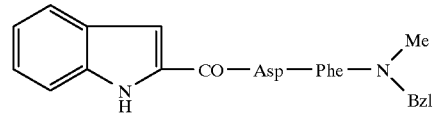 |
| | 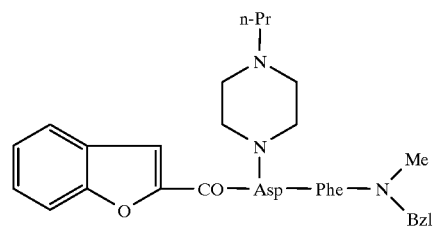 |
| 4-(30) | 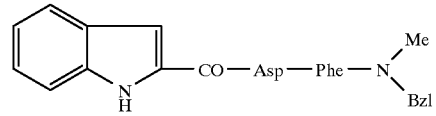 |
| | 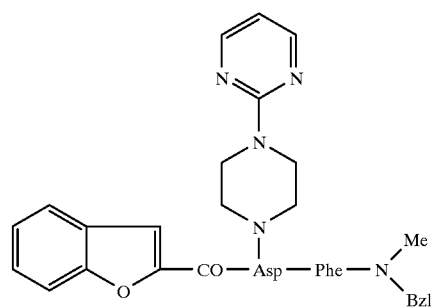 |

-continued
| Example No. | Formula |
|---|---|
| 4-(31) | 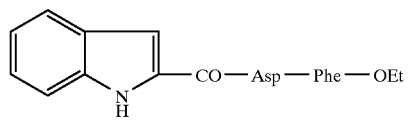 |
|  | 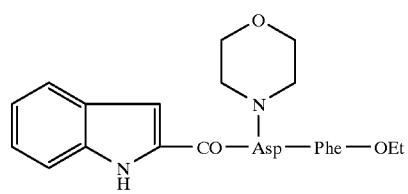 |
| 5 | 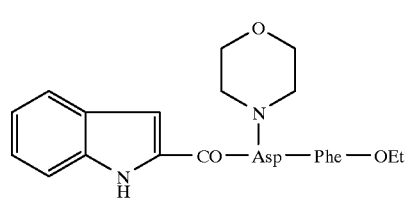 |
|  | 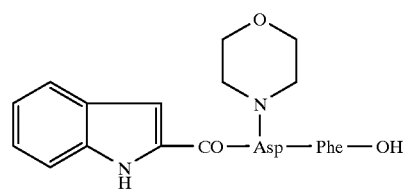 |
| 6 | 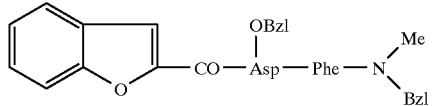 |
|  | 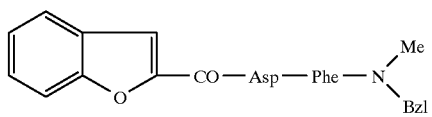 |
| 7 | 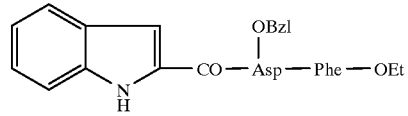 |
|  | 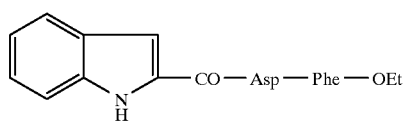 |
| 8 | 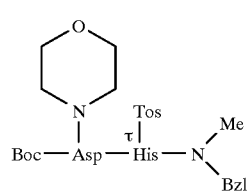 |

| Example No. | Formula |
|---|---|
| | Compound A |
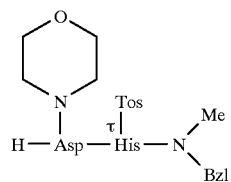
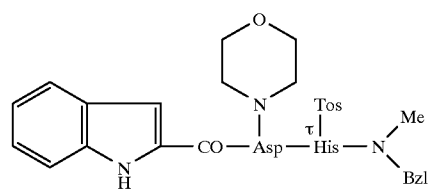
9-(1)
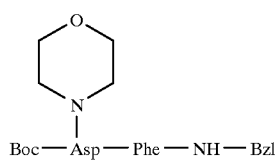
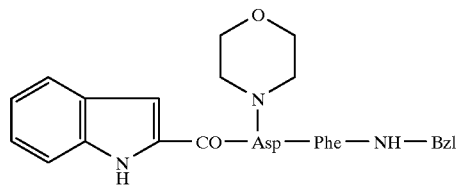
9-(2)
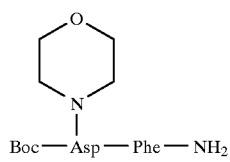
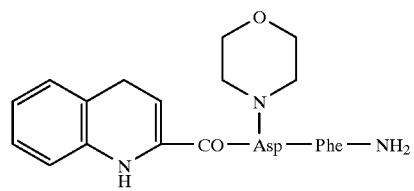
9-(3)
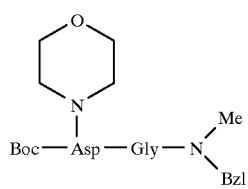

| Example No. | Formula |
|---|---|
| | 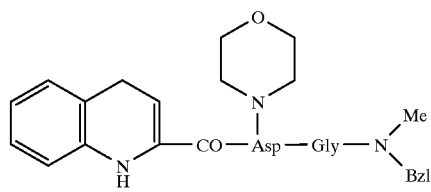 |
| 9-(4) | 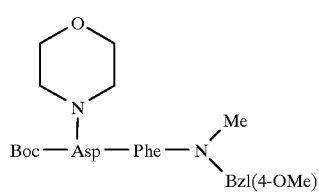 |
| | 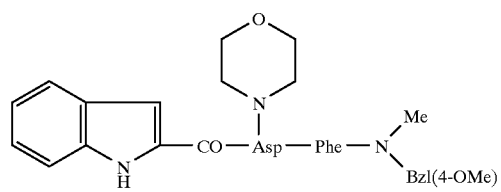 |
| 9-(5) | 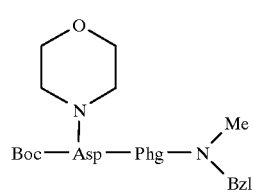 |
| | 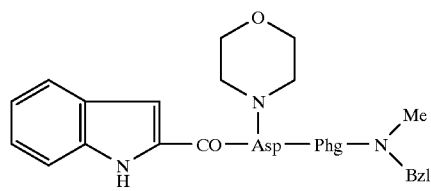 |
| 9-(6) | 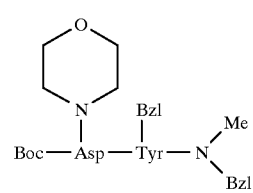 |
| | 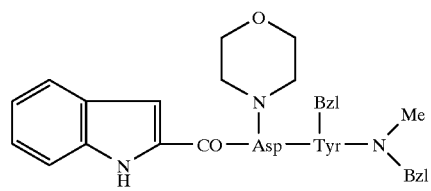 |

-continued
| Example No. | Formula |
|---|---|
| 9-(7) | 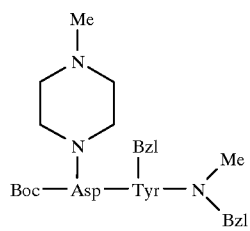 |
| | 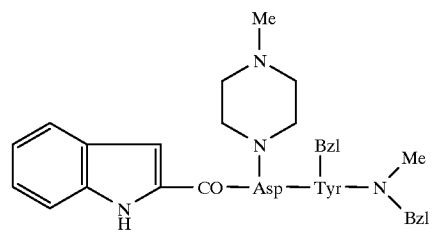 |
| 9-(8) | 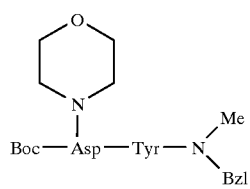 |
| | 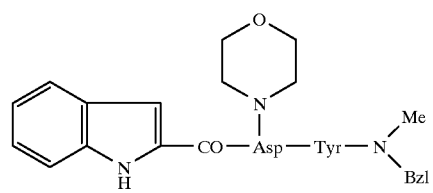 |
| 9-(9) | 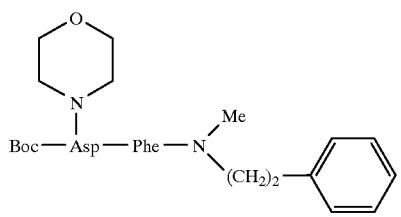 |
| | 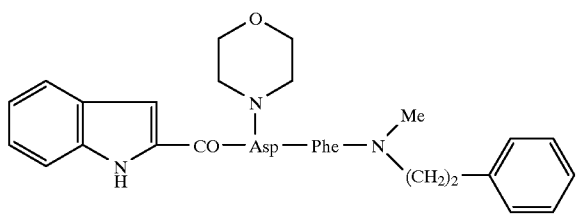 |
| 9-(10) | 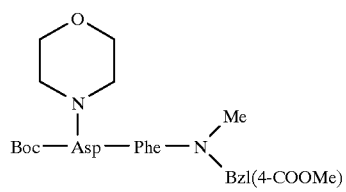 |

| Example No. | Formula |
|---|---|
| | 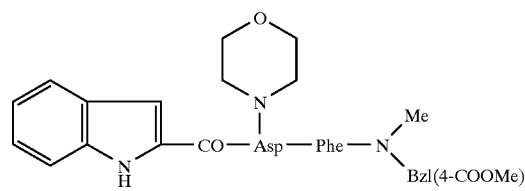 |
| 9-(11) | 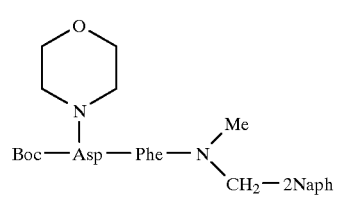 |
| | 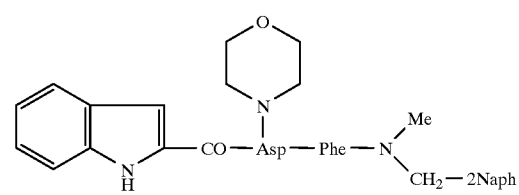 |
| 9-(12) | 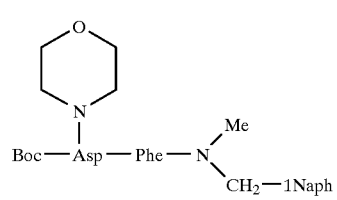 |
| | 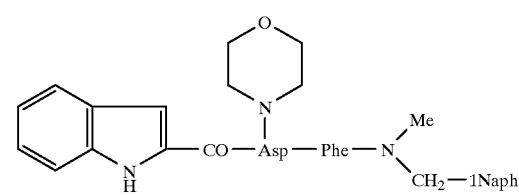 |
| 9-(13) | 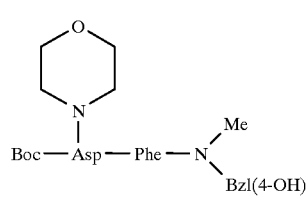 |
| | 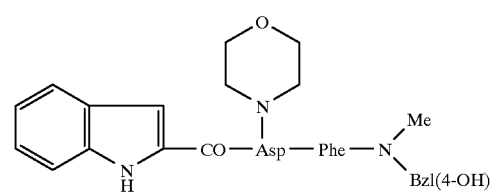 |

| Example No. | Formula |
|---|---|
| 9-(14) | 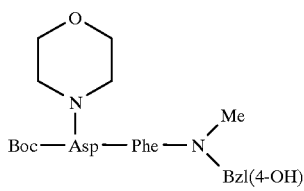 |
| | 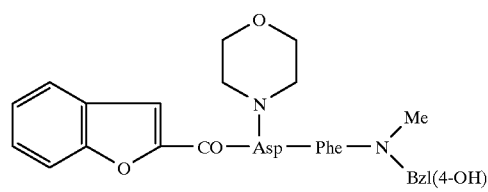 |
| 9-(15) | 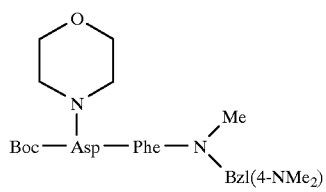 |
| | 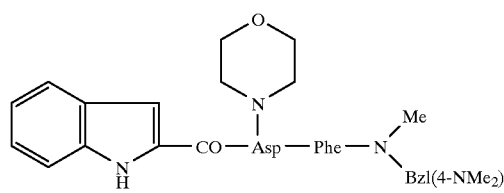 |
| 9-(16) | 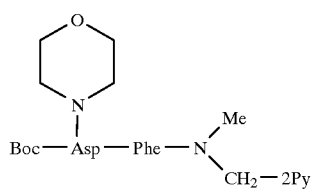 |
| | 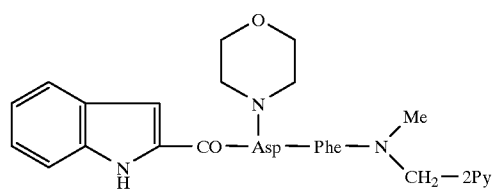 |
| 9-(17) | 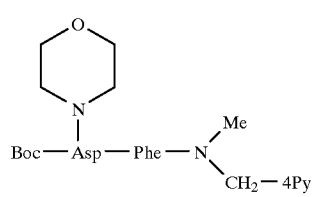 |

-continued

| Example No. | Formula |
|---|---|
| | Indole-CO—Asp—Phe—N(Me)(CH₂—4Py), with morpholine N attached to indole 2-position (ring) |
| 9-(18) | (4-Me-piperazin-1-yl)—N—Boc—Asp—Phe—N(Me)(Bzl(4-COOMe)) |
| | Benzofuran-2-CO—Asp—Phe—N(Me)(Bzl(4-COOMe)), with 4-Me-piperazin-1-yl substituent |
| 9-(19) | Morpholino—Boc—Asp—Phe—N(Me)(Bzl(4-COOMe)) |
| | Benzofuran-2-CO—Asp—Phe—N(Me)(Blz(4-COOMe)), with morpholino substituent |
| 10-(1) | (4-Me-piperazin-1-yl)—H—Asp—Phg—N(Me)(Bzl) |
| | Indole-2-CO—Asp—Phe—N(Me)(Bzl), with 4-Me-piperazin-1-yl substituent |

| Example No. | Formula |
|---|---|
| 10-(2) | 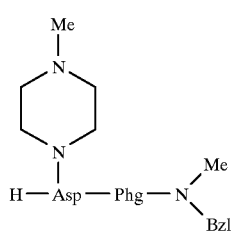 |
| | 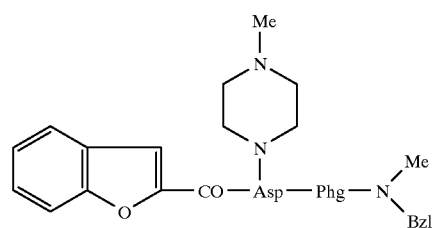 |
| 10-(3) | 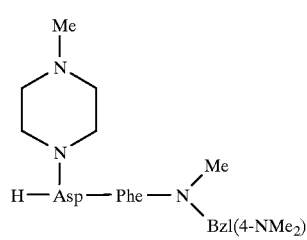 |
| | 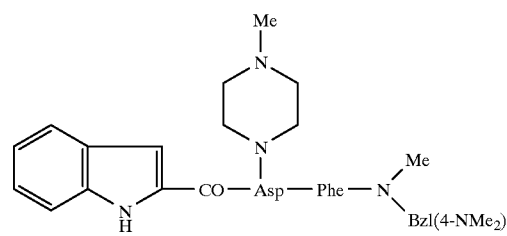 |
| 10-(4) | 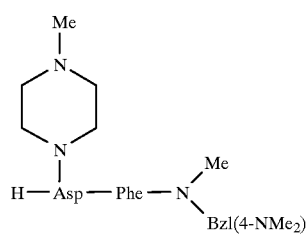 |
| | 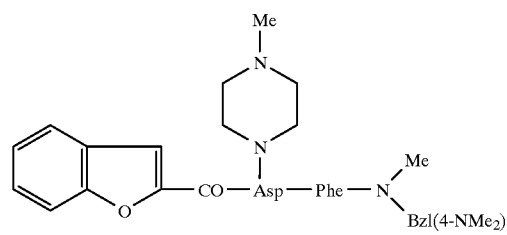 |

-continued
| Example No. | Formula |
|---|---|
| 10-(5) | 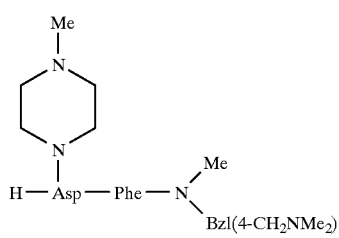 |
| | 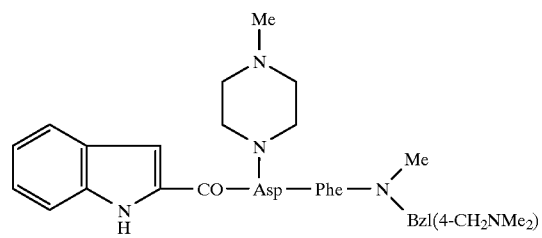 |
| 10-(6) | 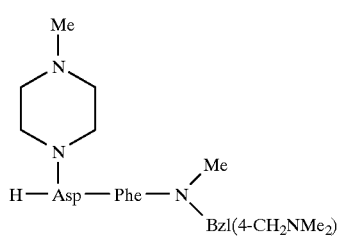 |
| | 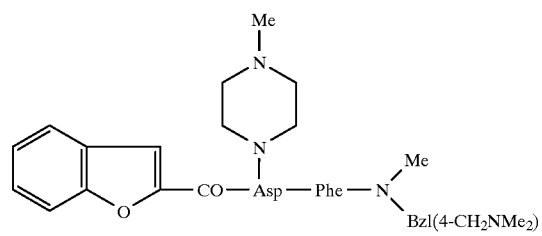 |
| 10-(7) | 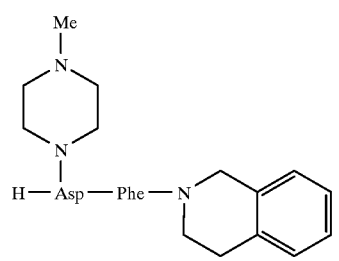 |
| | 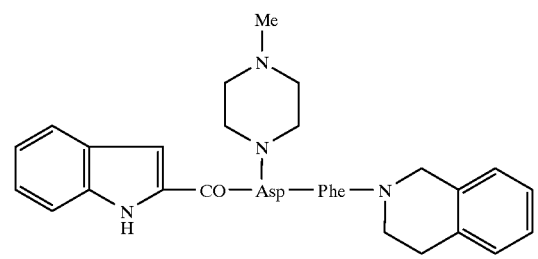 |

| Example No. | Formula |
|---|---|
| 10-(8) | 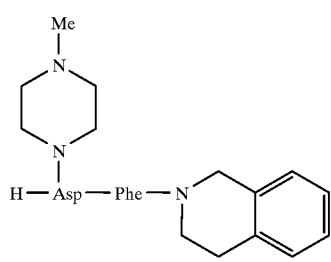 |
| | 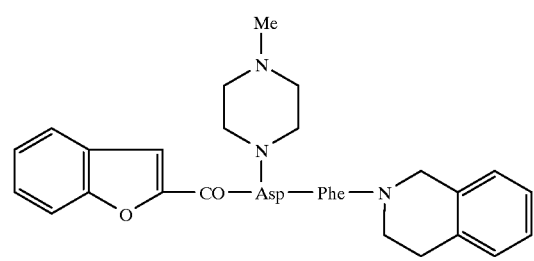 |
| 10-(9) | 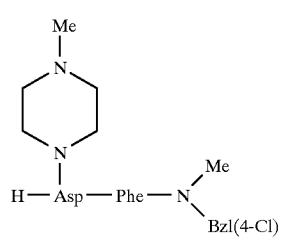 |
| | 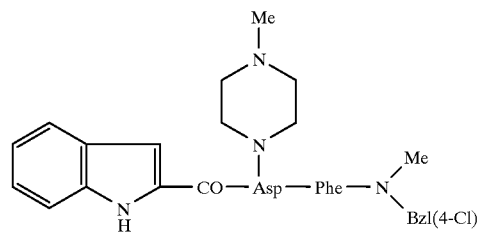 |
| 10-(10) | 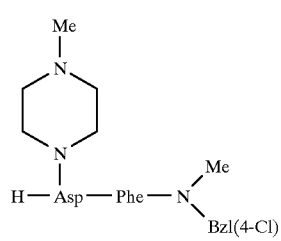 |
| | 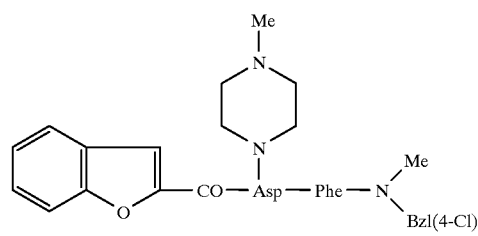 |

| Example No. | Formula |
|---|---|
| 10-(11) | 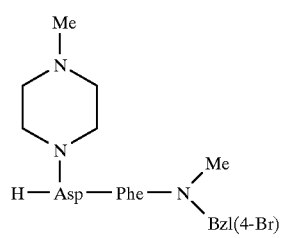 |
| | 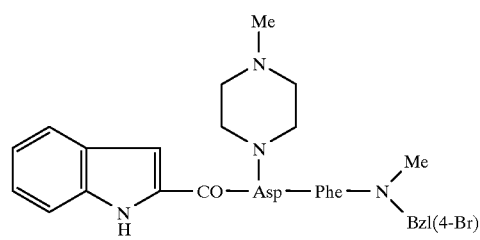 |
| 10-(12) | 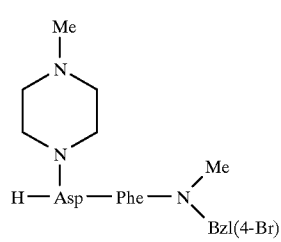 |
| | 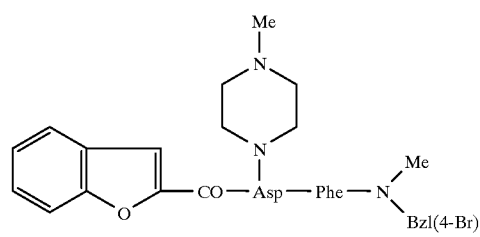 |
| 10-(13) | 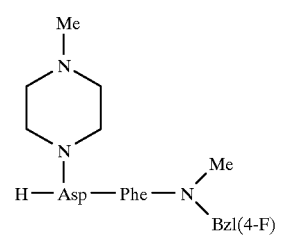 |
| | 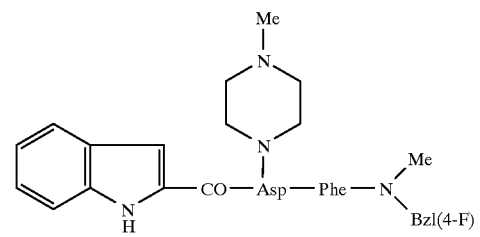 |

-continued
| Example No. | Formula |
| --- | --- |
| 10-(14) | 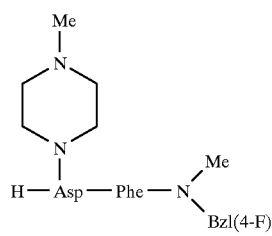 |
| | 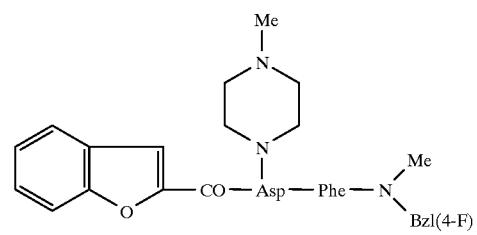 |
| 10-(15) | 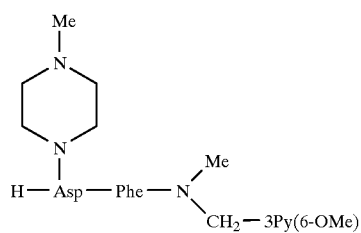 |
| | 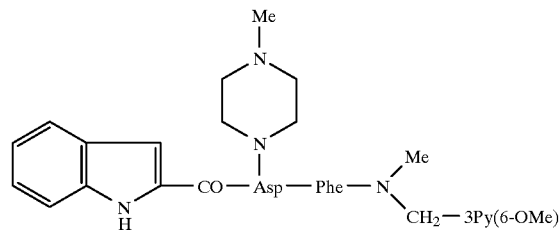 |
| 10-(16) | 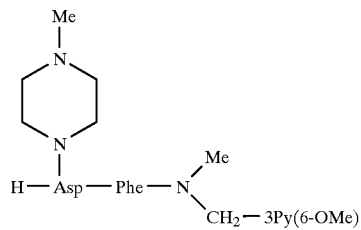 |
| | 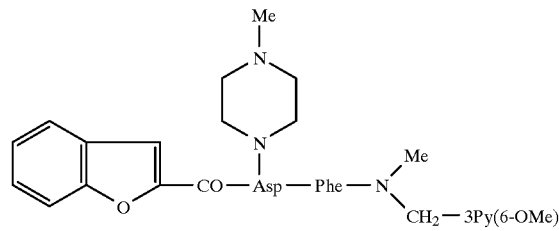 |

| Example No. | Formula |
|---|---|
| 10-(17) | 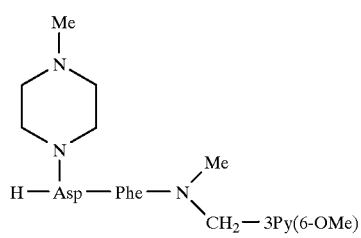 |
| | 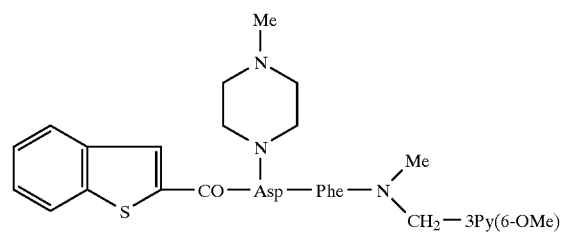 |
| 10-(18) | 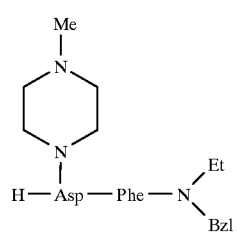 |
| | 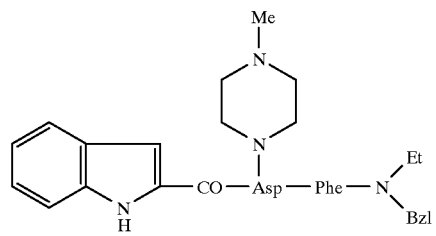 |
| 10-(19) | 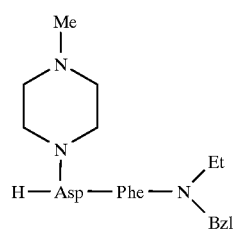 |
| | 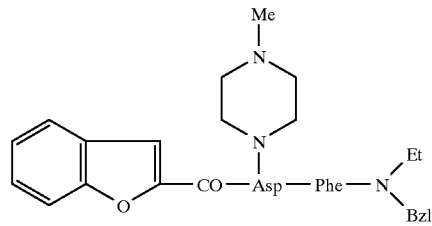 |

-continued
| Example No. | Formula |
|---|---|
| 10-(20) | 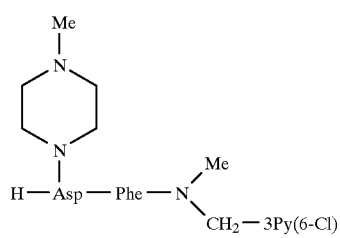 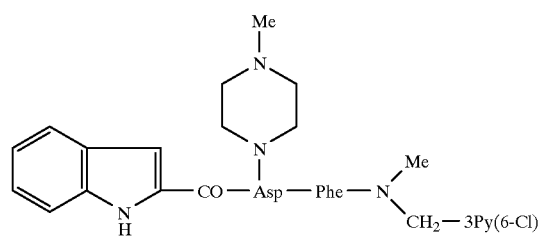 |
| 10-(21) | 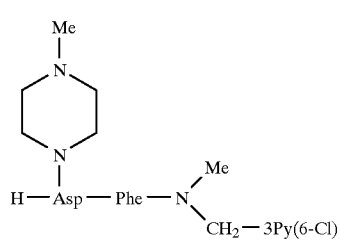 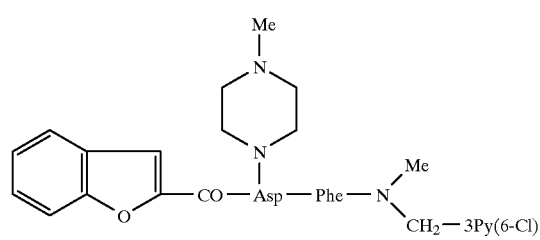 |
| 10-(22) | 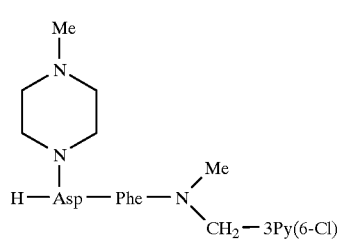 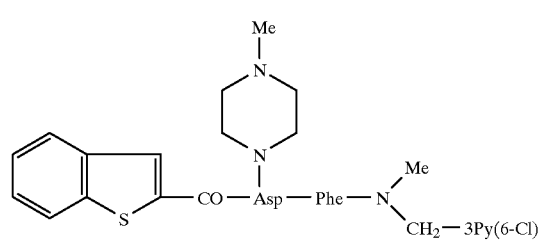 |

| Example No. | Formula |
|---|---|
| 10-(23) | 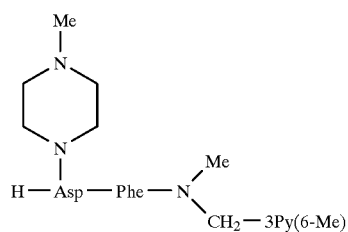 |
| | 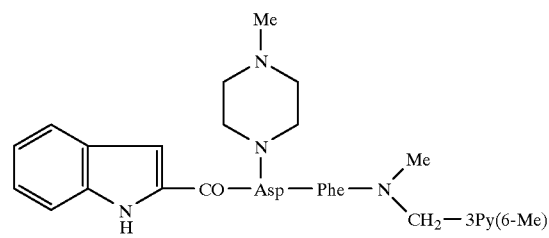 |
| 10-(24) | 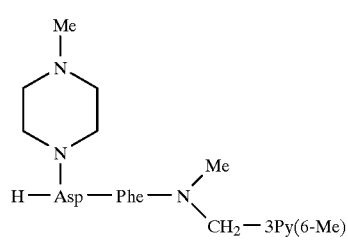 |
| | 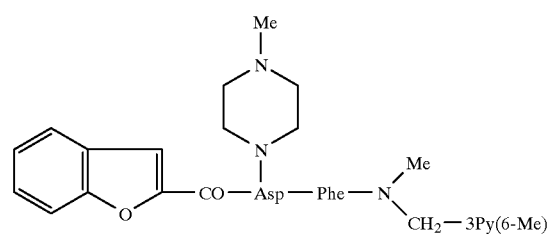 |
| 10-(25) | 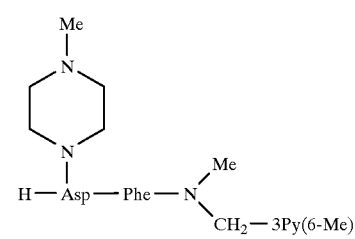 |
| | 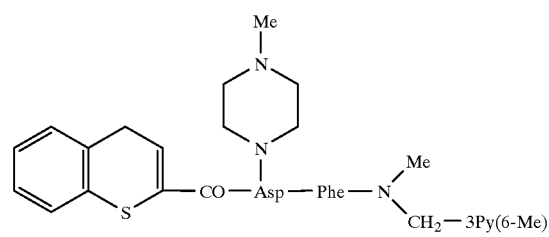 |

-continued
| Example No. | Formula |
|---|---|
| 10-(26) | 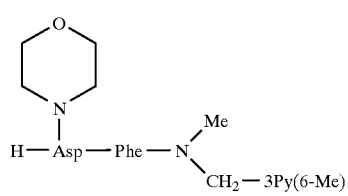 <br> 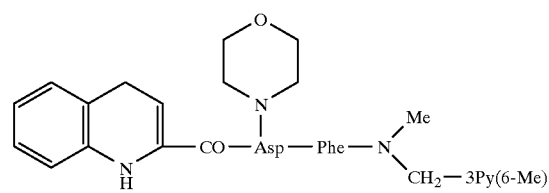 |
| 10-(27) | 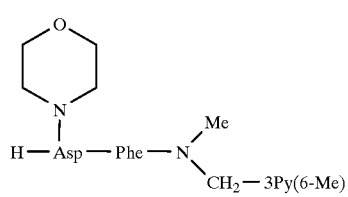 <br> 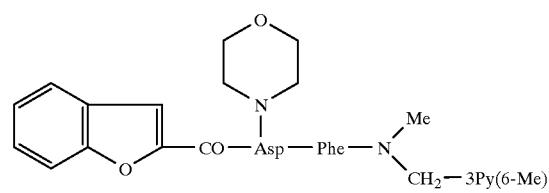 |
| 10-(28) | 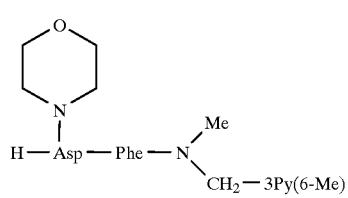 <br> 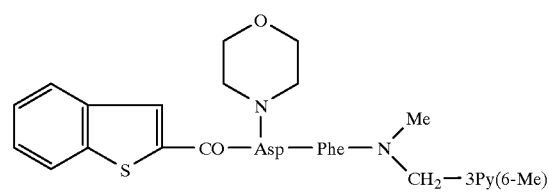 |
| 10-(29) | 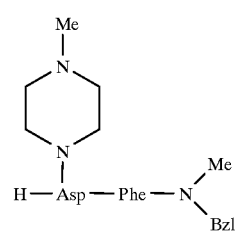 |

| Example No. | Formula |
|---|---|
| | 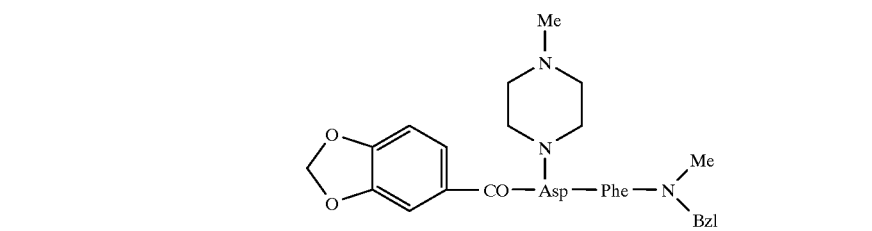 |
| 10-(30) | 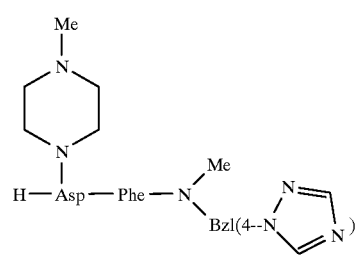 |
| | 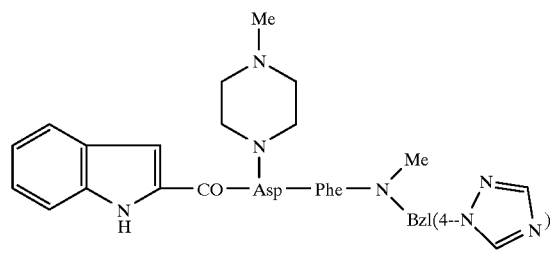 |
| 10-(31) | 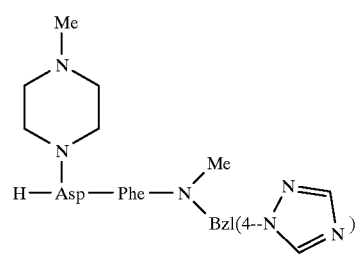 |
| | 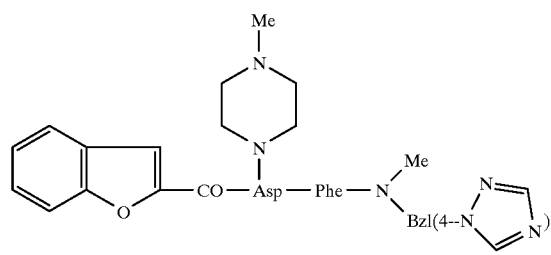 |
| 10-(32) | 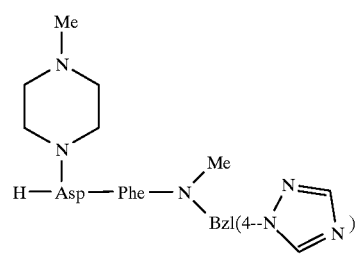 |

| Example No. | Formula |
| --- | --- |
| | 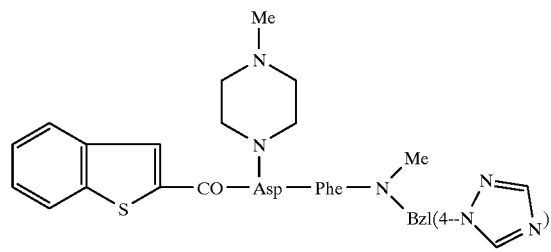 |
| 10-(33) | 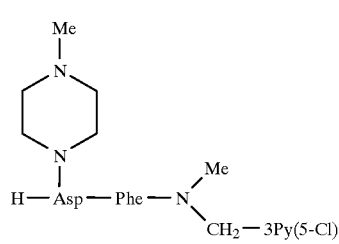 |
| | 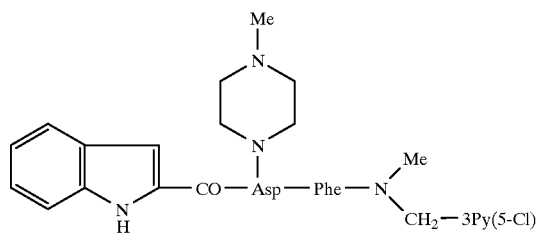 |
| 10-(34) | 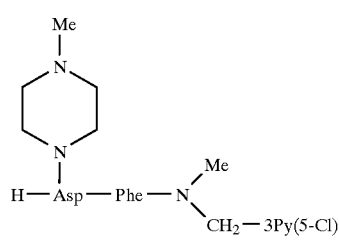 |
| | 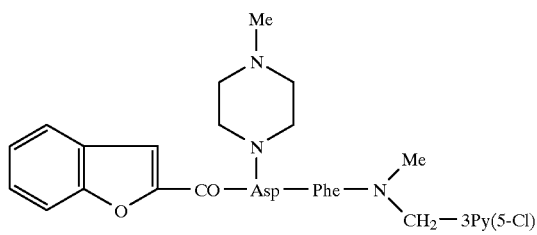 |
| 10-(35) | 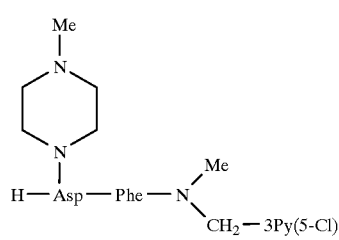 |

| Example No. | Formula |
|---|---|
| | 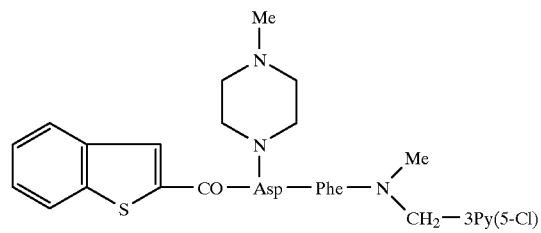 |
| 10-(36) | 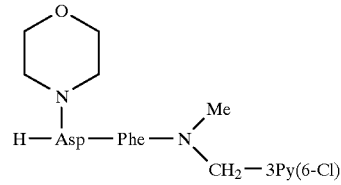 |
| | 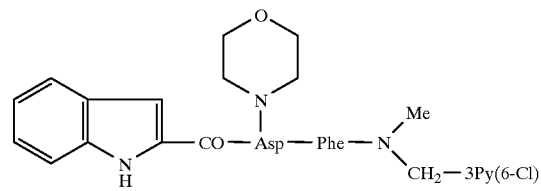 |
| 10-(37) | 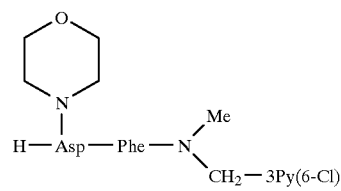 |
| | 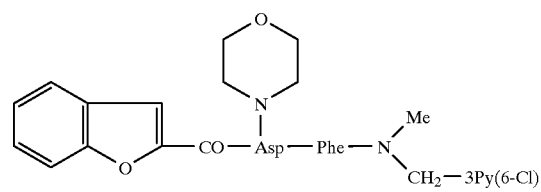 |
| 10-(38) | 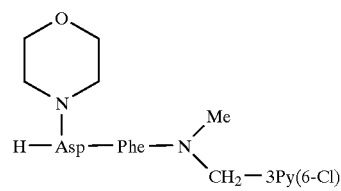 |
| | 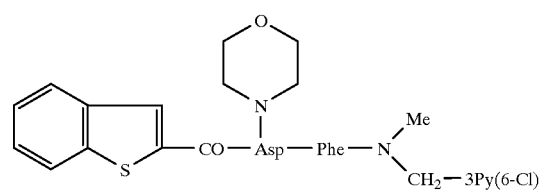 |

-continued
| Example No. | Formula |
|---|---|
| 10-(39) | 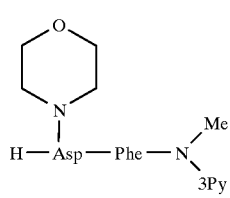 |
| | 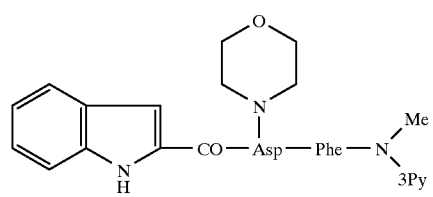 |
| 10-(40) | 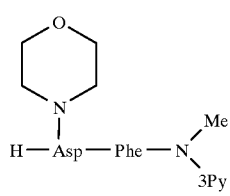 |
| | 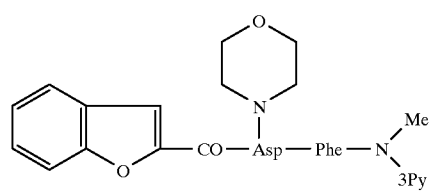 |
| 10-(41) | 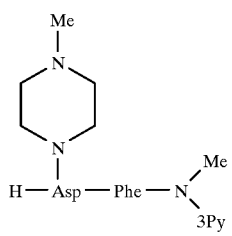 |
| | 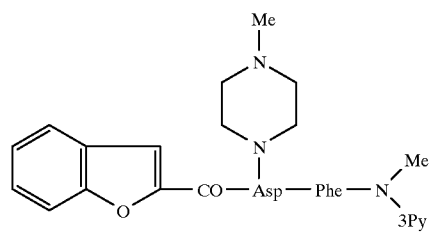 |
| 10-(42) | 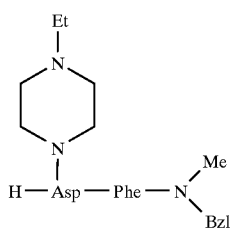 |

-continued
| Example No. | Formula |
|---|---|
| | 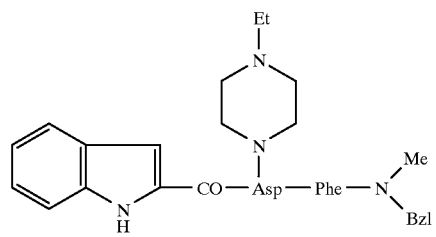 |
| 10-(43) | 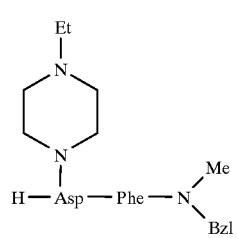 |
| | 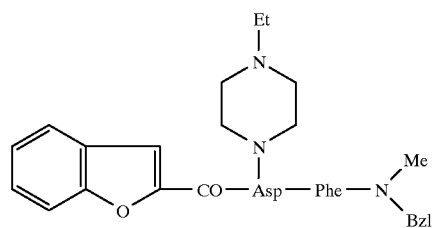 |
| 10-(44) | 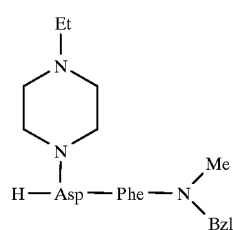 |
| | 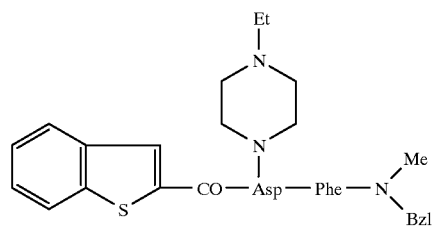 |
| 10-(45) | 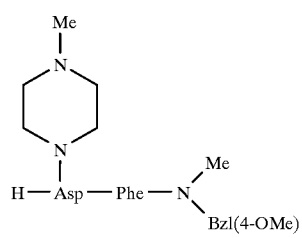 |

| Example No. | Formula |
|---|---|
| | 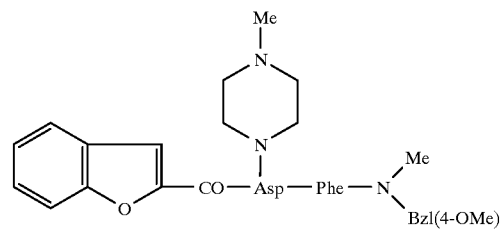 |
| 10-(46) | 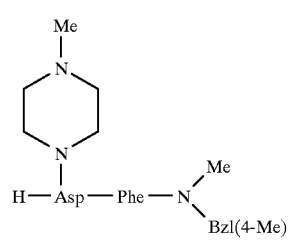 |
| | 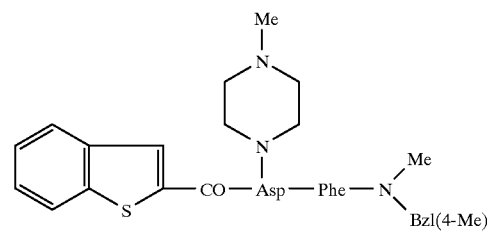 |
| 10-(47) | 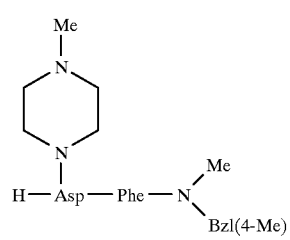 |
| | 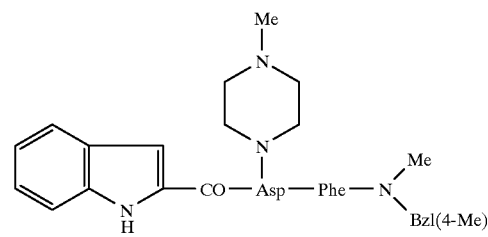 |
| 10-(48) | 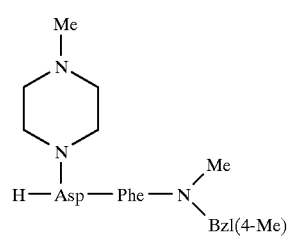 |

| Example No. | Formula |
|---|---|
|  | 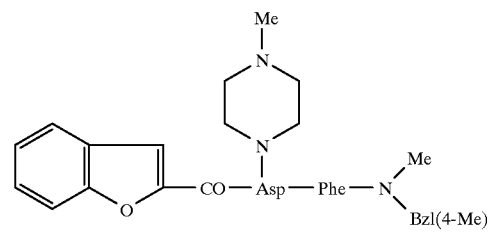 |
| 10-(49) | 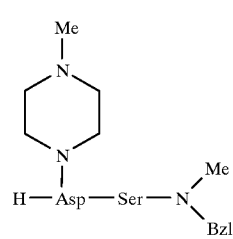 |
|  | 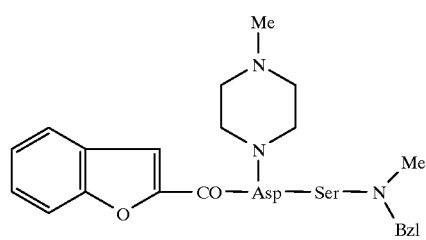 |
| 10-(50) | 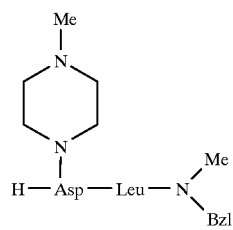 |
|  | 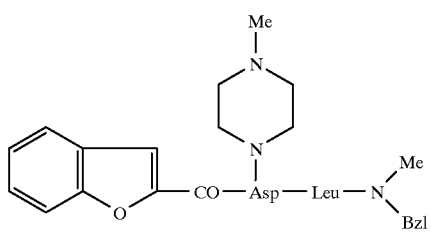 |
| 10-(51) | 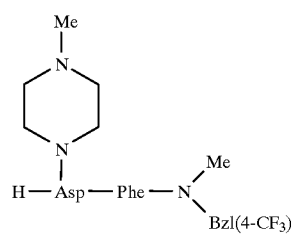 |

| Example No. | Formula |
|---|---|
| | 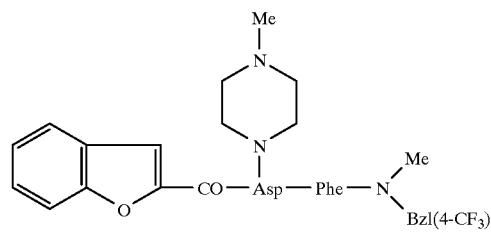 |
| 10-(52) | 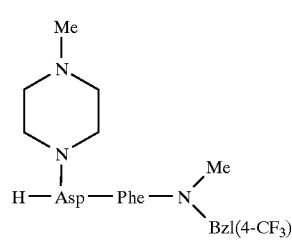 |
| | 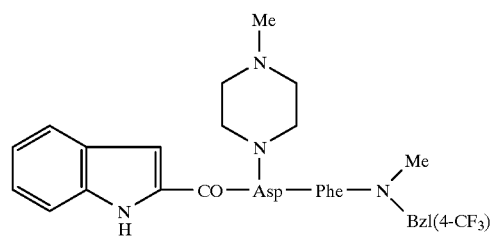 |
| 10-(53) | 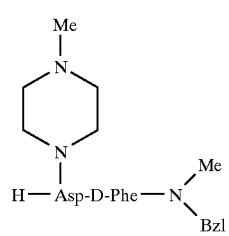 |
| | 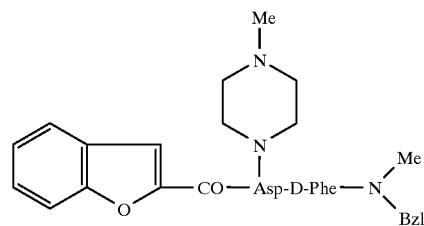 |
| 10-(54) | 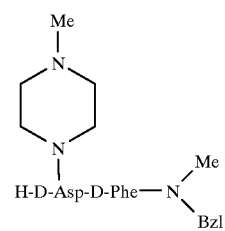 |

-continued
| Example No. | Formula |
|---|---|
| | 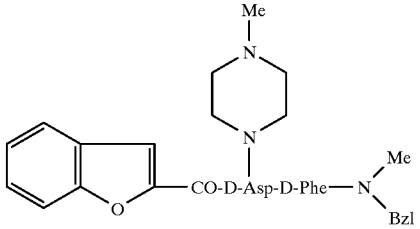 |
| 10-(55) | 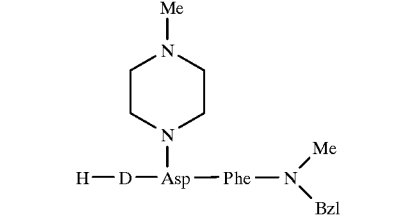 |
| 10-(56) | 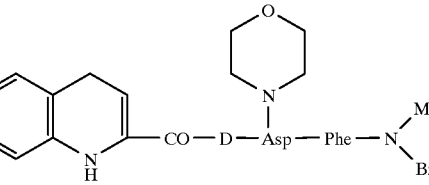 |
| 10-(57) | 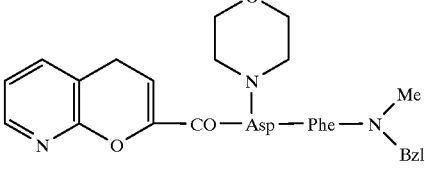 |
| 10-(58) | 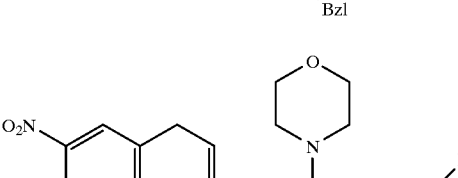 |

| Example No. | Formula |
|---|---|
| | 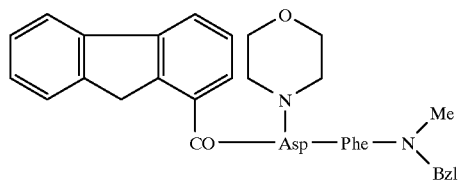 |
| 10-(59) | 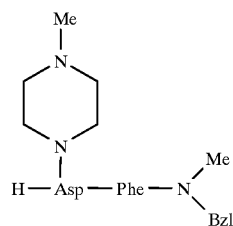 |
| | 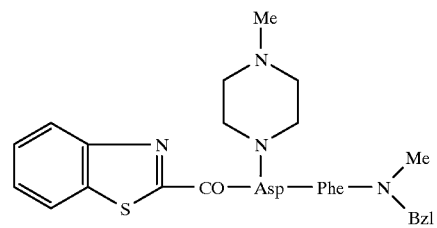 |
| 10-(60) | 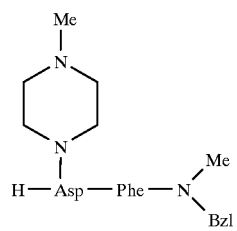 |
| | 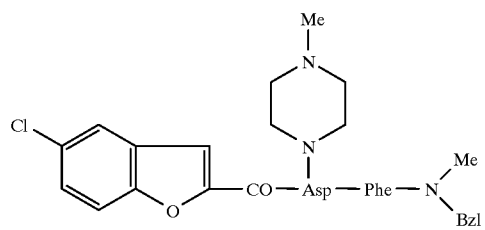 |
| 10-(61) | 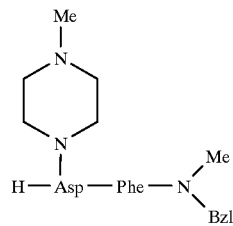 |

| Example No. | Formula |
|---|---|
| | 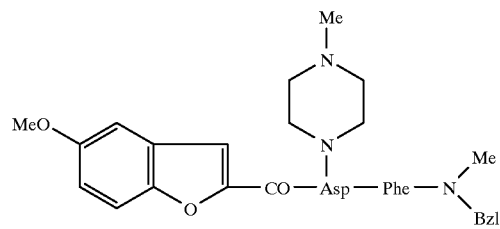 |
| 10-(62) | 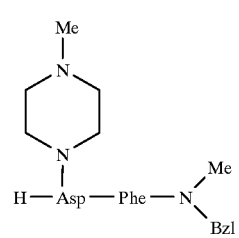 |
| | 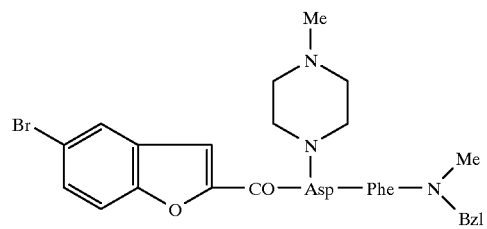 |
| 10-(63) | 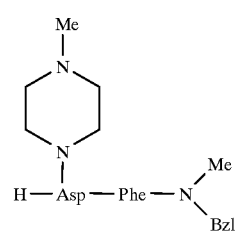 |
| | 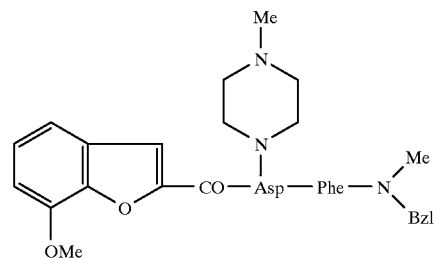 |
| 10-(64) | 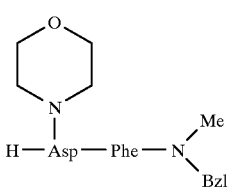 |

|Example No.|Formula|
|---|---|
| | (thiophene)-CO—Asp—Phe—N(Me)(Bzl), with Asp side chain as morpholine amide |
|10-(65)| H—Asp—Phe—N(Me)(Bzl), with Asp side chain as morpholine amide |
| | (furan-2-yl)-CO—Asp—Phe—N(Me)(Bzl), with Asp side chain as morpholine amide |
|10-(66)| H—Asp—Phe—N(Me)(Bzl), with Asp side chain as morpholine amide |
| | (pyridin-2-yl)-CO—Asp—Phe—N(Me)(Bzl), with Asp side chain as morpholine amide |
|10-(67)| H—Asp—Phe—N(Me)(Bzl), with Asp side chain as morpholine amide |
| | Ph-CO—Asp—Phe—N(Me)(Bzl), with Asp side chain as morpholine amide |
|10-(68)| H—Asp—Phe—N(Me)(Bzl), with Asp side chain as morpholine amide |

|Example No.|Formula|
|---|---|
| | 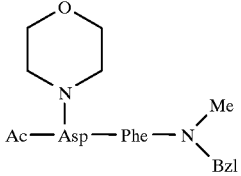 |
| 10-(69) | 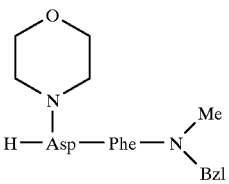 |
| | 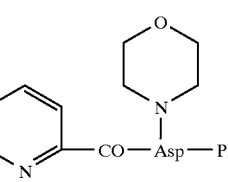 |
| 10-(70) | 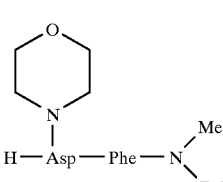 |
| | 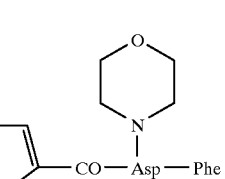 |
| 10-(71) | 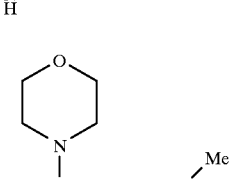 |
| | 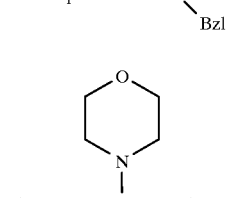 |
| 10-(72) | 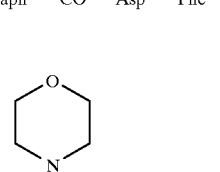 |

| Example No. | Formula |
| --- | --- |
| | 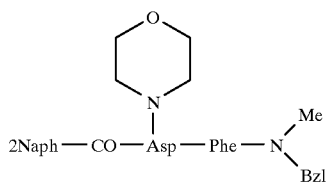 |
| 10-(73) | 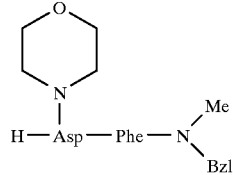 |
| | 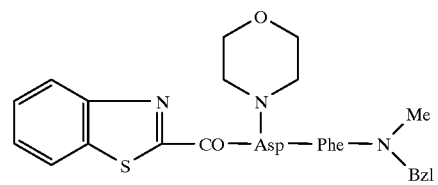 |
| 10-(74) | 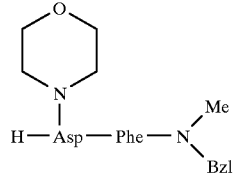 |
| | 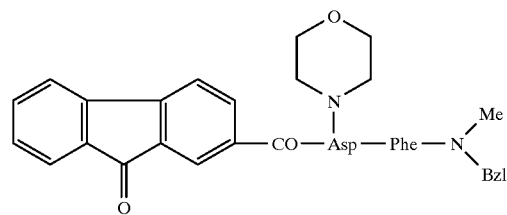 |
| 10-(75) | 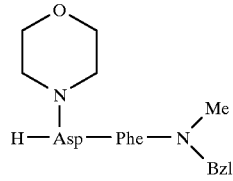 |
| | 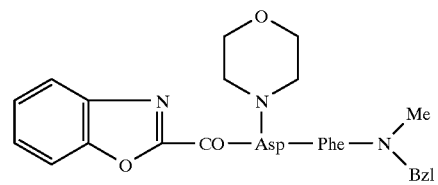 |

-continued
| Example No. | Formula |
| --- | --- |
| 10-(76) | 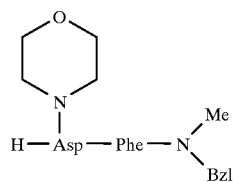<br>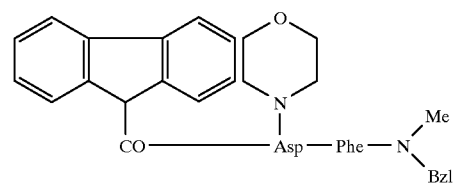 |
| 10-(77) | 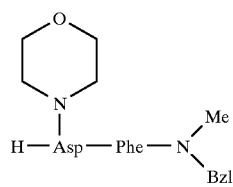<br>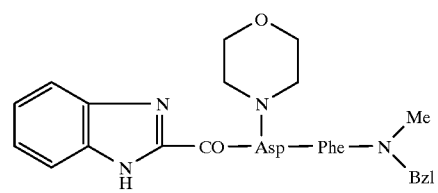 |
| 10-(78) | 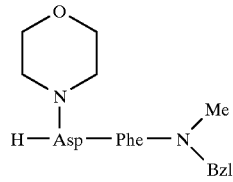<br>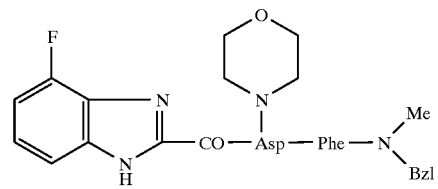 |
| 10-(79) | 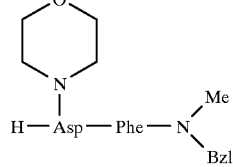<br>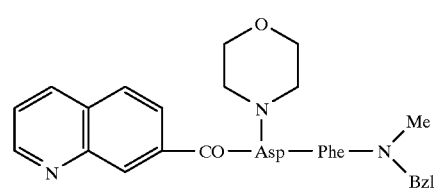 |

-continued
| Example No. | Formula |
|---|---|
| 10-(80) | 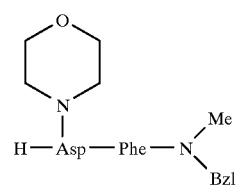 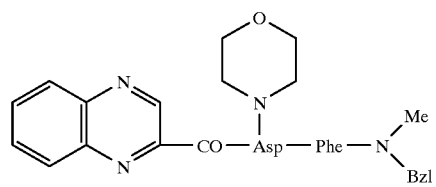 |
| 10-(81) | 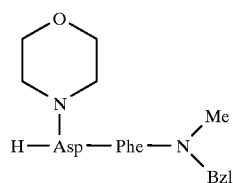 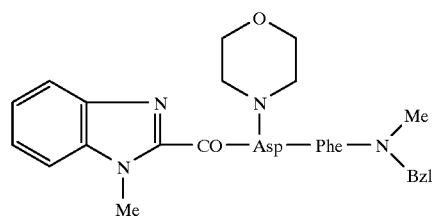 |
| 10-(82) | 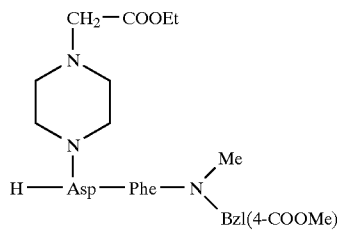 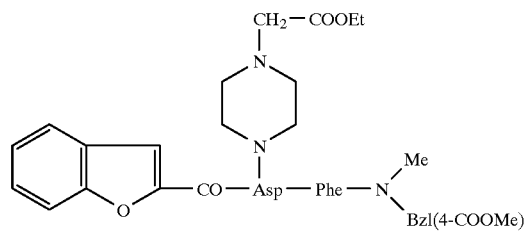 |
| 10-(83) | 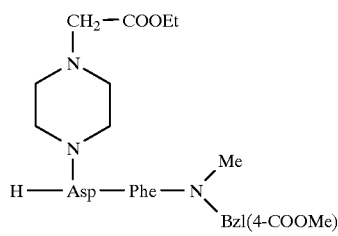 |

-continued
| Example No. | Formula |
|---|---|
| | 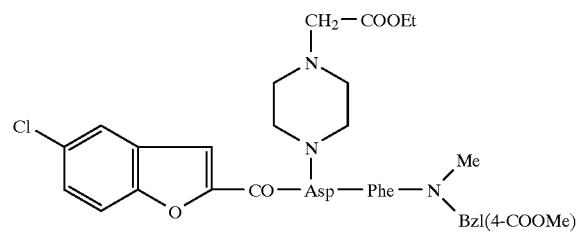 |
| 10-(84) | 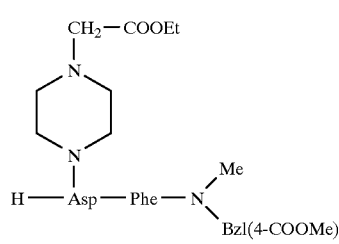 |
| | 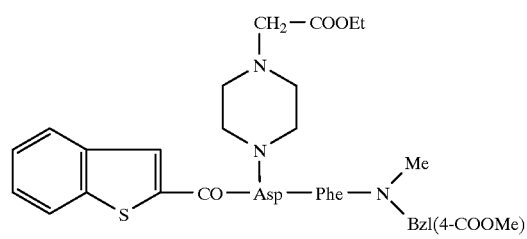 |
| 1-(85) | 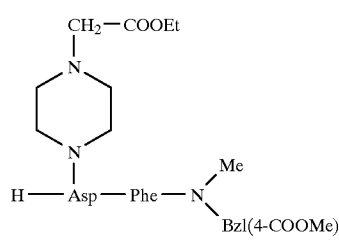 |
| | 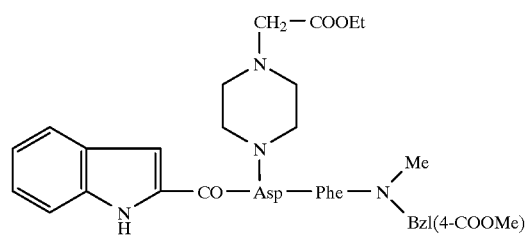 |
| 10-(86) | 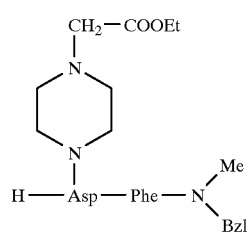 |

| Example No. | Formula |
|---|---|
| | 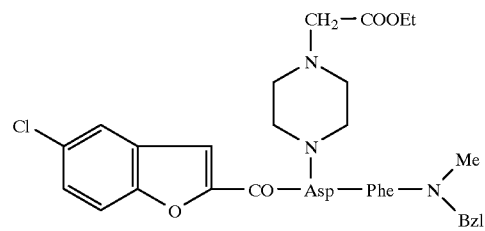 |
| 10-(87) | 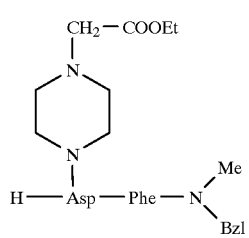 |
| | 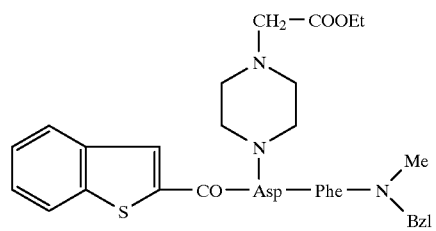 |
| 10-(88) | 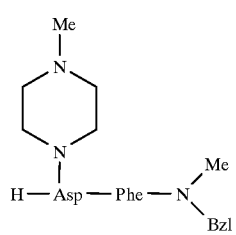 |
| | 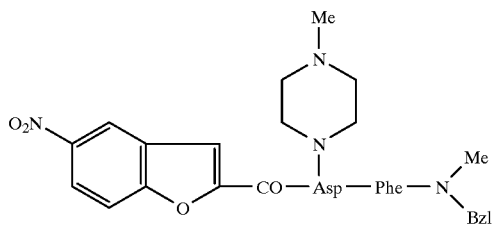 |
| 10-(89) | 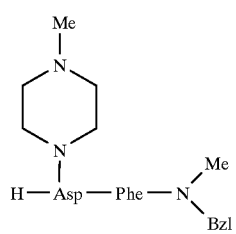 |

| Example No. | Formula |
|---|---|
| | 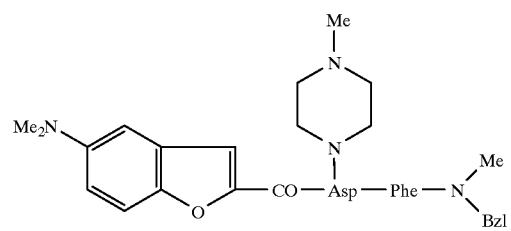 |
| 10-(90) | 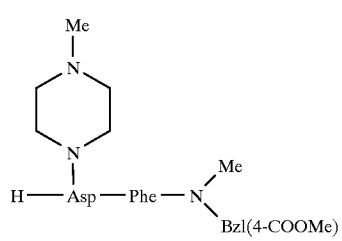 |
| | 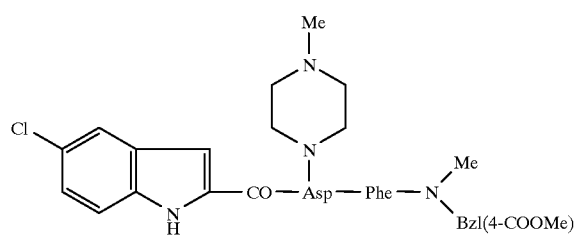 |
| 10-(91) | 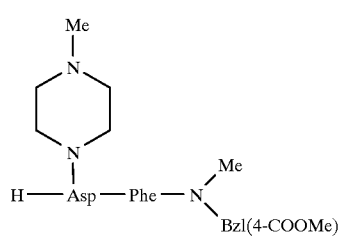 |
| | 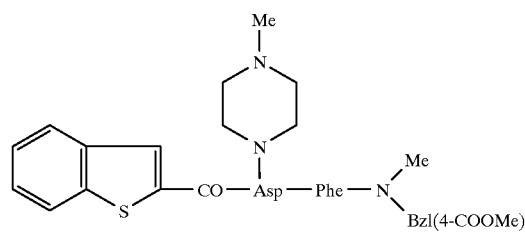 |
| 10-(92) | 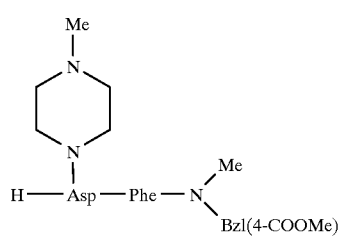 |

-continued
| Example No. | Formula |
|---|---|
| | 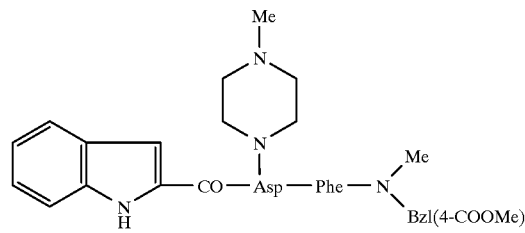 |
| 11-(1) | 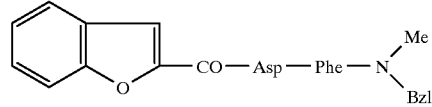 |
| 11-(2) | 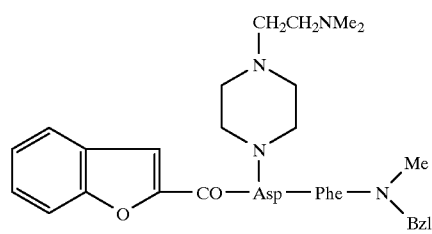 |
| | 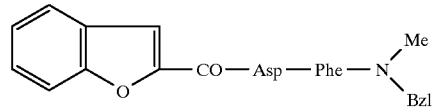 |
| 11-(3) | 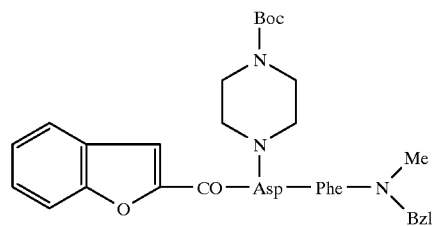 |
| | 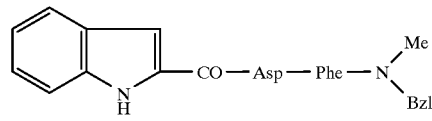 |
| 11-(4) | 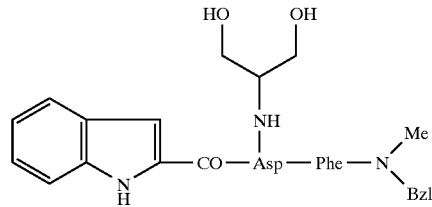 |
| | 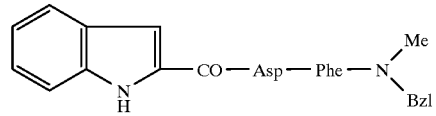 |

| Example No. | Formula |
|---|---|
| | 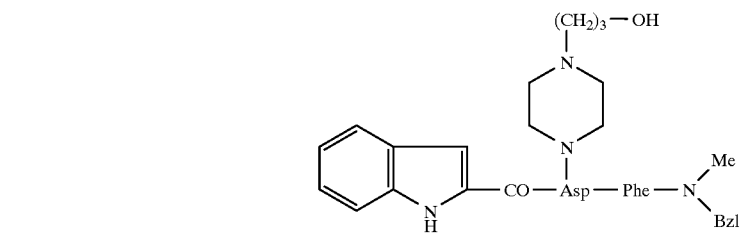 |
| 11-(5) | 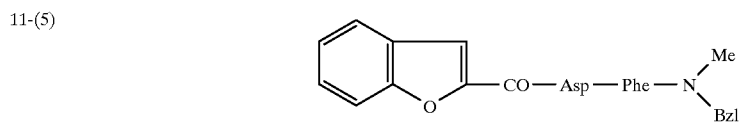 |
| 11-(6) | 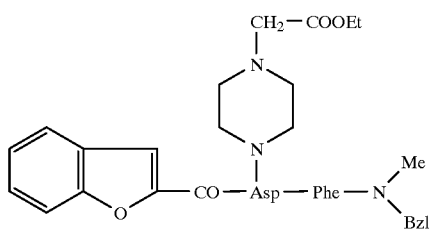 |
| 11-(7) | 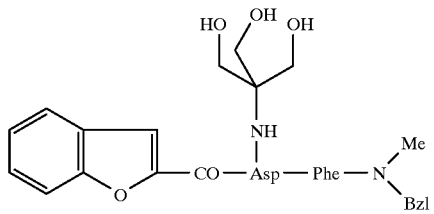 |
| 11-(8) | |

| Example No. | Formula |
|---|---|
| | 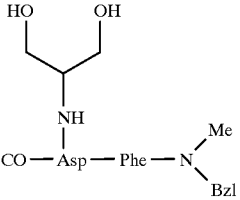 |
| 11-(9) | 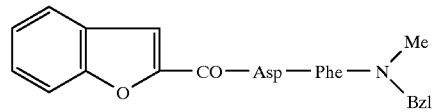 |
| | 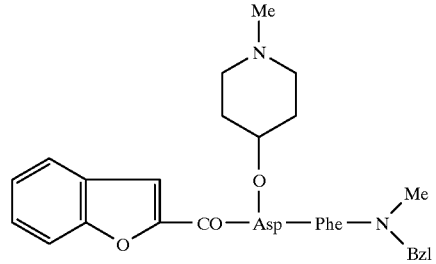 |
| 12 | 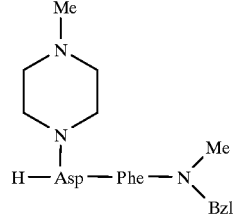 |
| | 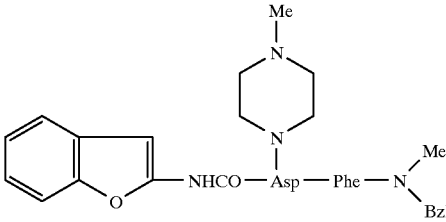 |
| 13 | 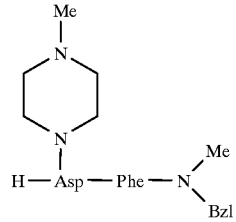 |
| | 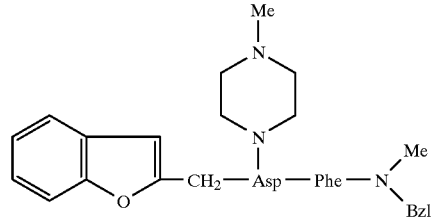 |

| Example No. | Formula |
| --- | --- |
| 14 | 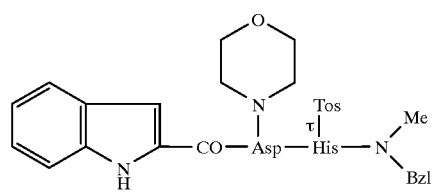 |
| 15 | 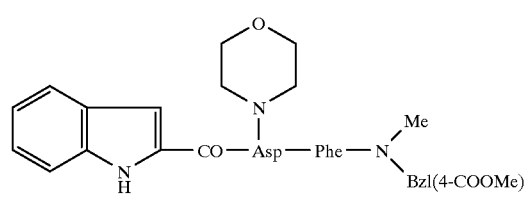 |
| 16 | 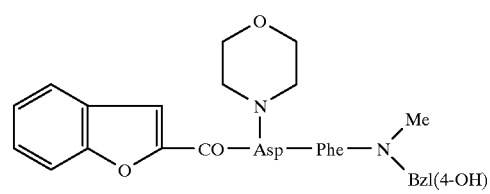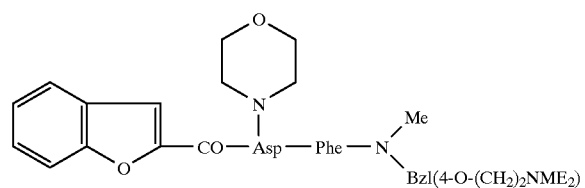 |
| 17 | 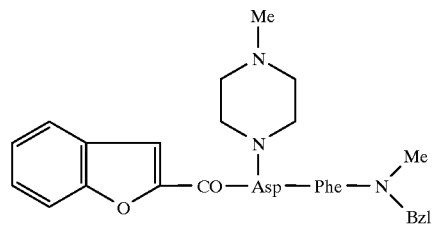 |

| Example No. | Formula |
|---|---|
| | benzofuran-2-CO—Asp—Phe—N(Me)(Bzl), with 4-(4,4-dimethylpiperazin-1-ium-1-yl) substituent on benzofuran, I⁻ counterion |
| 18-(1) | 5-nitro-furo[2,3-b]pyridine-2-CO—Asp—Phe—N(Me)(Bzl), with morpholino substituent; and 5-amino-furo[2,3-b]pyridine-2-CO—Asp—Phe—N(Me)(Bzl), with morpholino substituent |
| 18-(2) | 5-nitro-benzofuran-2-CO—Asp—Phe—N(Me)(Bzl), with 4-methylpiperazin-1-yl substituent; and 5-amino-benzofuran-2-CO—Asp—Phe—N(Me)(Bzl), with 4-methylpiperazin-1-yl substituent |
| 19 | benzofuran-2-CO—Asp—Phe—N(Me)(Bzl), with 4-methylpiperazin-1-yl substituent; and the same compound as citric acid salt monohydrate (HO–C(COOH)(CH$_2$COOH)$_2$ · H$_2$O) |

| Example No. | Formula |
|---|---|
| 20-(1) | 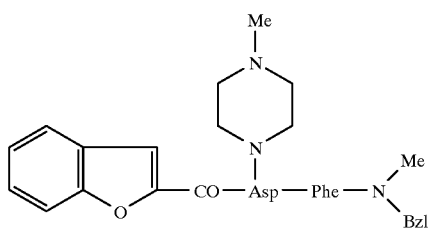 |
| | 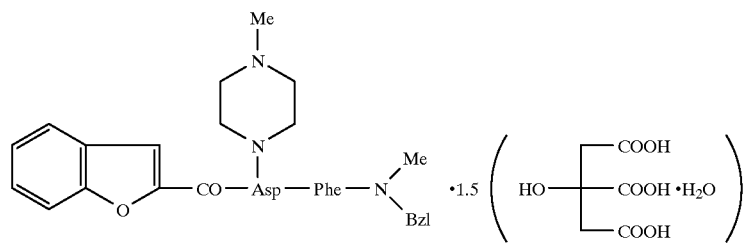 |
| 20-(2) | 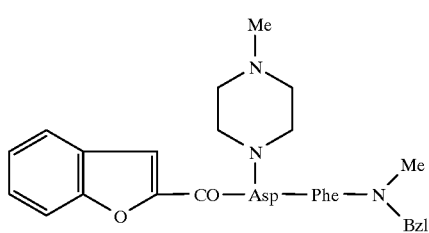 |
| | 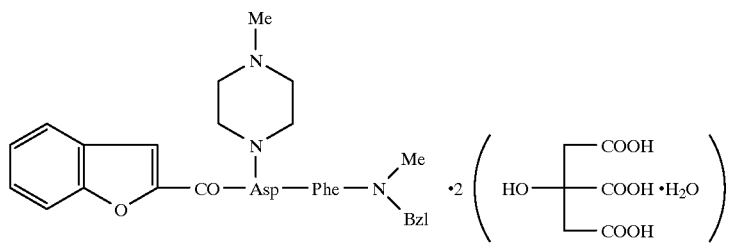 |
| 20-(3) | 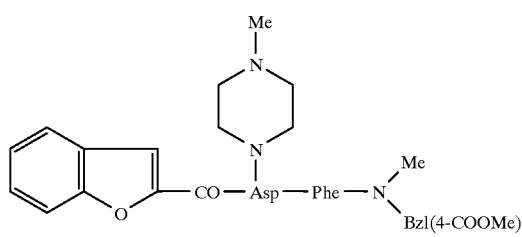 |
| | 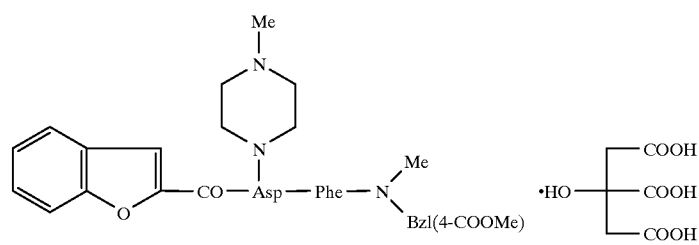 |

-continued
| Example No. | Formula |
|---|---|
| 21 | 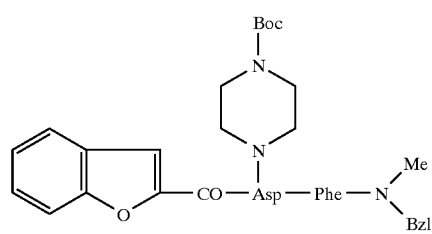 |
| 22 | 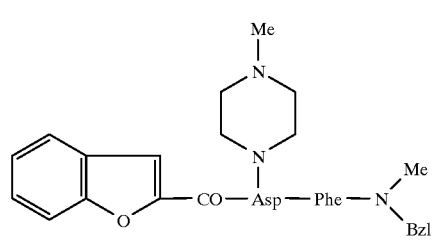 |
| 23 | 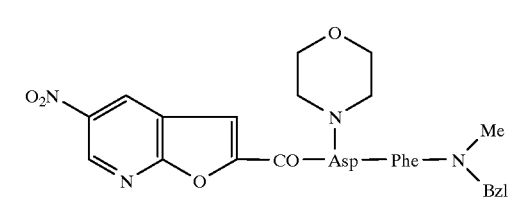 |
| | 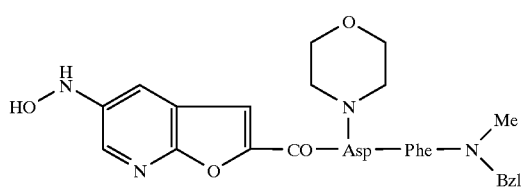 |
| 24 | 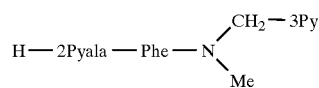 |
| | 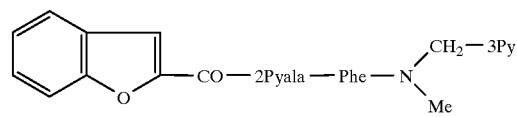 |

-continued
| Example No. | Formula |
|---|---|
| 25-(1) | 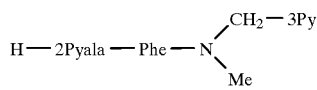 |
|  | 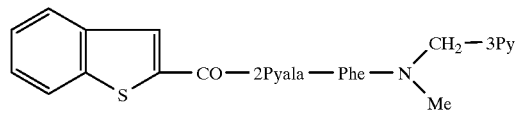 |
| 25-(2) | 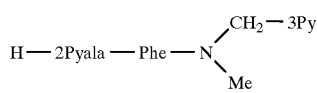 |
|  | 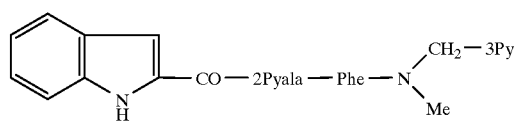 |
| 25-(3) | 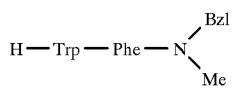 |
|  | 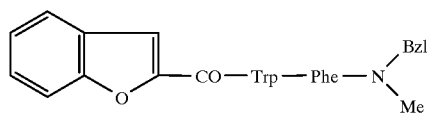 |
| 25-(4) | 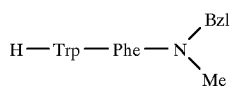 |
|  | 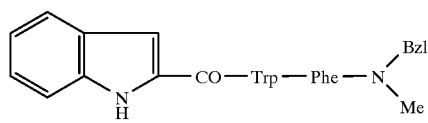 |
| 25-(5) | 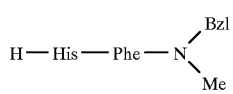 |
|  | 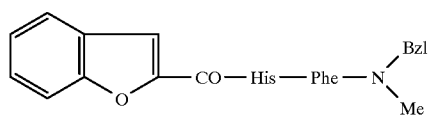 |
| 25-(6) | 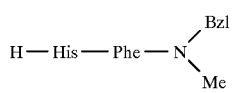 |
|  | 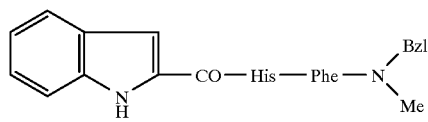 |
| 25-(7) | 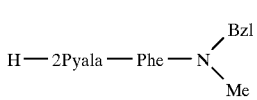 |

-continued

| Example No. | Formula |
|---|---|
| | benzofuran-CO—2Pyala—Phe—N(Bzl)(Me) |
| 25-(8) | H—2Pyala—Phe—N(CH₂—3Py(6-Cl))(Me) |
| | indole(NH)-CO—2Pyala—Phe—N(CH₂—3Py(6-Cl))(Me) |
| 25-(9) | H—2Pyala—Phe—N(CH₂—3Py(6-Cl))(Me) |
| | benzothiophene-CO—2Pyala—Phe—N(CH₂—3Py(6-Cl))(Me) |
| 25-(10) | H—2Pyala—Phe—N(CH₂—3Py(6-Cl))(Me) |
| | benzofuran-CO—2Pyala—Phe—N(CH₂—3Py(6-Cl))(Me) |
| 25-(11) | H—2Pyala—Phe—N(CH₂—4Py)(Me) |
| | benzothiophene-CO—2Pyala—Phe—N(CH₂—4Py)(Me) |
| 25-(12) | H—2Pyala—Phe—N(CH₂—4Py)(Me) |
| | benzothiazole-CO—2Pyala—Phe—N(CH₂—4Py)(Me) |
| 25-(13) | H—2Pyala—Phe—N(CH₂—4Py)(Me) |
| | benzofuran-CO—2Pyala—Phe—N(CH₂—4Py)(Me) |

-continued
| Example No. | Formula |
|---|---|
| 25-(14) | 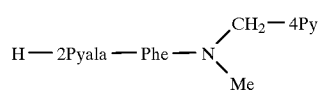 |
| | 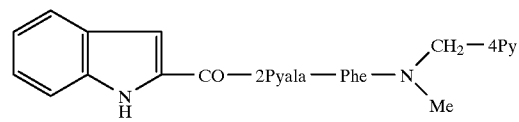 |
| 25-(15) | 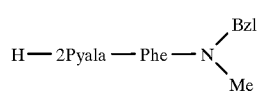 |
| | 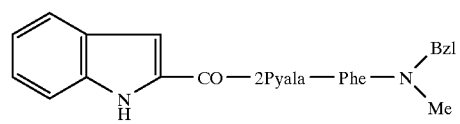 |
| 26-(1) | 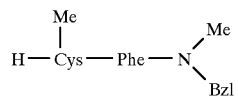 |
| | 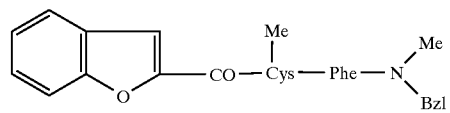 |
| 26-(2) | 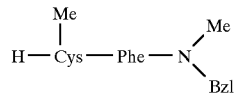 |
| | 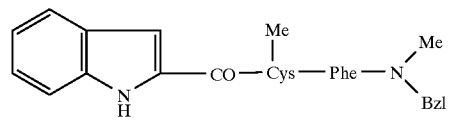 |
| 26-(3) | 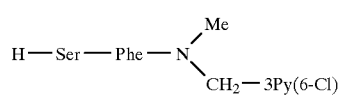 |
| | 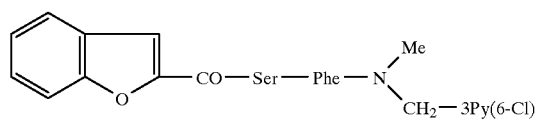 |
| 26-(4) | 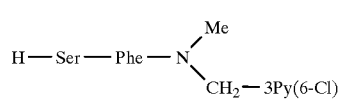 |
| | 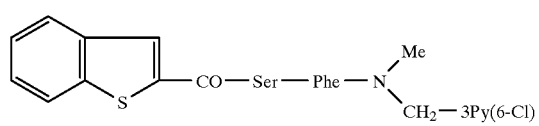 |

| Example No. | Formula |
|---|---|
| 26-(5) | 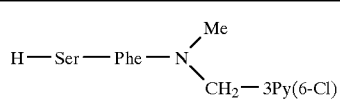<br>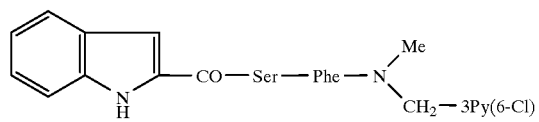 |
| 26-(6) | 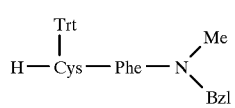<br>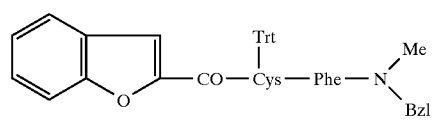 |
| 26-(7) | 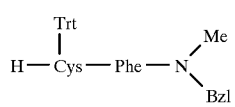<br>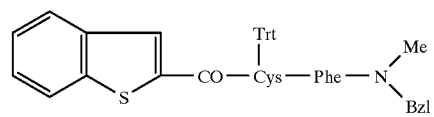 |
| 26-(8) | 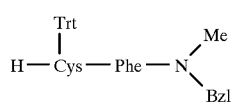<br>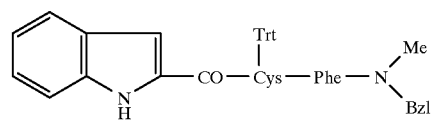 |
| 26-(9) | 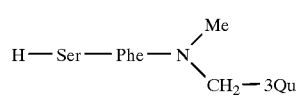<br>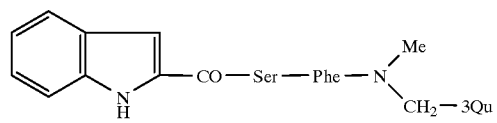 |
| 26-(10) | 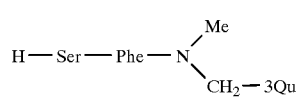<br>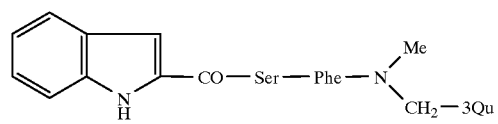 |

-continued

| Example No. | Formula |
|---|---|
| 26-(11) | H—Ser(Bzl)—2Pyala—N(Me)(Bzl) |
| | Indole-2-CO—Ser(Bzl)—2Pyala—N(Me)(Bzl) |
| 26-(12) | H—Ser(Bzl)—Phe—N(Me)(Bzl) |
| | Indole-2-CO—Ser(Bzl)—Phe—N(Me)(Bzl) |
| 26-(13) | H—Ser—Phe—N(Me)(CH₂—3Py) |
| | Indole-2-CO—Ser—Phe—N(Me)(CH₂—3Py) |
| 26-(14) | 2HCl·H—Ser—Phe—N(Me)(CH₂—3Py) |
| | Benzofuran-2-CO—Ser—Phe—N(Me)(CH₂—3Py) |
| 26-(15) | H—Ser—Phe—N(Me)(CH₂—3Py) |
| | Benzothiophene-2-CO—Ser—Phe—N(Me)(CH₂—3Py) |
| 26-(16) | H—Ser—Phe—N(Me)(CH₂—4Py) |
| | Benzothiazole-2-CO—Ser—Phe—N(Me)(CH₂—4Py) |

-continued
| Example No. | Formula |
|---|---|
| 26-(17) | 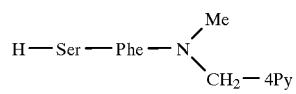 |
| | 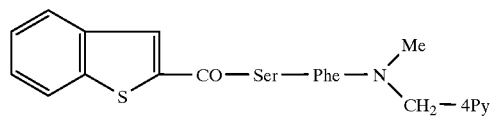 |
| 26-(18) | 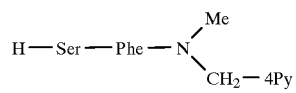 |
| | 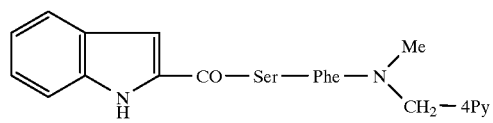 |
| 26-(19) | 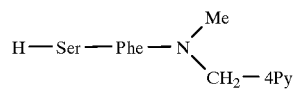 |
| | 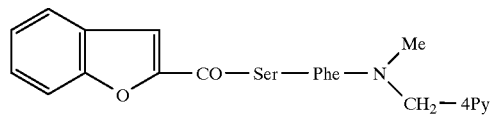 |
| 26-(20) | 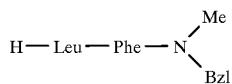 |
| | 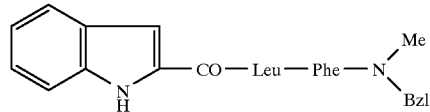 |
| 26-(21) | 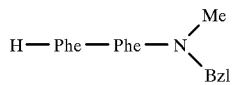 |
| | 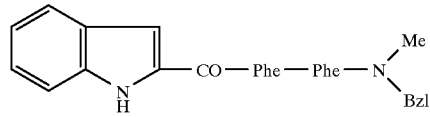 |
| 26-(22) | 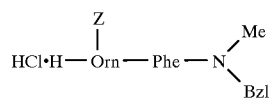 |
| | 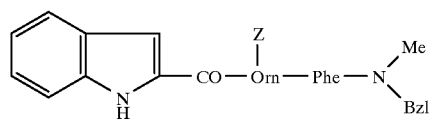 |
| 26-(23) | 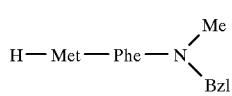 |

| Example No. | Formula |
|---|---|
| | 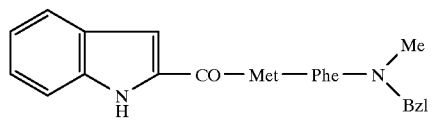 |
| 26-(24) | 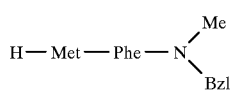 |
| | 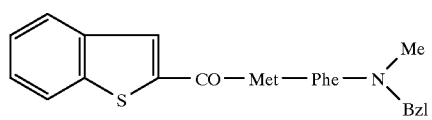 |
| 26-(25) | 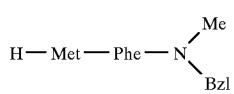 |
| | 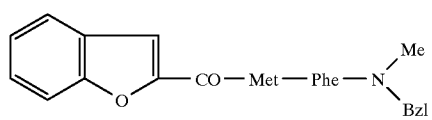 |
| 26-(26) | 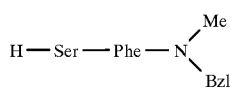 |
| | 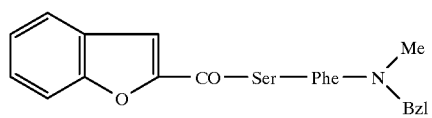 |
| 26-(27) | 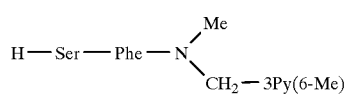 |
| | 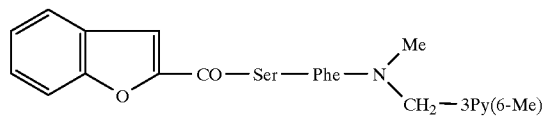 |
| 26-(28) | 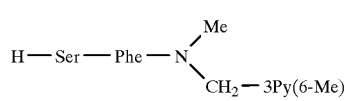 |
| | 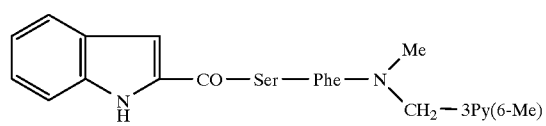 |
| 26-(29) | 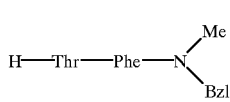 |

-continued
| Example No. | Formula |
|---|---|
| | 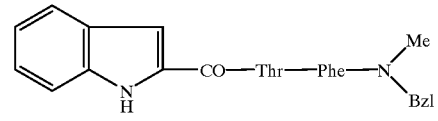 |
| 26-(30) | 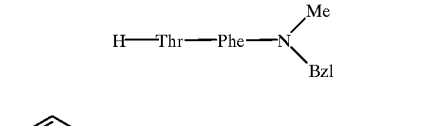 |
| | 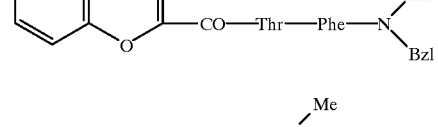 |
| 26-(31) | H—2Nal—Phe—N(Me)(Bzl) |
| |  |
| 26-(32) | H—2Nal—Phe—N(Me)(Bzl) |
| | 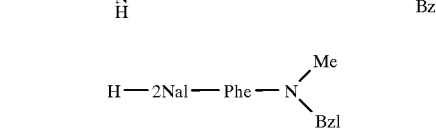 |
| 26-(33) | H—His—Phe—N(Me)(CH₂—3Py(6-Me)) |
| | 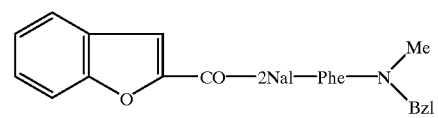 |
| 26-(34) | H—His—Phe—N(Me)(CH₂—3Py(6-Me)) |
| | (indole)-CO—His—Phe—N(Me)(CH₂—3Py(6-Me)) |
| 26-(35) | H—MePhe—Phe—Phe—N(Me)(Bzl) |
| | (benzofuran)-CO—MePhe—Phe—N(Me)(Bzl) |

-continued
| Example No. | Formula |
|---|---|
| 26-(36) | 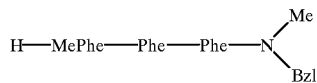<br>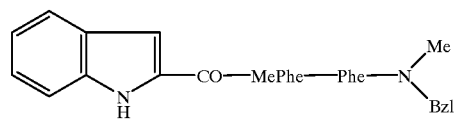 |
| 26-(37) | 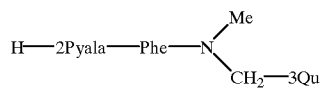<br>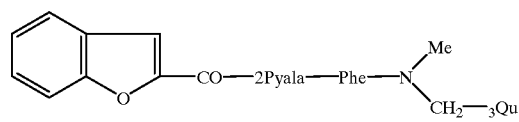 |
| 26-(38) | 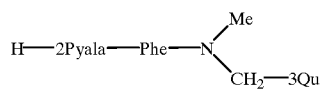<br>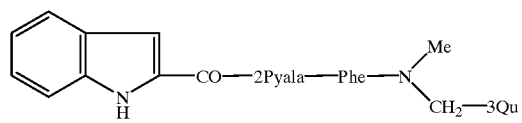 |
| 26-(39) | 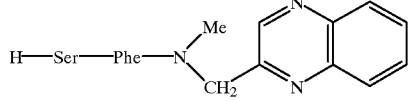<br>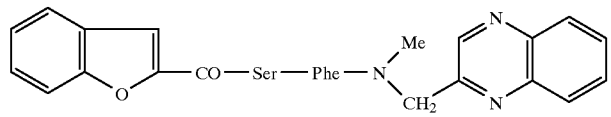 |
| 26-(40) | 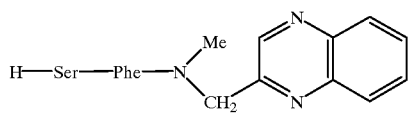<br>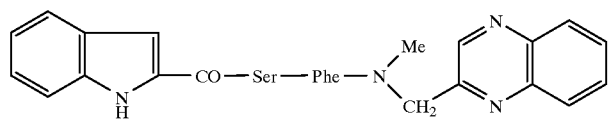 |
| 26-(41) | 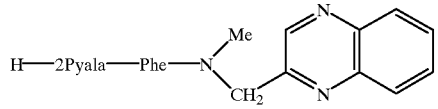<br>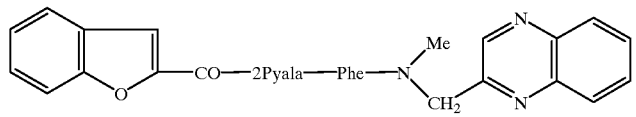 |

-continued
| Example No. | Formula |
|---|---|
| 26-(42) | 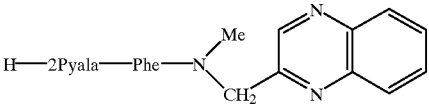 |
| | 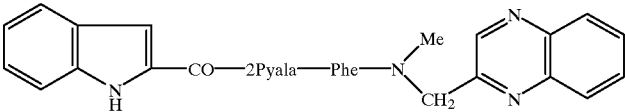 |
| 26-(43) | 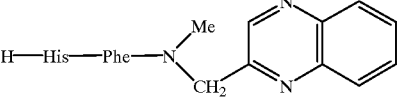 |
| | 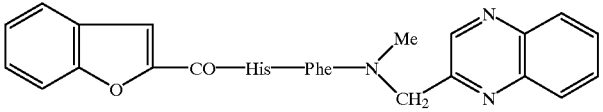 |
| 26-(44) | 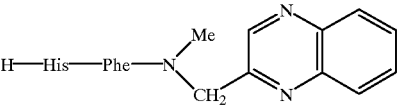 |
| | 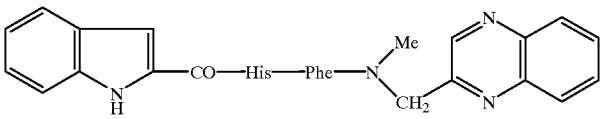 |
| 26-(45) | 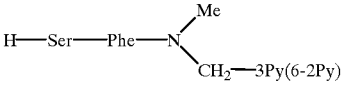 |
| | 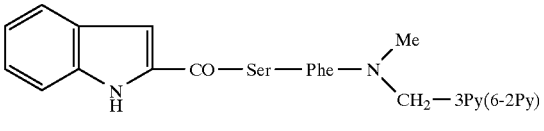 |
| 26-(46) | 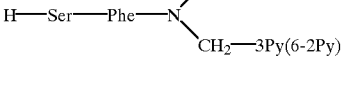 |
| | 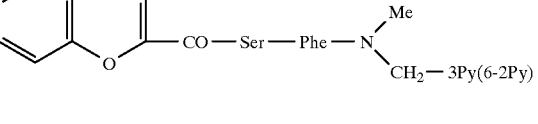 |
| 26-(47) | 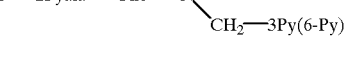 |
| | 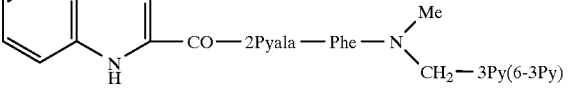 |

-continued
| Example No. | Formula |
|---|---|
| 26-(48) | 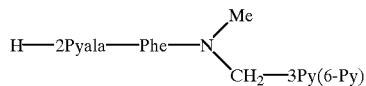 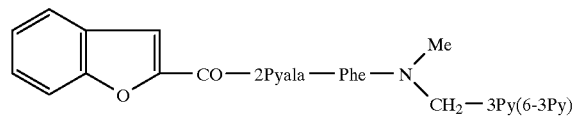 |
| 26-(49) | 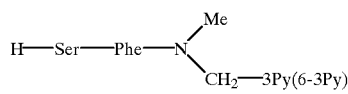 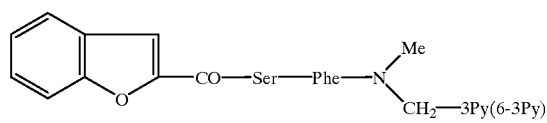 |
| 26-(50) | 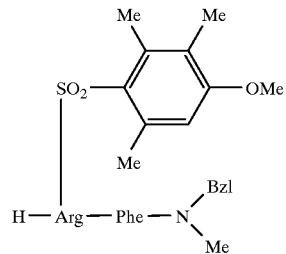 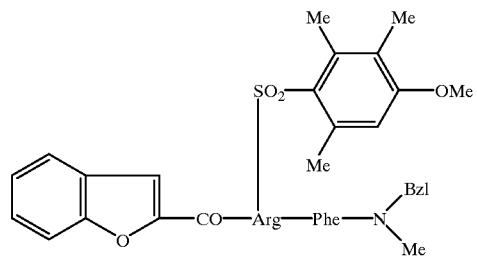 |
| 26-(51) | 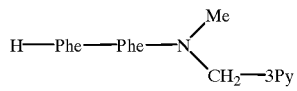 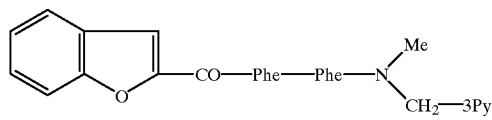 |
| 26-(52) | 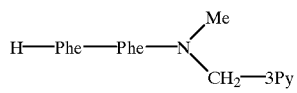 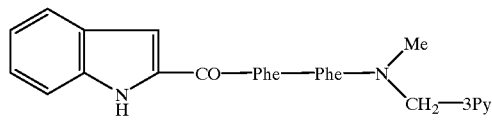 |

-continued
| Example No. | Formula |
|---|---|
| 26-(53) | 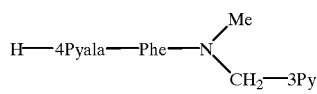<br>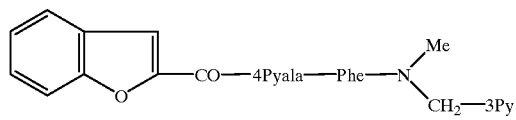 |
| 26-(54) | 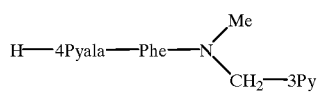<br>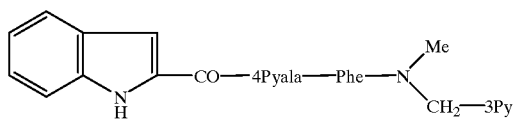 |
| 26-(55) | 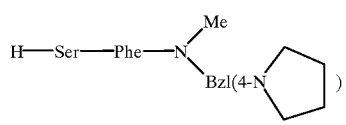<br>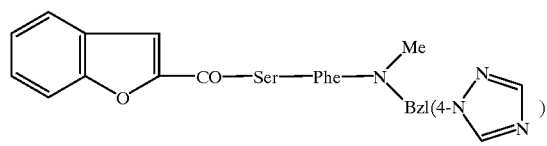 |
| 26-(56) | 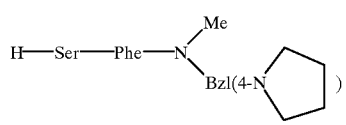<br>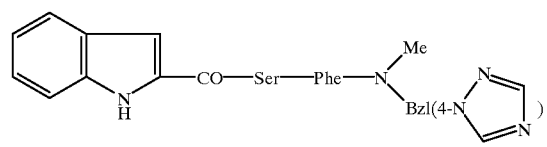 |
| 26-(57) | 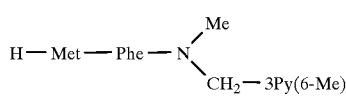<br>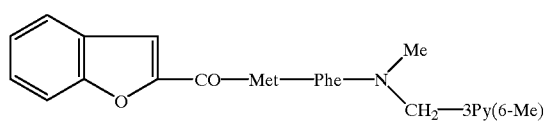 |
| 26-(58) | 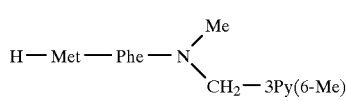<br>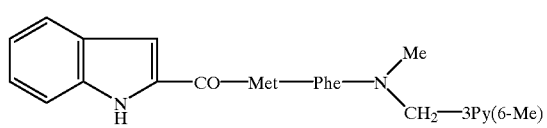 |

| Example No. | Formula |
|---|---|
| 26-(59) | 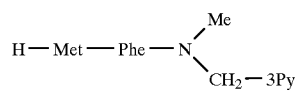<br>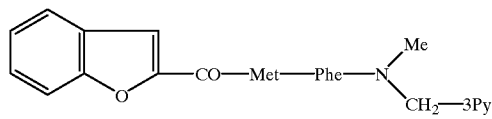 |
| 26-(60) | 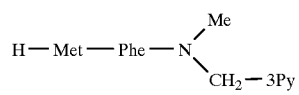<br>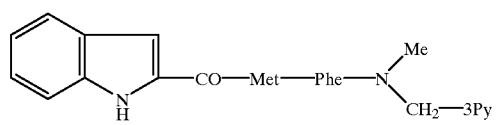 |
| 26-(61) | 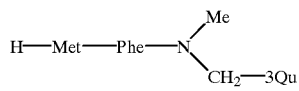<br>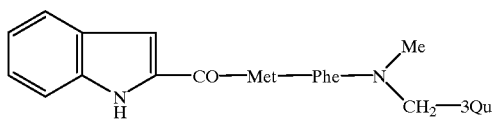 |
| 26-(62) | 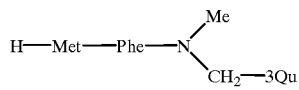<br>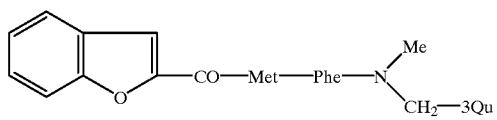 |
| 26-(63) | 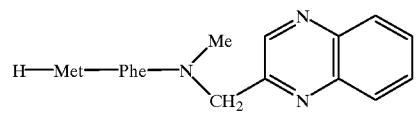<br>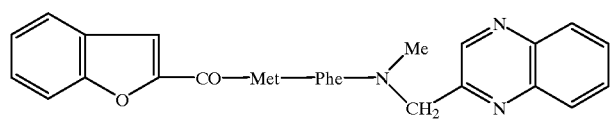 |
| 26-(64) | 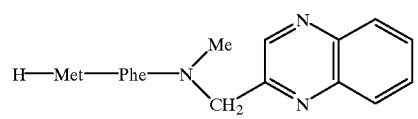<br>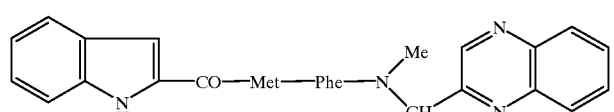 |

-continued

| Example No. | Formula |
|---|---|
| 26-(65) | H—Met—Phe—N(Me)(CH₂—3Py(6-3Py)) <br><br> Indole-2-CO—Met—Phe—N(Me)(CH₂—3Py(6-3Py)) |
| 26-(66) | H—Met—Phe—N(Me)(CH₂—3Py(6-3Py)) <br><br> Benzofuran-2-CO—Met—Phe—N(Me)(CH₂—3Py(6-3Py)) |
| 26-(67) | H—Ala(2-thienyl)—Phe—N(Me)(Bzl) <br><br> Benzofuran-2-CO—Ala(2-thienyl)—Phe—N(Me)(Bzl) |
| 26-(68) | H—Ala(2-thienyl)—Phe—N(Me)(Bzl) <br><br> Indole-2-CO—Ala(2-thienyl)—Phe—N(Me)(Bzl) |
| 26-(69) | H—Ser—Phe—N(Me)(CH₂—3Py(6-NMe₂)) <br><br> Indole-2-CO—Ser—Phe—N(Me)(CH₂—3Py(6-NMe₂)) |
| 26-(70) | H—Ser—Phe—N(Me)(CH₂—3Py(6-NMe₂)) |

| Example No. | Formula |
|---|---|
| | 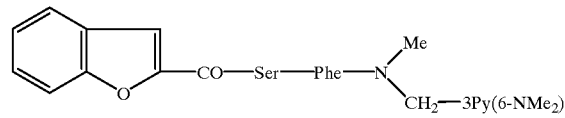 |
| 26-(71) | 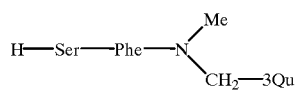 |
| | 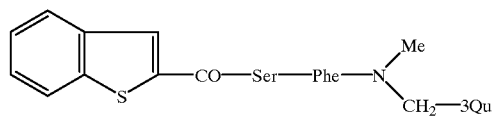 |
| 26-(72) | 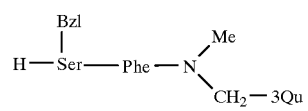 |
| | 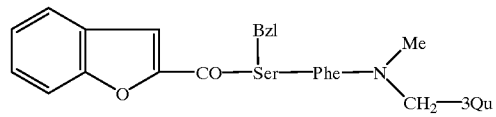 |
| 26-(73) | 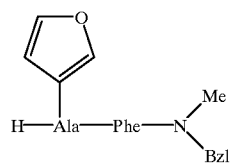 |
| | 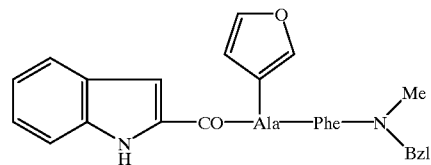 |
| 26-(74) | 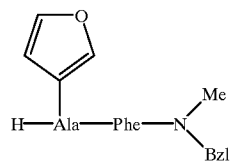 |
| | 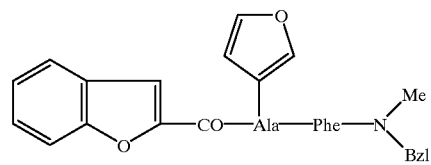 |
| 26-(75) | 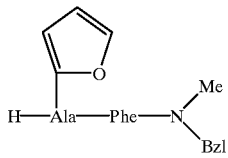 |

-continued
| Example No. | Formula |
|---|---|
| | 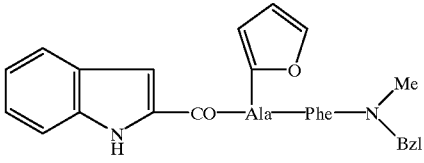 |
| 26-(76) | 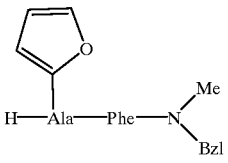 |
| 26-(77) | 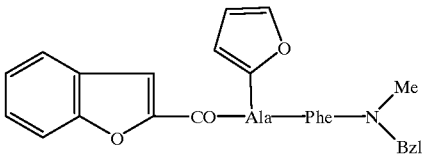 |
| 26-(78) | 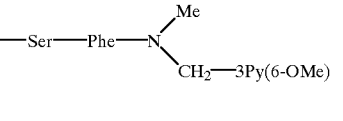 |
| 26-(79) | 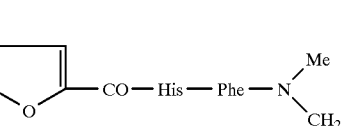 |
| 26-(80) | 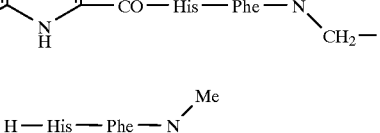 |

| Example No. | Formula |
|---|---|
| 26-(81) | 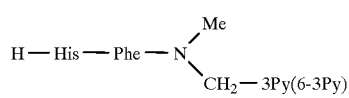 |
| | 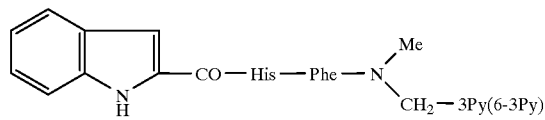 |
| 26-(82) | 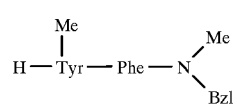 |
| | 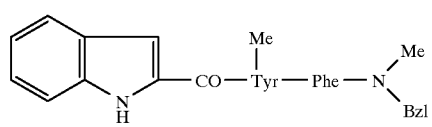 |
| 26-(83) | 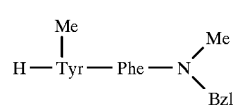 |
| | 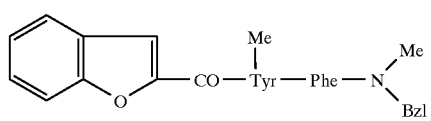 |
| 26-(84) | 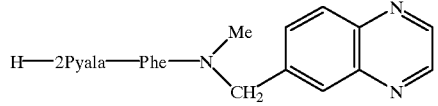 |
| | 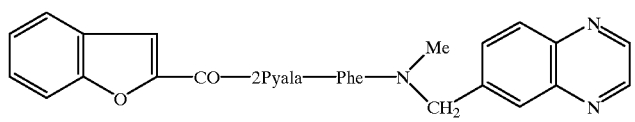 |
| 26-(85) | 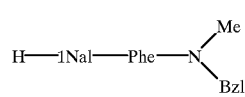 |
| | 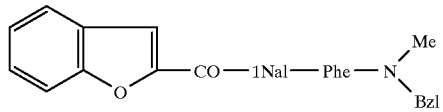 |
| 26-(86) | 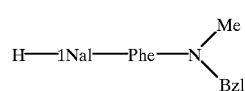 |
| | 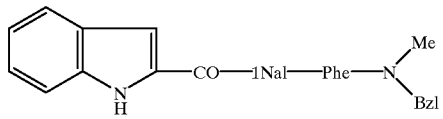 |

-continued
| Example No. | Formula |
|---|---|
| 26-(87) | 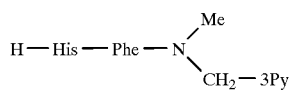 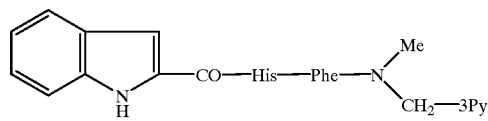 |
| 26-(88) | 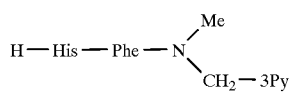 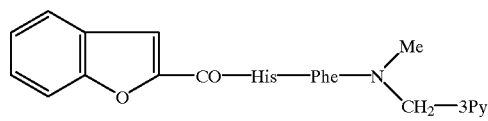 |
| 26-(89) | 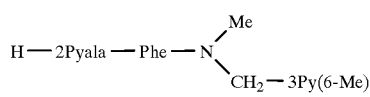 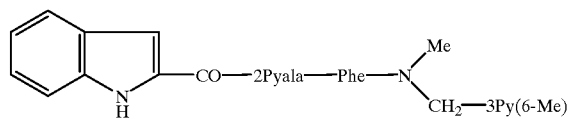 |
| 26-(90) | 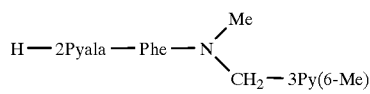 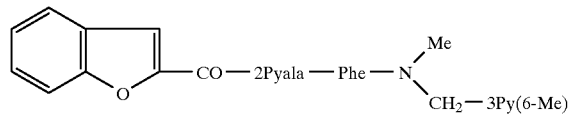 |
| 26-(91) | 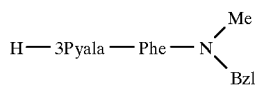 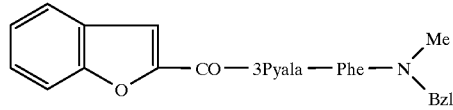 |
| 26-(92) | 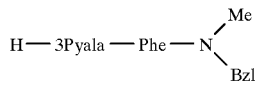 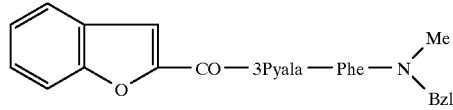 |
| 26-(93) | 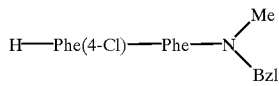 |

| Example No. | Formula |
|---|---|
| | 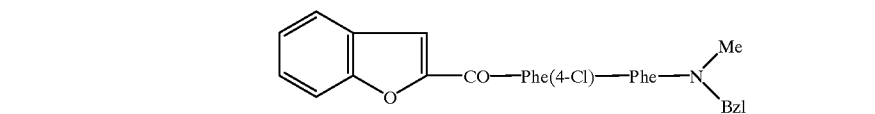 |
| 26-(94) | 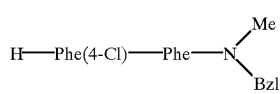 |
| | 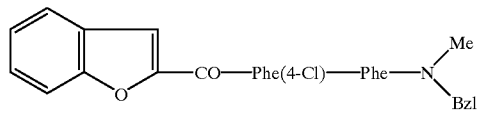 |
| 26-(95) | 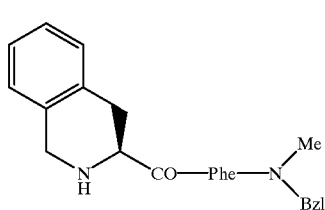 |
| | 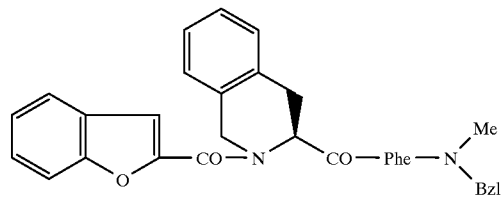 |
| 26-(96) | 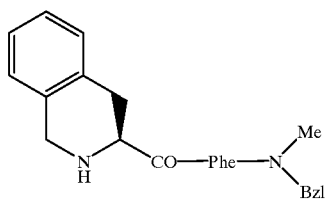 |
| | 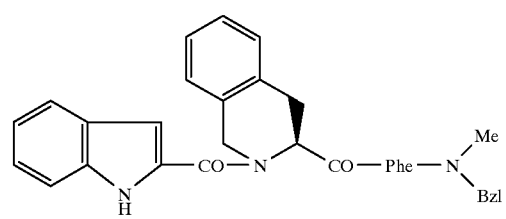 |
| 26-(97) | 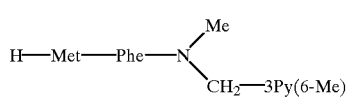 |
| | 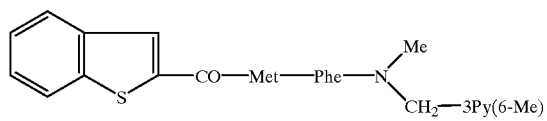 |
| 27 | 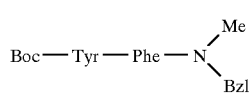 |

| Example No. | Formula |
|---|---|
| 28 | 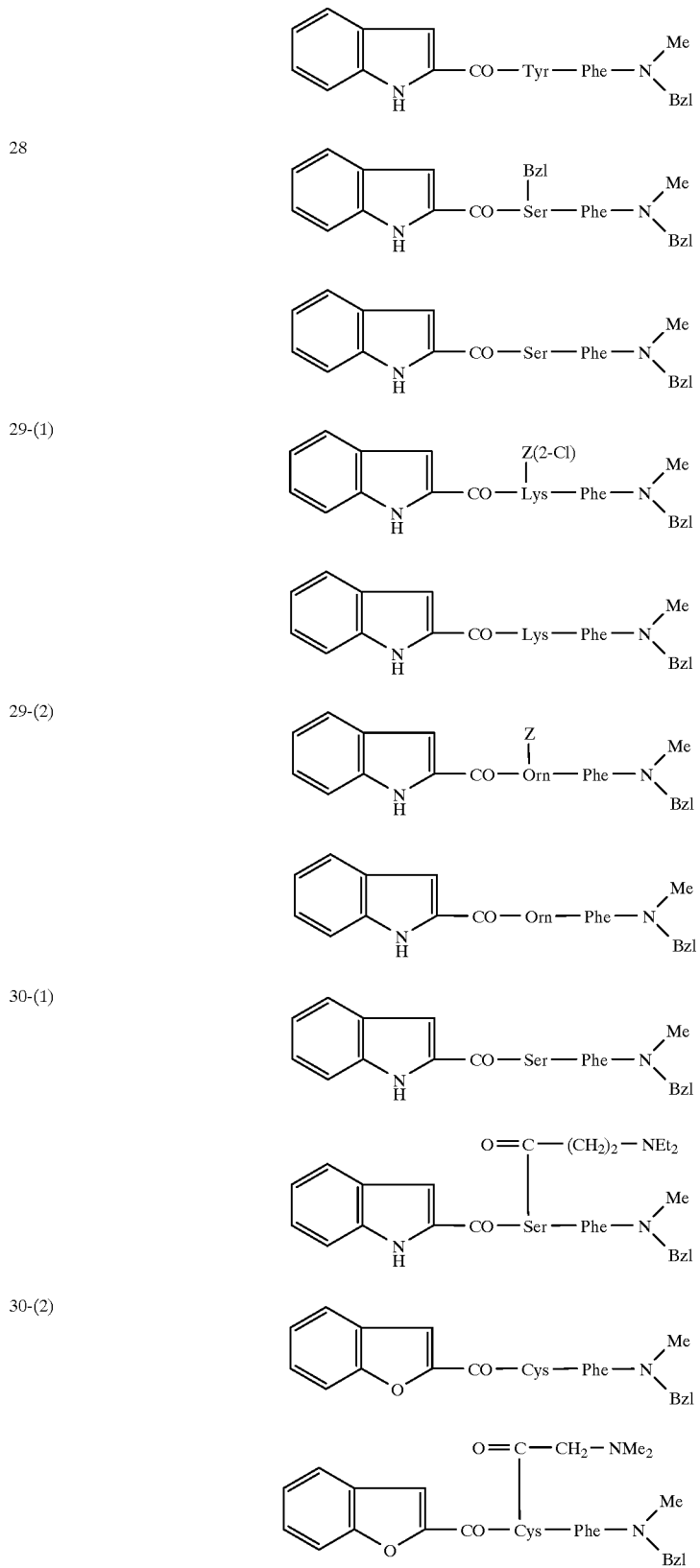 |
| 29-(1) | |
| 29-(2) | |
| 30-(1) | |
| 30-(2) | |

| Example No. | Formula |
|---|---|
| 30-(3) | 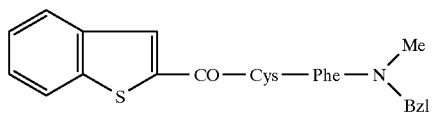 |
| | 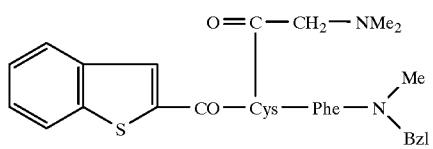 |
| 30-(4) | 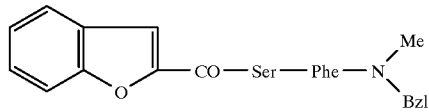 |
| | 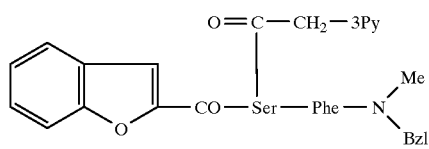 |
| 30-(5) | 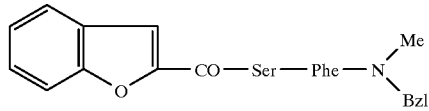 |
| | 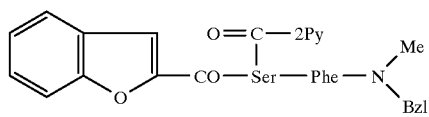 |
| 30-(6) | 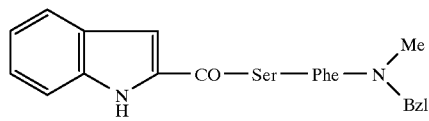 |
| | 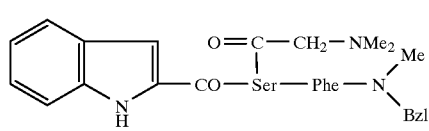 |
| 30-(7) | 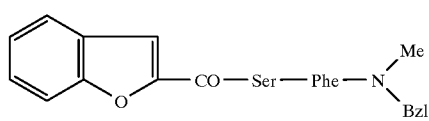 |
| | 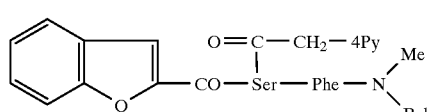 |
| 30-(8) | 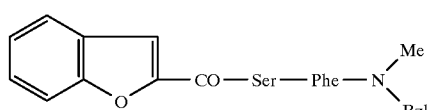 |

| Example No. | Formula |
|---|---|
| | 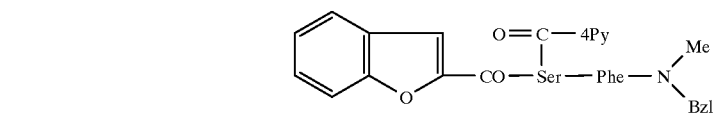 |
| 30-(9) | 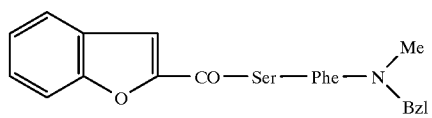 |
| | 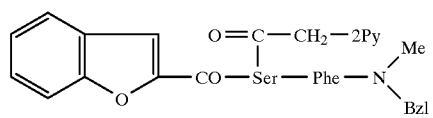 |
| 30-(10) | 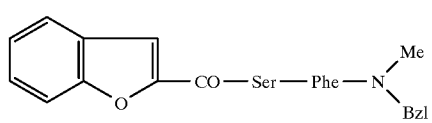 |
| | 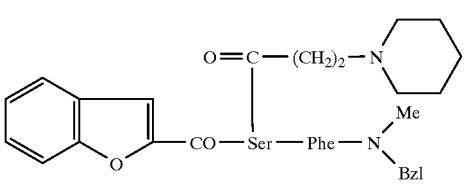 |
| 30-(11) | 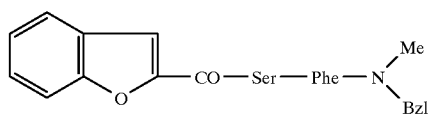 |
| | 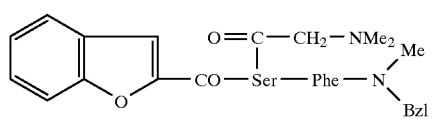 |
| 30-(12) | 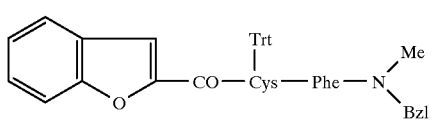 |
| 31 | 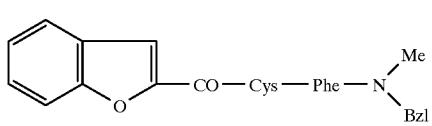 |

-continued
| Example No. | Formula |
|---|---|
| 32-(1) | 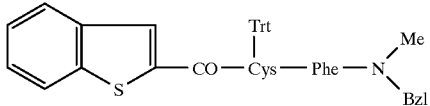 |
| 32-(2) | 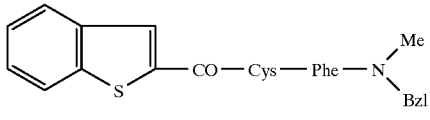 |
| 33 | 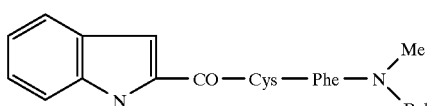 |
| 34-(1) | 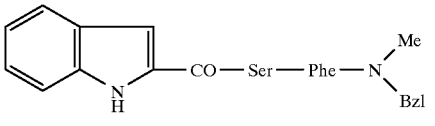 |
| 34-(2) | 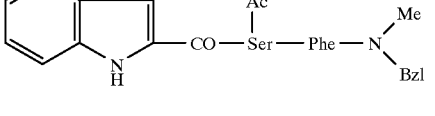 |
| 34-(3) | 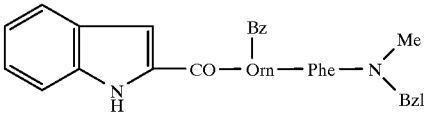 |

| Example No. | Formula |
|---|---|
| | 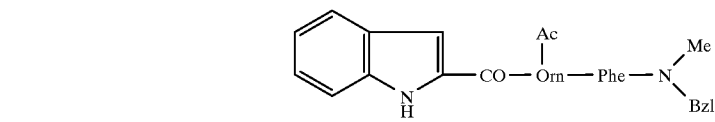 |
| 34-(4) | 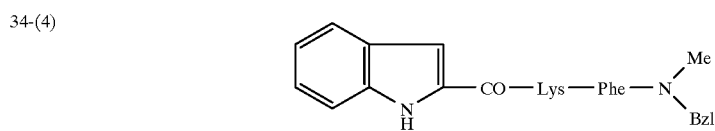 |
| | 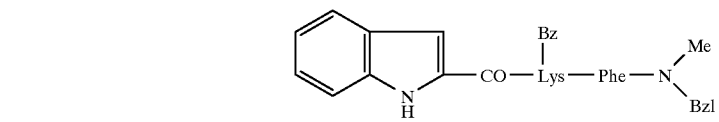 |
| 35 | 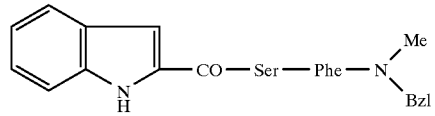 |
| | 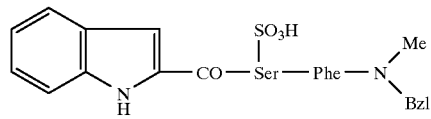 |
| 36 | 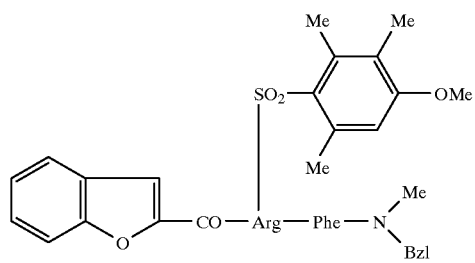 |
| | 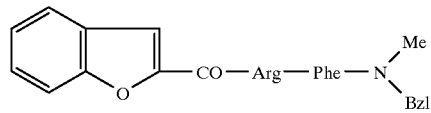 |
| 37-(1) | 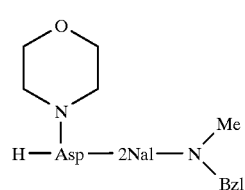 |
| | 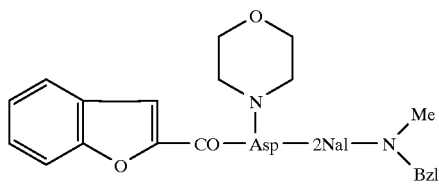 |

-continued
| Example No. | Formula |
|---|---|
| 37-(2) | 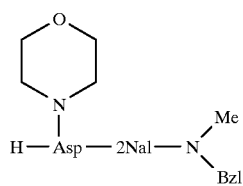 |
| | 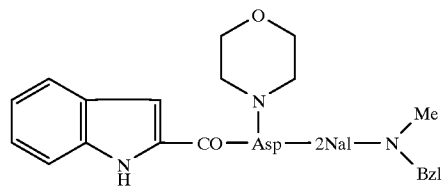 |
| 37-(3) | 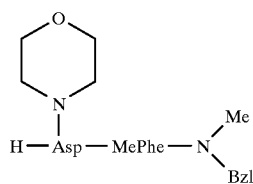 |
| | 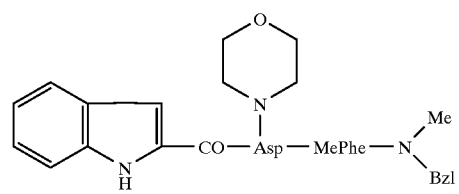 |
| 37-(4) | 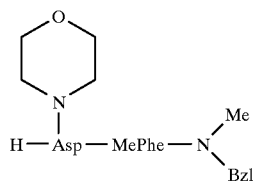 |
| | 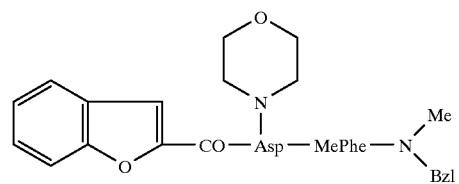 |
| 37-(5) | 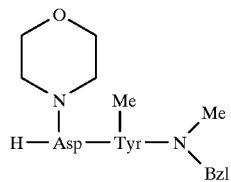 |
| | 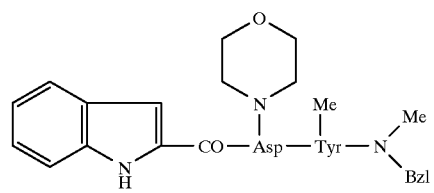 |

-continued
| Example No. | Formula |
|---|---|
| 37-(6) | 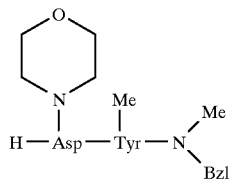 |
| | 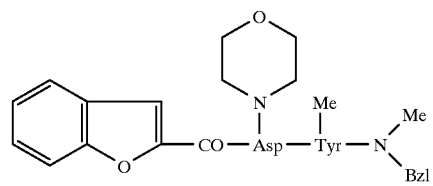 |
| 37-(7) | 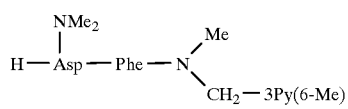 |
| | 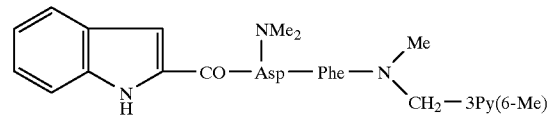 |
| 37-(8) | 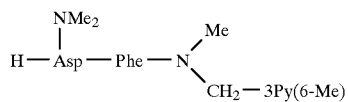 |
| | 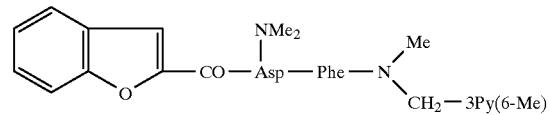 |
| 37-(9) | 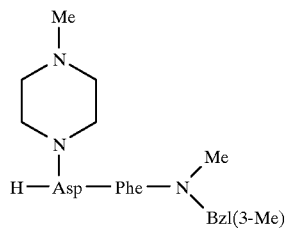 |
| | 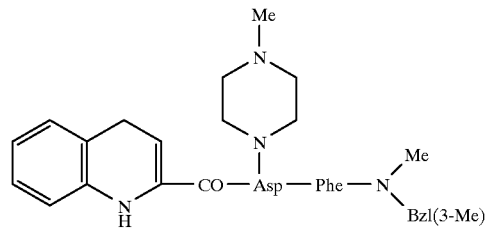 |

-continued
| Example No. | Formula |
|---|---|
| 37-(10) | 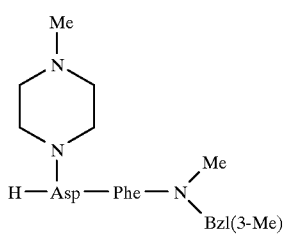 |
| | 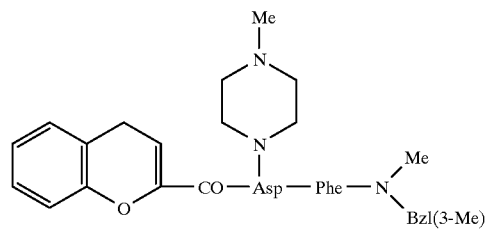 |
| 37-(11) | 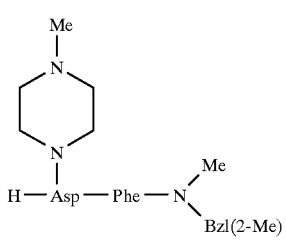 |
| | 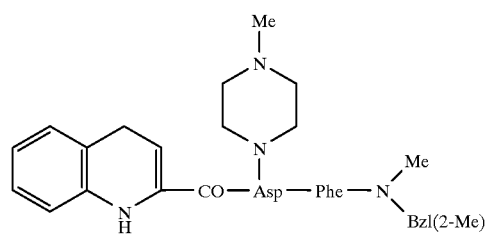 |
| 37-(12) | 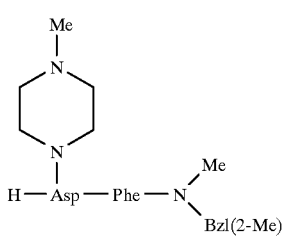 |
| | 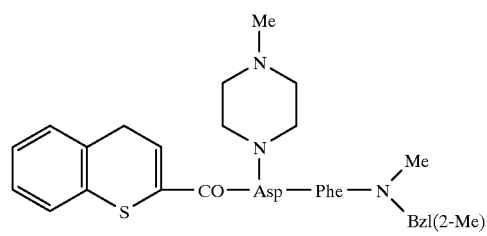 |

-continued
| Example No. | Formula |
|---|---|
| 37-(13) | 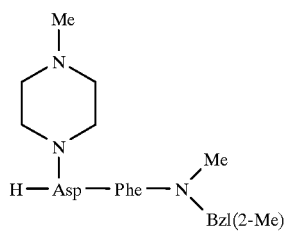 |
| | 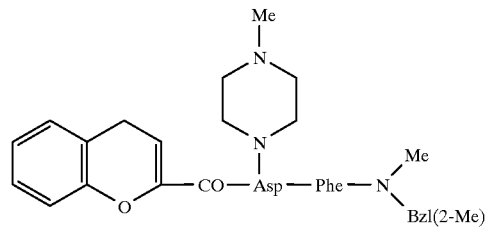 |
| 37-(14) | 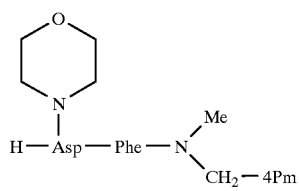 |
| | 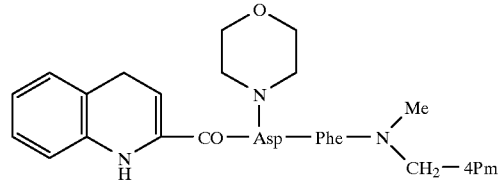 |
| 37-(15) | 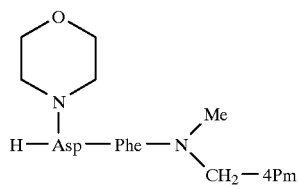 |
| | 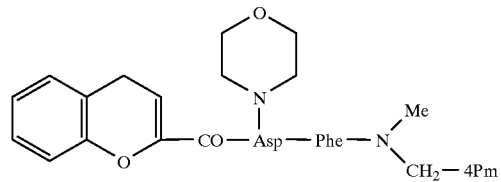 |
| 37-(16) | 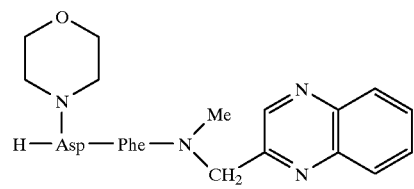 |

| Example No. | Formula |
|---|---|
| | 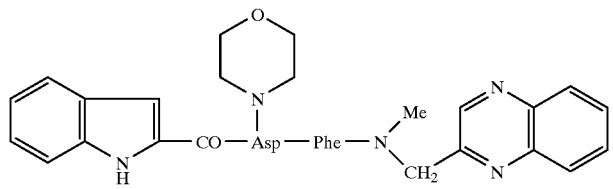 |
| 37-(17) | 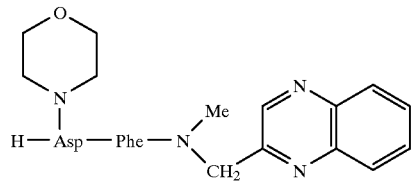 |
| | 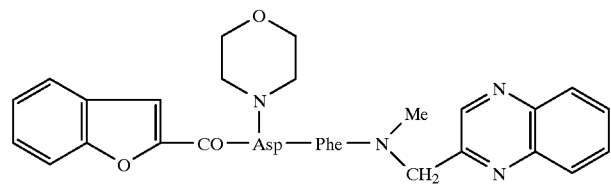 |
| 37-(18) | 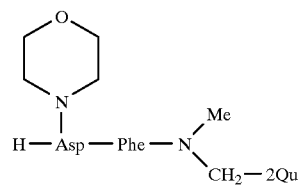 |
| | 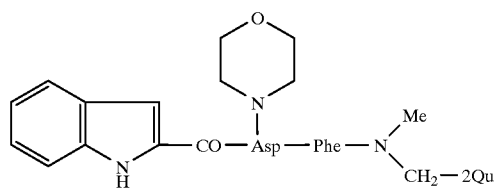 |
| 37-(19) | 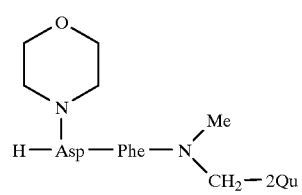 |
| | 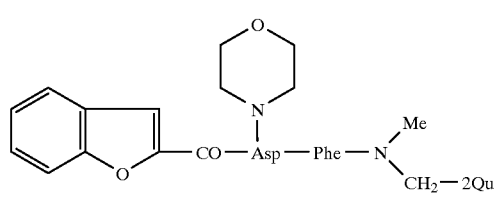 |

-continued
| Example No. | Formula |
|---|---|
| 37-(20) | 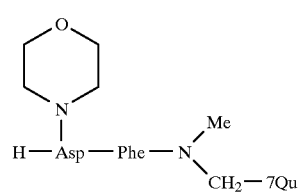<br>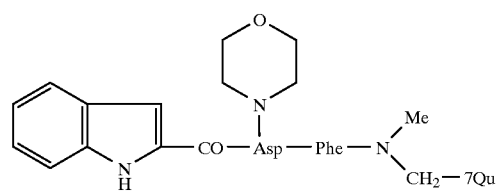 |
| 37-(21) | 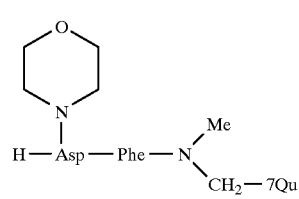<br>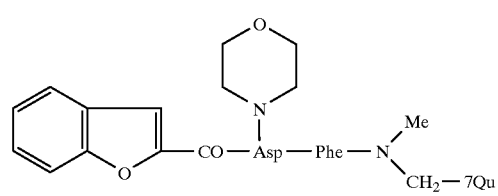 |
| 37-(22) | 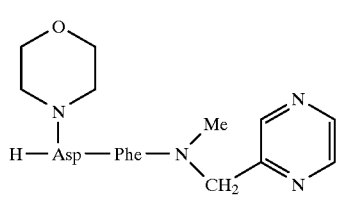<br>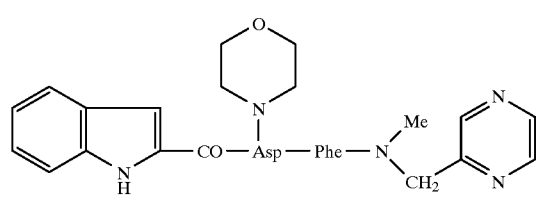 |
| 37-(23) | 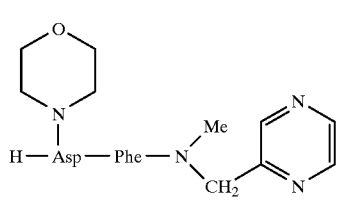 |

| Example No. | Formula |
|---|---|
| | 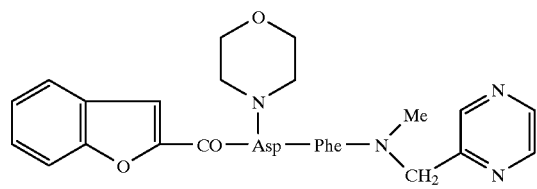 |
| 37-(24) | 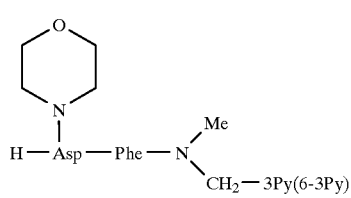 |
| | 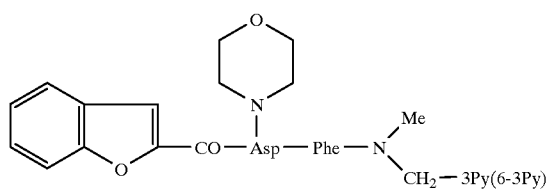 |
| 37-(25) | 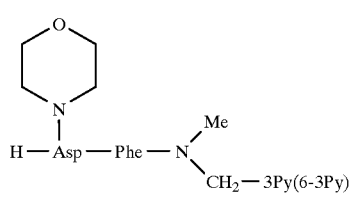 |
| | 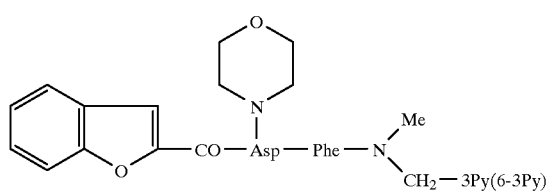 |
| 37-(26) | 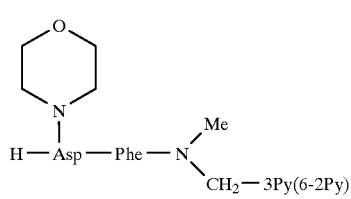 |
| | 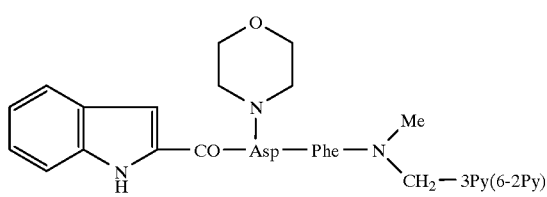 |

-continued
| Example No. | Formula |
|---|---|
| 37-(27) | 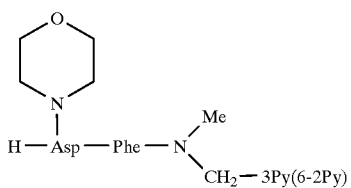 |
| | 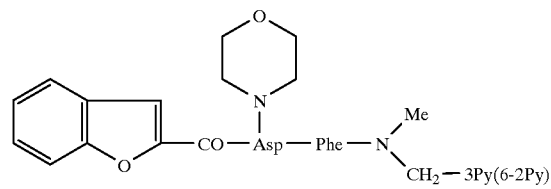 |
| 37-(28) | 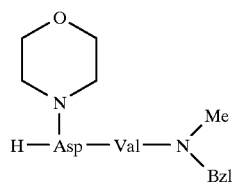 |
| | 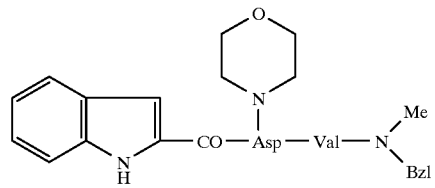 |
| 37-(29) | 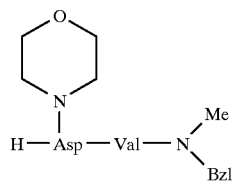 |
| | 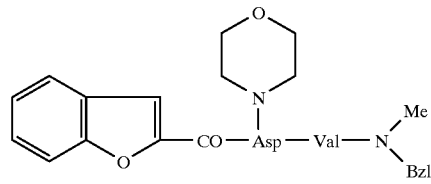 |
| 37-(30) | 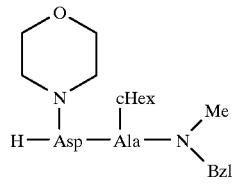 |
| | 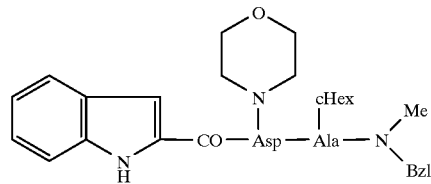 |

| Example No. | Formula |
|---|---|
| 37-(31) | 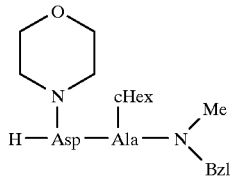<br>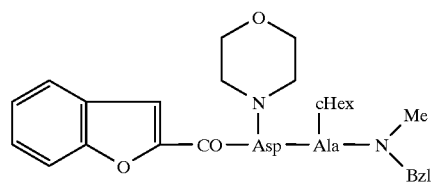 |
| 37-(32) | 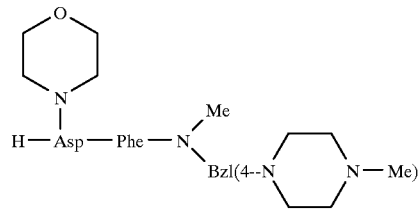<br>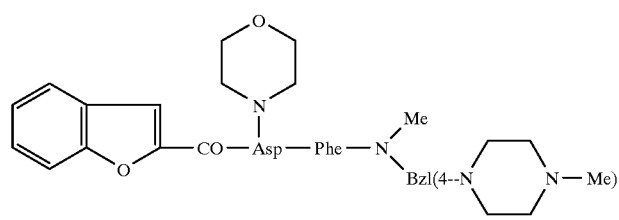 |
| 37-(33) | 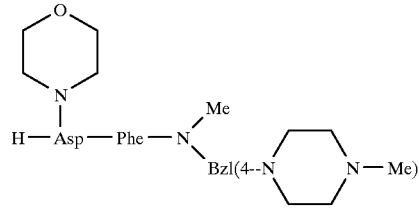<br>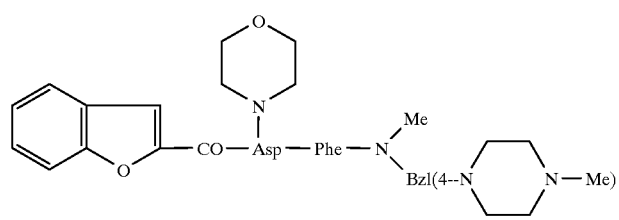 |
| 37-(34) | 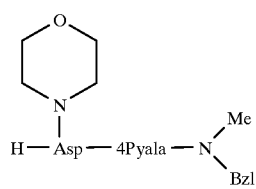 |

| Example No. | Formula |
|---|---|
| | 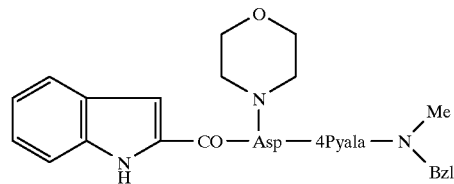 |
| 37-(35) | 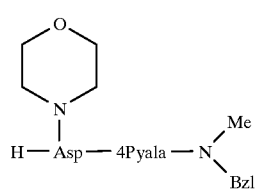 |
| | 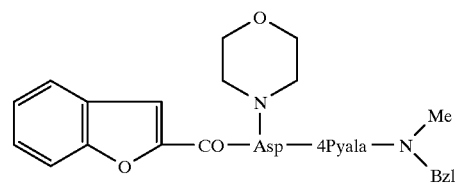 |
| 37-(36) | 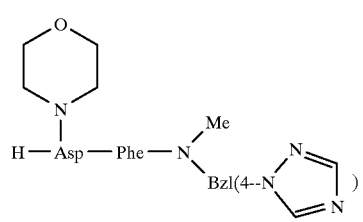 |
| | 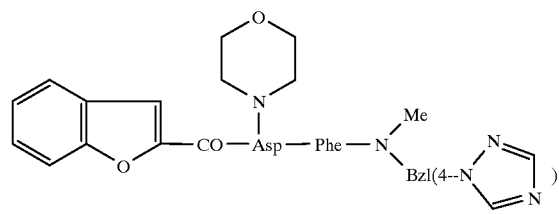 |
| 37-(37) | 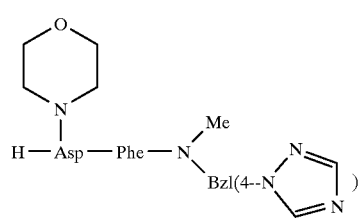 |
| | 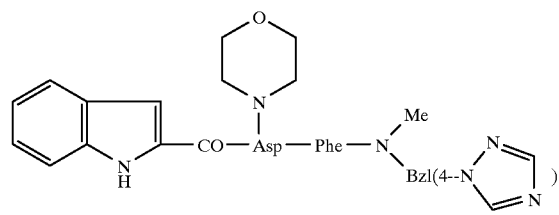 |

| Example No. | Formula |
|---|---|
| 37-(38) | 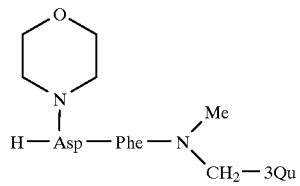 |
| | 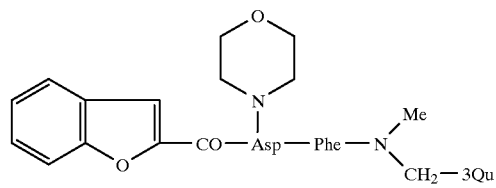 |
| 37-(39) | 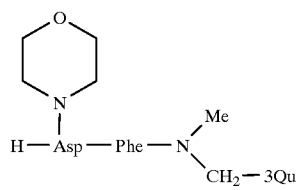 |
| | 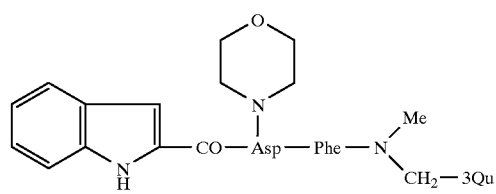 |
| 37-(40) | 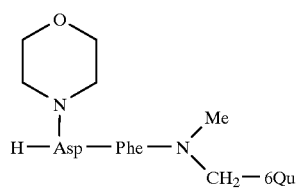 |
| | 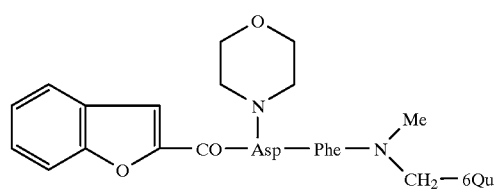 |
| 37-(41) | 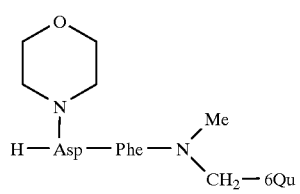 |

-continued
| Example No. | Formula |
|---|---|
| | 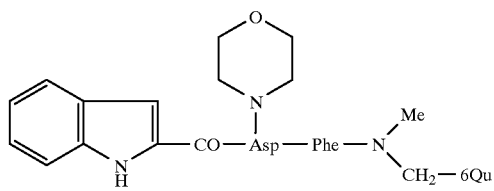 |
| 37-(42) | 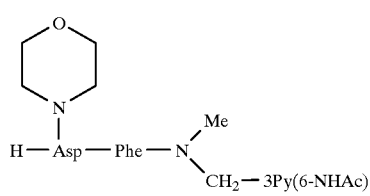 |
| | 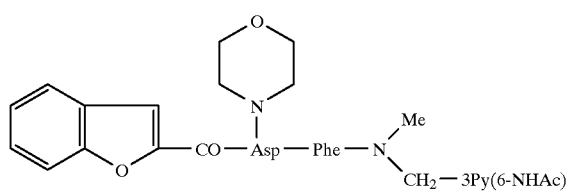 |
| 37-(43) | 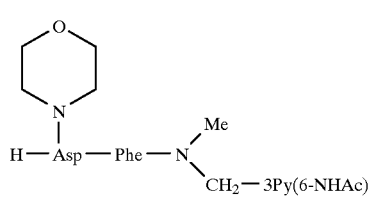 |
| | 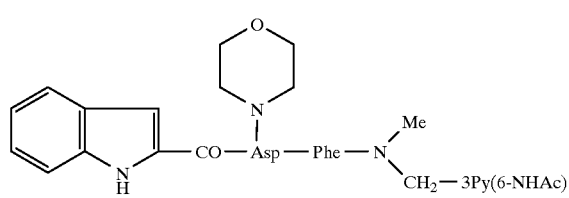 |
| 37-(44) | 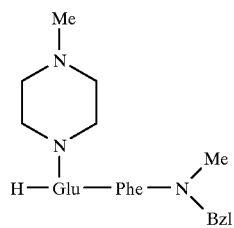 |
| | 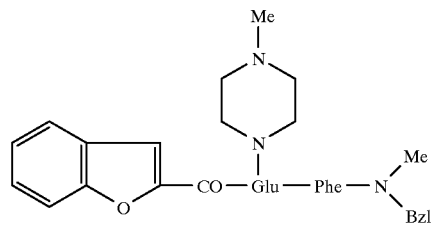 |

-continued
| Example No. | Formula |
|---|---|
| 37-(45) | 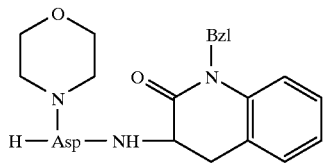<br>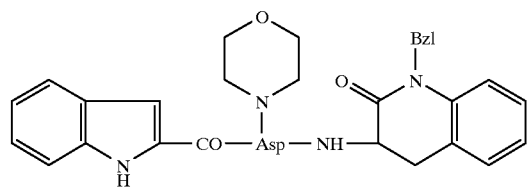 |
| 37-(46) | 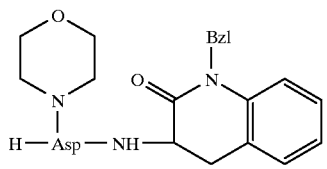<br>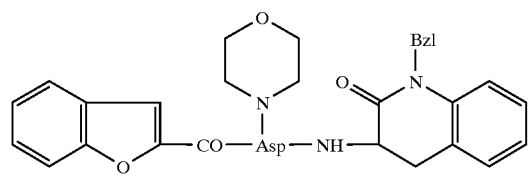 |
| 37-(47) | 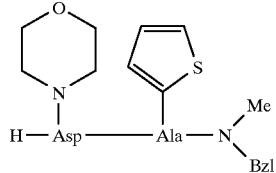<br>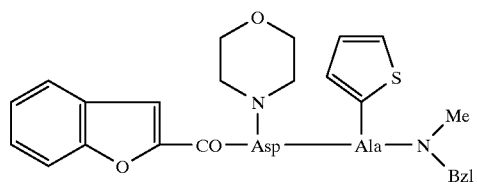 |
| 37-(48) | 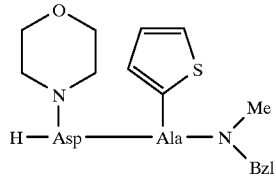<br>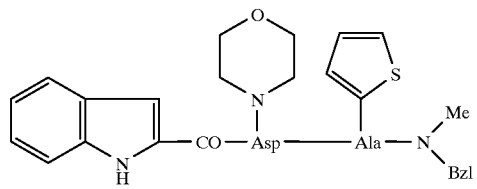 |

-continued
| Example No. | Formula |
|---|---|
| 37-(49) | 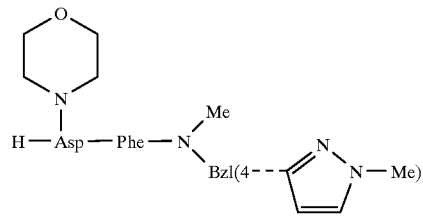 |
| | 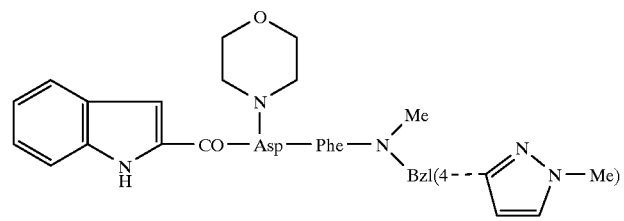 |
| 37-(50) | 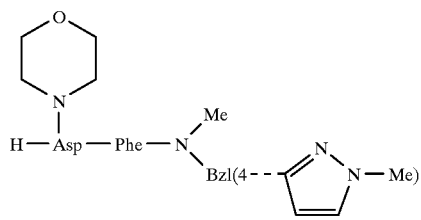 |
| | 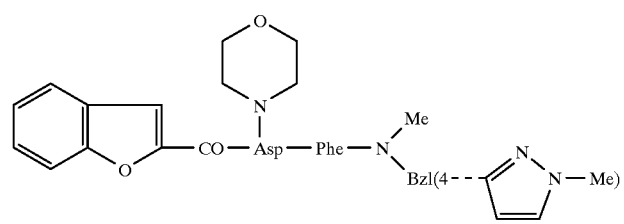 |
| 37-(51) | 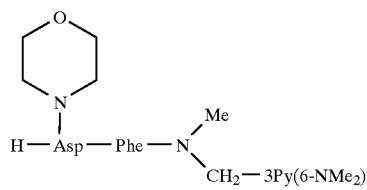 |
| | 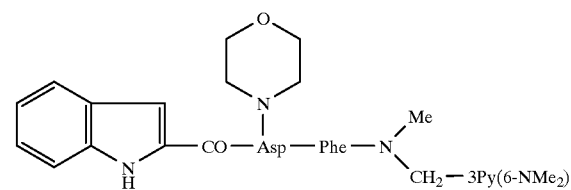 |
| 37-(52) | 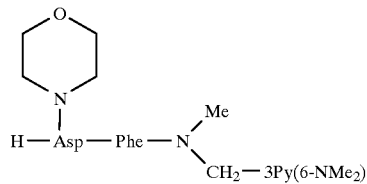 |

| Example No. | Formula |
|---|---|
| | ![benzofuran-CO-Asp(morpholine)-Phe-N(Me)-CH₂-3Py(6-NMe₂)] |
| 37-(53) | ![H-Asp(morpholine)-Phe-N(Me)-Bzl(4-pyrazol-N)] |
| | ![indole-2-CO-Asp(morpholine)-Phe-N(Me)-Bzl(4-pyrazol-N)] |
| 37-(54) | ![H-Asp(morpholine)-Phe-N(Me)-Bzl(4-pyrazol-N)] |
| | ![benzofuran-2-CO-Asp(morpholine)-Phe-N(Me)-Bzl(4-pyrazol-N)] |
| 37-(55) | ![H-Asp(morpholine)-Phe-N(Me)-CH₂-(1,2-dimethylbenzimidazole)] |
| | ![indole-2-CO-Asp(morpholine)-Phe-N(Me)-CH₂-(1,2-dimethylbenzimidazole)] |

| Example No. | Formula |
|---|---|
| 37-(56) | 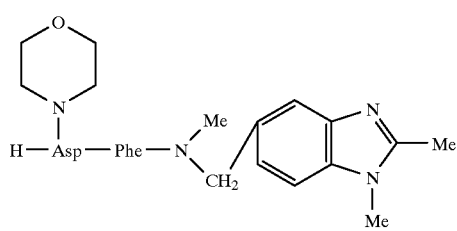 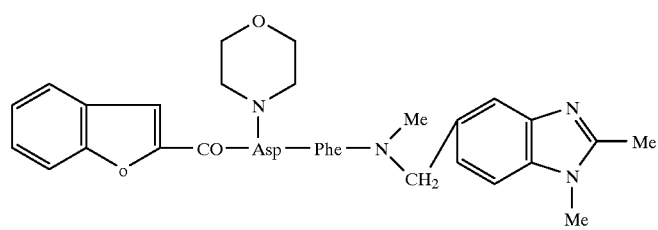 |
| 37-(57) | 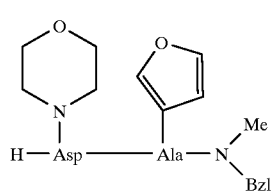 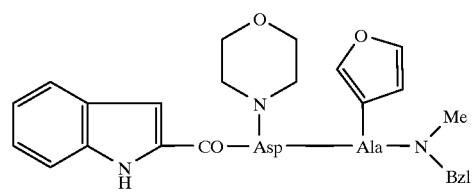 |
| 37-(58) | 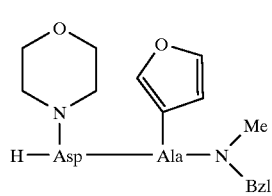 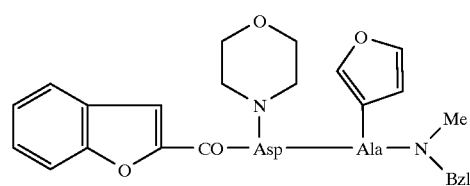 |
| 37-(59) | 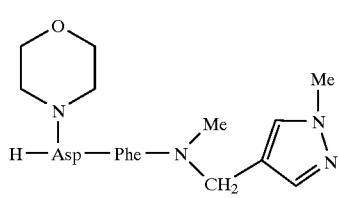 |

| Example No. | Formula |
|---|---|
| 37-(60) | indol-2-yl-CO—Asp(morpholine)—Phe—N(Me)—CH₂-(1-methylpyrazol-4-yl) |
| | H—Asp(morpholine)—Phe—N(Me)—CH₂-(1-methylpyrazol-4-yl) |
| | benzofuran-2-yl-CO—Asp(morpholine)—Phe—N(Me)—CH₂-(1-methylpyrazol-4-yl) |
| 37-(61) | H—Asp(morpholine)—Phe(4-Cl)—N(Me)(Bzl) |
| | indol-2-yl-CO—Asp(morpholine)—Phe(4-Cl)—N(Me)(Bzl) |
| 37-(62) | H—Asp(morpholine)—Phe(4-Cl)—N(Me)(Bzl) |
| | benzofuran-2-yl-CO—Asp(morpholine)—Phe(4-Cl)—N(Me)(Bzl) |
| 37-(63) | H—Asp(morpholine)—Ala(furan-2-yl)—N(Me)(Bzl) |

| Example No. | Formula |
|---|---|
| | 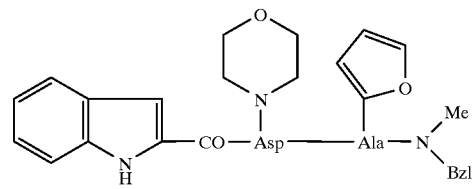 |
| 37-(64) | 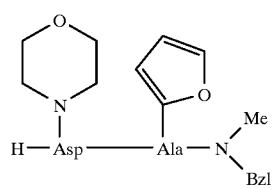 |
| | 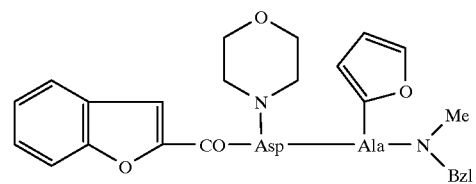 |
| 37-(65) | 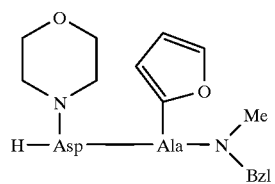 |
| | 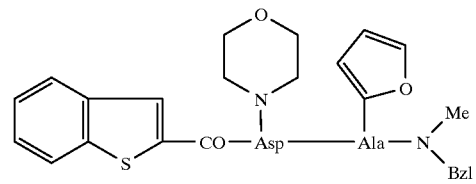 |
| 37-(66) | 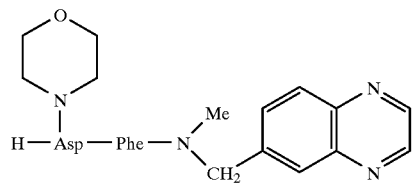 |
| | 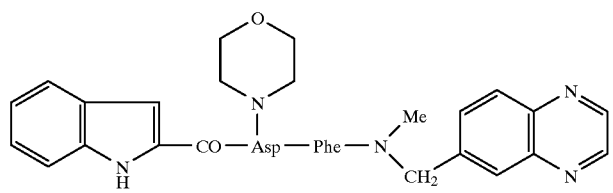 |

| Example No. | Formula |
|---|---|
| 37-(67) | 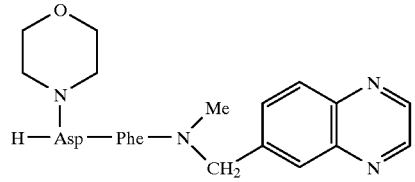<br>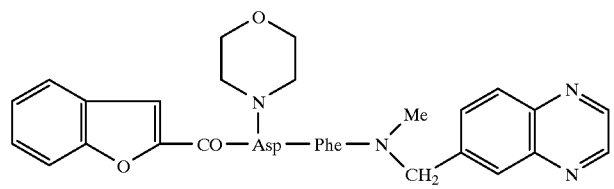 |
| 37-(68) | 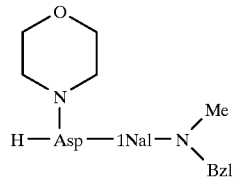<br>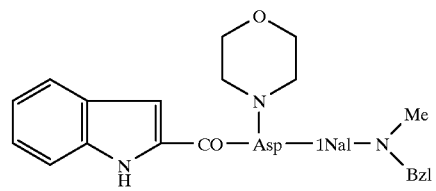 |
| 37-(69) | 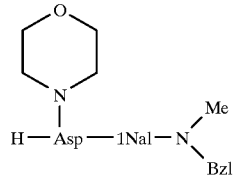<br>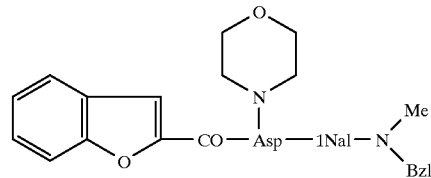 |
| 37-(70) | 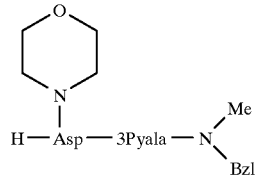<br>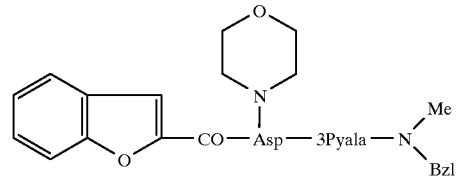 |

| Example No. | Formula |
|---|---|
| 37-(71) | 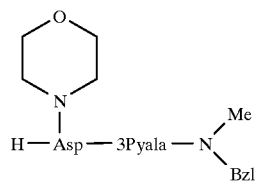 |
| | 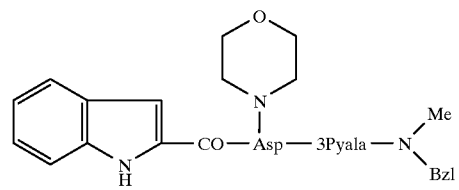 |
| 37-(72) | 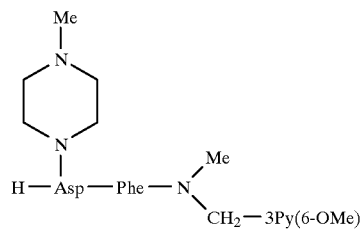 |
| | 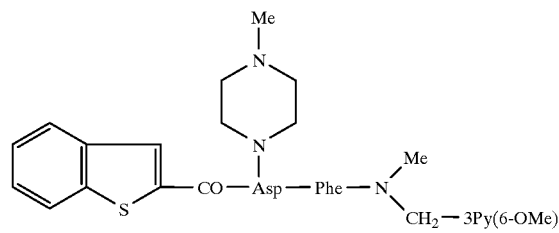 |
| 37-(73) | 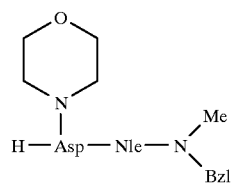 |
| | 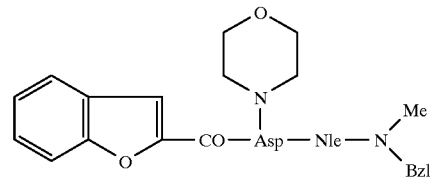 |
| 37-(74) | 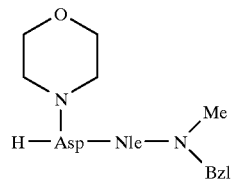 |

| Example No. | Formula |
|---|---|
| | 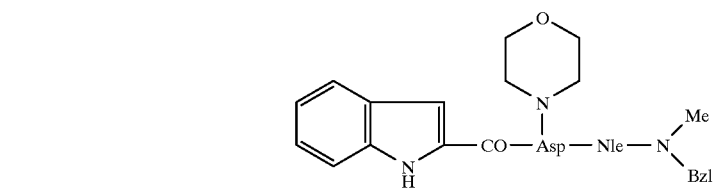 |
| 37-(75) | 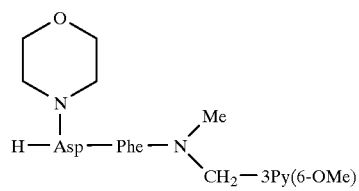 |
| | 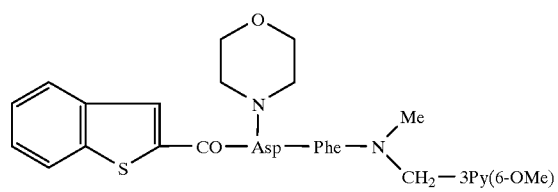 |
| 38 | 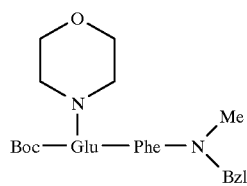 |
| | 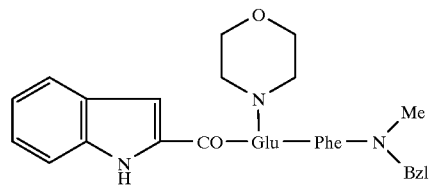 |
| 39 | 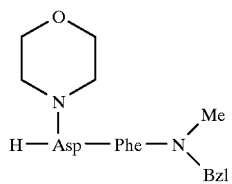 |
| | 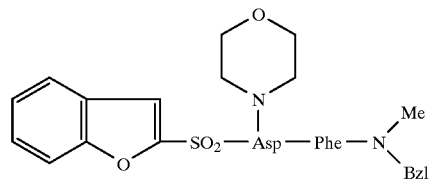 |
| 40-(1) | 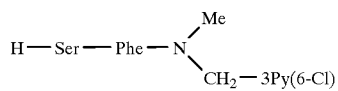 |

| Example No. | Formula |
|---|---|
| | 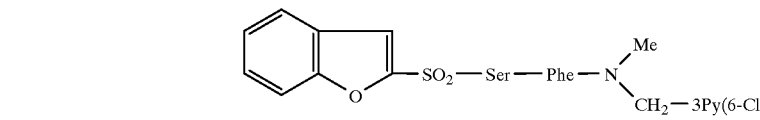 |
| 40-(2) | 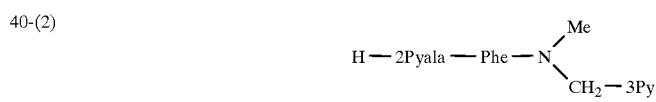 |
| | 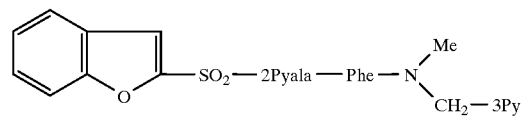 |
| 40-(3) | 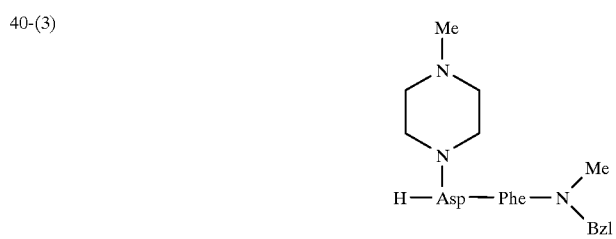 |
| | 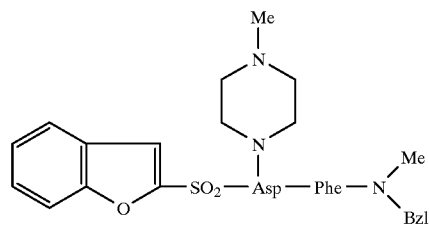 |
| 41-(1) |  |
| | 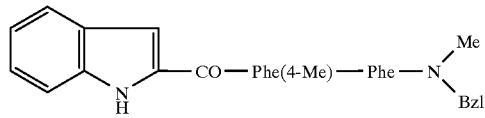 |
| 41-(2) | 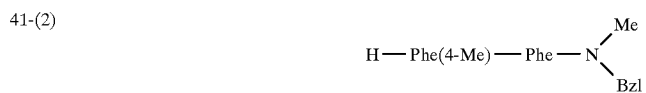 |
| | 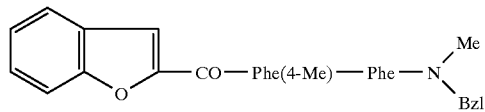 |
| 41-(3) | 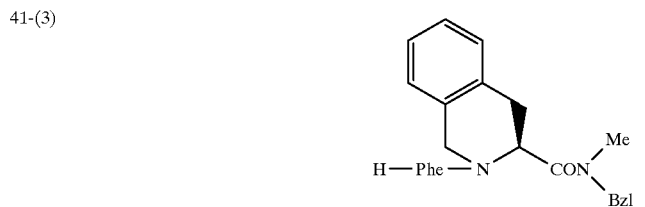 |

-continued
| Example No. | Formula |
|---|---|
| | 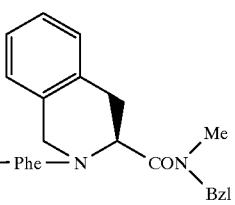 |
| 41-(4) | 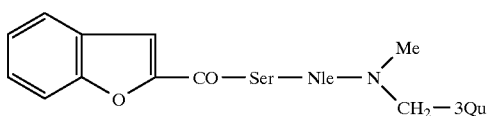 |
| 41-(5) | 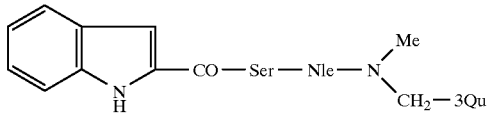 |
| 41-(6) | 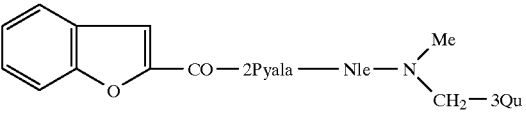 |
| 41-(7) | 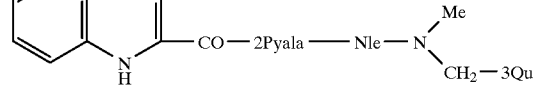 |
| 41-(8) | 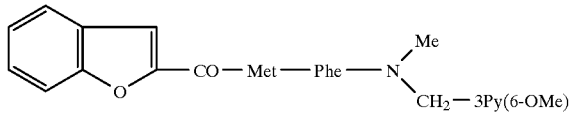 |
| 41-(9) |  |

-continued
| Example No. | Formula |
|---|---|
| | 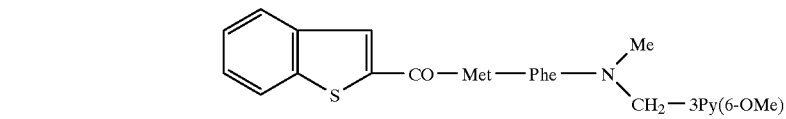 |
| 41-(10) | 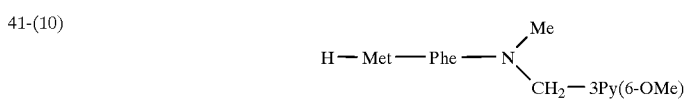 |
| | 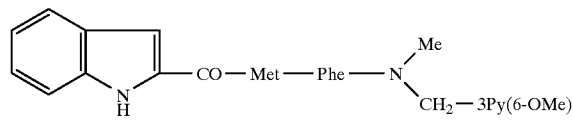 |
| 41-(11) | 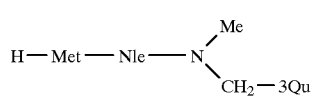 |
| | benzofuran-CO—Met—Nle—N(Me)(CH₂—3Qu) |
| 41-(12) | H—Met—Nle—N(Me)(CH₂—3Qu) |
| | 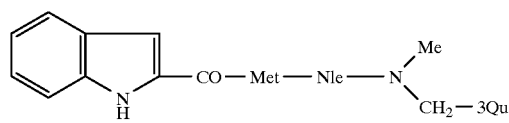 |
| 41-(13) | H—His—Nle—N(Me)(CH₂—3Qu) |
| | indole-CO—His—Nle—N(Me)(CH₂—3Qu) |
| 41-(14) | H—His—Nle—N(Me)(CH₂—3Qu) |
| | benzofuran-CO—His—Nle—N(Me)(CH₂—3Qu) |
| 41-(15) |  |

-continued
| Example No. | Formula |
|---|---|
| | 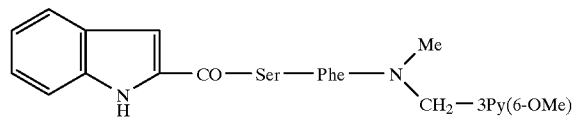 |
| 41-(16) | 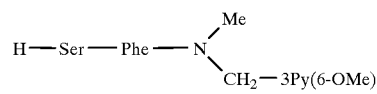 |
| | 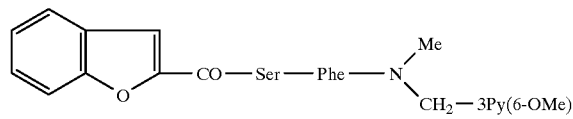 |
| 41-(17) | 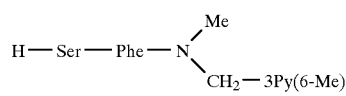 |
| | 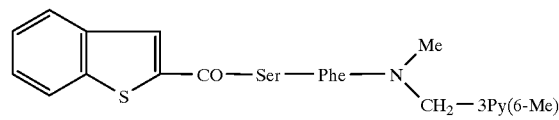 |
| 41-(18) | 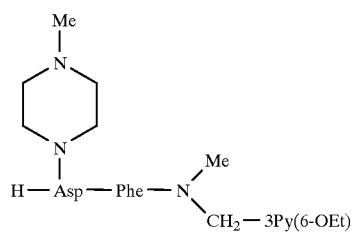 |
| | 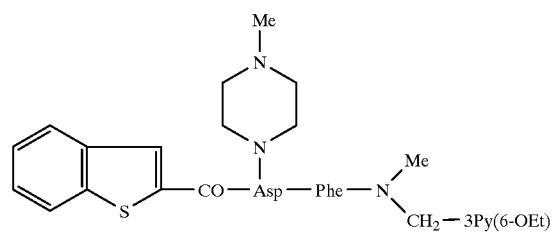 |
| 41-(19) | 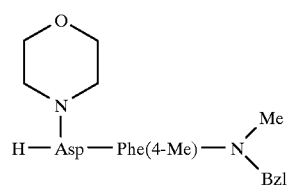 |
| | 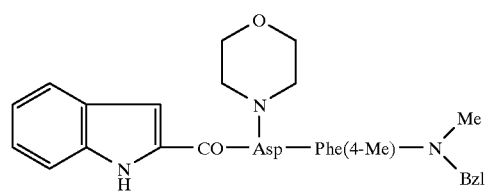 |

| Example No. | Formula |
|---|---|
| 41-(20) | 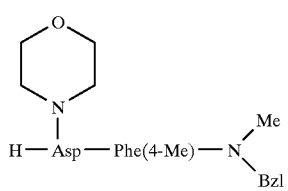 |
| | 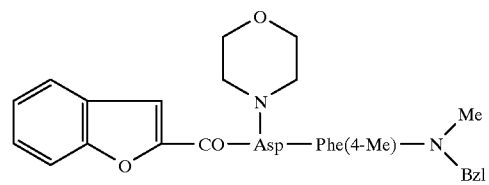 |
| 41-(21) | 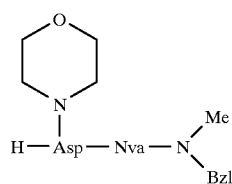 |
| | 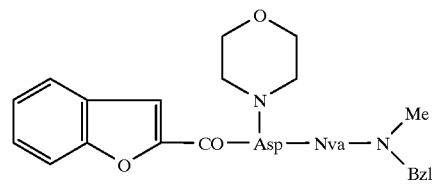 |
| 41-(22) | 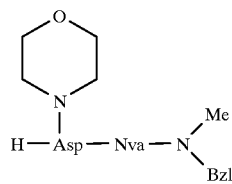 |
| | 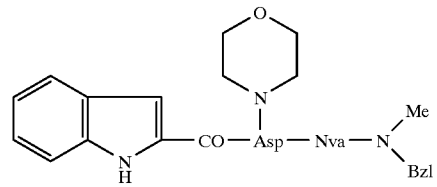 |
| 41-(23) | 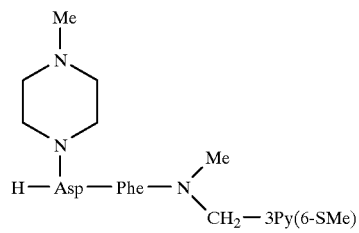 |

| Example No. | Formula |
|---|---|
| | 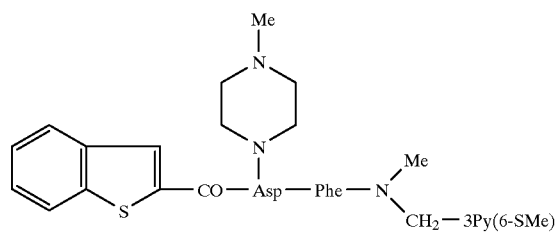 |
| 41-(24) | 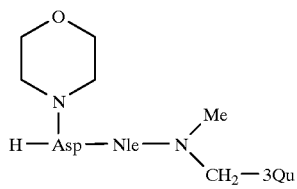 |
| | 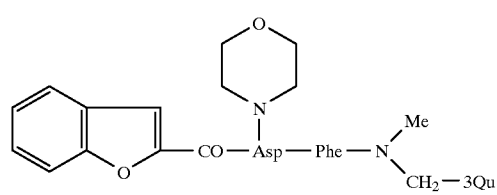 |
| 41-(25) | 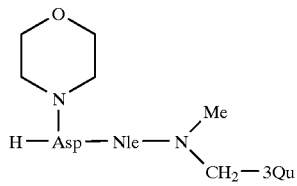 |
| | 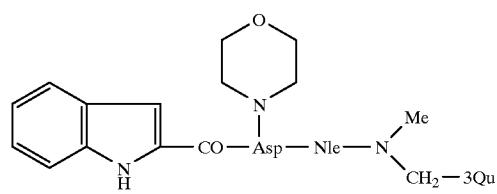 |
| 41-(26) | 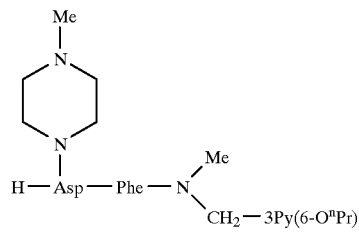 |
| | 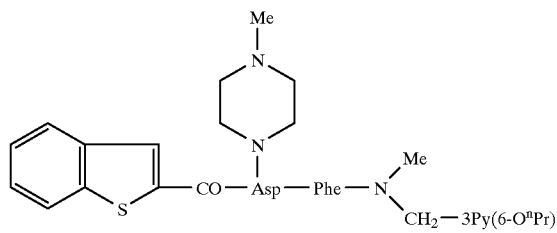 |

| Example No. | Formula |
|---|---|
| 41-(27) | 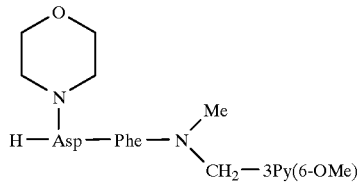 |
| | 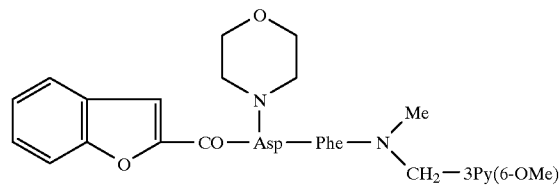 |
| 41-(28) | 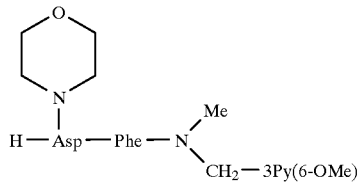 |
| | 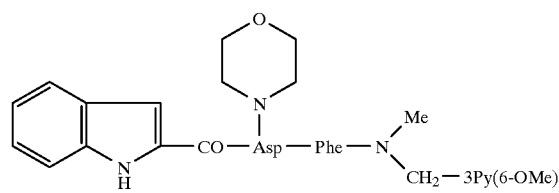 |
| 41-(29) | 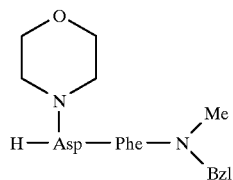 |
| | 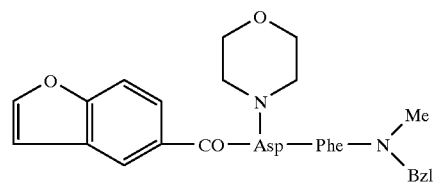 |
| 41-(30) | 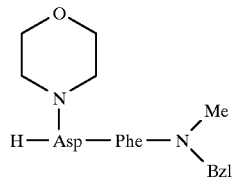 |

| Example No. | Formula |
|---|---|
| | 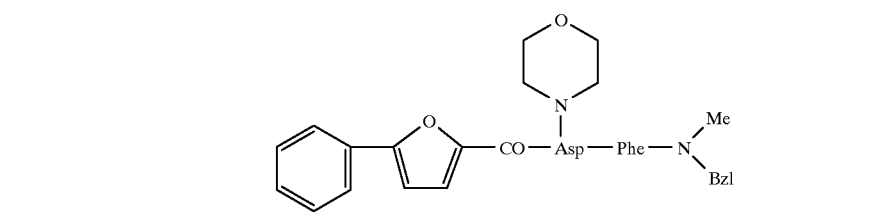 |
| 41-(31) | 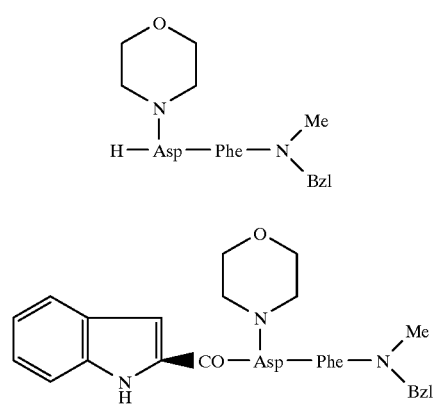 |
| 42-(1) | 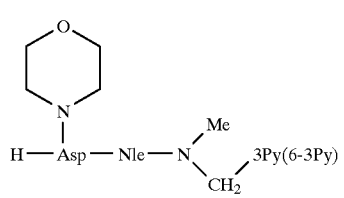 |
| | 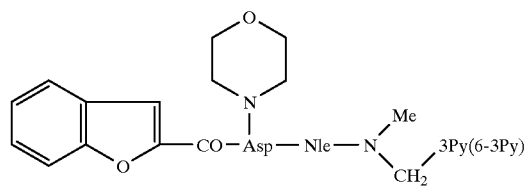 |
| 42-(2) | 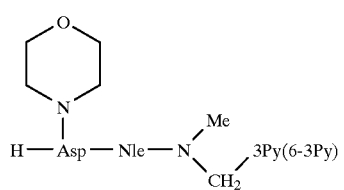 |
| | 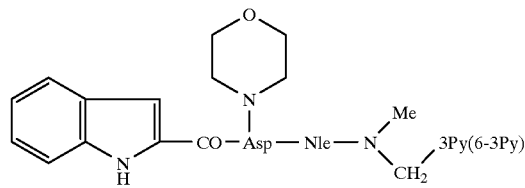 |
| 42-(3) | 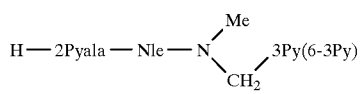 |

-continued
| Example No. | Formula |
|---|---|
| | 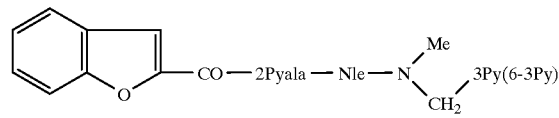 |
| 42-(4) | 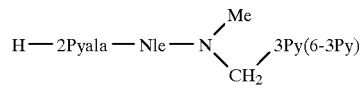 |
| | 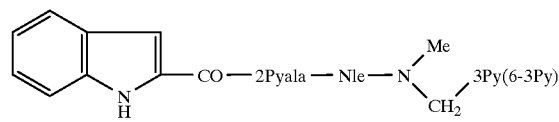 |
| 42-(5) | 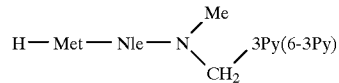 |
| | 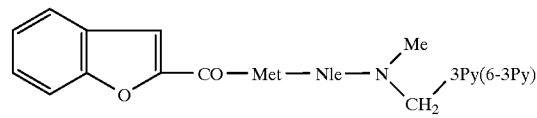 |
| 42-(6) | 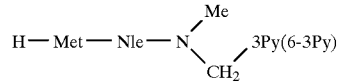 |
| | 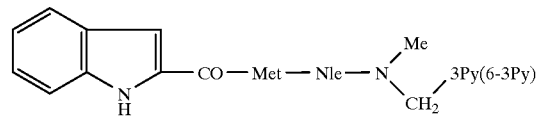 |
| 42-(7) | 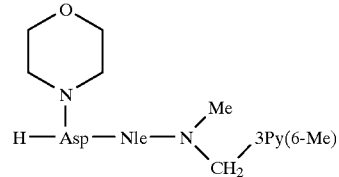 |
| | 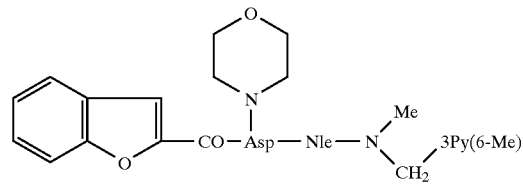 |
| 42-(8) | 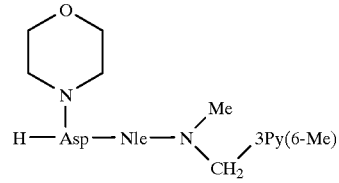 |

-continued
| Example No. | Formula |
|---|---|
| | 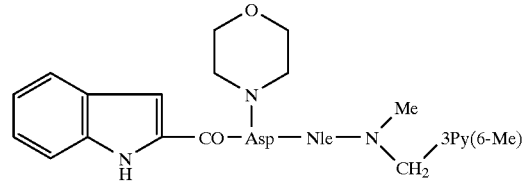 |
| 42-(9) | 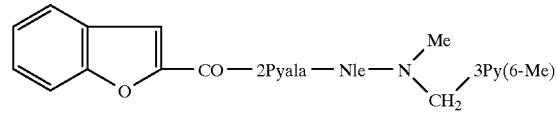 |
| | 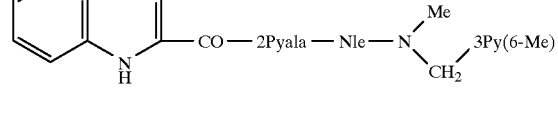 |
| 42-(10) | H—2Pyala—Nle—N(Me)(CH₂-3Py(6-Me)) |
| | 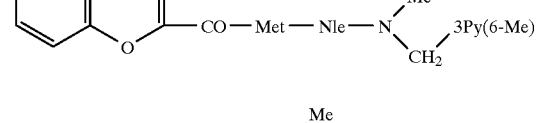 |
| 42-(11) | H—Met—Nle—N(Me)(CH₂-3Py(6-Me)) |
| | 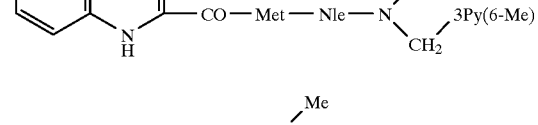 |
| 42-(12) | H—Met—Nle—N(Me)(CH₂-3Py(6-Me)) |
| | 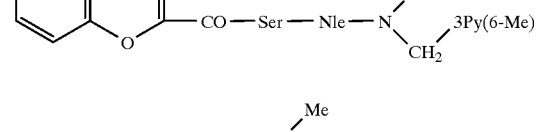 |
| 42-(13) | H—Ser—Nle—N(Me)(CH₂-3Py(6-Me)) |
| | (benzofuran-2-yl)CO—Ser—Nle—N(Me)(CH₂-3Py(6-Me)) |
| 42-(14) | H—Ser—Nle—N(Me)(CH₂-3Py(6-Me)) |

| Example No. | Formula |
|---|---|
| | 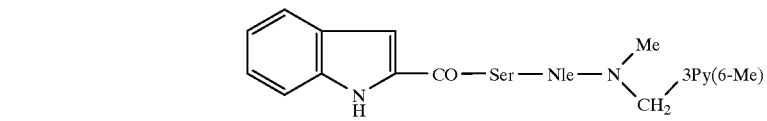 |
| 42-(15) | 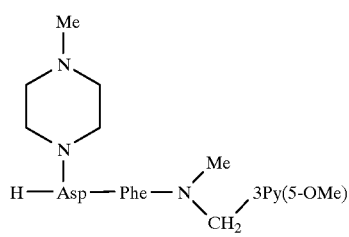 |
| | 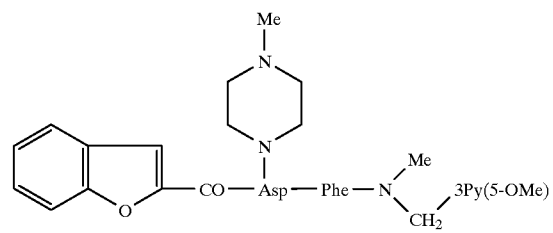 |
| 42-(16) | 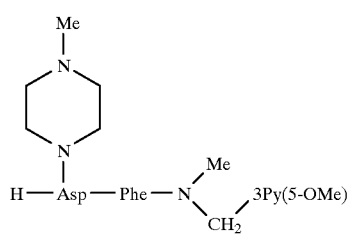 |
| | 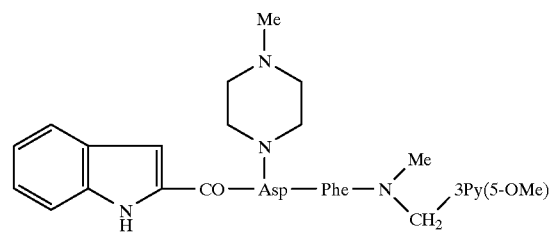 |
| 42-(17) | 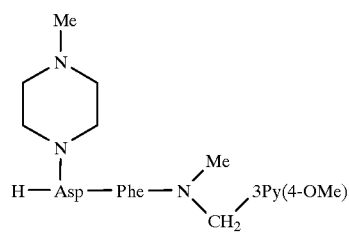 |
| | 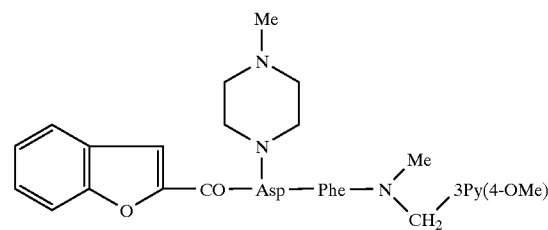 |

| Example No. | Formula |
|---|---|
| 42-(18) | 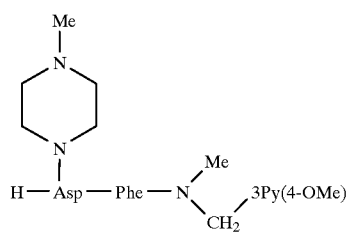 |
| | 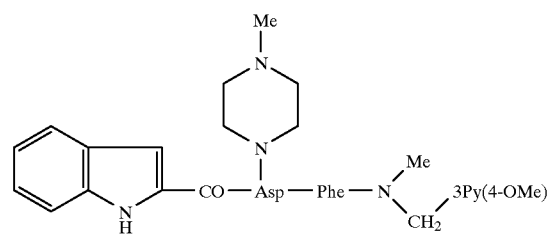 |
| 42-(19) | 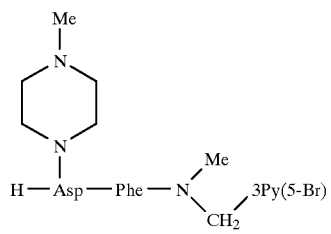 |
| | 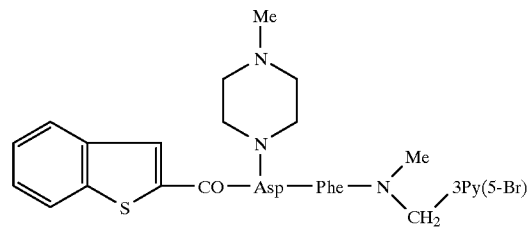 |
| 43 | 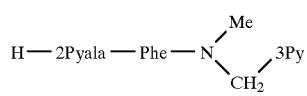 |
| | 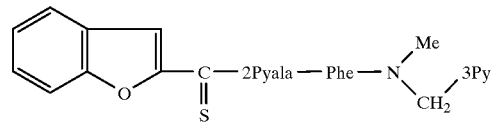 |
| 44-(1) | 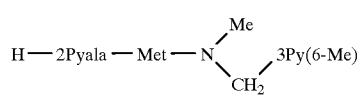 |
| | 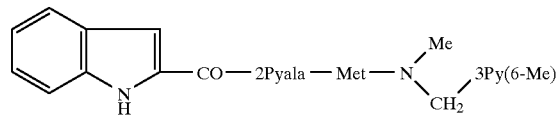 |

-continued
| Example No. | Formula |
|---|---|
| 44-(2) | 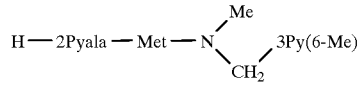<br>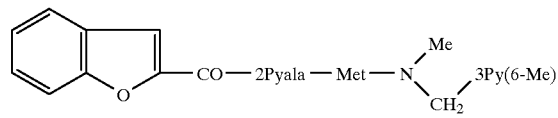 |
| 44-(3) | 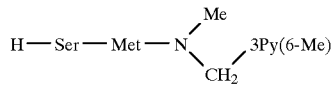<br>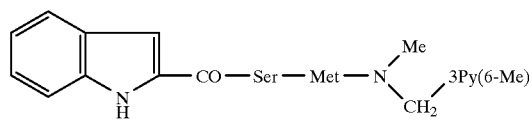 |
| 44-(4) | 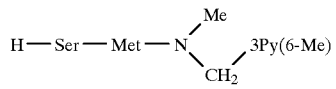<br>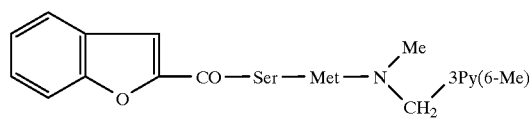 |
| 44-(5) | 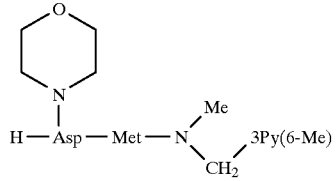<br>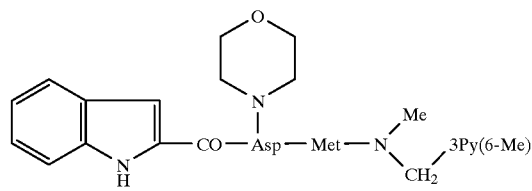 |
| 44-(6) | 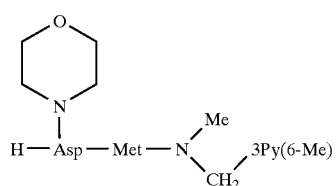<br>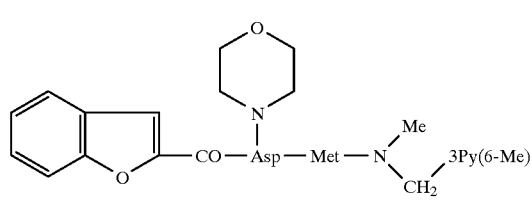 |

-continued

| Example No. | Formula |
|---|---|
| 44-(7) | H—Met—Met—N(Me)(CH₂-3Py(6-Me)) |
| | Indole-2-CO—Met—Met—N(Me)(CH₂-3Py(6-Me)) |
| 44-(8) | H—Met—Met—N(Me)(CH₂-3Py(6-Me)) |
| | Benzofuran-2-CO—Met—Met—N(Me)(CH₂-3Py(6-Me)) |

Preparation 1

Starting Compound (2.00 g), 1-methylpiperazine (414 mg), and 1-hydroxybenzotriazole (559 mg) were dissolved in methylene chloride (50 ml). The mixture was ice-cooled and 1-ethyl-3-(3-dimethylaminopropyl)carbodiimide hydrochloride (793 mg) was added thereto. The mixture was stirred at this temperature for 1 hour and at room temperature for 4 hours. The mixture was concentrated under vacuum and the residue was diluted in water and extracted with chloroform. The organic layer was washed with saturated sodium hydrogencarbonate solution and brine. After evaporation, the crude material obtained was purified on a column of silica gel eluting with chloroform-methanol (60:1) to give Object Compound (2.34 g) as an amorphous solid.

MASS (FAB) (m/z): 566 (M+H)$^+$; NMR (CDCl$_3$, δ): 1.42 (9H, s), 2.29 (3H, s), 2.32–2.47 (4H, m), 2.52 (3×⅔H, s), 2.55–2.61 (1H, m), 2.77 (3×⅓H, s), 2.95–3.10 (2H, m), 3.16–3.27 (1H, m), 3.42–3.50 (2H, m), 3.57–3.63 (2H, m), 4.07–4.32 (2×⅔H, m), 4.47–4.58 (1H, m), 4.62 (2×⅓H, d, J=15 Hz), 5.09–5.17 (1H, m), 6.00–6.07 (1H, m), 6.83–6.90 (1H, m), 7.00–7.05 (1H, m), 7.18–7.30 (8H, m), 7.40 (1×⅓H, d, J=8 Hz), 7.43 (1×⅔H, d, J=8 Hz)

Preparation 2

The following object compound was obtained according to a similar manner to that of Preparation 1.

Mass (FAB) (m/z): 553 (M+H)$^+$; NMR (CDCl$_3$, δ): 1.43 (9H, s), 2.50–2.62 (1H, m), 2.54 (3×⅔H, s), 2.79 (3×⅓H, s), 2.96–3.10 (2H, m), 3.15–3.25 (1H, m), 3.42–3.48 (2H, m), 3.58–3.62 (2H, m), 3.65–3.72 (4H, m), 4.04–4.33 (2×⅔H, m), 4.50–4.58 (1H, m), 4.62 (2×⅓H, d, J=15 Hz), 5.08–5.17 (1H, m), 6.00 (1H, d, J=8 Hz), 6.87–7.05 (2H, m), 7.18–7.27 (8H, m), 7.40 (1×⅓H, d, J=8 Hz), 7.46 (1×⅔H, d, J=8 Hz)

Preparation 3

Starting Compound (2.34 g) was dissolved in methylene chloride (20 ml) and the solution was ice-cooled. To this solution was added trifluoroacetic acid (10 ml). The mixture was stirred at this temperature for 10 minutes and at room temperature for 1 hour and was concentrated under reduced pressure. The residue was made alkaline with saturated sodium hydrogencarbonate solution and extracted with chloroform. The organic layer was washed with brine and evaporated under reduced pressure to give Object Compound (1.46 g) as an amorphous solid.

Mass (FAB) (m/z): 466 (M+H)$^+$; NMR (CDCl$_3$, δ): 2.23–2.50 (5H, m), 2.29 (3H, s), 2.63 (3×⅔H, s), 2.70–2.85 (1H, m), 2.87 (3×⅓H, s), 2.93–3.13 (2H, m), 3.39 (1H, t, J=5 Hz), 3.46 (1H, t, J=5 Hz), 3.52–3.73 (3H, m), 4.31–4.38 (2×⅔H, m), 4.67 (2×⅓H, d, J=15 Hz), 5.11–5.20 (1H, m), 6.94–7.13 (2H, m), 7.18–7.31 (8H, m), 8.04 (1×⅓H, d, J=8 Hz), 8.15 (1×⅔H, d, J=8 Hz)

Preparation 4

A mixture of Starting Compound (0.15 g) and trifluoroacetic acid (0.5 ml) was stirred at room temperature for 1 hour. Trifluoroacetic acid was removed under reduced pressure. The residue was dissolved in 10% hydrochloric acid-methanol (0.2 ml). Evaporation of solvent gave Object Compound (0.15 g) as powder.

NMR (CD$_3$OD, δ): 2.90 (3×⅔H, s), 2.97 (3H, s), 3.05 (3×⅓H, s), 3.03–3.16 (4H, m), 3.42–3.62 (8H, m), 4.27 (1H, m), 4.50–4.68 (2H, m), 5.46 (1H, t, J=7 Hz), 7.18–7.36 (5H, m), 7.83–8.04 (2H, m), 8.48 (1H, m), 8.76 (1H, d, J=6 Hz)

Preparation 5

The following object compounds were obtained according to a similar manner to that of Preparation 3 or 4.

(1) MASS (FAB) (m/z): 453 (M+H)$^+$; NMR (CDCl$_3$, δ): 2.43–2.53 (1H, m), 2.67 (3×⅔H, s), 2.71–2.83 (1H, m), 2.87 (3×⅓H, s), 2.93–3.13 (2H, m), 3.37–3.45 (2H, m), 3.54–3.73 (7H, m), 4.29–4.43 (2×⅔H, m), 4.68 (2×⅓H, d, J=15 Hz), 5.12–5.21 (1H, m), 6.95–7.15 (2H, m), 7.20–7.31 (8H, m), 8.07 (1×⅓H, d, J=8 Hz), 8.15 (1×⅔H, d, J=8 Hz)

(2) MASS (FAB) (m/z): 474 (M+H)$^+$; NMR (CDCl$_3$, δ): 2.42–2.63 (1H, m), 2.67 (3×⅔H, s), 2.81–2.91 (1H, m), 2.86 (3×⅓H, s), 2.95–3.15 (2H, m), 3.60–3.65 (1×⅓H, m), 3.70–3.74 (1×⅔H, m), 4.22–4.41 (2×⅔H, m), 4.67 (2×⅓H, d, J=15 Hz), 5.08–5.18 (3H, m), 6.96–7.29 (12H, m), 7.30–7.41 (3H, m), 8.00 (1×⅓H, d, J=8 Hz), 8.08 (1×⅔H, d, J=8 Hz)

(3) NMR (CDCl$_3$, δ): 2.36 (1H, dd, J=7, 15 Hz), 2.72–2.78 (2H, m), 2.95 (1H, dd, J=7, 15 Hz), 3.22 (3H, s), 3.37 (2H, m), 3.50–3.70 (7H, m), 4.77 (1H, q, J=7 Hz), 6.87 (2H, m), 6.93 (2H, m), 7.20–7.22 (4H, m), 7.31–7.34 (4H, m), 7.94 (1H, d, J=7 Hz)

(4) NMR (CD$_3$OD, δ): 2.91–3.00 (2H, m), 2.92 (3×⅓H, s), 3.03 (3×⅔H, s), 3.41–3.68 (10H, m), 4.24 (1H, m), 4.50–4.60 (2H, m), 5.42 (1H, m), 7.18–7.21 (2H, m), 7.29–7.36 (3H, m), 7.76–7.80 (2H, m), 8.28 (1H, m), 8.67 (1H, m)

(5) NMR (CD$_3$OD, δ): 2.87 (6×⅔H, s), 2.97 (3H, s), 2.98 (6×⅓H, s), 3.05–3.14 (4H, m), 3.22 (1H, m), 3.35 (1H, m), 3.49–3.74 (9H, m), 4.02 (1H, m), 4.27 (1H, m), 4.94 (1H, t, J=7 Hz), 7.27–7.36 (5H, m)

(6) NMR (CDCl$_3$, δ): 1.77 (1H, m), 2.18 (3H, s), 2.13–2.33 (3H, m), 2.49 (1H, dd, J=7, 15 Hz), 2.78 (1H, dd, J=3, 15 Hz), 3.00 (2H, d, J=7 Hz), 3.02 (1H, m), 3.33 (1H, m), 3.43 (2H, m), 3.52–3.72 (9H, m), 5.12 (1H, q, J=7 Hz), 7.19–7.31 (5H, m), 8.14 (1H, d, J=7 Hz)

(7) NMR (DMSO-d$_6$, δ): 1.11 (3H, t, J=7 Hz), 2.81–3.10 (4H, m), 4.03 (2H, q, J=7 Hz), 4.13 (1H, m), 4.52 (1H, q, J=7 Hz), 5.14 (1H, d, J=15 Hz), 5.19 (1H, d, J=15 Hz), 7.24–7.32 (5H, m), 7.37–7.41 (4H, m), 8.28 (3H, m), 8.94 (1H, d, J=8 Hz)

Preparation 6

To a stirred mixture of Starting Compound (2.00 g), 1-methylpiperazine (0.62 g) and 1-hydroxybenzotriazole (0.84 g) in methylene chloride (30 ml) was added 1-(3-dimethylaminopropyl)-3-ethylcarbodiimide hydrochloride (1.20 g) in some portions at 0° C. and the mixture was stirred at room temperature for 4 hours. The reaction mixture was washed with 5% aqueous sodium bicarbonate twice and dried. Evaporation of solvent gave a residue which was purified by silica gel column chromatography. Elution with chloroform~3% methanol-chloroform afforded Object Compound (2.50 g) as powder.

MASS (FAB) (m/z): 406 (M$^+$+1); NMR (CDCl$_3$, δ): 1.42 (9H, s), 2.30 (3H, s), 2.35 (4H, m), 2.77 (1H, dd, J=4, 16 Hz), 3.15 (1H, dd, J=4, 16 Hz), 3.42 (2H, t, J=5 Hz), 3.57 (2H, m), 4.60 (1H, m), 5.13 (1H, d, J=15 Hz), 5.22 (1H, d, J=15 Hz), 5.82 (1H, d, J=7 Hz), 7.33 (5H, m)

Preparation 7

The following object compound was obtained according to a similar manner to that of Preparation 6.

NMR (CDCl$_3$, δ): 1.44 (9H, s), 2.78 (1H, dd, J=4, 16 Hz), 3.11 (1H, dd, J=4, 16 Hz), 3.43 (2H, t, J=7 Hz), 3.58 (2H, m), 3.67 (4H, m), 3.76 (3H, s), 4.58 (1H, td, J=4, 7 Hz), 5.75 (1H, d, J=7 Hz)

Preparation 8

A mixture of Starting Compound (0.7 g) and trifluoroacetic acid (1.5 ml) was stirred at room temperature for 1 hour. Evaporation of trifluoroacetic acid gave a residue which was made alkaline with 1N aqueous sodium hydroxide and extracted with chloroform. The extract was washed with water and dried. Evaporation of solvent gave Object Compound (0.39 g).

NMR (CDCl$_3$, δ): 1.85 (1H, m), 2.22 (3H, s), 2.20–2.37 (3H, m), 2.80 (1H, dd, J=7, 12 Hz), 2.92 (1H, dd, J=7, 12 Hz), 3.09 (1H, m), 3.34 (1H, m), 3.60 (2H, m), 3.94 (1H, t, J=7 Hz), 7.17–7.32 (5H, m)

Preparation 9

The following object compounds were obtained according to a similar manner to that of Preparation 3, 4 or 8.

(1) NMR (CD$_3$OD, δ): 2.95 (3×⅓H, s), 2.97 (3×⅔H, s), 3.45–3.59 (2H, m), 4.50 (1H, d, J=15 Hz), 4.66 (1H, d, J=15 Hz), 5.02 (1H, m), 7.20–7.37 (5H, m), 7.75–7.82 (2H, m), 8.28 (1H, m), 8.71 (1H, d, J=4 Hz)

(2) NMR (CDCl$_3$, δ): 2.18 (6×⅖H, s), 2.26 (6×⅗H, s), 2.12–2.33 (1H, m), 2.40 (1H, t, J=7 Hz), 2.79 (3×⅗H, s), 2.77 (1H, m), 2.92 (3×⅖H, s), 2.94 (1H, m), 3.02 (1×⅖H, m), 3.23 (1×⅖H, m), 3.46 (2×⅗H, m), 3.87 (1×⅖H, t, J=7 Hz), 3.91 (1×⅗H, t, J=7 Hz), 7.19–7.32 (5H, m)

Preparation 10

A solution of Starting Compound (2.6 g) in methanol (50 ml) was hydrogenated over 10% palladium on carbon (0.7 g) at 4 kg/cm$^{-2}$ for 6 hours. The catalyst was filtered off and washed with methanol. The combined filtrate and washings were evaporated to give Object Compound (2.00 g) as powder.

MASS (FAB) (m/z): 316 (M$^+$+1); NMR (CDCl$_3$, δ): 1.42 (9H, s), 2.78 (3H, s), 2.82 (1H, m), 3.02–3.20 (5H, m), 3.83 (4H, m), 4.43 (1H, m), 5.89 (1H, d, J=7 Hz)

Preparation 11

To a stirred solution of Starting Compound (0.5 g) and triethylamine (0.24 ml) in N,N-dimethylformamide (6 ml) was added dropwise trimethylacetyl chloride (0.21 ml) at −10° C. and the mixture was stirred at 0° C. for 5 minutes. To this solution was added dropwise a solution of N-methylaniline (0.18 g) in N,N-dimethylformamide (1 ml) at −10° C. and the mixture was stirred at room temperature overnight. The reaction mixture was diluted with water and extracted with chloroform. The extract was washed with 1N aqueous hydrochloric acid and 5% aqueous sodium bicarbonate, and dried. Evaporation of solvent gave a residue which was chromatographed on silica gel. Elution with chloroform gave Object Compound (0.49 g).

MASS (FAB) (m/z): 389 (M$^+$+1); NMR (CDCl$_3$, δ): 2.72 (1H, dd, J=7, 12 Hz), 2.90 (1H, dd, J=7, 12 Hz), 3.20 (3H, s), 4.57 (1H, q, J=7 Hz), 5.00 (1H, d, J=15 Hz), 5.06 (1H, d, J=15 Hz), 5.43 (1H, d, J=7 Hz), 6.83–6.90 (4H, m), 7.21 (3H, m), 7.32–7.33 (8H, m)

Preparation 12

The following object compounds were obtained according to a similar manner to that of Preparation 1, 6 or 11.

(1) MASS (FAB) (m/z): 370 (M$^+$+1); NMR (CDCl$_3$, δ): 1.39 (9H, s), 2.87 (3×¼H, s), 2.95 (3×¾H, s), 3.06 (1H, dd, J=7, 14 Hz), 3.22 (1H, dd, J=7, 14 Hz), 4.40 (1H, d, J=15 Hz), 4.71 (1H, d, J=15 Hz), 5.14 (1H, m), 5.48 (1H, d, J=7 Hz), 7.14–7.16 (4H, m), 7.23–7.32 (3H, m), 7.55 (1H, m), 8.51 (1H, d, J=4 Hz)

(2) MASS (FAB) (m/z): 350 (M$^+$+1); NMR (CDCl$_3$, δ): 1.40 (9H, s), 2.16 (6×⅓H, s), 2.23 (6×⅔H, s), 2.10–2.37 (2H, m), 2.68 (3×⅔H, s), 2.88 (3×⅓H, s), 2.95 (2H, d, J=7 Hz), 2.97–3.12 (2×⅓H, m), 3.27–3.50 (2×⅔H, m), 4.80 (1H, m), 5.32 (1×⅓H, d, J=7 Hz), 5.38 (1×⅔H, d, J=7 Hz), 7.19–7.28 (5H, m)

(3) MASS (FAB) (m/z): 348 (M$^+$+1); NMR (CDCl$_3$, δ): 1.42 (9H, s), 1.75 (1H, m), 2.18 (3H, s), 2.14–2.32 (3H, m), 2.89–3.02 (3H, m), 3.26–3.34 (1H, m), 3.52–3.57 (2H, m), 4.82 (1H, m), 5.42 (1H, d, J=7 Hz), 7.17–7.30 (5H, m)

(4) MASS (FAB) (m/z): 406 (M$^+$+1); NMR (CDCl$_3$, δ): 1.43 (9H, s), 2.47 (1H, dd, J=7, 16 Hz), 2.80 (2H, t, J=7 Hz), 3.18 (1H, dd, J=4, 16 Hz), 3.35–3.70 (10H, m), 4.51 (1H, m), 6.03 (1H, d, J=7 Hz), 6.82 (1H, m), 7.18–7.32 (5H, m)

Preparation 13

To a stirred solution of Starting Compound (3.8 g) in methanol (30 ml) was added dropwise 1N aqueous sodium hydroxide (12 ml) at 0° C. and the mixture was stirred at room temperature for 4 hours. The reaction mixture was diluted with water and extracted with ether. The aqueous solution was acidified with 10% aqueous citric acid and extracted with chloroform 4 times and dried. Evaporation of solvent gave Object Compound (3.55 g) as powder.

NMR (CDCl$_3$, δ): 1.44 (9H, s), 2.70 (1H, dd, J=7, 16 Hz), 3.20 (1H, dd, J=4, 16 Hz), 3.48 (2H, m), 3.64–3.75 (6H, m), 4.55 (1H, dt, J=4, 7 Hz), 5.82 (1H, d, J=7 Hz)

Preparation 14

The following object compounds were obtained according to a similar manner to that of Preparation 1, 6 or 11.

(1) MASS (FAB) (m/z): 567 (M$^+$+1); NMR (CDCl$_3$, δ): 1.46 (9H, s), 2.29 (3H, s), 2.38 (4H, m), 2.55 (1H, dd, J=5, 15 Hz), 2.82 (3×⅓H, s), 2.90 (3×⅔H, s), 3.07–3.32 (3H, m), 3.45 (2H, m), 3.58 (2H, m), 4.25 (1H, m), 4.46–4.65 (2H, m), 4.79 (1H, dd, J=4, 15 Hz), 5.40 (1H, m), 6.03 (1H, m), 7.06–7.32 (6H, m), 7.51–7.62 (2H, m), 8.47 (1H, d, J=5 Hz)

(2) MASS (FAB) (m/z): 554 (M$^+$+1); NMR (CDCl$_3$, δ): 1.46 (9H, s), 2.82 (3×⅓H, s), 2.91 (3×⅔H, s), 3.07–3.33 (4H, m), 3.42 (2H, m), 3.56–3.67 (6H, m), 4.17 (1H, d, J=15 Hz), 4.28 (1H, d, J=15 Hz), 4.51 (1H, m), 4.79 (1H, m), 5.40 (1H, m), 6.02 (1H, m), 7.07–7.31 (6H, m), 7.51–7.62 (2H, m), 8.48 (1H, d, J=5 Hz)

(3) MASS (FAB) (m/z): 539 (M$^+$+1); NMR (CDCl$_3$, δ): 1.45 (9H, s), 2.53 (1H, dd, J=5, 15 Hz), 2.72 (1H, dd, J=7, 13 Hz), 2.93 (1H, dd, J=7, 13 Hz), 3.16 (3H, s), 3.16 (1H, m), 3.43 (2H, m), 3.57 (2H, m), 3.66 (4H, m), 4.52 (1H, m), 4.74 (1H, m), 5.97 (1H, d, J=7 Hz), 6.72 (1H, m), 6.97 (2H, m), 7.21–7.33 (7H, m)

(4) MASS (FAB) (m/z): 534 (M$^+$+1); NMR (CDCl$_3$, δ): 1.45 (9H, s), 2.13 (6×⅔H, s), 2.22 (6×⅓H, s), 2.28 (1H, m), 2.52 (1×⅔H, m), 2.58 (1×⅓H, m), 2.62 (3×⅓H, s), 2.85 (3×⅔H, s), 2.94–3.05 (3H, m), 3.16–3.29 (2H, m), 3.41–3.51 (3H, m), 3.59 (2H, m), 3.67 (4H, m), 4.51 (1H, m), 5.02 (1H, m), 5.98 (1H, d, J=7 Hz), 7.22–7.27 (5H, m), 7.35 (1×⅔H, d, J=7 Hz), 7.41 (1×⅓H, d, J=7 Hz)

(5) MASS (FAB) (m/z): 532 (M$^+$+1); NMR (CDCl$_3$, δ): 1.46 (9H, s), 1.70 (1H, m), 2.17 (3H, s), 2.11–2.19 (2H, m), 2.28 (1H, m), 2.55 (1H, dd, J=5, 16 Hz), 2.86–3.06 (3H, m), 3.18–3.28 (2H, m), 3.43–3.72 (10H, m), 4.53 (1H, m), 5.06 (1H, m), 6.00 (1H, d, J=7 Hz), 7.20–7.30 (5H, m), 7.42 (1H, d, J=7 Hz)

(6) NMR (CDCl$_3$, δ): 1.20 (3H, t, J=7 Hz), 1.42 (9H, s), 2.70 (1H, dd, J=7, 16 Hz), 3.08 (2H, d, J=7 Hz), 3.07 (1H, dd, J=4, 16 Hz), 4.13 (2H, q, J=7 Hz), 4.52 (1H, m), 4.77 (1H, q, J=7 Hz), 5.10 (1H, d, J=15 Hz), 5.15 (1H, d, J=15 Hz), 5.62 (1H, d, J=7 Hz), 6.93 (1H, d, J=7 Hz), 7.14 (2H, d, J=8 Hz), 7.23–7.35 (8H, m)

Preparation 15

The following object compound was obtained according to a similar manner to that of Preparation 1, 6 or 11.

MASS (FAB) (m/z): 360 (M$^+$+1); NMR (CDCl$_3$, δ): 2.88 (1H, dd, J=4, 16 Hz), 3.25 (1H, dd, J=4, 16 Hz), 3.42–3.45 (2H, m), 3.58–3.62 (2H, m), 3.65–3.69 (4H, m), 3.77 (3H, s), 5.13 (1H, dt, J=4, 7 Hz), 6.99 (1H, s), 7.14 (1H, t, J=8 Hz), 7.29 (1H, t, J=8 Hz), 7.42 (1H, d, J=8 Hz), 7.55 (1H, d, J=8 Hz), 7.66 (1H, d, J=8 Hz), 9.25 (1H, br s)

Preparation 16

The following object compound was obtained according to a similar manner to that of Preparation 13.

MASS (FAB) (m/z): 346 (M$^+$+1); NMR (CDCl$_3$, δ): 2.83 (1H, dd, J=7, 16 Hz), 3.33 (1H, m), 3.44 (2H, m), 3.65 (6H, m), 5.02 (1H, t, J=7 Hz), 7.04 (1H, s), 7.12 (1H, t, J=8 Hz), 7.27 (1H, t, J=8 Hz), 7.42 (1H, d, J=8 Hz), 7.64 (1H, d, J=8 Hz), 7.69 (1H, br s), 9.57 (1H, br s)

Preparation 17

The following object compound was obtained according to a similar manner to that of Preparation 10.

NMR (CDCl$_3$, δ): 2.59 (1H, dd, J=7, 14 Hz), 2.94 (1H, dd, J=7, 14 Hz), 3.22 (3H, s), 3.55 (1H, t, J=7 Hz), 6.82 (2H, m), 6.90 (2H, m), 7.20–7.22 (4H, m), 7.32–7.35 (4H, m)

Preparation 18

The following object compounds were obtained according to a similar manner to that of Preparation 3, 4 or 8.

(1) NMR (CD$_3$OD, δ): 2.77–2.92 (4H, m), 3.37–3.47 (3H, m 3.52–3.67 (7H, m), 4.13 (1H, t, J=7 Hz), 7.17–7.32 (5H, m)

(2) NMR (CD$_3$OD, δ): 3.03 (1H, dd, J=4, 16 Hz), 3.18 (1H, dd, J=7, 16 Hz), 3.50 (2H, t, J=7 Hz), 3.56(2H, t, J=7 Hz), 3.63–3.70 (4H, m), 3.82 (3H, s), 4.32 (1H, dd, J=4, 7 Hz)

Preparation 19

The following object compound was obtained according to a similar manner to that of Preparation 1, 6 or 11.

MASS (FAB) (m/z): 449 (M$^+$+1); NMR (CDCl$_3$, δ): 2.51 (1H, dd, J=7, 16 Hz), 2.79 (2H, t, J=7 Hz), 3.31 (1H, dd, J=4, 16 Hz), 3.36–3.60 (6H, m), 3.62–3.68 (4H, m), 5.03 (1H, dd, J=4, 7 Hz), 6.95 (1H, d, J=2 Hz), 7.03 (1H, t, J=7 Hz), 7.09–7.22 (5H, m), 7.32 (1H, t, J=8 Hz), 7.45 (1H, d, J=8 Hz), 7.67 (1H, d, J=8 Hz), 8.11 (1H, d, J=8 Hz), 9.43 (1H, br s)

Preparation 20

The following object compound was obtained according to a similar manner to that of Preparation 1, 6 or 11.

MASS (FAB) (m/z): 438 (M$^+$+1);

NMR (CDCl$_3$, δ): 2.47–2.65 (2H, m), 2.62 (3×⅔H, s), 2.67 (3×⅓H, s), 3.05 (4H, m), 3.48 (2H, m), 3.62–3.70 (6H, m), 4.17 (1×⅓H, d, J=15 Hz), 4.38 (1×⅔H, d, J=15 Hz), 4.45 (1×⅓H, d, J=15 Hz), 4.62 (1×⅔H, d, J=15 Hz), 5.17 (1H, m), 7.11–7.31 (11H, m)

Preparation 21

A mixture of Starting Compound (6.22 g), 1H-1,2,4-triazole (4.15 g), and potassium carbonate (8.29 g) in N,N-dimethylformamide (50 ml) was heated to 120° C. for 1.5 hours. The mixture was concentrated, thereto added water (150 ml), and extracted three times with ethyl acetate. The organic layer was washed with water, brine, and dried over magnesium sulfate. The solvent was evaporated, and the residue was passed through a short column of silica gel eluting with a mixture of methylene chloride and ethyl acetate. Evaporation of the solvent gave Object Compound as white crystals.

MASS (m/z): 174 (M+H)$^+$; NMR (CDCl$_3$, δ): 7.92 (2H, d, J=9 Hz), 8.06 (2H, d, J=9 Hz), 8.17 (1H, s), 8.69 (1H, s), 10.07 (1H, s)

Preparation 22

Starting Compound (5.19 g) was dissolved in 30% methylamine in methanol (30 ml), and heated to 60° C. for 1 hour.

Preparation 22 (continued)

Evaporation of the solvent gave a solid, and the solid was suspended in ethanol (150 ml), then cooled with ice. To this suspension was added sodium borohydride (1.13 g) in some portions and the mixture was stirred at room temperature for 1 hour. The mixture was concentrated, thereto added some water, and extracted five times with dichloromethane. The organic layer was washed with brine, and dried over potassium carbonate. Evaporation of the solvent, followed by distillation (bp 136–137° C./0.45 mmHg) afforded Object Compound as colorless prisms (4.00 g).

mp: 55–56° C.; MASS (m/z): 189 (M+H)$^+$; NMR (CDCl$_3$, δ): 2.46 (3H, s), 3.80 (2H, s), 7.46 (2H, d, J=8 Hz), 7.62 (2H, d, J=8 Hz), 8.10 (1H, s), 8.52 (1H, s)

Preparation 23

Starting Compound (729 mg) was dissolved in 30% methylamine in methanol (3 ml), and heated to 60° C. for 1.5 hours. Evaporation of the solvent gave an oil, and the residue was redissolved in ethanol (5 ml), then cooled with ice. To this solution was added sodium borohydride (204 mg) in some portions and the mixture was stirred at room temperature for 1 hour. After the mixture was concentrated, added aqueous sodium hydroxide, and extracted three times with chloroform. The organic layer was dried over magnesium sulfate and evaporated. The product was purified by column chromatography (silica gel) eluting with a mixture of chloroform and methanol to give Object Compound as a pale-yellow oil (316 mg).

MASS (m/z): 153 (M+H)$^+$; NMR (CDCl$_3$, δ): 2.45 (3H, s), 3.69 (2H, s), 3.92 (3H, s), 6.72 (1H, d, J=9 Hz), 7.58 (1H, dd, J=9, 2 Hz), 8.08 (1H, d, J=2 Hz)

Preparation 24

Object Compound was obtained according to a similar manner to that of Preparation 23.

MASS (m/z): 157 (M+H)$^+$; NMR (CDCl$_3$, δ): 2.46 (3H, s), 3.77 (2H, s), 7.71 (1H, s), 8.42 (1H, s), 8.48 (1H, s)

Preparation 25

A mixture of Starting Compound (3.0 g) and 30% methylamine-methanol (30 ml) was stirred at 60° C. for 2 hours. Evaporation of methanol gave a residue, which was redissolved in methanol (30 ml). To this mixture was added sodium borohydride (0.5 g) in some portions at 0° C. The mixture was stirred at room temperature for 30 minutes. The reaction mixture was made acidic with 1N hydrochloric acid and extracted with ether. The aqueous solution was made alkaline with 1N aqueous sodium hydroxide and extracted with chloroform. The extract was washed with water and dried. Evaporation of solvent gave Object Compound (2.4 g).

MASS (m/z): 190 (M$^+$+1); NMR (CDCl$_3$, δ): 2.45 (3H, s), 3.81 (2H, s), 7.43 (2H, d, J=8 Hz), 7.57 (2H, d, J=8 Hz)

Preparation 26

To an ice-cooled solution of di-tert-butyl dicarbonate (4.50 g) in dichloromethane (10 ml) was added Starting Compound (2.51 g), and the mixture was stirred at room temperature for 1 hour. The mixture was diluted with dichloromethane, washed with water, brine, and dried over magnesium sulfate. Evaporation of the solvent afforded Object Compound (4.51 g) as a pale-yellow crystal.

mp: 55–57° C.; MASS (m/z): 226 (M+H)$^+$; NMR (CDCl$_3$, δ): 1.45 (9H, s), 4.28 (2H, br d), 4.84 (1H, br s), 6.93–7.05 (2H, m), 7.20–7.30 (2H, m)

Preparation 27

To an ice-cooled suspension of Starting Compound (6.05 g) in dichloromethane (40 ml) was added triethylamine (5 ml). Di-tert-butyl dicarbonate (6.78 g) in dichloromethane (20 ml) was added thereto dropwise, and the mixture was stirred at room temperature for 8 hours. The mixture was washed twice with 10% citric acid, once with aqueous sodium hydrogencarbonate, once with brine, and dried over magnesium sulfate. Evaporation of the solvent gave Object Compound (7.89 g) as a white solid.

MASS (m/z): 266 (M+H)$^+$; NMR (CDCl$_3$, δ): 1.45 (9H, s), 3.89 (3H, s), 4.35 (2H, br s), 4.95 (1H, br s), 7.33 (2H, d, J=8 Hz), 7.98 (2H, d, J=8 Hz)

Preparation 28

To an ice-cooled suspension of sodium hydride (600 mg) in anhydrous tetrahydrofuran (10 ml) was added dropwise Starting Compound (4.51 g) in anhydrous tetrahydrofuran (10 ml) for 5 minutes. The mixture was heated to 60° C. for 2 hours. During the heating, the mixture turned into light yellow. After the mixture was allowed to cool to room temperature, iodomethane (4.56 g) was added thereto dropwise and heated to 30° C. for 2 hours. The reaction mixture was allowed to cool to room temperature. Water was added thereto, and the mixture was extracted three times with ether. The organic layer was washed with brine and dried over magnesium sulfate. After the solvent was evaporated, the residue was subjected to column chromatography (silica gel, hexane—ethyl acetate) to give Object Compound (3.09 g) as a colorless oil.

MASS (m/z): 240 (M+H)$^+$; NMR (CDCl$_3$, δ): 1.48 (9H, s), 2.80 (3H, s), 4.38 (2H, s), 6.92–7.05 (2H, m), 7.10–7.27 (2H, m)

Preparation 29

To an ice-cooled suspension of sodium hydride (0.86 g) in anhydrous tetrahydrofuran (30 ml) was added dropwise Starting Compound (7.89 g) in anhydrous tetrahydrofuran (15 ml) for 10 minutes. The mixture was heated to 40° C. for 2 hours. During the heating, the mixture turned into light yellow. After the mixture was allowed to cool to room temperature, iodomethane (5.02 g) was-added dropwise and heated to 40° C. for 2 hours. The reaction mixture was allowed to cool to room temperature. Water was added to the mixture, and the mixture was extracted three times with ether. The organic layer was washed with brine and dried over magnesium sulfate. After the solvent was evaporated, the residue was subjected to column chromatography (silica gel, hexane—ethyl acetate) to give Object Compound (5.21 g) as a colorless oil.

MASS (m/z): 280 (M+H)$^+$; NMR (CDCl$_3$, δ): 1.46 (9H, br s), 2.80 (½×2H, br s), 2.88 (½×2H, br s), 3.90 (3H, s), 4.47 (2H, br s), 7.28 (2H, d, J=8 Hz), 8.00 (2H, d, J=8 Hz)

Preparation 30

10% Hydrogen chloride in methanol (50 ml) was added to Starting Compound (7.56 g) and heated to 60° C. for 3 hours. The mixture was allowed to cool to room temperature. The white precipitate formed was collected by filtration and washed with ether. The product was recrystallized from ethanol-water (10:1) to give Object Compound (6.15 g).

NMR (D$_2$O, δ): 3.95 (3H, s), 4.28 (2H, s), 7.59 (2H, d, J=8 Hz), 8.11 (2H, d, J=8 Hz)

Preparation 31

Starting Compound (12.09 g), 37% formaldehyde solution (16.5 ml), and formic acid (9.1 ml) were mixed with ice-cooling and heated to 80° C. for 20 hours. After the mixture was allowed to cool to room temperature, 6N hydrochloric acid (20 ml) was added and washed with ether. The aqueous layer was adjusted to pH 6–7 by adding 28% aqueous ammonia and then concentrated. Acetone was added to the solution, and the white precipitate formed was filtered, washed with acetone and ether, and evaporated in vacuo to give Object Compound (4.34 g).

mp: >300° C. (dec.); NMR (D$_2$O): 2.89 (6H, s), 4.38 (2H, s), 7.57 (2H, d, J=8 Hz), 7.96 (2H, d, J=8 Hz)

Preparation 32

A mixture of Starting Compound (3.59 g), methylamine hydrochloride (1.36 g), and 1-ethyl-3-(3-dimethylaminopropyl)carbodiimide hydrochloride (4.22 g) in dichloromethane-N,N-dimethylformamide (1:1, 40 ml) was stirred at room temperature for 12 hours. The reaction mixture was diluted with ethyl acetate, washed with aqueous sodium hydrogencarbonate, with brine, and dried over magnesium sulfate. After the solvent was evaporated, the residue was subjected to column chromatography (silica gel chloroform-methanol) to give Object Compound as a colorless crystal (185 mg).

mp: 51–52° C.; MASS (m/z): 193 (M+H)$^+$; NMR (CDCl$_3$, δ): 2.50 (6H, s), 3.01 (3H, d, J=6 Hz), 3.48 (2H, s), 6.16 (1H, br s), 7.38 (2H, d, J=8 Hz), 7.72 (2H, d, J=8 Hz)

Preparation 33

To a suspension of lithium aluminum hydride (56 mg) in anhydrous tetrahydrofuran (2 ml) was added Starting Compound (180 mg) at 0° C. The mixture was heated to reflux for 1.5 hours. The mixture was allowed to cool to room temperature and diluted with ether. To this mixture was added water (56 mg), 15% aqueous sodium hydroxide (56 mg), and water (110 mg). Filtration followed by evaporation of the solvent afforded Object Compound (125 mg) as a colorless oil.

MASS (m/z): 179 (M+H)$^+$; NMR (CDCl$_3$, δ): 2.23 (6H, s), 2.45 (3H, s), 3.40 (2H, s), 3.73 (2H, s), 7.27 (4H, s)

Preparation 34

The following object compound was obtained according to a similar manner to that of Preparation 6.

MASS (FAB) (m/z): 478 (M+H)$^+$; NMR (CDCl$_3$, δ): 1.28 (3H, t, J=8 Hz), 1.39 (9H, s), 2.45–2.61 (4H, m), 2.76 (1H, dd, J=15, 5 Hz), 3.13 (1H, dd, J=15, 5 Hz), 3.20 (2H, s), 3.43–3.50 (2H, m), 3.60–3.64 (2H, m), 4.08–4.22 (2H, m), 4.56–4.62 (1H, m), 5.17 (2H, q, J=8 Hz), 5.80 (1H, d, J=8 Hz), 7.33 (5H, br s)

Preparation 35

The following object compound was obtained according to a similar manner to that of Preparation 10.

MASS (FAB) (m/z): 387 (M+H)$^+$; NMR (CDCl$_3$, δ): 1.26 (3H, t, J=8 Hz), 1.39 (9H, s), 2.50–3.90 (5H, m), 3.04–3.12 (1H, m), 3.23 (2H, s), 3.52–3.62 (3H, m), 3.68–3.80 (1H, m), 4.18 (2H, q, J=8 Hz), 4.38–4.50 (1H, m), 5.94 (1H, br s)

Preparation 36

Starting Compound (573 mg) was dissolved in a mixture of hydrochloric acid (1 ml) and methanol (5 ml), and stirred at 50° C. for 1 hour. The reaction mixture was evaporated and the remaining solid was dried in vacuo. To this solid was added dichloromethane (5 ml), Boc—Phe—OH (531 mg), 1-hydroxybenzotriazole (284 mg) and 1-ethyl-3-(3-dimethylaminopropyl)carbodiimide hydrochloride (416 mg), and the mixture was stirred at room temperature for 12 hours. The mixture was diluted with ethyl acetate, washed with aqueous sodium hydrogencarbonate, washed with brine, and dried over magnesium sulfate. Evaporation of the solvent followed by subjecting to column chromatography (silica gel, chloroform-methanol) afforded Object Compound (820 mg) as a colorless oil.

MASS (m/z): 427 (M+H)$^+$; NMR (CDCl$_3$, δ): 1.40 (9H, s), 2.63 (⅔×3H, s), 2.80 (⅓×3H, s), 3.0–3.1 (2H, m), 3.70 (⅓×3H, s), 3.90 (⅔×3H, s), 4.19 (⅓×1H, d, J=17 Hz), 4.38 (⅓×1H, d, J=17 Hz), 4.53 (⅔×2H, ABq, Δ=0.11, J=15 Hz), 4.8–4.9 (1H, m), 5.30 (⅓×1H, br d, J=8 Hz), 5.38 (⅔×1H, br d, J=8 Hz), 6.9–7.3 (7H, m), 7.9–8.0 (2H, m)

Preparation 37

The following object compound was obtained according to a similar manner to that of Preparation 36.

MASS (m/z): 387 (M+H)$^+$; NMR (CDCl$_3$, δ): 1.42 (9H, s), 2.61 (¾×3H, s), 2.79 (¼×3H, z), 2.93–3.03 (2H, m), 4.05 (¼×1H, d, J=17 Hz), 4.32 (¼×1H, d, J=17 Hz), 4.45 (¾×2H, ABq, Δ=0.12, J=15 Hz), 4.78–5.00 (1H, m), 5.30–5.45 (1H, m), 6.80–7.30 (9H, m)

Preparation 38

Starting Compound (4.09 g) was dissolved in tetrahydrofuran (45 ml) and cooled to −15° C. N-Methyl-morpholine (1.1 ml) and isobutylchloroformate (1.38 g) were added successively to the solution, and stirred at the temperature for 3 minutes. N-Methyl benzylamine (1.22 g) in tetrahydrofuran (5 ml) was added to the mixture, and the whole was stirred at 0° C. for 30 minutes. The reaction mixture was diluted with chloroform, washed with aqueous sodium hydrogencarbonate, washed with brine, and dried over magnesium sulfate. Evaporation of the solvent gave Object Compound (5.13 g) as white powder.

NMR (CDCl$_3$, δ): 1.40 (9H, s), 2.42 (3H, s), 2.72–3.04 (2H, m), 2.83 (⅓×3H, s), 2.88 (⅔×3H, s), 4.30–4.65 (2H, m), 4.85–5.04 (1H, m), 5.32–5.50 (1H, m), 7.00–7.95 (11H, m)

Preparation 39

The following object compounds were obtained according to a similar manner to that of Preparation 1, 6, 11 or 38.

(1) NMR (CDCl$_3$, δ): 1.40 (9H, s), 2.80 (¾×3H, s), 2.85 (¼×3H, s), 4.33 (¼×1H, d, J=15 Hz), 4.55 (¼×1H, d, J=15 Hz), 4.60 (¾×2H, ABq, Δ=0.10, J=14 Hz), 5.59 (¾×1H, d, J=8 Hz), 5.62 (¼×1H, d, J=8 Hz), 6.05 (1H, d, J=8 Hz), 6.9–7.4 (10H, m)

(2) MASS (m/z): 389 (M+H)$^+$; NMR (CDCl$_3$, δ): 2.93–3.22 (2H, m), 4.32 (2H, d, J=16 Hz), 4.33–4.47 (1H, m), 5.06 (2H, s), 5.33 (1H, br s), 5.92 (1H, br s), 6.98–7.41 (15H, m)

(3) MASS (m/z): 279 (M+H)$^+$; NMR (CDCl$_3$, δ): 1.43 (⅖×9H, s), 1.48 (⅗×9H, s), 2.88 (⅗×3H, s), 2.99 (⅖×3H, s), 3.95–4.08 (2H, m), 4.46 (⅖×2H, s), 4.61 (⅗×2H, s), 5.50–5.62 (1H, br s), 7.10–7.42 (5H, m)

(4) MASS (m/z): 399 (M+H)$^+$; NMR (CDCl$_3$, δ): 1.42 (9H, s), 2.60 (⅔×3H, s), 2.78 (⅓×3H, s), 2.95–3.02 (2H, m), 3.76 (⅓×3H, s), 3.79 (⅔×3H, s), 3.98 (⅓×1H, d, J=17 Hz), 4.30 (⅓×1H, d, J=17 Hz), 4.42 (⅔×2H, ABq, Δ=0.13, J=15 Hz), 4.8–5.0 (1H, m), 5.33 (⅓×1H, br d, J=9 Hz), 5.40 (⅔×1H, br d, J=9 Hz), 6.78 (⅓×2H, d, J=9 Hz), 6.80 (⅔×2H, d, J=9 Hz), 6.88 (⅓×2H, d, J=9 Hz), 7.03 (⅔×2H, d, J=9 Hz), 7.1–7.3 (5H, m)

(5) MASS (m/z): 475 (M+H)⁺; NMR (CDCl₃, δ): 1.40 (¼×9H, s), 1.43 (¾×9H, s), 2.60 (¾×3H, s), 2.81 (¼×3H, s), 2.88–2.98 (2H, m), 4.22 (¼×2H, ABq, Δ=0.24, J=17 Hz), 4.48 (¾×2H, ABq, Δ=0.13, J=15 Hz), 4.75–4.88 (1H, m), 5.01 (¾×2H, s), 5.05 (¼×2H, s), 5.26–5.44 (1H, m), 6.77–7.45 (14H, m)

(6) MASS (m/z): 383 (M+H)⁺; NMR (CDCl₃, δ): 1.42 (9H, s), 2.45–2.98 (4H, m), 2.60 (⅗×3H, s), 2.80 (⅖×3H, s), 3.10–3.63 (2H, m), 4.68–4.85 (1H, m), 5.25 (⅖×1H, br d, J=9 Hz), 5.35 (⅗×1H, br d, J=9 Hz), 7.02–7.32 (10H, m)

(7) MASS (m/z): 419 (M+H)⁺; NMR (CDCl₃, δ): 1.41 (9H, s), 2.66 (¾×3H, s), 2.87 (¼×3H, s), 3.02 (2H, m), 4.24 (¼×1H, d, J=17 Hz), 4.53 (¼×1H, d, J=17 Hz), 4.67 (¾×2H, ABq, Δ=0.09, J=15 Hz), 4.9–5.0 (1H, m), 5.40 (¼×1H, d, J=9 Hz), 5.46 (¾×1H, d, J=9 Hz), 7.0–7.3 (6H, m), 7.4–7.9 (6H, m)

(8) MASS (m/z): 419 (M+H)⁺; NMR (CDCl₃, δ): 1.38 (¼×9H, s), 1.43 (¾×9H, s), 2.60 (¾×3H, s), 2.90 (¼×3H, s), 2.93–3.08 (2H, m), 4.63 (¼×2H, ABq, Δ=0.20, J=17 Hz), 4.80–4.98 (1H, m), 5.00 (¾×2H, ABq, Δ=0.16, J=15 Hz), 5.32–5.50 (1H, m), 6.90–8.10 (12H, m)

(9) MASS (m/z): 411 (M⁺); NMR (CDCl₃, δ): 1.40 (9H, s), 2.59 (⅔×3H, s), 2.80 (⅓×3H, s), 2.93 (6H, s), 2.98 (2H, m), 3.95 (⅓×1H, d, J=17 Hz), 4.30 (⅓×1H, d, J=17 Hz), 4.39 (⅔×2H, ABq, Δ=0.08, J=15 Hz), 4.7–4.8 (⅔×1H, m), 4.9–5.0 (⅓×1H, m), 5.38 (⅓×1H, d, J=9 Hz), 5.43 (⅔×1H, d, J=9 Hz), 6.63 (2H, d, J=8 Hz), 6.8–7.3 (7H, m)

(10) MASS (m/z): 426 (M+H)⁺; NMR (CDCl₃, δ): 1.39 (⅓×9H, s), 1.42 (⅔×9H, s), 2.20 (⅓×6H, s), 2.22 (⅔×6H, s), 2.61 (⅔×3H, s), 2.82 (⅓×3H, s), 2.92–3.04 (2H, m), 3.37 (⅓×2H, s), 3.39 (⅔×2H, s), 4.08 (⅓×1H, d, J=17 Hz), 4.34 (⅓×1H, d, J=17 Hz), 4.48 (⅔×2H, ABq, Δ=0.10, J=15 Hz), 4.80–4.95 (1H, m), 5.30–5.45 (1H, m), 6.88–7.30 (9H, m)

(11) MASS (m/z): 381 (M+H)⁺; NMR (CDCl₃, δ): 1.42 (9H, s), 2.25–2.42 (1H, m), 2.65–2.80 (1H, m), 2.90–3.20 (2H, m), 3.48–3.90 (2H, m), 3.96 (⅓×1H, d, J=17 Hz), 4.48 (⅓×1H, d, J=17 Hz), 4.65 (⅔×2H, ABq, Δ=0.19, J=17 Hz), 4.85–5.00 (1H, m), 5.38–5.52 (1H, m), 6.80–7.22 (9H, m)

(12) mp: 100–101° C.; MASS (m/z): 403 (M+H)⁺; NMR (CDCl₃, δ): 1.43 (9H, s), 2.62 (¾×3H, s), 2.78 (¼×3H, s), 2.90–3.10 (2H, m), 4.19 (¼×2H, ABq, Δ=0.21, J=17 Hz), 4.45 (¾×2H, ABq, Δ=0.12, J=15 Hz), 4.78–4.92 (1H, m), 5.32 (¼×1H, d, J=9 Hz), 5.38 (¾×1H, d, J=9 Hz), 6.80–7.05 (2H, m), 7.09–7.32 (7H, m)

(13) MASS (m/z): 447, 449 (M+H)⁺; NMR (CDCl₃, δ): 1.42 (9H, s), 2.62 (¾×3H, s), 2.79 (¼×3H, s), 2.90–3.08 (2H, m), 4.17 (¼×2H, ABq, Δ=0.21, J=17 Hz), 4.42 (¾×2H, ABq, Δ=0.12, J=15 Hz), 4.78–4.93 (1H, m), 5.25–5.42 (1H, m), 6.73–7.00 (2H, m), 7.08–7.45 (7H, m)

(14) MASS (m/z): 400 (M+H)⁺; NMR (CDCl₃, δ): 1.40 (9H, s), 2.59 (¾×3H, s), 2.75 (¼×3H, s), 2.90–3.08 (2H, m), 3.90 (¼×3H, s), 3.93 (¾×3H, s), 4.34 (¼×2H, ABq, Δ=0.10, J=17 Hz), 4.40 (¾×2H, ABq, Δ=0.11, J=15 Hz), 4.74–5.05 (1H, m), 5.30–5.45 (1H, m), 6.55–6.70 (1H, m), 7.03–7.38 (6H, m), 7.80–8.00 (1H, m)

(15) NMR (CDCl₃, δ): 0.95 (⅗×3H, t, J=7.5 Hz), 1.02 (⅖×3H, t, J=7.5 Hz), 1.40 (⅖×9H, s), 1.42 (⅗×9H, s), 2.85–3.55 (4H, m), 4.19 (⅖×2H, ABq, Δ=0.18, J=17 Hz), 4.33 (⅗×1H, d, J=15 Hz), 4.73 (⅗×1H, d, J=15 Hz), 4.75–4.92 (1H, m), 5.25–5.42 (1H, m), 6.93–7.35 (10H, m)

(16) MASS (m/z): 404 (M+H)⁺; NMR (CDCl₃, δ): 1.42 (9H, s), 2.63 (⅚×3H, s), 2.76 (⅙×3H, s), 2.88–3.09 (2H, m), 4.04 (⅙×1H, d, J=17 Hz), 4.30 (⅙×1H, d, J=17 Hz), 4.44 (⅚×2H, ABq, Δ=0.08, J=15 Hz), 4.76–4.92 (1H, m), 5.22–5.38 (1H, m), 7.03–7.40 (7H, m), 8.05 (⅙×1H, d, J=2 Hz), 8.18 (⅚×1H, d, J=2 Hz)

(17) MASS (m/z): 384 (M+H)⁺; NMR (CDCl₃, δ): 1.42 (9H, s), 2.51 (⅕×3H, s), 2.53 (⅘×3H, s), 2.60 (⅘×3H, s), 2.78 (⅕×3H, s), 2.90–3.06 (2H, m), 3.98 (⅕×1H, d, J=17 Hz), 4.32 (⅕×1H, d, J=17 Hz), 4.44 (⅘×2H, ABq, Δ=0.06, J=15 Hz), 4.75–4.98 (1H, m), 5.25–5.42 (1H, m), 6.98–7.33 (7H, m), 8.18 (⅕×1H, d, J=2 Hz), 8.31 (⅘×1H, d, J=2 Hz)

(18) MASS (m/z): 436 (M+H)⁺; NMR (CDCl₃, δ): 1.42 (9H, s), 2.67 (¾×3H, s), 2.82 (¼×3H, s), 2.95–3.07 (2H, m), 4.26 (¼×2H, ABq, Δ=0.22, J=17 Hz), 4.53 (¾×2H, s), 4.82–4.95 (1H, m), 5.28–5.42 (1H, m), 7.00–7.32 (7H, m), 7.50–7.62 (2H, m), 8.10 (1H, s), 8.52 (1H, s)

(19) MASS (m/z): 404 (M+H)⁺; NMR (CDCl₃, δ): 1.42 (9H, s), 2.61 (⅚×3H, s), 2.78 (⅙×3H, s), 2.92–3.08 (2H, m), 3.96 (⅙×1H, d, J=17 Hz), 4.38 (⅙×1H, d, J=17 Hz), 4.47 (⅚×2H, ABq, Δ=0.07, J=15 Hz), 4.76–4.92 (1H, m), 5.25–5.40 (1H, m), 7.10–7.35 (5H, m), 7.50 (1H, s), 8.12 (⅙×1H, s), 8.28 (⅚×1H, s), 8.48 (1H, s)

(20) MASS (m/z): 370 (M+H)⁺; NMR (CDCl₃, δ): 1.38 (⅓×9H, s), 1.42 (⅔×9H, s), 2.77 (⅔×3H, s), 2.89 (⅓×3H, s), 2.90–3.10 (2H, m), 4.38 (⅓×2H, ABq, Δ=0.10, J=17 Hz), 4.61 (⅔×2H, s), 4.81–4.97 (1H, m), 5.25–5.44 (1H, m), 6.87–7.67 (8H, m), 8.43–8.57 (1H, m)

(21) MASS (m/z): 370 (M+H)⁺; NMR (CDCl₃, δ): 1.39 (¼×9H, s), 1.42 (¾×9H, s), 2.69 (¾×3H, s), 2.82 (¼×3H, s), 2.90–3.12 (2H, m), 4.28 (¼×2H, s), 4.48 (¾×2H, ABq, Δ=0.06, J=15 Hz), 4.68–4.98 (1H, m), 5.20–5.40 (1H, m), 6.73–7.35 (7H, m), 8.40–8.52 (2H, m)

(22) MASS (m/z): 370 (M+H)⁺; NMR (CDCl₃, δ): 1.40 (⅕×9H, s), 1.42 (⅘×9H, s), 2.63 (⅘×3H, s), 2.79 (⅕×3H, s), 2.92–3.06 (2H, m), 4.08 (⅕×1H, d, J=17 Hz), 4.35 (⅕×1H, d, J=17 Hz), 4.49 (⅘×2H, ABq, Δ=0.09, J=15 Hz), 4.79–4.98 (1H, m), 5.28–5.42 (1H, m), 7.10–7.35 (7H, m), 8.28 (⅕×1H, s), 8.42 (⅘×1H, s), 8.50–8.55 (1H, m)

(23) MASS (m/z): 399 (M⁺+1); NMR (CDCl₃, δ): 1.43 (9H, s), 2.59 (3H×⅔, s), 2.78 (3H×⅓, s), 2.98 (2H, d, J=7 Hz), 3.78 (3H, s), 3.99 (1H×⅓, d, J=15 Hz), 4.31 (1H×⅓, d, J=15 Hz), 4.35 (1H×⅔, d, J=15 Hz), 4.48 (1H×⅔, d, J=15 Hz), 4.83 (1H, m), 5.40 (1H, m), 6.80–7.04 (4H, m), 7.16–7.25 (5H, m)

(24) MASS (ESI)(m/z): 383 (M+H)⁺; NMR (CDCl₃, 1δ): 1.42 (9H, s), 2.32 (3H, s), 2.59 (3×⅔H, s), 2.83 (3×⅓H, s), 2.90–3.06 (2H, m), 4.02–4.53 (2H, m), 4.82–4.96 (1H, m), 5.40–5.50 (1H, m), 6.88 (2×⅓H, d, J=8 Hz), 6.99 (2×⅔H, d, J=8 Hz), 7.05–7.10 (2H, m), 7.13–7.30 (5H, m)

(25) MASS (m/z): 309 (M⁺+1); NMR (CDCl₃, δ): 1.38 (9H×⅓, s), 1.45 (9H×⅔, s), 2.93 (3H×⅓, s), 3.05 (3H×⅔, s), 3.26 (1H×⅔, m), 3.44 (1H×⅓, m), 3.67–3.88 (2H, m), 4.60–4.71 (3H, m), 5.70 (1H, m), 7.17–7.38 (5H, m)

(26) MASS (m/z): 335 (M⁺+1); NMR (CDCl₃, δ): 0.84 (6H×²⁄₇, t, J=7 Hz), 0.94 (3H×⅝, d, J=7 Hz), 1.00 (3H×⁵⁄₇, d, J=7 Hz), 1.45 (9H, s), 1.34–1.76 (3H, m), 2.92 (3H×⅔, s), 2.97 (3H×⅖, s), 4.48 (1H×⁵⁄₇, d, J=15 Hz), 4.67 (1H×⁵⁄₇, d, J=15 Hz), 4.65–4.72 (2H×⅔, m), 5.19 (1H×⅔, d, J=7 Hz), 5.28 (1H×⅝, d, J=7 Hz), 7.20–7.34 (5H, m)

(27) MASS (m/z): 437 (M⁺+1); NMR (CDCl₃, δ): 1.40 (9H×⅓, s), 1.45 (9H×⅔, s), 2.67 (3H×⅔, s), 2.83 (3H×⅓, s), 3.02 (2H, d, J=8 Hz), 4.22 (1H×⅓, d, J=15 Hz), 4.37 (1H×⅓, d, J=15 Hz), 4.50 (1H×⅔, d, J=15 Hz), 4.58 (1H×⅔, d, J=15 Hz), 4.90 (1H, m), 5.36 (1H, m), 7.02–7.28 (7H, m), 7.53 (2H, d, J=8 Hz)

(28) MASS (m/z): 369 (M⁺+1); NMR (CDCl₃, δ): 1.42 (9H, s), 2.62 (3H×⅔, s), 2.82 (3H×⅓, s), 3.00 (2H, d, J=7

Hz), 4.11 (1H×⅓, d, J=15 Hz), 4.36 (1H×⅓, d, J=15 Hz), 4:43 (1H×⅔, d, J=15 Hz), 4.54 (1H×⅔, d, J=15 Hz), 4.86 (1H, m), 5.41 (1H, m), 6.96–7.28 (10H, m)

Preparation 40

Starting Compound (801 mg) was dissolved in dichloromethane (10 ml). Boron tribromide solution in dichloromethane (0.43 ml) was added to the above solution at room temperature, and the whole was stirred at the same temperature for 12 hours. Water (5 ml) was added to the mixture and stirred for 30 minutes. The mixture was neutralized by adding aqueous sodium hydrogencarbonate and then extracted three times with chloroform. The organic layer was dried over potassium carbonate. Evaporation of the solvent gave Object Compound (406 mg) as an oil.

MASS (m/z): 285 (M+H)$^+$; NMR (CDCl$_3$, δ): 2.74 (⅔×3H, s), 2.75–2.85 (1H, m), 2.90 (⅓×3H, s), 3.00–3.10 (1H, m), 3.92 (⅓×1H, d, J=17 Hz), 3.95–4.05 (1H, m), 4.10 (⅔×1H, d, J=15 Hz), 4.34 (⅓×1H, d, J=17 Hz), 4.82 (⅔×1H, d, J=15 Hz), 6.60–7.35 (9H, m)

Preparation 41

Starting Compound (2.56 g) was dissolved in dichloromethane (5 ml) and cooled to 0° C. Trifluoroacetic acid (5 ml) was added to the solution and the mixture was stirred at 0° C. for 3 hours. Aqueous sodium hydroxide was added to the solution with ice-cooling to make basic, and the solution was extracted three times with chloroform. The organic layer was washed with brine and dried over magnesium sulfate. Evaporation of the solvent gave Object Compound (2.02 g) as an oil.

MASS (m/z): 413 (M+H)$^+$; NMR (CDCl$_3$, δ): 2.43 (3H, s), 2.61–2.75 (1H, m), 2.80–2.95 (4H, m), 3.98–4.18 (1H, m), 4.33 (⅓×1H, d, J=17 Hz), 4.57 (⅔×2H, ABq, Δ=0.16, J=15 Hz), 4.61 (⅓×1H, d, J=17 Hz), 7.00–7.43 (11H, m), 7.75–7.97 (3H, m)

Preparation 42

The following object compounds were obtained according to a similar manner to- that of Preparation 31 4 or 8.

(1) MASS (m/z): 255 (M+H)$^+$; NMR (CDCl$_3$, δ): 2.75 (⅔×3H, s), 2.95 (⅓×3H, s), 4.22 (⅓×1H, d, J=17 Hz), 4.58 (⅓×1H, d, J=17 Hz), 4.63 (⅔×2H, ABq, Δ=0.09, J=15 Hz), 4.74 (⅓×1H, s), 4.77 (⅔×3H, s), 6.92–7.45 (10H, m)

(2) NMR (CDCl$_3$, δ): 2.70 (⅗×3H, s), 2.72–2.85 (1H, m), 2.89 (⅖×3H, s), 2.93 (⅗×6H, s), 2.95–3.05 (1H, m), 3.90–4.00 (1H, m), 4.08 (⅖×1H, d, J=17 Hz), 4.35 (⅖×1H, d, J=17 Hz), 4.48 (⅗×2H, ABq, Δ=0.11, J=15 Hz), 6.62–7.33 (9H, m)

(3) MASS (m/z): 326 (M+H)$^+$; NMR (CDCl$_3$, δ): 2.23 (6H, s), 2.71 (⅗×3H, s), 2.72–2.85 (1H, m), 2.91 (⅖×3H, s), 2.92–3.05 (1H, m), 3.41 (2H, s), 3.88 (⅖×1H, t, J=7 Hz), 3.97 (⅗×1H, t, J=7 Hz), 4.28 (⅖×2H, ABq, Δ=0.21, J=17 Hz), 4.55 (⅗×2H, ABq, Δ=0.16, J=15 Hz), 6.95–7.34 (9H, m)

(4) MASS (m/z): 281 (M+H)$^+$; NMR (CDCl$_3$, δ): 2.42–3.06 (4H, m), 3.22–3.88 (2H, m), 3.97–4.05 (1H, m), 4.14 (⅓×1H, d, J=17 Hz), 4.52 (⅓×1H, d, J=17 Hz), 4.71 (⅔×2H, ABq, Δ=0.12, J=17 Hz), 6.88–7.32 (9H, m)

(5) MASS (m/z): 303 (M+H)$^+$; NMR (CDCl$_3$, δ): 2.70 (¾×3H, s), 2.73–3.08 (2H, m), 2.89 (¼×3H, s), 3.80–4.02 (1H, m), 4.25 (¼×2H, ABq, Δ=0.17, J=17 Hz), 4.50 (¾×2H, ABq, Δ=0.21, J=15 Hz), 6.88–7.34 (9H, m)

(6) MASS (m/z): 347, 349 (M+H)$^+$; NMR (CDCl$_3$, δ): 2.70 (¾×3H, s), 2.73–3.08 (2H, m), 2.89 (¼×3H, s), 3.79–4.02 (1H, m), 4.23 (¼×2H, ABq, Δ=0.17, J=17 Hz), 4.39 (¾×1H, d, J=15 Hz), 4.59 (¾×1H, d, J=15 Hz), 6.82–7.45 (9H, m)

(7) MASS (m/z): 287 (M+H)$^+$; NMR (CDCl$_3$, δ): 2.70 (¾×3H, s), 2.73–3.08 (2H, m), 2.88 (¼×3H, s), 3.84–4.02 (1H, m), 4.25 (¼×2H, ABq, Δ=0.20, J=17 Hz), 4.52 (¾×2H, ABq, Δ=0.20, J=17 Hz), 6.90–7.35 (9H, m)

(8) MASS (m/z): 300 (M+H)$^+$; NMR (CDCl$_3$, δ): 2.69 (¾×3H, s), 2.74–3.10 (2H, m), 2.87 (¼×3H, s), 3.88–3.98 (1H, m), 3.93 (3H, s), 4.20 (¼×2H, ABq, Δ=0.25, J=17 Hz), 4.44 (¾×2H, ABq, Δ=0.20, J=15 Hz), 6.64–6.72 (1H, m), 7.10–7.45 (8H, m), 7.85–8.02 (1H, m)

(9) MASS (m/z): 283 (M+H)$^+$; NMR (CDCl$_3$, δ): 1.03 (½×3H, t, J=7 Hz), 1.07 (½×3H, t, J=7 Hz), 2.70–3.25 (3H+½×1H, m), 3.50–3.97 (1H+½×1H, m), 4.22 (½×2H, ABq, Δ=0.13, J=17 Hz), 4.33 (½×1H, d, J=15 Hz), 4.80 (½×1H, d, J=15 Hz), 7.00–7.39 (10H, m)

(10) MASS (m/z): 303 (M+H)$^+$; NMR (CDCl$_3$, δ): 2.49 (⅚×3H, s), 2.72 (⅙×3H, s), 2.98–3.23 (2H, m), 3.70 (⅙×1H, d, J=17 Hz), 4.23 (⅙×1H, d, J=17 Hz), 4.40 (1H, t, J=7 Hz), 4.42 (⅚×2H, ABq, Δ=0.07, J=15 Hz), 7.08–7.52 (7H, m), 8.06 (⅙×1H, d, J=2 Hz), 8.20 (⅚×1H, d, J=2 Hz)

(11) MASS (m/z): 284 (M+H)$^+$; NMR (CDCl$_3$, δ): 2.53 (3H, s), 2.70 (¾×3H, s), 2.73–3.08 (2H, m), 2.88 (¼×3H, s), 3.84–4.02 (1H, m), 4.12 (¼×1H, d, J=17 Hz), 4.37 (¼×1H, d, J=17 Hz), 4.51 (¾×2H, ABq, Δ=0.17, J=15 Hz), 7.02–7.45 (7H, m), 8.26 (¼×1H, s), 8.34 (¾×1H, s)

(12) MASS (m/z): 336 (M+H)$^+$; NMR (CDCl$_3$, δ): 2.72 (⅔×3H, s), 2.72–3.10 (2H, m), 2.91 (⅓×3H, s), 3.88 (⅓×1H, t, J=7 Hz), 4.01 (⅔×1H, t, J=7 Hz), 4.34 (⅓×2H, ABq, Δ=0.17, J=17 Hz), 4.60 (⅔×2H, ABq, Δ=0.16, J=15 Hz), 7.08–7.37 (7H, m), 7.53–7.65 (2H, m), 8.09 (1H, s), 8.52 (1H, s)

(13) MASS (m/z): 304 (M+H)$^+$; NMR (CDCl$_3$, δ): 2.70 (⅚×3H, s), 2.78–3.08 (2H, m), 2.88 (⅙×3H, s), 3.84 (⅙×1H, t, J=7 Hz), 3.97 (⅚×1H, t, J=7 Hz), 4.28 (⅙×2H, ABq, Δ=0.22, J=17 Hz), 4.52 (⅚×2H, ABq, Δ=0.24, J=15 Hz), 7.10–7.36 (5H, m), 7.54 (1H, s), 8.22 (⅙×1H, s), 8.32 (⅚×1H, s), 8.50 (1H, s)

(14) MASS (m/z): 270 (M+H)$^+$; NMR (CDCl$_3$, δ): 2.71 (¾×3H, s), 2.76–3.10 (2H, m), 2.88 (¼×3H, s), 3.82–4.02 (1H, m), 4.28 (¼×2H, ABq, Δ=0.20, J=17 Hz), 4.55 (¾×2H, ABq, Δ=0.21, J=15 Hz), 7.11–7.55 (7H, m), 8.32–8.58 (2H, m)

(15) NMR (CDCl$_3$, δ): 2.69 (3H×⅔, s), 2.78 (1H, m), 2.89 (3H×⅓, s), 2.97 (1H, m), 3.78 (3H, s), 3.93 (1H, m), 4.10 (1H×⅓, d, J=15 Hz), 4.35 (1H×⅓, d, J=15 Hz), 4.40 (1H×⅔, d, J=15 Hz), 4.57 (1H×⅔, d, J=15 Hz), 6.81–6.85 (2H, m), 6.94–7.29 (7H, m)

(16) MASS (ESI) (m/z): 283 (M+H)$^+$; NMR (CDCl$_3$, δ): 2.32 (3H, s), 2.68 (3×⅔H, s), 2.73–2.81 (1H, m), 2.89 (3×⅓H, s), 2.94–3.02 (1H, m), 3.82–4.00 (1H, m), 4.12 (2×¼H, d, J=16 Hz), 4.37 (2×¼H, d, J=16 Hz), 4.43 (2×¼H, d, J=15 Hz), 4.58 (2×¼H, d, J=15 Hz), 6.92 (1H, d, J=8 Hz), 7.02–7.31 (8H, m)

(17) NMR (CDCl$_3$, δ): 2.68 (3H×²⁄₇, s), 2.85 (3H×⁵⁄₇, s), 3.92–4.61 (4H, m), 4.86 (1H, br s), 7.11–7.20 (5H, m), 8.30 (2H, br s)

(18) NMR (CDCl$_3$, δ): 0.86 (6H×⅖, t, J=7 Hz), 0.96 (3H×⁷⁄₁₀, d, J=7 Hz), 1.02 (3H×⁷⁄₁₀, d, J=7 Hz), 1.52 (1H, m), 2.05 (2H, m), 2.86 (3H×⅓, s), 2.91 (3H×⅔, s), 3.95 (2H×½, s), 4.20 (1H×½, d, J=15 Hz), 4.62 (1H, m), 4.85 (1H×½, d, J=15 Hz), 7.18–7.34 (5H, m), 8.57 (2H, br s)

(19) NMR (CDCl$_3$, δ): 2.53 (3H×⅕, s), 2.80 (3H×⅕, s), 3.06 (1H, dd, J=8, 13 Hz), 3.32 (1H, dd, J=6, 13 Hz), 3.77

(1H×⅕, d, J=15 Hz), 4.31 (1H×⅕, d, J=15 Hz), 4.54 (2H×⅘, s), 4.68 (1H, dd, J=6, 8 Hz), 7.10–7.39 (7H, m), 7.56 (2H, t, J=8 Hz)

(20) NMR (CDCl₃, δ): 2.37 (3H×¾, s), 2.65 (3H×¼, s), 3.22 (1H, m), 3.60 (1H, m), 3.60 (1H×¼, d, J=16 Hz), 4.11 (1H×¾, d, J=15 Hz), 4.28 (1H×¼, d, J=16 Hz), 4.67 (1H×¾, d, J=15 Hz), 4.89 (1H, m), 6.98–7.26 (10H, m), 8.77 (2H, br s)

Preparation 43

The following object compounds were obtained according to a similar manner to that of Preparation 10.

(1) MASS (m/z): 482 (M⁺−1); NMR (CDCl₃, δ): 1.45 (9H, s), 2.60 (3H×⅔, s), 2.78 (3H×⅓, s), 2.72–3.16 (4H, m), 4.21 (1H×⅔, d, J=15 Hz), 4.23 (1H×⅓, d, J=15 Hz), 4.31 (1H×⅓, d, J=15 Hz), 4.52 (1H, m), 4.67 (1H×⅔, d, J=15 Hz), 5.22 (1H, m), 6.17 (1H, m), 6.82–7.25 (10H, m), 7.99 (1H, d, J=8 Hz)

(2) MASS (m/z): 484 (M⁺+1); NMR (CDCl₃, δ): 1.47 (9H, s), 2.62 (1H, m), 2.69 (3H×⅔, s), 2.78 (3H×⅓, s), 2.93–3.05 (3H, m), 4.23–4.33 (1H, m), 4.48–4.62 (2H, m), 5.14 (1H, m), 5.92–6.01 (1H, m), 6.92 (2H, m), 7.06 (1H, m), 7.18–7.22 (7H, m), 7.83–7.94 (1H, m)

Preparation 44

1-tert-Butoxycarbonyl-4-ethylpiperazine (477 mg) was dissolved in a mixture of hydrochloric acid (1 ml) and methanol (2 ml), and heated to reflux for 3 hours. The reaction mixture was allowed to cool to room temperature, evaporated, and dried in vacuo to give a white solid. To this solid was added dichloromethane (5 ml), Starting Compound (972 mg), 1-hydroxybenzotriazole (278.1 mg), and triethylamine (0.3 ml). The mixture was cooled in ice, added 1-ethyl-3-(3-dimethylaminopropyl)carbodiimide hydrochloride (360 mg), then stirred at room temperature for 12 hours. The reaction mixture was diluted with ethyl acetate, washed with aqueous sodium hydrogencarbonate, washed with brine, and dried over magnesium sulfate. Evaporation of the solvent followed by subjecting to column chromatography (silica gel, chloroform-methanol) afforded Object Compound (961 mg) as a white powder.

MASS (m/z): 580 (M+H)⁺; NMR (CDCl₃, δ): 1.09 (3H, t, J=7 Hz), 1.48 (9H, s), 2.34–2.65 (7H, m), 2.54 (⅔×3H, s), 2.78 (⅓×3H, s), 2.93–3.30 (3H, m), 3.40–3.68 (4H, m), 4.18 (⅓×2H, ABq, Δ=0.17, J=17 Hz), 4.30 (⅔×1H, d, J=15 Hz), 4.45–4.60 (1H, m), 4.62 (⅔×1H, d, J=15 Hz), 5.08–5.20 (1H, m), 5.97–6.11 (1H, m), 6.82–7.32 (10H, m), 7.32–7.50 (1H, m)

Preparation 45

The following object compounds were obtained according to a similar manner to that of Preparation 1, 6 or 11.

(1) MASS (m/z): 566 (M⁺1); NMR (CDCl₃, δ): 1.46 (9H, s), 2.30 (3H, s), 2.35–2.45 (4H, m), 2.53 (3H×⅔, s), 2.60 (1H, m), 2.78 (3H×⅓, s), 2.95–3.13 (2H, m), 3.22 (1H, m), 3.46 (2H, m), 3.61 (2H, m), 4.08 (1H×⅓, d, J=15 Hz), 4.27 (1H×⅓, d, J=15 Hz), 4.29 (1H×⅔, d, J=15 Hz), 4.52 (1H, m), 4.63 (1H×⅔, d, J=15 Hz), 5.12 (1H, m), 6.03 (1H, d, J=7 Hz), 6.87–7.04 (2H, m), 7.20–7.27 (8H, m), 7.38 (1H×⅓, d, J=8 Hz), 7.45 (1H×⅔, d, J=8 Hz)

(2) MASS (m/z): 566 (M⁺+1); NMR (CDCl₃, δ): 1.46 (9H, s), 2.29 (3H, s), 2.33–2.53 (5H, m), 2.58 (3H×⅔, s), 2.84 (3H×⅓, s), 2.94–3.21 (3H, m), 3.43 (2H, m), 3.59 (2H, m), 4.15 (1H×⅓, d, J=15 Hz), 4.30 (1H×⅓, d, J=15 Hz), 4.33 (1H×⅔, d, J=15 Hz), 4.54 (1H, m), 4.66 (1H×⅔, d, J=15 Hz), 5.13 (1H, m), 5.92–5.99 (1H, m), 6.94–7.29 (10H, m), 7.52 (1H, d, J=8 Hz)

(3) MASS (FAB) (m/z): 638 (M+H)⁺; NMR (CDCl₃, δ): 1.27 (3H, t, J=8 Hz), 1.47 (9H, s), 2.53 (3×⅔H, s), 2.50–2.62 (5H, m), 2.78 (3×⅓H, s), 2.95–3.13 (2H, m), 3.17–3.26 (1H, m), 3.22 (2H, s), 3.47–3.52 (2H, m), 3.62–3.69 (2H, m), 4.08–4.32 (2×⅔H, m), 4.19 (2H, q, J=8 Hz), 4.47–4.57 (1H, m), 4.62 (2×⅓H, d, J=15 Hz), 5.08–5.17 (1H, m), 6.02 (1H, d, J=8 Hz), 6.85–6.89 (2×⅓H, m), 7.01–7.03 (2×⅔H, m), 7.16–7.30 (8H, m), 7.40 (1×⅓H, d, J=8 Hz), 7.45 (1×⅔H, d, J=8 Hz)

Preparation 46

The following object compounds were obtained according to a similar manner to that of Preparation 1, 6, 11 or 38.

(1) MASS (m/z): 697 (M+H)⁺; NMR (CDCl₃, δ): 1.46 (9H, s), 2.42 (3H, s), 2.48–2.62 (1H, m), 2.80–2.95 (1H, m), 2.82 (⅓×3H, s), 2.88 (⅔×3H, s), 2.95–3.10 (1H, m), 3.10–3.26 (1H, m), 3.35–3.72 (8H, m), 4.28–4.68 (3H, m), 5.10–5.25 (1H, m), 5.94–6.06 (1H, m), 7.02–7.90 (12H, m)

(2) MASS (m/z): 552 (M+H)⁺; NMR (CDCl₃, δ): 1.44 (9H, s), 2.23–2.42 (4H, m), 2.26 (3H, s), 2.45–2.70 (1H, m), 2.81 (⅔×3H, s), 2.85 (⅓×3H, s), 3.00–3.25 (1H, m), 3.30–3.65 (4H, m), 4.32 (⅓×1H, d, J=17 Hz), 4.42–4.61 (1H+⅓×1H, m), 4.60 (⅔×2H, ABq, Δ=0.16, J=15 Hz), 5.73–5.87 (1H, m), 5.98–6.12 (1H, m), 6.90–7.47 (10H, m), 8.03–8.25 (1H, m)

(3) MASS (m/z): 569 (M+H)⁺; NMR (CDCl₃, δ): 1.48 (9H, s), 2.50 (⅔×3H, s), 2.50–2.65 (1H, m), 2.74 (⅓×3H, s), 2.95–3.25 (3H, m), 3.38–3.70 (8H, m), 3.77 (⅖×1H, d, J=17 Hz), 4.20 (⅖×1H, d, J=17 Hz), 4.35 (⅗×2H, ABq, Δ=0.10, J=15 Hz), 4.48–4.62 (1H, m), 5.02–5.22 (1H, m), 6.02 (1H, br d), 6.28 (⅔×1H, br s), 6.60–7.55 (10H+⅓×1H, m)

(4) MASS (m/z): 608 (M⁺); NMR (CDCl₃, δ): 1.46 (9H, s), 2.30 (3H, s), 2.30–2.63 (5H, m), 2.50 (⅗×3H, s), 2.73 (⅖×3H, s), 2.90 (⅖×6H, s), 2.92 (⅗×6H, s), 2.97–3.12 (2H, m), 3.12–3.30 (1H, m), 3.37–3.70 (4H, m), 3.87 (⅖×1H, d, J=17 Hz), 4.19 (⅖×1H, d, J=17 Hz), 4.22 (⅗×1H, d, J=15 Hz), 4.47–4.58 (1H, m), 4.50 (⅗×1H, d, J=15 Hz), 5.00–5.25 (1H, m), 5.93–6.10 (1H, br d), 6.42–7.52 (10H, m)

(5) MASS (m/z): 623 (M+H)⁺; NMR (CDCl₃, δ): 1.47 (9H, s), 2.23 (⅓×6H, s), 2.25 (⅔×6H, s), 2.30 (3H, s), 2.32–2.50 (4H, m), 2.50–2.64 (1H, m), 2.53 (⅔×3H, s), 2.78 (⅓×3H, s), 2.92–3.30 (3H, m), 3.39 (⅓×2H, s), 3.42 (⅔×2H, s), 3.42–3.70 (4H, m), 4.17 (⅓×2H, ABq, Δ=0.17, J=17 Hz), 4.28 (⅔×1H, d, J=15 Hz), 4.43–4.60 (1H, m), 4.62 (⅔×1H, d, J=15 Hz), 5.03–5.20 (1H, m), 5.96–6.10 (1H, m), 6.80–7.50 (10H, m)

(6) MASS (m/z): 578 (M+H)⁺; NMR (CDCl₃, δ): 1.46 (9H, s), 2.18–2.82 (7H, m), 2.30 (3H, s), 2.92–3.12 (2H, m), 3.12–3.30 (1H, m), 3.37–3.85 (6H, m), 3.89 (⅓×1H, d, J=17 Hz), 4.32 (⅓×1H, d, J=17 Hz), 4.45–4.58 (1H, m), 4.62 (⅔×2H, ABq, Δ=0.15, J=17 Hz), 5.10–5.21 (1H, m), 5.98–6.10 (1H, m), 6.78–7.57 (10H, m)

(7) MASS (m/z): 600 (M+H)⁺; NMR (CDCl₃, δ): 1.48 (9H, s), 2.30 (3H, s), 2.32–2.50 (4H, m), 2.52–2.63 (1H, m), 2.55 (⅔×3H, s), 2.75 (⅓×3H, s), 2.95–3.30 (3H, m), 3.38–3.68 (4H, m), 4.14 (⅓×2H, ABq, Δ=0.09, J=17 Hz), 4.22 (⅔×1H, d, J=15 Hz), 4.45–4.58 (1H, m), 4.58 (⅔×1H, d, J=15 Hz), 5.05–5.20 (1H, m), 5.95–6.10 (1H, m), 6.70–6.95 (2H, m), 7.12–7.45 (8H, m)

(8) MASS (m/z): 644, 646 (M+H)⁺; NMR (CDCl₃, δ): 1.48 (9H, s), 2.30 (3H, s), 2.30–2.50 (4H, m), 2.50–2.63 (1H, m), 2.55 (¾×3H, s), 2.75 (¼×3H, s), 2.90–3.30 (3H, m), 3.38–3.68 (4H, m), 4.13 (¼×2H, ABq, Δ=0.07, J=17 Hz), 4.22 (¾×1H, d, J=15 Hz), 4.46–4.59 (1H, m), 4.58 (¾×1H, d, J=15 Hz), 5.03–5.17 (1H, m), 5.97–6.08 (1H, m), 6.62–6.91 (2H, m), 7.15–7.48 (8H, m)

(9) MASS (m/z): 584 (M+H)$^+$; NMR (CDCl$_3$, δ): 1.47 (9H, s), 2.30 (3H, s), 2.30–2.48 (4H, m), 2.50–2.65 (1H, m), 2.54 (¾×3H, s), 2.73 (¼×3H, s), 2.92–3.30 (3H, m), 3.38–3.68 (4H, m), 4.13 (¼×2H, ABq, Δ=0.14, J=17 Hz), 4.23 (¾×1H, d, J=15 Hz), 4.45–4.59 (1H, m), 4.58 (¾×1H, d, J=15 Hz), 5.05–5.18 (1H, m), 5.98–6.10 (1H, m), 6.72–7.03 (4H, m), 7.15–7.48 (6H, m)

(10) MASS (m/z): 597 (M+H)$^+$; NMR (CDCl$_3$, δ): 1.48 (9H, s), 2.30 (3H, s), 2.33–2.50 (4H, m), 2.50–2.63 (1H, m), 2.52 (¾×3H, s), 2.71 (¼×3H, s), 2.95–3.28 (3H, m), 3.38–3.68. (4H, m), 3.89 (¼×3H, s), 3.92 (¾×3H, s), 3.92 (¼×1H, d, J=17 Hz), 4.18 (¼×1H, d, J=17 Hz), 4.20 (¾×1H, d, J=15 Hz), 4.48–4.58 (1H, m), 4.51 (¾×1H, d, J=15 Hz), 5.01–5.27 (1H, m), 5.95–6.10 (1H, br d), 6.53–6.68 (1H, m), 7.12–7.48 (7H, m), 7.74–7.94 (1H, m)

(11) MASS (m/z): 580 (M+H)$^+$; NMR (CDCl$_3$, δ): 0.90 (⅗×3H, t, J=7 Hz), 0.98 (⅖×3H, t, J=7 Hz), 1.45 (9H, s), 2.32 (3H, s), 2.35–2.62 (5H, m), 2.83–3.32 (5H, m), 3.35–3.70 (4H, m), 4.12 (⅖×2H, ABq, Δ=0.18, J=17 Hz), 4.18 (⅗×1H, d, J=15 Hz), 4.42–4.62 (1H, m), 4.78 (⅗×1H, d, J=15 Hz), 4.96–5.18 (1H, m), 5.92–6.10 (1H, br d), 6.85–7.46 (11H, m)

(12) MASS (m/z): 601 (M+H)$^+$; NMR (CDCl$_3$, δ): 1.48 (9H, s), 2.30 (3H, s), 2.30–2.51 (4H, m), 2.51–2.63 (1H, m), 2.58 (⅘×3H, s), 2.73 (⅕×3H, s), 2.93–3.30 (3H, m), 3.40–3.70 (4H, m), 4.16 (⅕×2H, ABq, Δ=0.09, J=17 Hz), 4.25 (⅘×1H, d, J=15 Hz), 4.48–4.58 (1H, m), 4.57 (⅘×1H, d, J=15 Hz), 5.02–5.17 (1H, m), 5.97–6.10 (1H, m), 7.10–7.48 (8H, m), 8.01 (⅕×1H, d, J=2 Hz), 8.15 (⅘×1H, d, J=2 Hz)

(13) MASS (m/z): 581 (M+H)$^+$; NMR (CDCl$_3$, δ): 1.47 (9H, s), 2.30 (3H, s), 2.30–2.64 (5H, m), 2.51 (¼×3H, s), 2.53 (¾×3H×2, s), 2.72 (¼×3H, s), 2.94–3.30 (3H, m), 3.39–3.68 (4H, m), 4.00 (¼×1H, d, J=17 Hz), 4.22 (¼×1H, d, J=17 Hz), 4.27 (¾×1H, d, J=15 Hz), 4.46–4.60 (1H, m), 4.53 (¾×1H, d, J=15 Hz), 5.01–5.21 (1H, m), 5.95–6.10 (1H, br d), 6.91–7.50 (8H, m), 8.14 (¼×1H, d, J=2 Hz), 8.27 (¾×1H, d, J=2 Hz)

(14) MASS (m/z): 568 (M+H)$^+$; NMR (CDCl$_3$, δ): 1.47 (9H, s), 2.50–2.63 (1H, m), 2.51 (¼×3H, s), 2.53 (¾×3H×2, s), 2.73 (¼×3H, s), 2.95–3.28 (3H, m), 3.38–3.78 (8H, m), 3.98 (¼×1H, d, J=17 Hz), 4.23 (¼×1H, d, J=17 Hz), 4.28 (¾×1H, d, J=15 Hz), 4.46–4.62 (1H, m), 4.54 (¾×1H, d, J=15 Hz), 5.01–5.22 (1H, m), 5.93–6.08 (1H, m), 6.95–7.52 (8H, m), 8.15 (¼×1H, s), 8.28 (¾×1H, s)

(15) MASS (m/z): 633 (M+H)$^+$; NMR (CDCl$_3$, δ): 1.48 (9H, s), 2.30 (3H, s), 2.30–2.63 (5H, m), 2.61 (⅔×3H, s), 2.89 (⅓×3H, s), 2.93–3.30 (3H, m), 3.37–3.68 (4H, m), 4.23 (⅓×2H, ABq, Δ=0.12, J=17 Hz), 4.38 (⅔×1H, d, J=15 Hz), 4.45–4.60 (1H, m), 4.62 (⅔×1H, d, J=15 Hz), 5.08–5.21 (1H, m), 5.95–6.10 (1H, m), 6.91–7.62 (10H, m), 8.11 (1H, s), 8.52 (1H, s)

(16) MASS (m/z): 601 (M+H)$^+$; NMR (CDCl$_3$, δ): 1.47 (9H, s), 2.30 (3H, s), 2.30–2.50 (4H, m), 2.50–2.64 (1H, m), 2.56 (⅘×3H, s), 2.75 (⅕×3H, s), 2.93–3.30 (3H, m), 3.40–3.68 (4H, m), 4.18 (⅕×2H, ABq, Δ=0.09, J=17 Hz), 4.22 (⅘×1H, d, J=15 Hz), 4.46–4.62 (1H, m), 4.64 (⅘×1H, d, J=15 Hz), 5.02–5.15 (1H, m), 5.96–6.10 (1H, m), 7.10–7.52 (7H, m), 8.08 (⅕×1H, s), 8.23 (⅘×1H, s), 8.41–8.50 (1H, m)

(17) MASS (m/z): 588 (M+H)$^+$; NMR (CDCl$_3$, δ): 1.47 (9H, s), 2.50–2.62 (1H, m), 2.58 (¾×3H, s), 2.73 (¼×3H, s), 2.92–3.28 (3H, m), 3.39–3.78 (8H, m), 4.15 (¼×2H, ABq, Δ=0.13, J=17 Hz), 4.27 (¾×1H, d, J=15 Hz), 4.48–4.61 (1H, m), 4.55 (¾×1H, d, J=15 Hz), 5.02–5.15 (1H, m), 5.93–6.08 (1H, m), 6.92–7.50 (8H, m), 8.02 (¼×1H, m), 8.15 (¾×1H, m)

(18) MASS (m/z): 554 (M+H)$^+$; NMR (CDCl$_3$, δ): 1.47 (9H, s), 2.48–2.62 (1H, m), 2.55 (¾×3H, s), 2.75 (¼×3H, s), 2.92–3.28 (3H, m), 3.35–3.80 (8H, m), 4.18 (¼×2H, ABq, Δ=0.18, J=17 Hz), 4.29 (¾×1H, d, J=15 Hz), 4.46–4.62 (1H, m), 4.61 (¾×1H, d, J=15 Hz), 5.00–5.18 (1H, m), 5.93–6.07 (1H, m), 7.03–7.50 (8H, m), 8.18–8.53 (2H, m)

(19) MASS (m/z): 567 (M+H)$^+$; NMR (CDCl$_3$, δ): 1.47 (9H, s), 2.30 (3H, s), 2.32–2.48 (4H, m), 2.52–2.63 (1H, m), 2.54 (¾×3H, s), 2.74 (¼×3H, s), 2.93–3.30 (3H, m), 3.38–3.68 (4H, m), 4.18 (¼×2H, ABq, Δ=0.14, J=17 Hz), 4.28 (¾×1H, d, J=15 Hz), 4.45–4.60 (1H, m), 4.62 (¾×1H, d, J=15 Hz), 5.03–5.20 (1H, m), 5.93–6.10 (1H, m), 7.00–7.50 (8H, m), 8.18–8.53 (2H, m)

(20) MASS (m/z): 596 (M$^+$+1); NMR (CDCl$_3$, δ): 1.44 (9H, s), 2.28 (3H, s), 2.37 (4H, m), 2.51 (3H×⅔, s), 2.60–2.79 (1H, m), 2.73 (3H×⅓, s), 2.95–3.07 (2H, m), 3.22 (1H, m), 3.46 (2H, m), 3.61 (2H, m), 3.77 (3H×⅓, s), 3.78 (3H×⅔, s), 3.96 (1H×⅓, d, J=15 Hz), 4.22 (1H×⅔, d, J=15 Hz), 4.41 (1H×⅓, d, J=15 Hz), 4.54 (1H×⅔, d, J=15 Hz), 4.54 (1H, m), 5.06–5.18 (1H, m), 6.02 (1H, m), 6.77–7.00 (4H, m), 7.08–7.25 (5H, m), 7.43 (1H, m)

(21) MASS (ESI) (m/z): 580 (M+H)$^+$; NMR (CDCl$_3$, δ): 1.43 (9H, s), 2.25 (3H, s), 2.31 (3H, s), 2.35–2.48 (4H, m), 2.52 (3×⅔H, s), 2.54–2.62 (1H, m), 2.76 (3×⅓H, s), 2.97–3.10 (2H, m), 3.17–3.28 (1H, m), 3.42–3.50 (2H, m), 3.58–3.64 (2H, m), 4.02 (2×¼H, d, J=16 Hz), 4.22 (2×¼H, d, J=16 Hz), 4.27 (2×¼H, d, J=15 Hz), 4.58 (2×¼H, d, J=15 Hz), 4.48–4.57 (1H, m), 5.08–5.19 (1H, m), 6.03 (1H, d, J=8 Hz), 6.78 (2×⅓H, d, J=8 Hz), 6.91 (2×⅔H, d, J=8 Hz), 7.03 (2H, t, J=8 Hz), 7.18–7.30 (5H, m), 7.40 (1×⅓H, d, J=8 Hz), 7.47 (1×⅔H, d, J=8 Hz)

(22) MASS (m/z): 506 (M$^+$+1); NMR (CDCl$_3$, δ): 1.46 (9H, s), 2.28 (3H, s), 2.35–2.42 (4H, m), 2.57 (1H, m), 2.93 (3H×⅓, s), 2.98 (3H×⅔, s), 3.29–3.75 (6H, m), 3.86–3.94 (1H, m), 4.52 (1H×⅔, d, J=15 Hz), 4.54 (1H, m), 4.63 (2H×⅓, s), 4.71 (1H×⅔, d, J=15 Hz), 5.02 (1H, m), 5.89 (1H, d, J=8 Hz), 7.15–7.35 (5H, m), 7.53 (1H×⅓, d, J=8 Hz), 7.61 (1H×⅔, d, J=8 Hz)

(23) MASS (m/z): 532 (M$^+$+1); NMR (CDCl$_3$, δ): 0.78 (3H×⅓, d, J=7 Hz), 0.83 (3H×⅓, d, J=7 Hz), 0.92 (3H×⅔, d, J=7 Hz), 0.96 (3H×⅔, d, J=7 Hz), 1.44 (9H, s), 1.43–1.70 (3H, m), 2.30 (3H, s), 2.38 (4H, m), 2.57 (1H, m), 2.92 (3H×⅓, s), 2.97 (3H×⅔, s), 3.17 (1H, m), 3.46 (2H, m), 3.59 (2H, m), 4.42 (1H×⅔, d, J=15 Hz), 4.53 (1H, m), 4.57 (1H×⅓, d, J=15 Hz), 4.69 (1H×⅓, d, J=15 Hz), 4.73 (1H×⅔ d, J=15 Hz), 4.96 (1H, m), 6.05 (1H, m), 7.17–7.35 (6H, m)

(24) MASS (m/z): 634 (M$^+$+1); NMR (CDCl$_3$, δ): 1.47 (9H, s), 2.30 (3H, s), 2.35–2.46 (4H, m), 2.52–2.61 (1H, m), 2.59 (3H×¾, s), 2.78 (3H×¼, s), 2.93–3.26 (3H, m), 3.45 (2H, m), 3.60 (2H, m), 4.27 (2H×¼, s), 4.33 (1H×¾, d, J=15 Hz), 4.53 (1H, m), 4.65 (1H×¾, d, J=15 Hz), 5.05 (1H×¼, m), 5.14 (1H×¾, q, J=7 Hz), 6.02 (1H, m), 6.90–7.23 (7H, m), 7.33–7.52 (3H, m)

(25) MASS (m/z): 566 (M$^+$+1); NMR (CDCl$_3$, δ): 1.46 (9H, s), 2.29 (3H, s), 2.33–2.53 (5H, m), 2.58 (3H×⅔, s), 2.84 (3H×⅓, s), 2.94–3.21 (3H, m), 3.43 (2H, m), 3.59 (2H, m), 4.15 (1H×⅓, d, J=15 Hz), 4.30 (1H×⅓, d, J=15 Hz), 4.33 (1H×⅔, d, J=15 Hz), 4.54 (1H, m), 4.66 (1H×⅔, d, J=15 Hz), 5.13 (1H, m), 5.92–5.99 (1H, m), 6.94–7.29 (10H, m), 7.52 (1H, d, J=8 Hz)

(26) MASS (m/z): 574 (M$^+$+1); NMR (CDCl$_3$, δ): 1.45 (9H, s), 2.54 (3H×⅔, s), 2.71 (1H, m), 2.81 (3H×⅓, s), 2.92–3.12 (3H, m), 4.05 (1H×⅓, d, J=15 Hz), 4.28 (1H×⅓, d, J=15 Hz), 4.32 (1H×⅔, d, J=15 Hz), 4.53 (1H, m), 4.61 (1H×⅔, d, J=15 Hz), 5.07–5.18 (3H, m), 5.58 (1H, m), 6.89–7.34 (16H, m)

(27) MASS (m/z): 574 (M$^+$+1); NMR (CDCl$_3$, δ): 1.45 (9H, s), 2.59 (3H×⅔, s), 2.68 (1H, dd, J=5, 16 Hz), 2.84 (3H×⅓, s), 2.95–3.05 (3H, m), 4.09 (1H×⅓, d, J=15 Hz), 4.31 (1H×⅓, d, J=15 Hz), 4.37 (1H×⅔, d, J=15 Hz), 4.53 (1H, m), 4.62 (1H×⅔, d, J=15 Hz), 5.07–5.17 (3H, m), 5.56 (1H, m), 6.93–7.36 (16H, m)

Preparation 47

Starting Compound (194 mg) was dissolved in methanol (20 ml), and hydrogenated (3 kg/cm$^2$) over 10% palladium on carbon (20 mg) at room temperature for 3 hours. The palladium on carbon was filtered off, and the remaining solution was evaporated and dried in vacuo. The residue was dissolved in dichloromethane (5 ml), and to this solution was added Compound A (153 mg), 1-hydroxybenzotriazole (65 mg), and 1-ethyl-3-(3-dimethylaminopropyl)carbodiimide hydrochloride (104 mg) with ice-cooling, then the mixture was stirred at room temperature for 15 hours. The reaction mixture was diluted with chloroform, washed with aqueous sodium hydrogencarbonate, washed with brine, and dried over magnesium sulfate. Evaporation of the solvent followed by subjecting to column chromatography (silica gel, chloroform-methanol) afforded Object Compound (173 mg) as white powder.

MASS (m/z): 539 (M+H)$^+$; NMR (CDCl$_3$, δ): 1.36 (9H, s), 2.58–2.68 (1H, m), 2.90–3.00 (1H, m), 3.03–3.12 (1H, m), 3.25–3.45 (5H, m), 3.50–3.66 (4H, m), 4.30–4.45 (3H, m), 4.60–4.72 (1H, m), 5.66 (1H, br d), 6.72–6.90 (2H, m), 7.08–7.30 (10H, m)

Preparation 48

The following object compound was obtained according to a similar manner to that of Preparation 47.

MASS (m/z): 449 (M+H)$^+$; NMR (CDCl$_3$, δ): 1.39 (9H, s), 2.62–2.72 (1H, m), 2.87–3.14 (2H, m), 3.22–3.32 (1H, m), 3.40–3.47 (2H, m), 3.50–3.57 (2H, m), 3.62–3.70 (4H, m), 4.37–4.50 (1H, m), 4.60–4.70 (1H, m), 5.31 (1H, br s), 5.75 (1H, br d), 6.48 (12H, br d), 6.83 (1H, br d), 7.20–7.35 (5H, m)

Preparation 49

Trifluoroacetic acid (4 ml) was added to Starting Compound (700 mg) with ice-cooling, and stirred at room temperature for 1 hour. The reaction mixture was evaporated, and to the remaining oil was added hydrogen chloride in methanol and evaporated, then the remaining solid was dried in vacuo. To this solid was added dichloromethane (4 ml), Compound A (535 mg), 1-hydroxybenzotriazole (244 mg), and 1-ethyl-3-(3-dimethylaminopropyl)carbodiimide (322 mg), and the mixture was stirred at room temperature for 12 hours. The reaction mixture was diluted with chloroform, washed with aqueous sodium hydrogencarbonate, washed with brine, and dried over magnesium sulfate. Evaporation of the solvent followed by subjecting to column chromatography (silica gel, chloroform-methanol) afforded Object Compound (728 mg) as white powder.

MASS (m/z): 583 (M+H)$^+$; NMR (CDCl$_3$, δ): 1.48 (9H, s), 2.50 (⅔×3H, s), 2.5–2.6 (1H, m), 2.73 (⅓×3H, s), 3.0–3.1 (2H, m), 3.1–3.2 (1H, m), 3.4–3.7 (8H, m), 3.75 (⅓×3H, s), 3.78 (⅔×3H, s), 3.95 (⅓×1H, d, J=17 Hz), 4.22 (⅔×1H, d, J=15 Hz), 4.22 (⅓×1H, d, J=17 Hz), 4.54 (⅔×1H, d, J=15 Hz), 4.5–4.6 (1H, m), 5.1–5.2 (1H, m), 6.00 (1H, br d, J=9 Hz), 6.7–6.8 (⅓×4H, m), 6.78 (⅔×2H, d, J=9 Hz), 6.98 (⅔×2H, d, J=9 Hz), 7.1–7.2 (5H, m), 7.40 (⅓×1H, d, J=8 Hz), 7.45 (⅔×1H, d, J=8 Hz)

Preparation 50

The following object compounds were obtained according to a similar manner to that of Preparation 49.

(1) MASS (m/z): 463 (M+H)$^+$; NMR (CDCl$_3$, δ): 1.45 (9H, s), 2.48–2.63 (1H, m), 2.87 (⅔×3H, s), 2.98 (⅓×3H, s), 3.17–3.78 (9H, m), 4.02–4.22 (3H, m), 4.47 (⅓×2H, s), 4.61 (⅔×2H, ABq, Δ=0.09, J=15 Hz), 6.00–6.13 (1H, m), 7.10–7.70 (6H, m)

(2) MASS (m/z): 539 (M+H)$^+$; NMR (CDCl$_3$, δ): 1.43 (9H, s), 2.5–2.6 (2H, m), 2.80 (⅔×3H, s), 2.85 (⅓×3H, s), 3.0–3.1 (1H, m), 3.3–3.6 (8H, m), 4.32 (⅓×1H, d, J=15 Hz), 4.42 (⅓×1H, d, J=15 Hz), 4.60 (⅔×2H, ABq, Δ=0.15, J=15 Hz), 5.78 (⅔×1H, d, J=7 Hz), 5.82 (⅓×1H, d, J=7 Hz), 6.10 (1H, br d, J=7 Hz), 6.9–7.4 (10H, m), 8.12 (1H, br d, J=7 Hz)

(3) MASS (m/z): 659 (M+H)$^+$; NMR (CDCl$_3$, δ): 1.48 (9H, s), 2.48–2.62 (1H, m), 2.54 (⅔×3H, s), 2.78 (⅓×3H, s), 2.90–3.05 (2H, m), 3.10–3.28 (1H, m), 3.37–3.75 (8H, m), 4.10 (⅓×1H, d, J=17 Hz), 4.27 (⅓×1H, d, J=17 Hz), 4.28 (⅔×1H, d, J=15 Hz), 4.46–4.60 (1H, m), 4.60 (⅔×1H, d, J=15 Hz), 5.01 (⅔×2H, s), 5.02–5.13 (1H, m), 5.07 (⅓×2H, s), 6.00 (1H, br d), 6.75–7.48 (15H, m)

(4) MASS (m/z): 672 (M+H)$^+$; NMR (CDCl$_3$, δ): 1.46 (9H, s), 2.29 (3H, s), 2.30–2.49 (4H, m), 2.50–2.63 (1H, m), 2.54 (⅔×3H, s), 2.77 (⅓×3H, s), 2.85–3.10 (2H, m), 3.13–3.30 (1H, m), 3.35–3.68 (4H, m), 4.19 (⅓×2H, ABq, Δ=0.16, J=17 Hz), 4.27 (⅔×1H, d, J=15 Hz), 4.42–4.62 (1H, m), 4.62 (⅔×1H, d, J=15 Hz), 4.94–5.17 (3H, m), 5.93–6.10 (1H, m), 6.72–7.50 (15H, m)

(5) MASS (m/z): 569 (M+H)$^+$; NMR (CDCl$_3$, δ): 1.47 (9H, s), 2.48–2.72 (1H, m), 2.62 (⅔×3H, s), 2.81 (⅓×3H, s), 2.82–3.05 (2H, m), 3.05–3.28 (1H, m), 3.30–3.75 (8H, m), 4.28 (⅓×2H, ABq, Δ=0.15, J=17 Hz), 4.33 (⅔×1H, d, J=15 Hz), 4.45–4.63 (1H, m), 4.60 (⅔×1H, d, J=15 Hz), 4.98–5.15 (1H, m), 5.92–6.12 (1H, br d), 6.42–7.60 (11H, m)

(6) MASS (m/z): 567 (M+H)$^+$; NMR (CDCl$_3$, δ): 1.49 (9H, s), 2.39–2.77 (4H, m), 2.58 (⅗×3H, s), 2.80 (⅖×3H, s), 2.90–3.05 (2H, m), 3.10–3.40 (2H, m), 3.40–3.80 (8H, m), 4.45–4.60 (1H, m), 4.93–5.10 (1H, m), 5.92–6.08 (1H, m), 6.98–7.48 (11H, m)

(7) MASS (m/z): 611 (M+H)$^+$; NMR (CDCl$_3$, δ): 1.45 (9H, s), 2.59 (⅔×3H, s), 2.5–2.6 (1H, m), 2.79 (⅓×3H, s), 3.0–3.1 (2H, m), 3.1–3.2 (1H, m), 3.4–3.7 (8H, m), 3.90 (3H, s), 4.33 (1H, d, J=15 Hz), 4.5–4.6 (1H, m), 4.69 (1H, d, J=15 Hz), 5.1–5.2 (1H, m), 6.02 (1H, br s), 6.90 (1H, br d, J=9 Hz), 7.0–7.3 (7H, m), 7.8–7.9 (2H, m)

(8) MASS (m/z): 603 (M+H)$^+$; NMR (CDCl$_3$, δ): 1.47 (9H, s), 2.5–2.6 (1H, m), 2.58 (⅗×3H, s), 2.83 (⅖×3H, s), 3.0–3.1 (2H, m), 3.2–3.3 (1H, m), 3.4–3.7 (8H, m), 4.23 (⅖×1H, d, J=17 Hz), 4.45 (⅖×1H, d, J=17 Hz), 4.47 (⅗×1H, d, J=15 Hz), 4.5–4.6 (1H, m), 4.77 (⅗×1H, d, J=15 Hz), 5.1–5.3 (1H, m), 6.03 (1H, br d, J=9 Hz), 7.1–7.3 (6H, m), 7.4–7.6 (4H, m), 7.7–7.9 (3H, m)

(9) MASS (m/z): 603 (M+H)$^+$; NMR (CDCl$_3$, δ): 1.48 (9H, s), 2.42–2.62 (1H, m), 2.52 (⅔×3H, s), 2.88 (⅓×3H, s), 2.93–3.25 (3H, m), 3.35–3.75 (8H, m), 4.40–4.60 (1H, m), 4.65 (⅓×2H, ABq, Δ=0.05, J=17 Hz), 4.82 (⅔×1H, d, J=15 Hz), 4.95–5.20 (1H, m), 5.15 (⅔×1H, d, J=15 Hz), 6.03 (1H, br d), 6.78–8.05 (13H, m)

(10) MASS (m/z): 554 (M+H)⁺; NMR (CDCl₃, δ): 1.48 (9H, s), 2.48–2.62 (1H, m), 2.70 (⅔×3H, s), 2.85 (⅓×3H, s), 2.95–3.26 (3H, m), 3.38–3.75 (8H, m), 4.30 (⅓×2H, ABq, Δ=0.11, J=17 Hz), 4.50–4.60 (1H, m), 4.58 (⅔×2H, ABq, Δ=0.15, J=15 Hz), 5.05–5.20 (1H, m), 5.98 (1H, br d), 6.82–7.63 (9H, m), 8.48 (1H, m)

(11) MASS (m/z): 554 (M+H)⁺; NMR (CDCl₃, δ): 1.48 (9H, s), 2.48–2.65 (1H, m), 2.64 (⅔×3H, s), 2.80 (⅓×3H, s), 2.90–3.28 (3H, m), 3.35–3.76 (8H, m), 4.25 (⅓×2H, ABq, Δ=0.12, J=17 Hz), 4.31 (⅔×1H, d, J=15 Hz), 4.50–4.60 (1H, m), 4.59 (⅔×1H, d, J=15 Hz), 4.92–5.22 (1H, m), 6.01 (1H, br d), 6.55–6.90 (2H, m), 7.13–7.48 (6H, m), 8.38–8.51 (2H, m)

(12) MASS (FAB) (m/z): 624 (M+H)⁺; NMR (CDCl₃, δ): 1.49 (9H, s), 2.30 (3H, s), 2.35–2.48 (4H, m), 2.52–2.62 (1H, m), 2.59 (3×⅔H, s), 2.68 (3×⅓H, s), 2.94–3.13 (2H, m), 3.20–3.27 (1H, m), 3.42–3.50 (2H, m), 3.58–3.65 (2H, m), 3.90 (3H, s), 4.23–4.34 (2×⅔H, m), 4.49–4.58 (1H, m), 4.70 (2×⅓H, d, J=15 Hz), 5.04–5.19 (1H, m), 5.99–6.07 (1H, m), 6.88 (2×⅓H, d, J=8 Hz), 7.03 (2×⅔H, d, J=8 Hz), 7.18–7.30 (5H, m), 7.37 (1×⅓H, d, J=8 Hz), 7.43 (1×⅔H, d, J=8 Hz), 7.88 (2×⅓H, d, J=8 Hz), 7.92 (2×⅔H, d, J=8 Hz)

(13) MASS (FAB) (m/z): 696 (M+H)⁺; NMR (CDCl₃, δ): 1.27 (3H, t, J=8 Hz), 1.47 (9H, s), 2.52–2.65 (5H, m), 2.62 (3×⅔H, s), 2.78 (3×⅓H, s), 2.92–3.12 (2H, m), 3.14–3.30 (1H, m), 3.26 (2H, s), 3.47–3.54 (2H, m), 3.61–3.70 (2H, m), 3.92 (3H, s), 4.19 (2H, q, J=8 Hz), 4.27–4.32 (2×⅔H, m), 4.48–4.58 (1H, m), 4.70 (2×⅓H, d, J=15 Hz), 5.03–5.18 (1H, m), 5.95–6.08 (1H, m), 6.88 (2×⅓H, d, J=8 Hz), 7.03 (2×⅔H, d, J=8 Hz), 7.17–7.28 (5H, m), 7.37 (1×⅓H, d, J=8 Hz), 7.44 (1×⅔H, d, J=8 Hz), 7.88 (2×⅓H, d, J=8 Hz), 7.92 (2×⅔H, d, J=8 Hz)

(14) MASS (m/z): 595 (M+); NMR (CDCl₃, δ): 1.48 (9H, s), 2.50 (⅔×3H, s), 2.5–2.6 (2H, m), 2.75 (⅓×3H, s), 2.91 (⅓×6H, s), 2.94 (⅔×6H, s), 3.03 (2H, m), 3.1–3.2 (1H, m), 3.4–3.7 (8H, m), 3.87 (⅓×2H, d, J=16 Hz), 4.24 (1H, d, J=15 Hz), 4.47 (⅔×2H, d, J=15 Hz), 4.5–4.6 (1H, m), 5.0–5.1 (⅔×1H, m), 5.1–5.2 (⅓×1H, m), 6.00 (1H, d, J=9 Hz), 6.60 (⅓×2H, d, J=7 Hz), 6.63 (⅔×2H, d, J=7 Hz), 6.80 (⅓×2H, d, J=7 Hz), 6.95 (⅔×2H, d, J=7 Hz), 7.1–7.2 (5H, m), 7.45 (1H, d, J=7 Hz)

Preparation 51

The following object compounds were obtained according to a similar manner to that of Preparation 3, 4 or 8.

(1) MASS (m/z): 452 (M+H)⁺; NMR (CDCl₃, δ): 2.28 (3H, s), 2.30–2.65 (5H, m), 2.81 (⅔×3H, s), 2.85–2.98 (1H, m), 2.89 (⅓×3H, s), 3.30–3.88 (5H, m), 4.44 (⅓×2H, ABq, Δ=0.22, J=17 Hz), 4.60 (⅔×2H, ABq, Δ=0.14, J=15 Hz), 5.78–5.92 (1H, m), 6.90–7.47 (10H, m), 8.60–8.78 (1H, m)

(2) MASS (m/z): 509 (M+H)⁺; NMR (CDCl₃, δ): 2.20–2.48 (5H, m), 2.31 (3H, s), 2.63 (⅗×3H, s), 2.70–2.88 (1H, m), 2.82 (⅖×3H, s), 2.90–3.15 (2H, m), 2.92 (⅖×6H, s), 2.94 (⅗×6H, s), 3.35–3.76 (5H, m), 4.23 (⅖×2H, ABq, Δ=0.21, J=17 Hz), 4.28 (⅗×1H, d, J=15 Hz), 4.54 (⅗×1H, d, J=15 Hz), 5.06–5.32 (1H, m), 6.45–7.33 (9H, m), 8.02–8.20 (1H, m)

(3) MASS (m/z): 523 (M+H)⁺; NMR (CDCl₃, δ): 2.22 (⅖×6H, s), 2.24 (⅗×6H, s), 2.25–2.52 (5H, m), 2.30 (3H, s), 2.66(⅗×3H, s), 2.70–2.90 (1H, m), 2.88 (⅖×3H, s), 2.90–3.18 (2H, m), 3.33–3.75 (7H, m), 4.32 (⅗×1H, d, J=15 Hz), 4.33 (⅖×2H, s), 4.66 (⅗×1H, d, J=15 Hz), 5.10–5.23 (1H, m), 6.90–7.32 (9H, m), 8.02–8.20 (1H, m)

(4) MASS (m/z): 478 (M+H)⁺; NMR (CDCl₃, δ): 2.30 (3H, s), 2.30–2.87 (7H, m), 2.95–3.30 (3H, m), 3.38–3.85 (7H, m), 4.04 (½×1H, d, J=17 Hz), 4.53 (½×1H, d, J=17 Hz), 4.67 (½×2H, ABq, Δ=0.17, J=17 Hz), 5.14–5.28 (1H, m), 6.82–7.25 (9H, m), 8.10–8.22 (1H, m)

(5) MASS (m/z): 500 (M+H)⁺; NMR (CDCl₃, δ): 2.30 (3H, s), 2.30–2.57 (5H, m), 2.68 (¾×3H, s), 2.70–2.88 (1H, m), 2.82 (¼×3H, s), 2.90–3.18 (2H, m), 3.35–3.75 (5H, m), 4.25 (¾×1H, d, J=15 Hz), 4.30 (¼×2H, ABq, Δ=0.05, J=17 Hz), 4.64 (¾×1H, d, J=15 Hz), 5.05–5.22 (1H, m), 6.80–7.01 (2H, m), 7.10–7.30 (7H, m), 8.05–8.20 (1H, m)

(6) MASS (m/z): 544, 546 (M+H)⁺; NMR (CDCl₃, δ): 2.30 (3H, s), 2.30–2.57 (5H, m), 2.67 (¾×3H, s), 2.70–2.88 (1H, m), 2.82 (¼×3H, s), 2.90–3.18 (2H, m), 3.35–3.75 (5H, m), 4.23 (¾×1H, d, J=15 Hz), 4.29 (¼×2H, ABq, Δ=0.06, J=17 Hz), 4.62 (¾×1H, d, J=15 Hz), 5.05–5.21 (1H, m), 6.74–6.95 (2H, m), 7.11–7.42 (7H, m), 8.05–8.20 (1H, m)

(7) MASS (m/z): 484 (M+H)⁺; NMR (CDCl₃, δ): 2.30 (3H, s), 2.3–2.55 (5H, m), 2.68 (¾×3H, s), 2.72–2.88 (1H, m), 2.83 (¼×3H, s), 2.90–3.18 (2H, m), 3.35–3.75 (5H, m), 4.27 (¾×1H, d, J=15 Hz), 4.30 (¼×2H, s), 4.62 (¾×1H, d, J=15 Hz), 5.10–5.22 (1H, m), 6.83–7.08 (4H, m), 7.13–7.32 (5H, m), 8.05–8.20 (1H, m)

(8) MASS (m/z): 497 (M+H)⁺; NMR (CDCl₃, δ): 2.30 (3H, s), 2.30–2.55 (4H, m), 2.65 (¾×3H, s), 2.75–2.88 (1H, m), 2.78 (¼×3H, s), 2.93–3.15 (2H, m), 3.35–3.75 (6H, m), 3.90 (¼×3H, s), 3.92 (¾×3H, s), 4.20 (¼×2H, ABq, Δ=0.18, J=17 Hz), 4.24 (¾×1H, d, J=15 Hz), 4.55 (¾×1H, d, J=15 Hz), 5.05–5.25 (1H, m), 6.58–6.70 (1H, m), 7.02–7.35 (6H, m), 7.80–8.20 (2H, m)

(9) MASS (m/z): 480 (M+H)⁺; NMR (CDCl₃, δ): 0.99 (⅗×3H, t, J=7 Hz), 1.04 (⅖×3H, t, J=7 Hz), 2.20–2.50 (5H, m), 2.28 (3H, s), 2.68–2.88 (1H, m), 2.90–3.30 (4H, m), 3.32–3.75 (5H, m), 4.23 (⅗×1H, d, J=15 Hz), 4.33 (⅖×2H, ABq, Δ=0.05, J=17 Hz), 4.83 (⅗×1H, d, J=15 Hz), 5.00–5.22 (1H, m), 6.92–7.40 (10H, m), 8.00–8.20 (1H, m)

(10) MASS (m/z): 501 (M+H)⁺; NMR (CDCl₃, δ): 2.30–2.60 (5H, m), 2.31 (3H, s), 2.68 (⅘×3H, s), 2.72–2.88 (1H, m), 2.78 (⅕×3H, s), 2.92–3.24 (2H, m), 3.37–3.75 (5H, m), 4.28 (⅘×1H, d, J=15 Hz), 4.29 (⅕×2H, s), 4.60 (⅘×1H, d, J=15 Hz), 5.05–5.20 (1H, m), 7.00–7.37 (9H, m), 8.02–8.22 (2H, m)

(11) MASS (m/z): 481 (M+H)⁺; NMR (CDCl₃, δ): 2.31 (3H, s), 2.31–2.50 (5H, m), 2.51 (¼×3H, s), 2.54 (¾×3H, s), 2.66 (¾×3H, s), 2.72–2.88 (1H, m), 2.80 (¼×3H, s), 2.93–3.20 (2H, m), 3.38–3.76 (5H, m), 4.28 (¼×2H, ABq, Δ=0.14, J=17 Hz), 4.31 (¾×1H, d, J=15 Hz), 4.59 (¾×1H, d, J=15 Hz), 5.06–5.24 (1H, m), 6.98–7.32 (7H, m), 8.08–8.33 (2H, m)

(12) MASS (m/z): 468 (M+H)⁺; NMR (CDCl₃, δ): 2.38–2.59 (1H, m), 2.51 (¼×3H, s), 2.53 (¾×3H, s), 2.65 (¾×3H, s), 2.69–2.86 (1H, m), 2.79 (¼×3H, s), 2.92–3.18 (2H, m), 3.32–3.76 (9H, m), 4.27 (¼×2H, ABq, Δ=0.16, J=17 Hz), 4.32 (¾×1H, d, J=15 Hz), 4.57 (¾×1H, d, J=15 Hz), 5.03–5.22 (1H, m), 6.98–7.33 (7H, m), 8.05–8.34 (2H, m)

(13) MASS (m/z): 533 (M+H)⁺; NMR (CDCl₃, δ): 2.27–2.58 (5H, m), 2.30 (3H, s), 2.70–2.88 (1H, m), 2.72 (⅔×3H, s), 2.85 (⅓×3H, s), 2.92–3.21 (2H, m), 3.33–3.78 (5H, m), 4.38 (⅓×2H, s), 4.41 (⅔×1H, d, J=15 Hz), 4.67 (⅔×1H, d, J=15 Hz), 5.08–5.24 (1H, m), 7.00–7.36 (7H, m), 7.50–7.64 (2H, m), 8.10 (1H, s), 8.10–8.22 (1H, m), 8.52 (1H, s)

(14) MASS (m/z): 501 (M+H)⁺; NMR (CDCl₃, δ): 2.31 (3H, s), 2.31–2.62 (5H, m), 2.68 (⅘×3H, s), 2.71–2.88 (1H, m), 2.82 (⅕×3H, s), 2.95–3.20 (2H, m), 3.35–3.78 (5H, m), 4.30 (⅘×1H, d, J=15 Hz), 4.32 (⅕×2H, ABq, Δ=0.05, J=17

Hz), 4.62 (⅕×1H, d, J=15 Hz), 5.03–5.20 (1H, m), 7.10–7.32 (5H, m), 7.48 (1H, s), 8.08–8.31 (2H, m), 8.40–8.52 (1H, m)

(15) MASS (m/z): 488 (M+H)⁺;

NMR (CDCl₃, δ): 2.33–2.62 (1H, m), 2.68 (⅘×3H, s), 2.71–2.85 (1H, m), 2.79 (⅕×3H, s), 2.90–3.22 (2H, m), 3.34–3.77 (9H, m), 4.28 (⅕×2H, ABq, Δ=0.05, J=17 Hz), 4.29 (⅘×1H, d, J=15 Hz), 4.58 (⅘×1H, d, J=15 Hz), 5.02–5.18 (1H, m), 7.00–7.38 (7H, m), 8.00–8.21 (2H, m)

(16) MASS (m/z): 454 (M+H)⁺; NMR (CDCl₃, δ): 2.38–2.61 (1H, m), 2.67 (¾×3H, s), 2.67–2.85 (1H, m), 2.82 (¼×3H, m), 2.92–3.20 (2H, m), 3.35–3.76 (9H, m), 4.32 (¼×2H, ABq, Δ=0.10, J=17 Hz), 4.32 (¾×1H, d, J=15 Hz), 4.64 (¾×1H, d, J=15 Hz), 5.07–5.21 (1H, m), 7.05–7.43 (7H, m), 8.06–8.22 (7H, m), 8.29(¼×1H, s), 8.40 (¾×1H, s), 8.46–8.56 (1H, m)

(17) MASS (m/z): 467 (M+H)⁺; NMR (CDCl₃, δ): 2.31 (3H, s), 2.31–2.58 (5H, m) 2.67 (¾×3H, s), 2.70–2.86 (1H, m), 2.82 (¼×3H, s), 2.94–3.20 (2H, m), 3.38–3.75 (5H, m), 4.32 (¾×1H, d, J=5 Hz), 4.34 (¼×2H, ABq, Δ=0.06, J=17 Hz), 4.65 (¾×1H, d, J=15 Hz), 5.08–5.20 (1H, m), 7.11–7.42 (7H, m), 8.07–8.22 (1H, m), 8.28 (¼×1H, s), 8.41 (¾×1H, s), 8.48–8.56 (1H, m)

(18) MASS (m/z): 480 (M+H)⁺; NMR (CDCl₃, δ): 1.09 (3H, t, J=7 Hz), 2.22–2.52 (7H, m), 2.67 (⅔×3H, s), 2.69–2.92 (1H, m), 2.87 (⅓×3H, s), 2.92–3.15 (2H, m), 3.34–3.78 (5H, m), 4.33 (⅔×1H, d, J=15 Hz), 4.38 (⅓×2H, ABq, Δ=0.07, J=17 Hz), 4.68 (⅔×1H, d, J=15 Hz), 5.09–5.23 (1H, m), 6.92–7.32 (10H, m), 8.02–8.22 (1H, m)

(19) NMR (CDCl₃, δ): 2.30 (3H, s), 2.37 (4H, m), 2.44 (1H, dd, J=7, 16 Hz), 2.65 (3H×⅔, s), 2.72–2.85 (1H, m), 2.83 (3H×⅓, s), 2.94–3.12 (2H, m), 3.43 (2H, m), 3.57–3.74 (3H, m), 3.79 (3H, s), 4.20 (1H×⅓, d, J=15 Hz), 4.26 (1H×⅔, d, J=15 Hz), 4.33 (1H×⅓, d, J=15 Hz), 4.61 (1H×⅔, d, J=15 Hz), 5.11–5.24 (1H, m), 6.77–7.28 (9H, m), 8.08 (1H×⅓, d, J=8 Hz), 8.15 (1H×⅔, d, J=8 Hz)

(20) MASS (ESI) (m/z): 480 (M+H); NMR (CDCl₃, δ): 2.29 (3H, s), 2.30 (3H, s), 2.23–2.48 (6H, m), 2.63 (3×⅔H, s), 2.70–2.80 (1H, m), 2.84 (3×⅓H, s), 2.89–3.13 (2H, m), 3.38–3.47 (2H, m), 3.50–3.72 (2H, m), 4.23–4.31 (2×⅔H, m), 4.62 (2×⅓H, d, J=15 Hz), 5.10–5.22 (1H, m), 6.87 (2×⅓H, d, J=8 Hz), 6.94 (2×⅔H, d, J=8 Hz), 7.07 (2H, d, J=8 Hz), 7.12–7.29 (5H, m), 8.08 (1×⅓H, d, J=8 Hz), 8.15 (1×⅔H, d, J=8 Hz)

(21) NMR (CDCl₃, δ): 2.29 (3H, s), 2.36 (4H, m), 2.66–2.77 (1H, m), 2.87–3.09 (1H, m), 2.95 (3H×⅓, s), 3.02 (3H×⅔, s), 3.42–3.69 (5H, m), 3.76–3.93 (3H, m), 4.57 (1H×⅔, d, J=15 Hz), 4.66 (2H×⅓, s), 4.67 (1H×⅔, d, J=15 Hz), 5.03 (1H, m), 7.16–7.36 (5H, m), 8.42 (1H×⅓, d, J=8 Hz), 8.50 (1H×⅔, d, J=8 Hz)

(22) NMR (CDCl₃, δ): 0.81 (3H×⅓, d, J=7 Hz), 0.84 (3H×⅓, d, J=7 Hz), 0.94 (3H×⅔, d, J=7 Hz), 0.98 (3H×⅔, d, J=7 Hz), 1.42–1.72 (3H, m), 2.29 (3H, s), 2.33–2.42 (4H, m), 2.51–2.62 (1H, m), 2.86–2.97 (1H, m), 2.93 (3H×⅓, s), 3.01 (3H×⅔, s), 3.46–3.77 (5H, m), 4.43 (1H×⅔, d, J=15 Hz), 4.61 (1H×⅓, d, J=16 Hz), 4.73 (1H×⅓, d, J=16 Hz), 4.74 (1H×⅔, d, J=15 Hz), 4.98 (1H, dt, J=4, 8 Hz), 7.18–7.37 (5H, m), 7.97 (1H×⅓, d, J=8 Hz), 8.04 (1H×⅔, d, J=8 Hz)

(23) NMR (CDCl₃, δ): 2.30 (3H, s), 2.35–2.44 (4H, m), 2.52 (1H, dd, J=8, 16 Hz), 2.71 (3H×⅔, s), 2.77 (1H, dd, J=3, 16 Hz), 2.85 (3H×⅓, s), 2.93–3.17 (2H, m), 3.41–3.47 (2H, m), 3.54–3.74 (3H, m), 4.35 (1H×⅓, d, J=15 Hz), 4.37 (1H×⅔, d, J=15 Hz), 4.50 (1H×⅓, d, J=15 Hz), 4.72 (1H×⅔, d, J=15 Hz), 5.07 (1H×⅓, q, J=7 Hz), 5.18 (1H×⅔, q, J=7 Hz), 7.01 (1H×⅔, d, J=8 Hz), 7.13 (2H, d, J=8 Hz), 7.20–7.25 (3×⅓H, m), 7.50 (2H, t, J=8 Hz)

(24) NMR (CDCl₃, δ): 2.30 (3H, s), 2.36 (4H, m), 2.50 (1H, dd, J=7, 16 Hz), 2.67 (3H×⅗, s), 2.81 (1H×⅖, dd, J=4, 16 Hz), 2.88 (3H×⅖, s), 2.90 (1H×⅗, dd, J=4, 16 Hz), 2.97–3.12 (2H, m), 3.39–3.46 (2H, m), 3.56–3.77 (3H, m), 4.32 (1H×⅗, d, J=15 Hz), 4.32 (1H×⅖, d, J=15 Hz), 4.44 (1H×⅖, d, J=15 Hz), 4.70 (1H×⅗, d, J=15 Hz), 5.15 (1H, m), 7.00–7.28 (10H, m), 8.02 (1H×⅖, d, J=8 Hz), 8.13 (1H×⅗, d, J=8 Hz)

(25) NMR (CDCl₃, δ): 2.29 (3H, s), 2.25–2.50 (5H, m), 2.66 (3H×⅔, s), 2.73 (1H×⅓, dd, J=3, 16 Hz), 2.82 (1H×⅔, dd, J=3, 16 Hz), 2.87 (3H×⅓, s), 2.92–3.13 (2H, m), 3.38–3.47 (2H, m), 3.54–3.73 (3H, m), 4.33 (1H×⅔, d, J=15 Hz), 4.34 (1H×⅓, d, J=15 Hz), 4.41 (1H×⅓, d, J=15 Hz), 4.67 (1H×⅔, d, J=15 Hz), 5.17 (1H, m), 6.97–7.15 (3H, m), 7.21 (3H, s), 7.22–7.27 (4H, m), 8.06 (1H×⅓, d, J=7 Hz), 8.16 (1H×⅔, d, J=7 Hz)

(26) NMR (CDCl₃, δ): 2.30 (3H, s), 2.36 (4H, m), 2.50 (1H, dd, J=7, 16 Hz), 2.67 (3H×⅗, s), 2.81 (1H×⅖, dd, J=4, 16 Hz), 2.88 (3H×⅖, s), 2.90 (1H×⅗, dd, J=4, 16 Hz), 2.97–3.12 (2H, m), 3.39–3.46 (2H, m), 3.56–3.77 (3H, m), 4.32 (1H×⅗, J=15 Hz), 4.32 (1H×⅖, J=15 Hz), 4.44 (1H×⅖, J=15 Hz), 4.70 (1H×⅗, J=15 Hz), 5.15 (1H, m), 7.00–7.28 (10H, m), 8.02 (1H×⅖, d, J=8 Hz), 8.13 (1H×⅗, d, J=8 Hz)

(27) MASS (FAB) (m/z): 538 (M+H)⁺; NMR (CDCl₃, δ): 1.28 (3H, t, J=8 Hz), 2.25–2.33 (1×⅓H, m), 2.41–2.49 (1×⅔H, m), 2.51–2.62 (4H, m), 2.63 (3×⅔H, s), 2.70–2.85 (1H, m), 2.86 (3×⅓H, s), 2.92–3.13 (2H, m), 3.23 (2H, s), 3.42–3.51 (2H, m), 3.57–3.77 (3H, m), 4.19 (2H, q, J=8 Hz), 4.31–4.42 (2×⅔H, m), 4.68 (2×⅓H, d, J=15 Hz), 5.11–5.20 (1H, m), 6.98 (2×⅓H, d, J=8 Hz), 7.05 (2×⅔H, d, J=8 Hz), 7.12–7.31 (8H, m), 8.07 (1×⅓H, d, J=8 Hz), 8.15 (1×⅔H, d, J=8 Hz)

(28) MASS: 524 (M+1); NMR (CDCl₃, δ): 2.29 (3H, s), 2.33–2.45 (4H, m), 2.48–2.57 (1H, m), 2.63 (3×⅔H, s), 2.71–2.81 (1H, m), 2.83 (3×⅓H, s), 2.92–3.14 (2H, m), 3.39–3.47 (2H, m), 3.52–3.73 (3H, m), 3.88 (3H, s), 4.33–4.49 (2×⅔H, m), 4.72 (2×⅓H, d, J=15 Hz), 5.07–5.22 (1H, m), 6.98 (2×⅓H, d, J=8 Hz), 7.08 (2×⅔H, d, J=8 Hz), 7.13–7.30 (5H, m), 7.92 (2H, t, J=8 Hz), 8.10 (1×⅓H, d, J=8Hz), 8.17 (1×⅔H, d, J=8 Hz)

(29) MASS (FAB) (m/z): 596 (M+H)⁺; NMR (CDCl₃, δ): 1.22 (3H, t, J=8 Hz), 2.33–2.42 (1H, m), 2.48–2.62 (4H, m), 2.63 (3×⅔H, s), 2.69–2.78 (1H, m), 2.80 (3×⅓H, s), 2.92–3.13 (2H, m), 3.20 (2H, s), 3.42–3.51 (2H, m), 3.57–3.72 (3H, m), 3.90 (3H, s), 4.19 (2H, q, J=8 Hz), 4.31–4.50 (2×⅔H, m), 4.72 (2×⅓H, d, J=15 Hz), 5.07–5.12 (1H, m), 6.98 (2×⅓H, d, J=8 Hz), 7.08 (2×⅔H, d, J=8 Hz), 7.12–7.17 (1H, m), 7.20–7.28 (4H, m), 7.92 (2H, t, J=8 Hz), 8.10 (1×⅓H, d, J=8 Hz), 8.17 (1×⅔H, d, J=8 Hz)

Preparation 52

To a solution of Starting compound (53.06 g) in dichloromethane (400 ml) were added N-methyl-N-(3-pyridylmethyl)amine (25.65 g) and 1-hydroxybenzotriazole (27.02 g) and the mixture was cooled with ice. 1-Ethyl-3-(3-dimethylaminopropyl)carbodiimide hydrochloride (42.18 g) was added to the mixture in small portions, then the whole was stirred at room temperature for 8 hours. After the mixture was concentrated, 1N sodium hydroxide (300 ml) was added thereto, and the mixture was extracted three times with ethyl acetate. The organic layer was washed once with brine and dried over magnesium sulfate. Evaporation of the solvent followed by silica gel column chromatography (chloroform-methanol) gave Object compound (81.37 g) as a colorless oil.

MASS: m/z 370 (M+H)⁺; NMR (CDCl₃, δ): 1.40 (⅕×9H, s), 1.42 (⅘×3H, s), 2.63 (⅘×3H, s), 2.79 (⅕×3H, s), 2.92–3.06 (2H, m), 4.08 (⅕×1H, d, J=17 Hz), 4.35 (⅕×1H, d, J=17 Hz), 4.49 (⅘×2H, ABq, Δ=0.09, J=15 Hz), 4.79–4.98 (1H, m), 5.28–5.42 (1H, m), 7.10–7.35 (7H, m), 8.28 (⅕×1H, s), 8.42 (⅕×1H, s), 8.50–8.55 (1H, m)

Preparation 53

Object compounds were obtained according to a similar manner to that of Preparation 1, 6, 11 or 52.

(1) MASS: m/z 404 (M+H)⁺; NMR (CDCl₃, δ): 1.42 (9H, s), 2.63 (⅝×3H, s), 2.76 (⅜×3H, s), 2.88–3.09 (2H, m), 4.04 (⅜×1H, d, J=17 Hz), 4.30 (⅜×1H, d, J=17 Hz), 4.44 (⅝×2H, ABq, Δ=0.08, J=15 Hz), 4.76–4.92 (1H, m), 5.22–5.38 (1H, m), 7.03–7.40 (7H, m), 8.05 (⅜×1H, d, J=2 Hz), 8.18 (⅝×1H, d, J=2 Hz)

(2) MASS: m/z 370 (M+H)⁺; NMR (CDCl₃, δ): 1.39 (¼×9H, s), 1.42 (¾×9H, s), 2.69 (¾×3H, s), 2.82 (¼×3H, s), 2.90–3.12 (2H, m), 4.28 (¼×2H, s), 4.48 (¾×2H, ABq, Δ=0.06, J=15 Hz), 4.68–4.98 (1H, m), 5.20–5.40 (1H, m), 6.73–7.35 (7H, m), 8.40–8.52 (2H, m)

Preparation 54

Trifluoroacetic acid (150 ml) was slowly added to ice-cooled Starting compound (72.82 g), and the mixture was stirred at room temperature for 2.5 hours. The trifluoroacetic acid was evaporated and the residue was cooled with ice. 1510 Aqueous sodium hydroxide (about 400 ml) was added to the residue, and the mixture was extracted three times with chloroform. The organic layer was dried over magnesium sulfate. Evaporation of the solvent gave Object compound (62.01 g) as a colorless oil.

MASS: m/z 270 (M+H)⁺; NMR (CDCl₃, δ): 2.71 (¾×3H, s), 2.76–3.10 (2H, m), 2.88 (¼×3H, s), 3.82–4.02 (1H, m), 4.28 (¼×2H, ABq, Δ=0.20, J=17 Hz), 4.55 (¾×2H, ABq, Δ=0.21, J=15 Hz), 7.11–7.55 (7H, m), 8.32–8.58 (2H, m)

Preparation 55

Object compound was obtained according to a similar manner to that of Preparation 3, 4, 8, 41 or 54.

MASS: m/z 303 (M+H)⁺; NMR (CDCl₃, δ): 2.49 (⅝×3H, s), 2.72 (⅜×3H, s), 2.98–3.23 (2H, m), 3.70 (⅜×1H, d, J=17 Hz), 4.23 (⅜×1H, d, J=17 Hz), 4.40 (1H, t, J=7 Hz), 4.42 (⅝×2H, ABq, Δ=0.07, J=15 Hz), 7.08–7.52 (7H, m), 8.06 (⅜×1H, d, J=2 Hz), 8.20 (⅝×1H, d, J=2 Hz)

Preparation 56

To a stirred solution of (2S)-3-(2-pyridyl)-2-(tert-butoxycarbonylamino)propionic acid (1.19 g) and Starting Compound (1.20 g) in N,N-dimethylformamide (3 ml) was added dropwise diphenylphosphoryl azide (1.25 g) followed by triethylamine (1.36 ml) at 0° C. The mixture was stirred at room temperature for 3 hours. The reaction mixture was diluted with water and extracted with chloroform. The extract was dried and evaporated. The residue was purified by column chromatography on silica gel in chloroform ~2% methanol-chloroform. Recrystallization from ethyl acetate—n-hexane gave Object Compound (1.69 g).

MASS: m/z 518 (M⁺+1); NMR (CDCl₃, δ): 1.44 (9H, s), 2.52 (3H×¾, s), 2.74 (3H×¼, s), 2.80 (2H×¾, d, J=7 Hz), 2.93 (2H×¼, m), 3.19 (1H, m), 3.35 (1H, m), 4.08 (1H×¼, d, J=16 Hz), 4.21 (1H×¼, d, J=16 Hz), 4.27 (1H×¾, d, J=15 Hz), 4.56 (1H×¾, d, J=15 Hz), 4.57 (1H, m), 5.06 (1H, q, J=7 Hz), 6.43 (1H, m), 7.05–7.35 (9H, m), 7.60 (2H, m), 8.21 (1H×¼, d, J=2 Hz), 8.35 (1H×¾, d, J=2 Hz), 8.51 (2H, m)

Preparation 57

Object compounds were obtained according to a similar manners to that of Preparation 1, 6, 11, 38, 52 or 56.

(1) MASS: m/z 555 (M⁺+1); NMR (CDCl₃, δ): 1.42 (9H, s), 2.47 (3H×⅔, s), 2.75 (3H×⅓, s), 2.85 (2H, m), 3.12–3.32 (2H, m), 4.11 (1H×⅓, d, J=16 Hz), 4.18 (1H×⅓, d, J=16 Hz), 4.22 (1H×⅔, d, J=15 Hz), 4.52 (1H×⅔, d, J=15 Hz), 5.02 (1H, m), 5.13 (1H, m), 6.68 (1H, t, J=8 Hz), 6.87–7.35 (15H, m), 7.62 (1H, m), 8.13 (1H×⅔, s), 8.16 (1H×⅓, s)

(2) MASS: m/z 506 (M⁺+1); NMR (CDCl₃, δ): 1.43 (9H, s), 2.63 (3H×⅔, s), 2.83 (3H×⅓, s), 2.91–3.02 (3H, m), 3.12 (1H, m), 4.16 (1H×⅓, d, J=16 Hz), 4.34–4.54 (2×⅔H, m), 5.05 (1H, m), 6.81 (1H, s), 6.99–7.13 (4H, m), 7.21–7.28 (7H, m), 7.47 (1H, d, J=8 Hz)

(3) MASS: m/z 552 (M⁺); NMR (CDCl₃, δ): 1.44 (9H, s), 2.53 (3H×⅔, s), 2.71 (3H×⅓, s), 2.79 (2H, d, J=8 Hz), 3.19 (1H, m), 3.33 (1H, m), 4.23 (1H×⅔, d, J=15 Hz), 4.26 (1H×⅓, d, J=16 Hz), 4.48 (1H×⅓, d, J=16 Hz), 4.51 (1H×⅔, d, J=15 Hz), 4.57 (1H, m), 5.05 (1H, m), 6.43 (1H, m), 7.06–7.25 (10H, m), 7.60 (1H, m), 8.12 (1H, m), 8.51 (1H, m)

(4) MASS: m/z 518 (M⁺+1); NMR (CDCl₃, δ): 1.45 (9H, s), 2.62 (3H×¾, s), 2.77 (3H×¼, s), 2.82–2.98 (2H, m), 3.12–3.33 (2H, m), 4.02–4.54 (3H, m), 4.93 (1H×¼, m), 5.12 (1H×¾, m), 6.63–6.68 (2H×¼, m), 6.82–6.84 (2H×¾, m), 7.06–7.24 (7H, m), 7.54–7.62 (2H, m), 8.37–8.52 (3H, m)

(5) MASS: m/z 517 (M⁺+1); NMR (CDCl₃, δ): 1.44 (9H, s), 2.49 (3H×¾, s), 2.76 (3H×¼, s), 2.72–2.95 (2H, m), 3.08–3.37 (2H, m), 4.17 (1H×¼, d, J=15 Hz), 4.30 (1H×¾, d, J=15 Hz), 4.34 (1H×¼, d, J=15 Hz), 4.53 (1H×¾, d, J=15 Hz), 4.57 (1H, m), 5.08 (1H, m), 6.84–7.26 (13H, m), 7.53–7.62 (2H, m), 8.49–8.52 (1H, m)

Preparation 58

Object compounds were obtained according to a similar manner to that of Preparation 3, 4, 8, 41 or 54.

(1) NMR (CDCl₃, δ): 2.77 (3H×¾, s), 2.86 (3H×¼, s), 2.87–3.08 (3H, m), 3.17–3.35 (1H, m), 3.74–3.85 (1H, m), 4.32 (1H×¾, d, J=15 Hz), 4.37 (1H×¼, d, J=15 Hz), 4.58 (1H×¼, d, J=15 Hz), 4.62 (1H×¾, d, J=15 Hz), 4.97–5.06 (1H×¼, m), 5.15–5.25 (1H×¾, m), 6.75–6.79 (2H×¼, m), 6.87–6.89 (2H×¾, m), 7.14–7.27 (7H, m), 7.56–7.64 (1H, m), 8.08–8.23 (1H, m), 8.44–8.52 (3H, m)

(2) NMR (CDCl₃, δ): 2.67 (3H×⅔, s), 2.85 (3H×⅓, s), 2.88–3.07 (3H, m), 3.17–3.31 (1H, m), 3.72–3.87 (1H, m), 4.32 (1H×⅔, d, J=15 Hz), 4.33 (1H×⅓, d, J=15 Hz), 4.63 (1H×⅓, d, J=15 Hz), 4.65 (1H×⅔, d, J=15 Hz), 6.96–7.29 (12H, m), 7.55–7.63 (1H, m), 8.17–8.28 (1H, m), 8.48–8.52 (1H, m)

(3) NMR (CDCl₃, δ): 2.67 (3H×⅔, s), 2.75 (3H×⅓, s), 2.92 (3H, m), 3.18–3.31 (1H, m), 3.74 (1H, m), 4.23 (1H×⅓, d, J=16 Hz), 4.25 (1H×⅔, d, J=15 Hz), 4.53 (1H×⅓, d, J=16 Hz), 4.56 (1H×⅔, d, J=15 Hz), 7.10–7.30 (10H, m), 7.56 (1H, m), 8.00–8.20 (2H, m), 8.49 (1H, m)

(4) NMR (CDCl₃, δ): 2.72 (3H×⅔, s), 2.79–3.06 (4H, m), 2.87 (3H×⅓, s), 3.49 (1H×⅓, dd, J=4, 7 Hz), 3.58 (1H×⅔, t, J=6 Hz), 4.32 (1H×⅓, d, J=16 Hz), 4.37 (1H×⅔, d, J=15 Hz), 4.44 (1H×⅓, d, J=16 Hz), 4.65 (1H×⅔, d, J=15 Hz), 5.15 (1H, q, J=7 Hz), 6.78 (1H, d, J=10 Hz), 7.01–7.28 (10H, m), 7.47 (1H, d, J=2 Hz), 8.03 (1H×⅓, d, J=8 Hz), 8.07 (1H×⅔, d, J=8 Hz)

(5) NMR (CDCl₃, δ): 2.71 (3H×⅔, s), 2.86 (3H×⅓, s), 2.85–3.04 (3H, m), 3.23 (1H×⅓, dd, J=3, 15 Hz), 3.30

(1H×⅔, dd, J=3, 15 Hz), 3.61 (1H×⅓, dd, J=4, 15 Hz), 3.69 (1H×⅔, dd, J=4, 15 Hz), 4.29 (1H×⅔, d, J=15 Hz), 4.41 (2H×⅓, s), 4.68 (1H×⅔, d, J=15 Hz), 5.21 (1H, m), 6.96–7.37 (14H, m), 7.67 (1H, m), 7.94–8.16 (2H, m)

(6) NMR (CDCl$_3$, δ): 2.69 (3H×¾, s), 2.82 (3H×¼, s), 2.85–3.03 (3H, m), 3.18–3.30 (1H, m), 3.69 (1H×¼, dd, J=3, 7 Hz), 3.77 (1H×¾, dd, J=3, 7 Hz), 4.30 (1H×¼, d, J=16 Hz), 4.32 (1H×¾, d, J=15 Hz), 4.38 (1H×¼, d, J=16 Hz), 4.65 (1H×¾, d, J=15 Hz), 5.15 (1H, m), 7.14–7.27 (8H, m), 7.37 (1H, m), 7.61 (1H, m), 8.21–8.53 (4H, m)

Preparation 59

The following object compound was obtained according to a similar manner to that of Preparation 1, 6, 11, 38, 52 or 58.

MASS: 486 (M+1); NMR (CDCl$_3$, δ): 1.43 (9H, s), 2.09 (3×⅓H, s), 2.11 (3×⅔H, s), 2.57 (3×⅔H, s), 2.82 (3×⅓H, s), 2.79–2.88 (2H, m), 2.99–3.04 (2H, m), 4.08 (2×⅙H, d, J=16 Hz), 4.31 (2×⅙H, d, J=16 Hz), 4.39 (2×⅓H, d, J=15 Hz), 4.59 (2×⅓H, d, J=15 Hz), 4.20–4.32 (1H, m), 5.11–5.20 (1H, m), 5.22–5.37 (1H, m), 6.93–7.32 (11H, m)

Preparation 60

The following object compounds were obtained according to a similar manner to that of Preparation 1, 6, 11, 38, 52 or 56.

(1) MASS: 491 (M+1); NMR (CDCl$_3$, δ): 1.43 (9H, s), 2.69 (3×⅘H, s), 2.77 (3×⅕H, s), 2.92–3.13 (2H, m), 3.35 (1H, t, J=8 Hz), 3.57–3.63 (1H, m), 3.90–4.03 (1H, m), 4.12–4.25 (1H, m), 4.35 (2×⅒H, d, J=16 Hz), 4.40 (2×⅒H, d, J=16 Hz), 4.39 (2×⅖H, d, J=15 Hz), 4.50 (2×⅖H, d, J=15 Hz), 5.10 (1H, q, J=8 Hz), 5.43 (1H, d, J=8 Hz), 7.09–7.19 (2H, m), 7.20–7.32 (5H, m), 7.39 (1H, d, J=8 Hz), 8.10 (1×⅕H, s), 8.19 (1×⅘H, s)

(2) MASS: 714 (M+1); NMR (CDCl$_3$, δ): 1.42 (9H, s), 1.48–1.53 (1H, m), 1.54 (3×⅔H, s), 2.64–2.73 (1H, m), 2.77 (3×⅓H, s), 2.89–3.03 (2H, m), 3.85–3.95 (1H, m), 4.17–4.34 (2×⅔H, m), 4.54 (2×⅓H, d, J=15 Hz), 4.67–4.77 (1H, m), 5.04–5.13 (1H, m), 6.72–7.31 (20H, m), 7.39–7.43 (6H, m)

(3) MASS: 507 (M+1); NMR (CDCl$_3$, δ): 1.45 (9H, s), 2.73 (3×¾H, s), 2.88 (3×¼H, s), 2.93–3.12 (2H, m), 3.24–3.33 (1H, m), 3.52–3.64 (1H, m), 3.92–4.08 (1H, m), 4.13–4.24 (1H, m), 4.60 (2×½H, d, J=15 Hz), 4.78 (2×½H, d, J=15 Hz), 5.10–5.20 (1H, m), 5.38–5.47 (1H, m), 7.10–7.20 (6H, m), 7.58 (1H, t, J=8 Hz), 7.71 (1H, t; J=8 Hz), 7.80 (1H, d, J=8 Hz), 7.82 (1×¼H, s), 7.92 (1×¾H, s), 8.10 (1H, dd, J=8, 2 Hz), 8.70 (1×¼H, d, J=2 Hz), 8.76 (1×¾H, d, J=2 Hz)

(4) MASS: (m/z): 516 (M$^+$+1); NMR (CDCl$_3$, δ): 2.52 (3H×⅔, s), 2.79 (3H×⅓, s), 2.97 (2H, m), 3.04 (2H, m), 4.02 (1H×⅓, d, J=15 Hz), 4.25 (1H×⅓, d, J=15 Hz), 4.34 (1H×⅔, d, J=15 Hz), 4.37 (1H, m), 4.54 (1H×⅔, d, J=15 Hz), 4.92 (1H, m), 5.11 (1H, m), 6.68 (1H×⅓, d, J=8 Hz), 6.79 (1H×⅔, d, J=8 Hz), 6.91 (1H, m), 7.04–7.30 (14H, m)

(5) MASS: (m/z): 457 (M$^+$+1); NMR (CDCl$_3$, δ): 1.46 (9H, s), 2.75 (3H×¾, s), 2.86 (3H×¼, s), 2.91–3.12 (2H, m), 3.57–3.65 (1H, m), 3.97 (1H, m), 4.20 (1H, m), 4.28 (1H×¼, d, J=15 Hz), 4.33 (1H×¼, d, J=15 Hz), 4.44 (1H×¾, d, J=15 Hz), 4.54 (1H×¾, d, J=15 Hz), 4.98–5.07 (1H×¼, m), 5.13–5.21 (1H×¾, m), 5.46 (1H, t, J=7 Hz), 6.88 (1H×¼, d, J=7 Hz), 6.94 (1H×¾, d, J=7 Hz), 7.10–7.28 (5H, m), 8.49 (2H, d, J=7 Hz)

(6) MASS: (m/z): 457 (M$^+$+1); NMR (CDC$_3$, δ): 1.46 (9H, s), 2.70 (3H×¾, s), 2.82 (3H×¼, s), 3.02 (2H, m), 3.38 (1H, m), 3.61 (1H, m), 3.97 (1H, m), 4.07 (1H×¼, d, J=15 Hz), 4.21 (1H, m), 4.42 (1H×¼, d, J=15 Hz), 4.44 (1H×¾, d, J=15 Hz), 4.57 (1H×¾, d, J=15 Hz), 5.12 (1H, m), 5.44 (1H, m), 7.13–7.29 (7H, m), 7.44 (1H, m), 8.34 (1H×¼, d, J=2 Hz), 8.42 (1H×¾, d, J=2 Hz), 8.53 (1H, dd, J=2, 6 Hz)

(7) MASS (m/z): 546 (M$^+$+1); NMR (CDCl$_3$, δ): 1.44 (9H, s), 2.60 (3H×⅔, s), 2.82 (3H×⅓, s), 2.91–3.07 (2H, m), 3.58 (1H, dd, J=7, 16 Hz), 3.89 (1H, m), 4.11–4.37 (2H, m), 4.48–4.61 (2H, m), 5.15 (1H, q, J=7 Hz), 5.33 (1H, m), 6.94 (1H, m), 7.07–7.34 (16H, m)

(8) MASS (m/z): 482 (M$^+$+1); NMR (CDCl$_3$, δ): 0.96 (6H, m), 1.45 (9H, s), 1.55–1.71 (3H, m), 2.60 (3H×⅔, s), 2.83 (3H×⅓, s), 2.98–3.03 (2H, m), 4.09 (1H×⅓, d, J=15 Hz), 4.31 (1H×⅓, d, J=15 Hz), 4.39 (1H×⅔, d, J=15 Hz), 4.56 (1H×⅔, d, J=15 Hz), 4.82 (1H, m), 5.15 (1H, m), 6.82–6.96 (2H, m), 7.07–7.28 (10H, m)

(9) MASS (m/z): 547 (M$^+$+1); NMR (CDCl$_3$, δ): 1.45 (9H, s), 2.85 (3H×⅓, s), 2.93 (3H×⅔, s), 3.08 (1H, m), 3.26 (1H, m), 3.56 (1H, m), 3.87 (1H, m), 4.26–4.32 (2H, m), 4.46–4.67 (3H, m), 4.75 (1H, m), 5.38 (2H, m), 6.87–7.16 (4H, m), 7.24–7.53 (9H, m), 8.47 (1H, m)

(10) MASS (m/z): 500 (M+H); NMR (CDCl$_3$, δ): 1.41 (9H, s), 1.81–1.97 (1H, m), 1.98–2.07 (1H, m), 2.10 (3H, s), 2.46–2.55 (2H, m), 2.61 (3×⅔H, s), 2.84 (3×⅓H, s), 2.98–3.07 (2H, m), 4.09–4.43 (2×⅔H, m), 4.20–4.30 (1H, m), 4.58 (2×⅓H, d, J=15 Hz), 5.12 (2H, q, J=8 Hz), 6.93–7.32 (11H, m)

(11) MASS (m/z): 532 (M+H)$^+$; NMR (CDCl$_3$, δ): 1.42 (9H, s), 2.53 (⅔×3H, z), 2.79 (⅓×3H, s), 2.85–3.04 (4H, m), 4.13 (⅓×2H, ABq, Δ=0.18, J=17 Hz), 4.22–4.38 (1H, m), 4.32 (⅔×1H, d, J=15 Hz), 4.58 (⅔×1H, d, J=15 Hz), 4.90–5.18 (1H, m), 6.22 (1H, br s), 6.60–7.32 (16H, m)

(12) MASS (m/z): 471 (M$^+$+1); NMR (CDCl$_3$, δ): 1.46 (9H, s), 2.52 (3H×¼, s), 2.54 (3H×¾, s), 2.68 (3H×¾, s), 2.81 (3H×¼, s), 2.93–3.07 (2H, m), 3.41 (1H, m), 3.61 (1H, m), 4.00 (1H, m), 4.21 (1H, m), 4.41 (1H, d, J=15 Hz), 4.52 (1H, d, J=15 Hz), 5.11 (1H×¾, m), 5.17 (1H×¼, m), 5.43 (1H, d, J=6 Hz), 7.08–7.37 (7H, m), 8.24 (1H×¼, br s), 8.31 (1H×¾, br s)

(13) MASS (m/z): 470 (M$^+$+1); NMR (CDCl$_3$, δ): 1.11 (3H×⅓, d, J=7 Hz), 1.14 (3H×⅔, d, J=7 Hz), 1.46 (9H, s), 2.68 (3H×⅔, s), 2.86 (3H×⅓, s), 2.93–3.10 (2H, m), 4.03 (1H×⅓, d, J=8 Hz), 4.12 (1H×⅔, d, J=8 Hz), 4.22 (1H×⅓, d, J=16 Hz), 4.25 (1H, br s), 4.41 (1H×⅔, d, J=15 Hz), 4.42 (1H×⅓, d, J=16 Hz), 4.61 (1H×⅔, d, J=15 Hz), 5.15 (1H, m), 5.34 (1H, m), 7.02–7.29 (12H, m)

(14) MASS: 566 (M+1); NMR (CDCl$_3$, δ): 1.37 (9H, s), 2.47 (3×⅔H, s), 2.69 (3×⅓H, s), 2.88–3.02 (2H, m), 3.13–3.27 (2H, m), 3.09 (2×⅙H, d, J=16 Hz), 4.09 (2×⅓H, d, J=15 Hz), 4.13 (2×⅙H, d, J=16 Hz), 4.40–4.52 (1H, m), 4.51 (2×⅓H, d, J=15 Hz), 4.92–5.01 (1H, m), 5.02–5.13 (1H, m), 6.68 (1×⅓H, d, J=8 Hz), 6.78 (1×⅔H, d, J=8 Hz), 6.81–6.90 (1H, m), 6.98–7.20 (6H, m), 7.21–7.30 (3H, m), 7.31 (1H, t, J=8 Hz), 7.40–7.48 (2H, m), 7.62 (1H, s), 7.70–7.82 (3H, m)

(15) MASS: 521 (M+1); NMR (CDCl$_3$, δ): 1.47 (9H, s), 2.53 (3H, s), 2.58 (3×¾H, s), 2:72 (3×¼H, s), 2.78–3.01 (3H, m), 3.03–3.20 (1H, m), 3.95 (2×⅛H, d, J=16 Hz), 4.30 (2×⅛H, d, J=16 Hz), 4.32 (2×⅜H, d, J=15 Hz), 4.48 (2×⅜H, d, J=15 Hz), 4.32–4.50 (1H, m), 4.97–5.12 (1H, m), 5.70–5.90 (1H, m), 6.80 (1H, s), 7.02–7.40 (8H, m), 7.50 (1×⅘H, s), 7.52 (1×⅕H, s), 8.17 (1×⅕H, s), 8.27 (1×⅘H, s)

(16) MASS: 530 (M+1); NMR (CDCl$_3$, δ): 1.33 (9×½H, s), 1.37 (9×½H, s), 2.43–2.70 (5H, m), 2.77–3.10 (4H, m), 3.17–3.37 (1H, m), 4.29 (2×⅙H, d, J=16 Hz), 4.31 (2×⅓H, d, J=15 Hz), 4.36 (2×⅙H, d, J=16 Hz), 4.62 (2×⅓H, d, J=15 Hz), 4.69–4.80 (1×½H, m), 4.81–4.99 (1×½H, m), 5.12–5.23 (1H, m), 6.50–6.90 (1H, m), 6.93–7.37 (15H, m)

(17) MASS: 568 (M+1); NMR (CDCl$_3$, δ): 1.42 (9H, s), 2.59 (3×¾H, s), 2.83 (3×¼H, s), 2.71–2.88 (2H, m), 3.15–3.40 (2H, m), 4.30 (2×⅙H, d, J=16 Hz), 4.41 (2×⅙H, d, J=16 Hz), 4.43 (2×⅓H, d, J=15 Hz), 4.78 (2×⅓H, d, J=15 Hz), 4.52–4.63 (1H, m), 5.03–5.20 (1H, m), 6.37–6.46 (1H, m), 7.02–7.22 (7H, m), 7.51–7.80 (5H, m), 7.87 (1H, s), 8.06 (1×¼H, d, J=8 Hz), 8.10 (1×¾H, d, J=8 Hz), 8.51 (1×¾H, d, J=2 Hz), 8.54 (1×¼H, d, J=2 Hz), 8.70 (1H, d, J=8 Hz)

(18) MASS: 508 (M+1); NMR (CDCl$_3$, δ): 1.45 (9H, s), 2.92 (3×¾H, s), 2.98 (3×¼H, s), 3.00–3.22 (2H, m), 3.30 (1H, t, J=5 Hz), 3.52–3.64 (1H, m), 3.87–4.02 (1H, m), 4.12–4.25 (1H, m), 4.68 (2×⅙H, d, J=16 Hz), 4.71 (2×⅓H, d, J=15 Hz), 4.73 (2×⅙H, d, J=16 Hz), 4.98 (2×⅓H, d, J=15 Hz), 5.14–5.32 (1H, m), 5.38–5.48 (1H, m), 7.12–7.22 (6H, m), 7.73–7.80 (2H, m), 7.99–8.06 (1H, m), 8.10–8.14 (1H, m), 8.78 (1×⅙H, s), 8.80 (1×⅚H, s)

(19) MASS: 569 (M+1); NMR (CDCl$_3$, δ): 1.43 (9H, s), 2.73 (3×⅘H, s), 2.80–3.10 (2H, m), 2.91 (3×⅕H, s), 3.12–3.40 (2H, m), 4.50–4.70 (1H, m), 4.59 (2×½H, d, J=15 Hz), 4.91 (2×½H, d, J=15 Hz), 5.03–5.28 (1H, m), 6.23–6.41 (1H, m), 7.00–7.23 (7H, m), 7.59 (1H, t, J=8 Hz), 7.67–7.80 (3H, m), 7.92–8.03 (1H, m), 8.04–8.14 (1H, m), 8.48–8.52 (1H, m), 8.58 (1×⅘H, s), 8.71 (1×⅕H, s)

(20) MASS: 558 (M+1); NMR (CDCl$_3$, δ): 1.47 (9H, s), 2.83 (3×⅘H, s), 2.90–3.20 (5H, m), 2.98 (3×⅕H, s), 4.33–4.45 (1H, m), 4.63 (2×⅓H, s), 4.74 (2×⅖H, d, J=15 Hz), 4.83 (2×⅖H, d, J=15 Hz), 5.02–5.12 (1×⅘H, m), 5.13–5.22 (1×⅕H, m), 6.81 (1H, s), 7.08–7.30 (6H, m), 7.51 (1H, s), 7.73–7.80 (2H, m), 7.98–8.03 (1H, m), 8.10–8.17 (1H, m), 8.72 (1×⅕H, s), 8.77 (1×⅘H, s)

(21) MASS: 534 (M+1); NMR (CDCl$_3$, δ): 1.48 (9H, s), 2.83 (3×¾H, s), 2.87 (3×¼H, s), 2.95–3.12 (2H, m), 3.55–3.63 (1H, m), 3.95–4.02 (1H, m), 4.15–4.25 (1H, m), 4.42 (2×⅙H, d, J=16 Hz), 4.43 (2×⅓H, d, J=15 Hz), 4.47 (2×⅙H, d, J=16 Hz), 4.70 (2×⅓H, d, J=15 Hz), 5.10–5.22 (1H, m), 5.38–5.48 (1H, m), 7.08–7.32 (7H, m), 7.45 (1×¼H, dd, J=8, 2 Hz), 7.58 (1×¾H, dd, J=8, 2 Hz), 7.81 (1H, dd, J=8, 5 Hz), 8.31–8.40 (2H, m), 8.41 (1×¼H, s), 8.50 (1×¾H, s), 8.67–8.71 (1H, m)

(22) MASS: 595 (M+1); NMR (CDCl$_3$, δ): 1.44 (9H, s), 2.59 (3×⅘H, s), 2.70–3.02 (2H, m), 2.68 (3×⅕H, s), 3.13–3.40 (2H, m), 4.16 (2×⅙H, d, J=16 Hz), 4.30 (2×⅙H, d, J=16 Hz), 4.37 (2×⅓H, d, J=15 Hz), 4.53 (2×⅓H, d, J=15 Hz), 4.54–4.63 (1H, m), 5.01–5.13 (1H, m), 6.35–6.48 (1H, m), 7.03–7.28 (7H, m), 7.37–7.47 (2H, m), 7.53–7.70 (3H, m), 8.23–8.33 (1H, m), 8.47 (1H, s), 8.51 (1H, d, J=3 Hz), 8.67 (1H, d, J=8 Hz), 9.18 (1H, s)

(23) MASS: 534 (M+1); NMR (CDCl$_3$, δ): 1.47 (9H, s), 2.73 (3×⅘H, s), 2.83 (3×⅕H, s), 2.97–3.17 (2H, m), 3.23–3.32 (1H, m), 3.58–3.66 (1H, m), 3.94–4.07 (1H, m), 4.11 (2×⅙H, d, J=16 Hz), 4.17–4.25 (1H, m), 4.48 (2×⅙H, d, J=16 Hz), 4.50 (2×⅓H, d, J=15 Hz), 4.59 (2×⅓H, d, J=15 Hz), 5.10–5.22 (1H, m), 5.38–5.45 (1H, m), 7.12–7.32 (6H, m), 7.38–7.48 (1H, m), 7.55 (1H, dd, J=8, 2 Hz), 7.68 (1H, dd, J=8, 2 Hz), 8.27–8.32 (1H, m), 8.43 (1×⅕H, s), 8.52 (1×⅘H, s), 8.67 (1H, d, J=2 Hz), 9.19 (1H, s)

(24) MASS (m/z): 737 (M$^+$+1); NMR (CDCl$_3$, δ): 1.42 (9H, s), 1.44 (2H, m), 1.82 (2H, m), 2.14 (3H, m), 2.66 (3H, s), 2.73 (3H, s), 2.75 (2H, m), 2.78 (3H, s), 3.12 (2H, m), 3.82 (3H, s), 4.14 (1H, d, J=16 Hz), 4.41 (1H, d, J=16 Hz), 4.54 (1H, m), 4.92 (1H, m), 4.52 (1H, m), 6.55 (1H, m), 7.00–7.24 (10H, m)

(25) MASS (m/z): 517 (M$^+$+1); NMR (CDCl$_3$, δ): 1.43 (9H, s), 2.55 (3H×¾, s), 2.77 (3H×¼, s), 2.97 (2H, m), 3.06 (2H, m), 4.03 (1H×¼, d, J=16 Hz) 4.24 (1H×¼, d, J=16 Hz), 4.32 (1H×¾, d, J=15 Hz), 4.37 (1H, m), 4.57 (1H×¾, d, J=15 Hz), 4.92 (1H, m), 5.10 (1H, m), 6.72 (1H, m), 7.10–7.39 (12H, m), 8.26 (1H×¼, br s), 8.40 (1H×¾, br s), 8.53 (1H, m)

(26) MASS (m/z): 518 (M$^+$+1); NMR (CDCl$_3$, δ): 1.41 (9H, s), 2.59 (3H×¾, s), 2.78 (3H×¼, s), 2.92–3.03 (3H, m), 3.12 (1H, m), 3.99 (1H×¼, d, J=16 Hz), 4.27 (1H×¼, d, J=16 Hz), 4.33 (1H×¾, d, J=15 Hz), 4.43 (1H, m), 4.61 (1H×¾, d, J=15 Hz), 4.95 (1H, d, J=7 Hz), 5.09 (1H, m), 6.90 (1H, d, J=7 Hz), 7.09–7.40 (9H, m), 8.27 (1H×⅕, br s), 8.41 (1H×⅘, br s), 8.50 (2H, d, J=5 Hz), 8.53 (1H, d, J=5 Hz)

(27) MASS (m/z): 523 (M$^+$+1); NMR (CDCl$_3$, δ): 1.46 (9H, s), 2.73 (3H×¾, s), 2.85 (3H×¼, s), 2.93–3.11 (2H, m), 3.59 (1H, m), 3.98 (1H, m), 4.17 (1H×¼, d, J=15 Hz), 4.20 (1H, m), 4.47 (1H×¼, d, J=15 Hz), 4.52 (1H×¾, d, J=15 Hz), 4.58 (1H×¾, d, J=15 Hz), 5.14 (1H, m), 5.40 (1H, m), 7.17–7.27 (7H, m), 7.61 (2H, d, J=8 Hz), 8.10 (1H, s), 8.54 (1H, s)

(28) MASS (m/z): 515 (M+1)$^+$; NMR (CDCl$_3$, δ): 1.46 (9H, s), 1.90 (1H, m), 2.03 (1H, m), 2.10 (3H, s), 2.47–2.57 (2H, m), 2.54 (3H, m), 2.60 (3H×⅘, s), 2.79 (3H×⅕, s), 3.01 (2H, d, J=7.5 Hz), 4.27 (1H, m), 4.36 (1H, d, J=14.5 Hz), 4.52 (1H, d, J=14.5 Hz), 5.07–5.23 (2H, m), 6.90–7.01 (1H, m), 7.05–7.23 (6H, m), 7.25–7.34 (1H, m), 8.20 (⅕H, d, J=2.5 Hz), 8.31 (⅘H, d, J=2.5 Hz)

(29) MASS (m/z): 501 (M+1)$^+$; NMR (CDCl$_3$, δ): 1.47 (9H, s), 1.91 (1H, m), 2.04 (1H, m), 2.10 (3H, s), 2.47–2.57 (2H, m), 2.63 (3H×⅘, s), 2.80 (3H×⅕, s), 3.02 (2H, d, J=8.5 Hz), 4.26 (1H, m), 4.37 (1H, d, J=14.5 Hz), 4.59 (1H, d, J=14.5 Hz), 5.09–5.20 (2H, m), 6.92–7.02 (1H, m), 7.10–7.30 (6H, m), 7.39–7.45 (1H, m), 8.29 (1H×⅕, d, J=1.5 Hz), 8.41 (1H×⅘, d, J=1.5 Hz), 8.53 (1H, d, J=5.5 Hz)

(30) MASS (m/z): 551 (M+1)$^+$; NMR (CDCl$_3$, δ): 1.46 (9H, s), 1.92 (1H, m), 2.05 (1H, m), 2.09 (3H, s), 2.46–2.58 (2H, m), 2.69 (3H×⅘, s), 2.88 (3H×⅕, s), 3.03 (2H, d, J=7.5 Hz), 4.21–4.35 (1H, m), 4.28 (1H×⅕, d, J=14.5 Hz), 4.51 (1H×⅕, d, J=14.5 Hz), 4.56 (1H×⅘, d, J=14.5 Hz), 4.78 (1H×⅘, d, J=8.0 Hz), 5.07–5.29 (2H, m), 6.93–7.04 (1H, m), 7.10–7.20 (5H, m), 7.51–7.60 (1H, m), 7.68–7.78 (1H, m), 7.80 (1H, d, J=7.5 Hz), 7.93 (1H×⅘, d, J=0.75 Hz), 8.06 (1H×⅕, d, J=0.75 Hz), 8.11 (1H, d, J=7.5 Hz), 8.61 (1H×⅕, d, J=1.5 Hz), 8.77 (1H×⅘, d, J=1.5 Hz)

(31) MASS (m/z): 552 (M+1)$^+$; NMR (CDCl$_3$, δ): 1.46 (9H, s), 1.83–2.11 (2H, m), 2.08 (3H, s), 2.41–2.57 (1H, m), 2.52 (1H, t, J=7.5 Hz), 2.87 (3H×⅕, s), 2.96 (3H×⅕, s), 3.01–3.10 (2H, m), 4.20–4.32 (1H, m), 4.61 (2H×⅕, s), 4.69 (1H×⅕, d, J=14.5 Hz), 4.93 (1H×⅕, d, J=14.5 Hz), 5.08–5.29 (2H, m), 6.97 (1H, m), 7.11–7.24 (5H, m), 7.73–7.80 (2H, m), 7.97–8.04 (1H, m), 8.07–8.15 (1H, m), 8.66 (1H×⅕, s), 8.79 (1H×⅘, s)

(32) MASS (m/z): 578 (M+1)$^+$; NMR (CDCl$_3$, δ): 1.47 (9H, s), 1.86–1.97 (1H, m), 2.00–2.12 (1H, m), 2.10 (3H, s), 2.52 (2H, t, J=7.5 Hz), 2.69 (3H×⅘, s), 2.83 (3H×⅕, s), 3.03 (2H, d, J=7.5 Hz), 4.13 (1H×⅕, d, J=14.5 Hz), 4.39 (1H×⅕, d, J=14.5 Hz), 4.48 (1H×⅘, d, J=14.5 Hz), 4.59. (1H×⅘, d, J=14.5 Hz), 5.08–5.23 (2H, m), 6.92–7.01 (1H, m), 7.13–7.33 (6H, m), 7.40 (1H, dd, J=7.5, 5.5 Hz), 7.52 (1H, dd, J=8.5, 1.5 Hz), 7.65 (1H×⅕, d, J=7.5 Hz), 7.69 (1H×⅘, d, J=7.5 Hz), 8.31 (1H, dd, J=8.5, 1.5 Hz), 8.40 (1H×⅕, d, J=1.5 Hz), 8.52 (1H×⅘, d, J=1.5 Hz), 8.65 (1H, d, J=5.5 Hz), 9.17 (1H×⅕, d, J=1.5 Hz), 9.19 (1H×⅘, d, J=1.5 Hz)

(33) MASS (m/z): 522 (M+1)$^+$; NMR (CDCl$_3$, δ): 1.43 (9H, s), 2.53 (3H×⅔, s), 2.80 (3H×⅓, s), 2.91–3.06 (2H, m), 3.18–3.39 (2H, m), 4.00 (1H×⅓, d, J=14.5 Hz), 4.26 (1H×⅓, d, J=14.5 Hz), 4.30–4.45 (1H, br s), 4.38 (1H×⅔, d, J=14.5 Hz), 4.53 (1H×⅔, d, J=14.5 Hz), 5.00 (1H, br s), 5.14 (1H, m), 6.81 (1H, dd, J=8.5, 1.5 Hz), 6.87–6.95 (2H, m), 7.07 (1H, dd, J=7.0, 1.5 Hz), 7.09–7.32 (10H, m)

(34) MASS: 500 (M+H)⁺; NMR (CDCl₃, δ): 1.45 (9H, s), 2.66 (⅔×3H, s), 2.78 (⅓×3H, s), 2.87–3.07 (2H, m), 3.05 (⅓×6H, s), 3.07 (⅔×6H, z), 3.52–3.65 (1H, m), 3.82 (⅓×1H, d, J=17 Hz), 3.90–4.05 (1H, m), 4.11–4.26 (1H, m), 4.34 (⅓×1H, d, J=17 Hz), 4.35 (⅔×2H, ABq, Δ=0.11, J=15 Hz), 5.01–5.32 (1H, m), 5.32–5.48 (1H, m), 6.47 (1H, d, J=9 Hz), 7.05–7.35 (7H, m), 7.90 (⅓×1H, d, J=2 Hz), 7.98 (⅔×1H, d, J=2 Hz)

(35) MASS (m/z): 597 (M+H)⁺; NMR (CDCl₃, δ): 1.46 (9H, s), 2.68 (¾×3H, s), 2.86 (¼×3H, s), 2.92–3.16 (2H, m), 3.53–3.66 (1H, m), 3.81–4.00 (1H, m), 4.21–4.62 ((2 +¼)H, m), 4.56 (2H, s), 4.81 (¾×1H, d, J=15 Hz), 5.10–5.45 (2H, m), 7.03–8.16 (16H, m), 8.61 (¼×1H, d, J=2 Hz), 8.75 (¾×1H, d, J=2 Hz)

(36) MASS (m/z): 506 (M+H)⁺; NMR (CDCl₃, δ): 1.43 (9H, s), 2.56 (⅔×3H, s), 2.80–3.06 (4H, m), 2.82 (⅓×3H, s), 4.15 (⅓×2H, ABq, Δ=0.24, J=17 Hz), 4.20–4.39 (1H, m), 4.46 (⅔×2H, ABq, Δ=0.15, J=15 Hz), 4.91 (1H, br s), 5.05–5.20 (1H, m), 6.21 (⅓×1H, s), 6.26 (⅔×1H, s), 6.70–7.40 (13H, m)

(37) MASS (m/z): 506 (M+H)⁺; NMR (CDCl₃, δ): 1.44 (9H, s), 2.52 (⅔×3H, s), 2.78 (⅓×3H, s), 2.87–3.22 (4H, m), 4.13 (⅓×2H, ABq, Δ=0.24, J=17 Hz), 4.34–4.48 (1H, m), 4.43 (⅔×2H, ABq, Δ=0.16, J=15 Hz), 5.00–5.23 (2H, m), 6.02–6.13 (1H, m), 6.27 (1H, m), 6.80–7.37 (12H, m)

(38) MASS.: 487 (M+1); NMR (CDCl₃, δ): 1.43 (9H, s), 2.64 (3×¾H, s), 2.78 (3×¼H, s), 2.90–3.11 (2H, m), 3.25–3.43 (1H, m), 3.52–3.63 (1H, m), 3.90 (3H, s), 3.84–4.02 (1H, m), 4.12–4.23 (1H, m), 4.23 (2×⅙H, d, J=16 Hz), 4.30 (2×⅓H, d, J=15 Hz), 4.35 (2×⅙H, d, J=16 Hz), 4.50 (2×⅓H, d, J=15 Hz), 5.02–5.25 (1H, m), 5.37–5.48 (1H, m), 6.68 (1H, d, J=8 Hz), 7.07–7.40 (7H, m), 7.88 (1×⅓H, s), 7.95 (1×⅓H, s)

(39) MASS: 557 (M+1); NMR (CDCl₃, δ): 1.40 (9H, s), 2.63 (3×⅓H, s), 2.84 (3×⅓H, s), 2.88–3.20 (4H, m), 4.22 (2×⅙H, d, J=16 Hz), 4.33–4.50 (1H, m), 4.53 (2×⅙H, d, J=16 Hz), 4.60 (2×⅓H, d, J=15 Hz), 4.68 (2×⅓H, d, J=15 Hz), 5.00–5.18 (1H, m), 5.71–5.90 (1H, m), 6.80 (1H, s), 7.04–7.22 (5H, m), 7.44–7.60 (3H, m), 7.68–7.80 (2H, m), 7.90 (1H, s), 8.04–8.11 (1H, m), 8.61 (1×⅓H, s), 8.71 (1×⅓H, s)

(40) MASS: 584 (M+1); NMR (CDCl₃, δ): 1.43 (9H, s), 2.68 (3×⅓H, s), 2.81 (3×⅓H, s), 2.87–3.02 (3H, m), 3.08–3.20 (1H, m), 4.11 (2×⅙H, d, J=16 Hz), 4.32–4.45 (1H, m), 4.48 (2×⅓H, d, J=15 Hz), 4.51 (2×⅓H, d, J=15 Hz), 4.58 (2×⅙H, d, J=16 Hz), 5.00–5.13 (1H, m), 6.82 (1H, s), 7.08–7.16 (2H, m), 7.18–7.28 (4H, m), 7.30–7.43 (2H, m), 7.46–7.53 (2H, m), 7.62–7.70 (1H, m), 8.29 (1H, d, J=8 Hz), 8.39 (1×⅓H, s), 8.50 (1×⅓H, s), 8.63 (1H, d, J=5 Hz), 9.18 (1H, s)

(41) MASS: 546 (M+1); NMR (CDCl₃, δ): 1.42 (9H, s), 2.54 (3×⅔H, s), 2.79 (3×⅓H, s), 2.90–3.03 (4H, m), 3.77 (3H, s), 4.02 (2×⅙H, d, J=16 Hz), 4.23 (2×⅙H, d, J=16 Hz), 4.31 (2×⅓H, d, J=15 Hz), 4.58 (2×⅓H, d, J=15 Hz), 4.25–4.40 (1H, m), 4.87–4.98 (1H, m), 5.03–5.18 (1H, m), 6.63–6.93 (4H, m), 7.01–7.17 (5H, m), 7.17–7.21 (2H, m), 7.22–7.32 (4H, m)

(42) MASS: 569 (M+1); NMR (CDCl₃, δ): 1.48 (9H, s), 2.60 (3×⅔H, s), 2.82 (3×⅓H, s), 2.73–2.90 (2H, m), 3.17–3.42 (2H, m), 4.40 (2×⅙H, d, J=16 Hz), 4.55 (2×⅙H, d, J=16 Hz), 4.56 (2×⅓H, d, J=15 Hz), 4.56–4.67 (1H, m), 4.75 (2×⅓H, d, J=15 Hz), 5.08–5.19 (1H, m), 6.30–6.50 (1H, m), 7.07–7.23 (7H, m), 7.38 (1H, d, J=8 Hz), 7.60 (1H, t, J=8 Hz), 7.62–7.75 (1H, m), 7.81 (1×⅔H, s), 8.01 (1×⅓H, s), 7.99 (1H, d, J=8 Hz), 8.51 (1H, d, J=3 Hz), 8.82 (2H, s)

(43) MASS: 566 (M+1); NMR (CDCl₃, δ): 1.38 (9H, s), 2.43 (3×¾H, s), 2.71 (3×¼H, s), 2.80–2.98 (2H, m), 3.35–3.67 (2H, m), 4.03 (2×⅛H, d, J=16 Hz), 4.16 (2×⅛H, d, J=16 Hz), 4.18 (2×⅜H, d, J=15 Hz), 4.54 (2×⅜H, d, J=15 Hz), 4.42–4.53 (1H, m), 4.90–5.18 (2H, m), 6.50–6.65 (1H, m), 6.83–7.40 (12H, m), 7.42–7.60 (2H, m), 7.74 (1H, d, J=8 Hz), 7.83 (1H, t, J=8 Hz), 8.12 (1H, d, J=8 Hz)

(44) MASS: 507 (M+1); NMR (CDCl₃, δ): 1.44 (9H, s), 2.60 (3×¾H, s), 2.71 (3×¼H, s), 2.74–3.03 (3H, m), 3.04–3.19 (1H, m), 4.32–4.40 (1H, m), 4.41 (2×⅜H, d, J=15 Hz), 4.47 (2×⅜H, d, J=15 Hz), 4.50 (2×⅛H, d, J=16 Hz), 4.63 (2×⅛H, d, J=16 Hz), 4.99–5.12 (1H, m), 5.72–5.90 (1H, m), 6.81 (1H, s), 7.08–7.32 (7H, m), 7.32–7.43 (1H, m), 7.47–7.53 (1H, m), 8.27 (1×¼H, s), 8.38 (1×¾H, s), 8.49–8.53 (1H, m)

(45) MASS: 532 (M+1); NMR (CDCl₃, δ): 1.41 (9H, s), 2.49 (3H, s), 2.52 (3×¾H, s), 2.71 (3×¼H, s), 2.87–3.00 (2H, m), 3.14–3.41 (2H, m), 3.98 (2×⅛H, d, J=16 Hz), 4.20 (2×⅛H, d, J=16 Hz), 4.23 (2×⅜H, d, J=15 Hz), 4.50 (2×⅜H, d, J=15 Hz), 4.52–4.63 (1H, m), 5.00–5.17 (1H, m), 6.30–6.47 (1H, m), 6.92–7.30 (9H, m), 7.53–7.68 (2H, m), 8.12 (1×¼H, s), 8.25 (1×¾H, s), 8.48–8.52 (1H, m)

(46) MASS: 517 (M+1); NMR (CDCl₃, δ): 1.40 (9H, s), 2.58 (3×⅔H, s), 2.82 (3×⅓H, s), 2.83–3.19 (4H, m), 4.09 (2×⅙H, d, J=15 Hz), 4.30 (2×⅙H, d, J=15 Hz), 4.33 (2×⅓H, d, J=16 Hz), 4.33–4.50 (1H, m), 4.60 (2×⅓H, d, J=16 Hz), 5.00–5.20 (2H, m), 6.90–7.40 (12H, m), 7.50 (1H, t, J=8 Hz), 8.40 (1H, s), 8.48 (1H, s)

(47) MASS: 550 (M+1); NMR (CDCl₃, δ): 1.41 (9H, s), 2.57 (3×⅔H, s), 2.81 (3×⅓H, s), 2.87–3.10 (4H, m), 3.99 (2×⅙H, d, J=16 Hz), 4.27 (2×⅙H, d, J=16 Hz), 4.32 (2×⅓H, d, J=15 Hz), 4.60 (2×⅓H, d, J=15 Hz), 4.28–4.43 (1H, m), 4.85–5.00 (1H, m), 5.02–5.18 (1H, m), 6.69–6.99 (2H, m), 7.02–7.15 (5H, m), 7.16–7.40 (8H, m)

(48) MASS: 528 (M+1); NMR (CDCl₃, δ): 1.46 (9×⅔H, s), 1.50 (9×⅓H, s), 2.48–2.73 (2H, m), 2.51 (3×⅔H, s), 2.78 (3×⅓H, s), 2.90–3.37 (2H, m), 4.26–4.70 (4H, m), 4.82–5.10 (2H, m), 6.52–6.73 (1H, m), 6.83–7.08 (5H, m), 7.09–7.40 (9H, m)

Preparation 61

The following object compounds were obtained according to a similar manner to that of Preparation 3, 4, 8, 41 or 54.

(1) NMR (CDCl₃, δ): 1.99 (3×⅓H, s), 2.03 (3×⅔H, s), 2.38–2.58 (1H, m), 2.72 (3×⅔H, s), 2.82–3.12 (3H, m), 2.90 (3×⅓H, s), 3.38 (1×⅓H, dd, J=12, 4 Hz), 3.49 (1×⅔H, dd, J=12, 4 Hz), 4.35 (2×⅔H, d, J=15 Hz), 4.36 (2×⅙H, d, J=16 Hz), 4.43 (2×⅙H, d, J=16 Hz), 4.68 (2×⅓H, d, J=15 Hz), 5.19 (1H, q, J=12 Hz), 7.00–7.32 (10H, m), 8.04 (1×⅓H, d, J=8 Hz), 8.13 (1×⅔H, d, J=8 Hz)

(2) MASS: 391 (M+1); NMR (CDCl₃, δ): 2.71 (3×¾H, s), 2.79 (3×¼H, s), 2.93–3.17 (2H, m), 3.35–3.49 (1H, m), 3.58–3.68 (1H, m), 3.70–3.81 (1H, m), 4.20 (2×⅛H, d, J=16 Hz), 4.39 (2×⅛H, d, J=16 Hz), 4.35 (2×⅜H, d, J=15 Hz), 4.58 (2×⅜H, d, J=15 Hz), 5.12 (1H, q, J=8 Hz), 7.10–7.18 (2H, m), 7.20–7.30 (4H, m), 7.38 (1H, d, J=8 Hz), 7.97 (1H, d, J=8 Hz), 8.09 (1×¼H, s), 8.19 (1×¾H, s)

(3) MASS: 614 (M+1); NMR (CDCl₃, δ): 2.31–2.50 (1H, m), 2.57–2.68 (1H, m), 2.63 (3×⅔H, s), 2.81 (3×⅓H, s), 2.88–3.04 (3H, m), 4.28 (2×⅔H, d, J=15 Hz), 4.63 (2×⅓H, d, J=15 Hz), 5.09 (1H, q, J=8 Hz), 6.93–7.31 (19H, m), 7.40–7.45 (6H, m), 7.70 (1×⅓H, d, J=8 Hz), 7.80 (1×⅔H, d, J=8 Hz)

(4) MASS: 407 (M+1); NMR (CDCl$_3$, δ): 2.73 (3×¾H, s), 2.89 (3×¼H, s), 2.94–3.18 (2H, m), 3.38–3.86 (3H, m), 4.39 (2×⅙H, d, J=16 Hz), 4.59 (2×⅙H, d, J=16 Hz), 4.60 (2×⅓H, d, J=15 Hz), 4.73 (2×⅓H, d, J=15 Hz), 5.11–5.31 (1H, m), 7.08–7.28 (5H, m), 7.56 (1H, t, J=8 Hz), 7.69 (1H, t, J=8 Hz), 7.77 (1H, d, J=8 Hz), 7.90 (1H, s), 8.00–8.12 (2H, m), 8.68 (1×¼H, d, J=2 Hz), 8.74 (1×¾H, d, J=2 Hz)

(5) NMR (CDCl$_3$, δ): 2.55 (3H×⅔, s), 2.73 (3H×⅓, s), 3.00 (2H, t, J=7 Hz), 3.88 (2H, m), 4.06–4.61 (5H, m), 5.12 (1H, d, J=7 Hz), 6.84–7.25 (15H, m), 8.14 (1H, d, J=7 Hz)

(6) NMR (CDCl$_3$, δ): 0.88 (6H, m), 1.57–1.85 (3H, m), 2.62 (3H×⅔, s), 2.80 (3H×⅓, s), 2.95–3.14 (2H, m), 4.15 (1H, m), 4.18 (1H×⅓, d, J=15 Hz), 4.27 (1H×⅔, d, J=15 Hz), 4.32 (1H×⅓, d, J=15 Hz), 4.58 (1H×⅔, d, J=15 Hz), 5.18 (1H, t, J=7 Hz), 6.90–6.99 (3H, m), 7.11–7.23 (7H, m), 8.14 (1H×⅔, d, J=8 Hz), 8.22 (1H×⅓, d, J=8 Hz)

(7) NMR (CD$_3$OD, δ): 2.90 (3H×⅔, s), 3.04 (3H×⅓, s), 3.41 (1H, m), 3.56 (1H, m), 3.65–3.73 (2H, m), 3.80 (1H, m), 4.13 (1H, m), 4.37–4.67 (4H, m), 5.47 (1H, m), 7.18–7.37 (8H, m), 7.76 (1H, m), 7.89–8.02 (2H, m), 8.26 (1H, m), 8.48 (1H, m), 8.73 (1H, m)

(8) NMR (CDCl$_3$, δ): 2.81 (3H×¾, s), 2.89 (3H×¼, s), 2.92–3.14 (2H, m), 3.29 (1H×¼, t, J=5 Hz), 3.44 (1H×¾, t, J=5 Hz), 3.52–3.64 (1H, m), 3.72–3.83 (1H, m), 4.37 (1H×¼, d, J=15 Hz), 4.41 (1H×¾, d, J=15 Hz), 4.47 (1H×¼, d, J=15 Hz), 4.62 (1H×¾, d, J=15 Hz), 5.04 (1H×¼, q, J=5 Hz), 5.21 (1H×¾, q, J=5 Hz), 6.88 (2H×¼, d, J=7 Hz), 6.94 (2H×¾, d, J=7 Hz), 7.11–7.28 (5H, m), 7.92 (1H, d, J=5 Hz), 8.51 (2H, d, J=7 Hz)

(9) NMR (CDCl$_3$, δ): 2.45 (1H×⅓, dd, J=8, 15 Hz), 2.60 (1H×⅔, dd, J=8, 15 Hz), 2.70 (3H×⅔, s), 2.85 (3H×⅓, s), 2.91–3.22 (3H, m), 3.50 (1H×⅓, dd, J=4, 8 Hz), 3.59 (1H×⅔, dd, J=4, 8 Hz), 4.32 (1H×⅔, d, J=15 Hz), 4.33 (1H×⅓, d, J=15 Hz), 4.42 (1H×⅓, d, J=15 Hz), 4.67 (1H×⅔, d, J=15 Hz), 5.22 (1H, m), 6.97–7.34 (15H, m), 7.92 (1H×⅓, d, J=8 Hz), 8.00 (1H×⅔, d, J=8 Hz)

(10) NMR (CD$_3$OD, δ): 2.93 (3H×¾, s), 3.07 (2H, d, J=7 Hz), 3.34 (3H×¼, s), 3.85 (1H, dd, J=7, 12 Hz), 3.93–4.01 (2H, m), 4.41 (1H×¼, d, J=15 Hz), 4.53 (1H×¾, d, J=15 Hz), 4.75 (1H×¼, d, J=15 Hz), 4.81 (1H×¾, d, J=15 Hz), 5.11 (1H, t, J=7 Hz), 7.24–7.31 (5H, m), 8.02 (1H, dd, J=6, 8 Hz), 8.30 (1H, d, J=8 Hz), 8.67 (1H, d, J=2 Hz), 8.77 (1H, d, J=6 Hz)

(11) MASS (m/z): 400 (M+H); NMR (CDCl$_3$, δ): 1.62–1.78 (1H, m), 1.90–2.02 (1H, m), 2.05 (3×⅓H, s), 2.09 (3×⅔H, s), 2.42 (1H, t, J=8 Hz), 2.51 (1H, t, J=8 Hz), 2.70 (3×⅔H, s), 2.90 (3×⅓H, s), 2.97–3.11 (2H, m), 3.38–3.41 (1×⅓H, m), 3.47–3.51 (1×⅔H, m), 4.31–4.39 (2×⅔H, m), 4.69 (2×⅓H, d, J=15 Hz), 5.19 (1H, q, J=8 Hz), 7.01–7.32 (10H, m), 7.83 (1×⅓H, d, J=8 Hz), 7.91 (1×⅔H, d, J=8 Hz)

(12) MASS (m/z): 356 (M+1); NMR (CDCl$_3$, δ): 2.73 (3×⅔H, s), 2.89 (3×⅓H, s), 2.92–3.12 (2H, m), 3.30 (1×⅓H, t, J=8 Hz), 3.42 (1H×⅔H, t, J=8 Hz), 3.48–3.62 (1H, m), 3.67–3.81 (1H, m), 4.31–4.51 (2×⅔H, m), 4.69 (2×⅓H, d, J=15 Hz), 5.19 (1H, q, J=8 Hz), 7.06 (2×⅓H, d, J=8 Hz), 7.11 (2×⅔H, d, J=8 Hz), 7.13–7.33 (8H, m), 7.82–7.93 (1H, m)

(13) NMR (CDCl$_3$, δ): 2.52 (3H×¼, s), 2,54 (3H×¾, s), 2.72 (3H×¾, s), 2.82 (3H×¼, s), 2.93–3.09 (2H, m), 3.36 (1H×¼, t, J=6 Hz), 3.42 (1H×¾, t, J=6 Hz), 3.61 (1H, m), 3.77 (1H, m), 4.15 (1H×¼, d, J=16 Hz), 4.37 (1H×¾, d, J=15 Hz), 4.42 (1H×¼, d, J=16 Hz), 4.56 (1H×¾, d, J=15 Hz), 5.15 (1H×¾, q, J=7 Hz), 5.20 (1H×¼, q, J=7 Hz), 7.05–7.35 (7H, m), 7.93 (1H, d, J=7 Hz), 8.23 (1H×¼, d, J=2 Hz), 8.31 (1H×¾, d, J=2 Hz)

(14) NMR (CDCl$_3$, δ): 1.05 (3H×⅓, d, J=7 Hz), 1.12 (3H×⅔, d, J=7 Hz), 2.77 (3H×⅔, s), 2.92 (3H×⅓, s), 2.94–3.12 (2H, m), 4.12 (1H, m), 4.37 (1H×⅓, d, J=16 Hz), 4.39 (1H×⅔, d, J=15 Hz), 4.45 (1H, m), 4.60 (1H×⅓, d, J=16 Hz), 4.67 (1H×⅔, d, J=15 Hz), 5.13 (1H×⅓, q, J=7 Hz), 5.22 (1H×⅔, q, J=7 Hz), 7.05–7.31 (10H, m), 7.97 (1H, m)

(15) MASS: 466 (M+1); NMR (CDCl$_3$, δ): 2.58–2.83 (1H, m), 2.68 (3×⅔H, s), 2.81 (3×⅓H, s), 2.90–3.10 (2H, m), 3.28 (1×⅓H, dd, J=15, 5 Hz), 3.33 (1×⅔H, dd, J=15, 5 Hz), 3.60 (1×⅓H, dd, J=12, 5 Hz), 3.70 (1×⅔H, dd, J=12, 5 Hz), 4.28 (2×⅓H, d, J=15 Hz), 4.32 (2×⅙H, d, J=16 Hz), 4.41 (2×⅙H, d, J=16 Hz), 4.68 (2×⅓H, d, J=15 Hz), 5.18–5.28 (1H, m), 7.00 (2×⅓H, d, J=7 Hz), 7.07 (2×⅔H, d, J=7 Hz), 7.10–7.39 (9H, m), 7.41–7.51 (2H, m), 7.61 (1×⅓H, s), 7.64 (1×⅔H, s), 7.73–7.85 (3H, m), 7.92 (1×⅓H, d, J=8 Hz), 8.01 (1×⅔H, d, J=8 Hz)

(16) MASS: 421 (M+1); NMR (CDCl$_3$, δ): 2.50 (3H, s), 2.63 (3×¾H, s), 2.80 (3×¼H, s), 2.82–3.10 (4H, m), 3.50–3.62 (1H, m), 4.11 (2×⅛H, d, J=16 Hz), 4.39 (2×⅛H, d, J=16 Hz), 4.41 (2×⅜H, d, J=15 Hz), 4.49 (2×⅜H, d, J=15 Hz), 5.07–5.23 (1H, m), 6.81 (1H, s), 7.03–7.37 (7H, m), 7.53 (1H, s), 7.95–8.08 (1H, m), 8.22 (1×¼H, s), 8.30 (1×¾H, s)

(17) MASS: 430 (M+1); NMR (CDCl$_3$, δ): 2.26 (3H, s), 2.43–2.61 (1H, m), 2.71 (3×⅔H, s), 2.86 (3×⅓H, s), 2.90–3.21 (4H, m), 4.37 (2×⅙H, d, J=16 Hz), 4.40 (2×⅓H, d, J=15 Hz), 4.41 (2×⅙H, d, J=16 Hz), 4.61 (2×⅓H, d, J=15 Hz), 5.18–5.28 (1H, m), 7.00–7.38 (15H, m), 7.80 (1×⅓H, d, J=8 Hz), 7.88 (1×⅔H, d, J=8 Hz)

(18) MASS: 468 (M+1); NMR (CDCl$_3$, δ): 2.72 (3×⅔H, s), 2.82–3.12 (3H, m), 2.88 (3×⅓H, s), 3.19–3.32 (1H, m), 3.69 (1×¼H, dd, J=8, 2 Hz), 3.80 (1×¾H, dd, J=8, 2 Hz), 4.51 (2×⅓H, d, J=15 Hz), 4.52 (2×⅙H, d, J=16 Hz), 4.59 (2×⅙H, d, J=16 Hz), 4.81 (2×⅓H, d, J=15 Hz), 5.12–5.30 (1H, m), 7.10–7.23 (7H, m), 7.51–7.80 (4H, m), 7.92 (1H, s), 8.09 (1×¼H, d, J=8 Hz), 8.11 (1×¾H, d, J=8 Hz), 8.22 (1×¼H, d, J=8 Hz), 8.24 (1×¾H, d, J=8 Hz), 8.49–8.56 (1H, m), 8.63 (1×¼H, d, J=2 Hz), 8.74 (1×¾H, d, J=2 Hz)

(19) mp: 165–167° C. MASS: 408 (M+1); NMR (CDCl$_3$, δ): 2.96 (3H, s), 2.98–3.35 (2H, m), 3.42–3.82 (3H, m), 4.72 (2×⅙H, d, J=16 Hz), 4.73 (2×⅓H, d, J=15 Hz), 4.82 (2×⅙H, d, J=16 Hz), 4.93 (2×⅓H, d, J=15 Hz), 5.15–5.32 (1H, m), 7.10–7.23 (5H, m), 7.72–7.80 (2H, m), 7.90–8.03 (2H, m), 8.06–8.13 (1H, m), 8.73 (1×⅕H, s), 8.80 (1×⅘H, s)

(20) MASS: 469 (M+1); NMR (CDCl$_3$, δ): 2.73–3.09 (2H, m), 2.91 (3×⅘H, s), 2.97 (3×⅕H, s), 3.11–3.30 (2H, m), 3.67 (1×⅕H, dd, J=8, 4 Hz), 3.79 (1×⅘H, dd, J=8, 4 Hz), 4.67 (2×⅓H, d, J=15 Hz), 4.68 (2×⅙H, d, J=16 Hz), 4.89 (2×⅙H, d, J=16 Hz), 4.93 (2×⅓H, d, J=15 Hz), 5.16–5.31 (1H, m), 7.08–7.22 (7H, m), 7.52–7.63 (1H, m), 7.72–7.80 (2H, m), 7.97–8.03 (1H, m), 8.08–8.14 (1H, m), 8.17–8.26 (1H, m), 8.48–8.53 (1H, m), 8.68 (1×⅕H, s), 8.76 (1×⅘H, s)

(21) MASS: 458 (M+1); NMR (CDCl$_3$, δ): 2.70–3.20 (3H, m), 2.91 (3×¾H, s), 2.98 (3×¼H, s), 3.45–3.65 (2H, m), 4.70 (2×⅙H, d, J=16 Hz), 4.73 (2×⅓H, d, J=15 Hz), 4.83 (2×⅙H, d, J=16 Hz), 4.89 (2×⅓H, d, J=15 Hz), 5.12–5.32 (1H, m), 4.72 (1×¼H, s), 4.89 (1×¾H, s), 6.72 (1×¼H, s), 6.80 (1×¾H, s), 7.05–7.23 (5H, m), 7.49 (1×¼H, s), 7.52 (1×¾H, s), 7.71–7.80 (2H, m), 7.96–8.07 (1H, m), 8.08–8.13 (1H, m), 8.72 (1×¼H, s), 8.78 (1×¾H, s)

(22) MASS: 434 (M+1); NMR (CDCl$_3$, δ): 2.78 (3×⅔H, s), 2.89 (3×⅓H, s), 2.96–3.18 (2H, m), 3.33 (1×⅓H, t, J=8

Hz), 3.42 (1×⅔H, t, J=8 Hz), 3.52–3.67 (1H, m), 3.71–3.81 (1H, m), 4.35 (2×⅙H, d, J=16 Hz), 4.42 (2×⅓H, d, J=15 Hz), 4.51 (2×⅙H, d, J=16 Hz), 4.71 (2×⅓H, d, J=15 Hz), 5.11–5.19 (1H, m), 7.11–7.33 (6H, m), 7.56 (1H, dd, J=8, 2 Hz), 7.81 (1H, t, J=8 Hz), 7.94 (1H, d, J=8 Hz), 8.29–8.42 (2H, m), 8.49 (1H, s), 8.63–8.70 (1H, m)

(23) MASS: 495 (M+1); NMR (CDCl$_3$, δ): 2.77 (3×⅓H, s), 2.81 (3×⅓H, s), 2.86–3.14 (3H, m), 3.20–3.32 (1H, m), 3.70–3.82 (1H, m), 4.35 (2×⅙H, d, J=16 Hz), 4.40 (2×⅓H, d, J=15 Hz), 4.43 (2×⅙H, d, J=16 Hz), 4.63 (2×⅓H, d, J=15 Hz), 5.11–5.23 (1H, m), 7.10–7.32 (7H, m), 7.40 (1H, dd, J=8, 4 Hz), 7.48 (1H, dd, J=8, 2 Hz), 7.56–7.70 (2H, m), 8.18–8.32 (2H, m), 8.40 (1×⅓H, s), 8.49 (1×⅓H, s), 8.51 (1H, d, J=2 Hz), 8.63 (1H, d, J=8 Hz), 8.19 (1H, s)

(24) MASS: 434 (M+1); NMR (CDCl$_3$, δ): 2.79 (3×¾H, s), 2.88 (3×¼H, s), 2.96–3.18 (2H, m), 3.33–3.45 (1H, m), 3.52–3.67 (1H, m), 3.74–3.83 (1H, m), 4.30 (2×⅙H, d, J=16 Hz), 4.48 (2×⅓H, d, J=15 Hz), 4.49 (2×⅙H, d, J=16 Hz), 4.66 (2×⅓H, d, J=15 Hz), 5.12–5.25 (1H, m), 7.12–7.30 (4H, m), 7.38–7.43 (2H, m), 7.55 (1H, dd, J=8, 2 Hz), 7.68 (1H, t, J=8 Hz), 7.92 (1H, d, J=8 Hz), 8.29–8.33 (1H, m), 8.44 (1×¼H, s), 8.53 (1×¾H, s), 8.67 (1H, d, J=5 Hz), 9.16–9.20 (1H, m)

(25) MASS (m/z): 637 (M$^+$+1);

(26) NMR (CDCl$_3$, δ): 2.52 (1H×¼, dd, J=8, 14 Hz), 2.65 (1H×¾, dd, J=8, 14 Hz), 2.70 (3H×¾, s), 2.82 (3H×¼, s), 3.01 (2H, m), 3.15 (1H×¼, dd, J=4, 14 Hz), 3.21 (1H×¾, dd, J=4, 14 Hz), 3.53 (1H×¼, dd, J=4, 8 Hz), 3.60 (1H×¾, dd, J=4, 8 Hz), 4.29 (1H×¼, d, J=16 Hz), 4.32 (1H×¾, d, J=15 Hz), 4.40 (1H×¼, d, J=16 Hz), 4.66 (1H×¾, d, J=15 Hz), 5.17 (1H, q, J=7 Hz), 7.13–7.40 (12H, m), 7.98 (1H, m), 8.30 (1H×¼, d, J=2 Hz), 8.41 (1H×¾, d, J=2 Hz), 8.52 (1H, m)

(27) NMR (CDCl$_3$, δ): 2.53–2.67 (1H, m), 2.71 (3H×¾, s), 2.83 (3H×¼, s), 2.94–3.21 (3H, m), 3.56 (1H×⅓, dd, J=4, 9 Hz), 3.64 (1H×⅔, dd, J=4, 12 Hz), 4.25 (1H×¼, d, J=16 Hz), 4.34 (1H×¾, d, J=15 Hz), 4.42 (1H×¼, d, J=16 Hz), 4.64 (1H×¾, d, J=15 Hz), 5.17 (1H, m), 7.08–7.42 (9H, m), 7.97 (1H, d, J=8 Hz), 8.31 (1H×¼, br s), 8.43 (1H×¾, br s), 8.53 (2H, d, J=5 Hz)

(28) NMR (CDCl$_3$, δ): 2.78 (3H×¾, s), 2.88 (3H×¼, s), 2.99 (1H, m), 3.11 (1H, m), 3.36 (1H×¼, t, J=5 Hz), 3.43 (1H×¾, t, J=5 Hz), 3.58 (1H, m), 3.78 (1H, m), 4.35 (1H×¼, d, J=15 Hz), 4.47 (1H×¾, d, J=15 Hz), 4.48 (1H×¼, d, J=15 Hz), 4.66 (1H×¾, d, J=15 Hz), 7.13–7.28 (7H, m), 7.60 (2H, d, J=8 Hz), 7.93 (1H, d, J=8 Hz), 8.11 (1H, s), 8.53 (1H, s)

(29) mp: 96–99° C.; MASS (m/z): 415 (M+1)$^+$; NMR (CDCl$_3$, δ): 1.70 (1H, m), 2.05 (1H, m), 2.07 (3H×¼, s), 2.09 (3H×¾, s), 2.43–2.58 (2H, m), 2.52 (3H×¼, s), 2.55 (3H×¾, s), 2.70 (3H×¾, s), 2.81 (3H×¼, s), 2.92–3.15 (2H, m), 3.38–3.52 (1H, m), 4.21 (1H×¼, d, J=14.5 Hz), 4.32 (1H×¾, d, J=14.5 Hz), 4.39 (1H×¼, d, J=14.5 Hz), 4.60 (1H×¾, d, J=14.5 Hz), 5.10–5.27 (1H, m), 7.01–7.10 (1H, m), 7.11–7.34 (6H, m), 7.90 (1H, d, J=9.0 Hz), 8.21 (1H×¼, d, J=1.5 Hz), 8.30 (1H×¾, d, J=1.5 Hz)

(30) MASS (m/z): 401 (M+1)$^+$; NMR (CDCl$_3$, δ): 1.73 (1H, m), 2.07 (3H×¼, s), 2.10 (3H×¾, s), 1.99–2.16 (1H, m), 2.48 (2H×¼, t, J=7.5 Hz), 2.53 (2H×¾, t, J=7.5 Hz), 2.72 (3H×¾, s), 2.84 (3H×¼, s), 2.94–3.12 (2H, m), 3.38–3.44 (1H×¼, m), 3.46–3.52 (1H×¾, m), 4.31 (1H×¼, d, J=14.5 Hz), 4.35 (1H×¾, d, J=14.5 Hz), 4.41 (1H×¼, d, J=14.5 Hz), 4.65 (1H×¾, d, J=14.5 Hz), 5.12–5.23 (1H, m), 7.12–7.30 (8H, m), 7.38–7.44 (1H, m), 7.93 (1H, d, J=8.5 Hz), 8.31 (1H×¼, d, J=1.5 Hz), 8.43 (1H×¾, d, J=1.5 Hz), 8.49–8.56 (1H, m)

(31) MASS (m/z): 451 (M+1)$^+$; NMR (CDCl$_3$, δ): 1.65–1.79 (1H, m), 1.98–2.14 (1H, m), 2.05 (3H×¼, s), 2.10 (3H×¾, s), 2.47 (2H×¼, t, J=7.5 Hz), 2.53 (2H×¾, t, J=7.5 Hz), 2.78 (3H×¾, s), 2.92 (3H×¼, s), 2.96–3.17 (2H, m), 3.39 (1H×¼, dd, J=7.5, 4.5 Hz), 3.50 (1H×¾, dd, J=7.5, 4.5 Hz), 4.52 (1H×¼, d, J=14.5 Hz), 4.53 (1H×¾, d, J=14.5 Hz), 4.62 (1H×¼, d, J=14.5 Hz), 4.82 (1H×¾, d, J=14.5 Hz), 5.13–5.32 (1H, m), 7.11–7.25 (5H, m), 7.51–7.60 (1H, m), 7.67–7.98 (4H, m), 8.09 (1H×¼, d, J=7.5 Hz), 8.11 (1H×¾, d, J=7.5 Hz), 8.66 (1H×¼, d, J=1.5 Hz), 8.78 (1H×¾, d, J=1.5 Hz)

(32) mp: 110–111° C.; MASS (m/z): 452 (M+1)$^+$; NMR (CDCl$_3$, δ): 1.63–1.78 (1H, m), 1.99–2.12 (1H, m), 2.02 (3H×⅕, s), 2.08 (3H×⅘, s), 2.39 (2H×⅕, t, J=7.5 Hz), 2.52 (2H×⅘, t, J=7.5 Hz), 2.94 (3H×⅕, s), 2.97–3.28 (2H, m), 3.01 (3H×⅘, s), 3.38 (1H×⅕, dd, J=7.5, 5.5 Hz), 3.50 (1H×⅘, dd, J=7.5, 5.5 Hz), 4.69 (1H, d, J=14.5 Hz), 4.95 (1H×⅕, d, J=14.5 Hz), 4.98 (1H×⅘, d, J=14.5 Hz), 5.17–5.33 (1H, m), 7.11–7.23 (5H, m), 7.74–7.81 (2H, m), 7.87–7.96 (1H, m), 7.99–8.04 (1H, m), 8.08–8.15 (1H, m), 8.70 (1H×⅕, s), 8.80 (1H×⅘, s)

(33) MASS (m/z): 478 (M+1)$^+$; NMR (CDCl$_3$, δ): 1.63–1.80 (1H, m), 1.99–2.14 (1H, m), 2.08 (3H×¼, s), 2.10 (3H×¾, s), 2.49 (2H×¼, t, J=7.5 Hz), 2.53 (2H×¾, t, J=7.5 Hz), 2.78 (3H×¾, s), 2.88 (3H×¼, s), 2.93–3.20 (2H, m), 3.44 (1H×¼, dd, J=7.5, 4.5 Hz), 3.51 (1H×¾, dd, J=7.5, 4.5 Hz), 4.37 (1H×¼, d, J=14.5 Hz), 4.43 (1H×¼, d, J=14.5 Hz), 4.47 (1H×¾, d, J=14.5 Hz), 4.67 (1H×¾, d, J=14.5 Hz), 5.13–5.27 (1H, m), 7.14–7.38 (21/4H, m), 7.41 (1H, dd, J=8.5, 5.5 Hz), 7.51 (1H×¾, dd, J=8.5, 1.5 Hz), 7.65 (1H×¼, d, J=7.5 Hz), 7.68 (1H×¾, d, J=7.5 Hz), 7.88–8.01 (1H, m), 8.31 (1H, dd, J=8.5, 1.5 Hz), 8.42 (1H×¼, d, J=1.5 Hz), 8.53 (1H×¾, d, J=1.5 Hz), 8.67 (1H, d, J=5.5 Hz), 9.17 (1H×¼, d, J=1.5 Hz), 9.20 (1H×¾, d, J=1.5 Hz)

(34) MASS (m/z): 422 (M+1)$^+$; NMR (CDCl$_3$, δ): 2.69 (3H×⅔, s), 2.87 (3H×⅓, s), 2.93–3.09 (3H, m), 3.26 (1H×⅓, dd, J=14.5, 4.5 Hz), 3.31 (1H×⅔, dd, J=14.5, 4.5 Hz), 3.49 (1H×⅓, dd, J=8.5, 4.5 Hz), 3.59 (1H×⅔, dd, J=8.5, 4.5 Hz), 4.29 (1H×⅓, d, J=14.5 Hz), 4.33 (1H×⅔, d, J=14.5 Hz), 4.40 (1H×⅓, d, J=14.5 Hz), 4.67 (1H×⅔, d, J=14.5 Hz), 5.20 (1H, q, J=7.5 Hz), 6.78–7.02 (3H, m), 7.05–7.33 (10H, m), 7.94 (1H×⅓, br d, J=8.5 Hz), 8.02 (1H×⅔, br d, J=8.5 Hz)

(35) MASS (m/z): 400 (M+H)$^+$; NMR (CDCl$_3$, δ): 2.69 (⅔×3H, s), 2.81 (⅓×3H, s), 2.86–3.10 (2H, m), 3.06 (⅓×6H, s), 3.08 (⅔×6H, s), 3.34–3.82 (3H, m), 3.92 (⅓×1H, d, J=17 Hz), 4.35 (⅔×2H, ABq, Δ=0.15, J=15 Hz), 4.36 (⅓×1H, d, J=17 Hz), 5.02–5.35 (1H, m), 6.44 (⅓×1H, d, J=9 Hz), 6.47 (⅔×1H, d, J=9 Hz), 7.06–7.36 (6H, m), 7.80–8.04 (2H, m)

(36) MASS (m/z): 497 (M+H)$^+$; NMR (CDCl$_3$, δ): 2.74 (¾×3H, s), 2.90 (¼×3H, s), 2.92–3.20 (2H, m), 3.44–3.75 (3H, m), 4.42–4.88 (4H, m), 5.10–5.30 (1H, m), 7.03–8.23 (16H, m), 8.62 (¼×1H, d, J=2 Hz), 8.77 (¾×1H, d, J=2 Hz)

(37) MASS (m/z): 406 (M+H)$^+$; NMR (CDCl$_3$, δ): 2.46–2.69 (1H, m), 2.68 (⅔×3H, s), 2.77–3.10 (3H, m), 2.87 (⅓×3H, s), 3.38–3.58 (1H, m), 4.33 (⅔×1H, d, J=15 Hz), 4.36 (⅓×2H, ABq, Δ=0.10, J=17 Hz), 4.67 (⅔×1H, d, J=15 Hz), 5.12–5.26 (1H, m), 6.21 (⅓×1H, s), 6.27 (⅔×1H, s), 6.95–7.40 (12H, m), 7.86–8.05 (1H, m)

(38) MASS (m/z): 406 (M+H)$^+$; NMR (CDCl$_3$, δ): 2.61–2.84 (1H, m), 2.66 (⅔×3H, s), 2.86 (⅓×3H, s), 2.89–3.20 (3H, m), 3.50–3.68 (1H, m), 4.32 (⅔×1H, d, J=15 Hz), 4.34 (⅓×2H, ABq, Δ=0.22, J=17 Hz), 4.67 (⅔×1H, d, J=15 Hz), 5.12–5.26 (1H, m), 6.04 (⅓×1H, d, J=2 Hz), 6.10 (⅔×1H, d, J=2 Hz), 6.24–6.32 (1H, m), 6.93–7.38 (11H, m), 7.98 (⅓×1H, d, J=8 Hz), 8.05 (⅔×1H, d, J=8 Hz)

(39) MASS: 387 (M+1); NMR (CDCl$_3$, δ): 2.71 (3×¾H, s), 2.81 (3×¼H, s), 2.90–3.13 (2H, m), 3.33–3.43 (1H, m), 3.51–3.61 (1H, m), 3.70–3.81 (1H, m), 3.89 (3H, s), 4.09

(2×⅙H, d, J=16 Hz), 4.29 (2×⅓H, d, J=15 Hz), 4.39 (2×⅓H, d, J=15 Hz), 4.53 (2×⅙H, d, J=16 Hz), 5.08–5.29 (1H, m), 6.68 (1×¼H, d, J=8 Hz), 6.69 (1×¾H, d, J=8 Hz), 7.10–7.30 (5H, m), 7.38 (1H, d, J=8 Hz), 7.90 (1H, s), 7.91 (1×¼H, s), 7.98 (1×¾H, s)

(40) MASS: 457 (M+1); NMR (CDCl$_3$, δ): 2.72 (3×¾H, s), 2.87 (3×¼H, s), 2.89–3.12 (4H, m), 3.50–3.70 (1H, m), 4.40 (2×⅙H, d, J=16 Hz), 4.60 (2×⅙H, d, J=16 Hz), 4.62 (2×⅓H, d, J=15 Hz), 4.68 (2×⅓H, d, J=15 Hz), 5.05–5.30 (1H, m), 6.81 (1H, s), 7.03–7.23 (5H, m), 7.48–7.60 (2H, m), 7.67–7.81 (2H, m), 7.91 (1H, s), 8.00–8.20 (2H, m), 8.68 (1×¼H, s), 8.72 (1×¾H, s)

(41) MASS: 484 (M+1); NMR (CDCl$_3$, δ): 2.77 (3×⅔H, s), 2.87 (3×⅓H, s), 2.81–3.20 (4H, m), 3.58–3.70 (1H, m), 4.30 (2×⅙H, d, J=16 Hz), 4.48 (2×⅙H, d, J=16 Hz), 4.51 (2×⅓H, d, J=15 Hz), 4.58 (2×⅓H, d, J=15 Hz), 5.08–5.22 (1H, m), 6.78–6.88 (1H, m), 7.10–7.31 (5H, m), 7.33–7.46 (1H, m), 7.49–7.60 (2H, m), 7.61–7.70 (1H, m), 8.00–8.10 (1H, m), 8.23–8.33 (1H, m), 8.41 (1×¼H, s), 8.51 (1×¾H, s), 8.65 (1H, s), 9.17 (1H, s)

(42) MASS: 446 (M+1); NMR (CDCl$_3$, δ): 2.38–2.60 (1H, m), 2.69 (3×⅔H, s), 2.83 (3×⅓H, s), 2.90–3.15 (3H, m), 3.40–3.60 (1H, m), 3.78 (3H, s), 4.31 (2×⅙H, d, J=16 Hz), 4.32 (2×⅓H, d, J=15 Hz), 4.41 (2×⅙H, d, J=16 Hz), 4.69 (2×⅓H, d, J=15 Hz), 5.13–5.26 (1H, m), 6.80–6.90 (2H, m), 6.95–7.32 (12H, m), 7.90 (1×⅓H, d, J=8 Hz), 7.99 (1×⅔H, d, J=8 Hz)

(43) MASS: 469 (M+1); NMR (CDCl$_3$, δ): 2.77 (3×⅔H, s), 2.90 (3×⅓H, s), 2.82–3.12 (3H, m), 3.14–3.31 (1H, m), 3.65–3.72 (1×⅓H, m), 3.78–3.85 (1×⅔H, m), 4.52 (2×⅙H, d, J=16 Hz), 4.61 (2×⅙H, d, J=16 Hz), 4.62 (2×⅓H, d, J=15 Hz), 4.80 (2×⅓H, d, J=15 Hz), 5.16–5.28 (1H, m), 7.10–7.33 (7H, m), 7.43 (1H, d, J=8 Hz), 7.53–7.65 (1H, m), 7.77 (1×⅓H, s), 7.83 (1×⅔H, s), 8.01 (1H, d, J=8 Hz), 8.23 (1H, t, J=8 Hz), 8.49–8.58 (1H, m), 8.83 (2H, s)

(44) MASS: 466 (M+1); NMR (CDCl$_3$, δ): 2.53–2.81 (1H, m), 2.78 (3×⅔H, s), 2.89 (3×⅓H, s), 2.93–3.13 (2H, m), 3.62–3.90 (2H, m), 4.30 (2×⅓H, d, J=15 Hz), 4.41 (2×⅓H, s), 4.71 (2×⅓H, d, J=15 Hz), 5.20–5.29 (1H, m), 7.00–7.10 (2H, m), 7.12–7.33 (9H, m), 7.36–7.43 (1H, m), 7.45–7.60 (2H, m), 7.77 (1H, d, J=8 Hz), 7.85 (1H, d, J=8 Hz), 7.98–8.22 (2H, m)

(45) MASS: 407 (M+1); NMR (CDCl$_3$, δ): 2.70 (3×¾H, s), 2.81 (3×¼H, s), 2.78–3.10 (4H, m), 3.47–3.65 (1H, m), 4.22 (2×⅛H, d, J=16 Hz), 4.41 (2×⅜H, d, J=15 Hz), 4.52 (2×⅜H, d, J=15 Hz), 4.63 (2×⅛H, d, J=16 Hz), 5.07–5.20 (1H, m), 6.72–6.85 (1H, m), 7.09–7.31 (6H, m), 7.41 (1H, d, J=7 Hz), 7.47–7.60 (1H, m), 7.97–8.05 (1H, m), 8.31 (1×¼H, s), 8.39 (1×¾H, s), 8.43 (1×¼H, s), 8.51 (1×¾H, s)

(46) MASS: 432 (M+1); NMR (CDCl$_3$, δ): 2.52 (3H, s), 2.67 (3×¾H, s), 2.78 (3×¼H, s), 2.80–3.10 (3H, m), 3.18–3.30 (1H, m), 3.68–3.80 (1H, m), 4.19 (2×⅛H, d, J=16 Hz), 4.28 (2×⅜H, d, J=15 Hz), 4.33 (2×⅛H, d, J=16 Hz), 4.58 (2×⅜H, d, J=15 Hz), 5.09–5.22 (1H, m), 6.99–7.30 (9H, m), 7.61 (1H, t, J=8 Hz), 8.19 (1H, s), 8.21 (1×¼H, s), 8.29 (1×¾H, s), 8.49–8.53 (1H, m)

(47) MASS: 417 (M+1); NMR (CDCl$_3$, δ): 2.49–2.73 (1H, m), 2.70 (3×⅔H, s), 2.89 (3×⅓H, s), 2.91–3.22 (3H, m), 3.48–3.53 (1×⅓H, m), 3.55–3.63 (1×⅔H, m), 4.31 (2×⅙H, d, J=16 Hz), 4.33 (2×⅓H, d, J=15 Hz), 4.41 (2×⅙H, d, J=16 Hz), 4.68 (2×⅓H, d, J=15 Hz), 5.12–5.26 (1H, m), 6.98–7.35 (11H, m), 7.48 (1×⅓H, d, J=8 Hz), 7.52 (1×⅔H, d, J=8 Hz), 7.88 (1×⅓H, d, J=8 Hz), 7.92 (1×⅔H, d, J=8 Hz), 8.42 (1×⅓H, s), 8.48 (1×⅔H, s), 8.50 (1H, s)

(48) MASS: 450 (M+1); NMR (CDCl$_3$, δ): 2.43–2.68 (1H, m), 2.69 (3×⅔H, s), 2.88 (3×⅓H, s), 2.90–3.18 (3H, m), 3.42–3.50 (1×⅓H, m), 3.52–3.60 (1×⅔H, m), 4.31 (2×⅙H, d, J=16 Hz), 4.32 (2×⅓H, d, J=15 Hz), 4.41 (2×⅙H, d, J=16 Hz), 4.69 (2×⅓H, d, J=15 Hz), 5.12–5.23 (1H, m), 6.97–7.43 (14H, m), 7.87 (1×⅓H, d, J=8 Hz), 7.94 (1×⅔H, d, J=8 Hz)

(49) MASS: 428 (M+1); NMR (CDCl$_3$, δ): 2.52–2.78 (1H, m), 2.69 (3×⅔H, s), 2.70–3.12 (3H, m), 2.89 (3×⅓H, s), 3.38–3.49 (1×⅓H, m), 4.49–3.58 (1×⅔H, m), 3.80–4.04 (2H, m), 4.33 (2×⅓H, d, J=15 Hz), 4.41 (2×⅓H, s), 4.69 (2×⅓H, d, J=15 Hz), 5.14–5.27 (1H, m), 6.93–7.33 (14H, m), 7.87 (1×⅓H, d, J=8 Hz), 7.93 (1×⅔H, d, J=8 Hz)

Preparation 62

The following object compounds were obtained by reacting each Starting compound with di-tert-butyl-dicarbonate in a conventional manner.

(1) MASS: 236 (M+1); NMR (CDCl$_3$, δ): 1.45 (9H, s), 2.14 (3H, s), 2.93–3.03 (2H, m), 4.48–4.58 (1H, m), 5.41 (1H, br s)

(2) mp: 50–53° C.; MASS: 222 (M+1); NMR (CDCl$_3$, δ): 1.46 (9H, s), 2.32 (3H, s), 4.31 (2H, d, J=6 Hz), 4.68 (1H, br s), 7.12–7.27 (4H, m)

(3) MASS: 222 (M+1); NMR (CDCl$_3$, δ): 1.42 (9H, s), 2.33 (3H, s), 4.28 (2H, d, J=8 Hz), 4.72 (1H, br s), 7.07 (2H, d, J=8 Hz), 7.09 (1H, s), 7.23 (1H, dd, J=15, 8 Hz)

Preparation 63

The following object compounds were obtained according to a similar manner to that of Preparation 1, 6, 11, 38, 52 or 56.

(1) MASS: 419 (M+1); NMR (CDCl$_3$, δ): 1.38 (9×⅓H, s), 1.42 (9×⅔H, s), 2.60 (3×⅔H, s), 2.81 (3×⅓H, s), 3.07–3.22 (2H, m), 4.14 (2×⅙H, d, J=16 Hz), 4.32 (2×⅙H, d, J=16 Hz), 4.36 (2×⅓H, d, J=15 Hz), 4.59 (2×⅓H, d, J=15 Hz), 4.92–5.06 (1H, m), 5.37 (1×⅓H, d, J=10 Hz), 5.45 (1×⅔H, d, J=10 Hz), 6.82 (2×⅓H, d, J=8 Hz), 6.92 (2×⅔H, d, J=8 Hz), 7.02–7.21 (3H, m), 7.27 (1×⅓H, d, J=8 Hz), 7.32 (1×⅔H, d, J=8 Hz), 7.40–7.50 (2H, m), 7.60 (1×⅓H, s), 7.63 (1×⅔H, s), 7.69–7.82 (3H, m)

(2) MASS: 383 (M+1); NMR (CDCl$_3$, δ): 1.08 (9×⅔H, s), 1.19 (9×⅘H, s), 1.32 (9×⅗H, s), 2.79–2.93 (6H, m), 2.93–3.29 (2H, m), 4.37–4.75 (2H, m), 4.97–5.08 (1×½H, m), 5.30–5.45 (1×½H, m), 6.90–7.00 (1H, m), 7.03–7.40 (9H, m)

(3) MASS: 399 (M+1); NMR (CDCl$_3$, δ): 1.38 (9×¼H, s), 1.40 (9×¾H, s), 2.61 (3×¾H, s), 2.81 (3×¼H, s), 2.92 (1H, d, J=8 Hz), 3.77 (3×¾H, s), 3.79 (3×¼H, s), 4.17 (2×⅙H, d, J=16 Hz), 4.37 (2×⅙H, d, J=16 Hz), 4.40 (2×⅓H, d, J=15 Hz), 4.59 (2×⅓H, d, J=15 Hz), 4.78–4.90 (1H, m), 5.31 (1×¼H, d, J=8 Hz), 5.40 (1×¾H, d, J=8 Hz), 6.70–6.82 (2H, m), 6.92–7.13 (4H, m), 7.20–7.32 (3H, m)

(4) MASS: 383 (M+1); NMR (CDCl$_3$, δ): 1.39 (9×⅓H, s), 1.41 (9×⅔H, s), 2.30 (3×⅓H, s), 2.32 (3×⅔H, s), 2.59 (3×⅓H, s), 2.82 (3×⅔H, s), 2.97–3.03 (2H, m), 4.00 (2×⅙H, d, J=16 Hz), 4.37 (2×⅙H, d, J=16 Hz), 4.42 (2×⅓H, d, J=15 Hz), 4.49 (2×⅓H, d, J=15 Hz), 4.82–4.97 (1H, m), 5.32–5.43 (1H, m), 6.77–7.30 (9H, m)

(5) MPSS 383 (M+1); NMR (CDCl$_3$, δ): 1.38 (9×⅓H, s), 1.41 (9×⅔H, s), 2.13 (3×⅓H, s), 2.22 (3×⅔H, s), 2.63 (3×⅔H, s), 2.87 (3×⅓H, s), 2.97–3.08 (2H, m), 3.99 (2×⅙H, d, J=16 Hz), 4.22 (2×⅙H, d, J=16 Hz), 4.41 (2×⅓H, d, J=15 Hz), 4.62 (2×⅓H, d, J=15 Hz), 4.70–4.79 (1×⅓H, m), 4.88–4.96 (1×⅔H, m), 5.38 (1H, t, J=8 Hz), 6.78 (1×⅓H, d, J=8 Hz), 6.82 (1×⅔H, d, J=8 Hz), 7.05–7.18 (4H, m), 7.22–7.32 (4H, m)

(6) MASS: 371 (M+1); NMR (CDCl$_3$, δ): 1.38 (9×1/3H, s), 1.40 (9×2/3H, s), 2.83 (3×1/3H, s), 2.90 (3×1/3H, s), 2.93–3.12 (2H, m), 4.52 (2×1/2H, d, J=15 Hz), 4.61 (2×1/2H, d, J=15 Hz), 4.89–4.97 (1H, m), 5.29–5.33 (1H, m), 6.80 (1×1/5H, d, J=5 Hz), 6.92 (1×1/5H, d, J=5 Hz), 7.12–7.31 (5H, m), 8.57 (1×1/5H, d, J=5 Hz), 8.59 (1×1/5H, d, J=5 Hz), 9.10 (1H, s)

(7) MASS: 421 (M+1); NMR (CDCl$_3$, δ): 1.31 (9×1/3H, s), 1.40(9×2/3H, s), 2.85 (3×5/6H, s), 2.94 (3×1/6H, s), 2.98–3.15 (2H, m), 4.55 (2×1/6H, d, J=16 Hz), 4.68 (2×1/6H, d, J=16 Hz), 4.73 (2×1/3H, d, J=15 Hz), 4.88 (2×1/3H, d, J=15 Hz), 4.88–5.02 (1H, m), 5.32–5.42 (1H, m), 7.10–7.23 (5H, m), 7.70–7.80 (2H, m), 7.97–8.03 (1H, m), 8.07–8.13 (1H, m), 8.61 (1×1/4H, s), 8.78 (1×3/4H, s)

(8) MASS: 420 (M+1); NMR (CDCl$_3$, δ): 1.34 (9×1/3H, s), 1.39 (9×2/3H, s), 2.80 (3×3/4H, s), 2.92 (3×1/4H, s), 2.98–3.18 (2H, m), 4.51 (2×1/6H, d, J=16 Hz), 4.63 (2×1/6H, d, J=16 Hz), 4.81 (2×2/3H, s), 4.90–5.04 (1H, m), 5.34–5.43 (1H, m), 7.09–7.29 (6H, m), 7.51 (1H, t, J=8 Hz), 7.69 (1H, t, J=8 Hz), 7.79 (1H, d, J=8 Hz), 8.01 (1H, d, J=8 Hz), 8.07 (1H, d, J=8 Hz)

(9) MASS: 420 (M+1); NMR (CDCl$_3$, δ): 1.39 (9×1/4H, s), 1.45 (9×3/4H, s), 2.68 (3×3/4H, s), 2.88 (3×1/4H, s), 2.97–3.05 (2H, m), 4.25 (2×1/6H, d, J=16 Hz), 4.58 (2×1/6H, d, J=16 Hz), 4.68 (2×1/3H, d, J=15 Hz), 4.72 (2×1/3H, d, J=15 Hz), 4.82–5.00 (1H, m), 5.33–5.47 (1H, m), 7.08–7.32 (6H, m), 7.37–7.42 (1H, m), 7.70–7.80 (1H, m), 7.88 (1H, s), 8.13 (1H, d, J=8 Hz), 8.88–8.92 (1H, m)

(10) MASS: 371(M+1); NMR (CDCl$_3$, δ): 1.40 (9×1/3H, s), 1.42 (9×2/3H, s), 2.81 (3×5/6H, s), 2.90 (3×1/6H, s), 2.93–3.08 (2H, m), 4.38 (2×1/6H, d, J=16 Hz), 4.44 (2×1/6H, d, J=16 Hz), 4.58 (2×1/3H, d, J=15 Hz), 4.68 (2×1/3H, d, J=15 Hz), 4.83–4.93 (1H, m), 5.29–5.40 (1H, m), 7.13–7.28 (5H, m), 8.43–8.50 (3H, m)

(11) MASS: 447 (M+1); NMR (CDCl$_3$, δ): 1.40 (9×1/4H, s), 1.41 (9×3/4H, s), 2.68 (3×3/4H, s), 2.83 (3×1/4H, s), 2.92–3.12 (2H, m), 4.16 (2×1/6H, d, J=16 Hz), 4.41 (2×1/6H, d, J=16 Hz), 4.53 (2×2/3H, s), 4.82–4.98 (1H, m), 5.32–5.42 (1H, m), 7.12–7.30 (5H, m), 7.38–7.42 (1H, m), 7.48–7.52 (1H, m), 7.62 (1×1/4H, d, J=8 Hz), 7.68 (1×3/4H, d, J=8 Hz), 8.25–8.32 (1H, m), 8.40 (1×1/4H, s), 8.51 (1×3/4H, s), 8.63 (1H, d, J=5 Hz), 9.12–9.20 (1H, m)

(12) MASS: 447 (M+1); NMR (CDCl$_3$, δ): 1.40 (9×1/4H, s), 1.42 (9×3/4H, s), 2.63 (3×1/4H, s), 2.80 (3×3/4H, s), 2.93–3.10 (2H, m), 4.13 (2×1/6H, d, J=16 Hz), 4.42 (2×1/6H, d, J=16 Hz), 4.49 (2×1/3H, d, J=15 Hz), 4.62 (2×1/3H, d, J=15 Hz), 4.82–4.99 (1H, m), 5.32–5.41 (1H, m), 7.15–7.23 (4H, m), 7.27–7.32 (2H, m), 7.52 (1H, d, J=8 Hz), 7.70–7.76 (1H, m), 8.25–8.40 (2H, m), 8.49 (1H, s), 8.68 (1H, d, J=5 Hz)

(13) MASS (m/z): 321 (M$^+$+1); NMR (CDCl$_3$, δ): 0.89–1.00 (6H, m), 1.43 (9H, s), 1.97 (1H, m), 2.90 (3H×1/3, s), 3.02 (3H×2/3, s), 4.47 (1H×2/3, d, J=15 Hz), 4.50 (1H×1/3, d, J=16 Hz), 4.53 (1H, m), 4.70 (1H×1/3, d, J=16 Hz), 4.74 (1H×2/3, d, J=15 Hz), 5.32 (1H, m), 7.21–7.34 (5H, m)

(14) MASS (m/z): 375 (M$^+$+1); NMR (CDCl$_3$, δ): 0.85–2.00 (13H, m), 1.45 (9H, s), 2.92 (3H×1/3, s), 2.98 (3H×2/3, s), 4.48 (1H×2/3, d, J=15 Hz), 4.65 (1H×2/3, d, J=15 Hz), 4.72 (2H×1/3, s), 4.74 (1H, m), 5.17 (1H×1/3, d, J=7 Hz), 5.24 (1H×2/3, d, J=7 Hz), 7.20–7.37 (5H, m)

(15) MASS (m/z): 467 (M$^+$+1); NMR (CDCl$_3$, δ): 1.41 (9H, s), 2.34 (3H, s), 2.55 (4H, m), 2.58 (3H, s), 2.97 (2H, d, J=7 Hz), 3.18 (4H, m), 3.98 (1H×1/3, d, J=16 Hz), 4.30 (1H×1/3, d, J=16 Hz), 4.36 (1H×2/3, d, J=15 Hz), 4.45 (1H×2/3, d, J=15 Hz), 4.83 (1H×2/3, q, J=7 Hz), 4.94 (1H×1/3, q, J=7 Hz), 5.37 (1H×1/3, d, J=7 Hz), 5.42 (1H×2/3, d, J=7 Hz), 6.79–6.90 (3H, m), 7.02 (1H, d, J=8 Hz), 7.13–7.24 (5H, m)

(16) MASS (m/z): 370 (M$^+$+1); NMR (CDCl$_3$, δ): 1.37 (9H×1/3s), 1.41 (9H×2/3, s), 2.77 (3H×2/3, s), 2.91 (3H×1/3, s), 2.88–3.06 (2H, m), 4.40 (1H×1/5, d, J=15 Hz), 4.42 (2H×1/5, s), 4.63 (1H×1/5, d, J=15 Hz), 4.90 (1H, m), 5.28 (1H×1/3, d, J=8 Hz), 5.39 (1H×2/3, d, J=8 Hz), 7.02–7.12 (4H, m), 7.27–7.32 (3H, m), 8.45 (2H×4/5, d, J=6 Hz), 8.52 (2H×1/5, d, J=6 Hz)

(17) MASS (m/z): 420 (M+H)$^+$; NMR (CDCl$_3$, δ): 1.39 (1/5×9H, s), 1.45 (4/5×9H, s), 2.68 (4/5×3H, s), 2.86 (1/5×3H, s), 2.92–3.08 (2H, m), 4.22 (1/5×1H, d, J=17 Hz), 4.58 (1/5×1H, d, J=17 Hz), 4.68 (4/5×2H, ABq, Δ=0.09, J=15 Hz), 4.80–5.05 (1H, m), 5.30–5.47 (1H, m), 7.06–7.26 (5H, m), 7.50–8.15 (5H, m), 8.62 (1/5×1H, s), 8.76 (4/5×1H, s)

(18) MASS (m/z): 420 (M+H)$^+$; NMR (CDCl$_3$, δ): 1.38 (1/4×9H, s), 1.43 (3/4×9H, s), 2.68 (3/4×3H, s), 2.88 (1/4×3H, s), 2.92–3.12 (2H, m), 4.40 (1/4×2H, ABq, Δ=0.24, J=17 Hz), 4.68 (3/4×2H, ABq, Δ=0.08, J=15 Hz), 4.83–5.02 (1H, m), 5.28–5.48 (1H, m), 7.08–7.62 (8H, m), 7.96–8.15 (2H, m), 8.90 (1H, d, J=2 Hz)

(19) MASS (m/z): 427 (M+H)$^+$; NMR (CDCl$_3$, δ): 1.42 (9H, s), 2.21 (3H, s), 2.62 (4/5×3H, s), 2.76 (1/5×3H, s), 2.89–3.08 (2H, m), 3.99 (1/5×1H, d, J=17 Hz), 4.32 (1/5×1H, d, J=17 Hz), 4.43 (4/5×2H, ABq, Δ=0.15, J=15 Hz), 4.77–5.00 (1H, m), 5.51 (1H, br d), 7.06–7.48 (6H, m), 7.92–8.28 (3H, m)

(20) MASS (m/z): 449 (M+H)$^+$; NMR (CDCl$_3$, δ): 1.39 (1/3×9H, s), 1.43 (2/3×9H, s), 2.61 (2/3×3H, s), 2.82 (1/3×3H, s), 2.90–3.08 (2H, m), 3.95 (3H, s), J=4.11 (1/3×1H, d, =17 Hz), 4.39 (1/3×1H, d, J=17 Hz), 4.51 (2/3×2H, ABq, Δ=0.19, J=15 Hz), 4.78–5.02 (1H, m), 5.30–5.50 (1H, m), 6.51 (1H, m), 6.93–7.32 (7H, m), 7.38 (1H, s), 7.62–7.78 (2H, m)

(21) MASS (m/z): 413 (M+H)$^+$; NMR (CDCl$_3$, δ): 1.41 (9H, s), 2.56 (3/4×3H, s), 2.74 (1/4×3H, s), 2.88–3.04 (2H, m), 3.05 (1/4×6H, s), 3.07 (3/4×6H, s), 3.79 (1/4×1H, d, J=17 Hz), 4.26 (1/4×1H, d, J=17 Hz), 4.32 (3/4×2H, ABq, Δ=0.06, J=15 Hz), 4.72–5.05 (1H, m), 5.31–5.45 (1H, m), 6.40 (1/4×1H, d, J=9 Hz), 6.45 (3/4×1H, d, J=9 Hz), 7.00–7.33 (6H, m), 7.86 (1/4×1H, d, J=2 Hz), 7.97 (3/4×1H, d, J=2 Hz)

(22) MASS (m/z): 435 (M+H)$^+$; NMR (CDCl$_3$, δ): 1.38 (1/4×9H, s), 1.42 (3/4×9H, s), 2.67 (3/4×3H, s), 2.83 (1/4×3H, s), 2.91–3.11 (2H, m), 4.25 (1/4×2H, ABq, Δ=0.22, J=17 Hz), 4.52 (3/4×2H, ABq, Δ=0.06, J=15 Hz), 4.81–4.96 (1H, m), 5.28–5.44 (1H, m), 6.98–7.35 (11H, m), 7.80 (1/4×1H, s), 7.82 (3/4×1H, s)

(23) MASS (m/z): 437 (M+H)$^+$; NMR (CDCl$_3$, δ): 1.39 (1/4×9H, s), 1.42 (3/4×9H, s), 2.58 (3/4×3H, s), 2.60 (3H, s), 2.81 (1/4×3H, s), 2.88–3.07 (2H, m), 3.71 (3H, s), 4.12 (1/4×1H, d, J=17 Hz), 4.52 (1/4×1H, d, J=17 Hz), 4.60 (3/4×2H, s), 4.75–5.08 (1H, m), 5.34–5.52 (1H, m), 6.82–7.50 (8H, m)

(24) MASS (m/z): 359 (M+H)$^+$; NMR (CDCl$_3$, δ): 1.40 (1/4×9H, s), 1.43 (3/4×9H, s), 2.68–2.95 (2H, m), 2.88 (3/4×3H, s), 2.90 (1/4×3H, s), 4.48 (1/4×2H, ABq, Δ=0.10, J=17 Hz), 4.56 (3/4×2H, ABq, Δ=0.15, J=15 Hz), 4.75–4.90 (1H, m), 5.23–5.43 (1H, m), 6.21 (1/4×1H, s), 6.28 (3/4×1H, s), 7.05–7.40 (7H, m)

(25) MASS (m/z): 373 (M+H)$^+$; NMR (CDCl$_3$, δ): 1.41 (9H, s), 2.62 (3/4×3H, s), 2.81 (1/4×3H, s), 2.88–3.10 (2H, m), 3.80 (1/4×3H, s), 3.86 (3/4×3H, s), 3.90 (1/4×1H, d, J=17 Hz), 4.17 (1/4X 1H, d, J=17 Hz), 4.30 (3/4×2H, ABq, Δ=0.11, J=15 Hz), 4.70–5.02 (1H, m), 5.28–5.42 (1H, m), 7.02–7.35 (7H, m)

(26) MASS (m/z): 403 (M+H)$^+$; NMR (CDCl$_3$, δ): 1.38 (1/3×9H, s), 1.41 (2/3×9H, s), 2.71 (2/3×3H, s), 2.81–3.17 (2H, m), 2.87 (1/3×3H, s), 4.36 (1/3×2H, ABq, Δ=0.02, J=17 Hz), 4.50 (2/3×2H, ABq, Δ=0.24, J=15 Hz), 4.84 (1H, q, J=8 Hz), 5.31 (1/3×1H, d, J=8 Hz), 5.42 (2/3×1H, d, J=8 Hz), 6.90–7.85 (9H, m)

(27) MASS (m/z): 359 (M+H)⁺; NMR (CDCl₃, δ): 1.40 (¼×9H, s), 1.42 (¾×9H, s), 2.80 (¾×3H, s), 2.88 (¼×3H, s), 2.90–3.12 (2H, m), 4.41 (¾×1H, d, J=15 Hz), 4.43 (¼×2H, ABq, Δ=0.19, J=17 Hz), 4.68 (¾×1H, d, J=15 Hz), 4.87–5.06 (1H, m), 5.30–5.51 (1H, m), 6.08 (1H, s), 6.23 (¾×1H, s), 6.28 (¼×1H, s), 7.05–7.40 (6H, m)

(28) MASS: 421 (M+1); NMR (CDCl₃, δ): 1.33 (9×⅓H, s), 1.40 (9×⅔H, s), 2.69 (3×⅔H, s), 2.89 (3×⅓H, s), 3.02 (2H, d, J=8 Hz), 4.31 (2×⅙H, d, J=16 Hz), 4.58 (2×⅙H, d, J=16 Hz), 4.70 (2×⅔H, s), 4.84–4.98 (1H, m), 5.32–5.46 (1H, m), 7.10–7.32 (5H, m), 7.47 (1H, d, J=8 Hz), 7.75 (1×⅓H, s), 7.83 (1×⅔H, s), 7.97–8.07 (1H, m), 8.82 (2H, s)

(29) MASS: 419 (M+1); NMR (CDCl₃, δ): 1.41 (9×⅓H, s), 1.43 (9×⅔H, s), 2.03 (3×⅔H, s), 2.65 (3×⅓H, s), 3.27–3.41 (1H, m), 3.57–3.72 (1H, m), 3.92 (2×⅙H, d, J=16 Hz), 4.24 (2×⅓H, d, J=15 Hz), 4.31 (2×⅙H, d, J=16 Hz), 4.37 (2×⅓H, d, J=15 Hz), 5.02–5.16 (1H, m), 5.51 (1×⅓H, d, J=8 Hz), 5.60 (1×⅔H, d, J=8 Hz), 6.70–6.79 (2×⅓H, m), 6.90–7.00 (2×⅔H, m), 7.10–7.40 (5H, m), 7.41–7.63 (2H, m), 7.68–7.90 (2H, m), 8.11 (1×⅓H, d, J=8 Hz), 8.30 (1×⅔H, d, J=8 Hz)

(30) MASS: 370 (M+1); NMR (CDCl₃, δ): 1.32 (9×⅓H, s), 1.38 (9×⅔H, s), 2.78 (3×⅔H, s), 2.82–3.10 (2H, m), 2.89 (3×⅓H, s), 4.38 (2×⅙H, d, J=16 Hz), 4.46 (2×⅙H, d, J=16 Hz), 4.49 (2×⅓H, d, J=15 Hz), 4.52 (2×⅓H, d, J=15 Hz), 4.81–4.92 (1H, m), 5.32 (1×⅓H, d, J=8 Hz), 5.42 (1×⅔H, d, J=8 Hz), 7.00–7.20 (3H, m), 7.21–7.34 (3H, m), 7.39 (1×⅓H, d, J=8 Hz), 7.44 (1×⅔H, d, J=8 Hz), 8.32 (1×⅓H, s), 8.48 (1×⅔H, s), 8.41–8.50 (1H, m)

(31) MASS: 335 (M+1); NMR (CDCl₃, δ): 0.78–0.98 (3H, m), 1.18–1.40 (4H, m), 1.41 (9×⅓H, s), 1.42 (9×⅔H, s), 1.49–1.78 (2H, m), 2.91 (3×⅓H, s), 2.98 (3×⅔H, s), 4.50 (2×⅓H, d, J=15 Hz), 4.62 (2×⅓H, d, J=15 Hz), 4.68 (2×⅓H, d, J=17 Hz), 4.58–4.73 (1H, m), 5.31 (1×⅓H, d, J=8 Hz), 5.39 (1×⅔H, d, J=8 Hz), 7.13–7.40 (5H, m)

Preparation 64

The following object compounds were obtained according to a similar manner to that of Preparation 3, 4, 8, 41 or 54.

(1) MASS: 319 (M+1); NMR (CDCl₃, δ): 2.72 (3×⅔H, s), 2.91 (3×⅓H, s), 2.89–3.02 (1H, m), 3.12–3.23 (1H, m), 3.99 (1×⅓H, t, J=8 Hz), 4.10 (1×⅔H, t, J=8 Hz), 4.22 (2×⅙H, d, J=16 Hz), 4.39 (2×⅙H, d, J=16 Hz), 4.42 (2×⅓H, d, J=15 Hz), 4.69 (2×⅓H, d, J=15 Hz), 6.92–7.39 (6H, m), 7.40–7.51 (2H, m), 7.59 (1×⅓H, s), 7.68 (1×⅔H, s), 7.71–7.85 (3H, m)

(2) MASS: 283 (M+1); NMR (CDCl₃, δ): 2.25 (3×⅓H, s), 2.37 (3×⅔H, s), 2.50 (3×⅔H, s), 2.90 (3×⅓H, s), 2.81–2.91 (1H, m), 2.91–3.05 (1H, m), 3.62–3.78 (1H, m), 3.79 (2×⅙H, d, J=16 Hz), 4.21 (2×⅙H, d, J=16 Hz), 4.49 (2×⅓H, d, J=15 Hz), 4.59 (2×⅓H, d, J=15 Hz), 6.96 (2×⅓H, d, J=8 Hz), 7.08 (2×⅔H, d, J=8 Hz), 7.13–7.32 (8H, m)

(3) MASS: 299 (M+1); NMR (CDCl₃, δ): 2.68–2.80 (1H, m), 2.71 (3×⅔H, s), 2.88–2.98 (1H, m), 2.91 (3×⅓H, s), 2.76 (3×⅔H, s), 2.78 (3×⅓H, s), 3.81 (1×⅓H, t, J=8 Hz), 3.91 (1×⅔H, t, J=8 Hz), 4.20 (2×⅙H, d, J=16 Hz), 4.39 (2×⅙H, d, J=16 Hz), 4.41 (2×⅓H, d, J=15 Hz), 4.67 (2×⅓H, d, J=15 Hz), 6.78 (2H, d, J=8 Hz), 7.00 –7.18 (4H, m), 7.22–7.37 (3H, m)

(4) MASS: 283 (M+1); NMR (CDCl₃, δ): 2.32 (3H, s), 2.69 (3×⅔H, s), 2.72–2.81 (1H, m), 2.90 (3×⅓H, s), 2.93–3.03 (1H, m), 3.86–4.00 (1H, m), 4.12 (2×¼H, d, J=16 Hz), 4.37 (2×¼H, d, J=16 Hz), 4.46 (2×¼H, d, J=15 Hz), 4.59 (2×¼H, d, J=15 Hz), 6.82–7.31 (9H, m)

(5) MASS: 283 (M+1); NMR (CDCl₃, δ): 2.13 (3×⅓H, s), 2.27 (3×⅔H, s), 2.72 (3×⅔H, s), 2.78–2.85 (1H, m), 2.97 (3×⅓H, s), 2.98–3.08 (1H, m), 3.70 (1×½H, t, J=8 Hz), 4.02 (1×½H, t, J=8 Hz), 4.03 (2×¼H, d, J=16 Hz), 4.73 (2×¼H, d, J=16 Hz), 4.55 (2×¼H, d, J=15 Hz), 4.63 (2×¼H, d, J=15 Hz), 6.88–6.93 (1H, m), 7.09–7.18 (4H, m), 7.22–7.32 (4H, m)

(6) MASS: 271 (M+1); NMR (CDCl₃, δ): 2.78–2.88 (1H, m), 2.95 (3×⅔H, s), 2.96 (3×⅓H, s), 3.00–3.09 (1H, m), 3.80 (1×¼H, t, J=7 Hz), 4.05 (1×¾H, t, J=7 Hz), 4.32 (2×⅙H, d, J=17 Hz), 4.42 (2×⅙H, d, J=17 Hz), 4.53 (2×⅓H, d, J=15 Hz), 4.69 (2×⅓H, d, J=15 Hz), 6.92 (1×¼H, d, J=5 Hz), 7.0 (1×¾H, d, J=5 Hz), 7.12–7.32 (5H, m), 8.62 (1H, d, J=5 Hz), 9.11 (1×¾H, s), 9.13 (1×¼H, s)

(7) MASS: 321 (M+1); NMR (CDCl₃, δ): 2.78–2.88 (1H, m), 2.90 (3×¾H, s), 3.00 (3×¼H, s), 2.98–3.15 (1H, m), 4.02 (1H, t, J=8 Hz), 4.51 (2×⅙H, d, J=16 Hz), 4.70 ( 2×⅙H, d, J=16 Hz), 4.78 (2×⅓H, d, J=15 Hz), 4.98 (2×⅓H, d, J=15 Hz), 7.11–7.30 (5H, m), 7.71–7.80 (2H, m), 7.98–8.04 (1H, m), 8.08–8.15 (1H, m), 8.66 (1×¼H, s), 8.82 (1×¾H, s)

(8) MASS: 320 (M+1); NMR (CDCl₃, δ): 2.79–2.88 (1H, m), 2.85 (3×⅔H, s), 2.97 (3×⅓H, s), 3.02–3.11 (1H, m), 3.98–4.07 (1H, m), 4.51 (2×⅙H, d, J=16 Hz), 4.70 (2×⅙H, d, J=16 Hz), 4.80 (2×⅓H, d, J=15 Hz), 4.92 (2×⅓H, d, J=15 Hz), 7.11–7.29 (6H, m), 7.51–7.58 (1H, m), 7.68–7.73 (1H, m), 7.81 (1H, d, J=8 Hz), 8.01 (1H, d, J=8 Hz), 8.10 (1H, t, J=8 Hz)

(9) MASS: 320 (M+1); NMR (CDCl₃, δ): 2.77 (3×¾H, s), 2.80–2-88 (1H, m), 2.99 (3×¼H, s), 3.00–3.09 (1H, m), 3.92–4.05 (1H, m), 4.36 (2×⅙H, d, J=16 Hz), 4.59 (2×⅙H, d, J=16 Hz), 4.73 (2×⅓H, d, J=15 Hz), 4.80 (2×⅓H, d, J=15 Hz), 7.11–7.31 (5H, m), 7.38–7.42 (2H, m), 7.79 (1H, dd, J=8, 2 Hz), 7.85 (1×¼H, s), 7.89 (1×¾H, s), 8.15 (1H, d, J=8 Hz), 8.90–8.93 (1H, m)

(10) MASS: 271 (M+1); NMR (CDCl₃, δ): 2.77–2.84 (1H, m), 2.88 (3×¾H, s), 2.92 (3×¼H, s), 2.97–3.09 (1H, m), 4.00 (1H, t, J=8 Hz), 4.29 (2×⅙, d, J=17 Hz), 4.51 (2×⅙H, d, J=17 Hz), 4.61 (2×⅓H, d, J=15 Hz), 4.75 (2×⅓H, d, J=15 Hz), 7.16–7.32 (5H, m), 8.38–8.53 (3H, m)

(11) MASS: 347 (M+1); NMR (CDCl₃, δ): 2.79 (3×⅘H, s), 2.68–2.87 (1H, m), 2.91 (3×⅕H, s), 2.96–3.10 (1H, m), 3.88–4.03 (1H, m), 4.26 (2×⅙H, d, J=16 Hz), 4.43 (2×⅙H, d, J=16 Hz), 4.51 (2×⅓H, d, J=15 Hz), 4.69 (2×⅓H, d, J=15 Hz), 7.13–7.32 (5H, m), 7.40 (1H, dd, J=8, 5 Hz), 7.61 (1H, dd, J=8, 5 Hz), 7.69 (1H, t, J=8 Hz), 8.30 (1H, d, J=8 Hz), 8.47 (1×⅕H, s), 8.53 (1×⅘H, s), 8.63 (1H, d, J=5 Hz), 9.18 (1H, s)

(12) MASS: 347 (M+1); NMR (CDCl₃, δ): 2.73 (3×⅘H, s), 2.80–2.90 (1H, m), 2.92 (3×⅕H, s), 2.97–3.09 (1H, m), 3.92–4.02 (1H, m), 4.26 (2×⅙H, d, J=16 Hz), 4.45 (2×⅙H, d, J=16 Hz), 4.50 (2×⅓H, d, J=15 Hz), 4.74 (2×⅓H, d, J=15 Hz), 7.17–7.42 (6H, m), 7.62 (1H, dd, J=8, 2 Hz), 7.82 (1H, t, J=8 Hz), 8.32–8.42 (2H, m), 8.52 (1H, s), 8.70 (1H, d, J=5 Hz)

(13) NMR (CDCl₃, δ): 0.95 (6H×⅔, d, J=7 Hz), 0.99 (6H×⅓, d, J=7 Hz), 1.91 (1H, m), 2.94 (3H, s), 3.46 (1H×⅓, d, J=7 Hz), 3.53 (1H×⅔, d, J=7 Hz), 4.43 (1H×⅓, d, J=16 Hz), 4.46 (1H×⅔, d, J=15 Hz), 4.72 (1H×⅓, d, J=16 Hz), 4.77 (1H×⅔, d, J=15 Hz), 7.17–7.38 (5H, m)

(14) NMR (CDCl₃, δ): 0.75–1.02 (2H, m), 1.11–1.33 (3H, m), 1.39 (2H, m), 1.53–1.88 (6H, m), 2.92 (3H×⅔, s), 2.97 (3H×⅓, s), 3.73 (1H×⅓, dd, J=4, 7 Hz), 3.80 (1H×⅔, dd, J=4, 7 Hz), 4.43 (1H×⅓, d, J=16 Hz), 4.48 (1H×⅔, d, J=15 Hz), 4.65 (1H×⅓, d, J=16 Hz), 4.73 (1H×⅔, d, J=15 Hz), 7.16–7.39 (5H, m)

(15) NMR (CDCl₃, δ): 2.35 (3H, s), 2.56 (4H, m), 2.69 (3H×⅗, s), 2.77 (1H, dd, J=7, 12 Hz), 2.90 (3H×⅖, s), 2.98

(1H, dd, J=7, 12 Hz), 3.19 (4H, m), 3.92 (1H, q, J=7 Hz), 4.07 (1H×⅖, d, J=16 Hz), 4.33 (1H×⅖, d, J=16 Hz), 4.39 (1H×⅗, d, J=15 Hz), 4.52 (1H×⅗, d, J=15 Hz), 6.85–6.96 (3H, m), 7.08 (1H, d, J=8 Hz), 7.13–7.31 (5H, m) (16) NMR (CDCl$_3$, δ): 2.78 (1H, m), 2.80 (3H×⅗, s), 2.97 (3H×⅖, s), 3.00 (1H, m), 3.86 (1H×⅖, t, J=7 Hz), 3.97 (1H×⅗, t, J=7 Hz), 4.37 (1H×⅖, d, J=16 Hz), 4.43 (1H×⅖, d, J=16 Hz), 4.43 (1H×⅗, d, J=15 Hz), 4.68 (1H×⅗, d, J=15 Hz), 7.03 (2H, m), 7.15 (2H, m), 7.31 (3H, m), 8.48 (2H, m)

(17) MASS (m/z): 320 (M+H)$^+$; NMR (CDCl$_3$, δ): 2.72–3.12 (2H, m), 2.77 (¾×3H, s), 2.97 (¼×3H, s), 3.90–4.07 (1H, m), 4.49 (¼×2H, ABq, Δ=0.18, J=17 Hz), 4.72 (¾×2H, ABq, Δ=0.19, J=15 Hz), 7.07–8.17 (10H, m), 8.68 (¼×1H, s), 8.80 (¾×1H, s)

(18) MASS (m/z): 320 (M+H)$^+$; NMR (CDCl$_3$, δ): 2.76 (¾×3H, s), 2.79–3.10 (2H, m), 2.98 (¼×3H, s), 3.87–4.08 (1H, m), 4.48 (¼×2H, ABq, Δ=0.16, J=17 Hz), 4.73 (¾×2H, ABq, Δ=0.18, J=15 Hz), 7.08–7.65 (8H, m), 7.98–8.15 (2H, m), 8.91 (1H, d, J=2 Hz)

(19) MASS (m/z): 327 (M+H)$^+$; NMR (CDCl$_3$, δ): 2.21 (3H, s), 2.70 (¾×3H, s), 2.75–3.10 (2H, m), 2.86 (¼×3H, s), 3.85–4.01 (1H, m), 4.22 (¼×2H, ABq, Δ=0.22, J=17 Hz), 4.49 (¾×2H, ABq, Δ=0.23, J=15 Hz), 7.10–7.55 (6H, m), 7.95–8.20 (3H, m)

(20) MASS (m/z): 275 (M+1)$^+$; NMR (CDCl$_3$, δ): 2.86 (3H×⅔, s), 2.96 (3H×⅓, s), 2.95–3.05 (1H, m), 3.16–3.29 (1H, m), 3.89 (1H×⅓, t, J=7.0 Hz), 3.97 (1H×⅔, t, J=7.0 Hz), 4.38 (1H×⅓, d, J=14.5 Hz), 4.51 (1H, d, J=14.5 Hz), 4.69 (1H×⅔, d, J=14.5 Hz), 6.80 (1H×⅓, d, J=1.5 Hz), 6.84 (1H×⅔, d, J=1.5 Hz), 6.89–6.97 (1H, m), 7.09 (1H×⅔, d, J=7.5 Hz), 7.13–7.19 (2H, m), 7.23–7.38 (10/3H, m)

(21) MASS (m/z): 349 (M+H)$^+$; NMR (CDCl$_3$, δ): 2.71 (⅔×3H, s), 2.73–2.87 (1H, m), 2.92 (⅓×3H, s), 2.95–3.06 (1H, m), 3.84–4.02 (1H, m), 3.93 (3H, s), 4.30 (⅓×2H, ABq, Δ=0.20, J=17 Hz), 4.57 (⅔×2H, ABq, Δ=0.22, J=15 Hz), 6.52 (1H, m), 6.98–7.41 (8H, m), 7.65–7.78 (2H, m)

(22) MASS (m/z): 313 (M$^+$+H); NMR (CDCl$_3$, δ): 2.68 (¾×3H, s), 2.72–2.82 (1H, m), 2.84 (¼×3H, s), 2.90–3.03 (1H, m), 3.07 (6H, s), 3.88–4.04 (1H, m), 3.99 (¼×1H, d, J=17 Hz), 4.30 (¼×1H, d, J=17 Hz), 4.40 (¾×2H, ABq, Δ=0.11, J=15 Hz), 6.43 (¼×1H, d, J=9 Hz), 6.47 (¾×1H, d, J=9 Hz), 7.06–7.40 (6H, m), 7.92 (¼×1H, d, J=2 Hz), 7.99 (¾×1H, d, J=2 Hz)

(23) MASS (m/z): 335 (M+H)$^+$; NMR (CDCl$_3$, δ): 2.77 (⅔×3H, s), 2.77–2.88 (1H, m), 2.92 (⅓×3H, s), 2.96–3.10 (1H, m), 3.82–4.05 (1H, m), 4.33 (⅓×2H, ABq, Δ=0.18, J=17 Hz), 4.58 (⅔×2H, ABq, Δ=0.13, J=17 Hz), 7.06–7.37 (11H, m), 7.82 (1H, s)

(24) MASS (m/z): 337 (M+H)$^+$; NMR (CDCl$_3$, δ): 2.60 (3H, s), 2.72 (⅗×3H, s), 2.73–2.85 (1H, m), 2.92 (⅖×3H, s), 2.93–3.05 (1H, m), 3.71 (3H, s), 3.88–4.05 (1H, m), 4.26 (⅖×1H, d, J=17 Hz), 4.54 (⅖×1H, d, J=17 Hz), 4.68 (⅗×2H, ABq, Δ=0.01, J=15 Hz), 6.88–7.52 (8H, m)

(25) MASS (m/z): 259 (M+H)$^+$; NMR (CDCl$_3$, δ): 2.62–2.88 (2H, m), 2.91 (⅔×3H, s), 2.97 (⅓×3H, s), 3.79–4.04 (1H, m), 4.33–4.73 (2H, m), 6.19 (⅓×1H, s), 6.27 (⅔×1H, s), 7.08–7.41 (7H, m)

(26) MASS (m/z): 273 (M+H)$^+$; NMR (CDCl$_3$, δ): 2.69–3.10 (2H, m), 2.72 (⅔×3H, s), 2.89 (⅓×3H, s), 3.82 (⅓×3H, s), 3.87 (⅔×3H, s), 3.89–4.00 (1H, m), 4.16 (⅓×2H, ABq, Δ=0.15, J=17 Hz), 4.35 (⅔×2H, ABq, Δ=0.12, J=15 Hz), 6.95–7.38 (7H, m)

(27) MASS (m/z): 303 (M+H)$^+$; NMR (CDCl$_3$, δ): 2.68–3.04 (2H, m), 2.76 (⅗×3H, s), 2.93 (⅖×3H, s), 3.78–4.05 (1H, m), 4.36 (⅖×2H, ABq, Δ=0.11, J=17 Hz), 4.42 (⅗×1H, d, J=15 Hz), 4.68 (⅗×1H, d, J=15 Hz), 6.95–7.42 (9H, m)

(28) MASS (m/z): 259 (M+H)$^+$; NMR (CDCl$_3$, δ): 2.76–3.08 (2H, m), 2.85 (⅔×3H, s), 2.94 (⅓×3H, s), 4.02 (⅓×1H, t, J=7 Hz), 4.08 (⅔×1H, t, J=7 Hz), 4.45 (⅔×1H, d, J=15 Hz), 4.46 (⅓×2H, ABq, Δ=0.19, J=17 Hz), 4.72 (⅔×1H, d, J=15 Hz), 6.09 (1H, m), 6.28 (1H, m), 7.08–7.40 (6H, m)

(29) MASS: 321 (M+1); NMR (CDCl$_3$, δ): 2.80 (3×¾H, s), 2.81–2.91 (1H, m), 3.00 (3×¼H, s), 3.01–3.11 (1H, m), 3.91 (1×¼H, t, J=8 Hz), 4.03 (1×¾H, t, J=8 Hz), 4.40 (2×⅙H, d, J=16 Hz), 4.60 (2×⅙H, d, J=16 Hz), 4.72 (2×⅓H, d, J=15 Hz), 4.83 (2×⅓H, d, J=15 Hz), 7.10–7.45 (5H, m), 7.57 (1H, d, J=8 Hz), 7.82 (1×¼H, s), 7.88 (1×¾H, s), 8.00–8.10 (1H, m), 8.80–8.88 (2H, m)

(30) MASS: 319 (M+1); NMR (CDCl$_3$, δ): 2.31 (3×⅔H, s), 2.83 (3×⅓H, s), 3.28–3.47 (2H, m), 3.81 (2×⅙H, d, J=16 Hz), 4.02 (2×⅙H, d, J=16 Hz), 4.01–4.09 (1×⅓H, m), 4.13–4.23 (1×⅔H, m), 4.39 (2×⅓H, d, J=15 Hz), 4.46 (2×⅓H, d, J=15 Hz), 6.90 (2×⅓H, d, J=8 Hz), 7.03 (2×⅔H, d, J=8 Hz), 7.15–7.60 (7H, m), 7.69–7.80 (1H, m), 7.84 (1H, d, J=8 Hz), 7.84 (1×⅓H, d, J=8 Hz), 8.10 (1×⅔H, d, J=8 Hz)

(31) MASS: 270 (M+1); NMR (CDCl$_3$, δ): 2.70–2.89 (1H, m), 2.78 (3×⅔H, s), 2.90–3.03 (1H, m), 2.99 (3×⅓H, s), 3.82 (1×⅓H, t, J=8 Hz), 3.92 (1×⅔H, t, J=8 Hz), 4.32 (2×⅙H, d, J=16 Hz), 4.43 (2×⅙H, d, J=16 Hz), 4.49 (2×⅓H, t, J=15 Hz), 4.61 (2×⅓H, d, J=15 Hz), 7.02 (1×⅔H, d, J=7 Hz), 7.19 (1×⅓H, d, J=7 Hz), 7.11–7.40 (5H, m), 7.47 (1×⅓H, d, J=7 Hz), 7.51 (1×⅔H, d, J=7 Hz), 8.37 (1×⅓H, s), 8.47 (1×⅔H, s), 8.48 (1H, s)

(32) MASS: 235 (M+1); NMR (CDCl$_3$, δ): 0.82–0.95 (3H, m), 1.20–1.55 (5H, m), 1.56–1.73 (1H, m), 2.91 (3×⅔H, s), 2.93 (3×⅓H, s), 3.61–3.75 (1H, m), 4.44 (2×⅙H, d, J=16 Hz), 4.50 (2×⅓H, d, J=15 Hz), 4.66 (2×⅙H, d, J=16 Hz), 4.70 (2×⅓H, d, J=15 Hz), 7.10–7.40 (5H, m)

Preparation 65

The following object compounds were obtained according to a similar manner to that of Preparation 1, 6, 11, 38, 52 or 56.

(1) MASS: 603 (M+1); NMR (CDCl$_3$, δ): 1.45 (9H, s), 2–47–3.60 (1H, m), 2.51 (3×⅔H, s), 2.79 (3×⅓H, s), 3.08–3.31 (3H, m), 3.36–3.50 (2H, m), 3.50–3.60 (2H, m), 3.61–3.77 (4H, m), 4.18 (2×⅓H, d, J=15 Hz), 4.21 (2×⅙H, d, J=16 Hz), 4.28 (2×⅙H, d, J=16 Hz), 4.69 (2×⅓H, d, J=15 Hz), 4.49–4.60 (1H, m), 5.20–5.30 (1H, m), 5.96–6.05 (1H, m), 6.72 (2×⅓H, d, J=8 Hz), 6.88 (2×⅔H, d, J=8 Hz), 6.99–7.19 (3H, m), 7.28–7.55 (4H, m), 7.61–7.82 (4H, m)

(2) MASS: 567 (M+1); NMR (CDCl$_3$, δ): 1.43 (9H, s), 2.67–2.83 (1H, m), 2.79 (3×⅔H, s), 2.89 (3×⅓H, s), 2.92–3.07 (1H, m), 3.10 (3H, s), 3.14–3.27 (1H, m), 3.28–3.50 (4H, m), 3.50–3.70 (5H, m), 4.13 (2×⅙H, d, J=16 Hz), 4.20–4.31 (1H, m), 4.37 (2×⅙H, d, J=16 Hz), 4.40 (2×⅓H, d, J=15 Hz), 4.71 (2×⅓H, d, J=15 Hz), 4.80–5.00 (1H, m), 5.64–5.80 (1H, m), 6.92 (1H, d, J=5 Hz), 7.10–7.32 (9H, m)

(3) MASS: 583 (M+1); NMR (CDCl$_3$, δ): 1.48 (9H, s), 2.50–2.62 (1H, m), 2.60 (3×⅔H, s), 2.80 (3×⅓H, s), 2.88–3.08 (2H, m), 3.12–3.27 (1H, m), 3.40–3.50 (2H, m), 3.57–3.63 (2H, m), 3.64–3.72 (4H, m), 3.73 (3×⅔H, s), 3.79 (3×⅓H, s), 4.18 (2×⅙H, d, J=16 Hz), 4.28 (2×⅓H, d, J=15 Hz), 4.31 (2×⅙H, d, J=16 Hz), 4.50–4.70 (1H, m), 4.68 (2×⅓H, d, J=15 Hz), 5.00–5.14 (1H, m), 5.95–6.07 (1H, m), 6.72 (2×⅔H, d, J=8 Hz), 6.80 (2×⅓H, d, J=8 Hz), 6.83–6.92 (1H, m)

(4) MASS: 526 (M+1); NMR (CDCl$_3$, δ): 1.48 (9H, s), 2.51–2.62 (1H, m), 2.52 (3H, s), 2.53 (3×⅔H, s), 2.73 (3×⅓H, s), 2.94 (3H, s), 2.98–3.03 (2H, m), 3.01 (3H, s), 3.09–3.30 (1H, m), 4.00 (2×⅙H, d, J=17 Hz), 4.22 (2×⅙H, d, J=17 Hz), 4.27 (2×⅓H, d, J=15 Hz), 4.54 (2×⅓H, d, J=15 Hz), 4.50–4.58 (1H, m), 5.06–5.18 (1H, m), 6.08–6.14 (1H, m), 6.92–7.30 (7H, m), 7.51 (1H, t, J=8 Hz), 8.14 (1×¼H, s), 8.28 (1×¾H, s)

(5) MASS: 580 (M+1); NMR (CDCl$_3$, δ): 1.43 (9H, s), 2.27 (3×⅓H, s), 2.31 (3×⅔H, s), 2.29 (3H, s), 2.32–2.44 (4H, m), 2.49–2.61 (1H, m), 2.50 (3×⅔H, s), 2.80 (3×⅓H, s), 2.97–3.11 (2H, m), 3.17–3.28 (1H, m), 3.40–3.50 (2H, m), 3.57–3.65 (2H, m), 4.02 (2×⅙H, d, J=16 Hz), 4.23 (2×⅙H, d, J=16 Hz), 4.28 (2×⅓H, d, J=15 Hz), 4.58 (2×⅓H, d, J=15 Hz), 4.48–4.56 (1H, m), 5.08–5.18 (1H, m), 5.99–6.07 (1H, m), 6.66–7.47 (10H, m)

(6) MASS: 580 (M+1); NMR (CDCl$_3$, δ): 1.47 (9H, s), 2.17 (3×⅔H, s), 2.28 (3×⅓H, s), 2.28 (3H, s), 2.32–2.42 (4H, m), 2.48–2.61 (1H, m), 2.54 (3×⅔H, s), 2.80 (3×⅓H, s), 2.95–3.28 (3H, m), 3.40–3.50 (2H, m), 3.55–3.65 (2H, m), 4.00 (2×¼H, d, J=16 Hz), 4.13 (2×¼H, d, J=16 Hz), 4.49 (2×½H, s), 4.50–4.59 (1H, m), 4.93–5.02 (1×⅓H, m), 5.13–5.21 (1×⅔H, m), 6.00 (1H, d, J=8 Hz), 6.63 (1×⅓H, d, J=8 Hz), 6.71 (1×⅔H, d, J=8 Hz), 7.02–7.18 (4H, m), 7.20–7.30 (4H, m), 7.38–7.45 (1H, m)

(7) MASS: 555 (M+1); NMR (CDCl$_3$, δ): 1.47 (9×¾H, s), 1.48 (9×¼H, s), 2.51–2.62 (1H, m), 2.81 (3×¾H, s), 2.88 (3×¼H, s), 2.94–3.23 (3H, m), 3.43–3.49 (2H, m), 3.57–3.62 (2H, m), 3.63–3.73 (4H, m), 4.36 (2×⅙H, d, J=17 Hz), 4.40 (2×⅙H, d, J=17 Hz), 4.47 (2×⅓H, d, J=15 Hz), 4.51–4.60 (1H, m), 4.61 (2×⅓H, d, J=15 Hz), 4.92–5.00 (1×¼H, m), 5.13–5.22 (1×¾H, m), 5.97–6.05 (1H, m), 6.72 (1×¼H, d, J=5 Hz), 6.82 (1×¾H, d, J=5 Hz), 7.18–7.30 (5H, m), 7.33 (1×¼H, d, J=8 Hz), 7.40 (1×¾H, d, J=8 Hz), 8.54 (1×¼H, d, J=5 Hz), 8.59 (1×¾H, d, J=5 Hz), 9.08 (1×¼H, s), 9.10 (1×¾H, s)

(8) MASS: 605 (M+1); NMR (CDCl$_3$, δ): 1.42 (9H, s), 2.49–2.62 (1H, m), 2.79 (3×⅝H, s), 2.93 (3×⅜H, s), 3.00–3.23 (3H, m), 3.40–3.50 (2H, m), 3.53–3.62 (2H, m), 3.63–3.73 (6H, m), 4.51 (2×⅙H, d, J=16 Hz), 4.58 (2×⅙H, d, J=16 Hz), 4.62 (2×⅓H, d, J=15 Hz), 4.92 (2×⅓H, d, J=15 Hz), 4.50–4.63 (1H, m), 7.08–7.21 (5H, m), 7.47–7.53 (1H, m), 7.71–7.80 (2H, m), 7.98–8.03 (1H, m), 8.07–8.13 (1H, m), 8.61 (1×⅜H, s), 8.74 (1×⅝H, s)

(9) MASS: 604 (M+1); NMR (CDCl$_3$, δ): 1.42 (9H, s), 2.49–2.61 (1H, m), 2.72 (3×⅔H, s), 2.89 (3×⅓H, s), 3.00–3.25 (3H, m), 3.40–3.50 (2H, m), 3.56–3.62 (2H, m), 3.63–3.73 (4H, m), 4.48 (2×⅙H, d, J=17 Hz), 4.58 (2×⅙H, d, J=17 Hz), 4.50–4.61 (1H, m), 4.69 (2×⅓H, d, J=15 Hz), 4.85 (2×⅓H, d, J=15 Hz), 5.17–5.28 (1H, m), 5.97–6.04 (1H, m), 7.03 (1×¼H, d, J=8 Hz), 7.09 (1×¾H, d, J=8 Hz), 7.18–7.24 (5H, m), 7.41–7.56 (2H, m), 7.70 (1H, t, J=8 Hz), 7.80 (1H, d, J=8 Hz), 7.97–8.08 (2H, m)

(10) MASS: 604 (M+1); NMR (CDCl$_3$, δ): 1.49 (9H, s), 2.52–2.60 (1H, m), 2.62 (3×⅔H, s), 2.83 (3×⅓H, s), 2.99–3.27 (3H, m), 3.40–3.50 (2H, m), 3.58–3.62 (2H, m), 3.64–3.74 (4H, m), 4.21 (2×⅙H, d, J=16 Hz), 4.50 (2×⅙H, d, J=16 Hz), 4.53–4.62 (1H, m), 4.60 (2×⅓H, d, J=15 Hz), 4.73 (2×⅓H, d, J=15 Hz), 5.11–5.27 (1H, m), 5.97–6.08 (1H, m), 7.02–7.30 (6H, m), 7.40 (1H, dd, J=8, 5 Hz), 7.44–7.53 (1H, m), 7.70–7.80 (1H, m), 7.83 (1H, s), 8.14 (1H, t, J=5 Hz), 8.89 (1H, t, J=5 Hz)

(11) MASS: 555 (M+1); NMR (CDCl$_3$, δ): 1.43 (9H, s), 2.52–2.60 (1H, m), 2.78 (3×¾H, s), 2.88 (3×¼H, s), 3.02–3.22 (2H, m), 3.41–3.50 (2H, m), 3.57–3.72 (7H, m), 4.36 (2×⅓H, d, J=15 Hz), 4.47 (2×⅓H, d, J=15 Hz), 4.48–4.60 (1H, m), 4.70 (2×⅓H, d, J=15 Hz), 5.08–5.16 (1H, m), 6.00 (1H, br s), 7.13–7.28 (6H, m), 7.47 (1H, br s), 8.41–8.50 (2H, m)

(12) MASS: 631 (M+1); NMR (CDCl$_3$, δ): 1.43 (9H, s), 2.51–2.62 (1H, m), 2.62 (3×¾H, s), 2.80 (3×¼H, s), 2.98–3.28 (3H, m), 3.40–3.52 (2H, m), 3.55–3.62 (2H, m), 3.62–3.72 (4H, m), 4.14 (2×⅙H, d, J=16 Hz), 4.32 (2×⅙H, d, J=16 Hz), 4.40 (2×⅓H, d, J=15 Hz), 4.51–4.60 (1H, m), 4.61 (2×⅓H, d, J=15 Hz), 5.08–5.20 (1H, m), 5.99–6.06 (1H, m), 7.12–7.30 (5H, m), 7.38–7.50 (3H, m), 7.59 (1×¼H, d, J=8 Hz), 7.67 (1×¾H, d, J=8 Hz), 8.26–8.32 (1H, m), 8.33 (1×¼H, s), 8.48 (1×¾H, s), 8.64 (1H, d, J=5 Hz), 9.12–9.20 (1H, m)

(13) MASS: 631 (M+1); NMR (CDCl$_3$, δ): 1.43 (9H, s), 2.52–2.62 (1H, m), 2.59 (3×¾H, s), 2.80 (3×¼H, s), 2.99–3.22 (3H, m), 3.42–3.50 (2H, m), 3.58–3.62 (2H, m), 3.67–3.77 (4H, m), 4.18 (2×⅙H, d, J=16 Hz), 4.32 (2×⅙H, d, J=16 Hz), 4.31 (2×⅓H, d, J=15 Hz), 4.71 (2×⅓H, d, J=15 Hz), 4.51–4.60 (1H, m), 5.08–5.22 (1H, m), 6.02 (1H, br s), 7.18–7.22 (5H, m), 7.28–7.33 (1H, m), 7.41–7.51 (2H, m), 7.79–7.88 (1H, m), 8.22–8.46 (3H, m), 8.66–8.70 (1H, m)

(14) MASS: 505 (M$^+$+1); NMR (CDCl$_3$, δ): 0.88–0.99 (6H, m), 1.47 (9H, s), 2.07 (1H, m), 2.57 (1H, m), 2.91 (3H×⅓, s), 3.01 (3H×⅔, s), 3.21 (1H, dd, J=3, 15 Hz), 3.45 (2H, m), 3.58 (2H, m), 3.65 (4H, m), 4.37 (1H×⅔, d, J=15 Hz), 4.57 (1H, m), 4.63 (2H×⅓, s), 4.81 (1H, m), 4.82 (1H×⅔, d, J=15 Hz), 6.12 (1H, m), 7.21–7.35 (5H, m)

(15) MASS: 559 (M$^+$+1); NMR (CDCl$_3$, δ): 0.80–1.00 (2H, m), 1.07–1.25 (3H, m), 1.45 (9H, s), 1.43–1.94 (8H, m), 2.55 (1H, m), 2.92 (3H×⅓, s), 2.98 (3H×⅔, s), 3.17 (1H, dd, J=4, 15 Hz), 3.44 (2H, m), 3.60 (2H, m), 3.66 (4H, m), 4.38 (1H×⅔, d, J=15 Hz), 4.56 (1H×⅓, d, J=16 Hz), 4.55 (1H, m), 4.67 (1H×⅓, d, J=16 Hz), 4.75 (1H×⅔, d, J=15 Hz), 5.02 (1H, m), 6.03 (1H, d, J=7 Hz), 7.17–7.38 (5H, m)

(16) MASS: 651 (M$^+$+1); NMR (CDCl$_3$, δ): 1.47 (9H, s), 2.35 (3H, s), 2.51 (3H×⅔, s), 2.56 (5H, m), 2.74 (3H×⅓, s), 3.02 (2H, m), 3.18 (5H, m), 3.45 (2H, m), 3.60 (2H, m), 3.67 (4H, m), 3.92 (1H×⅓, d, J=16 Hz), 4.22 (1H×⅓, d, J=16 Hz), 4.23 (1H×⅔, d, J=15 Hz), 4.52 (1H×⅔, d, J=15 Hz), 4.54 (1H, m), 5.07 (1H×⅔, m), 5.17 (1H×⅓, m), 6.00 (1H, d, J=7 Hz), 6.80 (4H×⅓, s), 0.82 (2H×⅔, s), 6.97 (2H×⅔, s), 7.19 (4H, s), 7.44 (1H, m)

(17) MASS (m/z): 554 (M$^+$+1); NMR (CDCl$_3$, δ): 1.45 (9H, s), 2.46–2.58 (1H, m), 2.72 (3H×⅔, s), 2.88 (3H×⅓, s), 2.90–2.99 (1H, m), 3.08 (1H, dd, J=7, 13 Hz), 3.18 (1H, m), 3.43 (2H, m), 3.57 (2H, m), 3.65 (4H, m), 4.26 (1H×⅔, d, J=15 Hz), 4.35 (1H×⅓, d, J=16 Hz), 4.44 (1H×⅓, d, J=16 Hz), 4.52 (1H, m), 4.70 (1H×⅔, d, J=15 Hz), 5.15 (1H, m), 5.98 (1H, d, J=7 Hz), 6.92–7.13 (4H, m), 7.27–7.45 (3H, m), 8.43 (2H, m)

(18) MASS (m/z): 620 (M$^+$+1); NMR (CDCl$_3$, δ): 1.47 (9H, s), 2.61 (3H×¾, s), 2.80 (3H×¼, s), 2.95–3.23 (4H, m), 3.45 (2H, m), 3.60 (2H, m), 3.67 (4H, m), 4.16 (1H×¼, d, J=16 Hz), 4.30 (1H×¼, d, J=16 Hz), 4.38 (1H×¾, d, J=15 Hz), 4.54 (1H, m), 4.63 (1H×¾, d, J=15 Hz), 5.13 (1H, m), 6.02 (1H, m), 6.97–7.17 (2H, m), 7.21–7.28 (4H, m), 7.36–7.58 (3H, m), 8.09 (1H, s), 8.52 (1H, s)

(19) MASS (m/z): 604 (M+H)$^+$; NMR (CDCl$_3$, δ): 1.48 (9H, s), 2.49–2.66 (1H, m), 2.61 (¾×3H, s), 2.83 (¼×3H, s), 2.94–3.28 (3H, m), 3.35–3.76 (8H, m), 4.38 (¼×2H, ABq, Δ=0.19, J=17 Hz), 4.49 (¾×1H, d, J=15 Hz), 4.50–4.65 (1H, m), 4.80 (¾×1H d, J=15 Hz), 5.02–5.25 (1H, m), 5.93–6.10 (1H, br d), 7.03–7.30 (5H, m), 7.40–8.15 (6H, m), 8.58 (¼×1H, d, J=2 Hz), 8.72 (¾×1H, d, J=2 Hz)

(20) MASS: 604 (M+H)$^+$; NMR (CDCl$_3$, δ): 1.48 (9H, s), 2.48–2.68 (1H, m), 2.62 (⅔×3H, s), 2.84 (⅓×3H, s), 2.94–3.28 (3H, m), 3.37–3.78 (8H, m), 4.38 (⅓×2H, ABq,

Δ=0.11, J=17 Hz), 4.49 (⅔×1H, d, J=15 Hz), 4.50–4.64 (1H, m), 4.80 (⅔×1H, d, J=15 Hz), 5.10–5.24 (1H, m), 5.96–6.08 (1H, br d), 7.10–7.55 (9H, m), 7.93–8.15 (2H, m), 8.86–8.92 (1H, m)

(21) MASS (m/z): 611 (M+H)⁺; NMR (CDCl₃, δ): 1.46 (9H, s), 2.19 (¼×3H, s), 2.21 (¾×3H, s), 2.50–2.63 (1H, m), 2.55 (¾×3H, s), 2.72 (¼×3H, s), 2.93–3.28 (3H, m), 3.37–3.78 (8H, m), 4.11 (¼×2H, ABq, Δ=0.22, J=17 Hz), 4.21 (¾×1H, d, J=15 Hz), 4.48–4.60 (1H, m), 4.58 (¾×1H, d, J=15 Hz), 5.02–5.22 (1H, m), 5.95–6.10 (1H, br d), 7.05–7.52 (7H, m), 7.86–8.15 (3H, m)

(22) MASS (m/z): 588 (M+H)⁺; NMR (CDCl₃, δ): 1.43 (9H, s), 1.8–2.2 (2H, m), 2.3–2.5 (2H, m), 2.60 (⅔×3H, s), 2.82 (⅓×3H, s), 3.0–3.1 (2H, m), 4.10 (⅓×1H, d, J=15 Hz), 4.1–4.2 (1H, m), 4.32 (⅓×1H, d, J=15 Hz), 4.38 (⅔×1H, d, J=15 Hz), 4.60 (⅔×1H, d, J=15 Hz), 5.1–5.2 (2H, m), 5.13 (2H, s), 6.9–7.3 (16H, m)

(23) MASS (m/z): 537 (M⁺+1); NMR (CDCl₃, δ): 1.47 (9H, s), 2.52–3.28 (4H, m), 3.42–3.68 (8H, m), 4.52–4.68 (2H, m), 4.89–4.97 (1H, m), 5.39–5.47 (1H, m), 6.90 (1H, d, J=8 Hz), 7.01 (1H, t, J=8 Hz), 7.13 (1H, t, J=8 Hz), 7.18–7.34 (6H, m), 6.79–7.85 (1H, m)

(24) MASS (m/z): 559 (M+1)⁺; NMR (CDCl₃, δ): 1.47 (9H, s), 2.49–2.62 (1H, m), 2.76 (3H×⅔, s), 2.84 (3H×⅓, s), 3.11–3.26 (2H, m), 3.32 (1H×⅔, x, J=8.5 Hz), 3.38 (1H×⅓, d, J=8.5 Hz), 3.40–3.50 (2H, m), 3.55–3.76 (6H, m), 4.33 (1H×⅓, d, J=14.5 Hz), 4.37 (1H×⅔, d, J=14.5 Hz), 4.41 (1H×⅓, d, J=14.5 Hz), 4.47–4.60 (1H, m), 4.64 (1H×⅔, d, J=14.5 Hz), 5.10–5.19 (1H, m), 6.02 (1H, br d, J=7.5 Hz), 6.83–7.33 (8H, m), 7.40 (1H×⅓, br d, J=7.5 Hz), 7.47 (1H×⅔, br d, J=7.5 Hz)

(25) MASS (m/z): 633 (M+H)⁺; NMR (CDCl₃, δ): 1.47 (9H, s), 2.47–2.62 (1H, m), 2.54 (⅔×3H, s), 2.79 (⅓×3H, s), 2.93–3.11 (2H, m), 3.11–3.28 (1H, m), 3.35–3.75 (8H, m), 3.94 (3H, s), 4.20 (⅓×2H, ABq, Δ=0.21, J=17 Hz), 4.26 (⅔×1H, d, J=15 Hz), 4.49–4.62 (1H, m), 4.68 (⅔×1H, d, J=15 Hz), 5.05–5.23 (1H, m), 6.02 (1H, br d, J=8 Hz), 6.50 (⅓×1H, d, J=2 Hz), 6.52 (⅔×1H, d, J=2 Hz), 6.87–7.73 (11H, m)

(26) MASS (m/z): 597 (M+H)⁺; NMR (CDCl₃, δ): 1.47 (9H, s), 2.50 (⅔×3H, s), 2.51–2.62 (1H, m), 2.71 (⅓×3H, s), 2.97–3.06 (2H, m), 3.06 (⅓×6H, s), 3.08 (⅔×6H, s), 3.11–3.28 (1H, m), 3.36–3.80 (8H+⅓×2H, m), 4.31 (⅔×2H, ABq, Δ=0.21, J=15 Hz), 4.47–4.61 (1H, m), 4.98–5.32 (1H, m), 6.02 (1H, br d, J=8 Hz), 6.39 (⅓×1H, d, J=9 Hz), 6.43 (⅔×1H, d, J=9 Hz), 7.12–7.52 (7H, m), 7.82 (⅓×1H, d, J=2 Hz), 7.94 (⅔×tH, d, J=2 Hz)

(27) MASS (m/z): 619 (M+H)⁺; NMR (CDCl₃, δ): 1.47 (9H, s), 2.49–2.65 (1H, m), 2.61 (⅔×3H, s), 2.79 (⅓×3H, s), 2.92–3–30 (3H, m), 3.36–3.78 (8H, m), 4.22 (⅓×2H, ABq, Δ=0.15, J=17 Hz), 4.46–4.62 (1H, m), 4.49 (⅔×2H, ABq, Δ=0.16, J=15 Hz), 5.06–5.21 (1H, m), 5.92–6.08 (1H, m), 6.92–7.50 (12H, m), 7.82 (1H, s)

(28) MASS (m/z): 621 (M+H)⁺; NMR (CDCl₃, δ): 1.47 (9H, s), 2.48–2.65 (1H, m), 2.52 (⅔×3H, s), 2.58 (⅓×3H, s), 2.60 (⅔×3H, s), 2.76 (⅓×3H, s), 2.93–3.27 (3H, m), 3.36–3.77 (8H, m), 3.69 (⅓×3H, s), 3.71 (⅔×3H, s), 4.02 (⅓×1H, d, J=17 Hz), 4.47 (⅓×1H, d, J=17 Hz), 4.48–4.62 (1H, m), 4.57 (⅔×2H, ABq, Δ=0.16, J=15 Hz), 5.02–5.34 (1H, m), 6.02 (1H, br d), 6.75–7.56 (9H, m)

(29) MASS (m/z): 543 (M+H)⁺; NMR (CDCl₃, δ): 1.45 (9H, s), 2.46–2.62 (1H, m), 2.70–3.02 (2H, m), 2.85 (⅔×3H, s), 2.88 (⅓×3H, s), 3.11–3.30 (1H, m), 3.37–3.76 (8H, m), 4.36 (⅔×1H, d, J=15 Hz), 4.45–4.60 (1H, m), 4.48 (⅓×2H, s), 4.70 (⅔×1H, d, J=15 Hz), 5.00–5.12 (1H, m), 6.02 (1H, br d, J=8 Hz), 6.23 (⅓×1H, s), 6.28 (⅔×1H, s), 7.00–7.50 (8H, m)

(30) MASS (m/z): 557 (M+H)⁺; NMR (CDCl₃, δ): 1.48 (9H, s), 2.50–2.62 (1H, m), 2.56 (⅔×3H, s), 2.78 (⅓×3H, s), 2.92–3.28 (3H, m), 3.38–3.75 (8H, m), 3.79 (⅓×3H, s), 3.85 (⅔×3H, s), 4.01 (⅓×2H, ABq, Δ=0.16, J=17 Hz), 4.13 (⅔×1H, d, J=15 Hz), 4.40 (⅔×1H, d, J=15 Hz), 4.46–4.60 (1H, m), 4.98–5.23 (1H, m), 5.93–6.09 (1H, m), 6.88–7.50 (8H, m)

(31) MASS (m/z): 587 (M+H)⁺; NMR (CDCl₃, δ): 1.46 (9H, s), 2.45–2.62 (1H, m), 2.67 (⅔×3H, s), 2.83 (⅓×3H, s), 2.85–3.27 (3H, m), 3.35–3.76 (8H, m), 4.25 (⅔×1H, d, J=15 Hz), 4.34 (⅓×2H, ABq, Δ=0.06, J=17 Hz), 4.45–4.60 (1H, m), 4.71 (⅔×1H, d, J=15 Hz), 5.04–5.16 (1H, m), 6.00 (1H, d, J=8 Hz), 6.84–7.48 (10H, m)

(32) MASS (m/z): 543 (M+H)⁺; NMR (CDCl₃, δ): 1.48 (9H, s), 2.48–2.67 (1H, m), 2.78 (⅔×3H, s), 2.86 (⅓×3H, s), 2.94–3.28 (3H, m), 3.35–3.79 (8H, m), 4.31 (⅔×1H, d, J=15 Hz), 4.41 (⅓×2H, ABq, Δ=0.13, J=17 Hz), 4.46–4.63 (1H, m), 4.77 (⅔×1H, d, J=15 Hz), 5.10–5.30 (1H, m), 5.92–6.10 (1H, br d, J=8 Hz), 6.11 (⅔×1H, d, J=2 Hz), 6.13 (⅓×1H, d, J=2 Hz), 6.24 (⅔×1H, d, J=2 Hz), 6.30 (⅓×1H, d, J=2 Hz), 7.02–7.60 (7H, m)

(33) MASS: 605 (M+1); NMR (CDCl₃, δ): 1.49 (9H, s), 2.50–2.70 (1H, m), 2.63 (3×⅔H, s), 2.83 (3×⅓H, s), 2.97–3.30 (3H, m), 3.40–3.50 (2H, m), 3.58–3.64 (2H, m), 3.65–3.80 (4H, m), 4.32 (2×⅙H, d, J=16 Hz), 4.49 (2×⅙H, d, J=16 Hz), 4.51–4.63 (1H, m), 4.59 (2×⅓H, d, J=15 Hz), 4.80 (2×⅓H, d, J=15 Hz), 5.10–5.21 (1H, m), 5.95–6.08 (1H, m), 7.15–7.28 (5H, m), 7.39–7.53 (2H, m), 7.71 (1×⅓H, s), 7.82 (1×⅔H, s), 7.98 (1×⅓H, d, J=8 Hz), 8.00 (1×⅔H, d, J=8 Hz), 8.82 (2H, s)

(34) MASS: 603 (M+1);
NMR (CDCl₃, δ): 1.49 (9H, s), 1.91 (3×⅔H, s), 2.61 (3×⅓H, s), 3.20–3.53 (4H, m), 3.54–3–86 (8H, m), 4.22 (2×½H, d, J=15 Hz), 4.36 (2×½H, d, J=15 Hz), 4.50–4.63 (1H, m), 5.28–5.38 (1H, m), 6.00–6.10 (1H, m), 6.61–6.68 (2×⅓H, m), 6.88–7.00 (2×⅔H, m), 7.07–7.30 (5H, m), 7.31–7.72 (4H, m), 7.74–7.86 (1H, m), 8.19 (1×⅓H, d, J=8 Hz), 8.39 (1×⅔H, d, J=8 Hz)

(35) MASS: 554 (M+1) NMR (CDCl₃, δ): 1.41 (9H, s), 2.48–2.61 (1H, m), 2.71 (3×⅔H, s), 2.88 (3×⅓H, s), 2.89–3.27 (3H, m), 3.35–3.49 (1H, m), 3.52–3.75 (7H, m), 4.38 (2×⅓H, s), 4.39 (2×⅓H, d, J=15 Hz), 4.59 (2×⅓H, d, J=15 Hz), 4.44–4.58 (1H, m), 5.07–5.18 (1H, m), 5.96–6.06 (1H, m), 6.91–6.98 (2×⅓H, m), 7.08–7.11 (2×⅔H, m), 7.06–7.20 (1H, m), 7.22–7.33 (3H, m), 7.38–7.57 (2H, m), 8.38 (1×⅓H, s), 8.47 (1×⅔H, s), 8.47 (1H, s)

(36) MASS: 584 (M+1); NMR (CDCl₃, δ): 1.48 (9H, s), 2.51 (3×¾H, s), 2.71 (3×¼H, s), 2.49–2.63 (1H, m), 2.95–3.05 (2H, m), 3.06–3.25 (1H, m), 3.38–3.50 (2H, m), 3.53–3.62 (2H, m), 3.62–3.77 (4H, m), 3.88 (3×¼H, s), 3.99 (3×¾H, s), 4.20 (2×½H, d, J=16 Hz), 4.49 (2×½H, d, J=16 Hz), 4.50–4.60 (1H, m), 5.00–5.11 (1H, m), 5.95–6.07 (1H, m), 6.60–6.70 (1H, m), 7.00 (1×¼H, d, J=8 Hz), 7.18 (1×¾H, d, J=8 Hz), 7.10–7.30 (5H, m), 7.43 (1H, t, J=8 Hz), 7.80 (1×¼H, s), 7.92 (1×¾H, s)

(37) MASS: 519 (M+1); NMR (CDCl₃, δ): 0.78–1.00 (3H, m), 1.15–1.41 (4H, m), 1.47 (9H, s), 1.56–1.71 (2H, m), 2.48–2.62 (1H, m), 2.91 (3×⅓H, s), 2.97 (3×⅔H, s), 3.20 (1H, d, J=16 Hz), 3.35–3.50 (2H, m), 3.52–3.60 (2H, m), 3.61–3.78 (4H, m), 4.41 (2×⅓H, d, J=15 Hz), 4.49–4.63 (1H, m), 4.61 (2×⅓H, s), 4.77 (2×⅓H, d, J=15 Hz), 4.87–5.00 (1H, m), 6.08 (1H, d, J=8 Hz), 7.12–7.50 (6H, m)

Preparation 66

The following object compounds were obtained according to a similar manner to that of Preparation 3, 4, 8, 41 or 54.

(1) MASS: 503 (M+1); NMR (CDCl$_3$, δ): 1.97–2.03 (1×⅓H, m), 2.20–2.30 (1×⅔H, m), 2.47 (1×⅓H, dd, J=15, 2 Hz), 2.60 (1×⅔H, dd, J=15, 2 Hz), 2.72 (3×⅔H, s), 2.90 (3×⅓H, s), 2.98–3.33 (4H, m), 3.40–3.72 (7H, m), 4.30 (2×⅓H, d, J=15 Hz), 4.42 (2×⅙H, d, J=16 Hz), 4.50 (2×⅙H, d, J=16 Hz), 4.71 (2×⅓H, d, J=15 Hz), 5.26–5.38 (1H, m), 6.92–7.02 (2H, m), 7.10–7.23 (3H, m), 7.34–7.48 (3H, m), 7.59 (1×⅓H, s), 7.69 (1×⅔H, s), 7.70–7.81 (3H, m), 8.03 (1×⅓H, d, J=8 Hz), 8.19 (1×⅔H, d, J=8 Hz)

(2) MASS: 467 (M+1); NMR (CDCl$_3$, δ): 2.64 (1×⅔H, d, J=8 Hz), 2.71 (1×⅓H, d, J=8 Hz), 2.80 (3×⅔H, s), 2.89 (3×⅓H, s), 2.91–3.14 (2H, m), 3.11 (3H, s), 3.15–3.42 (3H, m), 3.43–3.70 (8H, m), 3.93 (1×⅓H, t, J=8 Hz), 4.08 (1×⅔H, t, J=8 Hz), 4.36 (2×⅙H, d, J=16 Hz), 4.47 (2×⅓H, d, J=15 Hz), 4.62 (2×⅓H, d, J=15 Hz), 4.68 (2×⅙H, d, J=16 Hz), 5.73–5.83 (1H, m), 6.97 (2×⅓H, d, J=7 Hz), 7.13 (2×⅔H, d, J=7 Hz), 7.18–7.33 (8H, m)

(3) MASS: 483 (M+1); NMR (CDCl$_3$, δ): 2.27–2.39 (1×⅓H, m), 2.42–2.53 (1×⅔H, m), 2.60–2.82 (1H, m), 2.68 (3×⅔H, s), 2.88 (3×⅓H, s), 2.90–3.08 (2H, m), 3.33–3.48 (2H, m), 3.50–3.72 (7H, m), 3.73 (3×⅔H, s), 3.76 (3×⅓H, s), 4.30 (2×⅓H, d, J=15 Hz), 4.40 (2×⅓H, s), 4.71 (2×⅓H, d, J=15 Hz), 5.08–5.19 (1H, m), 6.70–6.82 (2H, m), 6.93–7.15 (4H, m), 7.20–7.32 (3H, m), 8.01 (1×⅓H, d, J=8 Hz), 8.11 (1×⅔H, d, J=8 Hz)

(4) MASS: 426 (M+1); NMR (CDCl$_3$, δ): 2.50–2.62 (1H, m), 2.51 (3×⅓H, s), 2.52 (3×⅔H, s), 2.63 (3×⅔H, s), 2.72–2.85 (1H, m), 2.79 (3×⅓H, s), 2.91–3.22 (2H, m), 2.99 (3H, s), 3.00 (3H, s), 3.62–3.80 (1H, m), 4.22 (2×⅙H, d, J=17 Hz), 4.32 (2×⅓H, d, J=15 Hz), 4.38 (2×⅙H, d, J=17 Hz), 4.60 (2×⅓H, d, J=17 Hz), 5.10–5.23 (1H, m), 7.01–7.11 (1H, m), 7.14–7.31 (6H, m), 8.18 (1H, m), 8.21 (1×¼H, s), 8.30 (1×¾H, s)

(5) MASS: 480 (M+1); NMR (CDCl$_3$, δ): 2.30 (3H, s), 2.31 (3H, s), 2.22–2.48 (5H, m), 2.68 (3×⅔H, s), 2.72–2.85 (1H, m), 2.89 (3×⅓H, s), 2.92–3.16 (2H, m), 3.39–3.48 (2H, m), 3.52–3.73 (3H, m), 4.30 (2×⅙H, d, J=16 Hz), 4.37 (2×⅙H, d, J=16 Hz), 4.32 (2×⅓H, d, J=15 Hz), 4.62 (2×⅓H, d, J=15 Hz), 5.12–5.22 (1H, m), 6.78–7.27 (9H, m), 8.08 (1×⅓H, d, J=8 Hz), 8.17 (1×⅔H, d, J=8 Hz)

(6) NMR (CDCl$_3$, δ): 2.19 (3×⅓H, s), 2.21 (3×⅔H, s), 2.28 (3H, s), 2.31–2.47 (5H, m), 2.62–2.85 (1H, m), 2.72 (3×⅔H, s), 2.92 (3×⅓H, s), 2.95–3.18 (2H, m), 3.33–3.72 (5H, m), 4.30 (2×⅓H, s), 4.48 (2×⅓H, d, J=15 Hz), 4.59 (2×⅓H, d, J=15 Hz), 5.02 (1×⅓H, q, J=8 Hz), 5.12 (1×⅔H, q, J=8 Hz), 6.78–6.80 (1H, m), 7.07–7.17 (4H, m), 7.20–7.30 (4H, m), 7.97 (1×⅓H, d, J=8 Hz), 8.13 (1×⅔H, d, J=8 Hz)

(7) MASS: 455 (M+1); NMR (CDCl$_3$, δ): 2.39–2.61 (1H, m), 2.70–2.82 (1H, m), 2.88 (3×¾H, s), 2.89 (3×¼H, s), 2.93–3.22 (2H, m), 3.38–3.47 (2H, m), 3.51–3.73 (7H, m), 4.32 (2×⅙H, d, J=17 Hz), 4.48 (2×⅓H, d, J=15 Hz), 4.62 (2×⅙H, d, J=17 Hz), 4.64 (2×⅓H, d, J=15 Hz), 4.93–5.04 (1×¼H, m), 5.17–5.22 (1×¾H, m), 6.82 (1×¼H, d, J=5 Hz), 6.88 (1×¾H, d, J=5Hz), 7.17–7.31 (5H, m), 8.08–8.14 (1H, m), 8.58 (1×¼H, d, J=5 Hz), 8.60 (1×¾H, d, J=5 Hz), 9.10 (1H, s)

(8) MASS: 505 (M+1); NMR (CDCl$_3$, δ): 2.28–2.36 (1×¼H, m), 2.48–2.57 (1×¾H, m), 2.64–2.82 (1H, m), 2.86 (3×¾H, s), 2.97 (3×¼H, s), 3.00–3.26 (2H, m), 3.35–3.48 (2H, m), 3.50–3.77 (7H, m), 4.68 (2×⅙H, d, J=16 Hz), 4.70 (2×⅓H, d, J=15 Hz), 4.81 (2×⅙H, d, J=16 Hz), 4.92 (2×⅓H, d, J=15 Hz), 5.13–5.30 (1H, m), 7.09–7.22 (5H, m), 7.72–7.80 (2H, m), 7.97–8.03 (1H, m), 8.08–8.20 (2H, m), 8.69 (1×¼H, s), 8.78 (1×¾H, s)

(9) MASS: 504 (M+1); NMR (CDCl$_3$, δ): 2.23–2.33 (1×⅓H, m), 2.47–2.53 (1×⅔H, m), 2.69–2.83 (1H, m), 2.85 (3×¾H, s), 2.95 (3×¼H, s), 3.00–3.27 (2H, m), 3.37–3.47 (2H, m), 3.50–3.77 (7H, m), 4.65 (2×⅙H, d, J=16 Hz), 4.70 (2×⅓H, d, J=15 Hz), 4.72 (2×⅙H, d, J=16 Hz), 4.91 (2×⅓H, d, J=15 Hz), 5.20–5.30 (1H, m), 7.11–7.23 (6H, m), 7.52 (1H, t, J=8 Hz), 7.70 (1H, t, J=8 Hz), 7.80 (1H, d, J=8 Hz), 8.00–8.20 (3H, m)

(10) MASS: 504 (M+1);. NMR (CDCl$_3$, δ): 2.29–2.52 (1H, m), 2.69–2.83 (1H, m), 2.80 (3×¾H, s), 2.91 (3×¼H, s), 2.98–3.18 (2H, m), 3.35–3.47 (2H, m), 3.50–3.68 (7H, m), 4.42 (2×⅙H, d, J=16 Hz), 4.61 (2×⅙H, d, J=16 Hz), 4.68 (2×⅓H, d, J=15 Hz), 4.77 (2×⅓H, d, J=15 Hz), 5.14–5.28 (1H, m), 7.11–7.30 (6H, m), 7.40 (1H, dd, J=8, 5 Hz), 7.72 (1H, dd, J=8, 2 Hz), 7.78 (1×¼H, s), 7.82 (1×¾H, s), 8.08–8.20 (2H, m), 8.88–8.92 (1H, m)

(11) MASS: 455 (M+1); NMR (CDCl$_3$, δ): 2.31–2.40 (1×¼H, m), 2.48–2.56 (1×¾H, m), 2.69–2.82 (1H, m), 2.85 (3×⅘H, s), 2.91 (3×⅕H, s), 2.97–3.20 (2H, m), 3.36–3.42 (2H, m), 3.50–3.72 (7H, m), 4.43 (2×⅙H, d, J=16 Hz), 4.51 (2×⅓H, d, J=15 Hz), 4.62 (2×⅙H, d, J=16 Hz), 4.73 (2×⅓H, d, J=15 Hz), 5.12–5.22 (1H, m), 7.15–7.29 (5H, m), 8.08–8.16 (1H, m), 8.33–8.50 (3H, m)

(12) MASS: 531 (M+1); NMR (CDCl$_3$, δ): 2.47–2.60 (1H, m), 2.72 (3×¾H, s), 2.81 (1H, dd, J=15, 2 Hz) 2.85 (3×¼H, s), 2.97–3.11 (2H, m), 3.40–3.48 (2H, m), 3.51–3.77 (7H, m), 4.32 (2×⅙H, d, J=16 Hz), 4.41 (2×⅙H, d, J=16 Hz), 4.42 (2×⅓H, d, J=15 Hz), 4.65 (2×⅓H, d, J=15 Hz), 5.11–5.22 (1H, m), 7.18–7.30 (5H, m), 7.38–7.42 (1H, m), 7.49 (1H, d, J=8 Hz), 7.61 (1×¼H, d, J=8 Hz), 7.67 (1×¾H, d, J=8 Hz), 8.18 (1H, d, J=8 Hz), 8.27–8.32 (1H, m), 8.40 (1×¼H, s), 8.50 (1×¾H, s), 8.67 (1H, d, J=5 Hz), 9.16 (1×¼H, s), 9.18 (1×¾H, s)

(13) MASS: 531 (M+1); NMR (CDCl$_3$, δ): 2.42–2.58 (1H, m), 2.67 (3×⅚H, s), 2.72–2.82 (1H, m), 2.83 (3×⅙H, s), 2.99–3.20 (2H, m), 3.41–3.48 (2H, m), 3.52–3.77 (7H, m), 4.36 (2×⅙H, d, J=17 Hz), 4.38 (2×⅓H, d, J=15 Hz), 4.42 (2×⅙H, d, J=17 Hz), 4.71 (2×⅓H, d, J=15 Hz), 5.12–5.23 (1H, m), 7.15–7.32 (6H, m), 7.51 (1H, d, J=8 Hz), 7.79–7.85 (1H, m), 8.18 (1H, t, J=8 Hz), 8.27–8.40 (2H, m), 8.49 (1H, s), 8.70 (1H, d, J=5 Hz)

(14) NMR (CDCl$_3$, δ): 0.89–1.00 (6H, m), 2.10 (1H, m), 2.72 (1H, dd, J=7, 15 Hz), 2.84 (1H, dd, J=3, 15 Hz), 2.93 (3H×⅓, s), 3.04 (3H×⅔, s), 3.47 (2H, m), 3.58–3.76 (7H, m), 4.38 (1H×⅔, d, J=15 Hz), 4.66 (2H×⅓, s), 4.79 (1H, t, J=7 Hz), 4.83 (1H×⅔, d, J=15 Hz), 7.22–7.37 (5H m), 8.12 (1H, m)

(15) NMR (CDCl$_3$, δ): 0.84–1.23 (3H, m), 1.51–1.94 (10H, m), 2.56–2.67 (1H, m), 2.82–2.90 (1H, m), 2.94 (3H×⅓, s), 3.02 (3H×⅔, s), 3.46 (2H, m), 3.62–3.76 (7H, m), 4.41 (1H×⅔, d, J=15 Hz), 4.58 (1H×⅓, d, J=16 Hz), 4.73 (1H×⅓, d, J=16 Hz), 4.77 (1H×⅔, d, J=15 Hz), 5.01 (1H, m), 7.20–7.38 (5H, m), 7.91 (1H×⅓, d, J=7 Hz), 7.97 (1H×⅔, d, J=7 Hz)

(16) NMR (CDCl$_3$, δ): 2.34 (3H, s), 2.47 (1H, dd, J=7, 15 Hz), 2.57 (4H, m), 2.64 (3H×⅔, s), 2.76 (1H, dd, J=4, 7 Hz), 2.83 (3H×⅓, s), 2.93–3.12 (2H, m), 3.19 (4H, m), 3.42 (2H, m), 3.66 (7H, m), 4.17 (1H×⅓, d, J=16 Hz), 4.27 (1H×⅔, d, J=15 Hz), 4.33 (1H×⅓, d, J=16 Hz), 4.55 (1H×⅔, d, J=15 Hz), 5.10–5.25 (1H, m), 6.81–7.03 (4H, m), 7.15–7.25 (5H, m), 8.07 (1H×⅓, d, J=7 Hz), 8.13 (1H×⅔, d, J=7 Hz)

(17) NMR (CDCl$_3$, δ): 2.34–2.77 (2H, m), 2.79 (3H×⅔, s), 2.93 (3H×⅓, s), 2.87–3.14 (2H, m), 3.34–3.42 (2H, m), 3.50–3.68 (6H, m), 4.29 (1H×⅔, d, J=15 Hz), 4.42 (1H×⅓, d, J=16 Hz), 4.57 (1H×⅓, d, J=16 Hz), 4.72 (1H×⅔, d, J=15 Hz), 5.18 (1H, m), 6.97–7.15 (4H, m), 7.26–7.31 (3H, m), 8.08 (1H×⅓, d, J=8 Hz), 8.20 (1H×⅔, d, J=8 Hz), 8.43 (2H, d, J=5 Hz)

(18) NMR (CDCl₃, δ): 2.42–2.57 (1H, m), 2.72 (3H×¾, s), 2.77–2.83 (1H, m), 2.85 (3H×¼, s), 2.95–3.18 (2H, m), 3.43 (2H, m), 3.63 (6H, m), 3.72 (1H, m), 4.38 (2H×¼, s), 4.40 (1H×¾, s), 4.67 (1H×¾, s), 5.17 (1H, m), 7.05–7.25 (7H, m), 7.57 (2H, m), 8.10 (1H, s), 8.17 (1H, t, J=8 Hz), 8.54 (1H, s)

(19) MASS (m/z): 504 (M+H)⁺; NMR (CDCl₃, δ): 2.38–2.62 (1H, m), 2.69–2.86 (1H, m), 2.72 (¾×3H, s), 2.90 (¼×3H, s), 2.94–3.22 (2H, m), 3.35–3.78 (9H, m), 4.53 (¼×2H, ABq, Δ=0.10, J=17 Hz), 4.54 (¾×1H, d, J=15 Hz), 4.80 (¾×1H, d, J=15 Hz), 5.10–5.29 (1H, m), 7.06–7.30 (5H, m), 7.50–8.22 (6H, m), 8.64 (¼×1H, d, J=2 Hz), 8.76 (¾×1H, d, J=2 Hz)

(20) MASS (m/z): 504 (M+H)⁺; NMR (CDCl₃, δ): 2.36–2.61 (1H, m), 2.70–2.86 (1H, m), 2.72 (⅔×3H, s), 2.91 (⅓×3H, s), 2.92–3.20 (2H, m), 3.33–3.80 (9H, m), 4.51 (⅔×1H, d, J=15 Hz), 4.54 (⅓×2H, s), 4.85 (⅔×1H, d, J=15 Hz), 5.13–5.28 (1H, m), 7.10–7.60 (8H, m), 7.98–8.25 (3H, m), 8.90 (1H, d, J=2 Hz)

(21) MASS (m/z): 511. (M+H)⁺; NMR (CDCl₃, δ): 2.21 (3H, s), 2.40–2.61 (1H, m), 2.66 (¾×3H, s), 2.70–2.86 (1H, m), 2.78 (¼×3H, s), 2.92–3.20 (2H, m), 3.34–3.78 (9H, m), 4.24 (¼×2H, ABq, Δ=0.16, J=17 Hz), 4.28 (¾×1H, d, J=15 Hz), 4.59 (¾×1H, d, J=15 Hz), 5.05–5.22 (1H, m), 7.10–7.45 (6H, m), 7.91–8.24 (4H, m)

(22) NMR (CDCl₃, δ): 1.80–2.00 (2H, m), 2.22–2.32 (1H, m), 2.30 (3H, s), 2.33–2.42 (4H, m), 2.63 (3×⅔H, s), 2.90 (3×⅓H, s), 2.92–3.12 (2H, m), 3.27–3.40 (1H, m), 3.36–3.47 (2H, m), 3.53–3.70 (2H, m), 4.32–4.43 (3×⅔H, m), 4.70 (3×⅓H, d, J=15 Hz), 5.19 (1H, q, J=8 Hz), 7.01–7.12 (2H, m), 7.20–7.32 (8H, m), 7.93 (1×⅓H, d, J=8 Hz), 8.00 (1×⅔H, d, J=8 Hz)

(23) NMR (CDCl₃, δ): 2.53–3.03 (4H, m), 3.46 (2H, m), 3.66 (6H, m), 3.79–3.89 (1H, m), 4.61–4.71 (1H, m), 4.93 (1H, d, J=16 Hz), 5.42 (1H, d, J=16 Hz), 6.92 (1H, d, J=8 Hz), 7.01 (1H, t, J=8 Hz), 7.14 (1H, t, J=8 Hz), 7.20–7.32 (6H, m), 8.45 (1H, t, J=7 Hz)

(24) MASS (m/z): 459 (M+1)⁺; NMR (CDCl₃, δ): 2.40–2.63 (1H, m), 2.73–2.94 (1H, m), 2.84 (3H×⅔, s), 2.92 (3H×⅓, s), 3.11–3.50 (5H, m), 3.51–3.79 (7H, m), 4.39 (1H×⅔, d, J=14.5 Hz), 4.50 (1H×⅔, s), 4.70 (1H×⅔, d, J=14.5 Hz), 5.10–5.23 (1H, m), 6.79–6.96 (2H, m), 7.01–7.20 (3H, m), 7.22–7.35 (4H, m), 8.12 (1H×⅓, br d, J=7.5 Hz), 8.21 (1H×⅔, br d, J=7.5 Hz)

(25) MASS (m/z): 533 (M+H)⁺; NMR (CDCl₃, δ): 2.28–2.55 (1H, m), 2.67 (⅔×3H, s), 2.69–2.85 (1H, m), 2.87 (⅓×3H, s), 2.92–3.16 (2H, m), 3.33–3.79 (9H, m), 3.94 (3H, s), 4.32 (⅔×1H, d, J=15 Hz), 4.36 (⅓×2H, ABq, Δ=0.08, J=17 Hz), 4.71 (⅔×1H, d, J=15 Hz), 5.10–5.25 (1H, m), 6.50 (⅓×1H, d, J=2 Hz), 6.52 (⅔×1H, d, J=2 Hz), 6.95–7.42 (8H, m), 7.65–7.75 (2H, m), 8.02–8.21 (1H, m)

(26) MASS (m/z): 497 (M+H)⁺; NMR (CDCl₃, δ): 2.33–2.52 (1H, m), 2.61 (⅔×3H, s), 2.71–2.86 (1H, m), 2.76 (⅓×3H, s), 2.91–3.15 (2H, m), 3.05 (⅓×6H, s), 3.07 (⅔×6H, s), 3.35–3.76 (9H, m), 3.95 (⅓×1H, d, J=17 Hz), 4.28 (⅓×1H, d, J=17 Hz), 4.34 (⅔×2H, ABq, Δ=0.22, J=15 Hz), 5.03–5.33 (1H, m), 6.41 (⅓×1H, d, J=9 Hz), 6.46 (⅔×1H, d, J=9 Hz), 7.02–7.33 (6H, m), 7.88 (⅓×1H, d, J=2 Hz), 7.97 (⅔×1H, d, J=2 Hz), 8.06–8.19 (1H, m)

(27) MASS (m/z): 519 (M+H)⁺; NMR (CDCl₃, δ): 2.40–2.62 (1H, m), 2.70–2.85 (1H, m), 2.72 (¾×3H, s), 2.85 (¼×3H, s), 2.92–3.22 (2H, m), 3.35–3.79 (9H, m), 4.37 (¼×2H, s), 4.53 (¾×2H, ABq, Δ=0.22, J=15 Hz), 5.08–5.25 (1H, m), 6.98–7.33 (1H, m), 7.82 (1H, s), 8.10–8.22 (1H, m)

(28) MASS (m/z): 521 (M+H)⁺; NMR (CDCl₃, δ): 2.26–2.52 (1H, m), 2.59 (3H, s), 2.66 (⅗×3H, s), 2.68–2.82 (1H, m), 2.83 (⅖×3H, s), 2.92–3.16 (2H, m), 3.35–3.80 (9H, m), 3.70 (⅖×3H, s), 3.72 (⅗×3H, s), 4.23 (⅖×1H, d, J=17 Hz), 4.56 (⅖×1H, d, J=17 Hz), 4.61 (⅗×2H, ABq, Δ=0.07, J=15 Hz), 5.06–5.25 (1H, m), 6.86–7.50 (8H, m), 8.05–8.22 (1H, m)

(29) MASS (m/z): 443 (M+H)⁺; NMR (CDCl₃, δ): 2.43–2.67 (1H, m), 2.71–3.03 (3H, m), 2.90 (⅔×3H, s), 2.92 (⅓×3H, s), 3.33–3.78 (9H, m), 4.38 (⅔×1H, d, J=15 Hz), 4.54 (⅓×2H, ABq, Δ=0.08, J=17 Hz), 4.72 (⅔×1H, d, J=15 Hz), 5.02–5.16 (1H, m), 6.22 (⅓×1H, s), 6.29 (⅔×1H, s), 7.03–7.39 (7H, m), 8.02–8.23 (1H, m)

(30) MASS (m/z): 457 (M+H)⁺; NMR (CDCl₃, δ): 2.38–2.57 (1H, m), 2.69 (⅔×3H, s), 2.71–2.87 (1H, m), 2.84 (⅓×3H, s), 2.90–3.20 (2H, m), 3.36–3.75 (9H, m), 3.80 (⅓×3H, s), 3.87 (⅔×3H, s), 4.15 (⅔×1H, d, J=15 Hz), 4.15 (⅓×2H, ABq, Δ=0.07, J=17 Hz), 4.45 (⅔×1H, d, J=15 Hz), 5.02–5.29 (1H, m), 6.98–7.35 (7H, m), 8.04–8.20 (1H, m)

(31) MASS (m/z): 487 (M+H)⁺; NMR (CDCl₃, δ): 2.25–2.58 (1H, m), 2.58–2.80 (1H, m), 2.77 (⅔×3H, s), 2.82–3.14 (2H, m), 2.91 (⅓×3H, s), 3.30–3.80 (9H, m), 4.30 (⅔×1H, d, J=15 Hz), 4.49 (⅓×2H, ABq, Δ=0.15, J=17 Hz), 4.72 (⅔×1H, d, J=15 Hz), 5.05–5.23 (1H, m), 6.90–7.40 (9H, m), 8.04 (⅓×1H, d, J=9 Hz), 8.15 (⅔×1H, d, J=9 Hz)

(32) MASS (m/z): 443 (M+H)⁺; NMR (CDCl₃, δ): 2.41–2.64 (1H, m), 2.73–2.96 (1H, m), 2.83 (⅔×3H, s), 2.90 (⅓×3H, s), 2.96–3.20 (2H, m), 3.38–3.81 (9H, m), 4.33 (⅔×1H, d, J=15 Hz), 4.50 (⅓×2H, ABq, Δ=0.07, J=17 Hz), 4.79 (⅔×1H, d, J=15 Hz), 5.15–5.31 (1H, m), 6.10 (1H, m), 6.21–6.31 (1H, m), 7.07–7.40 (6H, m), 8.11 (⅓×1H, d, J=8 Hz), 8.19 (⅔×1H, d, J=8 Hz)

(33) MASS: 505 (M+1); NMR (CDCl₃, δ): 2.38–2.60 (1H, m), 2.78 (3×⅔H, s), 2.79 (1H, t, J=16 Hz), 2.91 (3×⅓H, s), 2.98–3.19 (2H, m), 3.38–3.49 (2H, m), 3.52–3.70 (6H, m), 3.71–3.80 (1H, m), 4.51 (2×⅙H, d, J=16 Hz), 4.60 (2×⅙H, d, J=16 Hz), 4.65 (2×⅓H, d, J=15 Hz), 4.81 (2×⅓H, d, J=15 Hz), 5.13–5.28 (1H, m), 7.13–7.29 (5H, m), 7.31 (1×⅓H, d, J=8 Hz), 7.43 (1×⅔H, d, J=8 Hz), 7.78 (1×⅓H, s), 7.83 (1×⅔H, s), 7.99–8.03 (1H, m), 8.14 (1×⅓H, d, J=8 Hz), 8.19 (1×⅔H, d, J=8 Hz), 8.82 (2H, s)

(34) MASS: 503 (M+1); NMR (CDCl₃, δ): 2.12 (3×⅔H, s), 2.19–2.30 (1×⅓H, s), 2.41–2.51 (1×⅔H, s), 2.68–2.89 (1H, m), 2.79 (3×⅓H, s), 3.30–3.48 (3H, m), 3.52–3.79 (8H, m), 4.03 (2×⅙H, d, J=16 Hz), 4.27 (2×⅙H, d, J=16 Hz), 4.28 (2×⅓H, d, J=15 Hz), 4.49 (2×⅓H, d, J=15 Hz), 5.29–5.41 (1H, m), 6.77–6.83 (2×⅓H, m), 6.93–7.02 (2×⅔H, m), 7.13–7.31 (5H, m), 7.32–7.60 (3H, m), 7.69–7.87 (2H, m), 8.30–8.39 (1H, m)

(35) MASS: 454 (M+1); NMR (CDCl₃, δ): 2.33–2.60 (1H, m), 2.62–2.79 (1H, m), 2.80 (3×⅔H, s), 2.92 (3×⅓H, s), 2.88–3.19 (2H, m), 3.33–3.48 (2H, m), 3.49–3.72 (7H, m), 4.40 (2×⅓H, d, J=15 Hz), 4.45 (2×⅙H, d, J=16 Hz), 4.53 (2×⅙H, d, J=16 Hz), 4.63 (2×⅓H, d, J=15 Hz), 5.08–5.22 (1H, m), 6.98–7.20 (3H, m), 7.22–7.37 (3H, m), 7.43 (1×⅓H, d, J=8 Hz), 7.51 (1×⅔H, d, J=8 Hz), 8.11 (1×⅓H, d, J=8 Hz), 8.22 (1×⅓H, d, J=8 Hz), 8.36 (1×⅓H, s), 8.45 (1×⅔H, s), 8.45 (1H, s)

(36) MASS: 484 (M+1); NMR (CDCl₃, δ): 2.43–2.70 (1H, m), 2.61 (3×¾H, s), 2.73–2.88 (1H, m), 2.79 (3×¼H, s), 2.93–3.18 (2H, m), 3.40–3.49 (2H, m), 3.51–3.70 (6H, m), 3.71–3.80 (1H, m), 3.91 (3H, s), 4.10 (2×⅙H, d, J=16 Hz), 4.23 (2×⅓H, d, J=15 Hz), 4.30 (2×⅙H, d, J=16 Hz), 4.53 (2×⅓H, d, J=15 Hz), 5.03–5.23 (1H, m), 6.59–6.70 (1H, m), 7.07–7.33 (6H, m), 7.83 (1×¼H, s), 7.93 (1×¾H, s), 8.10–8.22 (1H, m)

(37) MASS: 419 (M+1); NMR (CDCl₃, δ): 0.79–1.00 (3H, m), 1.15–1.48 (4H, m), 1.55–1.90 (2H, m), 2.58–2.72

(1H, m), 2.80–2.90 (1H, m), 2.92 (3×⅓H, s), 2.97 (3×⅔H, s), 3.40–3.50 (2H, m), 3.51–3.70 (6H, m), 3.71–3.79 (1H, m), 4.43 (2×⅓H, d, J=15 Hz), 4.60 (2×⅙H, d, J=16 Hz), 4.68 (2×⅙H, d, J=16 Hz), 4.75 (2×⅓H, d, J=15 Hz), 4.86–4.99 (1H, m), 7.17–7.40 (5H, m), 8.07 (1×⅓H, d, J=8 Hz), 8.12 (1×⅔H, d, J=8 Hz)

Preparation 67

Starting Compound (1.14 g) was dissolved in 30% methylamine in methanol (7 ml) and heated at 50° C. for 1 hour. After the mixture was allowed to cool to room temperature, the solvent was evaporated then suspended in ethanol (15 ml). Sodium borohydride (277 mg) was added to the suspension with ice-cooling, and the mixture was stirred at 0° C. for 1 hour. After the solvent was evaporated, the residue was diluted with water, extracted three times with chloroform, and dried over magnesium sulfate. Evaporation of the solvent followed by column chromatography (silica gel, chloroform/methanol=5/1) gave Object Compound (708 mg) as a colorless oil.

MASS (m/z): 173 (M+H)$^+$; NMR (CDCl$_3$, δ): 2.51 (3H, s), 3.96 (2H, s), 7.48–7.85 (3H, m), 8.05–8.14 (2H, m), 8.89 (1H, d, J=2 Hz)

Preparation 68

Starting Compound (1.30 g) was dissolved in 30% methylamine in methanol (8 ml) and heated at 60° C. for 1 hour. After the mixture was allowed to cool to room temperature, the solvent was evaporated then suspended in ethanol (20 ml). The suspension was cooled in ice and added sodium borohydride (305 mg). The mixture was stirred at the temperature for 1 hour and the solvent was evaporated. The residue was diluted with water, and extracted three times with chloroform. The organic layer was washed with brine and dried over potassium carbonate. Evaporation of the solvent followed by column chromatography (silica gel, chloroform/methanol=5/1) gave Object Compound (923 mg) as a light yellow oil.

MASS (m/z): 180 (M+H)$^+$; NMR (CDCl$_3$, δ): 2.18 (3H, s), 2.43 (3H, s), 3.70 (2H, s), 7.67 (1H, dd, J=9, 2 Hz), 8.15 (1H, d, J=9 Hz), 8.20 (1H, d, J=2 Hz), 8.31 (1H, br s)

Preparation 69

The following object compounds were obtained according to a similar manner to that of Preparation 22, 23, 25, 67 or 68.

(1) MASS (m/z): 2 20 (M$^+$+1); NMR (CDCl$_3$, δ): 2.35 (3H, s), 2.44 (3H, s), 2.57 (4H, t, J=5 Hz), 3.19 (4H, t, J=5 Hz), 3.65 (2H, s), 6.89 (2H, d, J=8 Hz), 7.21 (2H, d, J=8 Hz)

(2) MASS (m/z): 173 (M+H)$^+$; NMR (CDCl$_3$, δ): 2.51 (3H, s), 3.96 (2H, s), 7.40 (1H, dd, J=9, 5 Hz), 7.70 (1H, d, J=9 Hz), 7.77 (1H, s), 8.08 (1H, d, J=9 Hz), 8.13 (1H, d, J=9 Hz), 8.89 (1H, d, J=5 Hz)

(3) Mass: 200 (M+1); NMR (CDCl$_3$, δ): 2.45 (3H, s), 3.81 (2H, s), 7.28–7.32 (1H, m), 7.80 (2H, t, J=7 Hz), 8.36 (1H, d, J=7 Hz), 8.38 (1H, d, J=7 Hz), 8.61 (1H, s), 8.67 (1H, d, J=5 Hz)

(4) MASS: 200 (M+1); NMR (CDCl$_3$, δ): 2.49 (3H, s), 3.80 (2H, s), 7.39 (1H, dd, J=8, 5 Hz), 7.63 (1H, d, J=8 Hz), 7.80 (1H, dd, J=8, 2 Hz), 8.31 (1H, dd, J=8, 2 Hz), 8.63–8.68 (2H, m), 9.20 (1H, s)

(5) MASS: 125 (M+2); NMR (CDCl$_3$, δ): 2.50 (3H, s), 3.90 (2H, s), 8.51 (2H, d, J=16 Hz), 8.62 (1H, s)

(6) MASS: 173 (M+1); NMR (CDCl$_3$, δ): 2.52 (3H, s), 4.00 (2H, s), 7.38 (1H, dd, J=8, 3 Hz), 7.58 (1H, d, J=8 Hz), 7.80 (1H, d, J=8 Hz), 7.99 (1H, s), 8.13 (1H, d, J=8 Hz), 8.90 (1H, d, J=5 Hz)

(7) MASS: 173 (M+1); NMR (CDCl$_3$, δ): 2.52 (3H, s), 4.07 (2H, s), 7.46 (1H, d, J=8 Hz), 7.51 (1H, t, J=8 Hz), 7.70 (1H, t, J=8 Hz), 7.80 (1H, d, J=8 Hz), 8.07 (1H, d, J=8 Hz), 8.12 (1H, d, J=8 Hz)

(8) MASS: 174 (M+1); NMR (CDCl$_3$, δ): 2.58 (3H, s), 4.12 (2H, s), 7.70–7.80 (2H, m), 8.03–8.12 (2H, m), 8.90 (1H, s)

(9) MASS: 125 (M+1); NMR (CDCl$_3$, δ): 2.49 (3H, s), 3.89 (2H, s), 7.37 (1H, d, J=7 Hz), 8.67 (1H, d, J=7 Hz), 9.17 (1H, s)

(10) MASS: 173 (M+1); NMR (CDCl$_3$, δ): 2.48 (3H, s), 4.00 (2H, s), 7.80 (1H, d, J=8 Hz), 8.02 (1H, s), 8.09 (1H, d, J=8 Hz), 8.80–8.87 (2H, m)

(11) MASS (m/z): 126 (M+H)$^+$; NMR (CDCl$_3$, δ): 2.45 (3H, s), 3.61 (2H, s), 3.87 (3H, s), 7.29 (1H, s), 7.41 (1H, s)

(12) mp: 102–103° C.; MASS (m/z): 159 (M–30)$^+$, 190 (M+H)$^+$; NMR (CDCl$_3$, δ): 2.45 (3H, s), 2.58 (3H, s), 3.70 (3H, s), 3.85 (2H, s), 7.22 (2H, s), 7.58 (1H, s)

(13) MASS (m/z): 188 (M+H)$^+$; NMR (CDCl$_3$, δ): 2.48 (3H, s), 3.79 (2H, s), 7.19 (1H, s), 7.27 (1H, s), 7.35 (2H, d, J=8 Hz), 7.42 (2H, d, J=8 Hz), 7.83 (1H, s)

(14) MASS (m/z): 166 (M+H)$^+$; NMR (CDCl$_3$, δ): 2.42 (3H, s), 3.07 (6H, s), 3.61 (2H, s), 6.51 (1H, d, J=9 Hz), 7.46 (1H, dd, J=9, 2 Hz), 8.07 (1H, d, J=2 Hz)

(15) MASS (m/z): 202 (M+H)$^+$; NMR (CDCl$_3$, δ): 2.45 (3H, s), 3.78 (2H, s), 3.93 (3H, s), 6.52 (1H, d, J=2 Hz), 7.34 (2H, d, J=8 Hz), 7.37 (1H, d, J=2 Hz), 7.74 (2H, d, J=8 Hz)

Preparation 70

A slurry of Starting Compound (6.45 g), selenium dioxide (7.48 g), and water (1.2 ml) in 285 ml of dioxane was refluxed for 6 days. The mixture was filtered while still warm, and the filtrate was evaporated. The residue was purified using silica gel column chromatography (eluent: hexane/ethyl acetate (2:1)) yielding Object Compound (380 mg).

MASS: 158 (M+1); NMR (CDCl$_3$, δ): 7.52–7.67 (1H, m), 7.93 (1H, d, J=8 Hz), 8.07 (1H, d, J=8 Hz), 8.23 (1H, d, J=8 Hz), 8.53 (1H, s), 9.03 (1H, d, J=5 Hz), 10.25 (1H, s)

Preparation 71

The following object compounds were obtained according to a similar manner to that of Preparation 70.

(1) mp: 65–68° C.; NMR (CDCl$_3$, δ): 7.68 (1H, t, J=8 Hz), 7.82 (1H, t, J=8 Hz), 7.90 (1H, d, J=8 Hz), 8.02 (1H, d, J=8 Hz), 8.27 (1H, d, J=8 Hz), 8.31 (1H, d, J=8 Hz), 10.22 (1H, s)

(2) mp: 108–109° C.; MASS: 159 (M+1); NMR (CDCl$_3$, δ): 7.87–7.99 (2H, m), 8.18–8.29 (2H, m), 9.40 (1H, s), 10.29 (1H, s)

(3) NMR (CDCl$_3$, δ): 7.85 (1H, d, J=8 Hz), 9.04 (1H, d, J=8 Hz), 9.47 (1H, s)

(4) mp: 137–139° C.; MASS: 159 (M+1); NMR (CDCl$_3$, δ): 8.23 (1H, d, J=8 Hz), 8.29 (1H, d, J=8 Hz), 8.60 (1H, s), 8.97 (2H, s), 10.27 (1H, s)

Preparation 72

To a solution of-dimethylsulfoxide (0.86 ml) in dichloromethane (20 ml) was added oxalyl chloride (0.53 ml) at −78° C. After the solution was stirred at −78° C. for 10 minutes, Starting Compound (900 mg) in dichloromethane (10 ml) was added thereto. The solution was stirred at −78° C. for 15 minutes, and triethyl amine (3.7 ml) was added thereto. The solution was allowed to ambient temperature and stirred for 1 hour. Water was added thereto and the aqueous layer was extracted with chloroform. The organic layer was dried over magnesium sulfate and concentrated. The residue was purified by chromatography on silica gel [chloroform-methanol (30:1)] to give Object Compound (720 mg) as a solid.

mp: 85–88° C.; MASS: 185 (M+1); NMR (CDCl$_3$, δ): 7.37–7.42 (1H, m), 7.82–7.90 (1H, m), 8.29 (1H, d, J=8 Hz), 8.51 (1H, d, J=8 Hz), 8.62 (1H, d, J=8 Hz), 8.72 (1H, d, J=5 Hz), 9.11 (1H, s), 10.11 (1H, s)

Preparation 73

The following object compounds were obtained according to a similar manner to that of Preparation 72.

(1) NMR (CDCl$_3$, δ): 8.70 (2H, dd, J=12, 3 Hz), 9.19 (1H, s), 10.21 (1H, s)

(2) mp: 66–72° C.; MASS: 185 (M+1); NMR (CDCl$_3$, δ): 7.48 (1H, dd, J=8, 5 Hz), 7.95 (1H, d, J=8 Hz), 8.29 (1H, dd, J=8, 5 Hz), 8.42 (1H, dd, J=8, 2 Hz), 8.72 (1H, d, J=5 Hz), 9.17 (1H, d, J=2 Hz), 9.30 (1H, d, J=2 Hz), 10.20 (1H, s)

Preparation 74

To a solution of Starting Compound (1.15 g) in anhydrous tetrahydrofuran (20 ml) at −78° C. was added 5.04 ml of a 1M solution of lithium aluminium hydride in tetrahydrofuran. The reaction mixture was allowed to warm to the temperature (−20° C.) which the solution became completely homogeneous. The reaction mixture was stirred at this temperature for 30 minutes and then cooled back down to −78° C. and quenched slowly with 15 ml of 10% aqueous tetrahydrofuran. After being warmed to ambient temperature, the reaction mixture was stirred with dry Celite for 15 minutes and then filtered. The solution was then concentrated under reduced pressure. The residue was purified by chromatography on silica gel [chloroform-methanol (10:1)] to give Object Compound (900 mg) as an oil.

MASS: 187 (M+1); NMR (CDCl$_3$, δ): 3.07 (1H, br s), 4.74 (2H, s), 7.29–7.32 (1H, m), 7.78–7.85 (2H, m), 8.31 (2H, t, J=8 Hz), 8.57 (1H, s), 8.66 (1H, d, J=6 Hz)

Preparation 75

The following object compounds were obtained according to a similar manner to that of Preparation 74.

(1) mp: 92–95° C.; MASS: 187 (M+1); NMR (CDCl$_3$, δ): 2.57 (1H, br s), 4.80 (2H, s), 7.40 (1H, dd, J=12, 5 Hz), 7.70 (1H, dd, J=8 Hz), 7.81 (1H, dd, J=8, 2 Hz), 8.29 (1H, dd, J=8, 2 Hz), 8.60 (1H, d, J=5 Hz), 8.67 (1H, s), 9.02 (1H, s)

(2) MASS: 112 (M+2); NMR (CDCl$_3$, δ): 3.32 (1H, t, J=7 Hz), 4.87 (2H, d, J=7 Hz), 8.50–8.52 (2H, m), 8.62 (1H, s)

Preparation 76

To a mixture of Starting Compound (434 mg) and N,O-dimethylhydroxylaminehydrochloride (246 mg) in dichloromethane-N,N-dimethylformamide (1:1, 5 ml) was added 1-ethyl-3-(3-dimethylaminopropyl) carbodiimidehydrochloride (534 mg) at room temperature. The reaction mixture was stirred at room temperature for 12 hours. The solution was diluted with ethyl acetate, washed twice with saturated sodium bicarbonate, once with brine, and dried over magnesium sulfate. Purification by flash chromatography (silica gel, hexane/ethyl acetate 1/3) gave Object Compound (303 mg, 55.8%) as an oil.

MASS (m/z): 217 (M+H)$^+$; NMR (CDCl$_3$, δ): 3.42 (3H, s), 3.56 (3H, s), 7.46 (1H, dd, J=9, 5 Hz), 8.06 (2H, ABq, Δ=0.12, J=9 Hz), 8.21 (1H, s), 8.22 (1H, dd, J=9, 2 Hz), 8.98 (1H, dd, J=5, 2 Hz)

Preparation 77

To an ice-cooled solution of Starting Compound (543 mg) in dry ether (6.3 ml) was added lithium aluminum hydride (96 mg) and stirred at 0° C. for 1 hour. After the reaction mixture was diluted with ether, 10% citric acid (0.3 ml) was added dropwise with vigorous stirring. The precipitate was filtered off, and the residue was purified by column chromatography (silica gel, hexane/ethyl acetate=1/1) to give the product (268 mg) as white crystals.

mp: 70–71° C.; MASS (m/z): 158 (M+H)$^+$; NMR (CDCl$_3$, δ): 7.52 (1H, dd, J=9, 3 Hz), 8.21 (2H, ABq, Δ=0.04, J=9 Hz), 8.33 (1H, d, J=9 Hz), 8.36 (1H, s), 9.05 (1H, d, J=3 Hz), 10.21 (1H, s)

Preparation 78

A mixture of Starting Compound (3.0 g), 1-methylpiperazine (2.7 g) and potassium carbonate (4.0 g) in N,N-dimethylformamide (5 ml) was stirred at 120° C. for 2 hours. After cooling potassium carbonate was removed by filtration. Evaporation of N,N-dimethylformamide in vacuo gave a residue which was taken up in chloroform and water. The organic solution was washed with water, and dried. Evaporation of solvent gave a residue which was chromatographed on silica gel. Elution with methanol-chloroform (1:50) afforded Object Compound (2.63 g)

MASS (m/z): 205 (M$^+$+1); NMR (CDCl$_3$, δ): 2.36 (3H, s), 2.55 (4H, t, J=5 Hz), 3.41 (4H, t, J=5 Hz), 6.92 (2H, d, J=8 Hz), 7.75 (2H, d, J=8 Hz), 9.78 (1H, s)

Preparation 79

The following object compounds were obtained according to a similar manner to that of Preparation 29.

(1) MASS: 236 (M+1); NMR (CDCl$_3$, δ): 1.48 (9H, s), 2.26 (3H, s), 2.79 (3H, s), 4.43 (2H, s), 7.09–7.19 (4H, m)

(2) MASS: 336 (M+1); NMR (CDCl$_3$, δ): 1.47 (9H, s), 2.33 (3H, s), 2.80 (3H, br s), 4.38 (2H, s), 6.97–7.08 (3H, m), 7.22 (1H, dd, J=15, 8 Hz)

Preparation 80

The following object compounds were obtained according to a similar manner to that of Preparation 3, 4, 8 or 41.

(1) MASS: 136 (M+1); NMR (CDCl$_3$, δ): 2.37 (3H, s), 2.51 (3H, s), 2.71 (2H, s), 7.13–7.18 (3H, m), 7.23–7.30 (1H, m)

(2) MASS: 136 (M+1); NMR (CDCl$_3$, δ): 2.35 (3H, s), 2.43 (3H, s), 3.70 (2H, s), 7.06–7.27 (4H, m)

Preparation 81

The following object compound was obtained accordidng to a similar manner to that of Preparation 6.

MASS: 351 (M+1); NMR (CDCl$_3$, δ): 1.42 (9H, s), 2.87 (1H, dd, J=17, 5 Hz), 2.91 (3H, s), 2.97 (3H, s), 3.17 (1H, dd, J=16, 5 Hz), 4.58–4.63 (1H, m), 5.13 (2×½H, d, J=12 Hz), 5.21 (2×½H, d, J=12 Hz), 5.88 (1H, d, J=8 Hz), 7.29–7.37 (5H, s)

Preparation 82

The following object compound was obtained according to a similar manner to that of Preparation 10.

MASS: 261 (M+1); NMR (CDCl$_3$, δ): 1.38 (9H, s), 2.67–2.77 (1H, m), 3.00 (3H, s), 3.05 (3H, s), 3.21 (1H, d, J=15 Hz), 4.51 (1H, t, J=8 Hz), 5.88 (1H, br s)

Preparation 83

The following object compound was obtained according to a similar manner to that of Preparation 10.

NMR (CDCl$_3$, δ): 1.42 (9H, s), 1.82–1.98 (1H, m), 2.00–2.18 (1H, m), 2.38–2.60 (2H, m), 2.70 (3×⅔H, s), 2.83 (3×⅓H, s), 3.00–3.15 (2H, m), 4.28–5.20 (3H, m), 5.21–5.30 (1H, m), 5.50–5.60 (1H, m), 6.90–7.00 (2H, m), 7.09–7.30 (8H, m), 8.18–8.30 (1H, m)

Preparation 84

The following object compound was obtained according to a similar manner to that of Preparation 1.

NMR (CDCl$_3$, δ): 1.47 (9H, s), 1.90–2.00 (1H, m), 2.00–2.20 (1H, m), 2.31 (3H, s), 2.32–2.53 (6H, m), 2.63 (3×⅔H, s), 2.82 (3×⅓H, s), 2.98–3.10 (2H, m), 3.40–3.48 (2H, m), 3.60–3.70 (2H, m), 4.07–4.18 (1H, m), 4.20 (2×¼H, d, J=16 Hz), 4.32 (2×¼H, d, J=16 Hz), 4.35 (2×¼H, d, J=15 Hz), 4.61 (2×¼H, d, J=15 Hz), 5.11 (1H, q, J=8 Hz), 5.58–5.66 (1H, m), 6.98 (2×⅓H, d, J=8 Hz), 7.08 (2×⅔H, d, J=8 Hz), 7.12–7.31 (8H, m), 7.45–7.55 (1H, m)

Preparation 85

The following object compound was obtained according to similar manners to those of Preparations 10 and 6.

MASS (m/z): 567 (M+H)$^+$; NMR (CDCl$_3$, δ): 1.45 (9H, s), 1.8–2.2 (2H, m), 2.3–2.6 (2H, m), 2.63 (⅔×3H, s), 2.84 (⅓×3H, s), 3.0–3.1 (2H, m), 3.4–3.5 (2H, m), 3.6–3.7 (6H, m), 4.1–4.2 (1H, m), 4.28 (⅓×2H, ABq, Δ=0.20, J=15 Hz), 4.50 (⅔×2H, ABq, Δ=0.22, J=15 Hz), 5.1–5.2 (1H, m), 5.5–5.6 (1H, m), 7.0–7.6 (11H, m)

Preparation 86

To a stirred suspension of sodium hydride (0.31 g, 60%) in N,N-dimethylformamide (10 ml) was added a solution of Starting Compound (0.7 g) in dimethylformamide (2 ml) at 0° C. The mixture was stirred at room temperature for 1 hour. To this mixture was added dropwise benzylbromide (0.63 g) at 0° C. The mixture was stirred at room temperature for 1 hour. The reaction mixture was poured into water and extracted with ethyl acetate. The organic layer was washed with water and dried. Evaporation of solvent gave a residue which was chromatographed on silica gel. Elution with a mixture of methanol-chloroform (1:100) provided Object Compound (0.56 g).

MASS (m/z): 253 (M$^+$+1); NMR (CDCl$_3$, δ): 2.94 (1H, t, J=15 Hz), 3.15 (1H, dd, J=5, 15 Hz), 3.72 (1H, dd, J=5, 15 Hz), 4.97 (1H, d, J=16 Hz), 5.40 (1H, d, J=16 Hz), 6.88 (1H, d, J=8 Hz), 6.99 (1H, t, J=8 Hz), 7.13 (1H, t, J=8 Hz), 7.20–7.33 (6H, m)

Preparation 87

A mixture of Starting Compuond (4.85 g) and N,N-dimethylformamide dimethyl acetal (17 ml) in benzene (12.5 ml) was distilled. The distillation was continued by occasional addition of benzene until most of the starting material was consumed. Then water was added thereto, the mixture was extracted three times with ether, washed with brine, and dried over magnesium sulfate. The product was purified by column chromatography (silica gel, chloroform/methanol=30/1) followed by recrystallization from toluene to give Object Compound (4.48 g) of yellow crystals.

mp: 99–100° C.; MASS (m/z): 248 (M+H)$^+$; NMR (CDCl$_3$, δ): 1.40 (3H, t, J=7 Hz), 2.95 (3H, br s), 3.18 (3H, br s), 4.40 (2H, q, J=7 Hz), 6.22 (1H, d, J=13 Hz), 7.83 (1H, d, J=13 Hz), 7.92 (2H, d, J=7 Hz), 8.05 (2H, d, J=7 Hz)

Preparation 88

Starting compound (2.47 g) was dissolved in acetic acid (10 ml) and methylhydrazine (519 mg) was added dropwise at room temperature. The reaction mixture was stirred at the temperature for 1 hour. The mixture was neutralized with 15% sodium hydroxide with ice-cooling, extracted three times with ethyl acetate, washed with brine, and dried over magnesium sulfate. The crude product was the 57:43 isomeric mixture of Object Compound A and Object Compound B determined by NMR. The two isomers were separated by column chromatography (silica gel, chloroform), and the first eluate was Object Compound A as white crystals (1.11 g) and the second was Object Compound B as an oil (646 mg).

Object Compound A mp: 79–80° C.; MASS (m/z): 231 (M+H)$^+$; NMR (CDCl$_3$, δ): 1.41 (3H, t, J=7 Hz), 3.97 (3H, s), 4.38 (2H, q, J=7 Hz), 6.60 (1H, d, J=2 Hz), 7.40 (1H, d, J=2 Hz), 7.85 (2H, d, J=7 Hz), 8.06 (2H, d, J=7 Hz)

Object Compound B

MASS (m/z): 231(M+H)$^+$; NMR (CDCl$_3$, δ): 1.41 (3H, t, J=7 Hz), 3.91 (3H, s), 4.41 (2H, q, J=7 Hz), 6.37 (1H, d, J=1 Hz), 7.49 (2H, d, J=7 Hz), 7.52 (1H, d, J=1 Hz), 8.12 (2H, d, J=7 Hz)

Preparation 89

To an ice-cooled suspension of lithium aluminum hydride (183 mg) in tetrahydrofuran (12 ml) was added Starting Compound (1.08 g) in tetrahydrofuran (12 ml). After the mixture was stirred at 0° C. for 1 hour, sodium fluoride (790 mg) and water (0.25 ml) were successively added thereto and the whole was stirred at room temperature for 1 hour. The precipitate formed was filtered off, and the resulting solution was evaporated to give Object Compound (876 mg) as white crystals.

mp: 92–93° C.; MASS (m/z): 189 (M+H)$^+$; NMR (CDCl$_3$, δ): 3.92 (3H, s), 4.69 (2H, d, J=5 Hz), 6.52 (1H, d, J=1 Hz), 7.36 (1H, d, J=1 Hz), 7.38 (2H, d, J=8 Hz), 7.77 (2H, d, J=8 Hz)

Preparation 90

To an acetone (45 ml) solution of Starting Compound (846 mg) was added activated manganese dioxide powder (7.82 g) and the mixture was refluxed for 1 hour. After the mixture was filtered, the Object Compound was isolated by column chromatography (silica gel, hexane/ethyl acetate=1/1) as white crystals (550 mg).

mp: 88–90° C.; MASS (m/z): 187 (M+H)$^+$; NMR (CDCl$_3$, δ): 3.97 (3H, s), 6.62 (1H, d, J=2 Hz), 7.41 (1H, d, J=2 Hz), 7.82–8.03 (4H, m), 10.01 (1H, s)

Preparation 91

To a methanol (20 ml) solution of Starting Compound (2.36 g) was added 50% aqueous dimethylamine solution (20 ml), and the mixture was refluxed for 12 hours. After the methanol was evaporated, sodium chloride was added thereto, and the mixture was extracted three times with ether. The organic layer was dried over magnesium sulfate. Evaporation of the solvent followed by column chromatography (silica gel, hexane/ethyl acetate=20/1) gave Object Compound (1.39 g) as white crystals.

mp: 40–41° C.; MASS (m/z): 201, 203 (M+H)⁺; NMR (CDCl₃, δ): 3.03 (6H, s), 6.39 (1H, d, J=9 Hz), 7.47 (1H, dd, J=9, 2 Hz), 8.14 (1H, d, J=2 Hz)

Preparation 92

To a stirred solution of Starting Compound (1.33 g) in tetrahydrofuran (16.5 ml) at −78° C. was added n-butyllithium (1.6M in hexane, 4.4 ml). After 2 hours, N,N-dimethylformamide (968 mg) was added thereto and the stirring was continued for 1 hour at −78° C. To the cold mixture was added saturated sodium- hydrogen carbonate solution (20 ml) and the mixture was extracted three times with ether. The organic layer was dried over magnesium sulfate. Evaporation of the solvent followed by column chromatography (hexane/ethyl acetate=2/1) gave Object Compound (777 mg) as white crystals.

mp: 44–45° C.; MASS (m/z): 151 (M+H)⁺; NMR (CDCl₃, δ): 3.20 (6H, s), 6.56 (1H, d, J=9 Hz), 7.91 (1H, dd, J=9, 2 Hz), 8.55 (1H, d, J=2 Hz), 9.76 (1H, s)

Preparation 93

A mixture of 4-fluorobenzonitrile (6.05 g), imidazole (4.09 g), and potassium carbonate (8.33 g) in N,N-dimethylformamide (50 ml) was heated at 120° C. for 2 hours. The mixture was cooled and evaporated. Then the mixture was diluted with water (50 ml), added 1N sodium hydroxide solution to make basic, and extracted three times with ethyl acetate. The organic layer was dried over magnesium sulfate. Evaporation of the solvent followed by column chromatography (silica gel, ethyl acetate) gave Object Compound (7.75 g) as white crystals.

mp: 151–152° C.; MASS (m/z): 170 (M+H)⁺; NMR (CDCl₃, δ): 7.26 (1H, s), 7.32 (1H, s), 7.53 (2H, d, J=8 Hz), 7.80 (2H, d, J=8 Hz), 7.93 (1H, s)

Preparation 94

To a stirred solution of Starting Compound (4.23 g) in dichloromethane (125 ml) at 70° C. was added dropwise diisobutyl aluminum hydride in toluene (1.5M, 41.5 ml) for 10 minutes. The stirring was continued at −70° C. for 1 hour. To this cold mixture were added water (50 ml) and saturated ammonium chloride (50 ml). The precipitate formed was filtered off, and the remaining solution was extracted three times with dichloromethane. The organic layer was dried over magnesium sulfate. Evaporation of the solvent followed by column chromatography (silica gel, chloroform/methanol=20/1) gave Object Compound (1.44 g) as white crystals.

mp: 147–148° C.; MASS: 173 (M+H)⁺; NMR (CDCl₃, δ): 7.27 (1H, s), 7.37 (1H, s), 7.58 (2H, d, J=8 Hz), 7.98 (1H, s), 8.03 (2H, d, J=8 Hz), 10.05 (1H, s)

Preparation 95

A mixture of Starting Compound (7.72 g), iodomethane (5.47 g), and potassium carbonate (6.34 g) in N,N-dimethylformamide (30 ml) was heated at 60° C. for 3 hours. The mixture was evaporated, then diluted with water, and extracted three times with ethyl acetate. The organic layer was dried over magnesium sulfate. Evaporation of the solvent followed by column chromatography (silica gel, hexane/ethyl acetate=3/2) gave Object Compound (8.14 g) as a yellow oil.

MASS (m/z): 267 (M+H)⁺; NMR (CDCl₃, δ): 1.42 (⅖× 3H, t, J=7 Hz), 1.44 (⅗×3H, t, J=7 Hz), 1.82 (⅗×3H, s), 2.25 (⅖×3H, s), 3.22 (⅗×3H, s), 3.46 (⅖×3H, s), 4.42 (⅖×2H, q, J=7 Hz), 4.44 (⅗×2H, q, J=7 Hz), 7.40 (⅖×1H, d, J=8 Hz), 7.48 (⅗×1H, d, J=8 Hz), 8.30 (⅖×1H, dd, J=8, 2 Hz), 8.34 (⅗×1H, dd, J=8, 2 Hz), 8.58 (⅖×1H, d, J=2 Hz), 8.62 (⅗×1H, d, J=2 Hz)

Preparation 96

A mixture of Starting Compound (8.09 g) and powdered iron (17.0 g) in acetic acid-ethanol (1:1, 183 ml) was slowly heated until the reaction was initiated (about 70° C.). The inner temperature rose to 89° C. After the reaction subsided, the mixture was refluxed for 1 hour and allowed to cool to room temperature. The mixture was carefully poured into the suspension of sodium carbonate (145 g) in water (600 ml). The precipitate formed was filtered, then the filtrate was made basic by adding 1N sodium hydroxide, extracted three times with ethyl acetate, washed once with brine, and dried over magnesium sulfate. Evaporation of the solvent gave crude product (5.74 g) as crystals. This was recrystallized from toluene (18 ml)—hexane (36 ml) to give Object Compound (5.55 g) of colorless crystals.

mp: 130–131° C.; MASS (m/z): 219 (M+H)⁺; NMR (CDCl₃, δ): 1.41 (3H, t, J=7 Hz), 2.60 (3H, s), 3.73 (3H, s), 4.29 (2H, q, J=7 Hz), 7.26 (1H, d, J=9 Hz), 7.98 (1H, d, J=9 Hz), 8.39 (1H, s)

Preparation 97

To an ice-cooled suspension of lithium aluminum hydride (950 mg) in tetrahydrofuran (50 ml) was added Starting Compound (5.45 g), and the mixture was stirred at room temperature for 1 hour. The mixture was cooled with ice and diluted with ether (100 ml). Then, water (0.95 ml), 15% sodium hydroxide (0.95 ml), and water (1.9 ml) were added dropwise to the mixture and filtered. To the precipitate was added ethanol, and the insoluble matter was filtered off. The combined filtrate was evaporated to give Object Compound (4.29 g) as white crystals.

mp: 162–164° C.; MASS (m/z): 177 (M+H)⁺; NMR (CDCl₃, δ): 2.57 (3H, s), 3.69 (3H, s), 4.75 (2H, s), 7.25 (2H, ABq, Δ=0.05, J=8 Hz), 7.61 (1H, s)

Preparation 98

To a stirred solution of oxalyl chloride (5.85 g) in dichloromethane (23 ml) below −60° C. was added dimethyl sulfoxide (4.50 g) dropwise. To this solution was added dropwise Starting Compound (4.05 g) in dimethyl sulfoxide (20 ml)—dichloromethane (73 ml) with cooling below −55° C. The stirring was continued at −60° C. for 1 hour, then triethylamine (16.0 ml) was added dropwise, and the mixture was allowed to warm to room temperature. Water (50 ml) was added thereto, then the mixture was extracted four times with chloroform and dried over magnesium sulfate. Evaporation of the solvent followed by column chromatography (silica gel, chloroform/methanol 30/1) gave Object Compound (3.37 g) as off-white crystals.

mp: 73–74° C.; MASS (m/z): 175 (M+H)⁺; NMR (CDCl₃, δ): 2.64 (3H, s), 3.77 (3H, s), 7.37 (1H, d, J=8 Hz), 7.84 (1H, d, J=8 Hz), 8.16 (1H, s), 10.06 (1H, s)

Preparation 99

The following object compounds were obtained according to a similar manner to that of Preparation 1, 6, 11, 38, 52 or 56.

(1) MASS: 530 (M+1); NMR (CDCl₃, δ): 1.40 (9H, s), 2.29 (3H, s), 2.52 (3×⅔H, s), 2.80 (3×⅓H, s), 2.90–3.08 (4H, m), 4.02 (2×⅙H, d, J=16 Hz), 4.22 (2×⅙H, d, J=16

Hz), 4.30 (2×⅓H, d, J=15 Hz), 4.58 (2×⅓H, d, J=15 Hz), 4.23–4.42 (1H, m), 4.83–4.95 (1H, m), 5.07–5.18 (1H, m), 6.69 (1×⅓H, d, J=8 Hz), 6.80 (1×⅔H, d, J=8 Hz), 6.89 (1×⅔H, t, J=8 Hz), 7.08 (1×⅓H, t, J=8 Hz), 7.00–7.14 (8H, m), 7.15–7.21 (2H, m), 7.22–7.31 (3H, m)

(2) MASS: 528 (M+1); NMR (CDCl$_3$, δ): 1.30 (9×⅓H, s), 1.31 (9×⅔H, s), 2.70–3.25 (8H, m), 4.40–5.09 (5H, m), 5.13–5.28 (1H, m), 6.82–7.48 (14H, m)

(3) MASS: 473 (M+1); NMR (CDCl$_3$, δ): 0.80 (3×⅘H, t, J=8 Hz), 0.85 (3×⅕H, t, J=8 Hz), 1.18–1.40 (4H, m), 1.43 (9H, s), 1.57–1.82 (2H, m), 2.97 (3×⅕H, s), 3.08 (3×⅘H, s), 3.58–3.68 (1H, m), 3.90–4.03 (2H, m), 4.20–4.31 (1H, m), 4.19 (2×⅖H, d, J=15 Hz), 4.21 (2×¹⁄₁₀H, d, J=16 Hz), 4.84 (2×⅖H, d, J=15 Hz), 4.90 (2×¹⁄₁₀H, d, J=16 Hz), 4.86–5.00 (1H, m), 5.52 (1H, d, J=7 Hz), 7.08–7.20 (1H, m), 7.57 (1H, q, J=8 Hz), 7.70 (1H, t, J=8 Hz), 7.80 (1×⅘H, d, J=8 Hz), 7.83 (1×⅕H, d, J=8 Hz), 8.00 (1×⅘H, s), 8.12 (1×⅕H, s), 8.10 (1H, d, J=8 Hz), 8.78 (1×⅘H, s), 8.83 (1×⅕H, s)

(4) MASS: 534 (M+1); NMR (CDCl$_3$, δ): 0.73 (3×¼H, t, J=8 Hz), 0.79 (3×¾H, t, J=8 Hz), 0.98–1.30 (4H, m), 1.32–1.62 (1H, m), 1.47 (9H, s), 1.63–1.70 (1H, m), 2.92 (3×¼H, s), 3.00 (3×¾H, s), 3.19 (1×¼H, s), 3.22 (1×¾H, s), 3.28–3.42 (1H, m), 4.52 (2×⅜H, d, J=15 Hz), 4.53–4.63 (1H, m), 4.72 (2×⅛H, d, J=16 Hz), 4.87 (2×⅛H, d, J=16 Hz), 4.92 (2×⅜H, d, J=15 Hz), 4.81–4.92 (1H, m), 6.50–6.60 (1H, m), 7.10–7.21 (2H, m), 7.50–7.61 (3H, m), 7.70 (1H, t, J=8 Hz), 7.72–7.88 (1H, m), 7.98 (1H, s), 8.09 (1×¾H, d, J=8 Hz), 8.11 (1×¼H, d, J=8 Hz), 8.50 (1H, d, J=2 Hz), 8.78 (1H, s)

(5) MASS: 531 (M+1); NMR (CDCl$_3$, δ): 1.47 (9H, s), 1.82–1.98 (1H, m), 1.99–2.10 (1H, m), 2.09 (3H, s), 2.47–2.53 (2H, m), 2.58 (3×⅔H, s), 2.75 (3×⅓H, s), 3.00 (2H, d, J=8 Hz), 3.90 (3×⅓H, s), 3.91 (3×⅔H, s), 4.20–4.30 (1H, m), 4.29 (2×½H, d, J=15 Hz), 4.49 (2×½H, d, J=15 Hz), 5.02–5.27 (2H, m), 6.61 (1×⅓H, d, J=8 Hz), 6.67 (1×⅔H, d, J=8 Hz), 7.00 (1H, d, J=8 Hz), 7.07–7.30 (5H, m), 7.32 (1H, dd, J=8, 2 Hz), 7.82 (1×⅓H, d, J=2 Hz), 7.94 (1×⅔H, d, J=2 Hz)

(6) MASS: 517 (M+1); NMR (CDCl$_3$, δ): 0.80 (3×¼H, t, J=8 Hz), 0.84 (3×¾H, t, J=8 Hz), 1.18–1.40 (4H, m), 1.43 (9H, s), 1.53–1.70 (1H, m), 1.70–1.82 (1H, m), 1.86–1.99 (1H, m), 2.00–2.12 (1H, m), 2.08 (3H, s), 2.50–2.60 (2H, m), 2.98 (3×¼H, s), 3.09 (3×¾H, s), 4.22–4.38 (1H, m), 4.63 (2×⅜H, d, J=15 Hz), 4.87 (2×⅜H, d, J=15 Hz), 4.92 (2×¼H, s), 4.90–5.03 (1H, m), 5.14–5.28 (1H, m), 6.90–7.03 (1H, m), 7.56 (1H, q, J=8 Hz), 7.70 (1H, q, J=8 Hz), 7.80 (1H, q, J=8 Hz), 8.00 (1H, s), 8.10 (1×¾H, d, J=8 Hz), 8.11 (1×¼H, d, J=8 Hz), 8.78–8.82 (1H, m)

(7) MASS: 523 (M+1); NMR (CDCl$_3$, δ): 0.78 (3×¼H, t, J=8 Hz), 0.83 (3×¾H, t, J=8 Hz), 1.10–1.38 (4H, m), 1.40 (9H, s), 1.51–1.80 (2H, m), 2.92–3.20 (3H, m), 2.98 (3×¼H, s), 3.05 (3×¾H, s), 4.37–4.49 (1H, m), 4.68–4.92 (3H, m), 6.78–6.88 (1H, m), 7.21–7.30 (1H, m), 7.49 (1×¾H, s), 7.52 (1×¼H, s), 7.52–7.61 (1H, m), 7.71 (1H, t, J=8 Hz), 7.79 (1×¾H, d, J=8 Hz), 7.84 (1×¼H, d, J=8 Hz), 8.00 (1H, s), 8.09 (1×¾H, d, J=8 Hz), 8.11 (1×¼H, d, J=8 Hz), 8.79 (1×¾H, s), 8.81 (1×¼H, s)

(8) MASS: 611 (M+1); NMR (CDCl$_3$, δ): 1.39 (3H, t, J=8 Hz), 1.43 (9H, s), 2.29 (3H, s), 2.32–2.47 (4H, m), 2.50 (3×¾H, s), 2.71 (3×¼H, s), 2.49–2.62 (1H, m), 2.95–3.29 (3H, m), 3.40–3.52 (2H, m), 3.53–3.64 (2H, m), 3.92 (2×⅛H, d, J=16 Hz), 4.18 (2×⅜H, d, J=15 Hz), 4.28 (2×⅛H, d, J=16 Hz), 4.50 (2×⅜H, d, J=15 Hz), 4.31 (2H, q, J=8 Hz), 4.45–4.58 (1H, m), 5.00–5.22 (1H, m), 6.01 (1H, d, J=8 Hz), 6.53 (1×¼H, d, J=8 Hz), 6.63 (1×¾H, d, J=8 Hz), 6.92 (1×¼H, d, J=8 Hz), 7.20 (1H, m), 7.11–7.30 (5H, m), 7.40 (1×¼H, d, J=8 Hz), 7.43 (1×¾H, d, J=8 Hz), 7.78 (1×¼H, s), 7.89 (1×¾H, s)

(9) MASS: 567 (M+1); NMR (CDCl$_3$, δ): 1.48 (9H, s), 2.30 (3×¾H, s), 2.32 (3×¼H, s), 2.48–2.62 (1H, m), 2.58 (3×¾H, s), 2.80 (3×¼H, s), 2.88–3.09 (2H, m), 3.10–3.23 (1H, m), 3.38–3.49 (2H, m), 3.52–3.62 (2H, m), 3.63–3.76 (4H, m), 4.12 (2×⅛H, d, J=16 Hz), 4.30 (2×⅜H, d, J=5 Hz), 4.56 (2×⅛H, d, J=16 Hz), 4.62 (2×⅜H, d, J=15 Hz), 4.48–4.62 (1H, m), 5.02–5.13 (1H, m), 6.00 (1H, d, J=8 Hz), 6.83 (1×¾H, m), 6.98–7.03 (1×¼H, m), 6.98–7.13 (5H, m), 7.18–7.32 (3H, m), 7.39 (1×¼H, d, J=8 Hz), 7.43 (1×¾H, d, J=8 Hz)

(10) MASS: 505 (M+1); NMR (CDCl$_3$, δ): 0.83 (3×⅓H, t, J=8 Hz), 0.92 (3×⅔H, t, J=8 Hz), 1.22–1.50 (2H, m), 1.43 (9H, s), 1.53–1.78 (1H, m), 2.48–2.61 (1H, m), 2.90 (3×⅓H, s), 2.96 (3×⅔H, s), 3.11–3.23 (1H, m), 3.38–3.50 (2H, m), 3.53–3.61 (2H, m), 3.62–3.70 (4H, m), 4.40 (2×⅓H, d, J=15 Hz), 4.47–4.59 (2H, m), 4.60 (2×⅓H, s), 4.72 (2×⅓H, d, J=15 Hz), 4.84–4.99 (1H, m), 6.07 (1H, d, J=8 Hz), 7.13–7.48 (6H, m)

(11) MASS: 613 (M+1); NMR (CDCl$_3$, δ): 1.41 (9H, s), 2.28 (3H, s), 2.32–2.50 (4H, m), 2.50–2.62 (1H, m), 2.51 (3H, s), 2.52 (3×¾H, s), 2.71 (3×¼H, s), 2.93–3.30 (3H, m), 3.38–3.52 (2H, m), 3.54–3.65 (2H, m), 3.99 (2×⅛H, d, J=16 Hz), 4.19 (2×⅛H, d, J=16 Hz), 4.20 (2×⅜H, d, J=15 Hz), 4.51 (2×⅜H, d, J=15 Hz), 4.47–4.60 (1H, m), 5.01–5.20 (1H, m), 5.95–6.00 (1H, m), 6.81–7.21 (7H, m), 7.39 (1×¼H, d, J=8 Hz), 7.41 (1×¾H, d, J=8 Hz), 8.05 (1×¼H, s), 8.20 (1×¾H, s)

(12) MASS: 570 (M+1); NMR (CDCl$_3$, δ): 1.30 (3×¼H, t, J=8 Hz), 1.36 (3×¾H, t, J=8 Hz), 1.17–1.40 (4H, m), 1.48 (9H, s), 1.57–1.86 (2H, m), 2.58 (1H, dd, J=16, 4 Hz), 2.99 (3×¼H, s), 3.04 (3×¾H, s), 3.18 (1H, d, J=16 Hz), 3.38–3.50 (2H, m), 3.52–3.61 (2H, m), 3.62–3.78 (4H, m), 4.50–4.69 (1H, m), 4.61 (2×½H, d, J=16 Hz), 4.80–5.03 1H, m), 4.96 (2×½H, d, J=16 Hz), 6.09 (1H, d, J=8 Hz), 7.32–7.50 (1H, m), 7.58 (1H, q, J=8 Hz), 7.70 (1H, t, J=8 Hz), 7.78–7.84 (1H, m), 8.00 (1H, s), 8.08–8.16 (1H, m), 8.80 (1H, d, J=2 Hz)

(13) MASS: 625 (M+1); NMR (CDCl$_3$, δ): 0.91 (3×⅕H, t, J=8 Hz), 0.92 (3×⅘H, t, J=8 Hz), 1.43 (9H, s), 1.63–1.80 (2H, m), 2.30 (3H, s), 2.32–2.50 (4H, m), 2.50–2.63 (1H, m), 2.53 (3×⅘H, s), 2.72 (3×⅕H, s), 2.93–3.13 (2H, m), 3.14–3.30 (1H, m), 3.40–3.52 (2H, m), 3.54–3.63 (2H, m), 3.82 (2H, t, J=8 Hz), 3.97 (2×½H, d, J=15 Hz), 4.32 (2×½H, d, J=15 Hz), 4.48–4.60 (1H, m), 5.00–5.17 (1H, m), 6.01 (1H, d, J=8 Hz), 6.40 (1×⅕H, d. J=8 Hz), 6.48 (1×⅘H, d, J=8 Hz), 6.93–7.03 (1H, m), 7.08–7.30 (6H, m), 7.33–7.47 (1H, m)

(14) MASS: 584 (M+1); NMR (CDCl$_3$, δ): 1.41 (9H, s), 2.50 (3×⅔H, s), 2.50–2.60 (1H, m), 2.71 (3×⅓H, s), 2.92–3.03 (2H, m), 3.20 (1H, d, J=15 Hz), 3.38–3.50 (2H, m), 3.52–3.60 (2H, m), 3.60–3.73 (4H, m), 3.90 (3×⅓H, s), 3.91 (3×⅔H, s), 4.20 (2×½H, d, J=15 Hz), 4.49 (2×½H, d, J=15 Hz), 4.50–4.60 (1H, m), 5.01–5.11 (1×⅔H, m), 5.12–5.23 (1×⅓H, m), 6.01 (1H, d, J=8 Hz), 6.59 (1×⅓H, d, J=8 Hz), 6.64 (1×⅔H, d, J=8 Hz), 7.10–7.22 (4H, m), 7.22–7.30 (1H, m), 7.38–7.48 t1H, m), 7.79 (1×⅓H, d, J=2 Hz), 7.91 (1×⅔H, d, J=2 Hz)

Preparation 100

The following object compounds were obtained according to a similar manner to that of Preparation 3, 4, 8, 41 or 54.

(1) MASS: 430 (M+1); NMR (CDCl$_3$, δ): 2.30 (3H, s), 2.36–2.48 (1×⅓H, m), 2.50–2.60 (1×⅔H, m), 2.66 (3×⅔H, s), 2.82 (3×⅓H, s), 2.88–3.18 (3H, m), 3.46 (1×⅓H, dd, J=12, 4 Hz), 3.57 (1×⅔H, dd, J=12, 4 Hz), 4.30 (2×⅓H, d, J=15 Hz), 4.31 (2×⅙H, d, J=16 Hz), 4.40 (2×⅙H, d, J=16 Hz), 4.67 (2×⅓H, d, J=15 Hz), 5.19 (1H, q, J=12 Hz), 6.93–7.30 (14H, m), 7.91 (1×⅓H, d, J=8 Hz), 8.00 (1×⅔H, d, J=8 Hz)

(2) MASS: 428 (M+1); NMR (CDCl₃, δ): 2.70–2.85 (2H, m), 2.99–3.25 (3H, m), 3.00 (3×⅓H, s), 3.05 (3×⅔H, s), 3.92–4.15 (1H, m), 4.41–5.07 (3H, m), 5.30–5.40 (1H, m), 7.00–7.80 (14H, m)

(3) MASS: 373 (M+1); NMR (CDCl₃, δ): 0.81 (3×¼H, t, J=8 Hz), 0.85 (3×¾H, t, J=8 Hz), 1.17–1.42 (4H, m), 1.59–1.88 (2H, m), 3.00 (3×¼H, s), 3.07 (3×¾H, s), 3.41 (1×¼H, t, J=5 Hz), 3.50 (1×¾H, t, J=5 Hz), 3.60–3.75 (1H, m), 3.80–3.90 (1H, m), 4.63 (2×⅛H, d, J=16 Hz), 4.70 (2×⅜H, d, J=15 Hz), 4.81 (2×⅛H, d, J=16 Hz), 4.90 (2×⅜H, d, J=15 Hz), 4.81–5.07 (1H, m), 7.59 (1H, q, J=8 Hz), 7.68–7.90 (3H, m), 8.01 (1×¾H, s), 8.12 (1×¼H, s), 8.10 (1H, d, J=8 Hz), 8.80 (1×¾H, s), 8.82 (1×¼H, s)

(4) MASS: 434 (M+1); NMR (CDCl₃, δ): 0.79 (3×⅓H, t, J=8 Hz), 0.87 (3×⅔H, t, J=8 Hz), 1.10–1.35 (4H, m), 1.50–1.80 (2H, m), 2.98 (3×⅓H, s), 3.04 (3×⅔H, s), 3.00–3.12 (1H, m), 3.22–3.37 (1H, m), 3.63–3.71 (1×⅓H, m), 3.75–3.85 (1×⅔H, m), 4.61 (2×⅓H, d, J=15 Hz), 4.83 (2×⅙H, d, J=16 Hz), 4.92 (2×⅓H, d, J=15 Hz), 4.98 (2×⅙H, d, J=16 Hz), 4.90–5.05 (1H, m), 7.11–7.30 (2H, m), 7.51–7.66 (2H, m), 7.71 (1H, t, J=8 Hz), 7.80 (1H, d, J=8 Hz), 8.01 (1H, s), 8.10 (1×⅔H, d, J=8 Hz), 8.12 (1×⅓H, d, J=8 Hz), 8.20 (1×⅓H, d, J=8 Hz), 8.22 (1×⅔H, d, J=8 Hz), 8.50–8.58 (1H, m), 8.81 (1H, d, J=2 Hz)

(5) MASS: 431 (M+1); NMR (CDCl₃, δ): 1.62–1.79 (1H, m), 1.97–2.11 (1H, m), 2.09 (3×¼H, s), 2.10 (3×¾H, s), 2.48 (2×¼H, t, J=8 Hz), 2.51 (2×¾H, t, J=8 Hz), 2.68 (3×¾H, s), 2.78 (3×¼H, s), 2.90–3.18 (2H, m), 3.40–3.51 (1H, m), 3.90 (3×¼H, s), 3.91 (3×¾H, s), 4.11 (2×⅛H, d, J=16 Hz), 4.24 (2×⅜H, d, J=15 Hz), 4.33 (2×⅜H, d, J=15 Hz), 4.57 (2×⅛H, d, J=16 Hz), 5.08–5.18 (1×¾H, m), 5.20–5.30 (1×¼H, m), 6.62 (1×¼H, d, J=8 Hz), 6.68 (1×¾H, d, J=8 Hz), 7.10–7.37 (6H, m), 7.88 (1×¼H, d, J=2 Hz), 7.90 (1H, d, J=8 Hz), 7.94 (1×¾H, d, J=2 Hz)

(6) MASS: 417 (M+1); NMR (CDCl₃, δ): 0.80 (3×¼H, t, J=8 Hz), 0.84 (3×¾H, t, J=8 Hz), 1.17–1.47 (4H, m), 1.50–1.90 (3H, m), 2.08–2.22 (1H, m), 2.09 (3×¼H, s), 2.10 (3×¾H, s), 2.60 (2×¼H, t, J=8 Hz), 2.62 (2×¾H, t, J=8 Hz), 3.00 (3×¼H, s), 3.07 (3×¾H, s), 3.40–3.48 (1×¼H, m), 3.50–3.58 (1×¾H, m), 4.62 (2×½H, d, J=15 Hz), 4.92 (2×½H, d, J=15 Hz), 4.80–5.06 (1H, m), 7.53 (1×¾H, t, J=8 Hz), 7.57 (1×¼H, t, J=8 Hz), 7.70 (1H, t, J=8 Hz), 7.79 (1H, d, J=7 Hz), 7.90 (1H, d, J=8 Hz), 8.01 (1H, s), 8.09 (1×¾H, d, J=7 Hz), 8.11 (1×¼H, d, J=7 Hz), 8.81 (1H, d, J=2 Hz)

(7) MASS: 423 (M+1); NMR (CDCl₃, δ): 0.79 (3×¼H, t, J=8 Hz), 0.87 (3×¾H, t, J=8 Hz), 1.00–1.40 (4H, m), 2.53–2.80 (2H, m), 2.90–3.06 (2H, m), 2.98 (3×¼H, s), 3.04 (3×¾H, s), 3.49–3.58 (1×¼H, m), 3.60–3.70 (1×¾H, m), 4.78 (2×¾H, s), 4.81–4.93 (2×¼H, s), 4.81–5.02 (1H, m), 6.86 (1H, s), 7.50–7.60 (2H, m), 7.71 (1H, t, J=8 Hz), 7.79 (1H, q, J=8 Hz), 7.90 (1×¾H, d, J=8 Hz), 7.93 (1×¼H, d, J=8 Hz), 8.00 (1×¾H, s), 8.03 (1×¼H, s), 8.09 (1×¾H, d, J=8 Hz), 8.11 (1×¼H, d, J=8 Hz), 8.79 (1×¾H, s), 8.81 (1×¼H, s)

(8) MASS: 511 (M+1); NMR (CDCl₃, δ): 1.38 (3H, t, J=8 Hz), 2.29 (3H, s), 2.32–2.52 (5H, m), 2.61 (3×¾H, s), 2.77 (3×¼H, s), 2.70–2.88 (1H, m), 2.93–3.18 (2H, m), 3.37–3.48 (2H, m), 3.51–3.74 (3H, m), 4.11 (2×⅛H, d, J=16 Hz), 4.20 (2×⅜H, d, J=15 Hz), 4.32 (2×⅛H, d, J=16 Hz), 4.53 (2×⅜H, d, J=15 Hz), 4.29 (2H, q, J=8 Hz), 5.11 (1×¾H, q, J=8 Hz), 5.20 (1×¼H, q, J=8 Hz), 6.59 (1×¼H, d, J=8 Hz), 6.62 (1×¾H, d, J=8 Hz), 7.07 (1×¼H, d, J=8 Hz), 7.18 (1×¾H, d, J=8 Hz), 7.10–7.32 (5H, m), 7.81 (1×¼H, s), 7.91 (1×¾H, s), 8.12 (1×¼H, d, J=8 Hz), 8.16 (1×¾H, d, J=8 Hz)

(9) MASS: 467 (M+1); NMR (CDCl₃, δ): 2.28 (3H, s), 2.33–2.58 (1H, m), 2.68 (3×⅔H, s), 2.80 (1H, dd, J=17, 2 Hz), 2.83 (3×⅓H, s), 2.90–3.10 (2H, m), 3.33–3.48 (2H, m), 3.50–3.78 (7H, m), 4.32 (2×⅓H, d, J=15 Hz), 4.38 (2×⅓H, s), 4.69 (2×⅓H, d, J=15 Hz), 5.08–5.20 (1H, m), 6.93–7.13 (6H, m), 7.20–7.32 (3H, m), 8.03 (1×⅓H, d, J=8 Hz), 8.11 (1×⅔H, d, J=8 Hz)

(10) MASS: 405 (M+1); NMR (CDCl₃, δ): 0.87 (3×⅓H, t, J=8 Hz), 0.93 (3×⅔H, t, J=8 Hz), 1.22–1.50 (2H, m), 1.58–1.80 (2H, m), 2.58–2.72 (1H, m), 2.80–2.91 (1H, m), 2.92 ( 3×⅓H, s), 3.01 (3×⅔H, s), 3.40–3.51 (2H, m ), 3.52–3.71 (6H, m), 3.72–3.80 (1H, m), 4.46 (2×⅓H, d, J=15 Hz), 4.67 (2×⅓H, s), 4.77 (2×⅓H, d, J=15 Hz), 4.88–5.00 (1H, m), 7.17–7.42 (5H, m), 8.08 (1×⅓H, d, J=8 Hz), 8.12 (1×⅔H, d, J=8 Hz)

(11) MASS: 513 (M+1); NMR (CDCl₃, δ): 2.32 (3H, s), 2.38–2.52 (6H, m), 2.52 (3×⅓H, s), 2.53 (3×⅔H, s), 2.64 (3×⅔H, s), 2.79 (3×⅓H, s), 2.73–2.88 (1H, m), 2.93–3.20 (1H, m), 3.42–3.51 (2H, m), 3.53–3.78 (3H, m), 4.18 (2×⅙H, d, J=16 Hz), 4.28 (2×⅓H, d, J=15 Hz), 4.31 (2×⅙H, d, J=16 Hz), 4.55 (2×⅓H, d, J=15 Hz), 5.07–5.21 (1H, m), 6.97–7.32 (7H, m), 8.12 (1H, s), 8.16 (1×⅓H, s), 8.22 (1×⅔H, s)

(12) MASS: 470 (M+1); NMR (CDCl₃, δ): 0.80 (3×⅕H, t, J=8 Hz), 0.85 (3×⅘H, t, J=8 Hz), 1.15–1.40 (4H, m), 1.60–1.90 (2H, m), 2.63 (1×⅕H, d, J=8 Hz), 2.70 (1×⅘H, d, J=8 Hz), 2.80 (1H, t, J=15 Hz), 2.99 (3×⅕H, s), 3.03 (3×⅘H, s), 3.40–3.50 (2H, m), 3.50–3.70 (6H, m), 3.70–3.80 (1H, m), 4.63 (2×½H, d, J=15 Hz), 4.80–5.02 (1H, m), 4.90 (2×½H, d, J=15 Hz), 7.50–7.60 (1H, m), 7.71 (1H, t, J=8 Hz), 7.80 (1H, d, J=8 Hz), 8.01 (1H, s), 8.10 (2×⅘H, d, J=8 Hz), 8.12 (2×⅕H, d, J=8 Hz), 8.80 (1H, d, J=8 Hz)

(13) MASS: 525 (M+1); NMR (CDC₃, δ): 0.90 (3×⅕H, t, J=8 Hz), 0.92 (3×⅘H, t, J=8 Hz), 1.67–1.90 (2H, m), 2.29 (3H, s), 2.33–2.48 (4H, m), 2.49–2.60 (1H, m), 2.61 (3×⅘H, s), 2.76 (3×⅕H, s), 2.72–2.88 (1H, m), 2.92–3.09 (2H, m), 3.40–3.50 (2H, m), 3.51–3.72 (3H, m), 3.79 (2×¹⁄₁₀H, d, J=16 Hz), 3.85 (2H, t, J=8 Hz), 3.99 (2×⅖H, d, J=15 Hz), 4.08 (2×¹⁄₁₀H, d, J=16 Hz), 4.39 (2×⅖H, d, J=15 Hz), 5.01–5.20 (1H, m), 6.41 (1×⅕H, d, J=8 Hz), 6.49 (1×⅘H, d, J=8 Hz), 6.81 (1×⅕H, d, J=8 Hz), 7.03 (1×⅘H, d, J=8 Hz), 7.10–7.32 (6H, m), 8.15 (1H, d, J=8 Hz)

(14) MASS: 484 (M+1); NMR (CDCl₃, δ): 2.40–2.58 (1H, m), 2.63 (3×¾H, s), 2.70–2.82 (1H, m), 2.78 (3×¼H, s), 2.93–3.18 (2H, m), 3.38–3.50 (2H, m), 3.51–3.74 (7H, m), 3.90 (3×¼H, s), 3.91 (3×¾H, s), 4.10 (2×⅛H, d, J=16 Hz), 4.23 (2×⅜H, d, J=15 Hz), 4.31 (2×⅛H, d, J=16 Hz), 4.56 (2×⅜H, d, J=15 Hz), 5.04–5.27 (1H, m), 6.61 (1×¼H, d, J=8 Hz), 6.68 (1×¾H, d, J=8 Hz), 7.03–7.36 (6H, m), 7.84 (1×¼H, s), 7.93 (1×¾H, s), 8.11 (1×¼H, d, J=8 Hz), 8.13 (1×¾H, d, J=8 Hz)

Preparation 101

The following object compounds were obtained according to a similar manner to that of Preparation 1, 6, 11, 38, 52 or 56.

(1) MASS: 414 (M+1); NMR (CDCl₃, δ): 1.35 (3H, t, J=8 Hz), 1.39 (9H, s), 2.58 (3×¾H, s), 2.77 (3×¼H, s), 2.90–3.10 (2H, m), 3.90 (2×⅛H, d, J=16 Hz), 4.26 (2×⅛H, d, J=16 Hz), 4.31 (2H q, J=8 Hz), 4.33 (2×⅜H, d, J=15 Hz), 4.43 (2×⅜H, d, J=15 Hz), 4.73–4.88 (1×⅔H, m) 4.90–5.00

(1×⅓H, m), 5.30–5.43 (1H, m), 6.59 (1×¼H, d, J=8 Hz), 6.63 (1×¾H, d, J=8 Hz), 7.02–7.36 (6H, m), 7.81 (1×¼H, s), 7.92 (1×¾H, s)

(2) MASS: 383 (M+1); NMR (CDCl$_3$, δ): 1.40 (9×⅓H, s), 1–42 (9×⅔H, s), 2.28 (3×⅔H, s), 2.30 (3×⅓H, s), 2.61 (3×⅔H, s), 2.81 (3×⅓H, s), 2.87–3.00 (2H, m), 4.14 (2×⅙H, d, J=16 Hz), 4.37 (2×⅙H, d, J=16 Hz), 4.42 (2×⅓H, d, J=15 Hz), 4.56 (2×⅓H, d, J=15 Hz), 4.79–4.92 (1H, m), 5.32 (1×⅓H, d, J=8 Hz), 5.40 (1×⅔H, d, J=8 Hz), 6.91–7.18 (6H, m), 7.20–7.31 (3H, m)

(3) MASS: 321 (M+1); NMR (CDCl$_3$, δ): 0.83 (3×⅓H, t, J=8 Hz), 0.90 (3×⅔H, t, J=8 Hz), 1.20–1.78 (4H, m), 1.41 (9×⅓H, s), 1.43 (9×⅔H, s), 2.90 (3×⅓H, s), 2.94 (3×⅔H, s), 4.51 (2×½H, d, J=15Hz), 4.68 (2×½H, d, J=15 Hz), 4.59–4.73 (1H, m), 5.31 (1×⅓H, d, J=8 Hz), 5.39 (1×⅔H, d, J=8 Hz), 7.12–7.40 (5H, m)

(4) MASS: 416 (M+1); NMR (CDCl$_3$, δ): 1.40 (9H, s), 2.51 (3×⅕H, s), 2.53 (3×⅘H, s), 2.58 (3×⅕H, s), 2.76 (3×⅘H, s), 2.90–3.07 (2H, m), 3.97 (2×⅒H, d, J=16 Hz), 4.29 (2×⅒H, d, J=16 Hz), 4.32 (2×⅖H, d, J=15 Hz), 4.42 (2×⅖H, d, J=15 Hz), 4.77–4.97 (1H, m), 5.29–5.40 (1H, m), 6.93–7.30 (7H, m), 8.10 (1×⅕H, s), 8.21 (1×⅘H, s)

(5) MASS: 386 (M+1); NMR (CDCl$_3$, δ): 0.80 (3×¼H, t, J=8 Hz), 0.88 (3×¾H, t, J=8 Hz), 1.18–1.38 (3H, m), 1.39 (9×¼H, s), 1.41 (9×¾H, s), 1.51–1.63 (1H, m), 1.64–1.73 (2H, m), 2.99 (3×¼H, s), 3.08 (3×¾H, s), 4.60–4.69 (1H, m), 4.70 (2×⅜H, d, J=15 Hz), 4.78 (2×⅛H, d, J=17 Hz), 4.87 (2×⅜H, d, J=15 Hz), 4.89 (2×⅛H, d, J=17 Hz), 5.29 (1×¼H, d, J=8 Hz), 5.33 (1×¾H, d, J=8 Hz), 7.53 (1H, t, J=8 Hz), 7.70 (1H, t, J=8 Hz), 7.79 (1H, d, J=8 Hz), 8.00 (1H, s), 8.09 (1H, d, J=8 Hz), 8.81 (1H, d, J=2 Hz)

(6) MASS: 428 (M+1); NMR (CDCl$_3$, δ): 0.90 (3×⅕H, t, J=8 Hz), 0.93 (3×⅘H, t, J=8 Hz), 1.39 (9H, s), 1.65–1.82 (2H, m), 2.60 (3×⅘H, s), 2.75 (3×⅕H, s), 2.90–3.03 (2H, m), 3.51 (2×⅒H, d, J=16 Hz), 3.77–3.90 (2H, m), 4.10 (2×⅒H, d, J=16 Hz), 4.11 (2×⅖H, d, J=15 Hz), 4.22 (2×⅖H, d, J=15 Hz), 4.73–5.92 (1H, m), 5.32 (1H, d, J=8 Hz), 6.43 (1×⅕H, d, J=8 Hz), 6.49 (1×⅘H, d, J=8 Hz), 6.85 (1×⅕H, dd, J=12, 3 Hz), 7.10 (1×⅘H, dd, J=12, 3 Hz), 7.02–7.32 (6H, m)

(7) MASS: 381 (M+1); NMR (CDCl$_3$, δ): 1.35 (9×⅖H, s), 1.39 (9×⅖H, s), 1.49 (9×⅗H, s), 2.83–3.20 (2H, m), 3.03 (3H, s), 4.33–4.71 (2H, m), 4.73–5.00 (2H, m), 5.21–5.38 (1H, m), 7.08–7.45 (9H, m)

Preparation 102

The following object compounds were obtained according to a similar manner to that of Preparation 3, 4, 8, 41 or 54.

(1) MASS: 314 (M+1); NMR (CDCl$_3$, δ): 1.39 (3H, t, J=8 Hz), 2.62 (3×¾H, s), 2.88 (3×¼H, s), 2.72–2.88 (1H, m), 2.88–3.08 (1H, m), 3.88–4.00 (1H, m), 4.03 (2×⅛H, d, J=16 Hz), 4.30 (2×⅛H, d, J=16 Hz), 4.32 (2×⅜H, d, J=15 Hz), 4.32 (2H, q, J=8 Hz), 4.53 (2×⅜H, d, J=15 Hz), 6.63 (1×¼H, d, J=8 Hz), 6.67 (1×¾H, d, J=1 Hz), 7.10–7.32 (5H, m), 7.41 (1H, dd, J=8, 2 Hz), 7.88 (1×¼H, s), 7.97 (1×¾H, s)

(2) MASS: 283 (M+1); NMR (CDCl$_3$, δ): 2.28 (3H, s), 2.63–2.80 (1H, m), 2.71 (3×⅔H, s), 2.90 (3×⅓H, s), 2.88–3.00 (1H, m), 3.86 (1×⅓H, t, J=8 Hz), 3.97 (1×⅔H, t, J=8 Hz), 4.20 (2×⅙H, d, J=16 Hz), 4.40 (2×⅙H, d, J=16 Hz), 4.45 (2×⅓H, d, J=15 Hz), 4.63 (2×⅓H, d, J=15 Hz), 6.97–7.18 (6H, m) 7.20–7.38 (3H, m)

(3) MASS: 221 (M+1); NMR (CDCl$_3$, δ): 0.82–100 (3H, m), 1.30–1.70 (4H, m), 2.91 (3×⅔H, s), 2.94 (3×⅓H, s), 3.63–3.82 (1H, m), 4.46 (2×⅙H, d, J=16 Hz), 4.50 (2×⅓H, d, J=15 Hz), 4.68 (2×⅙H, d, J=16 Hz), 4.71 (2×⅓H, d, J=15 Hz), 7.13–7.41 (5H, m)

(4) MASS: 316 (M+1); NMR (CDCl$_3$, δ): 2.55 (3H, s), 2.59 (3×¾H, s), 2.73–2.89 (1H, m), 2.88 (3×¼H, s), 2.90–3.08 (1H, m), 3.87–4.00 (1H, m), 4.09 (2×⅛H, d, J=16 Hz), 4.31 (2×⅛H, d, J=16 Hz), 4.37 (2×⅜H, d, J=15 Hz), 4.57 (2×⅜H, d, J=15 Hz), 7.02–7.35 (7H, m), 8.18 (1×¼H, s), 8.27 (1×¾H, s)

(5) MASS: 286 (M+1); NMR (CDCl$_3$, δ): 0.9 0 (3H, t, J=8 Hz), 1.20–1.58 (6H, m), 3.00 (3H, s), 3.72 (1H, d, J=8 Hz), 4.68 (2×⅜H, d, J=15 Hz), 4.71 (2×⅛H, d, J=16 Hz), 4.83 (2×⅛H, d, J=16 Hz), 4.91 (2×⅜H, d, J=15 Hz), 7.53 (1H, t, J=8 Hz), 7.70 (1H, t, J=8 Hz), 7.80 (1H, d, J=8 Hz), 7.92 (1×¼H, s), 8.01 (1×¾H, s), 8.09 (1H, d, J=8 Hz), 8.80 (1H, s)

(6) MASS: 328 (M+1); NMR (CDCl$_3$, δ): 0.98 (3H, t, J=8 Hz), 1.70–1.84 (2H, m), 2.63 (3×¾H, s), 2.81 (3×¼H, s), 2.74–2.89 (1H, m), 2.90–3.00 (1H, m), 3.88 (2H, t, J=8 Hz), 3.92 (1H, t, J=8 Hz), 4.10 (2×½H, d, J=15 Hz), 4.38 (2×½H, d, J=8 Hz), 6.51 (1H, d, J=8 Hz), 7.10–7.21 (4H, m), 7.21–7.35 (3H, m)

(7) MASS: 281 (M+1); NMR (CDCl$_3$, δ): 2.70–2.91 (1H, m), 2.92–3.17 (1H, m), 2.99 (3×½H, s), 3.00 (3×½H, s), 3.88–4.18 (3H, m), 4.60 (2×⅓H, d, J=17 Hz), 4.66 (2×⅓H, s), 4.78 (2×⅓H, d, J=17 Hz), 6.98–7.40 (9H, m)

Preparation 103

The following object compounds were obtained according to a similar manner to that of Preparation 22, 23, 25, 67 or 68.

(1) MASS: 167 (M+1); NMR (CDCl$_3$, δ): 1.32 (3H, t, J=8 Hz), 2.42 (3H, s), 3.62 (2H, s), 4.31 (2H, q, J=8 Hz), 6.69 (1H, d, J=8 Hz), 7.57 (1H, dd, J=8, 2 Hz), 8.03 (1H, d, J=2 Hz)

(2) MASS: 169 (M+1); NMR (CDCl$_3$, δ): 2.43 (3H, s), 2.57 (3H, s), 3.68 (2H, s), 7.16 (1H, d, J=8 Hz), 7.49 (1H, dd, J=8, 3 Hz), 8.37 (1H, s)

(3) MASS: 181 (M+1); NMR (CDCl$_3$, δ): 1.43 (3H, t, J=8 Hz), 1.70–1.84 (2H, m), 2.39 (3H, s), 3.50 (2H, s), 3.89 (2H, t, J=8 Hz), 6.52 (1H, d, J=8 Hz), 7.20 (1H, d, J=2 Hz), 7.30 (1H, dd, J=8, 2 Hz)

Preparation 104

The following object compounds were obtained according to a similar manner to that of Preparation 1, 6, 11, 38, 52 or 56.

(1) MASS: 413 (M+1); NMR (CDCl$_3$, δ): 0.85 (3×⅙H, t, J=8 Hz), 0.90 (3×⅚H, t, J=8 Hz), 1.20–1.40 (4H, m), 1.41 (9×⅙H, s), 1.42 (9×⅚H, s), 1.50–1.78 (2H, m), 2.96 (3×⅙H, s), 3.09 (3×⅚H, s), 4.58–4.81 (3H, m), 5.29 (1×⅙H, d, J=8 Hz), 5.32 (1×⅚H, d, J=8 Hz), 7.37–7.43 (1H, m), 7.68–7.80 (2H, m), 8.30 (1H, d, J=8 Hz), 8.60 (1H, s), 8.65 (1H, d, J=2 Hz), 9.20 (1H, s)

(2) MASS (m/z): 350 (M$^+$+1); NMR (CDCl$_3$, δ): 0.89 (3H, m), 1.33 (4H, m), 1.54–1.67 (2H, m), 2.55 (3H, s), 2.89 (3H×¼, ), 3.01 (3H×¾, s), 4.46–4.66 (3H, m), 5.33 (1H, m), 7.12 (1H, d, J=8 Hz), 7.47 (1H, dd, J=2, 8 Hz), 8.37 (1H, d, J=2 Hz)

(3) MASS: 400 (M+1); NMR (CDCl$_3$, δ): 1.38 (9×¼H, s), 1.39 (9×¾H, s), 2.61 (3×¾H, s), 2.79 (3×¼H, s), 2.99 (2×¾H, d, J=8 Hz), 3.01 (2×¼H, d, J=8 Hz), 3.80 (3×1.4H, s), 3.81 (3×¾H, s), 3.78 (2×⅛H, d, J=16 Hz), 4.38 (2×⅛H, d, J=16 Hz), 4.41 (2×⅜H, d, J=15 Hz), 4.52 (2×⅜H, d, J=15 Hz), 4.82 (1×¾H, q, J=8 Hz), 4.93 (1×¼H, q, J=8 Hz), 5.29–5.40 (1H, m), 7.01 (1×¼H, s), 7.08 (1×¾H, s), 7.10–7.32 (5H, m), 7.89 (1×¼H, s), 8.01 (1×¾H, s), 8.21 (1×¼H, s), 8.23 (1×¾H, s)

(4) MASS: 400 (M+1); NMR (CDCl$_3$, δ): 1.41 (9H, s), 2.65 (3×⅔H, s), 2.71 (3×⅓H, s), 2.90–3.10 (2H, m), 3.50 (2×⅙H, d, J=16 Hz), 3.80 (3×⅓H, s), 3.82 (3×⅔H, s), 4.40 (2×⅙H, d, J=16 Hz), 4.42 (2×⅓H, d, J=15 Hz), 4.58 (2×⅓H, d, J=15 Hz), 4.83 (1×⅔H, m), 5.16 (1×⅓H, m), 5.40 (1×⅔H, d, J=8 Hz), 5.52 (1×⅓H, d, J=8 Hz), 6.72 (1×⅓H, d, J=6 Hz), 6.76 (1×⅔H, d, J=6 Hz), 7.09–7.32 (5H, m), 8.06 (1×⅓H, s), 8.23 (1×⅔H, s), 8.42 (1H, d, J=6 Hz)

(5) MASS: 448 (M+1); NMR (CDCl$_3$, δ): 1.41 (9×⅙H, s), 1.42 (9×⅚H, s), 2.61 (3×⅚H, s), 2.79 (3×⅙H, s), 2.91–3.10 (2H, m), 3.91 (2×1/12H, d, J=16 Hz), 4.38 (2×1/12H, d, J=16 Hz), 4.41 (2×5/12H, d, J=15 Hz), 4.50 (2×5/12H, d, J=15 Hz), 4.78–4.93 (1H, m), 5.28–5.41 (1H, m), 7.11–7.31 (5H, m), 7.51 (1×⅙H, s), 7.69 (1×⅚H, s), 8.18 (1×⅙H, s), 8.31 (1×⅚H, s), 8.61 (1H, s)

Preparation 105

The following object compounds were obtained according to a similar manner to that of Preparation 3, 4, 8, 41 or 54.

(1) MASS: 313 (M+1); NMR (CDCl$_3$, δ): 0.90 (3H, t, J=8 Hz), 1.20–1.58 (4H, m), 1.59–1.80 (2H, m), 3.00 (3H, s), 3.62–3.78 (1H, m), 4.57 (2×½H, d, J=15 Hz), 4.74 (2×½H, d, J=15 Hz), 7.35–7.44 (1H, m), 7.60–7.80 (2H, m), 8.30 (1H, d, J=8 Hz), 8.60 (1H, s), 8.66 (1H, d, J=3 Hz), 9.19 (1H, s)

(2) NMR (CDCl$_3$, δ): 0.92 (3H, t, J=7 Hz), 1.31–1.58 (6H, m), 2.54 (3H, s), 2.94 (3H, s), 3.68 (1H, m), 4.45 (1H, d, J=15 Hz), 4.67 (1H, d, J=15 Hz), 7.13 (1H, d, J=8 Hz), 7.50 (1H, dd, J=2, 8 Hz), 8.37 (1H, d, J=2 Hz)

(3) MASS: 300 (M+1); NMR (CDCl$_3$, δ): 2.70 (3×¾H, s), 2.73–2.87 (1H, m), 2.90 (3×¼H, s), 2.93–3.07 (1H, m), 3.82 (3×¼H, s), 3.86 (3×¾H, s), 3.88 (1×¼H, s), 3.96 (1×¾H, s), 4.12 (2×⅙H, d, J=16 Hz), 4.40 (2×⅙H, d, J=15 Hz), 4.48 (2×⅓H, d, J=15 Hz), 4.60 (2×⅓H, d, J=15 Hz), 6.91 (1×¼H, s), 7.11 (1×¾H, s), 7.09–7.33 (5H, m), 7.98 (1×¼H, s), 8.07 (1×¾H, s), 8.23 (1H, d, J=2 Hz)

(4) MASS: 300 (M+1); NMR (CDCl$_3$, δ): 2.38–2.45 (1H, m), 2.45–2.52 (1H, m), 2.41 (3×⅔H, s), 2.43 (3×⅓H, s), 3.93 (3H, s), 3.94–4.03 (1H, m), 3.98 (2×⅙H, d, J=16 Hz), 4.22 (2×⅙H, d, J=16 Hz), 4.23 (2×⅓H, d, J=15 Hz), 4.33 (2×⅓H, d, J=15 Hz), 6.38–6.41 (1H, m), 6.66–6.70 (5H, m), 8.07 (1×⅓H, s), 8.13 (1×⅔H, s), 8.20–8.27 (1H, m)

(5) MASS: 348 (M+1); NMR (CDCl$_3$, δ): 2.68 (3×⅚H, s), 2.85 (3×⅙H, s), 2.78–2.90 (1H, m), 2.92–3.08 (1H, m), 3.83 (1×⅙H, t, J=8 Hz), 3.97 (1×⅚H, t, J=8 Hz), 4.11 (2×1/12H, d, J=16 Hz), 4.38 (2×1/12H, d, J=16 Hz), 4.39 (2×5/12H, d, J=15 Hz), 4.61 (2×5/12H, d, J=15 Hz), 7.10–7.35 (5H, m), 7.50 (1×⅙H, s), 7.71 (1×⅚H, s), 8.26 (1×⅙H, s), 8.38 (1×⅚H, s), 8.60 (1H, d, J=2 Hz)

Preparation 106

The following object compounds were obtained according to a similar manner to that of Preparation 1, 6, 11, 38, 52 or 56.

(1) MASS: 597 (M+1); NMR (CDCl$_3$, δ): 0.85 (3×¼H, t, J=8 Hz), 0.89 (3×¾H, t, J=8 Hz), 1.20–1.41 (4H, m), 1.47 (9H, s), 1.58–1.85 (2H, m), 2.57 (1H, dd, J=17, 4 Hz), 2.92 (3×¼H, s), 3.04 (3×¾H, s), 3.19 (1H, dd, J=17, 2 Hz), 3.40–3.50 (2H, m), 3.52–3.61 (2H, m), 3.62–3.85 (4H, m), 4.50–4.60 (1H, m), 4.57 (2×½H, d, J=15 Hz), 4.71 (2×½H, d, J=15 Hz), 4.83–5.00 (1H, m), 6.08 (1H, d, J=8 Hz), 7.30–7.50 (2H, m), 7.65–7.81 (2H, m), 8.31 (1H, d, J=8 Hz), 8.59 (1H, s), 8.67 (1H, d, J=2 Hz), 9.20 (1H, s)

(2) MASS: 561 (M+1); NMR (CDCl$_3$, δ): 0.79 (3×¼H, t, J=8 Hz), 0.80 (3×¾H, t, J=8 Hz), 0.93–1.30 (4H, m), 1.30–1.52 (1H, m), 1.43 (9H, s), 1.52–1.70 (1H, m), 2.90 (3×¼H, s), 3.01 (3×¾H, s), 3.19 (1×¼H, d, J=5 Hz), 3.21 (1×¾H, d, J=5 Hz), 3.28–3.40 (1H, m), 4.51 (2×½H, d, J=15 Hz), 4.51–4.62 (1H, m), 4.69 (2×½H, d, J=15 Hz), 5.80–5.93 (1H, m), 6.50–6.60 (1H, m), 7.10–7.22 (2H, m), 7.37–7.45 (1H, m), 7.46–7.80 (4H, m), 8.31 (1H, d, J=7 Hz), 8.51 (1H, d, J=4 Hz), 8.58 (1H, s), 8.65 (1H, d, J=2 Hz), 9.19 (1H, s)

(3) MASS: 544 (M+1); NMR (CDCl$_3$, δ): 0.86 (3×⅕H, t, J=8 Hz), 0.90 (3×⅘H, t, J=8 Hz), 1.29 (4×⅕H, t, J=8 Hz), 1.31 (4×⅘H, t, J=8 Hz), 1.42 (9H, s), 1.55–1.70 (1H, m), 1.70–1.85 (1H, m), 1.87–2.18 (2H, m), 2.09 (3H, s), 2.58 (2H, t, J=8 Hz), 2.94 (3×⅕H, s), 3.09 (3×⅘H, s), 4.22–4.35 (1H, m), 4.59 (2×½H, d, J=15 Hz), 4.70 (2×½H, d, J=15 Hz), 4.88–5.02 (1H, m), 5.12–5.23 (1H, m), 6.83–6.98 (1H, m), 7.41 (1H, dd, J=8, 6 Hz), 7.67–7.81 (2H, m), 8.30 (1H, d, J=8 Hz), 8.59 (1H, s), 8.66 (1H, d, J=2 Hz), 9.19 (1H, s)

(4) MASS (m/z): 534 (M$^+$+1); NMR (CDCl$_3$, δ): 0.87 (3H, t, J=7 Hz), 1.31 (4H, m), 1.47 (9H, s), 1.60–1.75 (2H, m), 2.54 (3H, s), 2.87 (3H×¼, s), 2.98 (3H×¾, s), 3.17 (1H, m), 3.43–3.57 (5H, m), 3.65 (4H, m), 4.40 (1H×¾, d, J=15 Hz), 4.53 (1H, m), 4.68 (2H×¼, s), 4.67 (1H×¾, d, J=15 Hz), 4.87 (1H, m), 6.06 (1H, d, J=7 Hz), 7.11–7.17 (1H, m), 7.32–7.47 (2H, m), 8.35 (1H, m)

(5) MASS (m/z): 498 (M$^+$+1); NMR (CDCl$_3$, δ): 0.80 (3H, t, J=7 Hz), 1.03 (2H, m), 1.17 (2H, m), 1.40 (1H, m), 1.46 (9H, s), 1.57 (1H, m), 2.53 (3H×¾, s), 2.54 (3H×¼, s), 2.85 (3H×¼, s), 2.95 (3H×¾, s), 3.18 (1H, dd, J=5, 14 Hz), 3.35 (1H, m), 4.37 (1H×¾, d, J=15 Hz), 4.54 (2H×¼, s), 4.57 (1H, m), 4.63 (1H×¾, d, J=15 Hz), 4.82 (1H, m), 6.56 (1H, d, J=7 Hz), 7.08–7.20 (3H, m), 7.43 (1H, dd, J=2, 8 Hz), 7.53 (1H, m), 7.58 (1H, m), 8.33 (1H, d, J=2 Hz), 8.49 (1H, d, J=5 Hz)

(6) MASS: 481 (M$^+$+1); NMR (CDCl$_3$, f): 0.87 (3H, t, J=7 Hz), 1.31 (4H, m), 1.44 (9H, s), 1.61 (1H, m), 1.72 (1H, m), 1.94 (1H, m), 2.05 (1H, m), 2.11 (3H, s), 2.54 (3H, s), 2.56 (2H, m), 2.89 (3H×¼, s), 3.00 (3H×¾, s), 4.28 (1H, m), 4.44 (1H×¾, d, J=15 Hz), 4.54 (1H×¼, d, J=16 Hz), 4.63 (1H×¼, d, J=16 Hz), 4.65 (1H×¾, d, J=15 Hz), 4.89 (1H, m), 5.22 (1H, m), 6.94 (1H, d, J=7 Hz), 7.13 (1H×¾, d, J=8 Hz), 7.17 (1H×¼, d, J=8 Hz), 7.46 (1H, dd, J=2, 8 Hz), 8.35 (1H, d, J=2 Hz)

(7) MASS (m/z): 437 (M$^+$+1); NMR (CDCl$_3$, δ): 0.87 (3H, t, J=7 Hz), 1.33 (4H, m), 1.44 (9H, s), 1.67 (2H, m), 2.54 (3H×¾, s), 2.55 (3H×¼, s), 2.88 (3H×¼, s), 3.02 (3H×¾, s), 3.63 (1H, m), 3.96 (1H, m), 4.23 (2H, m), 4.47 (1H×¼, d, J=16 Hz), 4.51 (1H×¾, d, J=15 Hz), 4.61 (1H×¾, d, J=15 Hz), 4.70 (1H×¼, d, J=16 Hz), 4.85 (1H, m), 5.56 (1H, d, J=7 Hz), 7.13 (1H, d, J=8 Hz), 7.21 (1H, d, J=7 Hz), 7.46 (1H×¾, d, J=2, 8 Hz), 7.57 (1H×¼, d, J=2, 8 Hz), 8.34 (1H×¾, d, J=2 Hz), 8.48 (1H×¼, d, J=2 Hz)

(8) MASS: 597 (M+1); NMR (CDCl$_3$, δ): 1.47 (9H, s), 2.29 (3H, s), 2.33–2.50 (4H, m), 2.53 (3×¾H, s), 2.58 (1H, dd, J=16 and 2 Hz), 2.78 (3×¼H, s), 2.98–3.09 (2H, m), 3.12–3.28 (1H, m), 3.40–3.50 (2H, m), 3.58–3.65 (2H, m), 3.79 (3×¼H, s), 3.81 (3×¾H, s), 3.89 (2×⅛H, d, J=16 Hz), 4.28 (2×⅛H, d, J=16 Hz), 4.38 (2×⅜H, d, J=15 Hz), 4.50 (2×⅜H, d, J=15Hz), 4.49–4.59 (1H, m), 5.07 (1×¾H, q, J=8 Hz), 5.19 (1×¼H, q, J=8 Hz), 6.02 (1H, d, J=8 Hz), 6.88 (1×¼H, s), 7.03 (1×¾H, s), 7.13–7.23 (5H, m), 7.43 (1×¼H, d, J=8 Hz), 7.47 (1×¾H, d, J=8 Hz), 7.82 (1×¼H, s), 7.98 (1×¾H, s), 8.19 (1×¼H, d, J=2 Hz), 8.21 (1×¾H, d, J=2 Hz)

(9) NMR (CDCl$_3$, δ): 1.43 (9H, s), 2.29 (3H, s), 2.31–2.50 (4H, m), 2.60 (3×⅔H, s), 2.70 (3×⅓H, s), 2.90–3.30 (4H, m), 3.40–3.53 (2H, m), 3.53–3.70 (2H, m), 3.77 (3×⅓H, s), 3.81 (3×⅔H, s), 4.31 (2×½H, d, J=15 Hz), 4.43–4.58 (1×⅔H, m), 4.60 (2×½H, d, J=15 Hz), 5.08 (1×⅔H, q, J=8 Hz), 5.32–5.46 (1×⅓H, m), 5.77 (1×⅓H, q, J=8 Hz), 6.02 (1H, t, J=8 Hz), 6.70–6.80 (1H, m), 7.10–7.33 (5H, m), 7.43 (1×⅔H, d, J=8 Hz), 7.50 (1×⅓H, d, J=8 Hz), 8.00 (1×⅓H, s), 8.20 (1×⅔H, s), 8.38–8.47 (1H, m)

(10) MASS: 645 (M+1); NMR (CDCl$_3$, δ): 1.47 (9H, s), 2.30 (3H, s), 2.32–2.50 (4H, m), 2.50–2.71 (1H, m), 2.56 (3×⅕H, s), 2.78 (3×⅕H, s), 2.96–3.13 (2H, m), 3.14–3.29 (1H, m), 3.42–3.50 (2H, m), 3.58–3.67 (2H, m), 4.11 (2×⅒H, d, J=15 Hz), 4.19 (2×⅖H, d, J=16 Hz), 4.22 (2×⅒H, d, J=15 Hz), 4.61 (2×⅖H, d, J=16 Hz), 4.48–4.58 (1H, m), 5.00–5.13 (1H, m), 5.98–6.08 (1H, m), 7.12–7.23 (5H, m), 7.32 (1×⅕H, s), 7.62 (1×⅕H, s), 7.40 (1×⅕H, d, J=8 Hz), 7.47 (1×⅕H, d, J=8 Hz), 8.10 (1×⅕H, s), 8.27 (1×⅕H, s), 8.52 (1×⅕H, s), 8.58 (1×⅕H, s)

Preparation 107

The following object compounds were obtained according to a similar manner to that of Preparation 3, 4, 8, 41 or 54.

(1) MASS: 497 (M+1); NMR (CDCl$_3$, δ): 0.88 (3×¼H, t, J=8 Hz), 0.89 (3×¾H, t, J=8 Hz), 1.20–1.42 (4H, m), 1.58–1.82 (2H, m), 2.60–2.90 (2H, m), 2.93 (3×¼H, s), 3.06 (3×¾H, s), 3.40–3.50 (2H, m), 3.50–3.72 (6H, m), 3.80–3.98 (1H, m), 4.58 (2×⅛H, d, J=16 Hz), 4.59 (2×⅜H, d, J=15 Hz), 4.69 (2×⅜H, d, J=15 Hz), 4.71 (2×⅛H, d, J=16 Hz), 4.80–5.00 (1H, m), 7.33–7.45 (1H, m), 7.63–7.80 (2H, m), 8.18 (1H, d, J=8 Hz), 8.30 (1H, d, J=8 Hz), 8.53–8.70 (2H, m), 9.18 (1H, s)

(2) MASS: 461 (M+1); NMR (CDCl$_3$, δ): 0.83 (3×¼H, t, J=8 Hz), 0.89 (3×¾H, t, J=8 Hz), 1.10–1.40 (4H, m), 1.52–1.80 (2H, m), 2.97 (3×¼H, s), 3.10 (3×¾H, s), 3.00–3.13 (1H, m), 3.25–3.38 (1H, m), 3.70–3.79 (1×¼H, m), 3.80–3.85 (1×¾H, m), 4.57 (2×⅜H, d, J=15 Hz), 4.71 (2×⅜H, d, J=15 Hz), 4.73 (2×¼H, s), 4.87–5.01 (1H, m), 7.18 (1H, t, J=5 Hz), 7.22 (1H, d, J=8 Hz), 7.37–7.45 (1H, m), 7.61 (1H, t, J=8 Hz), 7.68–7.81 (2H, m), 8.18 (1×¼H, d, J=8 Hz), 8.20 (1×¾H, d, J=8 Hz), 8.31 (1H, d, J=8 Hz), 8.52 (1H, d, J=2 Hz), 8.59 (1H, s), 8.63 (1H, d, J=2 Hz), 9.18 (1H, s)

(3) MASS: 444 (M+1); NMR (CDCl$_3$, δ): 0.85 (3×¼H, t, J=8 Hz), 0.89 (3×¾H, t, J=8 Hz), 1.20–1.45 (4H, m), 1.57–1.90 (3H, m), 2.09–2.22 (1H, m), 2.10 (3H, s), 2.61 (2H, t, J=8 Hz), 2.94 (3×¼H, s), 3.09 (3×¾H, s), 3.43–3.60 (1H, m), 4.58 (2×⅜H, d, J=15 Hz), 4.71 (2×⅜H, d, J=15 Hz), 4.70 (2×⅛H, d, J=16 Hz), 4.75 (2×⅛H, d, J=16 Hz), 4.88–5.12 (1H, m), 7.40 (1H, dd, J=8, 5 Hz), 7.64–7.81 (2H, m), 7.87 (1H, d, J=8 Hz), 8.30 (1H, dd, J=8, 2 Hz), 8.59 (1H, s), 8.63 (1H, d, J=2 Hz), 9.18 (1H, s)

(4) NMR (CDCl$_3$, δ): 0.88 (3H, t, J=7 Hz), 1.33 (4H, m), 1.66 (2H, m), 2.55 (3H, s), 2.67 (1H, dd, J=7, 15 Hz), 2.86 (1H, dd, J=3, 15 Hz), 2.91 (3H×¼, s), 3.02 (3H×¾, s), 3.47 (2H, m), 3.67 (6H, m), 3.73 (1H, m), 4.43 (1H×¾, d, J=15 Hz), 4.63 (2H×¼, s), 4.68 (1H×¾, d, J=15 Hz), 4.89 (1H, m), 7.13 (1H×¾, d, J=8 Hz), 7.16 (1H×¼, d, J=8 Hz), 7.47 (1H, m), 8.10 (1H, s), 8.36 (1H, d, J=2 Hz)

(5) NMR (CDCl$_3$, δ): 0.86 (3H, t, J=7 Hz), 1.22 (4H, m), 1.52–1.73 (2H, m), 2.53 (3H, s), 2.90 (3H×¼, s), 3.01 (3H×¾, s), 3.02–3.07 (1H, m), 3.26–3.34 (1H, m), 3.73 (1H×¼, dd, J=3, 7 Hz), 3.80 (1H×¾, dd, J=3, 7 Hz), 4.42 (1H×¾, d, J=15 Hz), 4.63 (2H×¼, s), 4.67 (1H×¾, d, J=15 Hz), 4.90 (1H, m), 7.12–7.37 (3H, m), 7.47 (1H, m), 7.62 (1H, m), 8.17 (1H, m), 8.35 (1H, s)

(6) NMR (CDCl$_3$, δ): 0.89 (3H, t, J=7 Hz), 1.31 (4H, m), 1.70 (2H, m), 1.83 (1H, m), 2.11 (3H, s), 2.15 (1H, m), 2.54 (3H, s), 2.62 (2H, t, J=7 Hz), 2.92 (3H×¼, s), 3.03 (3H×¾, s), 3.47 (1H×¼, m), 3.53 (1H×¾, m), 4.43 (1H×¾, d, J=15 Hz), 4.60 (1H×¼, d, J=16 Hz), 4.66 (1H×¼, d, J=16 Hz), 4.67 (1H×¾, d, J=15 Hz), 4.92 (1H, m), 7.13 (1H×¾, d, J=8 Hz), 7.17 (1H×¼, d, J=8 Hz), 7.47 (1H, d, J=8 Hz), 7.84 (1H, d, J=8 Hz), 8.35 (1H, s)

(7) NMR (CDCl$_3$, δ): 0.88 (3H, t, J=7 Hz), 1.32 (4H, m), 1.73 (2H, m), 2.54 (3H, s), 2.91 (3H×¼, s), 3.02 (3H×¾, s), 3.47 (1H, m), 3.67 (1H, m), 3.82 (1H, m), 4.47 (1H×¾, d, J=15 Hz), 4.53 (1H×¼, d, J=16 Hz), 4.65 (1H×¾, d, J=15 Hz), 4.69 (1H×¼, d, J=16 Hz), 4.88 (1H, m), 7.13 (1H×¾, d, J=8 Hz), 7.19 (1H×¼, d, J=8 Hz), 7.47 (1H×¾, m), 7.53 (1H×¼, m), 7.71 (1H, m)

(8) MASS: 497 (M+1); NMR (CDCl$_3$, δ): 2.31 (3H, s), 2.33–2.45 (4H, m), 2.43–2.53 (1H, m), 2.68 (3×¾H, s), 2.71–2.85 (1H, m), 2.81 (3×¼H, s), 2.97–3.16 (2H, m), 3.38–3.50 (2H, m), 3.52–3.73 (3H, m), 3.80 (3×¼H, s), 3.83 (3×¾H, s), 4.10 (2×⅛H, d, J=16 Hz), 4.40 (2×⅛H, d, J=16 Hz), 4.41 (2×⅜H, d, J=15 Hz), 4.54 (2×⅜H, d, J=15 Hz), 5.10 (1×¾H, q, J=8 Hz), 5.19 (1×¼H, q, J=8 Hz), 6.94 (1×¼H, s), 7.06 (1×¾H, s), 7.13–7.33 (5H, m), 7.90 (1×¼H, s), 8.01 (1×¾H, s), 8.11 (1×¼H, s), 8.17 (1×¾H, s), 8.20 (1×¼H, s), 8.22 (1×¾H, s)

(9) NMR (CDCl$_3$, δ): 2.31 (3H, s), 2.39–2.60 (4H, m), 2.74 (3×⅔H, s), 2.80 (3×⅓H, s), 2.76–2.86 (1H, m), 2.92–3.10 (3H, m), 3.40–3.50 (2H, m), 3.52–3.72 (2H, m), 3.67–3.72 (1×⅔H, m), 3.75–3.81 (1×⅓H, m), 3.81 (3×⅓H, s), 3.82 (3×⅔H, s), 3.87 (2×⅙H, d, J=16 Hz), 4.41 (2×⅙H, d, J=16 Hz), 4.42 (2×⅓H, d, J=15 Hz), 4.56 (2×⅓H, d, J=15 Hz), 5.10 (1×⅔H, q, J=8 Hz), 5.37 (1×⅓H, q, J=8 Hz), 6.73 (1×⅓H, d, J=8 Hz), 6.78 (1×⅔H, d, J=8 Hz), 7.10–7.31 (5H, m), 8.06 (1×⅓H, s), 8.21 (1×⅔H, s), 8.11–8.20 (1H, m), 8.41 (1H, d, J=8 Hz)

(10) MASS: 545 (M+1); NMR (CDCl$_3$, δ): 2.40 (3H, s), 2.43–2.64 (5H, m), 2.68 (3×⅕H, s), 2.71–2.88 (1H, m), 2.81 (3×⅕H, s), 2.97–3.14 (2H, m), 3.47–3.58 (2H, m), 3.60–3.83 (3H, m), 4.18 (2×⅛H, d, J=16 Hz), 4.30 (2×⅜H, d, J=15 Hz), 4.38 (2×⅛H, d, J=16 Hz), 4.58 (2×⅜H, d, J=15 Hz), 5.10 (1H, q, J=8 Hz), 7.11–7.30 (5H, m), 7.46 (1×¼H, s), 7.68 (1×¾H, s), 8.18 (1H, q, J=8 Hz), 8.20 (1×¼H, s), 8.30 (1×¾H, s), 8.58 (1×¼H, s), 8.60 (1×¾H, s)

Preparation 108

The following compound was obtained according to a similar manner to that of Preparation 23.

MASS: 201 (M+1); NMR (CDCl$_3$, δ): 2.49 (3H, s), 3.77 (2H, s), 7.84 (1H, s), 8.47 (1H, s), 8.57 (1H, s)

Preparation 109

To a solution of Starting Compound (1.02 g) in toluene (6 ml) was added Lawesson's reagent (1.29 g), and the mixture was refluxed for 24 hours. After the mixture was allowed to cool to room temperature, it was subjected to silica gel column chromatography (hexane) to collect a yellow bond. The eluate was evaporated and recrystallized from hexane to give Object Compound (600 mg) as yellow crystals.

mp: 78–79° C.; NMR (CDCl$_3$, δ): 4.28 (3H, s), 7.22–7.74 (5H, m)

Preparation 110

The following object compound was obtained according to a similar manner to that of Preparation 1, 6, 11, 38, 52 or 56.

MASS (m/z): 368 (M+H)$^+$; NMR (CDCl$_3$, δ): 1.42 (9H, s), 1.72–2.00 (2H, m), 2.02 (¼×3H, s), 2.08 (¾×3H, s), 2.52

(3H, s), 2.53 (2H, m), 2.89 (¼×3H, s), 3.02 (¾×3H, s), 4.51 (¼×1H, d, J=17 Hz), 4.53 (¾×2H, ABq, Δ=0.12, J=15 Hz), 4.72 (¼×1H, d, J=17 Hz), 4.73–4.97 (1H, m), 5.25–5.44 (1H, m), 7.10 (¾×1H, d, J=8 Hz), 7.15 (¼×1H, d, J=8 Hz), 7.46 (1H, dd, J=8, 2 Hz), 8.36 (1H, d, J=2 Hz)

Preparation 111

The following object compound was obtained according to a similar manner to that of Preparation 3, 4, 8, 41 or 54.

MASS (m/z): 268 (M+H)$^+$; NMR (CDCl$_3$, δ): 1.58–1.95 (2H, m), 2.03 (¼×3H, s), 2.08 (¾×3H, s), 2.50–2.78 (2H, m), 2.53 (3H, s), 2.92 (¼×3H, s), 2.98 (¾×3H, s), 3.81–3.94 (1H, m), 4.45 (¼×1H, d, J=17 Hz), 4.56 (¾×2H, ABq, Δ=0.19, J=15 Hz), 4.72 (¼×1H, d, J=17 Hz), 7.11 (¾×1H, d, J=8 Hz), 7.16 (¼×1H, d, J=8 Hz), 7.41 (¼×1H, dd, J=8, 2 Hz), 7.48 (¾×1H, dd, J=8, 2 Hz), 8.37 (1H, d, J=2 Hz)

Preparation 112

The following compounds were obtained according to a similar manner to that of Preparation 1, 6, 11, 38, 52 or 56.

(1) MASS (m/z): 516 (M+H)$^+$; NMR (CDCl$_3$, δ): 1.44 (9H, s), 1.56–1.97 (2H, m), 1.92 (¼×3H, s), 1.98 (¾×3H, s), 2.11–2.26 (2H, m), 2.52 (3H, s), 2.83 (¼×3H, s), 2.97 (¾×3H, s), 3.08–3.46 (2H, m), 4.48–4.62 (1H, m), 4.50 (¾×2H, ABq, Δ=0.25, J=15 Hz), 4.58 (¼×2H, s), 4.90–5.13 (1H, m), 6.45–6.63 (1H, m), 7.03–7.68 (6H, m), 8.32 (1H, s), 8.51 (1H, s)

(2) MASS (m/z): 455 (M+H)$^+$; NMR (CDCl$_3$, δ): 1.44 (9H, s), 1.75–2.15 (2H, m), 2.02 (¼×3H, s), 2.07 (¾×3H, s), 2.45–2.59 (5H, m), 2.87 (¼×3H, s), 3.03 (¾×3H, s), 3.50–3.69 (1H, m), 3.78 (1H, br s), 3.85–4.10 (1H, m), 4.10–4.30 (1H, m), 4.46 (¼×1H, d, J=17 Hz), 4.53 (¾×2H, ABq, Δ=0.13, J=15 Hz), 4.78 (¼×1H, d, J=17 Hz), 4.98–5.22 (1H, m), 5.42–5.58 (1H, m), 7.03–7.62 (3H, m), 8.32 (¾×1H, s), 8.38 (¼×1H, s)

(3) MASS (m/z): 552 (M+H)$^+$; NMR (CDCl$_3$, δ): 1.47 (9H, s), 1.81–2.10 (2H, m), 2.02 (3H×¼, s), 2.08 (3H×¾, s), 2.46–2.61 (6H, m), 2.89 (3H×¼, s), 3.02 (3H×¾, s), 3.16–3.28 (1H, m), 3.37–3.49 (2H, m), 3.53–3.75 (6H, m), 4.40 (1H×¾, d, J=15.0 Hz), 4.48–4.60 (1H+1H×¼, m), 4.68 (1H, d, J=15.0 Hz), 5.01–5.11 (1H×¾, m), 5.13–5.22 (1H×¼, m), 6.02 (1H, d, J=8.5 Hz), 7.12 (1H×¾, d, J=8.5 Hz), 7.17 (1H×¼, d, J=8.5 Hz), 7.35 (1H×¼, d, J=8.5 Hz), 7.43 (1H×¾, d, J=8.5 Hz), 7.46 (1H, dd, J=8.5, 1.0 Hz), 8.36 (1H, d, J=1.0 Hz)

(4) MASS (m/z): 499 (M+H)$^+$; NMR (CDCl$_3$, δ): 1.47 (9H, s), 1.79–2.14 (4H, m), 2.03 (3H×¼, s), 2.08 (3H×¾, s), 2.11 (3H, s), 2.45–2.62 (7H, s), 2.89 (3H×¼, s), 3.03 (3H×¾, s), 4.20–4.33 (1H, m), 4.44 (1H×¾, d, J=15.0 Hz), 4.54 (1H×¼, d, J=15.0 Hz), 4.64 (1H×¾, d, J=15.0 Hz), 4.72 (1H×¼, d, J=15.0 Hz), 5.02–5.25 (2H, m), 6.93 (1H×¼, d, J=8.5 Hz), 6.98 (1H×¾, d, J=8.5 Hz), 7.13 (1H×¾, d, J=8.5 Hz), 7.19 (1H×¼, d, J=8.5 Hz), 7.46 (1H×¾, dd, J=8.5, 1.5 Hz), 7.48 (1H×¼, dd, J=8.5, 1.5 Hz), 8.37 (1H, d, J=11.5 Hz)

Preparation 113

The following compounds were obtained according to a similar manner to that of Preparation 3, 4, 8, 41 or 54.

(1) MASS (m/z): 416 (M+H)$^+$; NMR (CDCl$_3$, δ): 1.74–2.03 (2H, m), 2.00 (¼×3H, s), 2.06 (¾×3H, s), 2.30–2.46 (2H, m), 2.54 (3H, s), 2.88 (¼×3H, s), 3.02 (¾×3H, s), 3.07–3.38 (2H, m), 3.77–3.97 (1H, m), 4.53 (¾2H, ABq, Δ=0.18, J=15 Hz), 4.62 (¼×2H, ABq, Δ=0.13, J=17 Hz), 4.98–5.22 (1H, m), 7.07–7.68 (5H, m), 8.17–8.32 (1H, m), 8.36 (1H, s), 8.48–8.55 (1H, m)

(2) MASS (m/z): 355 (M+H)$^+$; NMR (CDCl$_3$, δ): 1.80–2.10 (2H, m), 2.02 (¼×3H, s), 2.06 (¾×3H, s), 2.42–2.58 (5H, m), 2.90 (¼×3H, s), 3.05 (¾×3H, s), 3.38–4.02 (3H, m), 4.46 (¼×1H, d, J=17 Hz), 4.54 (¾×2H, ABq, Δ=0.16, J=15 Hz), 4.78 (¼×1H, d, J=17 Hz), 5.01–5.22 (1H, m), 7.08–7.22 (1H, m), 7.42–7.57 (1H, m), 7.76–7.93 (1H, m), 8.37 (1H, s)

(3) MASS (m/z): 452 (M+H)$^+$; NMR (CDCl$_3$, δ): 1.85–2.21 (2H, m), 2.02 (3H×¼, s), 2.09 (3H×¾, s), 2.49–2.61 (5H, m), 2.73–2.82 (2H, m), 2.90 (3H×¼, s), 3.04 (3H×¾, s), 3.40–3.50 (2H, m), 3.54–3.74 (7H, m), 4.43 (1H×¾, d, J=15.0 Hz), 4.59 (1H×¼, d, J=15.0 Hz), 4.65 (1H×¾, d, J=15.0 Hz), 4.71 (1H×¼, d, J=15.0 Hz), 5.01–5.21 (1H, m), 7.11 (1H×¾, d, J=8.5 Hz), 7.17 (1H×¼, d, J=8.5 Hz), 7.48 (1H, dd, J=8.5, 1.0 Hz), 8.14 (1H×¼, d, J=8.5 Hz), 8.20 (1H×¾, d, J=8.5 Hz), 8.37 (1H, d, J=1.0 Hz)

(4) MASS (m/z): 399 (M+H)$^+$; NMR (CDCl$_3$, δ): 1.71–2.22 (4H, m), 2.03 (3H×¼, s), 2.09 (3H×¾, s), 2.10 (3H, s), 2.45–2.67 (4H, m), 2.55 (3H, s), 2.90 (3H×¼, s), 3.06 (3H×¾, s), 3.44 (1H×¼, dd, J=8.5, 5.5 Hz), 3.52 (1H×¾, dd, J=8.5, 5.5 Hz), 4.43 (1H×¾, d, J=14.5 Hz), 4.60 (1H×¼, d, J=16.0 Hz), 4.67 (1H×¾, d, J=14.5 Hz), 4.73 (1H×¼, d, J=16.0 Hz), 5.03–5.22 (1H, m), 7.12 (1H×¾, d, J=8.5 Hz), 7.17 (1H×¼, d, J=8.5 Hz), 7.47 (1H×¾, dd, J=8.5, 1.0 Hz), 7.50 (1H×¼, dd, J=8.5, 1.0 Hz), 7.88–7.98 (1H, m), 8.37 (1H, d, J=1.0 Hz)

Preparation 114

The following compound was obtained according to a similar manner to that of Preparation 23.

(1) MASS: 153 (M+1); NMR (CDCl$_3$, δ): 2.43 (3H, s), 3.78 (2H, s), 3.96 (3H, s), 6.76 (1H, d, J=7 Hz), 8.35 (1H, s), 8.43 (1H, d, J=7 Hz)

(2) MASS: 153 (M+1); NMR (CDCl$_3$, δ): 2.43 (3H, s), 3.72 (2H, s), 3.81 (3H, s), 7.20 (1H, s), 8.12 (1H, s), 8.19 (1H, d, J=2 Hz)

EXAMPLE 1

To an ice-cooled solution of benzo[b]furan-2-carboxylic acid (70 mg), Starting Compound (200 mg), and 1-hydroxybenzotriazole (58 mg) in methylene chloride (20 ml), was added 1-ethyl-3-(3-dimethylaminopropyl) carbodiimide hydrochloride (82 mg). The solution was stirred at the same temperature for an hour and at room temperature overnight. The mixture was concentrated under vacuum and the residue was diluted in water and extracted with chloroform. The organic layer was washed with saturated sodium hydrogencarbonate solution, water and brine, and was dried over magnesium sulfate. After evaporation, the crude material obtained was purified on a column of silica gel eluting with chloroform-methanol (30:1) to give Object Compound (260 mg) as an amorphous solid.

MASS (FAB) (m/z): 610 (M+H)$^+$; NMR (CDCl$_3$, δ): 2.28 (3H, s), 2.36–2.50 (4H, m), 2.58 (3×⅔H, s), 2.62–2.71 (1H, m), 2.80 (3×⅓H, s), 2.98–3.11 (2H, m), 3.27–3.38 (1H, m), 3.42–3.56 (2H, m), 3.66–3.70 (2H, m), 4.11–4.38 (2×⅔H, m), 4.65 (2×⅓H, d, J=15 Hz), 5.02–5.17 (2H, m), 6.93–7.06 (2H, m), 7.12–7.21 (6H, m), 7.22–7.32 (3H, m), 7.43 (1H, t, J=8 Hz), 7.50 (1H, s), 7.57 (1H, d, J=8 Hz), 7.63–7.72 (2H, m), 8.19–8.23 (1H, m)

EXAMPLE 2

The following object compounds were obtained according to a similar manner to that of Example 1.

(1) MASS (FAB) (m/z): 626 (M+H)$^+$; NMR (CDCl$_3$, δ): 2.28 (3H, s), 2.34–2.51 (4H, m), 2.56–2.68 (1H, m), 2.62

(3×⅔H, s), 2.80 (3×⅓H, s), 3.00–3.07 (2H, m), 3.31 (1H, t, J=15 Hz), 3.42–3.58 (2H, m), 3.62–3.70 (2H, m), 4.12–4.41 (2×⅔H, m), 4.64 (2×⅓H, d, J=15 Hz), 4.98–5.14 (2H, m), 6.98–7.08 (2H, m), 7.12–7.21 (6H, m), 7.23–7.31 (3H, m), 7.37–7.46 (2H, m), 7.68–7.75 (1H, m), 7.80–7.88 (2H, m), 8.13 (1H, d, J=8 Hz)

(2) MASS (FAB) (m/z): 613 (M+H)$^+$; NMR (CDCl$_3$, δ): 2.52–2.69 (1H, m), 2.63 (3×⅔H, s), 2.83 (3×⅓H, s), 3.01–3.09 (2H, m), 3.30 (1H, t, J=15 Hz), 3.41–3.53 (2H, m), 3.62–3.79 (6H, m), 4.12–4.43 (2×⅔H, m), 4.63 (2×⅓H, d, J=15 Hz), 4.98–5.13 (2H, m), 6.99–7.21 (7H, m), 7.23–7.33 (3H, m), 7.36–7.45 (2H, m), 7.67–7.90 (4H, m), 8.12 (1H, t, J=8 Hz)

(3) MASS (FAB) (m/z): 596 (M+H)$^+$; NMR (CDCl$_3$, δ): 2.58–2.70 (1H, m), 2.59 (3×⅔H, s), 2.82 (3×⅓H, s), 3.04 (2H, t, J=8 Hz), 3.29 (1H, t, J=15 Hz), 3.42–3.58 (2H, m), 3.63–3.77 (6H, m), 4.12–4.40 (2×⅔H, m), 4.66 (2×⅓H, d, J=15 Hz), 5.02–5.16 (2H, m), 6.97–7.33 (11H, m), 7.42–7.72 (5H, m), 8.11 (1H, d, J=8 Hz)

(4) MASS (FAB) (m/z): 630 (M+H)$^+$; NMR (CDCl$_3$, δ): 2.68 (3×⅔H, s), 2.72 (1H, dd, J=15, 7 Hz), 2.83 (3×⅓H, s), 2.95–3.08 (2H, m), 3.11–3.22 (1H, m), 3.33–3.48 (2H, m), 3.53–3.68 (6H, m), 4.19–4.42 (2×⅔H, m), 4.72 (2×⅓H, d, J=15 Hz), 5.13–5.32 (2H, m), 6.88 (1H, d, J=8 Hz), 6.98–7.12 (6H, m), 7.18 (1H, d, J=8 Hz), 7.22–7.29 (4H, m), 7.33 (1H, d, J=8 Hz), 7.59 (1H, s), 8.04–8.22 (2H, m)

(5) MASS (FAB) (m/z): 626 (M+H)$^+$; NMR (CDCl$_3$, δ): 2.62 (3×⅔H, s), 2.72 (1H, dd, J=15, 7 Hz), 2.83 (3×⅓H, s), 2.93–3.08 (2H, m), 3.13–3.22 (1H, m), 3.33–3.50 (2H, m), 3.52–3.68 (6H, m), 3.87 (3H, s), 4.17–4.40 (2×⅔H, m), 4.71 (2×⅓H, d, J=15 Hz), 5.12–5.30 (2H, m), 6.89–7.00 (3H, m), 7.02–7.16 (8H, m), 7.27–7.33 (3H, m), 7.95–8.13 (2H, m)

(6) MASS (FAB) (m/z): 614 (M+H)$^+$; NMR (CDCl$_3$, δ): 2.67 (3×⅔H, s), 2.72 (1H, dd, J=15, 8 Hz), 2.82 (3×⅓H, s), 2.99–3.03 (2H, m), 3.13–3.24 (1H, m), 3.33–3.49 (2H, m), 3.53–3.68 (6H, m), 4.19–4.41 (2×⅔H, m), 4.70 (2×⅓H, d, J=15 Hz), 5.13–5.31 (2H, m), 6.91–7.15 (9H, m), 7.25–7.29 (4H, m), 7.32–7.38 (1H, m), 8.02–8.17 (2H, m)

(7) MASS (FAB) (m/z): 597 (M$^+$+1); NMR (CDCl$_3$, δ): 2.42 (1×⅓H, d, J=15 Hz), 2.61 (1H, m), 2.88 (3×⅓H, s), 2.97 (3×⅔H, s), 3.05–3.28 (3H, m), 3.41 (2H, m), 3.55–3.64 (6H, m), 4.30 (1×⅓H, d, J=15 Hz), 4.75 (1×⅔H, d, J=15 Hz), 4.85 (1×⅔H, d, J=15 Hz), 5.17 (1H, m), 5.39 (1H, m), 6.98–7.17 (5H, m), 7.22–7.33 (3H, m), 7.37–7.66 (3H, m), 8.00–8.48 (3H, m)

(8) MASS (FAB) (m/z): 610 (M$^+$+1); NMR (CDCl$_3$, δ): 2.27 (3H, s), 2.24–2.38 (4H, m), 2.55–2.67 (1H, m), 2.85 (3×⅓H, s), 2.96 (3×⅔H, s), 3.07–3.32 (3H, m), 3.45 (2H, m), 3.62 (2H, m), 4.23 (1×⅔H, d, J=15 Hz), 4.53 (1×⅓H, d, J=15 Hz), 4.81 (1×⅔H, d, J=15 Hz), 4.88 (1×⅓H, d, J=15 Hz), 5.14 (1H, m)i, 5.38 (1H, q, J=7 Hz), 6.98–7.33 (10H, m), 7.38–7.53 (2H, m), 7.63 (1H, m), 8.03–8.16 (2H, m), 8.37 (1H, m)

(9) MASS (FAB) (m/z): 575 (M$^+$+1); NMR (CDCl$_3$, δ): 1.75 (1H, m), 2.17 (3H, s), 2.15–2.32 (3H, m), 2.69 (1H, dd, J=6, 15 Hz), 2.93–3.03 (3H, m), 3.23–3.67 (12H, m), 5.12 (1H, m), 5.17 (1H, m), 7.00 (1H, d, J=2 Hz), 7.12–7.22 (6H, m), 7.30 (1H, t, J=8 Hz), 7.44 (1H, d, J=8 Hz), 7.66 (1H, d, J=8 Hz), 7.91 (1H, d, J=7 Hz), 8.04 (1H, d, J=8 Hz)

(10) MASS (FAB) (m/z): 577 (M$^+$+1); NMR (CDCl$_3$, δ): 2.17 (6×⅓H, s), 2.21 (6×⅔H, s), 2.30 (1H, m), 2.65–2.75 (1H, m), 2.72 (3×⅔H, s), 2.89 (3×⅓H, s), 2.99 (2H, d, J=7 Hz), 3.09 (1H, m), 3.18–3.27 (2H, m), 3.44 (2H, m), 3.52 (1H, m), 3.62 (6H, m), 5.05 (1H, m), 5.18 (1H, m), 6.98 (1H, s), 7.12–7.17 (6H, m), 7.30 (1H, d, J=8 Hz), 7.45 (1H, d, J=8 Hz), 7.65 (1H, d, J=8 Hz), 7.88 (1H, m), 7.95–8.02 (1H, m)

(11) MASS (FAB) (m/z): 582 (M$^+$+1); NMR (CDCl$_3$, δ): 2.63–2.76 (2H, m), 2.90 (1H, dd, J=7, 13 Hz), 3.19 (3H, s), 3.18–3.25 (1H, m), 3.44 (2H, m), 3.65 (6H, m), 4.75 (1H, q, J=7 Hz), 5.12 (1H, m), 6.88–6.95 (5H, m), 7.12 (4H, m), 7.28–7.33 (4H, m), 7.44 (1H, d, J=8 Hz), 7.65 (1H, d, J=8 Hz), 7.80 (1H, d, J=7 Hz), 7.94 (1H, d, J=8 Hz)

(12) MASS (FAB) (m/z): 618 (M+H)$^+$; NMR (CDCl$_3$, δ): 2.60 (3×⅔H, s), 2.72–2.88 (1H, m), 2.82 (3×⅓H, s), 2.91–3.20 (3H, m), 4.16–4.40 (2×⅔H, m), 4.65 (2×⅓H, d, J=15 Hz), 4.99–5.17 (2H, m), 5.17 (2H, s), 6.98–7.15 (7H, m), 7.27–7.37 (10H, m), 7.45 (1H, t, J=8 Hz), 7.51–7.55 (2H, m), 7.68–7.78 (2H, m)

(13) mp: 154° C.; MASS (FAB) (m/z): 542 (M$^+$+1); NMR (CDCl$_3$, δ): 1.24 (3H, t, J=7 Hz), 2.77 (1H, dd, J=7, 16 Hz), 3.02–3.17 (3H, m), 4.17 (2H, q, J=7 Hz), 4.82 (1H, q, J=7 Hz), 5.07 (1H, m), 5.14 (1H, d, J=15 Hz), 5.20 (1H, d, J=15 Hz), 6.78 (1H, s), 7.05 (5H, s), 7.14–7.21 (2H, m), 7.29–7.37 (5H, m), 7.43 (1H, d, J=8 Hz), 7.54 (1H, d, J=8 Hz), 7.67 (1H, d, J=8 Hz), 9.15 (1H, br s)

EXAMPLE 3

Starting Compound (200 mg), 4-cyclohexylpiperazine (64 mg), and 1-hydrobenzotriazole (51 mg) were dissolved in a mixed solvent of methylene chloride (20 ml) and N,N-dimethylformamide (10 ml). The mixture was ice-cooled and 1-ethyl-3-(3-dimethylaminopropyl)carbodiimide hydrochloride (73 mg) was added thereto. The mixture was stirred at this temperature for 1 hour and at room temperature for overnight. The mixture was concentrated under vacuum and residue was diluted in water and extracted with chloroform. The organic layer was washed with saturated sodium hydrogencarbonate solution and brine. After evaporation, the crude material obtained was purified on a column of silica gel eluting with chloroform-methanol (60:1) to give Object Compound (210 mg) as an amorphous solid.

MASS (FAB) (m/z): 677 (M+H)$^+$; NMR (CDCl$_3$, δ): 0.98–1.21 (5H, m), 1.53–1.61 (1H, m), 1.70–1.80 (4H, m), 2.40–2.52 (4H, m), 2.50–2.65 (1H, m), 2.56 (3×⅔H, s), 2.62–2.77 (1H, m), 2.80 (3×⅓H, s), 2.94–3.08 (2H, m), 3.18–3.28 (1H, m), 3.35–3.47 (2H, m), 3.52–3.65 (2H, m), 4.17–4.36 (2×⅔H, m), 4.69 (2×⅓H, d, J=15 Hz), 5.11–5.27 (2H, m), 6.93–7.15 (9H, m), 7.22–7.29 (4H, m), 7.43 (1H, d, J=8 Hz), 7.66 (1H, d, J=8 Hz), 7.99–8.12 (2H, m)

EXAMPLE 4

The following object compounds were obtained according to a similar manner to that of Example 3.

(1) MASS (FAB) (m/z): 637 (M+H)$^+$; NMR (CDCl$_3$, δ): 0.84 (3H, t, J=8 Hz), 1.41–1.52 (2H, m), 2.27 (2H, t, J=8 Hz), 2.32–2.46 (4H, m), 2.58 (3×⅔H, s), 2.62–2.72 (1H, m), 2.80 (3×⅓H, s), 2.95–3.08 (2H, m), 3.22–3.31 (1H, m), 3.40–3.51 (2H, m), 3.56–3.70 (2H, m), 4.14–4.38 (2×⅔H, m), 4.69 (2×⅓H, d, J=15 Hz), 5.10–5.21 (2H, m), 6.95–7.18 (10H, m), 7.23–7.30 (3H, m), 7.43 (1H, d, J=8 Hz), 7.65 (1H, d, J=8 Hz), 7.89–7.97 (1H, m), 8.04–8.11 (1H, m), 9.87 (1H, br s)

(2) MASS (FAB) (m/z): 594 (M+H)$^+$; NMR (CDCl$_3$, δ): 1.28–1.53 (6H, m), 1.75–1.92 (2H, m), 2.62–2.76 (1H, m), 2.72 (3×⅔H, s), 2.92 (3×⅓H, s), 2.83–3.19 (3H, m), 4.09 (1H, m), 4.22 (2×⅓H, d, J=15 Hz), 4.39 (2×⅓H, s), 4.90 (2×⅓H, d, J=15 Hz), 5.23–5.41 (1H, m), 5.60–5.80 (1H, m), 6.85–7.11 (7H, m), 7.12–7.16 (3H, m), 7.22–7.30 (4H, m), 7.43–7.50 (1H, m), 7.62–7.68 (1H, m), 8.04 (1×⅓H, d, J=8 Hz), 8.22 (1×⅔H, d, J=8 Hz), 8.91 (1×⅓H, d, J=8 Hz), 9.00 (1×⅔H, d, J=8 Hz)

(3) MASS (FAB) (m/z): 667 (M+H)⁺; NMR (CDCl₃, δ): 1.27 (3H, t, J=8 Hz), 2.58–2.71 (1H, m), 2.65 (3×⅔H, s), 2.89 (3×⅓H, s), 2.99–3.04 (2H, m), 3.28 (1H, t, J=15 Hz), 3.40–3.58 (6H, m), 3.60–3.67 (2H, m), 4.15 (2H, q, J=8 Hz), 4.28–4.43 (2×⅔H, m), 4.68 (2×⅓H, d, J=15 Hz), 5.05–5.18 (2H, m), 6.98–7.20 (9H, m), 7.26–7.33 (4H, m), 7.45 (1H, d, J=8 Hz), 7.67–7.82 (2H, m), 8.03 (1H, d, J=8 Hz), 9.41 (1H, d, J=8 Hz)

(4) mp: 85–90° C.; MASS (FAB) (m/z): 609 (M+H)⁺; NMR (CDCl₃, δ): 2.30 (3H, s), 2.33–2.52 (4H, m), 2.57–2.69 (1H, m), 2.62 (3×⅔H, s), 2.73 (3×⅓H, s), 2.99–3.07 (2H, m), 3.27–3.36 (1H, m), 3.42–3.55 (2H, m), 3.58–3.75 (2H, m), 4.14–4.41 (2×⅔H, m), 4.67 (2×⅓H, m), 5.12 (2H, t, J=8 Hz), 6.95–7.21 (9H, m), 7.23–7.35 (4H, m), 7.43 (1H, d, J=8 Hz), 7.69 (1H, d, J=8 Hz), 7.78 (1H, t, J=8 Hz), 8.07 (1H, t, J=8 Hz), 9.37 (1H, br s)

(5) MASS (FAB) (m/z): 594 (M+H)⁺; NMR (CDCl₃, δ): 1.45–1.69 (6H, m), 2.60 (3×⅔H, s), 2.57–2.69 (1H, m), 2.82 (3×⅓H, s), 3.00–3.10 (2H, m), 3.25–3.43 (3H, m), 3.45–3.70 (2H, m), 4.15–4.40 (2×⅔H, m), 4.67 (2×⅓H, d, J=15 Hz), 5.02–5.18 (2H, m), 6.95–7.08 (3H, m), 7.12–7.19 (6H, m), 7.24–7.32 (4H, m), 7.43 (1H, d, J=8 Hz), 7.69 (1H, d, J=8 Hz), 7.73–7.82 (1H, m), 8.14 (1H, t, J=8 Hz), 9.41 (1H, br s)

(6) MASS (FAB) (m/z): 580 (M+H)⁺; NMR (CDCl₃, δ): 1.80–1.95 (4H, m), 2.53–2.68 (1H, m), 2.61 (3×⅔H, s), 2.82 (3×⅓H, s), 2.98–3.07 (2H, m), 3.17 (1H, t, J=15 Hz), 3.29–3.40 (1H, m), 3.42–3.57 (3H, m), 4.18–4.39 (2×⅔H, m), 4.68 (2×⅓H, d, J=15 Hz), 5.10–5.17 (2H, m), 6.94–7.16 (9H, m), 7.21–7.30 (4H, m), 7.43 (1H, d, J=8 Hz), 7.66 (1H, d, J=8 Hz), 7.98–8.02 (1H, m), 8.40 (1H, t, J=8 Hz), 9.80 (1H, d, J=10 Hz)

(7) MASS (FAB) (m/z): 612 (M+H)⁺; NMR (CDCl₃, δ): 2.52–2.62 (4H, m), 2.63 (3×⅔H, s), 2.66–2.73 (1H, m), 2.86 (3×⅓H, s), 2.99–3.08 (2H, m), 3.15–3.26 (1H, m), 3.63–3.70 (2H, m), 3.79–3.93 (2H, m), 4.18–4.42 (2×⅔H, m), 4.70 (2×⅓H, d, J=15 Hz), 5.12–5.28 (2H, m), 6.97–7.15 (9H, m), 7.24–7.30 (4H, m), 7.46 (1H, d, J=8 Hz), 7.67 (1H, d, J=8 Hz), 7.98–8.08 (2H, m)

(8) MASS (FAB) (m/z): 566 (M+H)⁺; NMR (CDCl₃, δ): 0.38–0.61 (4H, m), 2.52–2.69 (2H, m), 2.71 (3×⅔H, s), 2.89–3.09 (2H, m), 2.92 (3×⅓H, s), 3.11–3.22 (1H, m), 4.19–4.51 (2×⅔H, m), 4.97 (2×⅓H, d, J=15 Hz), 5.30–5.50 (1H, m), 5.71–5.94 (1H, m), 6.87–7.08 (6H, m), 7.12–7.18 (3H, m), 7.22–7.28 (4H, m), 7.39–7.50 (2H, m), 7.62 (1H, d, J=8 Hz), 8.18 (1×⅓H, d, J=8 Hz), 8.35 (1×⅔H, d, J=8 Hz), 9.10 (1×⅓H, d, J=8 Hz), 9.21 (1×⅔H, d, J=8 Hz)

(9) MASS (FAB) (m/z): 673 (M+H)⁺; NMR (CDCl₃, δ): 2.63 (3×⅔H, s), 2.67–2.80 (1H, m), 2.81 (3×⅓H, s), 2.98–3.08 (2H, m), 3.26 (1H, t, J=8 Hz), 3.47–3.53 (2H, m), 3.63–3.92 (6H, m), 4.18–4.39 (2×⅔H, m), 4.72 (2×⅓H, d, J=15 Hz), 5.12–5.31 (2H, m), 6.49–6.53 (1H, m), 6.97–7.13 (9H, m), 7.2–7.30 (4H, m), 7.47 (1H, d, J=8 Hz), 7.67 (1H, d, J=8 Hz), 8.00–8.10 (2H, m), 8.30 (2H, d, J=5 Hz)

(10) MASS (FAB) (m/z): 681 (M+H)⁺; NMR (CDCl₃, δ): 1.23 (3H, t, J=8 Hz), 2.46–2.58 (4H, m), 2.60 (3×⅔H, s), 2.59–2.75 (1H, m), 2.81 (3×⅓H, s), 2.99–3.03 (2H, m), 3.17 (2H, s), 3.20–3.28 (1H, m), 3.47–3.51 (3H, m), 3.60–3.73 (2H, m), 4.17 (2H, q, J=8 Hz), 4.19–4.39 (2×⅔H, m), 4.71 (2×⅓H, d, J=15 Hz), 5.11–5.25 (2H, m), 6.94–7.14 (9H, m), 7.21–7.29 (4H, m), 7.43 (1H, d, J=8 Hz), 7.63 (1H, d, J=8 Hz), 7.93–8.07 (2H, m)

(11) MASS (FAB) (m/z): 677 (M+H)⁺; NMR (CDCl₃, δ): 1.32–1.47 (4H, m), 1.50–1.60 (4H, m), 1.78–1.82 (2H, m), 2.42–2.52 (6H, m), 2.55–3.03 (4H, m), 2.62 (3×⅔H, s), 2.81 (3×⅓H, s), 3.18–3.30 (1H, m), 3.80–3.90 (1H, m), 4.18–4.37 (2×⅔H, m), 4.69 (2×⅓H, d, J=15 Hz), 4.58–4.62 (1H, m), 5.11–5.25 (2H, m), 6.93–7.03 (2H, m), 7.08–7.18 (7H, m), 7.25–7.30 (4H, m), 7.44 (1H, d, J=8 Hz), 7.65 (1H, d, J=8 Hz), 7.98–8.13 (2H, m)

(12) MASS (FAB) (m/z): 580 (M+H)⁺; NMR (CDCl₃, δ): 1.47–1.62 (2H, m), 1.70–1.88 (2H, m), 2.04–2.15 (1H, m), 2.20–2.30 (1H, m), 2.62–2.73 (1H, m), 2.70 (3×⅔H, s), 2.86–3.17 (3H, m), 2.92 (3×⅓H, s), 4.21–4.46 (2×⅔H, m), 4.23–4.32 (1H, m), 4.93 (2×⅓H, d, J=15 Hz), 5.27–5.43 (1H, m), 5.67–5.88 (1H, m), 6.90–7.13 (9H, m), 7.22–7.30 (5H, m), 7.48 (1H, d, J=8 Hz), 7.64 (1H, d, J=8 Hz), 8.03 (1×⅓H, d, J=8 Hz), 8.21 (1×⅔H, d, J=8 Hz), 9.00 (1×⅓H, d, J=8 Hz), 9.10 (1×⅔H, d, J=8 Hz)

(13) MASS (FAB) (m/z): 637 (M+H)⁺; NMR (CDCl₃, δ): 1.99 (3×⅓H, s), 2.02 (3×⅔H, s), 2.61 (3×⅔H, s), 2.72 (1H, dd, J=15, 5 Hz), 2.84 (3×⅓H, d, J=2 Hz), 2.97–3.07 (2H, m), 3.13–3.26 (1H, m), 3.32–3.42 (4H, m), 3.50–3.68 (4H, m), 4.15–4.42 (2×⅔H, m), 4.69 (2×⅓H, t, J=15 Hz), 5.11–5.32 (2H, m), 6.93–7.14 (9H, m), 7.22–7.31 (4H, m), 7.46 (1H, d, J=8 Hz), 7.65 (1H, d, J=8 Hz), 7.95–8.17 (2H, m)

(14) MASS (FAB) (m/z): 608 (M+H)⁺; NMR (CDCl₃, δ): 0.80–1.11 (3H, m), 1.17–1.31 (2H, m), 1.47–1.67 (3H, m), 1.78–1.91 (2H, m), 2.58–2.68 (1H, m), 2.69 (3×⅔H, s), 2.77–2.86 (1H, m), 2.89 (3×⅓H, s), 3.00–3.12 (2H, m), 3.61–3.75 (1H, m), 4.20–4.42 (2×⅔H, m), 4.88 (2×⅓H, d, J=15 Hz), 5.18–5.31 (1H, m), 5.38–5.52 (1H, m), 6.38 (1H, t, J=8 Hz), 6.98–7.10 (9H, m), 7.21–7.32 (4H, m), 7.45 (1H, dd, J=8, 2 Hz) 7.63 (1H, dd, J=8, 2 Hz), 7.96 (1×⅓H, d, J=8 Hz), 8.07 (1×⅔H, d, J=8 Hz), 8.60–8.67 (1H, m)

(15) MASS (FAB) (m/z): 610 (M+H)⁺; NMR (CDCl₃, δ): 2.21 (6×⅓H, s), 2.23 (6×⅔H, s), 2.41–2.57 (3H, m), 2.59 (3×⅔H, s), 2.64–2.73 (1H, m), 2.81 (3×⅓H, s), 2.97–3.03 (2H, m), 3.02 (3H, s), 3.18–3.60 (2H, m), 4.17–4.38 (2×⅔H, m), 4.69 (2×⅓H, d, J=15 Hz), 5.10–5.21 (2H, m), 6.94–7.06 (2H, m), 7.10–7.18 (7H, m), 7.23–7.31 (4H, m), 7.45 (1H, d, J=8 Hz), 7.65 (1H, d, J=8 Hz), 7.89–8.00 (1H, m), 8.11–8.23 (1H, m), 9.90 (1H, br s)

(16) MASS (FAB) (m/z): 623 (M+H)⁺; NMR (CDCl₃, δ): 1.82–1.97 (2H, m), 2.32 (3H, m), 2.51–2.73 (5H, m), 2.62 (3×⅔H, s), 2.81 (3×⅓H, s), 2.94–3.08 (2H, m), 3.20–3.30 (1H, m), 3.42–3.75 (4H, m), 4.14–4.39 (2×⅔H, m), 4.68 (2×⅓H, dd, J=15, 5 Hz), 5.09–5.21 (2H, m), 6.97–7.05 (2H, m), 7.10–7.15 (6H, m), 7.22–7.30 (5H, m), 7.45 (1H, d, J=8 Hz), 7.66 (1H, d, J=8 Hz), 7.91–8.00 (1H, m), 8.14–8.23 (1H, m)

(17) MASS (FAB) (m/z): 597; NMR (CDCl₃, δ): 2.13 (6H, s), 2.41 (2H, t, J=5 Hz), 2.70 (3×⅔H, s), 2.62–2.80 (1H, m), 2.90 (3×⅓H, s), 2.98–3.10 (3H, m), 3.27–3.35 (2H, m), 4.28–4.43 (2×⅔H, m), 4.83 (2×⅓H, d, J=15 Hz), 5.18–5.30 (1H, m), 5.35–5.49 (1H, m), 6.98–7.13 (9H, m), 7.22–7.31 (5H, m), 7.45 (1H, d, J=8 Hz), 7.65 (1H, d, J=8 Hz), 7.92–8.05 (1H, m), 8.62 (1H, d, J=8 Hz)

(18) MASS (FAB) (m/z): 615; NMR (CDCl₃, δ): 2.52–2.70 (1H, m), 2.73 (3×⅔H, s), 2.92 (3×⅓H, s), 2.75–2.90 (1H, m), 2.97–3.12 (2H, m), 4.12 (1H, d, J=15 Hz), 4.33 (1H, d, J=15 Hz), 4.22–4.39 (2×⅔H, m), 4.83 (2×⅓H, d, J=15 Hz), 5.22–5.34 (1H, m), 5.50–5.62 (1H, m), 6.86–7.14 (14H, m), 7.21–7.31 (5H, m), 7.48 (1H, d, J=8 Hz), 7.66 (1H, d, J=8 Hz), 7.86 (1×⅓H, d, J=8 Hz), 7.97 (1×⅔H, d, J=8 Hz) 8.75 (1H, d, J=8 Hz)

(19) MASS (FAB) (m/z): 611; NMR (DMSO-d₆, δ): 2.35–2.52 (1H, m), 2.68–2.73 (4H, m), 2.81 (3×½H, s), 2.83 (3×½H, s), 2.76–3.03 (4H, m), 3.40–3.80 (3H, m), 4.34–4.56 (2H, m), 4.80–5.02 (2H, m), 7.02–7.33 (13H, m), 7.45 (1H, d, J=8 Hz), 7.65 (1H, d, J=8 Hz), 8.12–8.40 (1H, m), 8.43–8.62 (1H, m), 8.87 (1H, m)

(20) MASS (FAB) (m/z): 540; NMR (CDCl$_3$, δ): 2.65–2.69 (4H, m), 2.73 (3×⅔H, s), 2.97 (3×⅓H, s), 2.87–3.15 (3H, m), 4.29–4.49 (2×⅔H, m), 4.82 (2×⅓H, d, J=15 Hz), 5.23–5.42 (1H, m), 5.61–5.78 (1H, m), 6.85–6,93 (2H, m), 7.02–7.14 (8H, m), 7.16 (1H, d, J=8 Hz), 7.18–7.30 (3H, m), 7.48 (1H, d, J=8 Hz), 7.65 (1H, d, J=8 Hz), 8.05 (1×⅓H, d, J=8 Hz), 8.17 (1×⅔H, d, J=8 Hz), 8.93 (1H, t, J=8 Hz) (21) NMR (CDCl$_3$, δ): 2.20–2.30 (1×½H, m), 2.52–2.62 (1×½H, m), 2.83 (3×⅔H, m), 2.94–2.99 (1H, m), 3.00 (3×⅓H, s), 3.42–3.95 (3H, m), 4.18–4.70 (2H, m), 5.26 (1H, t, J=8 Hz), 6.83–6.88 (2H, m), 7.02–7.38 (15H, m), 7.52 (1×½H, d, J=8 Hz), 7.60 (1×½H, d, J=8 Hz), 7.80 (1×½H, d, J=8 Hz), 8.00 (1×½H, s), 9.04 (1×½H, s), 9.22 (1×½H, s)

(22) MASS (FAB) (m/z): 672 (M+H)$^+$; NMR (CDCl$_3$, δ): 2.61 (3×⅔H, s), 2.67–2.80 (1H, m), 2.80 (3×⅓H, s), 2.97–3.04 (2H, m), 3.22–3.31 (1H, m), 3.42–3.62 (6H, m), 3.70–3.81 (2H, m), 4.17–4.38 (2×⅔H, m), 4.71 (2×⅓H, d, J=15 Hz), 5.12–5.22 (1H, m), 5.25–5.30 (1H, m), 6.57 (1H, d, J=8 Hz), 6.65 (1H, t, J=8 Hz), 6.95–7.05 (4H, m), 7.10–7.14 (6H, m), 7.23–7.28 (3H, m), 7.42–7.49 (2H, m), 7.67 (1H, d, J=8 Hz), 8.01–8.10 (2H, m), 8.18 (1H, d, J=5 Hz)

(23) MASS (FAB) (m/z): 639 (M+H)$^+$; NMR (CDCl$_3$, δ): 2.38–2.51 (6H, m), 2.61 (3×⅔H, s), 2.63–2.73 (1H, m), 2.82 (3×⅓H, s), 2.98–3.06 (2H, m), 3.18–3.28 (1H, m), 3.40–3.48 (2H, m), 3.60–3.70 (4H, m), 4.16–4.39 (2×⅔H, m), 4.70 (2×⅓H, d, J=15 Hz), 5.11–5.23 (2H, m), 6.96–7.13 (9H, m), 7.22–7.28 (4H, m), 7.43 (1H, d, J=8 Hz), 7.65 (1H, d, J=8 Hz), 7.97–8.09 (2H, m)

(24) MASS (FAB) (m/z): 554 (M+H)$^+$; NMR (CDCl$_3$, δ): 2.60 (3×⅔H, s), 2.56–2.70 (1H, m), 2.82 (3×⅓H, s), 2.95 (6H, s), 3.00–3.06 (2H, m), 3.24 (1H, t, J=15 Hz), 4.19–4.39 (2×⅔H, m), 4.68 (2×⅓H, d, J=15 Hz), 5.09–5.20 (2H, m), 6.93–7.05 (3H, m), 7.08–7.16 (6H, m), 7.23–7.30 (4H, m), 7.43 (1H, d, J=8 Hz), 7.63 (1H, d, J=8 Hz), 7.99 (1H, t, J=8 Hz), 8.17–8.25 (1H, m)

(25) MASS (FAB) (m/z): 671 (M+H)$^+$; NMR (CDCl$_3$, δ): 2.62 (3×⅔H, s), 2.65–2.81 (1H, m), 2.82 (3×⅓H, s), 3.02 (2H, t, J=8 Hz), 3.08–3.20 (4H, m), 3.22–3.38 (1H, m), 3.50–3.65 (2H, m), 3.70–3.82 (2H, m), 4.16–4.39 (2×⅔H, m), 4.69 (2×⅓H, d, J=15 Hz), 5.11–5.20 (1H, m), 5.21–5.28 (1H, m), 6.89 (3H, t, J=8 Hz), 6.95–7.13 (9H, m), 7.22–7.31 (6H, m), 7.45 (1H, d, J=8 Hz), 7.66 (1H, d, J=8 Hz), 7.98–8.11 (2H, m)

(26) MASS (FAB) (m/z): 596 (M+H)$^+$; NMR (CDCl$_3$, δ): 2.55–2.67 (1H, m), 2.61 (3×⅔H, s), 2.79 (3×⅓H, s), 2.92–3.09 (2H, m), 3.21–3.48 (3H, m), 3.62–3.68 (6H, m), 4.15–4.42 (2×⅔H, m), 4.65 (2×⅓H, d, J=15 Hz), 5.11–5.23 (2H, m), 6.96–7.37 (13H, m), 7.75–7.93 (3H, m), 8.07 (1H, d, J=8 Hz)

(27) MASS (FAB) (m/z): 624 (M+H)$^+$; NMR (CDCl$_3$, δ): 1.87–2.03 (2H, m), 2.35 (3H, s), 2.57–2.72 (5H, m), 2.60 (3×⅔H, s), 2.80 (3×⅓H, s), 3.00–3.12 (2H, m), 3.32 (1H, t, J=15 Hz), 3.47–3.76 (4H, m), 4.10–4.37 (2×⅔H, m), 4.65 (2×⅓H, dd, J=15, 8 Hz), 5.02–5.18 (2H, m), 6.92–7.08 (2H, m), 7.13–7.21 (5H, m), 7.23–7.32 (4H, m), 7.45 (1H, t, J=8 Hz), 7.52 (1H, s), 7.58 (1H, d, J=8 Hz), 7.69 (1H, d, J=8 Hz), 7.72–7.83 (1H, m), 8.27–8.33 (1H, m)

(28) MASS (FAB) (m/z): 678 (M+H)$^+$; NMR (CDCl$_3$, δ): 1.00–1.30 (5H, m), 1.58–1.68 (2H, m), 1.72–1.87 (4H, m), 2.50–2.61 (4H, m), 2.58 (3×⅔H, s), 2.67 (1H, dd, J=15, 7 Hz), 2.80 (3×⅓H, s), 2.99–3.11 (2H, m), 3.32 (1H, t, J=8 Hz), 3.40–3.55 (2H, m), 3.61–3.70 (2H, m), 4.12–4.38 (2×⅔H, m), 4.67 (2×⅓H, d, J=8 Hz), 5.02–5.18 (2H, m), 6.95–7.08 (2H, m), 7.13–7.20 (5H, m), 7.25–7.33 (4H, m), 7.45 (1H, s), 7.51 (1H, s), 7.58 (1H, d, J=8 Hz), 7.64–7.73 (2H, m), 8.22–8.28 (1H, m)

(29) MASS (FAB) (m/z): 638 (M+H)$^+$; NMR (CDCl$_3$, δ): 0.90 (3H, t, J=8 Hz), 1.51 (2H, q, J=8 Hz), 2.32 (2H, t, J=8 Hz), 2.38–2.52 (4H, m), 2.62 (3×⅔H, s), 2.68 (1H, dd, J=15, 7 Hz), 2.83 (3×⅓H, s), 3.02–3.12 (2H, m), 3.31 (1H, t, J=8 Hz), 3.43–3.58 (2H, m), 3.65–3.71 (2H, m), 4.12–4.40 (2×⅔H, m), 4.67 (2×⅓H, d, J=15 Hz), 5.02–5.18 (2H, m), 6.93–7.08 (2H, m), 7.14–7.20 (5H, m), 7.23–7.32 (4H, m), 7.43 (1H, t, J=8 Hz), 7.50 (1H, s), 7.58 (1H, d, J=8 Hz), 7.63–7.73 (2H, m), 8.20–8.26 (1H, m)

(30) MASS (FAB) (m/z): 674 (M+H)$^+$; NMR (CDCl$_3$, δ): 2.53 (3×⅔H, s), 2.72 (1H, dd, J=15, 7 Hz), 2.79 (3×⅓H, s), 2.97–3.12 (2H, m), 3.36 (1H, t, J=15 Hz), 3.48–3.62 (2H, m), 3.68–3.75 (2H, m), 3.79–3.99 (4H, m), 4.11–4.40 (2×⅔H, m), 4.63 (2×⅓H, d, J=15 Hz), 5.07–5.19 (2H, m), 6.53 (1H, t, J=5 Hz), 6.97–7.08 (2H, m), 7.12–7.20 (5H, m), 7.23–7.31 (4H, m), 7.42 (1H, t, J=8 Hz), 7.48 (1H, s), 7.57 (1H, d, J=8 Hz), 7.62–7.73 (2H, m), 8.23 (1H, d, J=8 Hz), 8.32 (2H, d, J=8 Hz)

(31) MASS (FAB) (m/z): 521 (M$^+$1); NMR (CDCl$_3$, δ): 1.21 (3H, t, J=7 Hz), 2.57 (1H, dd, J=7, 16 Hz), 3.08 (2H, m), 3.23 (1H, dd, J=4, 16 Hz), 3.38–3.52 (2H, m), 3.62–3.70 (6H, m), 4.13 (2H, q, J=7 Hz), 4.77 (1H, q, J=7 Hz), 5.08 (1H, m), 6.92 (1H, d, J=2 Hz), 7.13 (5H, s), 7.31 (1H, t, J=8 Hz), 7.43 (1H, d, J=8 Hz), 7.54 (1H, d, J=8 Hz), 7.67 (1H, d, J=8 Hz), 8.07 (1H, d, J=7 Hz), 9.38 (1H, br s)

EXAMPLE 5

The following object compound was obtained according to a similar manner to that of Preparation 13.

MASS: (FAB) (m/z): 493 (M$^+$+1); NMR (DMSO-d$_6$, δ): 2.78 (2H, m), 2.94 (1H, m), 3.04 (1H, m), 3.37–3.58 (8H, m), 4.47 (1H, m), 4.94 (1H, q, J=7 Hz), 7.02–7.09 (3H, m), 7.14–7.22 (5H, m), 7.45 (1H, d, J=8 Hz), 7.64 (1H, d, J=8 Hz), 7.95 (1H, d, J=8 Hz), 8.58 (1H, d, J=7 Hz)

EXAMPLE 6

The following object compound was obtained according to a similar manner to that of Preparation 10.

mp: 245–250° C.; NMR (DMSO-d$_6$, δ): 2.42–2.60 (1H, m), 2.71 (3×⅓H, s), 2.77 (3×⅔H, s), 2.81–2.93 (1H, m), 2.95–3.03 (1H, m), 3.40–3.48 (1H, m), 4.32 (2×⅓H, d, J=15 Hz), 4.43–4.57 (2×⅔H, m), 4.68–4.77 (1H, m), 4.84–5.00 (1H, m), 6.98–7.36 (11H, m), 7.47 (1H, t, J=8 Hz), 7.54 (1H, s), 7.68 (1H, d, J=8 Hz), 7.78 (1H, d, J=8 Hz), 8.71–8.98 (2H, m)

EXAMPLE 7

The following object compound was obtained according to a similar manner to that of Preparation 10.

MASS (m/z): 452 (M$^+$+1); NMR (CDCl$_3$, δ): 1.13 (3H, t, J=7 Hz), 2.82 (2H, m), 3.02 (2H, m), 4.07 (2H, q, J=7 Hz), 4.84 (1H, q, J=7 Hz), 5.25 (1H, m), 6.88–7.10 (7H, m), 7.22 (1H, d, J=8 Hz), 7.34 (1H, d, J=8 Hz), 7.55 (1H, d, J=8 Hz), 7.69 (1H, br s), 7.87 (1H, br s)

EXAMPLE 8

Starting Compound (496 mg) was dissolved in dichloromethane (1 ml) and cooled to 0° C. Trifluoroacetic acid (1 ml) was added to the solution and the mixture was stirred at 0° C. for 3 hours. The reaction mixture was made basic with ice cooling by adding aqueous sodium hydroxide, and extracted three times with chloroform. The organic layer was washed with brine and dried over magnesium sulfate. Evaporation of the solvent gave Compound A as white solid.

1H-Indole-2-carboxylic acid (75 mg) was dissolved in tetrahydrofuran (2 ml) and cooled to −15° C. N-Methylmorpholine (0.05 ml) and isobutyl chloroformate (73 mg) were added to the solution and stirred for 5 minutes. Compound A obtained above was dissolved in tetrahydrofuran (2.5 ml), added to the solution at −15° C., and stirred at 0° C. for 30 minutes. The reaction mixture was diluted with chloroform, washed with aqueous sodium hydrogen carbonate, washed with brine, and dried over magnesium sulfate. Evaporation of the solvent followed by column chromatography (silica gel, chloroform-methanol) afforded Object Compound (66 mg) as white powder.

MASS (m/z): 740 (M+H)$^+$; NMR (CDCl$_3$, δ): 2.36 (3H, s), 2.55–2.72 (1H, m), 2.80 (⅓×3H, s), 2.82–3.05 (2H, m), 2.90 (⅔×3H, s), 3.20–3.35 (1H, m), 3.35–3.73 (8H, m), 4.20 (⅔×1H, d, J=15 Hz), 4.53 (⅓×2H, ABq, Δ=0.12, J=17 Hz), 4.63 (⅔×1H, d, J=17 Hz), 5.00–5.22 (2H, m), 7.00–8.10 (18H, m), 9.65 (⅓×1H, s), 9.68 (⅔×1H, s)

EXAMPLE 9

The following object compounds were obtained according to a similar manner to that of Example 8.

(1) MASS (m/z): 582 (M+H)$^+$; NMR (CDCl$_3$, δ): 2.67–2.75 (1H, m), 3.02–3.15 (2H, m), 3.20–3.30 (1H, m), 3.30–3.50 (4H, m), 3.50–3.65 (4H, m), 4.29–4.51 (2H, m), 4.65–4.75 (1H, m), 4.85–4.92 (1H, m), 6.80–7.43 (16H, m), 7.63–7.75 (2H, m), 8.97 (1H, br s)

(2) MASS (m/z): 492 (M+H)$^+$; NMR (DMSO-d$_6$, δ): 2.67–2.92 (3H, m), 3.00–3.09 (1H, m), 3.38–3.60 (8H, m), 4.32–4.41 (1H, m), 4.82–4.92 (1H, m), 6.98–7.24 (10H, m), 7.38 (1H, br s), 7.47 (1H, d, J=8 Hz), 7.65 (1H, d, J=8 Hz), 8.00 (1H, d, J=8 Hz), 8.58 (1H, d, J=8 Hz)

(3) MASS (m/z): 506 (M+H)$^+$; NMR (CDCl$_3$, δ): 2.60–2.72 (1H, m), 2.80 (⅔×3H, s), 2.92 (⅓×3H, s), 3.28–3.78 (10H, m), 4.03–4.15 (2H, m), 4.40 (⅓×2H, s), 4.53 (⅔×2H, ABq, Δ=0.05, J=15 Hz), 5.10–5.23 (1H, m), 7.00–8.23 (11H, m), 9.18 (⅓×1H, br s), 9.22 (⅔×1H, br s)

(4) MASS (m/z): 626 (M+H)$^+$; NMR (CDCl$_3$, δ): 2.62 (⅔×3H, s), 2.6–2.7 (1H, m), 2.79 (⅓×3H, s), 3.0–3.1 (2H, m), 3.2–3.3 (1H, m), 3.4–3.7 (8H, m), 3.78 (3H, s), 4.03 (⅓×1H, d, J=17 Hz), 4.23 (⅔×1H, d, J=15 Hz), 4.34 (⅓×1H, d, J=17 Hz), 4.58 (⅔×1H, d, J=15 Hz), 5.1–5.2 (2H, m), 6.8–7.0 (4H, m), 7.1–7.2 (7H, m), 7.3–7.4 (1H, m), 7.44 (1H, d, J=9 Hz), 7.68 (1H, d, J=9 Hz), 7.72 (⅓×1H, d, J=9 Hz), 7.76 (⅔×1H, d, J=9 Hz), 8.05 (1H, d, J=9 Hz), 9.35 (⅓×1H, br s), 9.39 (⅔×1H, br s)

(5) MASS (m/z): 582 (M+H)$^+$; NMR (CDCl$_3$, δ): 2.63 (1H, dd, J=15, 7 Hz), 2.76 (⅔×3H, s), 2.82 (⅓×3H, s), 3.23 (1H, dd, J=15, 3 Hz), 3.4–3.7 (8H, m), 4.28 (⅓×1H, d, J=16 Hz), 4.42 (⅔×1H, d, J=14 Hz), 4.55 (⅓×1H, d, J=16 Hz), 4.70 (⅔×1H, d, J=14 Hz), 5.1–5.2 (1H, m), 5.78 (⅔×1H, d, J=7 Hz), 5.80 (⅓×1H, d, J=7 Hz), 6.9–7.4 (14H, m), 7.62 (1H, d, J=7 Hz), 8.07 (1H, d, J=7 Hz), 8.35 (1H, d, J=7 Hz), 9.33 (1H, br s)

(6) MASS (m/z): 702 (M+H)$^+$; NMR (CDCl$_3$, δ): 2.52–2.78 (1H, m), 2.67 (⅔×3H, s), 2.85 (⅓×3H, s), 2.88–3.05 (2H, m), 3.12–3.30 (1H, m), 3.32–3.75 (8H, m), 4.28 (⅔×1H, d, J=15 Hz), 4.33 (⅓×2H, ABq, Δ=0.16, J=17 Hz), 4.68 (⅔×1H, d, J=15 Hz), 4.82 (2H, s), 5.02–5.28 (2H, m), 6.62–8.15 (21H, m), 9.83 (⅓×1H, s), 9.87 (⅔×1H, s)

(7) MASS (m/z): 715 (M+H)$^+$; NMR (CDCl$_3$, δ): 2.28 (3H, s), 2.28–2.52 (4H, m), 2.52–2.71 (1H, m), 2.64 (⅔×3H, s), 2.82 (⅓×3H, s), 2.88–3.00 (2H, m), 3.20–3.38 (1H, m), 3.38–3.75 (4H, m), 4.28 (⅔×1H, d, J=15 Hz), 4.32 (⅓×2H, ABq, Δ=0.16, J=17 Hz), 4.67 (⅔×1H, d, J=15 Hz), 4.85 (2H, s), 4.98–5.18 (2H, m), 6.65–8.15 (21H, m), 9.42 (⅓×1H, s), 9.46 (⅔×1H, s)

(8) MASS (m/z): 612 (M+H)$^+$; NMR (CDCl$_3$, δ): 2.59–2.78 (1H, m), 2.74 (⅔×3H, s), 2.80–2.98 (2H, m), 2.83 (⅓×3H, s), 3.10–3.25 (1H, m), 3.30–3.70 (8H, m), 4.32 (⅔×1H, d, J=15 Hz), 4.41 (⅓×2H, ABq, Δ=0.14, J=17 Hz), 4.67 (⅔×1H, d, J=15 Hz), 5.02–5.25 (2H, m), 6.47–8.13 (17H, m), 9.95 (1H, s)

(9) MASS (m/z): 610 (M+H)$^+$; NMR (CDCl$_3$, δ): 2.45–2.85 (4H, m), 2.64 (⅗×3H, s), 2.84 (⅖×3H, s), 2.90–3.02 (2H, m), 3.18–3.40 (2H, m), 3.40–3.78 (8H, m), 4.91–5.19 (2H, m), 6.93–8.10 (17H, m), 9.50 (⅖×1H, s), 9.52 (⅗×1H, s)

(10) MASS (m/z): 654 (M+H)$^+$; NMR (CDCl$_3$, δ): 2.5–2.7 (1H, m), 2.65 (⅔×3H, s), 2.80 (⅓×3H, s), 3.0–3.1 (2H, m), 3.2–3.3 (1H, m), 3.4–3.7 (8H, m), 3.92 (3H, s), 4.35 (⅔×1H, d, J=15 Hz), 4.43 (⅓×1H, d, J=15 Hz), 4.65 (⅓×1H, d, J=15 Hz), 4.68 (⅔×1H, d, J=15 Hz), 4.8–5.2 (2H, m), 6.9–7.5 (11H, m), 7.6–8.1 (5H, m), 9.19 (⅓×1H, br s), 9.37 (⅔×1H, br s)

(11) MASS (m/z): 646 (M+H)$^+$; NMR (CDCl$_3$, δ): 2.5–2.7 (1H, m), 2.68 (⅔×3H, s), 2.88 (⅓×3H, s), 3.0–3.1 (2H, m), 3.1–3.3 (1H, m), 3.3–3.7 (8H, m), 4.30 (⅓×1H, d, J=17 Hz), 4.48 (⅔×1H, d, J=15 Hz), 4.56 (⅓×1H, d, J=17 Hz), 4.80 (⅔×1H, d, J=15 Hz), 5.0–5.2 (2H, m), 6.9–7.9 (18H, m), 8.08 (1H, d, J=9 Hz), 9.47 (⅓×1H, br s), 9.50 (⅔×1H, br s)

(12) MASS (m/z): 646 (M+H)$^+$; NMR (CDCl$_3$, δ): 2.40–2.65 (1H, m), 2.60 (⅔×3H, s), 2.94 (⅓×3H, s), 2.95–3.10 (2H, m), 3.20–3.80 (9H, m), 4.74 (⅓×2H, ABq, Δ=0.10, J=17 Hz), 4.77 (⅔×1H, d, J=15 Hz), 4.88–5.20 (2H, m), 5.22 (⅔×1H, d, J=15 Hz), 6.93–8.15 (19H, m), 9.28 (⅓×1H, s), 9.35 (⅔×1H, s)

(13) MASS (m/z): 612 (M+H)$^+$; NMR (CDCl$_3$, δ): 2.55–2.68 (1H, m), 2.59 (⅔×3H, s), 2.72 (⅓×3H, s), 2.95–3.08 (2H, m), 3.15–3.70 (9H, m), 3.75 (⅓×1H, d, J=17 Hz), 4.30 (⅓×1H, d, J=17 Hz), 4.35 (⅔×2H, ABq, Δ=0.06, J=15 Hz), 4.83–5.20 (2H, m), 6.65–8.35 (17H, m), 9.72 (1H, s)

(14) MASS (m/z): 613 (M+H)$^+$; NMR (CDCl$_3$, δ): 2.55–2.75 (1H, m), 2.59 (⅔×3H, s), 2.75 (⅓×3H, s), 2.95–3.15 (2H, m), 3.20–3.75 (9H, m), 3.84 (⅓×1H, d, J=17 Hz), 4.30 (⅓×1H, d, J=17 Hz), 4.38 (⅔×2H, ABq, Δ=0.13, J=15 Hz), 4.82–5.23 (2H, m), 6.68–8.30 (17H, m)

(15) MASS (m/z): 638 (M$^+$); NMR (CDCl$_3$, δ): 2.60 (⅔×3H, s), 2.6–2.7 (1H, m), 2.80 (⅓×3H, s), 2.92 (6H, s), 3.0–3.1 (2H, m), 3.2–3.3 (1H, m), 3.4–3.7 (8H, m), 3.98 (⅓×1H, d, J=17 Hz), 4.22 (⅔×1H, d, J=15 Hz), 4.34 (⅓×1H, d, J=17 Hz), 4.58 (⅔×1H, d, J=15 Hz), 5.0–5.2 (1H, m), 6.63 (2H, d, J=8 Hz), 6.91 (⅓×2H, d, J=8 Hz), 7.00 (⅔×2H, d, J=8 Hz), 7.1–7.2 (7H, m), 7.2–7.3 (1H, m), 7.43 (1H, d, J=7 Hz), 7.67 (1H, d, J=7 Hz), 7.80 (⅓×1H, d, J=8 Hz), 7.85 (⅔×1H, d, J=8 Hz), 8.05 (1H, d, J=8 Hz), 9.50 (⅓×1H, br s), 9.57 (⅔×1H, br s)

(16) MASS (m/z): 597 (M+H)$^+$; NMR (CDCl$_3$, δ): 2.55–2.72 (1H, m), 2.80 (⅔×3H, s), 2.90 (⅓×3H, s), 2.95–3.32 (3H, m), 3.37–3.74 (8H, m), 4.43 (⅓×2H, ABq, Δ=0.05, J=17 Hz), 4.48 (⅔×1H, d, J=15 Hz), 4.70 (⅔×1H, d, J=15 Hz), 5.07–5.21 (2H, m), 6.93–8.10 (15H, m), 8.45–8.55 (1H, m), 9.63 (⅓×1H, s), 9.65 (⅔×1H, s)

(17) MASS (m/z): 597 (M+H)$^+$; NMR (CDCl$_3$, δ): 2.55–2.72 (1H, m), 2.70 (¾×3H, s), 2.82 (¼×3H, s), 2.90–3.15 (2H, m), 3.18–3.34 (1H, m), 3.38–3.78 (8H, m), 4.28 (¼×2H, ABq, Δ=0.05, J=17 Hz), 4.31 (¾×1H, d, J=15 Hz), 4.58 (¾×1H, d, J=15 Hz), 4.93–5.22 (2H, m), 6.75–8.10 (14H, m), 8.43–8.51 (2H, m), 9.58 (1H, s)

(18) MASS (FAB) (m/z): 668 (M+H)⁺; NMR (CDCl₃, δ): 2.23 (3H, s), 2.30–2.46 (4H, m), 2.58–2.69 (1H, m), 2.58 (3×⅔H, s), 2.73 (3×⅓H, s), 2.92–3.10 (2H, m), 3.23–3.33 (1H, m), 3.38–3.52 (2H, m), 3.60–3.67 (2H, m), 3.88 (3H, s), 4.20–4.35 (2×⅔H, m), 4.66 (2×⅓H, d, J=15 Hz), 5.01–5.18 (2H, m), 6.95 (2×⅓H, d, J=8 Hz), 7.03 (2×⅔H, d, J=8 Hz), 7.10–7.20 (5H, m), 7.26 (1H, t, J=8 Hz), 7.38 (1H, t, J=8 Hz), 7.47 (1H, s), 7.52 (1H, d, J=8 Hz), 7.65 (1H, d, J=8 Hz), 7.73 (1H, d, J=8 Hz), 7.90 (2H, d, J=8 Hz), 8.19 (1H, t, J=8 Hz)

(19) MASS (FAB) (m/z): 655 (M+H)⁺; NMR (CDCl₃, δ): 2.58–2.70 (1H, m), 2.67 (3×⅔H, s), 2.80 (3×⅓H, s), 2.98–3.13 (2H, m), 3.31 (1H, t, J=15 Hz), 3.40–3.57 (2H, m), 3.63–3.77 (6H, m), 3.91 (3H, s), 4.20–4.40 (2×⅔H, m), 4.70 (2×⅓H, d, J=15 Hz), 5.03–5.18 (2H, m), 6.99 (2×⅓H, d, J=8 Hz), 7.09 (2×⅔H, d, J=8 Hz), 7.13–7.23 (6H, m), 7.31 (1H, t, J=8 Hz), 7.44 (1H, t, J=8 Hz), 7.51 (1H, s), 7.61 (1H, t, J=8 Hz), 7.70 (1H, d, J=8 Hz), 7.93 (2H, d, J=8 Hz), 8.20 (1H, t, J=8 Hz)

EXAMPLE 10

The following object compounds were obtained according to a similar manner to that of Example 1.

(1) MASS (m/z): 595 (M+H)⁺; NMR (CDCl₃, δ): 2.25–2.45 (4H, m), 2.27 (3H, s), 2.60–2.75 (1H, m), 2.80 (⅔×3H, s), 2.85 (⅓×3H, s), 3.17–3.75 (5H, m), 4.29 (⅓×1H, d, J=17 Hz), 4.43 (⅓×1H, d, J=17 Hz), 4.57 (⅔×1H, d, J=15 Hz), 4.72 (⅔×1H, d, J=15 Hz), 5.05–5.20 (1H, m), 5.70–5.87 (1H m), 6.75–7.48 (14H, m), 7.58–7.70 (1H, m), 7.98–8.18 (1H, m), 8.35–8.45 (1H, m), 9.42 (1H, br s)

(2) MASS (m/z): 596 (M+H)⁺; NMR (CDCl₃, δ): 2.27 (3H, s), 2.30–2.48 (4H, m), 2.65–2.80 (1H, m), 2.81 (⅔×3H, s), 2.85 (⅓×3H, s), 3.20–3.70 (5H, m), 4.30 (⅓×1H, d, J=17 Hz), 4.45 (⅔×1H, d, J=15 Hz), 4.58 (⅓×1H, d, J=17 Hz), 4.72 (⅔×1H, d, J=17 Hz), 5.04–5.18 (1H, m), 5.77–5.88 (1H, m), 6.80–7.70 (15H, m), 8.12–8.50 (2H, m)

(3) MASS (m/z): 651 (M+H)⁺; NMR (CDCl₃, δ): 2.28–2.52 (4H, m), 2.29 (3H, s), 2.55–2.72 (1H, m), 2.58 (⅔×3H, s), 2.78 (⅓×3H, s), 2.92 (6H, s), 2.95–3.10 (2H, m), 3.22–3.78 (5H, m), 3.98 (⅓×1H, d, J=17 Hz), 4.20 (⅔×1H, d, J=15 Hz), 4.31 (⅓×1H, d, J=17 Hz), 4.57 (⅔×1H, d, J=15 Hz), 5.02–5.25 (2H, m), 6.47–8.12 (16H, m), 9.25–9.58 (1H, br s)

(4) MASS (m/z): 652 (M+H)⁺; NMR (CDCl₃, δ): 2.30 (3H, s), 2.32–2.52 (4H, m), 2.58 (⅔×3H, s), 2.60–2.72 (1H, m), 2.78 (⅓×3H, s), 2.92 (6H, s), 2.96–3.10 (2H, m), 3.25–3.72 (5H, m), 3.98 (⅓×1H, d, J=17 Hz), 4.21 (⅔×1H, d, J=15 Hz), 4.30 (⅓×1H, d, J=17 Hz), 4.54 (⅔×1H, d, J=15 Hz), 5.02–5.25 (2H, m), 6.58–7.75 (15H, m), 8.15–8.28 (1H, m)

(5) MASS (m/z): 666 (M+H)⁺; NMR (CDCl₃, δ): 2.22 (6H, s), 2.29 (3H, s), 2.30–2.52 (4H, m), 2.55–2.70 (1H, m), 2.62 (⅔×3H, s), 2.82 (⅓×3H, s), 2.95–3.08 (2H, m), 3.22–3.78 (7H, m), 4.24 (⅓×2H, ABq, Δ=0.21, J=17 Hz), 4.29 (⅔×1H, d, J=15 Hz), 4.62 (⅔×1H, d, J=15 Hz), 5.00–5.19 (2H, m), 6.90–8.13 (16H, m), 9.35 (⅓×1H, s), 9.42 (⅔×1H, s)

(6). MASS (m/z): 667 (M+H)⁺; NMR (CDCl₃, δ): 2.22 (6H, s), 2.30 (3H, s), 2.32–2.53 (4H, m), 2.59 (⅔×3H, s), 2.59–2.72 (1H, m), 2.80 (⅓×3H, s), 2.94–3.12 (2H, m), 3.23–3.72 (7H, m), 4.22 (⅓×2H, ABq, Δ=0.19, J=17 Hz), 4.27 (⅔×1H, d, J=15 Hz), 4.63 (⅔×1H, d, J=15 Hz), 5.00–5.20 (2H, m), 6.88–7.75 (15H, m), 8.15–8.25 (1H, m)

(7) MASS (m/z): 621 (M+H)⁺; NMR (CDCl₃, δ): 2.20–2.50 (4H, m), 2.28 (3H, s), 2.55–2.82 (2H, m), 2.92–3.85 (10H, m), 3.98 (½×1H, d, J=17 Hz), 4.48 (½×1H, d, J=17 Hz), 4.62 (½×2H, ABq, Δ=0.15, J=17 Hz), 5.05–5.23 (2H, m), 6.80–8.15 (16H, m), 9.60 (1H, s)

(8) MASS (m/z): 622 (M+H)⁺; NMR (CDCl₃, δ): 2.30 (3H, s), 2.30–2.55 (4H, m), 2.55–3.82 (12H, m), 3.94 (⅖×1H, d, J=17 Hz), 4.48 (⅖×1H, d, J=17 Hz), 4.62 (⅗×2H, ABq, Δ=0.15, J=17 Hz), 5.02–5.23 (2H, m), 6.80–7.82 (15H, m), 8.15–8.28 (1H, m)

(9) MASS (m/z): 643 (M+H)⁺; NMR (CDCl₃, δ): 2.30 (3H, s), 2.30–2.53 (4H, m), 2.58–2.70 (1H, m), 2.62 (¾×3H, s), 2.78 (¼×3H, s), 2.97–3.10 (2H, m), 3.24–3.78 (5H, m), 4.20 (¼×2H, ABq, Δ=0.16, J=17 Hz), 4.25 (¾×1H, d, J=15 Hz), 4.60 (¾×1H, d, J=15 Hz), 5.02–5.17 (2H, m), 6.80–8.13 (16H, m), 9.33 (1H, br s)

(10) MASS (m/z): 644 (M+H)⁺; NMR (CDCl₃, δ): 2.30 (3H, s), 2.30–2.52 (4H, m), 2.60 (¾×3H, s), 2.60–2.72 (1H, m), 2.78 (¼×3H, s), 2.95–3.15 (2H, m), 3.25–3.74 (5H, m), 4.19 (¼×2H, ABq, Δ=0.1S, J=17 Hz), 4.24 (¾×1H, d, J=15 Hz), 4.59 (¾×1H, d, J=15 Hz), 5.02–5.18 (2H, m), 6.80–7.01 (2H, m), 7.17–7.74 (13H, m), 8.13–8.28 (1H, m)

(11) MASS (m/z): 687, 689 (M+H)⁺; NMR (CDCl₃, δ): 2.25–2.52 (4H, m), 2.30 (3H, s), 2.55–2.70 (1H, m), 2.62 (¾×3H, s), 2.77 (¼×3H, s), 2.92–3.12 (2H, m), 3.22–3.38 (1H, m), 3.40–3.78 (4H, m), 4.20 (¼×2H, ABq, Δ=0.15, J=17 Hz), 4.23 (¾×1H, d, J=15 Hz), 4.59 (¾×1H, d, J=15 Hz), 5.03–5.18 (2H, m), 6.73–8.12 (16H, m), 9.43 (1H, br s)

(12) MASS (m/z): 688, 690 (M+H)⁺; NMR (CDCl₃, δ): 2.30 (3H, s), 2.30–2.52 (4H, m), 2.60–2.71 (1H, m), 2.62 (¾×3H, s), 2.78 (¼×3H, s), 2.95–3.17 (2H, m), 3.26–3.75 (5H, m), 4.17 (¼×2H, ABq, Δ=0.14, J=17 Hz), 4.22 (¾×1H, d, J=15 Hz), 4.58 (¾×1H, d, J=15 Hz), 5.02–5.18 (2H, m), 6.72–6.96 (2H, m), 7.10–7.72 (13H, m), 8.15–8.27 (1H, m)

(13) MASS (m/z): 627 (M+H)⁺; NMR (CDCl₃, δ): 2.24–2.50 (4H, m), 2.28 (3H, s), 2.60 (¾×3H, s), 2.60–2.73 (1H, m), 2.78 (¼×3H, s), 2.93–3.13 (2H, m), 3.20–3.75 (5H, m), 4.20 (¼×2H, ABq, Δ=0.17, J=17 Hz), 4.21 (¾×1H, d, J=15 Hz), 4.61 (¾×1H, d, J=15 Hz), 5.06–5.21 (2H, m), 6.82–8.12 (16H, m), 9.23 (1H, br s)

(14) MASS (m/z): 628 (M+H)⁺; NMR (CDCl₃, δ): 2.30 (3H, s), 2.32–2.55 (4H, m), 2.59 (¾×3H, s), 2.60–2.72 (1H, m), 2.78 (¼×3H, s), 2.95–3.17 (2H, m), 3.26–3.75 (5H, m), 4.18 (¼×2H, ABq, Δ=0.20, J=17 Hz), 4.23 (¾×1H, d, J=15 Hz), 4.59 (¾×1H, d, J=15 Hz), 5.00–5.18 (2H, m), 6.82–7.73 (15H, m), 8.15–8.27 (1H, m)

(15) MASS (m/z): 640 (M+H)⁺; NMR (CDCl₃, δ): 2.30 (3H, s), 2.30–2.58 (4H, m), 2.59 (¾×3H, s), 2.60–2.70 (1H, m), 2.73 (¼×3H, s), 2.98–3.15 (2H, m), 3.20–3.35 (1H, m), 3.40–3.75 (4H, m), 3.92 (3H, s), 3.95 (¼×1H, d, J=17 Hz), 4.21 (¾×1H, d, J=15 Hz), 4.26 (¼×1H, d, J=17 Hz), 4.50 (¾×1H, d, J=15 Hz), 5.02–5.25 (2H, m), 6.58–6.68 (1H, m), 6.95–8.13 (14H, m), 9.73 (¼×1H, br s), 9.78 (¾×1H, br s)

(16) MASS (m/z): 641 (M+H)⁺; NMR (CDCl₃, δ): 2.30 (3H, s), 2.35–2.52 (4H, m), 2.58 (¾×3H, s), 2.60–2.72 (1H, m), 2.73 (¼×3H, s), 2.98–3.16 (2H, m), 3.28–3.40 (1H, m), 3.40–3.75 (4H, m), 3.92 (3H, s), 3.95 (¼×1H, d, J=17 Hz), 4.20 (¾×1H, d, J=15 Hz), 4.26 (¼×1H, d, J=17 Hz), 4.52 (¾×1H, d, J=15 Hz), 5.00–5.25 (2H, m), 6.60–6.70 (1H, m), 7.03–8.25 (14H, m)

(17) MASS (m/z): 657 (M+H)⁺; NMR (CDCl₃, δ): 2.30 (3H, s), 2.33–2.56 (4H, m), 2.56–2.68 (1H, m), 2.60 (¾×3H, s), 2.75 (¼×3H, s), 2.98–3.15 (2H, m), 3.25–3.42 (1H, m), 3.42–3.73 (4H, m), 3.91 (3H, s), 3.94 (¼×1H, d, J=17 Hz), 4.23 (¾×1H, d, J=15 Hz), 4.28 (¼×1H, d, J=17 Hz), 4.52 (¾×1H, d, J=15 Hz), 4.98–5.21 (2H, m), 6.60–6.70 (1H, m), 7.05–8.18 (14H, m)

(18) MASS (m/z): 623 (M+H)⁺; NMR (CDCl₃, δ): 0.98 (⅗×3H, t, J=7 Hz), 1.01 (⅖×3H, t, J=7 Hz), 2.25–2.74 (5H, m), 2.28 (3H, s), 2.92–3.18 (4H, m), 3.22–3.38 (1H, m), 3.40–3.75 (4H, m), 4.17 (⅗×1H, d, J=15 Hz), 4.19 (⅖×2H, ABq, Δ=0.18, J=17 Hz), 4.84 (⅗×1H, d, J=15 Hz), 5.00–5.20 (2H, m), 6.95–8.10 (17H, m), 9.48 (⅖×1H, br s), 9.53 (⅗×1H, br s)

(19) MASS (m/z): 624 (M+H)⁺; NMR (CDCl₃, δ): 0.97 (⅗×3H, t, J=7 Hz), 1.00 (⅖×3H, t, J=7 Hz), 2.30 (3H, s), 2.30–2.72 (5H, m), 2.93–3.20 (4H, m), 3.25–3.75 (5H, m), 4.17 (⅗×1H, d, J=15 Hz), 4.17 (⅖×2H, ABq, Δ=0.18, J=17 Hz), 4.81 (⅗×1H, d, J=15 Hz), 4.97–5.18 (2H, m), 6.93–7.72 (16H, m), 8.15–8.27 (1H, m)

(20) MASS (m/z): 644 (M+H)⁺; NMR (CDCl₃, δ): 2.28–2.55 (4H, m), 2.30 (3H, s), 2.60–2.71 (1H, m), 2.64 (⅘×3H, s), 2.74 (⅕×3H, s), 2.93–3.16 (2H, m), 3.21–3.35 (1H, m), 3.40–3.75 (4H, m), 4.18 (⅕×2H, ABq, Δ=0.21, J=17 Hz), 4.41 (⅕×2H, ABq, Δ=0.15, J=15 Hz), 5.02–5.17 (2H, m), 6.95–8.20 (15H, m), 9.59 (⅕×1H, s), 9.68 (⅘×1H, s)

(21) MASS (m/z): 645 (M+H)⁺; NMR (CDCl₃, δ): 2.30 (3H, s), 2.30–2.52 (4H, m), 2.58–2.71 (1H, m), 2.62 (⅕×3H, s), 2.73 (⅕×3H, s), 2.96–3.20 (2H, m), 3.25–3.40 (1H, m), 3.40–3.73 (4H, m), 4.20 (⅕×2H, ABq, Δ=0.19, J=17 Hz), 4.28 (⅘×1H, d, J=15 Hz), 4.54 (⅘×1H, d, J=15 Hz), 5.02–5.15 (2H, m), 7.05–7.73 (13H, m), 8.02–8.25 (2H, m)

(22) MASS (m/z): 661 (M+H)⁺; NMR (CDCl₃, δ): 2.30 (3H, s), 2.30–2.53 (4H, m), 2.53–2.68 (1H, m), 2.63 (⅘×3H, s), 2.75 (⅕×3H, s), 2.95–3.12 (2H, m), 3.26–3.40 (1H, m), 3.40–3.71 (4H, m), 4.20 (⅕×2H, ABq, Δ=0.24, J=17 Hz), 4.43 (⅘×2H, ABq, Δ=0.21, J=15 Hz ), 4.98–5.12 (2H, m), 7.10–8.20 (15H, m)

(23) MASS (m/z): 624 (M+H)⁺; NMR (CDCl₃, δ): 2.30 (3H, s), 2.30–2.50 (4H, m), 2.52 (⅕×3H, s), 2.55 (⅘×3H, s), 2.58–2.70 (1H, m), 2.61 (⅘×3H, s), 2.75 (⅕×3H, s), 2.95–3.12 (2H, m), 3.23–3.36 (1H, m), 3.41–3.75 (4H, m), 4.02 (⅕×1H, d, J=17 Hz), 4.32 (⅕×1H, d, J=17 Hz), 4.41 (⅘×2H, ABq, Δ=0.12, J=15 Hz), 5.00–5.20 (2H, m), 6.96–8.31 (15H, m), 9.34 (⅕×1H, m), 9.61 (⅘×1H, s)

(24) MASS (m/z): 625 (M+H)⁺; NMR (CDCl₃δ): 2.31 (3H, s), 2.32–2.50 (4H, m), 2.53 (3H, s), 2.59 (¾×3H, s), 2.60–2.71 (1H, m), 2.73 (¼×3H, s), 2.98–3.15 (2H, m), 3.25–3.73 (5H, m), 4.01 (¼×1H, d, J=17 Hz), 4.27 (¾×1H, d, J=15 Hz), 4.30 (¼×1H, d, J=17 Hz), 4.56 (¾×1H, d, J=15 Hz), 5.02–5.20 (2H, m), 7.02–7.75 (13H, m), 8.15–8.30 (2H, m)

(25) MASS (m/z): 641 (M+H)⁺; NMR (CDCl₃, δ): 2.31 (3H, s), 2.32–2.50 (4H, m), 2.52 (3H, s), 2.57–2.69 (1H, m), 2.62 (¾×3H, s), 2.76 (¼×3H, s), 2.98–3.14 (2H, m), 3.26–3.72 (5H, m), 4.02 (¼×1H, d, J=17 Hz), 4.30 (¾×1H, d, J=15 Hz), 4.32 (¼×1H, d, J=17 Hz), 4.56 (¾×1H, d, J=15 Hz), 4.99–5.18 (2H, m), 7.02–8.31 (15H, m)

(26) MASS (m/z): 6.11 (M+H)⁺; NMR (CDCl₃, δ): 2.53 (¼×3H, s), 2.55 (¾×3H, s), 2.60–2.71 (1H, m), 2.62 (¾×3H, s), 2.76 (¼×3H, s), 2.92–3.15 (2H, m), 3.18–3.35 (1H, m), 3.35–3.78 (8H, m), 4.02 (¼×1H, d, J=17 Hz), 4.32 (¼×1H, d, J=17 Hz), 4.42 (¾×2H, ABq, Δ=0.15, J=15 Hz), 5.02–5.22 (2H, m), 6.92–8.35 (15H, m), 9.62 (¼×1H, s), 9.81 (¾×1H, s)

(27) MASS (m/z): 612 (M+H)⁺; NMR (CDCl₃, δ): 2.52 (3H, s), 2.58–2.70 (1H, m), 2.60 (¾×3H, s), 2.75 (¼×3H, s), 2.95–3.15 (2H, m), 3.22–3.39 (1H, m), 3.39–3.80 (8H, m), 4.00 (¼×1H, d, J=17 Hz), 4.29 (¾×1H, d, J=15 Hz), 4.31 (¼×1H, d, J=17 Hz), 4.55 (¾×1H, d, J=15 Hz), 5.00–5.20 (2H, m), 7.00–7.78 (13H, m), 8.12–8.32 (2H, m)

(28) MASS (m/z): 628 (M+H)⁺; NMR (CDCl₃, δ): 2.52 (3H, s), 2.55–2.68 (1H, m), 2.62 (¾×3H, s), 2.76 (¼×3H, s), 2.95–3.14 (2H, m), 3.22–3.38 (1H, m), 3.40–3.80 (8H, m), 4.02 (¼×1H, d, J=17 Hz), 4.35 (¼×1H, d, J=17 Hz), 4.44 (¾×2H, ABq, Δ=0.23, J=15 Hz), 4.98–5.18 (2H, m), 7.00–8.33 (15H, m)

(29) MASS (m/z): 614 (M+H)⁺; NMR (CDCl₃, δ): 2.30 (3H, s), 2.30–2.63 (5H, m), 2.62 (¾×3H, s), 2.82 (¼×3H, s), 2.93–3.10 (2H, m), 3.22–3.40 (1H, m), 3.40–3.75 (4H, m), 4.26 (¼×2H, ABq, Δ=0.21, J=17 Hz), 4.32 (¼×1H, d, J=15 Hz), 4.64 (¼×1H, d, J=15 Hz), 4.93–5.15 (2H, m), 6.04 (2H, s), 6.80–7.98 (15H, m)

(30) MASS (m/z): 676 (M+H)⁺; NMR (CDCl₃, δ): 2.25–2.50 (4H, m), 2.28 (3H, s), 2.60–2.72 (1H, m), 2.66 (⅔×3H, s), 2.80 (⅓×3H, s), 2.92–3.16 (2H, m), 3.22–3.74 (5H, m), 4.27 (⅓×2H, ABq, Δ=0.18, J=17 Hz), 4.49 (⅔×2H, ABq, Δ=0.22, J=15 Hz), 5.05–5.21 (2H, m), 6.95–7.88 (15H, m), 8.01–8.13 (2H, m), 8.50 (⅔×1H, s), 8.52 (⅓×1H, s)

(31) MASS (m/z): 677 (M+H)⁺; NMR (CDCl₃, δ): 2.30 (3H, s), 2.30–2.54 (4H, m), 2.58–2.75 (1H, m), 2.67 (¾×3H, s), 2.80 (¼×3H, s), 2.97–3.21 (2H, m), 3.28–3.77 (5H, m), 4.28 (¼×2H, ABq, Δ=0.17, J=17 Hz), 4.52 (¾×2H, ABq, Δ=0.23, J=15 Hz), 5.02–5.22 (2H, m), 7.00–7.75 (15H, m), 8.10 (¾×1H, s), 8.18 (¼×1H, s), 8.20–8.28 (1H, m), 8.52 (¾×1H, s), 8.53 (¼×1H, s)

(32) MASS (m/z): 693 (M+H)⁺; NMR (CDCl₃, δ): 2.31 (3H, s), 2.31–2.70 (5H, m), 2.68 (¾×3H, s), 2.81 (¼×3H, s), 2.97–3.20 (2H, m), 3.25–3.73 (5H, m), 4.31 (¼×2H, ABq, Δ=0.21, J=17 Hz), 4.53 (¾×2H, ABq, Δ=0.18, J=15 Hz), 4.98–5.20 (2H, m), 7.03–7.94 (15H, m), 8.05–8.21 (2H, m), 8.52 (¾×1H, s), 8.53 (¼×1H, s)

(33) MASS (m/z): 644 (M+H)⁺; NMR (CDCl₃, δ): 2.30 (3H, s), 2.30–2.52 (4H, m), 2.58–2.70 (1H, m), 2.63 (⅘×3H, s), 2.78 (⅕×3H, s), 2.95–3.10 (2H, m), 3.22–3.75 (5H, m), 4.21 (⅕×2H, ABq, Δ=0.24, J=17 Hz), 4.43 (⅘×2H, ABq, Δ=0.20, J=15 Hz), 5.00–5.15 (2H, m), 6.93–8.18 (13H, m), 8.27 (1H, s), 8.48 (1H, s), 9.39 (⅕×1H, s), 9.51 (⅘×1H, s)

(34) MASS (m/z): 645 (M+H)⁺; NMR (CDCl₃, δ): 2.31 (3H, s), 2.31–2.52 (4H, m), 2.60–2.72 (1H, m), 2.62 (⅕×3H, s), 2.78 (⅕×3H, s), 2.98–3.17 (2H, m), 3.25–3.76 (5H, m), 4.21 (⅕×2H, ABq, Δ=0.22, J=17 Hz), 4.30 (⅖×1H, d, J=15 Hz), 4.59 (⅖×1H, d, J=15 Hz), 5.00–5.18 (2H, m), 7.10–7.85 (12H, m), 8.11–8.31 (2H, m), 8.48 (1H, s)

(35) MASS (m/z): 661 (M+H)⁺; NMR (CDCl₃, δ): 2.30 (3H, s), 2.30–2.53 (4H, m), 2.53–2.72 (1H, m), 2.65 (¾×3H, s), 2.79 (¼×3H, s), 2.96–3.16 (2H, m), 3.25–3.76 (5H, m), 4.08 (¼×1H, d, J=17 Hz), 4.32 (¾×1H, d, J=15 Hz), 4.34 (¼×1H, d, J=17 Hz), 4.58 (¾×1H, d, J=15 Hz), 4.95–5.12 (2H, m), 7.10–7.97 (12H, m), 8.05–8.30 (2H, m), 8.49 (1H, s)

(36) MASS (m/z): 631 (M+H)⁺; NMR (CDCl₃, δ): 2.54–2.70 (1H, m), 2.66 (⅘×3H, s), 2.73 (⅕×3H, s), 2.91–3.15 (2H, m), 3.15–3.32 (1H, m), 3.32–3.76 (8H, m), 4.18 (⅕×2H, ABq, Δ=0.24, J=17 Hz), 4.41 (⅘×2H, ABq, Δ=0.15, J=15 Hz), 5.00–5.20 (2H, m), 6.92–8.20 (15H, m), 9.74 (⅕×1H, s), 9.80 (⅘×1H, s)

(37) MASS (m/z): 632 (M+H)⁺; NMR (CDCl₃, δ): 2.58–2.72 (1H, m), 2.63 (⅘×3H, s), 2.75 (⅕×3H, s), 2.94–3.20 (2H, m), 3.22–3.80. (9H, m), 4.19 (⅕×2H, ABq, Δ=0.24, J=17 Hz), 4.42 (⅘×2H, ABq, Δ=0.22, J=15 Hz), 5.01–5.18 (2H, m), 7.08–7.77 (13H, m), 8.02–8.26 (2H, m)

(38) MASS (m/z): 648 (M+H)⁺; NMR (CDCl₃, δ): 2.52–2.70 (1H, m), 2.66 (⅘×3H, s), 2.77 (⅕×3H, s), 2.93–3.18 (2H, m), 3.22–3.82 (9H, m), 4.06 (⅕×1H, d, J=17 Hz), 4.32 (⅕×1H, d, J=17 Hz), 4.42 (⅖×2H, ABq, Δ=0.18, J=15 Hz), 4.97–5.15 (2H, m), 7.08–7.52 (9H, m), 7.65–7.93 (4H, m), 8.03–8.21 (2H, m)

(39) MASS (m/z): 597 (M+H)⁺; NMR (CDCl$_3$, δ): 2.55–2.70 (1H, m), 2.68 (⅘×3H, s), 2.79 (⅕×3H, s), 2.98–3.06 (2H, m), 3.22–3.33 (1H, m), 3.40–3.78 (8H, m), 4.09 (⅕×1H, d, J=17 Hz), 4.36 (⅕×1H, d, J=17 Hz), 4.48 (⅘×2H, ABq, Δ=0.15, J=15 Hz), 5.03–5.18 (2H, m), 6.95–7.48 (11H, m), 7.63–7.78 (2H, m), 8.00–8.12 (1H, m), 8.30–8.55 (2H, m), 9.33 (⅕×1H, br s), 9.51 (⅘×1H, br s)

(40) MASS (m/z): 598 (M+H)⁺; NMR (CDCl$_3$, δ): 2.57–2.72 (1H, m), 2.62 (¾×3H, s), 2.77 (¼×3H, s), 2.95–3.18 (2H, m), 3.22–3.81 (9H, m), 4.09 (¼×1H, d, J=17 Hz), 4.31 ( ¾×1H, d, J=15 Hz), 4.34 (¼×1H, d, J=17 Hz), 4.61 (¾×1H, d, J=15 Hz), 5.02–5.19 (2H, m), 7.10–7.76 (13H, m), 8.13–8.25 (1H, m), 8.30 (¼×1H, s), 8.38 (¾×1H, s), 8.46–8.55 (1H, m)

(41) MASS (m/z): 611 (M+H)⁺; NMR (CDCl$_3$, δ): 2.31 (3H, s), 2.31–2.52 (4H, m), 2.60–2.73 (1H, m), 2.62 (¾×3H, s), 2.77 (¼×3H, s), 2.98–3.18 (2H, m), 3.27–3.77 (5H, m), 4.22 (¼×2H, ABq, Δ=0.22, J=17 Hz), 4.29 (¾×1H, d, J=15 Hz), 4.62 (¾×1H, d, J=15 Hz), 5.03–5.20 (2H, m), 7.12–7.78 (13H, m), 8.16–8.25 (1H, m), 8.28 (¼×1H, s), 8.38 (¾×1H, s), 8.48–8.55 (1H, m)

(42) MASS (m/z): 623 (M+H)⁺; NMR (CDCl$_3$, δ): 1.07 (3H, t, J=7 Hz), 2.28–2.52 (6H, m), 2.61 (⅔×3H, s), 2.61–2.76 (1H, m), 2.81 (⅓×3H, s), 2.92–3.11 (2H, m), 3.18–3.35 (1H, m), 3.35–3.75 (4H, m), 4.26 (⅔×1H, d, J=15 Hz), 4.27 (⅓×2H, ABq, Δ=0.22, J=17 Hz), 4.68 (⅔×1H, d, J=15 Hz), 5.04–5.22 (2H, m), 6.92–8.12 (17H, m), 9.68 (⅓×1H, s), 9.72 (⅔×1H, s)

(43) MASS (m/z): 624 (M+H)⁺; NMR (CDCl$_3$, δ): 1.07 (3H, t, J=7 Hz), 2.32–2.54 (6H, m), 2.58 (⅔×3H, s), 2.58–2.70 (1H, m), 2.80 (⅓×3H, s), 2.94–3.14 (2H, m), 3.24–3.74 (5H, m), 4.24 (⅓×2H, ABq, Δ=0.22, J=17 Hz), 4.28 (⅔×1H, d, J=15 Hz), 4.63 (⅔×1H, d, J=15 Hz), 5.00–5.29 (2H, m), 6.90–7.74 (16H, m), 8.15–8.27 (1H, m)

(44) MASS (m/z): 640 (M+H)⁺; NMR (CDCl$_3$, δ): 1.08 (3H, t, J=7 Hz), 2.32–2.58 (6H, m), 2.58–2.70 (1H, m), 2.62 (⅔×3H, s), 2.82 (⅓×3H, s), 2.93–3.13 (2H, m), 3.24–3.75 (5H, m), 4.28 (⅓×2H, ABq, Δ=0.22, J=17 Hz), 4.32 (⅔×1H, d, J=15 Hz), 4.65 (⅔×1H, d, J=15 Hz), 4.95–5.18 (2H, m), 6.92–8.20 (17H, m)

(45) MASS (m/z): 640 (M⁺+1); NMR (CDCl$_3$, δ): 2.29 (3H, s), 2.42 (4H, m), 2.57 (3H×⅔, s), 2.66 (1H, dd, J=6, 16 Hz), 2.77 (3H×⅓, s), 3.04 (2H, m), 3.33 (1H, m), 3.49 (2H, m), 3.67 (2H, m), 3.77 (3H, s), 4.02 (1H×⅓, d, J=16 Hz), 4.21 (1H×⅔, d, J=15 Hz), 4.29 (1H×⅓, d, J=16 Hz), 4.57 (1H×⅔, d, J=15 Hz), 5.06–5.19 (2H, m), 6.80 (2H, d, J=8 Hz), 6.87–7.02 (2H, m), 7.17–7.21 (5H, m), 7.31 (1H, t, J=8 Hz), 7.44 (1H, t, J=8 Hz), 7.51 (1H, s), 7.56 (1H, d, J=8 Hz), 7.64–7.72 (2H, m), 8.22 (1H, m)

(46) MASS (ESI) (m/z): 640 (M+H)⁺; NMR (CDCl$_3$, δ): 2.27 (3H, s), 2.29 (3H, s), 2.23–2.52 (4H, m), 2.55–2.68 (1H, m), 2.61 (3×⅔H, s), 2.80 (3×⅓H, s), 2.97–3.10 (2H, m), 3.28–3.38 (1H, m), 3.42–3.58 (2H, m), 3.62–3.72 (2H, m), 4.09 (2×¼H, d, J=17 Hz), 4.27 (2×¼H, d, J=15 Hz), 4.33 (2×¼H, d, J=17 Hz), 4.60 (2×¼H, d, J=15 Hz), 4.99–5.15 (2H, m), 6.89 (2×⅓H, d, J=8 Hz), 6.98 (2×⅔H, d, J=8 Hz), 7.07 (2H, d, J=8 Hz), 7.12–7.20 (5H, m), 7.38–7.48 (2H, m), 7.71 (1H, t, J=8 Hz), 7.80–7.88 (3H, m), 8.12 (1H, d, J=8 Hz)

(47) MASS (ESI) (m/z): 623 (M+H)⁺; NMR (CDCl$_3$, δ): 2.21 (3H, s), 2.27 (3H, s), 2.28–2.40 (4H, m), 2.56 (3×⅔H, s), 2.62–2.78 (1H, m), 2.80 (3×⅓H, s), 2.93–3.08 (2H, m), 3.18–3.27 (1H, m), 3.35–3.48 (2H, m), 3.53–3.70 (2H, m), 4.13 (2×⅙H, d, J=17 Hz), 4.20 (2×⅓H, d, J=15 Hz), 4.31 (2×⅙H, d, J=17 Hz), 4.68 (2×⅓H, d, J=15 Hz), 5.12–5.30 (2H, m), 6.86 (2×⅓H, d, J=8 Hz), 6.93 (2×⅔H, d, J=8 Hz), 6.98–7.12 (9H, m), 7.22 (1H, t, J=8 Hz), 7.44 (1H, d, J=8 Hz), 7.63 (1H, d, J=8 Hz), 8.01–8.11 (2H, m)

(48) MASS (ESI) (m/z): 624 (M+H)⁺; NMR (CDCl$_3$, δ): 2.29 (3H, s), 2.31 (3H, s), 2.33–2.52 (4H, m), 2.58 (3×⅔H, s), 2.61–2.71 (1H, m), 2.79 (3×⅓H, s), 2.98–3.12 (2H, m), 3.28–3.38 (1H, m), 3.42–3.57 (2H, m), 3.62–3.72 (2H, m), 4.08 (2×¼H, d, J=17 Hz), 4.23 (2×¼H, d, J=15 Hz), 4.31 (2×¼H, d, J=17 Hz), 4.61 (2×¼H, d, J=15 Hz), 5.03–5.18 (2H, m), 6.86 (2×⅓H, d, J=8 Hz), 6.97 (2×⅔H, d, J=8 Hz), 7.09 (2H, d, J=8 Hz), 7.12–7.22 (5H, m), 7.29 (1H, t, J=8 Hz), 7.43 (1H, t, J=8 Hz), 7.49 (1H, s), 7.58 (1H, d, J=8 Hz), 7.67 (2H, q, J=8 Hz), 8.20–8.23 (1H, m)

(49) MASS (m/z): 550 (M⁺+1); NMR (CDCl$_3$, δ): 2.29 (3H, s), 2.39 (4H, m), 2.57–2.72 (1H, m), 2.89 (3H×⅓, s), 2.99 (3H×⅔, s), 3.38–3.51 (3H, m), 3.54–3.70 (3H, m), 3.78 (1H, dd, J=5, 11 Hz), 3.87–3.98 (1H, m), 4.44 (1H×⅔, d, J=15 Hz), 4.63 (2H×⅓, s), 4.67 (1H×⅔, d, J=15 Hz), 5.03 (1H, m), 5.09 (1H×⅓, m), 5.16 (1H×⅔, m), 7.16–7.19 (2H, m), 7.25–7.37 (4H, m), 7.44 (1H, t, J=8 Hz), 7.53 (1H, s), 7.58 (1H, d, J=8 Hz), 7.67 (1H, d, J=8 Hz), 7.74 (1H, d, J=8 Hz), 8.06 (1H, m)

(50) MASS (m/z): 576 (M⁺+1); NMR (CDCl$_3$, δ): 0.79 (3H×⅓, d, J=7 Hz), 0.83 (3H×⅓, d, J=7 Hz), 0.93 (3H×⅔, d, J=7 Hz), 0.96 (3H×⅔, d, J=7 Hz), 1.38–1.49 (1H, m), 1.58–1.75 (2H, m), 2.27 (3H, s), 2.38 (4H, m), 2.65 (1H, m), 2.89 (3H×⅓, s), 2.97 (3H×⅔, s), 3.29 (1H, dd, J=3, 16 Hz), 3.46 (2H, m), 3.65 (2H, m), 4.36 (1H×⅔, d, J=15 Hz), 4.60 (1H×⅓, d, J=15 Hz), 4.65 (1H×⅓, d, J=15 Hz), 4.73 (1H×⅔, d, J=15 Hz), 4.96 (1H, m), 5.11 (1H, m), 7.16–7.36 (5H, m), 7.41 (2H, t, J=8 Hz), 7.48 (1H, s), 7.53 (1H, d, J=8 Hz), 7.59–7.73 (2H, m), 8.24 (1H, d, J=8 Hz)

(51) MASS (m/z): 678 (M⁺+1); NMR (CDCl$_3$, δ): 2.30 (3H, s), 2.42 (4H, m), 2.64 (3H×¾, s), 2.67 (1H, dd, J=7, 16 Hz), 2.80 (3H×¼, s), 2.96–3.15 (2H, m), 3.34 (1H, dd, J=3, 16 Hz), 3.49 (2H, m), 3.67 (2H, m), 4.27 (1H×¼, d, J=16 Hz), 4.34 (1H×¼, d, J=16 Hz), 4.36 (1H×¾, d, J=15 Hz), 4.66 (1H×¾, d, J=15 Hz), 5.02–5.18 (2H, m), 6.99–7.21 (7H, m), 7.30 (1H, t, J=8 Hz), 7.44 (1H, t, J=8 Hz), 7.51–7.62 (4H, m), 7.67–7.71 (2H, m), 8.21 (1H, t, J=8 Hz)

(52) MASS (m/z): 677 (M⁺+1); NMR (CDCl$_3$, δ): 2.24 (3H, s), 2.30–2.39 (4H, m), 2.63 (3H×¾, s), 2.71 (1H, dd, J=5, 16 Hz), 2.78 (3H×¼, s), 2.93–3.12 (2H, m), 3.25 (1H, dd, J=3, 16 Hz), 3.43 (2H, m), 3.62 (2H, m), 4.27 (1H×¾, d, J=15 Hz), 4.32 (2H×¼, s), 4.67 (1H×¾, d, J=15 Hz), 5.06–5.25 (2H, m), 6.96–7.28 (10H, m), 7.43–7.49 (3H, m), 7.65 (1H, d, J=8 Hz), 8.03 (1H, d, J=7 Hz), 8.10 (1H, d, J=7 Hz)

(53) MASS (m/z): 610 (M⁺+1); NMR (CDCl$_3$, δ): 2.28 (3H, s), 2.37–2.40 (4H, m), 2.52 (1H, dd, J=7, 16 Hz), 2.64 (3H×⅔, s), 2.88 (3H×⅓, s), 2.97–3.09 (2H, m), 3.17 (1H×⅓, dd, J=3, 16 Hz), 3.28 (1H×⅔, dd, J=3, 16 Hz), 3.37–3.48 (2H, m), 3.56–3.74 (2H, m), 4.28 (1H×⅔, d, J=15 Hz), 4.29 (1H×⅓, d, J=15 Hz), 4.41 (1H×⅓, d, J=15 Hz), 4.72 (1H×⅔, d, J=15 Hz), 4.94 (1H×⅓, dt, J=4, 7 Hz), 5.10 (1H×⅔, dt, J=4, 7 Hz), 5.19 (1H, dt, J=7, 7 Hz), 7.02 (1H, d, J=7 Hz), 7.07–7.32 (10H, m), 7.42 (1H, t, J=8 Hz), 7.48–7.55 (2H, m), 7.66 (1H, d, J=8 Hz), 7.84 (1H×⅔, d, J=8 Hz), 7.92 (1H×⅓, d, J=8 Hz), 8.00 (1H×⅓, d, J=8 Hz), 8.16 (1H×⅔, d, J=8 Hz)

(54) MASS (m/z): 610 (M⁺+1); NMR (CDCl$_3$, δ): 2.27 (3H, s), 2.37–2.43 (4H, m), 2.58 (3H×⅔, s), 2.66 (1H, dd, J=7, 15 Hz), 2.79 (3H×⅓, s), 3.04 (2H, m), 3.29 (1H, dt, J=4, 15 Hz), 3.47 (2H, m), 3.65 (2H, m), 4.14 (1H×⅓, d, J=15 Hz), 4.26 (1H×⅔, d, J=15 Hz), 4.33 (1H×⅓, d, J=15 Hz), 4.63 (1H×⅔, d, J=15 Hz), 5.02–5.16 (2H, m), 6.92–7.05 (2H, m), 7.15 (5H, m), 7.23–7.30 (4H, m), 7.42 (1H, t, J=8 Hz), 7.48 (1H, s), 7.54 (1H, d, J=8 Hz), 7.64–7.74 (2H, m), 8.22 (1H, m)

(55) MASS (m/z): 610 (M$^+$+1); NMR (CDCl$_3$, δ): 2.28 (3H, s), 2.37–2.40 (4H, m), 2.52 (1H, dd, J=7, 16 Hz), 2.64 (3H×⅔, s), 2.88 (3H×⅓, s), 2.97–3.09 (2H, m), 3.17 (1H×⅓, dd, J=3, 16 Hz), 3.28 (1H×⅔, dd, J=3, 16 Hz), 3.37–3.48 (2H, m), 3.56–3.74 (2H, m), 4.28 (1H×⅔, d, J=15 Hz), 4.29 (1H×⅓, d, J=15 Hz), 4.41 (1H×⅓, d, J=15 Hz), 4.72 (1H×⅔, d, J=15 Hz), 4.94 (1H×⅓, dt, J=4, 7 Hz), 5.10 (1H×⅔, dt, J=4, 7 Hz), 5.19 (1H, dt, J=7, 7 Hz), 7.02 (1H, d, J=7 Hz), 7.07–7.32 (10H, m), 7.42 (1H, t, J=8 Hz), 7.48–7.55 (2H, m), 7.66 (1H, d, J=8 Hz), 7.84 (1H×⅔, d, J=8 Hz), 7.92 (1H×⅓, d, J=8 Hz), 8.00 (1H×⅓, d, J=8 Hz), 8.16 (1H×⅔, d, J=8 Hz)

(56) MASS (FAB) (m/z): 598 (M+H)$^+$; NMR (CDCl$_3$, δ): 2.67 (3×⅔H, s), 2.68–2.74 (1H, m), 2.83 (3×⅓H, s), 2.98–3.12 (2H, m), 3.20–3.31 (1H, m), 3.39–3.53 (2H, m), 3.60–3.75 (6H, m), 4.13–4.42 (2×⅔H, m), 4.63 (2×⅓H, d, J=15 Hz), 5.07–5.20 (2H, m), 6.99–7.08 (2H, m), 7.12–7.33 (9H, m), 7.49 (1H, s), 7.67 (1H, t, J=8 Hz), 8.03 (1H, d, J=8 Hz), 8.23 (1H, d, J=8 Hz), 8.48 (1H, d, J=5 Hz)

(57) MASS (FAB) (m/z): 643 (M+H)$^+$; NMR (CDCl$_3$, δ): 2.59–2.70 (1H, m), 2.65 (3×⅔H, s), 2.82 (3×⅓H, s), 2.98–3.07 (2H, m), 3.21–3.33 (1H, m), 3.40–3.53 (2H, m), 3.62–3.75 (6H, m), 4.11–4.46 (2×⅔H, m), 4.62 (2×⅓H, d, J=15 Hz), 5.02–5.17 (2H, m), 7.01–7.35 (10H, m), 7.63 (1H, s), 7.67 (1H, d, J=8 Hz), 8.40 (1H, d, J=8 Hz), 8.90 (1H, s), 9.38 (1H, s)

(58) MASS (FAB) (m/z): 645 (M+H)$^+$; NMR (CDCl$_3$, δ): 2.53–2.63 (1H, m), 2.67 (3×⅔H, s), 2.83 (3×⅓H, s), 2.97–3.11 (2H, m), 3.30 (1H, t, J=15 Hz), 3.42–3.59 (2H, m), 3.62–3.80 (6H, m), 4.13–4.45 (2×⅔H, m), 4.22 (2H, s), 4.63 (2×⅓H, d, J=15 Hz), 5.08–5.18 (2H, m), 7.00–7.32 (11H, m), 7.35 (1H, t, J=8 Hz), 7.47 (1H, t, J=8 Hz), 7.53–7.62 (2H, m), 7.70–7.83 (1H, m), 7.93 (1H, d, J=8 Hz), 8.06–8.11 (1H, m)

(59) MASS (FAB) (m/z): 627 (M+H)$^+$; NMR (CDCl$_3$, δ): 2.31 (3H, s), 2.36–2.49 (4H, m), 2.62 (3×⅔H, s), 2.66–2.78 (1H, m), 2.81 (3×⅓H, s), 2.98–3.12 (2H, m), 3.28–3.37 (1H, m), 3.42–3.55 (2H, m), 3.66–3.71 (2H, m), 4.13–4.40 (2×⅔H, m), 4.63 (2×⅓H, d, J=15 Hz), 5.02–5.20 (2H, m), 6.97–7.08 (2H, m), 7.16–7.22 (5H, m), 7.26–7.31 (3H, m), 7.48–7.73 (3H, m), 7.98 (1H, d, J=8 Hz), 8.15 (1H, d, J=8 Hz), 8.80–8.84 (1H, m)

(60) MASS (FAB) (m/z): 644 (M+H)$^+$; NMR (CDCl$_3$, δ): 2.29 (3H, s), 2.36–2.49 (4H, s), 2.60 (3×⅔H, s), 2.58–2.70 (1H, m), 2.82 (3×⅓H, s), 2.97–3.11 (2H, m), 3.31 (1H, t, J=15 Hz), 3.42–3.58 (2H, m), 3.66–3.72 (2H, m), 4.10–4.39 (2×⅔H, m), 4.65 (2×⅓H, d, J=15 Hz), 5.01–5.18 (2H, m), 6.97–7.08 (2H, m), 7.12–7.21 (5H, m), 7.23–7.30 (3H, m), 7.39–7.52 (3H, m), 7.65 (1H, s), 7.72 (1H, d, J=8 Hz), 8.27 (1H, d, J=8 Hz)

(61) MASS (FAB) (m/z): 640 (M+H)$^+$; NMR (CDCl$_3$, δ): 2.27 (3H, s), 2.33–2.49 (4H, m), 2.58–2.71 (1H, m), 2.59 (3×⅔H, s), 2.80 (3×⅓H, s), 2.98–3.12 (2H, m), 3.29 (1H, t, J=15 Hz), 3.42–3.55 (2H, m), 3.63–3.70 (2H, m), 3.84 (3H, s), 4.08–4.38 (2×⅔H, m), 4.65 (2×⅓H, d, J=15 Hz), 5.02–5.18 (2H, m), 6.94–7.08 (4H, m), 7.12–7.21 (5H, m), 7.23–7.30 (3H, m), 7.43 (1H, s), 7.45 (1H, d, J=8 Hz), 7.65 (1×⅓H, d, J=8 Hz), 7.71 (1×⅔H, d, J=8 Hz), 8.15–8.20 (1H, m)

(62) MASS (FAB) (m/z): 688 (M+H)$^+$; NMR (CDCl$_3$, δ): 2.30 (3H, s), 2.36–2.50 (4H, m), 2.58–2.70 (1H, m), 2.62 (3×⅔H, s), 2.82 (3×⅓H, s), 2.98–3.12 (2H, m), 3.32 (1H, t, J=15 Hz), 3.42–3.57 (2H, m), 3.63–3.71 (2H, m), 4.11–4.39 (2×⅔H, m), 4.65 (2×⅓H, d, J=15 Hz), 5.00–5.18 (2H, m), 6.97–7.08 (2H, m), 7.13–7.21 (4H, m), 7.23–7.32 (4H, m), 7.40–7.53 (2H, m), 7.63–7.96 (2H, m), 8.20–8.22 (2H, m)

(63) MASS (FAB) (m/z): 640 (M+H)$^+$; NMR (CDCl$_3$, δ): 2.29 (3H, s), 2.35–2.47 (4H, m), 2.61 (3×⅔H, s), 2.71 (1H, dd, J=15, 8 Hz), 2.83 (3×⅓H, s), 2.97–3.11 (2H, m), 3.19–3.29 (1H, m), 3.40–3.55 (2H, m), 3.63–3.72 (2H, m), 4.02 (3H, s), 4.17–4.40 (2×⅔H, m), 4.67 (2×⅓H, d, J=15 Hz), 5.02–5.15 (2H, m), 6.90 (1H, d, J=8 Hz), 6.97 (1H, d, J=8 Hz), 7.07 (1H, d, J=8 Hz), 7.12–7.21 (6H, m), 7.22–7.31 (4H, m), 7.48 (1H, s), 7.68 (1×⅓H, d, J=8 Hz), 7.75 (1×⅔H, d, J=8 Hz), 8.11 (1H, t, J=8 Hz)

(64) MASS (FAB) (m/z): 563 (M+H)$^+$; NMR (CDCl$_3$, δ): 2.50–2.71 (1H, m), 2.62 (3×⅔H, s), 2.82 (3×⅓H, s), 2.99–3.06 (2H, m), 3.28 (1H, t, J=15 Hz), 3.40–3.58 (2H, m), 3.62–3.79 (6H, m), 4.12–4.42 (2×⅔H, m), 4.65 (2×⅓H, d, J=15 Hz), 4.95–5.13 (2H, m), 6.98–7.33 (11H, m), 7.51–7.71 (3H, m), 7.90 (1H, t, J=8 Hz)

(65) MASS (FAB) (m/z): 547 (M+H)$^+$; NMR (CDCl$_3$, δ): 2.51–2.58 (1H, m), 2.59 (3×⅔H, s), 2.82 (3×⅓H, s), 3.00–3.10 (2H, m), 3.29 (1H, t, J=15 Hz), 3.40–3.55 (2H, m), 3.63–3.76 (6H, m), 4.09–4.39 (2×⅔H, m), 4.64 (2×⅓H, d, J=15 Hz), 4.98–5.17 (2H, m), 6.51–6.54 (1H, m), 6.93–7.32 (11H, m), 7.51 (1H, s), 7.58 (1H, dd, J=18, 8 Hz), 7.99 (1H, d, J=8 Hz)

(66) MASS (FAB) (m/z): 558 (M+H)$^+$; NMR (CDCl$_3$, δ): 2.59 (3×⅔H, s), 2.61–2.72 (1H, m), 2.77 (3×⅓H, s), 2.99–3.05 (2H, m), 3.22–3.33 (1H, m), 3.41–3.55 (2H, m), 3.62–3.72 (6H, m), 4.12–4.45 (2×⅔H, m), 4.63 (2×⅓H, d, J=15 Hz), 5.02–5.18 (2H, m), 6.92–7.22 (7H, m), 7.23–7.31 (3H, m), 7.42–7.56 (2H, m), 7.88 (1H, t, J=8 Hz), 8.20 (1H, d, J=8 Hz), 8.62 (1H, d, J=5 Hz), 9.18 (1H, d, J=8 Hz)

(67) MASS (FAB) (m/z): 556 (M+H)$^+$; NMR (CDCl$_3$, δ): 2.49–2.68 (1H, m), 2.65 (3×⅔H, s), 2.82 (3×⅓H, s), 2.98–3.05 (2H, m), 3.29 (1H, t, J=15 Hz), 3.41–3.59 (2H, m), 3.61–3.78 (6H, m), 4.12–4.42 (2×⅔H, m), 4.65 (2×⅓H, d, J=15 Hz), 5.00–5.13 (2H, m), 6.99–7.23 (7H, m), 7.25–7.32 (3H, m), 7.43–7.57 (3H, m), 7.62–7.72 (1H, m), 7.85 (2H, d, J=8 Hz), 8.07 (1H, t, J=8 Hz)

(68) MASS (FAB) (m/z): 495 (M+H)$^+$; NMR (CDCl$_3$, δ): 2.03 (3H, d, J=5 Hz), 2.43–2.55 (1H, m), 2.58 (3×⅔H, s), 2.82 (3×⅓H, s), 3.01 (2H, t, J=8 Hz), 3.18 (1H, t, J=8 Hz), 3.38–3.51 (2H, m), 3.58–3.63 (2H, m), 3.67–3.75 (4H, m), 4.08 (2×⅛H, d, J=15 Hz), 4.28–4.38 (2×⅛H, m), 4.63 (2×⅜H, d, J=15 Hz), 4.78–4.90 (1H, m), 5.01–5.12 (1H, m), 6.97 (1H, d, J=8 Hz), 7.05–7.31 (10H, m), 7.53 (1H, t, J=8 Hz)

(69) MASS (FAB) (m/z): 608 (M+H)$^+$; NMR (CDCl$_3$, δ): 2.60 (3×⅔H, s), 2.68–2.88 (1H, m), 2.80 (3×⅓H, s), 3.05 (2H, t, J=8 Hz), 3.12–3.33 (1H, m), 3.41–3.52 (2H, m), 3.62–3.73 (6H, m), 4.15–4.33 (2×⅔H, m), 4.65 (2×⅓H, d, J=15 Hz), 5.10–5.21 (2H, m), 6.96–7.08 (2H, m), 7.12–7.21 (5H, m), 7.23–7.31 (4H, m), 7.58–7.68 (2H, m), 7.80 (1H, t, J=8 Hz), 7.90 (1H, d, J=8 Hz), 8.21–8.35 (3H, m)

(70) MASS (FAB) (m/z): 546 (M+H)$^+$; NMR (CDCl$_3$, δ): 2.50–2.62 (1H, m), 2.61 (3×⅔H, s), 2.82 (3×⅓H, s), 2.96–3.08 (2H, m), 3.20–3.33 (1H, m), 3.43–3.50 (2H, m), 3.60–3.75 (6H, m), 4.11–4.40 (2×⅔H, m), 4.67 (2×⅓H, d, J=15 Hz), 4.98–5.15 (2H, m), 6.13–6.17 (1H, m), 6.67–6.71 (1H, m), 6.93–7.10 (3H, m), 7.12–7.32 (8H, m), 7.58–7.70 (2H, m), 9.48 (1H, br s)

(71) MASS (FAB) (m/z): 607 (M+H)$^+$; NMR (CDCl$_3$, δ): 2.62 (3×⅔H, s), 2.67–2.75 (1H, m), 2.82 (3×⅓H, s), 3.02–3.09 (2H, m), 3.29–3.78 (9H, m), 4.08–4.43 (2×⅔H, m), 4.63 (2×⅓H, d, J=15 Hz), 5.08–5.22 (2H, m), 7.00–7.33 (7H, m), 7.25–7.32 (3H, m), 7.43–7.96 (8H, m), 8.40 (1H, d, J=8 Hz)

(72) MASS (FAB) (m/z): 607 (M+H)$^+$; NMR (CDCl$_3$, δ): 2.56–2.70 (1H, m), 2.65 (3×⅔H, s), 2.83 (3×⅓H, s), 2.93–3.12 (2H, m), 3.31 (1H, t, J=15 Hz), 3.43–3.58 (2H, m), 3.62–3.80 (6H, m), 4.15–4.45 (2×⅔H, m), 4.64 (2×⅓H, d, J=15 Hz), 5.08–5.19 (2H, m), 7.01–7.22 (8H, m), 7.23–7.43 (2H, m), 7.52–7.62 (2H, m), 7.73–7.83 (1H, m), 7.89–7.92 (3H, m), 7.98 (1H, d, J=8 Hz), 8.22 (1H, d, J=8 Hz), 8.39 (1H, s)

(73) MASS (FAB) (m/z): 614 (M+H)⁺; NMR (CDCl₃, δ): 263 (3×⅔H, s), 2.64–2.78 (1H, m), 2.81 (3×⅓H, s), 2.97–3.12 (2H, m), 3.22–3.32 (1H, m), 3.40–3.55 (2H, m), 3.60–3.76 (6H, m), 4.12–4.39 (2×⅔H, m), 4.63 (2×⅓H, d, J=15 Hz), 5.01–5.18 (2H, m), 6.97–7.20 (7H, m), 7.23–7.30 (3H, m), 7.47–7.71 (3H, m), 7.97 (1H, d, J=8 Hz), 8.15 (1H, d, J=8 Hz), 8.82 (1H, d, J=8 Hz)

(74) MASS (FAB) (m/z): 659 (M+H)⁺; NMR (CDCl₃, δ): 2.53–2.62 (1H, m), 2.69 (2H, s), 2.82 (1H, s), 2.94–3.11 (2H, m), 3.26 (1H, t, J=15 Hz), 3.42–3.58 (2H, m), 3.62–3.78 (6H, m), 4.12–4.48 (2×⅔H, m), 4.64 (2×⅓H, d, J=15 Hz), 5.01–5.15 (2H, m), 7.01–7.22 (7H, m), 7.23–7.40 (5H, m), 7.52–7.60 (2H, m), 7.70 (1H, d, J=8 Hz), 7.78 (1H, d, J=8 Hz), 7.99–8.05 (2H, m), 8.12 (1H, d, J=8 Hz)

(75) MASS (FAB) (m/z): 598 (M+H)⁺; NMR (CDCl₃, δ): 2.60 (3×⅔H, s), 2.52–2.72 (1H, m), 2.80 (3×⅓H, s), 2.94–3.10 (2H, m), 3.28 (1H, t, J=15 Hz), 3.40–3.52 (2H, m), 3.62–3.76 (6H, m), 4.12–4.42 (2×⅔H, m), 4.62 (2×⅓H, d, J=15 Hz), 5.01–5.16 (2H, m), 6.98–7.18 (7H, m), 7.22–7.32 (3H, m), 7.41–7.52 (2H, m), 7.65 (1H, d, J=8 Hz), 7.72 (1H, d, J=8 Hz), 7.85 (1H, d, J=8 Hz), 8.82 (1H, d, J=8 Hz)

(76) MASS (FAB) (m/z): 645 (M+H)⁺; NMR (CDCl₃, δ): 2.28–2.42 (1H, m), 2.53 (3×⅔H, s), 2.81 (3×⅓H, s), 2.82–3.01 (3H, m), 3.27–3.38 (2H, m), 3.43–3.70 (6H, m), 4.03–4.35 (2×⅔H, m), 4.62 (2×⅓H, d, J=15 Hz), 4.75–4.88 (2H, m), 4.93–5.00 (1H, m), 6.90–6.98 (1H, m), 7.03–7.30 (12H, m), 7.32–7.55 (4H, m), 7.70–7.81 (3H, m)

(77) MASS (FAB) (m/z): 597 (M+H)⁺; NMR (CDCl₃, δ): 2.65 (3×⅔H, s), 2.83 (3×⅓H, s), 2.81–3.18 (4H, m), 3.40–3.47 (2H, m), 3.55–3.65 (6H, m), 4.28 (2×⅔H, t, J=15 Hz), 4.75 (2×⅓H, d, J=15 Hz), 5.20–5.30 (1H, m), 5.46–5.61 (1H, m), 6.93–7.11 (7H, m), 7.21–7.32 (5H, m), 7.46–7.52 (1H, m), 7.78–7.83 (1H, m), 8.40–8.49 (1H, m), 8.63–8.72 (1H, m)

(78) MASS (FAB) (m/z): 615 (M+H)⁺; NMR (CDCl₃, δ): 2.53 (3×⅔H, s), 2.75 (3×⅓H, s), 2.80–2.92 (1H, m), 3.00–3.13 (2H, m), 3.25 (1H, dd, J=15, 4 Hz), 3.43–3.51 (2H, m), 3.60–3.69 (6H, m), 3.99–4.30 (2×⅔H, m), 4.58 (2×⅓H, d, J=15 Hz), 4.81–4.92 (1H, m), 5.13–5.20 (1H, m), 6.83–6.97 (2H, m), 7.08–7.23 (10H, m), 7.35 (1H, d, J=8 Hz), 7.83–7.90 (1H, m), 8.17 (1H, d, J=8 Hz)

(79) MASS (FAB) (m/z): 608 (M+H)⁺; NMR (CDCl₃, δ): 2.60–2.73 (1H, m), 2.63 (3×⅔H, s), 2.81 (3×⅓H, s), 3.00–3.08 (2H, m), 3.30 (1H, t, J=15 Hz), 3.41–3.56 (2H, m), 3.60–3.78 (6H, m), 4.09–4.47 (2×⅔H, m), 4.63 (2×⅓H, d, J=15 Hz), 5.08–5.20 (2H, m), 7.00–7.33 (10H, m), 7.43–7.52 (1H, m), 7.67–7.83 (2H, m), 7.88–8.03 (1H, m), 8.20 (1H, d, J=8 Hz), 8.31 (1H, d, J=8 Hz), 8.58 (1H, s), 8.82–9.00 (1H, m)

(80) MASS (FAB) (m/z): 609 (M+H)⁺; NMR (CDCl₃, δ): 2.63 (3×⅔H, s), 2.81 (3×⅓H, s), 2.68–2.80 (1H, m), 3.01–3.08 (2H, m), 3.23–3.35 (1H, m), 3.40–3.57 (2H, m), 3.63–3.75 (6H, m), 4.10–4.42 (2×⅔H, m), 4.63 (2×⅓H, d, J=15 Hz), 5.11–5.22 (2H, m), 6.99–7.22 (6H, m), 7.24–7.32 (4H, m), 7.62–7.72 (1H, m), 7.83–7.92 (2H, m), 8.12 (2H, t, J=8 Hz), 9.11–9.17 (1H, m), 9.64 (1H, s)

(81) MASS (FAB) (m/z): 610 (M+H)⁺; NMR (CDCl₃, δ): 2.55–2.67 (1H, m), 2.61 (3×⅔H, s), 2.81 (3×⅓H, s), 2.99–3.06 (2H, m), 3.27 (1H, t, J=15 Hz), 3.40–3.58 (2H, m), 3.62–3.77 (6H, m), 4.03 (3H, s), 4.12–4.42 (2×⅔H, m), 4.63 (2×⅓H, d, J=15 Hz), 4.99–5.17 (2H, m), 6.98–7.41 (14H, m), 7.6i (2H, q, J=8 Hz), 8.01 (1H, t, J=8 Hz)

(82) MASS (FAB) (m/z): 7.40 (M+H)⁺; NMR (CDCl₃, δ): 1.23 (3H, t, J=8 Hz), 2.52–2.71 (5H, m), 2.62 (3×⅔H, s), 2.79 (3×⅓H, s), 2.97–3.14 (2H, m), 3.22 (2H, s), 3.28–3.39 (1H, m), 3.47–3.62 (2H, m), 3.68–3.78 (2H, m), 3.91 (3H, s), 4.18 (2H, q, J=8 Hz), 4.30–4.38 (2×⅔H, m), 4.70 (2×⅓H, d, J=15 Hz), 5.03–5.19 (2H, m), 6.97 (2×⅓H, d, J=8 Hz), 7.08 (2×⅔H, d, J=8 Hz), 7.13–7.23 (5H, m), 7.30 (1H, t, J=8 Hz), 7.43 (1H, t, J=8 Hz), 7.49 (1H, s), 7.53–7.63 (1H, m), 7.69 (2H, t, J=8 Hz), 7.92 (2H, d, J=8 Hz), 8.20 (1H, t, J=8 Hz)

(83) MASS (FAB) (m/z): 774 (M+H)⁺; NMR (CDCl₃, δ): 1.25 (3H, t, J=8 Hz), 2.52–2.69 (5H, m), 2.62 (3×⅔H, s), 2.79 (3×⅓H, s), 2.97–3.11 (2H, m), 3.20 (2H, s), 3.31 (1H, t, J=8 Hz), 3.43–3.60 (2H, m), 3.68–3.77 (2H, m), 3.91 (3H, s), 4.18 (2H, q, J=8 Hz), 4.22–4.38 (2×⅔H, m), 4.69 (2×⅓H, d, J=16 Hz), 5.01–5.18 (2H, m), 6.98 (2×⅓H, d, J=8 Hz), 7.08 (2×⅔H, d, J=8 Hz), 7.12–7.24 (5H, m), 7.40 (2H, t, J=8 Hz) 7.50 (1H, d, J=8 Hz), 7.60–7.70 (2H, m), 7.92 (2H, d, J=8 Hz), 8.23 (1H, t, J=8 Hz)

(84) MASS (FAB) (m/z): 756 (M+H)⁺; NMR (CDCl₃, δ): 1.25 (3H, t, J=8 Hz), 2.57–2.68 (5H, m), 2.63 (3×⅔H, s), 2.80 (3×⅓H, s), 2.97–3.11 (2H, m), 3.22 (2H, s), 3.32 (1H, t, J=8 Hz), 3.47–3.63 (2H, m), 3.68–3.75 (2H, m), 3.90 (3H, s), 4.18 (2H, q, J=8 Hz), 4.22–4.41 (2×⅔H, m), 4.70 (2×⅓H, d, J=15 Hz), 5.00–5.18 (2H, m), 7.00 (2×⅓H, d, J=8 Hz), 7.09 (2×⅔H, d, J=8 Hz), 7.11–7.23 (5H, m), 7.38–7.47 (2H, m), 7.69 (1×⅓H, d, J=8 Hz), 7.73 (1×⅔H, d, J=8 Hz), 7.80–7.89 (3H, m), 7.93 (2H, d, J=8 Hz), 8.10–8.15 (1H, m)

(85) MASS (FAB) (m/z): 739 (M+H)⁺; NMR (CDCl₃, δ): 1.21 (3H, t, J=8 Hz), 2.43–2.58 (4H, m), 2.63 (3×⅔H, s), 2.67–2.74 (1H, m), 2.80 (3×⅓H, s), 2.92–3.10 (2H, m), 3.16 (2H, s), 3.21 (1H, t, J=8 Hz), 3.40–3.52 (2H, m), 3.58–3.73 (2H, m), 3.90 (3H, s), 4.14 (2H, q, J=8 Hz), 4.28 (2×½H, d, J=8 Hz), 4.73 (2×½H, d, J=15 Hz), 5.08–5.28 (2H, m), 6.92–7.16 (8H, m), 7.27 (2H, t, J=8 Hz), 7.43 (1H, d, J=8 Hz), 7.63 (1H, d, J=8 Hz), 7.89 (2H, d, J=8 Hz), 8.01–8.10 (2H, m)

(86) MASS (FAB) (m/z): 716 (M+H)⁺; NMR (CDCl₃, δ): 1.23 (3H, t, J=8 Hz), 2.53–2.70 (5H, m), 2.62 (3×⅔H, s), 2.81 (3×⅓H, s), 2.97–3.11 (2H, m), 3.23 (2H, s), 3.31 (1H, t, J=15 Hz), 3.43–3.60 (2H, m), 3.68–3.73 (2H, m), 4.11–4.38 (2×⅔H, m), 4.18 (2H, q, J=8 Hz), 4.65 (2×⅓H, d, J=8 Hz), 5.02–5.17 (2H, m), 6.97 (2×⅓H, d, J=8 Hz), 7.04 (2×⅔H, d, J=8 Hz), 7.11–7.21 (5H, m), 7.23–7.30 (3H, m), 7.37–7.51 (3H, m), 7.63 (1H, s), 7.64 (1×⅓H, d, J=8 Hz), 7.71 (1×⅔H, d, J=8 Hz), 8.21–8.27 (1H, m)

(87) MASS (FAB) (m/z): 698 (M+H)⁺; NMR (CDCl₃, δ): 1.26 (3H, t, J=8 Hz), 2.56–2.69 (5H, m), 2.63 (3×⅔H, s), 2.83 (3×⅓H, s), 2.97–3.12 (2H, m), 3.12 (2H, s), 3.31 (1H, t, J=15 Hz), 3.48–3.62 (2H, m), 3.68–3.72 (2H, m), 4.17 (2H, q, J=8 Hz), 4.20–4.41 (2×⅔H, m), 4.65 (2×⅓H, d, J=15 Hz), 4.98–5.13 (2H, m), 6.98 (2×⅓H, d, J=8 Hz), 7.08 (2×⅔H, d, J=8 Hz), 7.12–7.32 (8H, m), 7.37–7.46 (2H, m), 7.70 (1×⅓H, d, J=8 Hz), 7.73 (1×⅔H, d, J=8 Hz), 7.80–7.86 (3H, m), 8.13 (1H, d, J=8 Hz)

(88) MASS (FAB) (m/z): 655 (M+H)⁺; NMR (CDCl₃, δ): 2.31 (3H, s), 2.37–2.52 (4H, m), 2.58–2.70 (1H, m), 2.59 (3×⅔H, s), 2.81 (3×⅓H, s), 2.98–3.10 (2H, m), 3.35 (1H, t, J=15 Hz), 3.43–3.58 (2H, m), 3.67–3.72 (2H, m), 4.07–4.39 (2×⅔H, m), 4.63 (2×⅓H, d, J=15 Hz), 5.02–5.17 (2H, m), 6.97 (2×⅓H, d, J=8 Hz), 7.07 (2×⅔H, d, J=8 Hz), 7.12–7.22 (6H, m), 7.24–7.32 (3H, m), 7.63 (1H, s), 7.65–7.72 (2H, m), 8.35–8.40 (1H, m), 8.62 (1H, s)

(89) MASS (FAB) (m/z): 653 (M+H)⁺; NMR (CDCl₃, δ): 2.29 (3H, s), 2.38–2.50 (4H, m), 2.61 (3×⅔H, s), 2.58–2.70 (1H, m), 2.81 (3×⅓H, s), 2.98 (6H, s), 3.02–3.08 (2H, m), 3.25–3.35 (1H, m), 3.42–3.58 (2H, m), 3.64–3.72 (2H, m), 4.13–4.38 (2×⅔H, m), 4.65 (2×⅓H, d, J=15 Hz), 5.00–5.16 (2H, m), 6.89–7.08 (5H, m), 7.13–7.22 (5H, m), 7.28–7.32 (2H, m), 7.38–7.46 (2H, m), 7.63 (1×⅓H, d, J=8 Hz), 7.70 (1×⅔H, d, J=8 Hz), 8.10–8.13 (1H, m)

(90) MASS (FAB) (m/z): 702 (M+H)⁺; NMR (CDCl₃, δ): 2.31 (3H, s), 2.38–2.50 (4H, m), 2.60–2.72 (1H, m), 2.65 (3×⅔H, s), 2.82 (3×⅓H, s), 3.00–3.12 (2H, m), 3.30–3.40 (1H, m), 3.45–3.58 (2H, m), 3.63–3.72 (2H, m), 3.93 (3H, s), 4.20–4.40 (2×⅔H, m), 4.69 (2×⅓H, d, J=15 Hz), 5.02–5.22 (2H, m), 7.00 (2×⅓H, d, J=8 Hz), 7.10 (2×⅔H, d, J=8 Hz), 7.14–7.32 (5H, m), 7.38–7.53 (3H, m), 7.60–7.72 (2H, m), 7.90–8.00 (2H, m), 8.22–8.30 (1H, m)

(91) MASS (FAB) (m/z): 684 (M+H)⁺; NMR (CDCl₃, δ): 2.28 (3H, s), 2.32–2.50 (4H, m), 2.58–2.70 (1H, m), 2.66 (3×⅔H, s), 2.81 (3×⅓H, s), 2.97–3.11 (2H, m), 3.31 (1H, t, J=15 Hz), 3.44–3.58 (2H, m), 3.62–3.70 (2H, m), 3.90 (3H, s), 4.23–4.41 (2×⅔H, m), 4.69 (2×⅓H, d, J=15 Hz), 5.00–5.18 (2H, m), 7.01 (2×⅓H, d, J=8 Hz), 7.09 (2×⅔H, d, J=8 Hz), 7.12–7.22 (5H, m), 7.38–7.47 (2H, m), 7.70–7.88 (4H, m), 7.92 (2H, d, J=8 Hz), 8.12–8.18 (1H, m)

(92) MASS (FAB) (m/z): 667 (M+H)⁺; NMR (CDCl₃, δ): 2.20 (3H, s), 2.27–2.42 (4H, m), 2.62 (3×⅔H, s), 2.67–2.76 (1H, m), 2.79 (3×⅓H, s), 2.93–3.10 (2H, m), 3.22 (1H, dd, J=15, 5 Hz), 3.32–3.47 (2H, m), 3.52–3.70 (2H, m), 3.90 (3H, s), 4.22 (2×⅓H, d, J=15 Hz), 4.29 (2×⅓H, d, J=18 Hz), 4.72 (2×⅓H, d, J=15 Hz), 5.09–5.30 (2H, m), 6.92–7.03 (4H, m), 7.04–7.18 (4H, m), 7.22 (2H, t, J=8 Hz), 7.42 (1H, d, J=8 Hz), 7.66 (1H, d, J=8 Hz), 7.90 (2H, d, J=8 Hz), 8.07–8.19 (2H, m)

EXAMPLE 11

The following object compounds were obtained according to a similar manner to that of Example 3.

(1) MASS (m/z): 667 (M+H)⁺; NMR (CDCl₃, δ): 2.34 (6H, s), 2.42–2.78 (9H, m), 2.61 (⅔×3H, s), 2.81 (⅓×3H, s), 2.93–3.15 (2H, m), 3.22–3.40 (1H, m), 3.40–3.75 (4H, m), 4.25 (⅓×2H, ABq, Δ=0.18, J=17 Hz), 4.29 (⅔×1H, d, J=15 Hz), 4.65 (⅔×1H, d, J=15 Hz), 5.00–5.22 (2H, m), 6.85–7.78 (16H, m), 8.15–8.25 (1H, m)

(2) MASS (m/z): 696 (M⁺+1); NMR (CDCl₃, δ): 1.45 (9H, s), 2.62 (3H×⅔, s), 2.67 (1H, m), 2.82 (3H×⅓, s), 3.04 (2H, m), 3.28 (1H, m), 3.44 (6H, m), 3.62 (2H, m), 4.14 (1H×⅓, d, J=16 Hz), 4.29 (1H×⅔, d, J=15 Hz), 4.37 (1H×⅓, d, J=16 Hz), 4.63 (1H×⅔, d, J=15 Hz), 5.11 (2H, m), 6.96–7.33 (11H, m), 7.44 (1H, t, J=8 Hz), 7.50 (1H, s), 7.56 (1H, d, J=8 Hz), 7.67 (2H, m), 8.19 (1H, d, J=8 Hz)

(3) MASS (FAB) (m/z): 600 (M+H)⁺; NMR (DMSO-d₆, δ): 2.55–2.67 (2H, m), 2.74 (3×⅓H, s), 2.82 (3×⅔H, s), 2.84–3.03 (2H, m), 3.42 (2H, t, J=5 Hz), 3.64–3.75 (1H, m), 4.37 (2×⅓H, d, J=15 Hz), 4.53 (2×⅔H, d, J=15 Hz), 4.57–4.63 (2H, m), 4.80–5.01 (2H, m), 7.03–7.10 (4H, m), 7.13–7.30 (9H, m), 7.45 (1H, d, J=8 Hz), 7.63 (2H, t, J=8 Hz), 8.32 (1×⅔H, d, J=8 Hz), 8.39 (1×⅓H, d, J=8 Hz), 8.49 (1H, t, J=8 Hz)

(4) MASS (FAB) (m/z): 653 (M+H)⁺; NMR (CDCl₃, δ): 1.66–1.73 (2H, m), 2.37–2.50 (4H, m), 2.55 (2H, t, J=5 Hz), 2.60 (3×⅔H, s), 2.59–2.72 (1H, m), 2.81 (3×⅓H, s), 3.02 (2H, d, J=8 Hz), 3.18–3.27 (1H, m), 3.40–3.47 (2H, m), 3.59–3.65 (2H, m), 3.76 (2H, t, J=5 Hz), 4.18–4.38 (2×⅔H, m), 4.69 (2×⅓H, d, J=15 Hz), 5.11–5.22 (2H, m), 6.96–7.17 (13H, m), 7.43 (1H, d, J=8 Hz), 7.63 (1H, d, J=8 Hz), 7.93–8.08 (2H, m)

(5) MASS (FAB) (m/z): 682 (M+H)⁺; NMR (CDCl₃, δ): 1.23 (3H, t, J=8 Hz), 2.52–2.66 (4H, m), 2.58 (3×⅔H, s), 2.67 (1H, dd, J=15, 8 Hz), 2.81 (3×⅓H, s), 2.97–3.11 (2H, m), 3.20 (2H, s), 3.31 (1H, t, J=15 Hz), 3.47–3.62 (2H, m), 3.70–3.74 (2H, m), 4.18 (2H, q, J=8 Hz), 4.20–4.38 (2×⅔H, m), 4.66 (2×⅓H, d, J=15 Hz), 5.02–5.18 (2H, m), 6.96 (2×⅓H, d, J=8 Hz), 7.06 (2×⅔H, d, J=8 Hz), 7.14–7.21 (6H, m), 7.25–7.32 (3H, m), 7.43 (1H, t, J=8 Hz), 7.50 (1H, s), 7.57 (1H, d, J=8 Hz), 7.63–7.72 (2H, m), 8.18–8.22 (1H, m)

(6) MASS (FAB) (m/z): 631 (M+H)⁺; NMR (CDCl₃, δ): 2.68–2.80 (1H, m), 2.70 (3×⅔H, s), 2.84 (3×⅓H, s), 2.90–3.08 (3H, m), 3.70–3.83 (6H, m), 4.28 (2×⅓H, d, J=15 Hz), 4.43–4.68 (2×⅔H, m), 4.54 (3H, br s), 5.03–5.19 (2H, m), 7.02–7.05 (4H, m), 7.09–7.16 (4H, m), 7.23–7.33 (4H, m), 7.39 (1H, t, J=8 Hz), 7.46 (2H, t, J=8 Hz), 7.62 (1H, d, J=8 Hz), 7.92 (1×⅓H, d, J=8 Hz), 8.00 (1×⅔H, d, J=8 Hz), 8.14 (1H, d, J=8 Hz)

(7) MASS (FAB) (m/z): 630 (M+H)⁺; NMR (CDCl₃, δ): 2.68–2.75 (1H, m), 2.77 (3×⅔H, s), 2.84–3.08 (3H, m), 2.92 (3×⅓H, s), 3.65–3.77 (6H, m), 4.24–4.52 (2×⅔H, m), 4.81 (2×⅓H, d, J=15 Hz), 5.10–5.40 (2H, m), 6.96–7.14 (11H, m), 7.23–7.33 (3H, m), 7.43 (1H, d, J=8 Hz), 7.64 (1H, d, J=8 Hz), 7.92 (1H, t, J=8 Hz), 8.27 (1×⅓H, d, J=8 Hz), 8.37 (1×⅔H, d, J=8 Hz)

(8) MASS (FAB) (m/z): 601 (M+H)⁺; NMR (CDCl₃, δ): 2.67 (3×⅔H, s), 2.62–2.81 (2H, m), 2.81 (3×⅓H, s), 2.88–3.07 (3H, m), 3.75–3.90 (4H, m), 3.99–4.08 (1H, m), 4.19–4.47 (2×⅔H, m), 4.21 (1H, br s), 4.33 (1H, br s), 4.70 (2×⅓H, d, J=15 Hz), 5.02–5.10 (1H, m), 5.12–5.21 (1H, m), 7.00 (3H, t, J=8 Hz), 7.09–7.15 (3H, m), 7.21–7.27 (4H, m), 7.30–7.49 (4H, m), 7.57 (1H, t, J=8 Hz), 8.03 (1×⅓H, d, J=8 Hz), 8.12 (1×⅔H, d, J=8 Hz), 8.21–8.23 (1H, m)

(9) MASS (ESI) (m/z): 510 (M+1); NMR (CDCl₃, δ): 1.99 (1H, dd, J=25, 8 Hz), 2.61 (1H, dd, J=25, 8 Hz), 2.80–3.12 (4H, m), 2.86 (3×⅔H, s), 2.92 (3×⅓H, s), 3.05 (3H, s), 3.49 (2H, d, J=8 Hz), 3.51–3.72 (1H, m), 4.00 (1H, q, J=8 Hz), 4.22–4.34 (2H, m), 4.52–4.70 (3H, m), 5.20–5.28 (2H, m), 6.58 (1H, d, J=8 Hz), 7.07 (2H, d, J=8 Hz), 7.16–7.32 (7H, m), 7.40–7.66 (7H, m)

EXAMPLE 12

To a solution of Starting Compound (107 mg) in dichloromethane (5 ml) was added (benzo[b]furan-2-yl)isocyanate (50 mg) at room temperature and stirred for 1 hour. Purification by column chromatography (silica gel, chloroform-methanol) afforded Object Compound (140 mg) as white powders.

MASS (m/z): 625 (M+H)⁺; NMR (CDCl₃, δ): 2.28 (3H, s), 2.30–2.48 (4H, m), 2.55 (⅔×3H, s), 2.65–2.82 (1H, m), 2.78 (⅓×3H, s), 2.95–3.15 (2H, m), 3.22–3.72 (4H, m), 4.14 (⅔×1H, d, J=15 Hz), 4.22 (⅓×2H, ABq, Δ=0.16, J=17 Hz), 4.65 (⅔×1H, d, J=15 Hz), 4.78–4.95 (1H, m), 5.05–5.22 (1H, m), 6.44 (1H, s), 6.82–7.82 (16H, m), 8.35–8.55 (2H, m)

EXAMPLE 13

Starting Compound (387 mg) and benzo[b]furan-2-carboxaldehyde (99 mg) were dissolved in benzene (10 ml) and heated to reflux for 2 hours. After the mixture was allowed to cool to room temperature, the solvent was evaporated and the remaining solid was redissolved in methanol (1 ml). To this solution was added sodium cyanoborohydride (45 mg) at room temperature, and added some drops of hydrogen chloride-methanol to adjust the solution to about pH 4. The reaction mixture was stirred at the room temperature for 2 days. The mixture was evaporated, added aqueous sodium hydrogen carbonate, and extracted three times with chloroform. The organic layer was washed with brine and dried over magnesium sulfate. Evaporation of the solvent followed by subjecting to column chromatography (silica gel, chloroform-tethanol) gave Object Compound (248 mg) as a viscous oil.

MASS (m/z): 596 (M+H)$^+$; NMR (CDCl$_3$, δ): 2.25 (3H, s), 2.25–2.78 (7H, m), 2.68 (⅔×3H, s), 2.85 (⅓×3H, s), 2.90–3.15 (2H, m), 3.25–3.68 (4H, m), 3.83 (⅔×2H, s), 3.90 (⅓×2H, ABq, Δ=0.12, J=17 Hz), 4.35 (⅔×1H, d, J=15 Hz), 4.38 (⅓×2H, s), 4.70 (⅔×1H, d, J=15 Hz), 5.05–5.22 (1H, m), 6.55 (⅓×1H, s), 6.60 (⅔×1H, s), 6.93–7.56 (15H, m), 8.02–8.22 (1H, m)

EXAMPLE 14

Starting Compound (53 mg) was dissolved in N,N-dimethylformamide (1 ml). Pyridinium chloride (98 mg) was added to the solution, and the mixture was stirred at room temperature for 2.5 hours. The solvent was evaporated, and the remaining oil was dissolved in ethyl acetate. The solution was washed twice with aqueous sodium hydrogen carbonate and dried over magnesium sulfate. Evaporation of the solvent followed by subjecting to column chromatography (silica gel, chloroform-methanol) afforded Object Compound (24 mg) as white powder.

MASS (m/z): 586 (M+H)$^+$; NMR (CDCl$_3$, δ): 2.58–3.20 (3H, m), 2.88 (⅓×3H, s), 3.01 (⅔×3H, s), 3.28–3.80 (9H, m), 4.27 (⅔×1H, d, J=15 Hz), 4.62 (⅓×2H, ABq, Δ=0.09, J=17 Hz), 4.80 (⅔×1H, d, J=15 Hz), 4.98–5.35 (2H, m), 6.45–8.22 (15H, m), 8.65 (1H, br s)

EXAMPLE 15

Starting Compound (347 mg) was dissolved in a mixture of 15% aqueous sodium hydroxide (1 ml) and ethanol (2 ml), and the solution was stirred at room temperature for 1 hour. The solution was acidified by adding 6N hydrochloric acid and extracted three times with chloroform. The organic layer was dried over sodium sulfate. Purification by column chromatography (silica gel, chloroform-methanol) gave Object Compound (151 mg) as white powder.

MASS (m/z): 640 (M+H)$^+$; NMR (CDCl$_3$, δ): 2.55–2.70 (1H, m), 2.73 (⅔×3H, s), 2.88 (⅓×3H, s), 2.92–3.75 (11H, m), 4.22 (⅓×1H, d, J=17 Hz), 4.28 (⅔×1H, d, J=15 Hz), 4.55 (⅓×1H, d, J=17 Hz), 4.62 (⅔×1H, d, J=15 Hz), 5.02–5.35 (2H, m), 6.75–8.45 (17H, m)

EXAMPLE 16

Starting Compound (155 mg), N-(2-chloroethyl)-dimethylamine hydrochloride (62 mg), and potassium carbonate were mixed in N,N-dimethylformamide (0.5 ml) and heated to 50° C. for 8 hours. The reaction mixture was diluted with ethyl acetate, washed twice with aqueous sodium hydrogencarbonate, twice with aqueous sodium hydroxide, once with brine, and dried over magnesium sulfate. Purification by column chromatography (chloroform-methanol) gave Object Compound (32 mg) as white powder.

MASS (m/z): 684 (M+H)$^+$; NMR (CDCl$_3$, δ): 2.34 (6H, s), 2.58 (⅔×3H, s), 2.58–2.80 (3H, m), 2.78 (⅓×3H, s), 2.95–3.12 (2H, m), 3.23–3.39 (1H, m), 3.39–3.80 (8H, m), 4.00–4.10 (2H, m), 4.02 (⅓×1H, d, J=17 Hz), 4.22 (⅔×1H, d, J=15 Hz), 4.31 (⅓×1H, d, J=17 Hz), 4.59 (⅔×1H, d, J=15 Hz), 5.02–5.20 (2H, m), 6.68–7.75 (15H, m), 8.15–8.26 (1H, m)

EXAMPLE 17

To a solution of Starting Compound (92 mg) in dichloromethane (0.5 ml) was added iodomethane (100 mg) at room temperature and stirred for 12 hours. Ether was added to the mixture and pale-yellow precipitate formed was removed by filtration and dried in vacuo to give Object Compound (103 mg).

MASS (m/z): 624 (M−I)$^+$; NMR (CDCl$_3$, δ): 2.70–2.88 (1H, m), 2.83 (3H, s), 2.90–3.25 (3H, m), 3.25–4.18 (14H, m), 4.45 (⅔×2H, ABq, Δ=0.05, J=15 Hz), 4.47 (⅓×2H, ABq, Δ=0.18, J=17 Hz), 4.98–5.25 (2H, m), 7.00–8.05 (17H, m)

EXAMPLE 18

The following object compounds were obtained according to a similar manner to that of Preparation 10.

(1) MASS (FAB) (m/z): 613 (M+H)$^+$; NMR (CDCl$_3$-DMSO-d$_6$, δ): 2.57–2.70 (1H, m), 2.72 (3×⅓H, s) 2.82 (3×⅔H, s), 2.83–3.05 (3H, m), 3.38–3.45 (4H, m), 3.49–3.53 (2H, m), 3.57–3.60 (2H, m), 4.38–4.52 (2H, m), 4.82–5.02 (2H, m), 5.29 (2H, s), 7.02–7.32 (11H, m), 7.38 (1H, s), 7.85 (1H, s), 8.27–8.37 (1H, m), 8.56–8.64 (1H, m)

(2) MASS (FAB) (m/z): 625 (M+H)$^+$; NMR (CDCl$_3$, δ): 2.29 (3H, s), 2.33–2.49 (4H, m), 2.58–2.70 (1H, m), 2.63 (3×⅔H, s), 2.81 (3×⅓H, s), 2.97–3.11 (2H, m), 3.25–3.35 (1H, m), 3.42–3.54 (2H, m), 3.61–3.70 (2H, m), 4.08–4.38 (2×⅔H, m), 4.63 (2×⅓H, d, J=15 Hz), 5.01–5.18 (2H, m), 6.81 (1H, dd, J=8, 2 Hz), 6.87 (1H, d, J=2 Hz), 6.95 (2×⅓H, d, J=8 Hz), 7.06 (2×⅔H, d, J=8 Hz), 7.12–7.22 (5H, m), 7.22–7.28 (3H, m), 7.30–7.33 (2H, m), 7.62–7.75 (1H, m), 8.10–8.15 (1H, m)

EXAMPLE 19

To an ethanol (5 ml) solution of Starting Compound (488 mg) was added ethanol (5 ml) solution of citric acid (169 mg) at room temperature. The mixture was concentrated to about 2 ml, and diluted with 300 ml of water. The water was removed by freeze dryer to give Object Compound (569 mg) as white powders.

NMR (D$_2$O, δ): 2.65 (4H, ABq, Δ=0.12, J=16 Hz), 2.5–3.5 (18H, m), 3.8–5.0 (4H, m), 6.8–7.7 (17H, m)

EXAMPLE 20

The following object compounds were obtained according to a similar manner to that of Example 19.

(1) NMR (D$_2$O, δ): 2.65 (6H, ABq, Δ=0.12, J=16 Hz), 2.5–3.5 (18H, m), 3.8–4.9 (4H, m), 6.6–7.6 (17H, m) (2) NMR (D$_2$O, δ): 2.73 (8H, ABq, Δ=0.12, J=16 Hz), 2.4–3.6 (18H, m), 3.8–5.0 (4H, m), 6.5–7.5 (17H, m)

(3) MASS (FAB) (m/z): 668; NMR (CD$_3$OD, δ): 2.72–2.78 (5H, m), 2.83–2.87 (5H, m), 2.89–3.10 (6H, m), 3.12–3.18 (2H, m), 3.77–3.85 (3H, m), 3.89 (3H, s), 4.48 (2×½H, d, J=15 Hz), 4.63 (2×½H, d, J=15 Hz), 4.98–5.15 (3H, m), 7.12–7.24 (7H, m), 7.33 (1H, t, J=8 Hz), 7.48 (1H, t, J=8 Hz), 7.52 (1H, s), 7.60 (1H, d, J=8 Hz), 7.73 (1H, d, J=8 Hz), 7.92 (2H, d, J=8 Hz)

EXAMPLE 21

The following object compound was obtained according to a similar manner to that of Preparation 3, 4 or 8.

MASS (m/z): 596 (M$^+$+1); NMR (CDCl$_3$, δ): 2.61 (3H× ⅔, s), 2.67 (1H, m), 2.81 (3H×⅓, s), 2.86 (4H, m), 3.05 (2H, m), 3.31 (1H, m), 3.44 (2H, m), 3.63 (2H, m), 4.15 (1H×⅓, d, J=16 Hz), 4.29 (1H×⅔, d, J=15 Hz), 4.35 (1H×⅓, d, J=16

Hz), 4.64 (1H×⅔, d, J=15 Hz), 5.10 (2H, m), 6.96 (2H×⅓, m), 7.05 (2H×⅔, m), 7.17 (5H, s), 7.25–7.33 (5H, m), 7.43 (1H, t, J=8 Hz), 7.50 (1H, s), 7.57 (1H, d, J=8 Hz), 7.66–7.74 (2H, m), 8.22 (1H, m)

EXAMPLE 22

To a solution of Starting Compound (1.0 g) in methanol (10 ml) was added dropwise 10% hydrochloric acid-methanol solution (1 ml). Evaporation of solvent gave Object Compound (1.06 g).

NMR (CDCl$_3$, δ): 2.56 (3H×⅔, s), 2.70 (3H×⅓, s), 2.78 (2H, m), 2.86 (3H×⅓, s), 2.93 (3H×⅔, s), 3.00–3.24 (4H, m), 3.35–3.57 (3H, m), 3.65–3.91 (1H, m), 4.02–4.05 (1H, m), 4.38 (1H, d, J=15 Hz), 4.55 (1H, d, J=15 Hz), 4.63–4.75 (1H, m), 5.06 (1H, m), 5.06 (1H×⅓, m), 5.28 (1H×⅔, m), 7.05–7.33 (11H, m), 7.40–7.58 (4H, m), 7.67 (1H, d, J=8 Hz), 7.76 (1H, t, J=4 Hz)

EXAMPLE 23

The following object compound was obtained according to a similar manner to that of Preparation 10.

MASS (FAB) (m/z): 629 (M+H)$^-$; NMR (CDCl$_3$, δ): 2.59–2.70 (1H, m), 2.67 (3×⅔H, s), 2.81 (3×⅓H, s), 3.04–3.14 (2H, m), 3.39 (1H, dd, J=15, 5 Hz), 3.44–3.51 (2H, m), 3.60–3.78 (6H, m), 4.11–4.42 (2×⅔H, m), 4.68 (2×⅓H, d, J=15 Hz), 5.08–5.15 (1H, m), 5.23–5.32 (1H, m), 6.93–7.03 (2H, m), 7.18–7.36 (9H, m), 7.51 (1H, d, J=8 Hz), 7.71 (1H, t, J=8 Hz), 7.95 (1H, s), 8.22 (1H, d, J=8 Hz)

EXAMPLE 24

The crude Object compound was obtained according to a similar manner to that of Example 1. About 30 g of the product was obtained, and it was recrystallized from ethanol-water (2:1) to give 28.47 g of white crystals.

mp: 92–93° C.; MASS: m/z 562 (M+H)$^+$; NMR (CDCl$_3$, δ): 2.59 (⅘×3H, s), 2.77 (⅕×3H, s), 2.91 (2H, d, J=7 Hz), 3.32 (1H, dd, J=14 and 7 Hz), 3.47 (1H, dd, J=14 and 4 Hz), 4.11 (⅘×1H, d, J=16 Hz), 4.27 (⅘×1H, d, J=15 Hz), 4.29 (⅕×1H, d, J=16 Hz), 4.60 (⅘×1H, d, J=15 Hz), 5.02–5.13 (2H, m), 7.08–7.37 (10H, m), 7.43 (1H, t, J=8 Hz), 7.48 (1H, s), 7.55–7.69 (3H, m), 8.18 (1H, m), 8.26 (⅕×1H, d, J=2 Hz), 8.37 (⅘×1H, d, J=2 Hz), 8.51 (1H, d, J=4 Hz), 8.58 (1H, d, J=4 Hz), 8.65 (1H, d, J=7 Hz)

EXAMPLE 25

Object compounds were obtained according to a similar manner to that of Example 1 or 24.

(1) MASS: m/z 578 (M$^+$+1); NMR (CDCl$_3$, δ): 2.60 (3H×¾, s), 2.76 (3H×¼, s), 2.87 (2H, d, J=7 Hz), 3.27 (1H, m), 3.42 (1H, m), 4.12 (1H×¼, d, J=16 Hz), 4.29 (1H×¾, d, J=15 Hz), 4.32 (1H×¼, d, J=16 Hz), 4.58 (1H×¾, d, J=15 Hz), 4.97–5.13 (2H, m), 7.09–7.29 (8H, m), 7.35–7.45 (3H, m), 7.63 (1H, t, J=8 Hz), 7.85–7.88 (3H, m), 8.10 (1H×¾, d, J=8 Hz), 8.22 (1H×¼, d, J=8 Hz), 8.37 (1H, s), 8.51 (1H, m), 8.57 (1H, m), 8.69 (1H, d, J=8 Hz)

(2) MASS: m/z 561 (M$^+$+1); NMR (CDCl$_3$, δ): 2.64 (3H×¾, s), 2.81 (3H×¼, s), 2.82–3.05 (2H, m), 3.37 (2H, m), 4.17 (1H×¼, d, J=16 Hz), 4.24 (1H×¼, d, J=16 Hz), 4.36 (1H×¾, d, J=15 Hz), 4.58 (1H×¾, d, J=15 Hz), 5.17 (1H, q, J=7 Hz), 5.35 (1H×¾, q, J=7 Hz), 5.44 (1H×¼, q, J=7 Hz), 7.03–7.32 (12H, m), 7.38–7.49 (2H, m), 7.67 (1H, d, J=8 Hz), 8.22–8.71 (5H, m)

(3) MASS: m/z 599 (M$^+$+1); NMR (CDCl$_3$, δ): 2.51 (3H×⅔, s), 2.78 (3H×⅓, s), 2.89 (2H, m), 3.26 (1H, m), 3.43 (1H×⅔, m), 3.47 (1H×⅓, m), 4.17 (2H×⅓, s), 4.21 (1H×⅔, d, J=15 Hz), 4.56 (1H×⅔, d, J=15 Hz), 4.96–5.08 (2H, m), 6.81 (1H, d, J=8 Hz), 6.92 (1H, m), 6.99–7.12 (8H, m), 7.16 (1H, t, J=8 Hz), 7.24–7.32 (5H, m), 7.35–7.50 (4H, m), 7.64 (1H, d, J=8 Hz), 7.73 (1H, m), 8.25 (1H×⅔, br s), 8.35 (1H×⅓, br s)

(4) MASS: m/z 598 (M$^+$+1); NMR (CDCl$_3$, δ): 2.46(3H×⅔, s), 2.80 (3H×⅓, s), 2.88–3.02 (2H, m), 3.21–3.37 (2H, m), 3.75 (1H×⅓, d, J=16 Hz), 4.15 (1H×⅔, d, J=15 Hz), 4.19 (1H×⅓, d, J=16 Hz), 4.77 (1H×⅔, d, J=15 Hz), 5.19 (1H, m), 5.62–5.73 (1H, m), 6.76 (1H, m), 6.90–7.26 (18H, m), 7.47 (1H, d, J=8 Hz), 7.55–7.67 (3H, m), 8.92 (1H, d, J=8 Hz)

(5) MASS: m/z 550 (M$^+$+1); NMR (CDCl$_3$, δ): 2.65 (3H×⅔, s), 2.85 (3H×⅓, s), 2.93–3.02 (2H, m), 3.12–3.31 (2H, m), 4.22 (1H×⅓, d, J=16 Hz), 4.39 (1H×⅓, d, J=16 Hz), 4.44 (1H×⅔, d, J=15 Hz), 4.58 (1H×⅔, d, J=15 Hz), 4.95–5.13 (2H, m), 6.81 (1H, s), 7.01–7.08 (3H, m), 7.13 (4H, s), 7.24–7.28 (5H, m), 7.38 (1H, t, J=8 Hz), 7.45–7.52 (3H, m), 7.62 (1H, br s), 7.96 (1H, br s), 8.20 (1H×⅓, d, J=8 Hz), 8.30 (1H×⅔, d, J=8 Hz)

(6) MASS: m/z 549 (M$^+$+1); NMR (CDCl$_3$, δ): 2.67 (3H×⅔, s), 2.91 (3H×⅓, s), 2.93–3.03 (2H, m), 3.16 (2H, m), 4.30 (1H×⅔, d, J=15 Hz), 4.31 (2H×⅓, s), 4.80 (1H×⅔, d, J=15 Hz), 5.26 (1H, m), 5.53 (1H, m), 6.65 (1H, s), 6.90–7.10 (10H, m), 7.19–7.27 (6H, m), 7.45 (1H, d, J=8 Hz), 7.62 (1H, d, J=8 Hz), 7.67 (1H, m), 8.95 (1H, br s)

(7) MASS: m/z 561 (M$^+$+1); NMR (CDCl$_3$, δ): 2.57 (3H×⅔, s), 2.80 (3H×⅓, s), 2.87–2.98 (2H, m), 3.23–3.49 (2H, m), 4.15 (1H×⅓, d, J=16 Hz), 4.28 (1H×⅔, d, J=15 Hz), 4.31 (1H×⅓, d, J=16 Hz), 4.60 (1H×⅔, d, J=15 Hz), 5.03–5.20 (2H, m), 6.92–7.31 (13H, m), 7.38–7.67 (5H, m), 8.17 (1H×⅔, d, J=8 Hz), 8.33 (1H×⅓, d, J=8 Hz), 8.52–8.62 (2H, m)

(8) MASS: m/z 595 (M$^+$); NMR (CDCl$_3$, δ): 2.64 (3H×⅚, s), 2.75 (3H×⅙, s), 2.79–2.97 (2H, m), 3.34 (2H, m), 4.11 (1H×⅙, d, J=16 Hz), 4.24 (1H×⅙, d, J=16 Hz), 4.34 (1H×⅚, d, J=15 Hz), 4.47 (1H×⅚, d, J=15 Hz), 5.10–5.23 (2H, m), 7.02–7.28 (12H, m), 7.44 (1H, dd, J=8, 10 Hz), 7.53 (1H, t, J=8 Hz), 7.68 (1H, d, J=8 Hz), 8.08–8.33 (2H, m), 8.52 (2H, m)

(9) MASS: m/z 612 (M$^+$); NMR (CDCl$_3$, δ): 2.62 (3H×⅘, s), 2.74 (3H×⅕, s), 2.87 (2H, d, J=7nz), 3.29 (1H, m), 3.43 (1H, m), 4.10 (1H×⅕, d, J=16 Hz), 4.22 (1H×⅕, d, J=16 Hz), 4.27 (1H×⅘, d, J=15 Hz), 4.52 (1H×⅘, d, J=15 Hz), 5.01 (1H, m), 5.08 (1H, m), 7.05–7.33 (9H, m), 7.38–7.47 (2H, m), 7.63 (1H, m), 7.87–7.90 (3H, m), 8.07–8.24 (2H, m), 8.57 (1H, m), 8.67 (1H×⅕, d, J=8 Hz), 8.73 (1H×⅘, d, J=8 Hz)

(10) MASS: m/z 596 (M$^+$); NMR (CDCl$_3$, δ): 2.62 (3H×⅚, s), 2.74 (3H×⅙, s), 2.91 (2H, d, J=7 Hz), 3.32 (1H, m), 3.45 (1H, m), 4.12 (1H×⅙, d, J=16 Hz), 4.22 (1H×⅙, d, J=16 Hz), 4.25 (1H×⅚, d, J=15 Hz), 4.52 (1H×⅚, d, J=15 Hz), 5.04–5.15 (2H, m), 7.08–7.32 (10H, m), 7.44 (1H, m), 7.49 (1H, s), 7.55 (1H, t, J=8 Hz), 7.62–7.69 (2H, m), 8.03 (1H×⅙, m), 8.14 (1H×⅚, m), 8.22 (1H, d, J=8 Hz), 8.58–8.68 (2H, m)

(11) MASS: m/z 578 (M$^+$+1); NMR (CDCl$_3$, δ): 2.17 (3H×¾, s), 2.82 (3H×¼, s), 2.91–3.02 (2H, m), 3.20–3.47 (2H, m), 4.16–4.55 (2H, m), 4.93–5.22 (2H, m), 6.73–6.87 (2H, m), 7.05–7.22 (6H, m), 7.37–7.45 (2H, m), 7.59–7.65 (1H, m), 7.84–7.88 (3H, m), 8.05–8.25 (2H, m), 8.33–8.71 (4H, m)

(12) MASS: m/z 579 (M$^+$+1); NMR (CDCl$_3$, δ): 2.67 (3H×⅔, s), 2.81 (3H×⅓, s), 2.88–3.06, (2H, m), 3.17–3.52 (2H, m), 4.21 (1H×¼, d, J=15 Hz), 4.37 (1H×¼, d, J=15 Hz), 4.35 (1H×¾, d, J=15 Hz), 4.52 (1H×¾, d, J=15 Hz), 4.96–5.27 (2H, m), 6.74–6.88 (2H, m), 7.03–7.25 (6H, m), 7.46–7.64 (3H, m), 7.95 (1H, m), 8.11–9.20 (5H, m)

(13) MASS: 562 (M⁺+1); NMR (CDCl₃, δ): 2.68 (3H×¾, s), 2.81 (3H×¼, s), 2.88–3.05 (2H, m), 3.13–3.48 (2H, m), 4.22 (1H×¼, d, J=15 Hz), 4.34 (1H×¾, d, J=15 Hz), 4.35 (1H×¼, d, J=15 Hz), 4.53 (1H×¾, d, J=15 Hz), 4.94–5.25 (2H, m), 6.73–6.76 (2H×¼, m), 6.86–6.88 (2H×¾, m), 7.03–7.22 (6H, m), 7.26–7.32 (2H, m), 7.40–7.68 (5H, m), 8.15–8.65 (5H, m)

(14) MASS m/z 561 (M⁺+1); NMR (CDCl₃, δ): 2.67 (3H×¾, s), 2.83 (3H×¼, s), 2.77–3.06 (2H, m), 3.22–3.44 (2H, m), 4.13 (1H×¼, d, J=15 Hz), 4.25 (1H×¾, d, J=15 Hz), 4.42 (1H×¼, d, J=15 Hz), 4.63 (1H×¾, d, J=15 Hz), 4.98–5.40 (2H, m), 6.68–6.72 (2H×¼, m), 6.82–6.84 (2H× ¾, m), 6.97–7.23 (10H, m), 7.37–7.53 (2H, m), 7.66–7.69 (1H, m), 8.24–8.62 (5H, m)

(15) MASS: m/z 560 (M⁺+1); NMR (CDCl₃, δ): 2.63 (3H×¾, s), 2.87 (3H×¼, s), 2.90–3.01 (2H, m), 3.32–3.37 (2H, m), 4.17 (1H×¼, d, J=15 Hz), 4.28 (1H×¾, d, J=15 Hz), 4.72 (1H×¼, d, J=15 Hz), 4.74 (1H×¾, d, J=15 Hz), 5.21 (1H, m), 5.46 (1H, m), 6.88–7.24 (15H, m), 7.37–7.48 (2H, m), 7.17–8.25 (1H, m), 8.40–8.61 (2H, m)

EXAMPLE 26

The following object compounds were obtained according to a similar manner to that of Example 1 or 24.

(1) MASS: 530 (M+1); NMR (CDCl₃, δ): 2.15 (3×⅓H, s), 2.17 (3×⅔H, s), 2.67 (3×⅔H, s), 2.91 (3×⅓H, s), 2.82–3.13 (4H, m), 4.12 (2×⅙H, d, J=16 Hz), 4.39 (2×⅙H, d, J=16 Hz), 4.41 (2×⅓H, d, J=15 Hz), 4.63 (2×⅓H, d, J=15 Hz), 4.78–4.88 (1H, m), 5.17–5.23 (1H, m), 6.99–7.57 (16H, m), 7.70 (1H, d, J=8 Hz)

(2) MASS: 529 (M+1); NMR (CDCl₃, δ): 2.17 (3H, s), 2.72 (3×⅔H, s), 2.98 (3×⅓H, s), 2.95–3.10 (4H, m), 4.19 (2×⅙H, d, J=16 Hz), 4.39 (2×⅙H, d, J=16 Hz), 4.52 (2×⅓H, d, J=15 Hz), 4.80 (2×⅓H, d, J=15 Hz), 5.38–5.49 (1H, m), 5.60–5.70 (1H, m), 6.97–7.18 (9H, m), 7.21–7.33 (5H, m), 7.51 (1H, d, J=8 Hz), 7.68 (1H, d, J=8 Hz ), 9.10 (1×⅓H, d, J=8 Hz), 9.15 (1×⅔H, d, J=8 Hz)

(3) MASS: 535 (M+1); NMR (CDCl₃, δ): 2.73 (3×⅔H, s), 2.80 (3×⅓H, s), 2.99–3.16 (2H, m), 3.72–3.82 (1H, m), 4.07–4.23 (2H, m), 4.42 (2×½H, d, J=15 Hz), 4.53 (2×½H, d, J=15 Hz), 4.82–4.90 (1H, m), 5.11–5.20 (1H, m), 7.09–7.31 (7H, m), 7.32–7.45 (2H, m), 7.50 (1H, d, J=8 Hz), 7.51 (1H, m), 7.57 (1H, t, J=8 Hz), 7.63 (1H, d, J=8 Hz), 7.79 (1H, d, J=8 Hz), 8.15 (1×⅓H, s), 8.20 (1×⅔H, s)

(4) MASS: 551 (M+1); NMR (CDCl₃, δ): 2.69 (3×⅔H, s), 2.78 (3×⅓H, s), 2.98–3.14 (2H, m), 3.73–3.82 (1H, m), 4.06–4.14 (1H, m), 4.18 (1H, t, J=8 Hz), 4.00 (2×⅙H, d, J=16 Hz), 4.41 (2×⅙H, d, J=16 Hz), 4.38 (2×⅓H, d, J=15 Hz), 4.51 (2×⅓H, d, J=15 Hz), 4.80–4.87 (1H, m), 5.09–5.18 (1H, m), 7.07–7.30 (6H, m), 7.31–7.43 (4H, m), 7.73–7.87 (4H, m), 8.12 (1×⅓H, s), 8.17 (1×⅔H, s)

(5) MASS: 534 (M+1); NMR (CDCl₃, δ): 2.91 (3×¼H, s), 2.93 (3×¾H, s), 3.01–3.25 (2H, m), 3.91–4.08 (2H, m), 4.09 (2×⅛H, d, J=16 Hz), 4.30 (2×⅛H, d, J=16 Hz), 4.35 (2×⅜H, d, J=15 Hz), 4.65 (2×⅜H, d, J=15 Hz), 5.20–5.38 (2H, m), 5.40–5.50 (1×¼H, m), 5.57–5.73 (1×¾H, m), 6.81 (1H, d, J=8 Hz), 7.00 (1H, s), 7.09–7.31 (9H, m), 7.42 (1H, d, J=8 Hz), 7.68 (1H, d, J=8 Hz), 8.08 (1×¼H, s), 8.13 (1×¾H, s), 9.19 (1H, d, J=8 Hz)

(6) MASS: 758 (M+1); NMR (CDCl₃, δ): 2.61 (3×⅔H, s), 2.62–2.68 (1H, m), 2.80 (3×⅓H, s), 2.82–2.91 (1H, m), 2.93–3.04 (2H, m), 4.20–4.30 (1H, m), 4.12 (2×¼H, d, J=16 Hz), 4.22 (2×¼H, d, J=16 Hz), 4.31 (2×¼H, d, J=15 Hz), 4.60 (2×¼H, d, J=15 Hz), 5.11 (1H, q, J=15 Hz), 6.69–7.71 (32H, m)

(7) MASS: 774 (M+1); NMR (CDCl₃, δ): 2.58–2.63 (1H, m), 2.61 (3×⅔H, s), 2.77 (3×⅓H, s), 2.81–3.06 (3H, m), 4.10–4.32 (1H, m), 4.10 (2×¼H, d, J=16 Hz), 4.22 (2×¼H, d, J=16 Hz), 4.30 (2×¼H, d, J=15 Hz), 4.59 (2×¼H, d, J=15 Hz), 5.10 (1H, q, J=8 Hz), 6.59 (1H, t, J=8 Hz), 6.78 (1×⅓H, d, J=8 Hz), 6.86 (1×⅔H, d, J=8 Hz), 6.90–7.20 (19H, m), 7.39–7.46 (8H, m), 7.68 (1H, d, J=8 Hz), 7.83 (2H, t, J=8 Hz)

(8) MASS: 757 (M+1); NMR (CDCl₃, δ): 2.51–2.69 (2H, m), 2.72 (3×⅔H, s), 2.90–3.06 (2H, m), 2.98 (3×⅓H, s), 4.25 (2×⅓H, s), 4.39 (2×⅓H, d, J=15 Hz), 4.88 (2×⅓H, d, J=15 Hz), 5.22–5.37 (2H, m), 6.78 (1H, d, J=8 Hz), 6.87–6.93 (2H, m), 6.98–7.20 (18H, m), 7.20–7.40 (8H, m), 7.51 (1H, d, J=8 Hz), 7.70 (1H, d, J=8 Hz), 8.63 (1H, t, J=8 Hz)

(9) MASS: 551 (M+1); NMR (CDCl₃, δ): 2.82 (3×⅔H, s), 2.91 (3×⅓H, s), 3.01–3.20 (2H, m), 3.73–3.87 (1H, m), 4.07–4.19 (1H, m), 4.32 (2×⅙H, d, J=16 Hz), 4.63 (2×⅙H, d, J=16 Hz), 4.67 (2×⅓H, d, J=15 Hz), 4.71 (2×⅓H, d, J=15 Hz), 4.61 (1H, br s), 4.85–4.98 (1H, m), 5.17–5.33 (1H, m), 7.03–7.20 (5H, m), 7.27 (1H, t, J=8 Hz), 7.36–7.80 (8H, m), 7.83–7.94 (2H, m), 8.08 (1×⅔H, d, J=8 Hz), 8.10 (1×⅓H, d, J=8 Hz), 8.77 (1H, s)

(10) MASS: 550 (M+1); NMR (CDCl₃, δ): 3.00 (3H, s), 3.04–3.20 (1H, m), 3.20–3.32 (1H, m), 3.93–4.15 (2H, m), 4.22 (2×⅙H, d, J=16 Hz), 4.52 (2×⅙H, d, J=15 Hz), 4.60 (2×⅙H, d, J=16 Hz), 4.92 (2×⅙H, d, J=15 Hz), 5.30–5.50 (1H, m), 5.58–5.77 (1H, m), 6.58 (1×¼H, s), 6.73 (1×¾H, s), 7.00–7.32 (8H, m), 7.33–7.49 (6H, m), 7.96 (1H, d, J=8 Hz), 8.64 (1H, s), 9.23 (1H, d, J=8 Hz)

(11) MASS (m/z): 590 (M+1); NMR (CDCl₃, δ): 2.90 (3H×¼, s), 3.03 (3H×¾, s), 3.14 (1H, m), 3.28 (1H, m), 3.70 (1H, m), 3.92 (1H, m), 4.21–4.69 (4H, m), 4.90 (1H, m), 5.22 (1H, m), 5.54 (1H, m), 6.92–7.27 (14H, m), 7.33–7.42 (2H, m), 7.66 (1H, d, J=8 Hz), 8.32–8.38 (2H, m)

(12) MASS (m/z): 589 (M⁺+1); NMR (CDCl₃, δ): 2.68 (3H×⅔, s), 2.90 (3H×⅓, s), 3.05 (2H, m), 3.77 (1H, m), 3.92 (1H, m), 4.14 (1H×⅓, d, J=15 Hz), 4.28 (1H×⅔, d, J=15 Hz), 4.38 (1H×⅓, d, J=15 Hz), 4.47 (1H, d, J=15 Hz), 4.54 (1H, d, J=15 Hz), 4.81 (1H×⅔, d, J=15 Hz), 5.34 (1H, q, J=7 Hz), 5.47 (1H, m), 6.92 (1H, m), 7.00 (1H, d, J=2 Hz), 7.08–7.33 (17H, m), 7.47 (1H, d, J=8 Hz), 7.68 (1H, d, J=8 Hz), 8.64 (1H, d, J=8 Hz)

(13) MASS (m/z): 500 (M⁺+1); NMR (CDCl₃ δ): 2.94 (3H×¾, s), 2.95 (3H×¼, s), 3.11 (1H, dd, J=5, 12 Hz), 3.24 (1H, dd, J=7, 12 Hz), 3.98 (2H, m), 4.38 (1H×¼, d, J=15 Hz), 4.39 (1H×¾, d, J=15 Hz), 4.48 (1H×¼, d, J=15 Hz), 4.79 (1H×¾, d, J=15 Hz), 5.33 (1H, m), 5.57 (1H, m), 6.96 (2H, m), 7.08–7.32 (9H, m), 7.47 (1H, d, J=8 Hz), 7.65 (1H, d, J=8 Hz), 8.32 (1H, dd, J=2, 6 Hz), 8.36 (1H, d, J=2 Hz), 9.05 (1H×¼, d, J=8 Hz), 9.12 (1H×¾, d, J=8 Hz)

(14) MASS: 501 (M⁺+1); NMR (CDCl₃, δ): 2.77 (3H×¾, s), 2.85 (3H×¼, s), 3.06 (2H, m), 3.77 (1H, dd, J=7, 12 Hz), 4.12 (1H, m), 4.25 (1H×¼, d, J=15 Hz), 4.48 (1H×¼, d, J=15 Hz), 4.47 (1H×¾, d, J=15 Hz), 4.57 (1H×¾, d, J=15 Hz), 4.83 (1H, m), 5.16 (1H, q, J=7 Hz), 7.14 (4H, s), 7.18–7.72 (10H, m), 8.39 (1H×¼, d, J=2 Hz), 8.42 (1H×¾, d, J=2 Hz), 8.51 (1H, m)

(15) MASS (m/z): 517 (M⁺+1); NMR (CDCl₃, δ): 2.77 (3H×¾, s), 2.87 (3H×¼, s), 3.04 (2H, m), 3.72 (1H, m), 3.89 (1H, m), 4.13 (1H, m), 4.48 (1H×¾, d, J=15 Hz), 4.49 (1H×¼, d, J=15 Hz), 4.52 (1H×¼, d, J=15 Hz), 4.58 (1H×¾, d, J=15 Hz), 4.72 (1H, m), 5.12 (1H, q, J=7 Hz), 7.11–7.51

(11H, m), 7.80–7.87 (3H, m), 8.42 (1H×¼, d, J=2 Hz), 8.45 (1H×¾, d, J=2 Hz), 8.53 (1H, m)

(16) MASS (m/z): 518 (M$^+$+1); NMR (CDCl$_3$, δ): 2.80 (3H×⅘, s), 2.88 (3H×⅕, s), 2.97–3.15 (2H, m), 3.80 (1H, t, J=7 Hz), 4.08–4.20 (2H, m), 4.34 (1H×⅕, d, J=15 Hz), 4.41 (1H×⅕, d, J=15 Hz), 4.46 (1H×⅘, d, J=15 Hz), 4.55 (1H×⅘, d, J=15 Hz), 4.71–4.82 (1H, m), 5.07 (1H×⅕, q, J=7 Hz), 5.22 (1H×⅘, q, J=7 Hz), 6.64–6.97 (2H, m), 7.08–7.21 (5H, m), 7.46–7.62 (3H, m), 7.95 (1H, d, J=8 Hz), 8.07 (1H, d, J=8 Hz), 8.04–8.32 (1H, m), 8.49–8.52 (2H, m)

(17) MASS (m/z): 517 (M$^+$+1); NMR (CDCl$_3$, δ): 2.77 (3H×¾, s), 2.85 (3H×¼, s), 2.95–3.14 (2H, m), 3.72–3.81 (1H, m), 4.08 (1H, dt, J=4, 12 Hz), 4.27 (1H×¼, d, J=15 Hz), 4.37 (1H×¼, d, J=15 Hz), 4.42 (1H×¾, d, J=15 Hz), 4.53 (1H×¾, d, J=15 Hz), 4.73–4.85 (1H, m), 5.05 (1H×¼, q, J=7 Hz), 5.18. (1H×¾, q, J=7 Hz), 6.90–6.93 (2H, m), 7.07–7.21 (5H, m), 7.33–7.42 (3H, m), 7.77–7.87 (4H, m), 8.46–8.50 (2H, m)

(18) MASS (m/z): 500 (M$^+$+1); NMR (CDCl$_3$, δ): 2.73 (3H×¾, s), 2.89 (3H×¼, s), 2.97–3.17 (2H, m), 3.83–4.02 (2H, m), 4.10 (1H×¼, d, J=15 Hz), 4.20 (1H×¼, d, J=15 Hz), 4.37 (1H×¾, d, J=15 Hz), 4.57 (1H×¾, d, J=15 Hz), 5.10–5.18 (1H×¼, m), 5.35–5.42 (1H×¾, m), 5.50–5.57 (1H, m), 6.71 (2H×¼, d, J=7 Hz), 6.83 (2H×¾, d, J=7 Hz), 7.06–7.23 (8H, m), 7.37 (1H, d, J=8 Hz), 7.56 (1H, d, J=8 Hz), 7.63 (1H, d, J=8 Hz), 8.37–8.40 (2H, m), 8.97–9.02 (1H, m)

(19) MASS (m/z): 501 (M$^+$+1); NMR (CDCl$_3$, δ): 2.80 (3H×¾, s), 2.88 (3H×¼, s), 2.95–3.15 (2H, m), 3.71–3.78 (1H, m), 4.11 (1H, dt, J=4, 12 Hz), 4.35 (1H×¼, d, J=15 Hz), 4.40 (1H×¼, d, J=15 Hz), 4.46 (1H×¾, d, J=15 Hz), 4.56 (1H×¾, d, J=15 Hz), 4.72–4.85 (1H, m), 5.06 (1H×¼, q, J=7 Hz), 5.21 (1H×¾, q, J=7 Hz), 6.92–6.97 (2H, m), 7.07–7.21 (5H, m), 7.28–7.78 (7H, m), 8.50–8.53 (2H, m)

(20) MASS (m/z): 525 (M$^+$+1); NMR (CDCl$_3$, δ): 0.96 (6H, d, J=6 Hz), 1.54–1.80 (3H, m), 2.70 (3H×⅓, s), 2.79 (3H×⅔, s), 2.95–3.11 (2H, m), 4.47 (1H×⅓, d, J=15 Hz), 4.55 (1H×⅔, d, J=15 Hz), 4.63 (1H×⅓, d, J=15 Hz), 4.73 (1H×⅔, d, J=15 Hz), 5.42 (2H, m), 6.92–7.15 (6H, m), 7.18–7.32 (4H, m), 7.51–7.66 (1H, m)

(21) MASS (m/z): 559 (M$^+$+1); NMR (CDCl$_3$, δ): 2.69 (3H×⅔, s), 2.95 (3H×⅓, s), 3.00 (2H, m), 3.21 (2H, t, J=7 Hz), 4.22 (2H×⅓, d), 4.32 (1H×⅔, d, J=15 Hz), 4.91 (1H×⅔, d, J=15 Hz), 5.31 (1H, m), 5.76 (1H, m), 6.92–7.15 (14H, m), 7.20–7.31 (5H, m), 7.48 (1H, d, J=8 Hz), 7.68 (1H, d, J=8 Hz), 8.94 (1H, d, J=8 Hz)

(22) MASS (m/z): 660 (M$^+$+1); NMR (CDCl$_3$, δ): 1.60–1.70 (2H, m), 1.80–1.98 (2H, m), 2.72 (3H×⅓, s), 2.78 (3H×⅔, s), 2.96–3.24 (4H, m), 4.23 (1H×⅓, d, J=15 Hz), 4.42 (1H×⅔, d, J=15 Hz), 4.63 (1H×⅓, d, J=15 Hz), 4.89 (1H×⅔, d, J=15 Hz), 5.02 (2H, s), 5.32–5.42 (2H, m), 6.97–7.17 (10H, m), 7.21–7.31 (9H, m), 7.47 (1H, d, J=8 Hz), 7.68 (1H, dd, J=2, 8 Hz), 8.81 (1H, br s)

(23) MASS (m/z): 543 (M+H); NMR (CDCl$_3$, δ): 2.08 (3H, s), 2.10–2.32 (2H, m), 2.57–2.68 (2H, m), 2.72 (3×⅔H, s), 3.05 (3×⅓H, s), 3.00–3.07 (2H, m), 4.16 (2×¼H, d, J=17 Hz), 4.41 (2×¼H, d, J=17 Hz), 4.50 (2×¼H, d, J=15 Hz), 4.89 (2×¼H, d, J=15 Hz), 5.34–5.48 (1H, m), 5.52–5.63 (1H, m), 6.98–7.18 (9H, m), 7.19–7.37 (5H, m), 7.49 (1H, d, J=8 Hz), 7.69 (1H, d, J=8 Hz), 9.08 (1H, , J=8 Hz)

(24) MASS (m/z): 560 (M+H); NMR (CDCl$_3$, δ): 2.02–2.26 (2H, m), 2.11 (3H, m), 2.57–2.63 (2H, m), 2.68 (3×⅔H, s), 2.89 (3×⅓H, s), 2.99–3.12 (2H, m), 4.17 (2×¼H, d, J=16 Hz), 4.41 (2×¼H, d, J=16 Hz), 4.42 (2×¼H, d, J=15 Hz), 4.62 (2×¼H, d, J=15 Hz), 4.90–5.01 (1H, m), 5.17–5.27 (1H, m), 7.02–7.43 (13H, m), 7.59 (1H, t, J=8 Hz), 7.78–7.87 (3H, m)

(25) MASS (m/z): 544 (M+H); NMR (CDCl$_3$, δ): 2.08 (3H, d, J=3 Hz), 2.10–2.28 (2H, m), 2.53–2.63 (2H, m), 2.68 (3×⅔H, s), 2.92 (3×⅓H, s), 2.98–3.12 (2H, m), 4.19 (2×¼H, d, J=16 Hz), 4.40 (2×¼H, d, J=16 Hz), 4.46 (2×¼H, d, J=15 Hz), 4.63 (2×¼H, d, J=15 Hz), 4.89–5.00 (1H, m), 5.18–5.23 (1H, m), 7.02–7.18 (7H, m), 7.24–7.31 (4H, m), 7.39–7.54 (5H, m), 7.69 (1H, d, J=8 Hz)

(26) MASS (m/z): 500 (M+1); NMR (CDCl$_3$, δ): 2.78 (3×⅔H, s), 2.91 (3×⅓H, s), 2.95–3.13 (2H, m), 3.62–3.80 (2H, m), 3.88 (1H, t, J=8 Hz), 4.03–4.17 (1H, m), 4.27–4.56 (2×⅔H, m), 4.69 (2×⅓H, d, J=15 Hz), 4.72–4.79 (1H, m), 5.12–5.22 (1H, m), 7.04–7.18 (6H, m), 7.26–7.37 (3H, m), 7.40 (2H, t, J=8 Hz), 7.50 (1H, s), 7.52 (2H, t, J=8 Hz), 7.62 (1H, d, J=8 Hz)

(27) MASS (m/z): 515 (M$^+$+1); NMR (CDCl$_3$, δ): 2.50 (3H×¾, s), 2.53 (3H×¼, s), 2.75 (3H×¾, s), 2.83 (3H×¼, s), 3.00–3.15 (2H, m), 3.81 (1H, m), 4.10 (1H, m), 4.05–4.14 (2H×¼, m), 4.44 (1H×¾, d, J=15 Hz), 4.50 (1H×¾, d, J=15 Hz), 4.79 (1H, br s), 4.94 (1H, m), 5.18 (1H, m), 7.00–7.18 (6H, m), 7.25–7.66 (7H, m), 7.88 (1H×¼, d, J=8 Hz), 7.96 (1H×¾, d, J=8 Hz), 8.28 (1H, d, J=2 Hz)

(28) MASS (m/z): 514 (M$^+$+1); NMR (CDCl$_3$, δ): 2.41 (3H×⁶⁄₇, s), 2.53 (3H×⅐, s), 2.93 (3H, s), 3.10 (1H, dd, J=5, 12 Hz), 3.26 (1H, dd, J=7, 12 Hz), 3.97 (2H, m), 4.28 (1H×⁶⁄₇, d, J=15 Hz), 4.28 (1H×⅐, d, J=16 Hz), 4.37 (1H×⁶⁄₇, d, J=16 Hz), 4.78 (1H×⁶⁄₇, d, J=15 Hz), 5.32 (1H, m), 5.64 (1H, m), 6.69 (1H, d, J=8 Hz), 6.88 (1H×⅐, s), 6.92 (1H×⁶⁄₇, s), 7.04–7.25 (9H, m), 7.48 (1H, d, J=8 Hz), 7.61 (1H×⅐, d, J=8 Hz), 7.65 (1H×⁶⁄₇, d, J=8 Hz), 8.22 (1H, s), 9.22 (1H×⅐, d, J=8 Hz), 9.28 (1H×⁶⁄₇, d, J=8 Hz)

(29) MASS (m/z): 513 (M$^+$+1); NMR (CDCl$_3$, δ): 1.21 (3H×⅓, d, J=7 Hz), 1.24 (3H×⅔, d, J=7 Hz), 2.76 (3H×⅔, s), 2.97 (3H×⅓, s), 3.00–3.14 (2H, m), 3.92–4.83 (4H, m), 5.26–5.41 (2H, m), 7.02–7.14 (8H, m), 7.16–7.31 (5H, m), 7.38–7.49 (2H, m), 7.65 (1H, d, J=8 Hz), 8.85 (1H×⅓, d, J=8 Hz), 8.93 (1H×⅔, d, J=8 Hz)

(30) MASS (m/z): 514 (M$^+$+1); NMR (CDCl$_3$, δ): 1.16 (3H×⅓, d, J=7 Hz), 1.21 (3H×⅔, d, J=7 Hz), 2.76 (3H×⅔, s), 2.93 (3H×⅓, s), 2.95–3.13 (2H, m), 3.87–3.97 (1H, m), 4.28–4.75 (4H, m), 5.18 (1H, m), 7.05–7.16 (6H, m), 7.21–7.32 (5H, m), 7.41–7.69 (5H, m)

(31) MASS: 609 (M+1); NMR (CDCl$_3$, δ): 2.42 (3×⅔H, s), 2.50 (3×⅓H, s), 2.82–3.08 (2H, m), 3.23–3.42 (2H, m), 3.47 (2×⅓H, d, J=15 Hz), 3.70 (2×⅙H, d, J=16 Hz), 4.09 (2×⅙H, d, J=16 Hz), 4.70 (2×⅓H, d, J=15 Hz), 5.10–5.30 (1H, m), 5.80–6.00 (1H, m), 6.71–6.80 (2×⅓H, m), 6.83–6.92 (2×⅔H, m), 6.93–7.30 (14H, m), 7.31–7.73 (7H, m), 8.97 (1H, d, J=8 Hz)

(32) MASS: 610 (M+1); NMR (CDCl$_3$, δ): 2.49 (3×⅔H, s), 2.68 (3×⅓H, s), 2.85–3.05 (2H, m), 3.22–3.48 (2H, m), 3.98 (2×⅓H, d, J=15 Hz), 4.07 (2×⅓H, s), 4.58 (2×⅓H, d, J=15 Hz), 5.01–5.22 (2H, m), 6.82–7.55 (19H, m), 7.60–7.70 (5H, m)

(33) MASS: 564 (M+1); NMR (CDCl$_3$, δ): 2.51 (3×¼H, s), 2.52 (3×¾H, s), 2.72 (3×¾H, s), 2.83 (3×¼H, s), 2.91–3.08 (2H, m), 3.10–3.28 (2H, m), 4.18 (2×⅛H, d, J=16 Hz), 4.29 (2×⅛H, d, J=16 Hz), 4.30 (2×⅜H, d, J=15 Hz), 4.72 (2×⅜H, d, J=15 Hz), 5.20–5.35 (1H, m), 5.42–5.60 (1H, m), 6.69 (1×¾H, s), 6.72 (1×¼H, s), 6.90–7.20 (8H, m), 7.20–7.30 (7H, m), 7.32–7.58 (3H, m), 7.62 (1H, d, J=8 Hz), 8.15 (1×¼H, s), 8.21 (1×¾H, s), 8.92 (1×¾H, d, J=8 Hz), 9.00 (1×¼H, d, J=8 Hz)

(34) MASS: 565 (M+1); NMR (CDCl$_3$, δ): 2.53 (3H, s), 2.60 (3×¾H, s), 2.78 (3×¼H, s), 2.90–3.07 (2H, m), 3.08–3.33 (2H, m), 3.99 (2×⅛H, d, J=16 Hz), 4.31 (2×⅛H, d, J=16 Hz), 4.39 (2×⅜H, d, J=15 Hz), 4.49 (2×⅜H, d, J=15

Hz), 4.95–5.18 (2H, m), 6.82 (1H, s), 7.00–7.30 (8H, m), 7.39 (1H, t, J=8 Hz), 7.43–7.58 (3H, m), 7.62 (1H, d, J=8 Hz), 8.00 (1H, br s), 8.20 (1×¼H, br s), 8.28 (1×¾H, s), 8.36 (1H, br s)

(35) MASS: 574 (M+1); NMR (CDCl₃, δ): 2.60–3.40 (4H, m), 2.71 (3H, s), 2.91 (3H, s), 4.32–4.60 (2×⅔H, m), 4.67 (2×⅓H, s), 4.90–5.48 (2H, m), 6.85–7.48 (19H, m), 7.49–7.75 (2H, m)

(36) MASS: 573 (M+1); NMR (CDCl₃, δ): 2.72 (3×⅔H, s), 2.91 (3×⅓H, s), 2.85–3.14 (3H, m), 3.15–3.50 (1H, m), 3.29 (3×⅓H, s), 3.40 (3×⅔H, s), 4.29 (2×⅓H, d, J=15 Hz), 4.33 (2×⅙H, d, J=16 Hz), 4.61 (2×⅙H, d, J=16 Hz), 4.79 (2×⅓H, d, J=15 Hz), 5.13–5.30 (1H, m), 4.48–4.58 (1×½H, m), 4.60–4.72 (1×½H, m), 6.70–6.82 (1H, m), 6.85–7.20 (12H, m), 7.21–7.40 (5H, m), 7.40–7.60 (1H, m), 7.60–7.72 (1H, m), 8.07–8.17 (1×½H, m), 8.30–8.42 (1×½H, m)

(37) MASS: 612 (M+1); NMR (CDCl₃, δ): 2.67 (3×⅕H, s), 2.83 (3×⅕H, s), 2.88–3.08 (2H, m), 3.22–3.50 (2H, m), 4.32 (2×⅙H, d, J=16 Hz), 4.48 (2×⅓H, d, J=15 Hz), 4.51 (2×⅙H, d, J=16 Hz), 4.78 (2×⅓H, d, J=15 Hz), 5.00–5.23 (2H, m), 7.00–7.21 (6H, m), 7.22–7.32 (2H, m), 7.40–7.80 (8H, m), 7.91 (1H, s), 8.10 (1H, d, J=8 Hz), 8.23 (1×¼H, d, J=8 Hz), 8.30 (1×¾H, d, J=8 Hz), 8.52–8.70 (2H, m), 8.72 (1H, d, J=2 Hz)

(38) MASS: 610 (M+1); NMR (CDCl₃, δ): 2.63 (3×⅔H, s), 2.80–3.10 (2H, m), 2.89 (3×⅓H, s), 3.30–3.43 (2H, m), 4.38 (2×⅙H, d, J=16 Hz), 4.43 (2×⅙H, d, J=16 Hz), 4.59 (2×⅓H, d, J=15 Hz), 4.70 (2×⅓H, d, J=15 Hz), 5.14–5.22 (1H, m), 5.23–5.49 (1H, m), 6.92–7.30 (11H, m), 7.32–7.58 (3H, m), 7.62–7.80 (3H, m), 7.90 (1H, s), 8.08–8.28 (1H, m), 8.38–8.52 (2H, m), 8.60 (1×¼H, s), 8.72 (1×¾H, s)

(39) MASS: 552 (M+1); NMR (CDCl₃, δ): 2.99–3.26 (2H, m), 3.00 (3H, s), 3.70–3.83 (1H, m), 4.01–4.18 (1H, m), 4.25 (1H, br s), 4.79 (2×½H, d, J=15 Hz), 4.87–4.93 (1H, m), 4.97 (2×½H, d, J=15 Hz), 5.20–5.38 (1H, m), 7.03–7.20 (5H, m), 7.23–7.30 (1H, m), 7.40 (1H, t, J=8 Hz), 7.48 (1H, d, J=8 Hz), 7.50 (1H, s), 7.58 (1H, d, J=8 Hz), 7.63 (1H, d, J=8 Hz), 7.71–7.81 (3H, m), 7.97–8.05 (1H, m), 8.06–8.17 (1H, m), 8.80 (1H, s)

(40) MASS: 551 (M+1); NMR (CDCl₃, δ): 3.04–3.30 (2H, m), 3.08 (3H, s), 3.90–4.08 (2H, m), 4.49 (2×⅙H, d, J=16 Hz), 4.62 (2×⅙H, d, J=16 Hz), 4.79 (2×⅓H, d, J=15 Hz), 4.99 (2×⅓H, d, J=15 Hz), 5.20 (1H, br s), 5.37–5.50 (1H, m), 5.60–5.73 (1H, m), 6.75 (1×¼H, s), 6.81 (1×¾H, s), 6.94–7.10 (4H, m), 7.12–7.22 (4H, m), 7.31 (1H, d, J=8 Hz), 7.42–7.78 (4H, m), 7.98 (1H, d, J=8 Hz), 8.61 (1×¼H, s), 8.69 (1×¾H, s), 9.18 (1H, d, J=8 Hz)

(41) MASS: 613 (M+1); NMR (CDCl₃, δ): 2.80 (3×¾H, s), 2.89–3.00 (2H, m), 2.94 (3×¼H, s), 3.22–3.50 (2H, m), 4.60 (2×⅓H, d, J=15 Hz), 4.59 (2×⅙H, d, J=16 Hz), 4.69 (2×⅙H, d, J=16 Hz), 4.93 (2×⅓H, d, J=15 Hz), 5.00–5.30 (2H, m), 6.99–7.20 (6H, m), 7.22–7.32 (2H, m), 7.42 (1H, t, J=8 Hz), 7.47 (1H, s), 7.52–7.70 (3H, m), 7.72–7.80 (2H, m), 7.94–8.03 (1H, m), 8.07–8.13 (1H, m), 8.27–8.39 (1H, m), 8.49–8.63 (m, 4H), 8.63 (1×¼H, s), 8.73 (1×¾H, s)

(42) MASS: 612 (M+1); NMR (CDCl₃, δ): 2.80–3.12 (2H, m), 2.85 (3×¾, s), 2.98 (3×¼H, m), 3.26–3.40 (2H, m), 4.57 (2×⅙H, d, J=16 Hz), 4.70 (2×⅙H, d, J=16 Hz), 4.71 (2×⅓H, d, J=15 Hz), 4.89 (2×⅓H, d, J=15 Hz), 5.19–5.41 (2H, m), 6.90–7.23 (10H, m), 7.33–7.50 (2H, m), 7.63–7.80 (3H, m), 7.97–8.03 (1H, m), 8.07–8.15 (1H, m), 8.22 (1×¼H, d, J=8 Hz), 8.33 (1×¾H, d, J=8 Hz), 8.41 (1×¾H, d, J=8 Hz), 8.50 (1H, d, J=5 Hz), 8.61 (1×¼H, s), 8.68 (1×¼H, d, J=8 Hz), 8.70 (1×¾H, s)

(43) MASS: 602 (M+1); NMR (CDCl₃, δ): 2.87 (3×⅘H, s), 2.94 (3×⅕H, s), 2.92–3.33 (4H, m), 4.68 (2×⅕H, d, J=15 Hz), 4.77 (2×⅖H, d, J=15 Hz), 4.83 (2×⅖H, d, J=15 Hz), 4.92–5.30 (2H, m), 6.82 (1H, s), 7.00–7.20 (5H, m), 7.20–7.31 (2H, t, J=8 Hz), 7.38 (1H, t, J=8 Hz), 7.44–7.59 (3H, m), 7.62 (1H, d, J=8 Hz), 7.70–7.82 (2H, m), 7.84–8.18 (2H, m), 8.22–8.40 (1H, m), 8.87 (1H, s)

(44) MASS: 601 (M+1); NMR (CDCl₃, δ): 2.78–3.30 (4H, m), 2.90 (3×⅘H, s), 3.01 (3×⅕H, s), 4.57 (2×⅙H, d, J=16 Hz), 4.78 (2×⅙H, d, J=16 Hz), 4.80 (2×⅓H, d, J=15 Hz), 4.88 (2×⅓H, d, J=15 Hz), 5.22–5.60 (2H, m), 6.69 (1×⅘H, s), 6.71 (1×⅕H, s), 6.85–7.20 (8H, m), 7.30–7.49 (2H, m), 7.57 (1H, t, J=8 Hz), 7.62–7.82 (3H, m), 7.92–8.02 (1H, m), 8.03–8.12 (1H, m), 8.59 (1×⅕H, s), 8.67 (1×⅘H, s), 8.90–9.18 (1H, m)

(45) MASS: 577 (M+1); NMR (CDCl₃, δ): 1.82 (1H, br s), 2.97 (3×¼H, s), 2.99 (3×¾H, s), 3.07–3.19 (1H, m), 3.20–3.30 (1H, m), 3.90–4.19 (2H, m), 4.42 (2×⅓H, d, J=15 Hz), 4.50 (2×⅙H, d, J=16 Hz), 4.60 (2×⅙H, d, J=16 Hz), 4.80 (2×⅓H, d, J=15 Hz), 5.30–5.40 (1H, m), 5.56–5.70 (1H, m), 6.51 (1×¼H, s), 6.71 (1×¾H, s), 7.03–7.40 (9H, m), 7.50 (1H, d, J=8 Hz), 7.59 (1H, d, J=8 Hz), 7.73 (1H, d, J=8 Hz), 7.80 (1H, t, J=8 Hz), 8.08 (1H, d, J=8 Hz), 8.25–8.49 (2H, m), 8.67 (1×¼H, d, J=2 Hz), 8.72 (1×¾H, d, J=2 Hz), 9.10 (1×¼H, d, J=8 Hz), 9.17 (1×¾H, d, J=8 Hz)

(46) MASS: 578 (M+1); NMR (CDCl₃, δ): 1.92 (1H, br s), 2.75 (3×¾H, s), 2.88 (3×¼H, s), 2.98–3.18 (2H, m), 3.70–3.82 (1H, m), 4.07–4.20 (1H, m), 4.23 (2×⅙H, d, J=16 Hz), 4.50 (2×⅓H, d, J=15 Hz), 4.55 (2×⅙H, d, J=16 Hz), 4.68 (2×⅓H, d, J=15 Hz), 4.73–4.90 (1H, m), 5.12–5.28 (1H, m), 7.10–7.36 (7H, m), 7.42 (1H, t, J=8 Hz), 7.47–7.70 (6H, m), 7.81 (1H, t, J=8 Hz), 8.27–8.40 (2H, m), 8.49 (1×¼H, s), 8.51 (1×¾, s), 8.62–8.68 (1H, m)

(47) MASS: 638 (M+1); NMR (CDCl₃, δ): 2.68 (3×⅘H, s), 2.79–3.10 (2H, m), 2.85 (3×⅕H, s), 3.30–3.47 (2H, m), 4.19 (2×⅙ Hz, d, J=16 Hz), 4.30 (2×⅙H, d, J=16 Hz), 4.43 (2×⅓H, d, J=15 Hz), 4.57 (2×⅓H, d, J=15 Hz), 5.11–5.28 (1H, m), 5.29–5.48 (1H, m), 6.90–7.14 (8H, m), 7.15–7.30 (2H, m), 7.31–7.52 (4H, m), 7.52–7.60 (1H, m), 7.67 (1H, d, J=8 Hz), 8.22–8.38 (2H, m), 8.40–8.53 (3H, m), 8.60–8.72 (1H, m), 9.10–9.22 (1H, m)

(48) MASS: 639 (M+1); NMR (CDCl₃, δ): 2.61 (3×⅘H, s), 2.80 (3×⅕H, s), 2.83–3.09 (2H, m), 3.28–3.50 (2H, m), 4.19 (2×⅙H, d, J=16 Hz), 4.36 (2×⅙H, d, J=16 Hz), 4.40 (2×⅓H, d, J=15 Hz), 4.58 (2×⅓H, d, J=15 Hz), 5.02–5.22 (2H, m), 7.05–7.33 (8H, m), 7.35–7.50 (4H, m), 7.51–7.70 (5H, m), 8.22 (1H, d, J=8 Hz), 8.28 (1H, d, J=8 Hz), 8.38 (1×⅕H, s), 8.45 (1×⅘H, s), 8.56 (1H, d, J=2 Hz), 8.61 (1H, d, J=4 Hz), 9.18 (1H, s)

(49) MASS: 578 (M+1); NMR (CDCl₃, δ): 2.80 (3×¾H, s), 2.89 (3×¼H, s), 3.00–3.19 (2H, m), 3.72–3.82 (1H, m), 4.08–4.20 (1H, m), 4.21–4.33 (1H, m), 4.13 (2×⅙H, d, J=16 Hz), 4.24 (2×⅙H, d, J=16 Hz), 4.53 (2×⅓H, d, J=15 Hz), 4.59 (2×⅓H, d, J=15 Hz), 4.78–4.90 (1H, m), 5.12–5.28 (1H, m), 7.11–7.22 (5H, m), 7.23–7.33 (2H, m), 7.35–7.47 (3H, m), 7.48–7.60 (3H, m), 7.62–7.73 (3H, m), 8.30 (1H, t, J=7 Hz), 8.49 (1×¼H, s), 8.51 (1×¾H, s), 8.65 (1H, br s), 9.17 (1H, br s)

(50) MASS (m/z): 781 (M⁺+1); NMR (CDCl₃, δ): 1.30–1.57 (2H, m), 1.98 (2H, m), 2.18 (3H, s), 2.65 (3H, s), 2.78 (2H, m), 2.85 (6H, s), 3.04–3.23 (2H, m), 3.72–3.90 (2H, m), 3.85 (3H, s), 4.88–4.93 (2H, m), 5.36 (1H, m), 6.42 (1H, m), 6.57 (1H, s), 7.03 (2H, d, J=8 Hz), 7.14–7.32 (9H, m), 7.41 (1H, t, J=8 Hz), 7.47 (1H, s), 7.52 (1H, d, J=8 Hz), 7.67 (1H, d, J=8 Hz)

(51) MASS (m/z): 561 (M⁺+1); NMR (CDCl₃, δ): 2.60 (3H×¾, s), 2.82 (3H×¼, s), 2.99 (2H, d, J=7 Hz), 3.20 (2H, m), 4.12 (1H×¼, d, J=16 Hz), 4.23 (1H×¼, d, J=16 Hz), 4.34

(1H×¾, d, J=15 Hz), 4.62 (1H×¾, d, J=15 Hz), 5.03 (1H, m), 5.11 (1H, m), 7.09–7.15 (5H, m), 7.19–7.32 (9H, m), 7.36–7.46 (2H, m), 7.52 (1H, d, J=8 Hz), 7.53 (1H, s), 7.67 (1H, d, J=8 Hz), 8.30 (1H×¼, br s), 8.41 (1H×¾, br s), 8.53 (1H, br s)

(52) MASS (m/z): 560 (M$^+$+1); NMR (CDCl$_3$, δ): 2.69 (3H×¾, s), 2.88 (3H×¼, s), 3.00 (2H, m), 3.20 (2H, m), 4.14 (1H×¼, d, J=16 Hz), 4.25 (1H×¼, d, J=16 Hz), 4.28 (1H×¾, d, J=15 Hz), 4.85 (1H×¾, d, J=15 Hz), 5.30 (1H, m), 5.73 (1H, m), 7.02–7.17 (14H, m), 7.20–7.31 (3H, m), 7.45 (1H, d, J=8 Hz), 7.67 (1H, d, J=8 Hz), 8.29 (1H×¼, br s), 8.43 (1H×¾, br s), 8.55 (1H, m), 8.88 (1H×¾, d, J=7 Hz), 9.03 (1H×¼, d, J=7 Hz)

(53) MASS (m/z): 562 (M$^+$+1); NMR (CDCl$_3$, δ): 2.62 (3H×¾, s), 2.82 (3H×¼, s), 2.96 (2H, m), 3.17 (2H, m), 4.06 (1H×¼, d, J=16 Hz), 4.27 (1H×¼, d, J=16 Hz), 4.35 (1H×¾, d, J=15 Hz), 4.62 (1H×¾, d, J=15 Hz), 5.07 (2H, m), 7.04–7.17 (7H, m), 7.20–7.51 (6H, m), 7.65 (1H, d, J=8 Hz), 8.30–8.53 (4H, m)

(54) MASS (m/z): 561 (M$^+$+1); NMR (CDCl$_3$, δ): 2.68 (3H×¾, s), 2.94 (3H×¼, s), 2.98 (2H, m), 3.20 (2H, m), 4.07 (1H×¼, d, J=16 Hz), 4.22 (1H×¼, d, J=16 Hz), 4.30 (1H×¾, d, J=15 Hz), 4.89 (1H×¾, d, J=15 Hz), 5.29 (1H, q, J=7 Hz), 5.83 (1H, q, J=7 Hz), 7.07–7.15 (10H, m), 7.21–7.44 (4H, m), 7.67 (1H, d, J=8 Hz), 8.32–8.57 (4H, m), 8.91 (1H×¾, d, J=8 Hz), 9.03 (1H×¼, d, J=8 Hz)

(55) MASS (m/z): 567 (M$^+$+1); NMR (CDCl$_3$, δ): 2.80 (3H×¾, s), 2.88 (3H×¼, s), 3.08 (2H, m), 3.76 (1H, m), 4.07–4.18 (2H, m), 4.24 (1×¼, d, J=16 Hz), 4.53 (1H×¾, d, J=15 Hz), 4.53 (1H×¼, d, J=16 Hz), 4.62 (1H×¾, d, J=15 Hz), 4.82 (1H, m), 5.21 (1H, q, J=7 Hz), 7.15–7.32 (7H, m), 7.42 (1H, t, J=8 Hz), 7.49–7.71 (7H, m), 8.10 (1H, m), 8.55 (1H×¾, s), 8.58 (1H×¼, s)

(56) MASS (m/z): 566 (M$^+$+1); NMR (CDCl$_3$, δ): 2.70 (3H×¾, s), 2.83 (3H×¼, s), 3.09 (2H, m), 3.97 (2H, m), 4.01 (1H×¼, d, J=16 Hz), 4.27 (1H×¼, d, J=16 Hz), 4.45 (1H×¾, d, J=15 Hz), 4.60 (1H×¾, d, J=15 Hz), 5.36 (1H, m), 5.61 (1H, m), 6.90–7.22 (11H, m), 7.37–7.46 (3H, m), 7.55 (1H×¾, d, J=8 Hz), 7.62 (1H, d, J=8 Hz), 7.75 (1H×¼, d, J=8 Hz), 8.02 (1H×¼, s), 8.06 (1H×¾s), 8.46 (1H×¾,s), 8.61 (1H×¼, s), 9.00 (1H×¾, d, J=8 Hz), 9.11 (1H×¼, d, J=8 Hz)

(57) MASS (m/z): 559 (M+1)$^+$; NMR (CDCl$_3$, δ): 2.04–2.21 (2H, m), 2.12 (3H, s), 2.52 (3H, s), 2.61 (2H, m), 2.67 (3H×⅕, s), 2.81 (3H×⅕, s), 3.02 (2H, d, J=7.0 Hz), 4.40 (1H, d, J=14.5 Hz), 4.54 (1H, d, J=14.5 Hz), 4.84 (1H, m), 5.09–5.26 (1H, m), 6.98–7.08 (1H, m), 7.09–7.56 (12H, m), 7.69 (1H, d, J=7.5 Hz), 8.24 (1H×⅕, d, J=1.5 Hz), 8.33 (1H×⅘, d, J=1.5 Hz)

(58) MASS (m/z): 558 (M+1)$^+$; NMR (CDCl$_3$, δ): 2.10 (3H, s), 2.19 (2H, m), 2.51–2.68 (2H, m), 2.56 (3H×¼, s), 2.58 (3H×¾, s), 2.76 (3H×¾, s), 2.98 (3H×¼, s), 3.03 (2H, d, J=7.5 Hz), 4.53 (1H, d, J=14.5 Hz), 4.68 (1H, d, J=14.5 Hz), 5.29–5.49 (2H, m), 6.98–7.03 (1H, m), 7.04–7.19 (9H, m), 7.22–7.37 (2H, m), 7.49 (1H, d, J=7.5 Hz), 7.70 (1H, d, J=7.5 Hz), 8.26 (1H×¼, d, J=1.5 Hz), 8.37 (1H×¾, d, J=1.5 Hz), 8.64 (1H, br d, J=7.5 Hz)

(59) MASS (m/z): 545 (M+1)$^+$; NMR (CDCl$_3$, δ): 2.06–2.21 (2H, m), 2.13 (3H, s), 2.63 (2H, m), 2.70 (3H×¾, s), 3.86 (3H×¼, s), 3.03 (2H, d, J=7.5 Hz), 4.11 (1H×¼, d, J=14.5 Hz), 4.39 (1H×¼, d, J=14.5 Hz), 4.42 (1H×¾, d, J=14.5 Hz), 4.61 (1H×¾, d, J=14.5 Hz), 4.87 (1H, m), 5.13 (1H, m), 7.03–7.35 (9H, m), 7.40–7.58 (4H, m), 7.70 (1H, d, J=7.5 Hz), 8.36 (1H×¼, d, J=1.5 Hz), 8.44 (1H×¾, d, J=1.5 Hz), 8.55 (1H, m)

(60) MASS (m/z): 544 (M+1)$^+$; NMR (CDCl$_3$, δ): 2.10 (3H, s), 2.20 (2H, m), 2.63 (2H, m), 2.77 (2H, m), 2.99 (3H×¼, s), 3.03 (2H, d, J=7.5 Hz), 4.18 (1H×¼, d, J=14.5 Hz), 4.52 (1H×¼, d, J=14.5 Hz), 4.53 (1H×¾, d, J=14.5 Hz), 4.77 (1H×¾, d, J=14.5 Hz), 5.39 (2H, m), 7.01 (1H, m), 7.06–7.19 (7H, m), 7.20–7.34 (4H, m), 7.40–7.51 (2H, m), 7.70 (1H, d, J=7.5 Hz), 8.35 (1H×¼, s), 8.48 (1H×¾, s), 8.53–8.68 (1H, m)

(61) MASS (m/z): 594 (M+1)$^+$; NMR (CDCl$_3$, δ): 2.08 (3H×¼, s), 2.10 (3H×¾, s), 2.11–2.29 (2H, m), 2.54–2.69 (2H, m), 2.83 (3H×¾, s), 3.02 (3H×¼, s), 3.07 (2H, s), 4.37 (1H×¼, d, J=14.5 Hz), 4.60 (1H×¼, d, J=14.5 Hz), 4.72 (1H×¾, d, J=14.5 Hz), 4.91 (1H×¾, d, J=14.5 Hz), 5.30–5.43 (2H, m), 6.97–7.20 (8H, m), 7.20–7.30 (1H, m), 7.43–7.62 (3H, m), 7.65–7.83 (13/4H, m), 7.98 (1H×¾, s), 8.09–8.19 (1H, m), 8.52 (1H, d, J=7.5 Hz), 8.68 (1H×¼, d, J=1.5 Hz), 8.82 (1H×¾, d, J=1.5 Hz)

(62) MASS (m/z): 595 (M+1)$^+$; NMR (CDCl$_3$, δ): 2.07–2.26 (2H, m), 2.11 (3H, s), 2.53–2.69 (2H, m), 2.73 (3H×⅘, s), 2.91 (3H×⅕, s), 3.02–3.10 (2H, m), 4.30 (1H×⅕, d, J=14.5 Hz), 4.60 (1H×⅕, d, J=14.5 Hz), 4.62 (1H×⅘, d, J=14.5 Hz), 4.78 (1H×⅘, d, J=14.5 Hz), 4.88 (1H, m), 5.18 (1H, m), 7.04–7.20 (6H, m), 7.23–7.37 (2H, m), 7.45 (1H, t, J=7.5 Hz), 7.49–7.62 (3H, m), 7.66–7.86 (¹⁶⁄₅H, m), 7.99 (1H×⅘, s), 8.13 (1H, d, J=7.5 Hz), 8.70 (1H×⅕, d, J=1.5 Hz), 8.80 (1H×⅘, d, J=1.5 Hz)

(63) MASS (m/z): 596 (M+1)$^+$; NMR (CDCl$_3$, δ): 2.03–2.22 (2H, m), 2.11 (3H, s), 2.52–2.67 (2H, m), 2.92 (3H×⅘, s), 3.00 (3H×⅕, s), 3.08 (2H, t, J=7.5 Hz), 4.73 (1H, d, J=14.5 Hz), 4.79–4.90 (1H, m), 4.96 (1H, d, J=14.5 Hz), 5.16–5.28 (1H, m), 7.02–7.17 (6H, m), 7.21–7.36 (2H, m), 7.43 (1H, t, J=7.5 Hz), 7.48–7.57 (2H, m), 7.69 (1H, d, J=7.5 Hz), 7.73–7.81 (2H, m), 7.99–8.06 (1H, m), 8.10–8.15 (1H, m), 8.73 (1H×⅕, s), 8.82 (1H×⅘, s)

(64) MASS (m/z): 595 (M+1)$^+$; NMR (CDCl$_3$, δ): 2.08 (3H, s), 2.10–2.27 (2H, m), 2.57–2.69 (2H, m), 3.01 (3H×⅘, s), 3.03–3.10 (2H, m), 3.15 (3H×⅕, s), 4.83 (1H, d, J=14.5 Hz), 5.09 (1H, d, J=14.5 Hz), 5.25–5.48 (2H, m), 6.89–7.24 (10H, m), 7.33–7.40 (1H, m), 7.62–7.70 (1H, m), 7.74–7.83 (2H, m), 8.01–8.08 (1H, m), 8.11–8.19 (1H, m), 8.39–8.47 (1H, m), 8.69 (1H×⅕, s), 8.83 (1H×⅘, s)

(65) MASS (m/z): 621 (M+1)$^+$; NMR (CDCl$_3$, δ): 2.07 (3H, s), 2.10–2.33 (2H, m), 2.59–2.68 (2H, m), 2.83 (3H×¾, s), 3.02 (3H×¼, s), 3.04 (2H, d, J=7.5 Hz), 4.22 (1H×¼, d, J=14.5 Hz), 4.46 (1H×¼, d, J=14.5 Hz), 4.63 (1H×¾, d, J=14.5 Hz), 4.75 (1H×¾, d, J=14.5 Hz), 5.33–5.49 (2H, m), 6.99 (1H×¼, d, J=1.5 Hz), 7.01 (1H×¾, d, J=1.5 Hz), 7.04–7.19 (7H, m), 7.23–7.32 (1H, m), 7.39–7.54 (3H, m), 7.67–7.73 (2H, m), 8.33 (1H, d, J=7.5 Hz), 8.45 (1H×¼, d, J=1.5 Hz), 8.57 (1H×¾, d, J=1.5 Hz), 8.63–8.88 (2H, m), 9.21 (1H, s), 10.32 (1H, br s)

(66) MASS (m/z): 622 (M+1)$^+$; NMR (CDCl$_3$, δ): 2.04–2.26 (2H, m), 2.13 (3H, s), 2.53–2.69 (2H, m), 2.74 (3H×⅘, s), 2.87 (3H×⅕, s), 2.99–3.14 (2H, m), 4.16 (1H×⅕, d, J=14.5 Hz), 4.44 (1H×⅕, d, J=14.5 Hz), 4.53 (1H×⅘, d, J=14.5 Hz), 4.61 (1H×⅘, d, J=14.5 Hz), 4.88 (1H, quint, J=7.5 Hz), 5.17 (1H, quint, J=7.5 Hz), 7.10–7.25 (6H, m), 7.27–7.60 (7H, m), 7.66–7.74 (2H, m), 8.28–8.34 (1H, m), 8.44 (1H×⅕, d, J=1.5 Hz), 8.54 (1H×⅘, d, J=1.5 Hz), 8.68 (1H, d, J=5.5 Hz), 9.20 (1H, m)

(67) MASS (m/z): 566 (M+1)$^+$; NMR (CDCl$_3$, δ): 2.60 (3H×⅔, s), 2.87 (3H×⅓, s), 3.00 (2H, t, J=7.5 Hz), 3.37–3.46 (2H, m), 4.06 (1H×⅓, d, J=14.5 Hz), 4.31 (1H×⅓, d, J=14.5 Hz), 4.41 (1H×⅔, d, J=14.5 Hz), 4.56 (1H×⅔, d, J=14.5 Hz), 4.85–4.99 (1H, m), 5.10–5.21 (1H, m), 6.83–7.21 (11H, m), 7.22–7.33 (5H, m), 7.43 (1H, t, J=7.5 Hz), 7.49–7.57 (2H, m), 7.70 (1H, d, J=7.5 Hz)

(68) MASS (m/z): 565 (M+1)$^+$; NMR (CDCl$_3$, δ): 2.69 (3H×⅔, s), 2.99 (3H×⅓, s), 3.03 (2H, d, J=7.5 Hz), 3.49 (2H, t, J=7.5 Hz), 4.10 (1H×⅓, d, J=14.5 Hz), 4.31 (1H×⅓, d, J=14.5 Hz), 4.43 (1H×⅔, d, J=14.5 Hz), 4.86 (1H×⅔, d, J=14.5 Hz), 5.22–5.37 (1H, m), 5.58–5.70 (1H, m), 6.78–6.88 (2H, m), 6.93–7.20 (11H, m), 7.23–7.39 (5H, m), 7.51 (1H, d, J=7.5 Hz), 7.70 (1H, m), 8.71 (1H, br d, J=7.5 Hz)

(69) MASS (m/z): 543 (M+H)$^+$; NMR (CDCl$_3$, δ): 2.83 (¾×3H, s), 2.91 (¼×3H, s), 2.95–3.30 (2H, m), 3.02 (¾×6H, s), 3.06 (¼×6H, s), 3.81 (¼×1H, d, J=17 Hz), 3.88–4.04 (2H, m), 4.24 (¾×1H, d, J=15 Hz), 4.36 ( ¼×1H, d, J=17 Hz), 4.65 (¾×1H, d, J=15 Hz), 5.18–5.64 (2H, m), 6.16 (¾×1H, d, J=9 Hz), 6.43 (¼×1H, d, J=9 Hz), 6.88–7.92 (13H, m), 8.88–9.12 (1H, m), 10.00 (1H, br s)

(70) MASS (m/z): 544 (M+H)$^+$; NMR (CDCl$_3$, δ): 2.72 (⅔×3H, s), 2.82 (⅓×3H, s), 2.91–3.12 (2H, m), 3.08 (6H, s), 3.63–3.80 (1H, m), 3.92 (⅓×1H, d, J=17 Hz), 4.05–4.20 (1H, m), 4.39 (⅔×2H, ABq, Δ=0.13, J=15 Hz), 4.42 (⅓×1H, d, J=17 Hz), 4.68–4.82 (1H, m), 5.04–5.32 (1H, m), 6.48 (⅔×1H, d, J=9 Hz), 6.50 (⅓×1H, d, J=9 Hz), 7.06–7.73 (13H, m), 7.94 (⅓×1H, d, J=2 Hz), 7.98 (⅔×1H, d, J=2 Hz)

(71) MASS (m/z): 567 (M+H)$^+$; NMR (CDCl$_3$, δ): 2.80 (¾×3H, s), 2.90 (¼×3H, s), 2.96–3.20 (2H, m), 3.50–3.85 (1H, m), 3.96–4.22 (1H, m), 4.26 (¼×1H, d, J=17 Hz), 4.55–4.88 (1H+¼×1H, m), 4.70 (¾×2H, s), 5.05–5.35 (1H, m), 7.00–8.18 (17H, m), 8.75 (1H, s)

(72) MASS (m/z): 641 (M+H)$^+$; NMR (CDCl$_3$, δ): 2.71 (¾×3H, s), 2.88 (¼×3H, s), 2.92–3.15 (2H, m), 3.56–3.73 (1H, m), 3.95–4.08 (1H, m), 4.44 (¼×2H, ABq, Δ=0.20, J=17 Hz), 4.51 (¾×1H, d, J=15 Hz), 4.62 (2H, s), 4.72–4.90 (1H, m), 4.82 (¾×1H, d, J=15 Hz), 5.10–5.32 (1H, m), 7.00–8.15 (22H, m), 8.64 (¼×1H, d, J=2 Hz), 8.77 (¾×1H, d, J=2 Hz)

(73) MASS (m/z): 549 (M+H)$^+$; NMR (CDCl$_3$, δ): 2.70 (⅔×3H, s), 2.90–3.13 (4H, m), 2.99 (⅓×3H, s), 4.21 (⅓×2H, ABq, Δ=0.09, J=17 Hz), 4.40 (⅔×1H, d, J=15 Hz), 4.89 (⅔×1H, d, J=15 Hz), 5.22–5.41 (1H, m), 5.56–5.72 (1H, m), 6.24 (⅓×1H, s), 6.28 (⅔×1H, s), 6.87–7.75 (18H, m), 8.84 (1H, d, J=9 Hz), 11.48 (1H, br s)

(74) MASS (m/z): 550 (M+H)$^+$; NMR (CDCl$_3$, δ): 2.63 (⅔×3H, s), 2.88 (⅓×3H, s), 2.92–3.10 (4H, m), 4.23 (⅓×2H, ABq, Δ=0.18, J=17 Hz), 4.52 (⅔×2H, ABq, Δ=0.14, J=15 Hz), 4.83–4.98 (1H, m), 5.09–5.22 (1H, m), 6.27 (⅓×1H, s), 6.31 (⅔×1H, s), 6.92–7.73 (19H, m)

(75) MASS (m/z): 549 (M+H)$^+$; NMR (CDCl$_3$, δ): 2.72 (⅔×3H, s), 2.95–3.13 (2H, m), 2.97 (⅓×3H, s), 3.22–3.34 (2H, m), 4.23 (⅓×2H, ABq, Δ=0.16, J=17 Hz), 4.42 (⅔×1H, d, J=15 Hz), 4.83 (⅔×1H, d, J=15 Hz), 5.23–5.40 (1H, m), 5.61–5.77 (1H, m), 6.04–6.22 (2H, m), 6.90–7.74 (17H, m), 8.88 (1H, d, J=8 Hz), 11.38 (⅔×1H, br s), 11.40 (⅓×1H, br s)

(76) MASS (m/z): 550 (M+H)$^+$; NMR (CDCl$_3$, δ): 2.59 (⅔×3H, s), 2.85 (⅓×3H, s), 2.88–3.33 (4H, m), 4.20 (⅓×2H, ABq, Δ=0.23, J=17 Hz), 4.48 (⅔×2H, ABq, Δ=0.16, J=15 Hz), 4.90–5.07 (1H, m), 5.07–5.25 (1H, m), 6.06–6.32 (2H, m), 6.88–7.72 (18H, m)

(77) MASS: 547 (M+1); NMR (CDCl$_3$, δ): 2.70 (3×¾H, s), 2.80 (3×¼H, s), 2.95–3.17 (2H, m), 3.71–3.85 (1H, m), 3.90 (3H, s), 3.98 (2×⅛H, d, J=16 Hz), 4.05–4.19 (1H, m), 4.28 (2×⅜H, d, J=15 Hz), 4.41 (2×⅛H, d, J=16 Hz), 4.57 (2×⅜H, d, J=15 Hz), 4.78–4.88 (1H, m), 5.08–5.18 (1×¼H, m), 5.20–5.28 (1×¼H, m), 6.69 (1×¾H, d, J=8 Hz), 6.70 (1×¼H, d, J=8 Hz), 7.05–7.21 (5H, m), 7.29–7.48 (4H, m), 7.69 (1H, d, J=7 Hz), 7.76–7.89 (3H, m), 7.90–8.00 (1H, m)

(78) MASS: 601 (M+1); NMR (CDCl$_3$, δ): 2.79 (3×¾H, s), 2.88 (3×¼H, s), 2.92–3.08 (2H, m), 3.10–3.33 (2H, m), 4.29 (2×⅛H, d, J=16 Hz), 4.53 (2×⅛H, d, J=16 Hz), 4.60 (2×⅜H, d, J=15 Hz), 4.71 (2×⅜H, d, J=15 Hz), 4.98–5.22 (2H, m), 6.82 (1H, s), 7.00–7.20 (5H, m), 7.27 (1H, t, J=8 Hz), 7.39 (1H, t, J=8 Hz), 7.45–7.60 (4H, m), 7.61–7.80 (3H, m), 7.91 (1H, s), 7.92–8.18 (1H, m), 8.09 (1H, d, J=8 Hz), 8.30–8.50 (1H, m), 8.67 (1×¼H, s), 8.71 (1×¾H, s)

(79) MASS: 600 (M+1); NMR (CDCl$_3$, δ): 2.78 (3×⅘H, s), 2.92 (3×⅕H, s), 2.97–3.10 (2H, m), 3.11–3.30 (2H, m), 4.47 (2×⅖H, d, J=15 Hz), 4.50 (2×⅕H, s), 5.00 (2×⅖H, d, J=15 Hz), 5.33 (1H, q, J=8 Hz), 5.43–5.60 (1H, m), 6.69 (1×⅕H, s), 6.79 (1×⅕H, s), 6.99 (1H, s), 7.02–7.19 (6H, m), 7.22 (1H, d, J=8 Hz), 7.32–7.60 (4H, m), 7.61–7.80 (3H, m), 7.89 (1H, s), 8.10 (1H, d, J=8 Hz), 8.61 (1×⅕H, s), 8.70 (1×⅕H, s), 8.97 (1×⅕H, d, J=8 Hz), 9.11 (1×⅕H, d, J=8 Hz)

(80) MASS: 628 (M+1); NMR (CDCl$_3$, δ): 2.70 (3×⅘H, s), 2.82 (3×⅕H, s), 2.90–3.10 (2H, m), 3.11–3.36 (2H, m), 4.12 (2×⅛H, d, J=16 Hz), 4.41 (2×⅛H, d, J=16 Hz), 4.43 (2×⅜H, d, J=15 Hz), 4.60 (2×⅜H, d, J=15 Hz), 4.96–5.20 (2H, m), 6.88 (1H, s), 7.05–7.31 (6H, m), 7.32–7.43 (2H, m), 7.44–7.70 (6H, m), 7.90–8.10 (1H, m), 8.20–8.33 (2H, m), 8.40 (1×⅕H, s), 8.47 (1×⅘H, s), 8.61 (1H, d, J=2 Hz), 9.13 (1H, s)

(81) MASS: 627 (M+1); NMR (CDCl$_3$, δ): 2.77 (3×⅔H, s), 2.90 (3×⅓H, s), 2.92–3.10 (2H, m), 3.10–3.30 (2H, m), 4.40 (2×½H, d, J=15 Hz), 4.79 (2×½H, d, J=15 Hz), 5.22–5.37 (1H, m), 5.38–5.50 (1H, m), 6.78 (1H, s), 6.92–7.30 (8H, m), 7.32–7.80 (7H, m), 8.22 (1H, d, J=5 Hz), 8.38 (1×⅓H, s), 8.46 (1×⅔H, s), 8.62 (1H, d, J=2 Hz), 8.70–8.90 (1H, m), 9.14 (1H,

(82) MASS: 589 (M+1); NMR (CDCl$_3$, δ): 2.69 (3×⅔H, s), 2.90 (3×⅓H, s), 2.95–3.05 (2H, m), 3.06–3.22 (2H, m), 3.39 (3×⅓H, s), 3.40 (3×⅔H, s), 4.20 (2×⅙H, d, J=16 Hz), 4.21 (2×⅓H, d, J=15 Hz), 4.27 (2×⅙H, d, J=16 Hz), 4.97 (2×⅓H, d, J=15 Hz), 5.20–5.40 (1H, m), 5.61–5.80 (1H, m), 6.45–5.60 (2H, m), 6.88–7.15 (10H, m), 7.16–7.40 (6H, m), 7.49 (1H, d, J=8 Hz), 7.68 (1H, d, J=8 Hz), 8.95 (1H, d, J=8 Hz)

(83) MASS: 590 (M+1); NMR (CDCl$_3$, δ): 2.59 (3×⅔H, s), 2.85 (3×⅓H, s), 2.90–3.04 (2H, m), 3.05–3.19 (2H, m), 3.70 (3H, s), 4.12 (2×⅙H, d, J=16 Hz), 4.28 (2×⅙H, d, J=16 Hz), 4.35 (2×⅓H, d, J=15 Hz), 4.63 (2×⅓H, d, J=15 Hz), 4.92–5.03 (1H, m), 5.07–5.20 (1H, m), 6.70–6.78 (2H, m), 6.91–7.20 (10H, m), 7.21–7.33 (5H, m), 7.41 (1H, t, J=8 Hz), 7.44–7.55 (2H, m), 7.68 (1H, d, J=8 Hz)

(84) MASS: 613 (M+1); NMR (CDCl$_3$, δ): 2.69 (3×¾H, s), 2.85 (3×¼H, s), 2.90–3.07 (2H, m), 3.35–3.50 (2H, m), 4.40 (2×⅛H, d, J=16 Hz), 4.51 (2×⅛H, d, J=16 Hz), 4.58 (2×⅜H, d, J=15 Hz), 4.78 (2×⅜H, d, J=15 Hz), 5.01–5.22 (1H, m), 7.03–7.21 (5H, m), 7.22–7.35 (3H, m), 7.37–7.50 (3H, m), 7.51–7.71 (4H, m), 7.72 (1×¼H, s), 7.81 (1×¾H, s), 7.99 (1H, t, J=8 Hz), 8.22–8.33 (1H, m), 8.49–8.69 (2H, m), 8.82 (2H, s)

(85) MASS: 610 (M+1); NMR (CDCl$_3$, δ): 2.48 (3×⅔H, s), 2.78 (3×⅓H, s), 2.80–2.97 (2H, m), 3.42–3.60 (1H, m), 3.66–3.80 (1H, m), 4.07 (2×⅙H, d, J=16 Hz), 4.11 (2×⅙H, d, J=16 Hz), 4.17 (2×⅙H, d, J=16 Hz), 4.58 (2×⅓H, d, J=15 Hz), 4.90–5.10 (2H, m), 6.48–6.60 (1H, m), 6.90–7.20 (7H, m), 7.21–7.60 (12H, m), 7.61–7.78 (2H, m), 7.79–7.85 (1H, m), 8.23–8.37 (1H, m)

(86) MASS: 609 (M+1); NMR (CDCl$_3$, δ): 2.52 (3×⅔H, s), 2.75–3.00 (2H, m), 2.83 (3×⅓H, s), 3.08–3.30 (1H, m), 3.52–3.68 (1H, m), 3.95 (2×⅙H, d, J=16 Hz), 4.09 (2×⅓H, d, J=15 Hz), 4.17 (2×⅙H, d, J=16 Hz), 4.90 (2×⅓H, d, J=15 Hz), 5.10–5.23 (1H, m), 5.59–5.80 (1H, m), 6.83–7.35 (18H, m), 7.40–7.60 (3H, m), 7.71 (1H, d, J=8 Hz), 7.88 (1×⅓H, d, J=8 Hz), 7.92 (1×⅔H, d, J=8 Hz), 8.91 (1H, d, J=7 Hz)

(87) MASS: 550 (M+1); NMR (CDCl₃, δ): 2.71 (3×⅘H, s), 2.82 (3×⅕H, s), 2.89–3.08 (2H, m), 3.09–3.30 (2H, m), 4.22 (2×¹⁄₁₀H, d, J=16 Hz), 4.31 (2×¹⁄₁₀H, d, J=16 Hz), 4.38 (2×⅖H, d, J=15 Hz), 4.70 (2×⅖H, d, J=15 Hz), 5.19–5.39 (1H, m), 5.42–5.59 (1H, m), 6.69 (1×⅕H, s), 6.72 (1×⅕H, s), 6.97–7.30 (9H, m), 7.31 (1H, d, J=8 Hz), 7.39–7.59 (3H, m), 7.62 (1H, d, J=8 Hz), 8.22 (1×⅕H, s), 8.33 (1×⅘H, s), 8.44–8.55 (1H, m), 8.88–9.10 (1H, m)

(88) MASS: 551 (M+1); NMR (CDCl₃, δ): 2.61 (3×⅘H, s), 2.78 (3×⅕H, s), 2.90–3.07 (2H, m), 3.08–3.33 (2H, m), 4.09 (2×¹⁄₁₀H, d, J=16 Hz), 4.34 (2×¹⁄₁₀H, d, J=16 Hz), 4.42 (2×⅖H, d, J=15 Hz), 4.51 (2×⅖H, d, J=15 Hz), 4.95–5.15 (2H, m), 6.81 (1H, s), 7.05–7.32 (7H, m), 7.39 (2H, t, J=8 Hz), 7.47–7.60 (3H, m), 7.62 (1H, d, J=8 Hz), 8.01 (1H, d, J=5 Hz), 8.29 (2×⅕H, s), 8.37 (2×⅘H, s), 8.48 (1H, d, J=3 Hz)

(89) MASS: 575 (M+1); NMR (CDCl₃, δ): 2.51 (3H, s), 2.61 (3×¾H, s), 2.79 (3×¼H, s), 2.81–3.07 (2H, m), 3.25–3.45 (2H, m), 4.08 (2×⅛H, d, J=16 Hz), 4.21 (2×⅛H, d, J=16 Hz), 4.36 (2×⅜H, d, J=15 Hz), 4.51 (2×⅜H, d, J=15 Hz), 5.08–5.28 (1H, m), 5.30–5.50 (1H, m), 6.93–7.30 (13H, m), 7.32–7.50 (2H, m), 7.69 (1H, d, J=8 Hz), 8.18 (1×¼H, s), 8.30 (1×¾H, s), 8.22 (1×¼H, d, J=8 Hz), 8.39 (1×¾H, d, J=8 Hz), 8.49 (1×¾H, d, J=8 Hz), 8.67 (1×¼H, d, J=8 Hz)

(90) MASS: 576 (M+1); NMR (CDCl₃, δ): 2.50 (3H, s), 2.55 (3×¾H, s), 2.72 (3×¼H, s), 2.78–3.02 (2H, m), 3.22–3.38 (1H, m), 3.38–3.50 (1H, m), 4.01 (2×⅛H, d, J=16 Hz), 4.22 (2×⅜H, d, J=15 Hz), 4.23 (2×⅛H, d, J=16 Hz), 4.51 (2×⅜H, d, J=15 Hz), 5.00–5.20 (2H, m), 6.98–7.37 (10H, m), 7.38–7.50 (2H, m), 7.50–7.70 (3H, m), 8.12–8.20 (1H, m), 8.18 (1×¼H, s), 8.22 (1×¾H, s), 8.50–8.68 (2H, m)

(91) MASS: 560 (M+1); NMR (CDCl₃, δ): 2.78 (3×⅔H, s), 2.94 (3×⅓H, s), 2.88–3.10 (2H, m), 3.10–3.30 (2H, m), 4.29 (2×⅓H, d, J=15 Hz), 4.31 (2×⅓H, s), 4.99 (2×⅓H, d, J=15 Hz), 5.17–5.40 (1H, m), 5.70–5.90 (1H, m), 6.84–6.94 (2H, m), 6.95–7.15 (8H, m), 7.16–7.33 (5H, m), 7.34–7.60 (2H, m), 7.60–7.70 (1H, m), 8.23 (1H, s), 8.43 (1H, s), 8.97 (1H, d, J=8 Hz)

(92) MASS: 561 (M+1); NMR (CDCl₃, δ): 2.62 (3×⅔H, s), 2.91 (3×⅓H, s), 2.88–3.30 (4H, m), 4.26 (2×⅙H, d, J=16 Hz), 4.33 (2×⅙H, d, J=16 Hz), 4.37 (2×⅓H, d, J=15 Hz), 4.70 (2×⅓H, d, J=15 Hz), 4.62–4.75 (2H, m), 6.92–7.20 (8H, m), 7.20–7.35 (4H, m), 7.35–7.73 (7H, m), 8.35–8.50 (2H, m)

(93) MASS: 594 (M+1); NMR (CDCl₃, δ): 2.61 (3×⅔H, s), 2.89 (3×⅓H, s), 2.92–3.05 (2H, m), 3.09–3.23 (2H, m), 4.09 (2×⅙H, d, J=16 Hz), 4.30 (2×⅙H, d, J=16 Hz), 4.39 (2×⅓H, d, J=15 Hz), 4.67 (2×⅓H, d, J=15 Hz), 4.98–5.21 (2H, m), 6.93–7.20 (11H, m), 7.21–7.38 (6H, m), 7.42 (1H, t, J=8 Hz), 7.48–7.60 (2H, m), 7.68 (1H, d, J=8 Hz)

(94) MASS: 593 (M+1); NMR (CDCl₃, δ): 2.68 (3×⅔H, s), 2.88–3.04 (2H, m), 2.99 (3×⅓H, s), 3.07–3.23 (2H, m), 4.09 (2×⅙H, d, J=16 Hz), 4.22 (2×⅙H, d, J=16 Hz), 4.25 (2×⅓H, d, J=15 Hz), 5.00 (2×⅓H, d, J=15 Hz), 5.22–5.38 (1H, m), 5.68–5.83 (1H, m), 6.90–7.16 (13H, m), 7.17–7.40 (5H, m), 7.49 (1H, d, J=8 Hz), 7.68 (1H, d, J=8 Hz), 8.91 (1H, d, J=8 Hz)

(95) MASS: 572 (M+1); NMR (CDCl₃, δ): 2.40–3.00 (2H, m), 2.57 (3H, s), 3.01–3.22 (1H, m), 3.30–3.47 (1H, m), 4.20–4.62 (1H, m), 4.30 (2×½H, d, J=15 Hz), 4.68 (2×½H, d, J=15 Hz), 4.90–5.20 (2H, m), 5.21–5.36 (1H, m), 6.80–7.37 (16H, m), 7.38–7.60 (2H, m), 7.62–7.78 (2H, m)

(96) MASS: 571 (M+1); NMR (CDCl₃, δ): 2.50–3.30 (2H, m), 2.89 (3H, s), 2.35–2.60 (1H, m), 4.20–4.40 (1H, m), 4.48 (2×½H, d, J=16 Hz), 4.60–4.80 (1H, m), 4.76 (2×½H, d, J=16 Hz), 4.85–5.30 (1H, m), 5.45–5.60 (1H, m), 6.20–6.60 (1H, m), 6.61–7.60 (18H, m), 8.60–8.90 (1H, m)

(97) MASS: 575 (M+1); NMR (CDCl₃, δ): 2.07 (3H, s), 2.11–2.25 (2H, m), 2.50 (3H, s), 2.56–2.73 (2H, m), 2.63 (3×⅔H, s), 2.80 (3×⅓H, s), 2.91–3.12 (2H, m), 4.01 (2×⅙H, d, J=16 Hz), 4.37 (2×⅙H, d, J=16 Hz), 4.38 (2×⅓H, d, J=15 Hz), 4.52 (2×⅓H, d, J=15 Hz), 4.87–5.00 (1H, m), 5.07–5.30 (1H, m), 7.00–7.22 (6H, m), 7.23–7.50 (4H, m), 7.59 (1×⅔H, d, J=8 Hz), 7.67 (1×⅓H, d, J=8 Hz), 7.70–7.90 (3H, m), 8.22 (1×⅓H, s), 8.29 (1×⅔H, s)

EXAMPLE 27

The following object compound was obtained according to a similar manner to that of Example 8.

MASS (m/z): 575 (M+H)⁺; NMR (CDCl₃, δ): 2.67 (⅔×3H, s), 2.90–3.15 (4H, m), 2.92 (⅓×3H, s), 4.28 (⅔×1H, d, J=15 Hz), 4.38 (⅓×1H, d, J=17 Hz), 4.64 (⅓×1H, d, J=17 Hz), 4.91 (⅔×1H, d, J=15 Hz), 5.20–5.70 (2H, m), 6.05–7.70 (22H, m), 8.70 (1H, s)

EXAMPLE 28

The following object compound was obtained according to a similar manner to that of Preparation 10.

MASS (m/z): 499 (M⁺+1); NMR (CDCl₃, δ): 2.62 (3H×⅔, s), 2.85 (3H×⅓s), 2.94–3.14 (2H, m), 3.79–4.08 (2H, m), 4.04 (1H×⅔, d, J=15 Hz), 4.28 (1H×⅓, d, J=15 Hz), 4.39 (1H×⅓, d, J=15 Hz), 4.92 (1H×⅔, d, J=15 Hz), 5.25–5.62 (2H, m), 6.92–7.13 (9H, m), 7.16–7.27 (3H, m), 7.42 (1H, m), 7.49–7.67 (2H, m), 8.67 (1H, m)

EXAMPLE 29

The following object compounds were obtained according to a similar manner to that of Preparation 10.

(1) MASS (m/z): 540 (M⁺+1); NMR (CDCl₃, δ): 1.24–1.96 (6H, m), 2.68 (3H×⅓, s), 2.70 (3H×⅔, s), 2.83–3.18 (4H, m), 4.22–4.83 (2H, m), 5.03–5.32 (2H, m), 6.78–7.60 (15H, m), 8.15 (2H, m)

(2) MASS (m/z): 526 (M⁺+1); NMR (CDCl₃, δ): 1.92 (4H, m), 2.72 (3H×⅔, s), 2.91 (3H×⅓, s), 2.83–3.09 (4H, m), 4.24 (1H×⅔, d, J=15 Hz), 4.47 (1H×⅔, d, J=15 Hz), 4.65 (1H×⅓, d, J=15 Hz), 4.85 (1H×⅔, d, J=15 Hz), 5.27–5.38 (2H, m), 6.85–7.26 (14H, m), 7.42 (1H, d, J=8 Hz), 7.55 (1H, d, J=8 Hz), 9.12 (1H, br s)

EXAMPLE 30

The following compounds were obtained according to a similar manner to that of Example 3.

(1) MASS: 626 (M+1); NMR (CDCl₃, δ): 0.89 (4H, t, J=8 Hz), 0.99 (2H, t, J=8 Hz), 2.29–2.56 (6H, m), 2.62–2.83 (2H, m), 2.75 (3×⅔H, s), 2.99 (3×⅓H, s), 3.02–3.12 (2H, m), 3.88–4.45 (2H, m), 4.63–4.72 (1H, m), 4.92 (1H, dd, J=15, 8 Hz), 5.32–5.70 (2H, m), 6.98–7.18 (9H, m), 7.20–7.36 (5H, m), 7.46 (1H, d, J=8 Hz), 7.68–7.71 (1H, m), 8.89 (1×⅓H, t, J=8 Hz), 9.17 (1×⅔H, d, J=8 Hz)

(2) MASS: 601 (M+1); NMR (CDCl₃, δ): 2.29 (6H, s), 2.67 (3×⅔H, s), 2.90 (3×⅓H, s), 3.00–3.10 (2H, m), 3.22–3.23 (2H, m), 3.28–3.39 (2H, m), 4.21 (2×⅙H, d, J=16 Hz), 4.38 (2×⅓H, d, J=15 Hz), 4.41 (2×⅙H, d, J=16 Hz), 4.70 (2×⅓H, d, J=15 Hz), 4.83–4.96 (1H, m), 5.12–5.22 (1H, m), 7.00–7.19 (7H, m), 7.23–7.32 (4H, m), 7.40–7.70 (6H, m)

(3) MASS: 617 (M+1); NMR (CDCl₃, δ): 2.31 (6H, s), 2.63 (3×⅔H, s), 2.89 (3×⅓H, s), 2.99–3.09 (2H, m), 3.11–3.43 (4H, m), 4.20 (2×⅙H, d, J=16 Hz), 4.37 (2×⅓H, d, J=15 Hz), 4.42 (2×⅙H, d, J=16 Hz), 4.69 (2×⅓H, d, J=15 Hz), 4.72–4.80 (1H, m), 5.10–5.22 (1H, m), 7.00–7.20 (8H, m), 7.21–7.35 (4H, m), 7.38–7.46 (2H, m), 7.72 (1×⅓H, s), 7.77 (1×⅔H, s), 7.83–7.88 (2H, m)

(4) MASS (m/z): 619 (M+1); NMR (CDCl₃, δ): 2.63 (3×⅔H, s), 2.87 (3×⅓H, s), 2.97–3.12 (2H, m), 3.62 (2H, s), 4.08–4.43 (2×⅔H, m), 4.32–4.41 (1H, m), 4.48–4.58 (1H, m), 4.65 (2×⅓H, d, J=15 Hz), 5.10–5.28 (2H, m), 6.98–7.20 (8H, m), 7.22–7.32 (5H, m), 7.39–7.49 (2H, m), 7.5.7 (2H, t, J=8 Hz), 7.69 (1H, d, J=8 Hz), 7.71 (1×⅔H, d, J=8 Hz), 7.79 (1×⅓H, d, J=8 Hz), 8.42 (1H, br s), 8.47 (1H, br s)

(5) MASS (m/z): 605 (M+1); NMR (CDCl₃, δ): 2.62 (3×⅔H, s), 2.80 (3×⅓H, s), 3.00–3.13 (2H, m), 4.08–4.40 (2×⅔H, m), 4.62 (2×⅓H, d, J=15 Hz), 4.63–4.72 (1H, m), 4.81–4.92 (1H, m), 5.20–5.33 (2H, m), 6.91–7.30 (11H, m), 7.42 (2H, t, J=7 Hz), 7.50 (2H, d, J=10 Hz), 7.66 (1H, d, J=8 Hz), 7.72–7.91 (3H, m), 8.10 (1H, t, J=8 Hz), 8.71 (1H, d, J=2 Hz)

(6) MASS (m/z): 584 (M+H)⁺; NMR (CDCl₃, δ): 2.23 (6H, s), 2.73 (3×⅔H, s), 3.00 (3×⅓H, s), 2.98–3.10 (2H, m), 3.13–3.22 (2H, m), 4.20 (2×¼H, d, J=16 Hz), 4.42 (2×¼H, d, J=16 Hz), 4.43 (2×¼H, d, J=15 Hz), 4.94 (2×¼H, d, J=15 Hz), 4.32–4.45 (1H, m), 4.68–4.80 (1H, m), 5.35–5.46 (1H, m), 5.75–5.88 (1H, m), 6.99–7.22 (10H, m), 7.23–7.38 (4H, m), 7.50 (1H, d, J=8 Hz), 7.70 (1H, d, J=8 Hz), 9.16 (1H, d, J=8 Hz)

(7) MASS (m/z): 619 (M+1); NMR (CDCl₃, δ): 2.65 (3×⅔H, s), 2.88 (3×⅓H, s), 2.99–3.12 (2H, m), 3.61 (2H, s), 4.10–4.42 (2×⅔H, m), 4.36–4.43 (1H, m), 4.49–4.58 (1H, m), 4.71 (2×⅓H, d, J=15 Hz), 5.09–5.29 (2H, m), 6.99–7.20 (9H, m), 7.22–7.38 (4H, m), 7.42 (2H, t, J=8 Hz), 7.52 (1H, s), 7.57 (1H, d, J=5 Hz), 7.63–7.73 (2H, m), 8.45 (2H, br s)

(8) MASS (m/z): 605 (M+1); NMR (CDCl₃, δ): 2.62 (3×⅔H, s), 2.82 (3×⅓H, s), 3.07 (2H, t, J=8 Hz), 4.08–4.38 (2×⅔H, m), 4.61 (2×⅓H, d, J=15 Hz), 4.63–4.78 (2H, m), 5.22–5.31 (1H, m), 5.33–5.40 (1H, m), 6.91–7.32 (11H, m), 7.42 (1H, t, J=8 Hz), 7.52–7.61 (3H, m), 7.68 (1H, d, J=8 Hz), 7.73–7.80 (2H, m), 7.92 (1×⅔H, d, J=8 Hz), 8.01 (1×⅓H, d, J=8 Hz), 8.70 (2H, br s)

(9) MASS (m/z): 619 (M+1); NMR (CDCl₃, δ): 2.59 (3×⅔H, s), 2.80 (3×⅓H, s), 2.91 (2H, t, J=8 Hz), 3.89 (2H, s), 4.08–4.34 (2×⅔H, m), 4.53–4.60 (2H, m), 4.62 (2×⅓H, d, J=15 Hz), 5.00–5.10 (1H, m), 5.13–5.22 (1H, m), 6.93–7.20 (13H, m), 7.40–7.48 (2H, m), 7.52 (1H, s), 7.58–7.62 (2H, m), 7.68 (1H, d, J=8 Hz), 7.83 (1H, t, J=8 Hz), 8.57 (1H, d, J=2 Hz)

(10) MASS (m/z): 639 (M+1); NMR (CDCl₃, δ): 1.31–1.62 (6H, m), 2.30–2.43 (4H, m), 2.50–2.57 (2H, m), 2.60–2.71 (2H, m), 2.63 (3×⅔H, s), 2.88 (3×⅓H, s), 2.97–3.13 (2H, m), 4.13–4.69 (4H, m), 5.01–5.11 (1H, m), 5.16–5.25 (1H, m), 6.98–7.20 (8H, m), 7.23–7.32 (2H, m), 7.40–7.70 (7H, m)

(11) MASS (m/z): 627 (M+1); NMR (CDCl₃, δ): 1.00 (6H, t, J=8 Hz), 2.48–2.57 (7H, m), 2.62 (3×⅔H, s), 2.82 (2H, t, J=8 Hz), 2.89 (3×⅓H, s), 3.04 (2H, t, J=8 Hz), 4.05–4.69 (3H, m), 4.89–5.00 (1H, m), 5.14–5.22 (1H, m), 7.00–7.22 (8H, m), 7.25–7.36 (4H, m), 7.44 (2H, q, J=8 Hz), 7.53 (1H, s), 7.56 (1H, dd, J=8, 2 Hz), 7.70 (1H, d, J=8 Hz)

(12) MASS (m/z): 585 (M+1); NMR (CDCl₃, δ): 2.28 (6H, s), 2.68 (3×⅔H, s), 2.91 (3×⅓H, s), 2.97–3.12 (2H, m), 3.17 (2H, d, J=8 Hz), 4.14–4.70 (4H, m), 5.09–5.27 (2H, m), 6.97–7.22 (7H, m), 7.24–7.32 (4H, m), 7.43 (1H, t, J=8 Hz), 7.49–7.58 (3H, m), 7.67–7.78 (2H, m)

EXAMPLE 31

Starting Compound (620 mg) was dissolved in methylenechloride (10 ml), and the solution was ice-cooled. To this solution was added trifluoroacetic acid (5 ml) and triethylsilane (476 mg). The mixture was stirred at this temperature for ten minutes and at ambient temperature for one hour and was concentrated under reduced pressure. The residue was dissolved in ethyl acetate and the organic layer was washed with sodium hydrogencarbonate solution and brine. After evaporation, the crude material obtained was purified on a column of silica gel eluting with chloroform-methanol (60:1) to give Object Compound (380 mg) as an amorphous solid.

MASS: 516 (M+1); NMR (CDCl₃, δ): 2.72 (3×⅔H, s), 2.78–2.88 (1H, m), 2.89 (3×⅓H, s), 2.99–3.18 (3H, m), 4.22 (2×⅙H, d, J=16 Hz), 4.41 (2×⅙H, d, J=16 Hz), 4.45 (2×⅓H, d, J=15 Hz), 4.63 (2×⅓H, d, J=15 Hz), 4.87–4.97 (1H, m), 5.21 (1H, q, J=8 Hz), 7.03–7.19 (7H, m), 7.26–7.35 (5H, m), 7.42–7.57 (4H, m), 7.69 (1H, d, J=8 Hz)

EXAMPLE 32

The following object compounds were obtained according to a similar manner to that of Example 31.

(1) MASS: 532 (M+1); NMR (CDCl₃, δ): 2.73 (3×⅔H, s), 2.78–2.90 (1H, m), 2.90 (3×⅓H, s), 2.99–3.18 (3H, m), 4.18 (2×⅙H, d, J=16 Hz), 4.43 (2×⅙H, d, J=16 Hz), 4.45 (2×⅓H, d, J=15 Hz), 4.61 (2×⅓H, d, J=15 Hz), 4.81–4.92 (1H, m), 5.17–5.27 (1H, m), 7.03–7.20 (7H, m), 7.22–7.47 (7H, m), 7.81–7.89 (3H, m)

(2) MASS: 515 (M+1); NMR (CDCl₃, δ): 2.77 (3×⅔H, s), 2.91–3.18 (4H, m), 3.03 (3×⅓H, s), 4.13 (2×⅙H, d, J=16 Hz), 4.41 (2×⅙H, d, J=16 Hz), 4.51 (2×⅓H, d, J=15 Hz), 4.86 (2×⅓H, d, J=15 Hz), 5.37–5.52 (1H, m), 5.63–5.73 (1H, m), 7.00–7.20 (9H, m), 7.22–7.40 (5H, m), 7.49 (1H, d, J=8 Hz), 7.70 (1H, d, J=8 Hz), 9.11 (1H, t, J=8 Hz)

EXAMPLE 33

To a stirred solution of Starting Compound (0.11 g) and triethylamine (0.05 ml) in methylene chloride (5 ml) was added dropwise acetyl chloride (0.02 g) at 0° C. and the mixture was stirred at room temperature for 1 hour. The reaction mixture was washed with 1N aqueous hydrochloric acid and 5% aqueous sodium bicarbonate, and dried. Evaporation of solvent gave a residue which was purified by column chromatography on silica gel. Elution with chloroform ~3% methanol-chloroform afforded Object Compound (0.05 g) as powder.

MASS (m/z): 582 (M⁺+1); NMR (CDCl₃, δ): 1.41–1.94 (6H, m), 1.84 (3H, s), 2.80 (3H×⅔, s), 3.02 (3H×⅓, s), 2.97–3.11 (3H, m), 3.22–3.33 (1H, m), 4.24 (1H×⅓, d, J=15 Hz), 4.45 (1H×⅔, d, J=15 Hz), 4.62 (1H×⅓, d, J=15 Hz), 4.85 (1H×⅔, d, J=15 Hz), 5.39 (2H, m), 6.31 (1H, m), 6.99–7.15 (8H, m), 7.17–7.32 (5H, m), 7.47 (1H, d, J=8 Hz), 7.67 (1H, d, J=8 Hz), 8.94 (1H, t, J=8 Hz)

EXAMPLE 34

The following object compounds were obtained according to a similar manner to that of Example 33.

(1) MASS (m/z): 541 (M⁺+1); NMR (CDCl₃, δ): 2.02 (3H, s), 2.74 (3H×⅔, s), 3.00 (3H×⅓, s), 3.06 (2H, m), 4.12 (1H×⅓, d, J=15 Hz), 4.37 (1H, m), 4.47 (1H×⅔, d, J=15 Hz), 4.57 (1H×⅓, d, J=15 Hz), 4.65 (1H, dd, J=4, 12 Hz), 4.88 (1H×⅔, d, J=15 Hz), 5.37 (1H, m), 5.70 (1H, m), 6.96–7.20 (10H, m), 7.25–7.32 (4H, m), 7.49 (1H, d, J=8 Hz), 7.70 (1H, dd, J=2, 8 Hz), 9.00 (1H, d, J=8 Hz)

(2) MASS (m/z): 630 (M⁺+1); NMR (CDCl₃, δ): 1.57–2.10 (4H, m), 2.79 (3H×⅔, s), 2.97 (3H×⅓, s), 2.94–3.07 (2H, m), 3.42–3.49 (2H, m), 4.27 (1H×⅓, d, J=15

Hz), 4.38 (1H×⅔, d, J=15 Hz), 4.43 (1H×⅓, d, J=15 Hz), 4.85 (1H×⅔, d, J=15 Hz), 5.35–5.62 (2H, m), 6.96–7.15 (9H, m), 7.17–7.33 (7H, m), 7.35–7.48 (3H, m), 7.56–7.82 (3H, m), 9.02 (1H, t, J=8 Hz)

(3) MASS: 568 (M$^+$+1); NMR (CDCl$_3$, δ): 1.61–1.71 (2H, m), 1.77–1.98 (2H, m), 1.90 (3H×⅔, s), 1.92 (3H×⅓, s), 2.81 (3H×⅔, s), 3.02 (3H×⅓, s), 2.95–3.05 (2H, m), 3.12–3.33 (2H, m), 4.26 (1H×⅓, d, J=15 Hz), 4.44 (1H×⅓, d, J=15 Hz), 4.46 (1H×⅔, d, J=15 Hz), 4.88 (1H×⅔, d, J=15 Hz), 5.34–5.52 (2H, m), 6.60 (1H, m), 6.99–7.15 (9H, m), 7.22–7.32 (5H, m), 7.46 (1H, d, J=8 Hz), 7.67 (1H, dd, J=2, 8 Hz), 9.01 (1H, t, J=8 Hz)

(4) MASS (m/z): 644 (M$^+$+1); NMR (CDCl$_3$, δ): 1.33–2.01 (6H, m), 2.77 (3H×⅔, s), 3.00 (3H×⅓, s), 2.98–3.07 (2H, m), 3.21–3.48 (2H, m), 4.26 (1H×⅓, d, J=15 Hz), 4.40 (1H×⅔, d, J=15 Hz), 4.62 (1H×⅓, d, J=15 Hz), 4.86 (1H×⅔, d, J=15 Hz), 5.42 (2H, m), 6.95–7.14 (8H, m), 7.18–7.37 (8H, m), 7.47 (1H, d, J=8 Hz), 7.64–7.77 (3H, m), 8.97 (1H, m)

EXAMPLE 35

To a solution of Starting Compound (243 mg) in N,N-dimethylformamide-pyridine (4:1, 5 ml) was added sulfur trioxide-pyridine complex (790 mg) at room temperature. The mixture was stirred at the temperature for 12 hours and the solvent was evaporated. To this residue was added 10% aqueous ammonia with ice-cooling, and the mixture was stirred for 30 minutes. The mixture was extracted three times with butanol, and the organic layer was washed with water. The solvent was evaporated, and the residue was redissolved in toluene, then evaporated to give a solid. The product was purified by column chromatography (silica gel, chloroform-methanol) to give Object Compound (191 mg) as white powders.

MASS (m/z): 499 (M–SO$_3$+H$^+$); NMR (CDCl$_3$, δ): 2.20–3.05 (5H, m), 3.70–5.50 (6H, m), 6.55–7.65 (17H, m), 8.50–8.75 (1H, m)

EXAMPLE 36

The following object compound was obtained by treating Starting Compound with trifluoroacetic acid according to a similar manner to that of Preparation 3, 4, 8 or 41.

MASS (m/z): 569 (M$^+$+1); NMR (CDCl$_3$, δ): 1.67 (2H, m), 1.98 (2H, m), 2.55 (3H×½, s), 2.58 (3H×½, s), 2.68–2.78 (2H, m), 2.97 (1H, m), 3.31 (1H, m), 3.68 (2H×½, s), 4.27–4.53 (2H×½, m), 4.99 (2H, m), 6.93–7.70 (17H, m)

EXAMPLE 37

The following object compounds were obtained according to a similar manner to that of Example 1 or 24.

(1) MASS: 647 (M+1); NMR (CDCl$_3$, δ): 2.52–2.72 (1H, m), 2.69 (3×⅔H, s), 2.80 (3×⅓H, s), 3.10–3.33 (3H, m), 3.37–3.52 (2H, m), 3.53–3.80 (6H, m), 4.21 (2×⅓H, d, J=15 Hz), 4.23 (2×⅙H, d, J=16 Hz), 4.37 (2×⅙H, d, J=16 Hz), 4.69 (2×⅓H, d, J=15 Hz), 5.02–5.30 (2H, m), 6.88 (2×⅓H, d, J=8 Hz), 6.93 (2×⅔H, d, J=8 Hz), 7.03–7.21 (3H, m), 7.22–7.33 (3H, m), 7.34–7.57 (4H, m), 7.58–7.83 (6H, m), 8.20 (1H, t, J=7 Hz)

(2) MASS: 646 (M+1); NMR (CDCl$_3$, δ): 2.52–2.77 (1H, m), 2.68 (3×⅔H, s), 2.83 (3×⅓H, s), 3.03–3.30 (3H, m), 3.30–3.48 (2H, m), 3.49–3.72 (6H, m), 4.15 (2×⅓H, d, J=15 Hz), 4.30 (2×⅙H, d, J=16 Hz), 4.38 (2×⅙H, d, J=16 Hz), 4.73 (2×⅓H, d, J=15 Hz), 5.13–5.38 (2H, m), 6.80–7.00 (3H, m), 7.01–7.30 (6H, m), 7.30–7.48 (3H, m), 7.50–7.80 (5H, m), 7.94–8.20 (2H, m)

(3) MASS: 610 (M+1); NMR (CDCl$_3$, δ): 2.50–2.72 (1H, m), 2.73–3.08 (2H, m), 2.81 (3×⅔H, s), 2.87 (3×⅓H, s), 3.09–3.30 (1H, m), 3.19 (3×⅓H, s), 3.20 (3×⅔H, s), 3.31–3.70 (8H, m), 4.23 (2×⅙H, d, J=16 Hz), 4.50 (2×⅓H, d, J=15 Hz), 4.65 (2×⅓H, d, J=15 Hz), 4.78 (2×⅙H, d, J=16 Hz), 5.37–5.50 (1×⅓H, m), 5.51–5.60 (1×⅔H, m), 5.70–5.87 (1H, m), 6.61 (1×⅔H, d, J=8 Hz), 6.78 (1H, s), 6.88 (1×⅓H, d, J=8 Hz), 6.91–7.33 (12H, m), 7.38–7.50 (1H, m), 7.60–7.72 (1H, m), 9.87 (1H, s)

(4) MASS: 611 (M+1); NMR (CDCl$_3$, δ): 2.51–2.70 (1H, m), 2.81 (3×⅔H, s), 2.89 (3×⅓H, s), 2.94–3.09 (2H, m), 3.13 (1H, t, J=8 Hz), 3.22 (3H, s), 3.30–3.42 (2H, m), 3.43–3.70 (6H, m), 4.21 (2×⅙H, d, J=16 Hz), 4.51 (2×⅓H, d, J=15 Hz), 4.67 (2×⅓H, d, J=15 Hz), 4.73 (2×⅙H, d, J=16 Hz), 5.34–5.58 (1H, m), 5.73 (1H, q, J=5 Hz), 6.54 (1×⅔H, d, J=8 Hz), 6.67 (1×⅓H, d, J=8 Hz), 6.80–6.93 (1H, m), 6.98–7.09 (2H, m), 7.11 (1H, d, J=8 Hz), 7.13–7.39 (7H, m), 7.40–7.60 (3H, m), 7.62–7.78 (1H, m)

(5) MASS: 626 (M+1); NMR (CDCl$_3$, δ): 2.58–2.80 (1H, m), 2.67 (3×⅔H, s), 2.83 (3×⅓H, s), 2.89–3.02 (2H, m), 3.10–3.22 (1H, m), 3.30–3.48 (2H, m), 3.49–3.72 (6H, m), 3.58 (3H, s), 4.22 (2×⅓H, d, J=15 Hz), 4.31 (2×⅙H, d, J=16 Hz), 4.40 (2×⅙H, d, J=16 Hz), 4.75 (2×⅓H, d, J=15 Hz), 5.09–5.20 (1H, m), 5.21–5.34 (1H, m), 6.61 (2H, t, J=8 Hz), 6.90–7.02 (3H, m), 7.03–7.14 (2H, m), 7.18–7.32 (5H, m), 7.42 (1H, d, J=8 Hz), 7.62 (1H, d, J=8 Hz), 8.02–8.20 (2H, m)

(6) MASS: 627 (M+1); NMR (CDCl$_3$, δ): 2.58–2.71 (1H, m), 2.68 (3×⅓H, s), 2.83 (3×⅔H, s), 2.88–3.08 (2H, m), 3.23–3.38 (1H, m), 3.40–3.60 (2H, m), 3.61–3.80 (6H, m), 3.70 (3H, s), 4.23 (2×⅙H, d, J=16 Hz), 4.29 (2×⅓H, d, J=15 Hz), 4.41 (2×⅙H, d, J=16 Hz), 4.69 (2×⅓H, d, J=15 Hz), 5.01–5.18 (2H, m), 6.69 (2×⅔H, d, J=15 Hz), 6.73 (2×⅓H, d, J=15 Hz), 6.97–7.14 (4H, m), 7.22–7.35 (5H, m), 7.43 (1H, t, J=8 Hz), 7.50 (1H, s), 7.54–7.61 (1H, m), 7.62–7.71 (1H, m), 8.22 (1H, d, J=8 Hz)

(7) MASS: 569 (M+1); NMR (CDCl$_3$, δ): 2.51 (3H, s), 2.57 (3×¾H, s), 2.61–2.69 (1H, m), 2.73 (3×¼H, s), 2.93 (6H, s), 2.99–3.12 (2H, m), 3.27 (1H, dd, J=16, 5 Hz), 4.09 (2×⅙H, d, J=16 Hz), 4.27 (2×⅓H, d, J=15 Hz), 4.29 (2×⅙H, d, J=16 Hz), 4.51 (2×⅓H, d, J=15 Hz), 5.09–5.22 (2H, m), 6.99–7.29 (10H, m), 7.46 (1H, d, J=8 Hz), 7.65 (1H, d, J=8 Hz), 7.99 (1×¾H, d, J=8 Hz), 8.06 (1×¼H, d, J=8 Hz), 8.19–8.27 (2H, m)

(8) MASS: 570 (M+1); NMR (CDCl$_3$, δ): 2.52 (3H, s), 2.58 (3×⅔H, s), 2.61–2.70 (1H, m), 2.73 (3×⅓H, s), 2.97 (3H, s), 3.00 (3H, s), 2.98–3.08 (2H, m), 3.34 (1H, d, J=17 Hz), 4.02 (2×⅙H, d, J=16 Hz), 4.27 (2×⅓H, d, J=15 Hz), 4.31 (2×⅙H, d, J=16 Hz), 4.57 (2×⅓H, d, J=15 Hz), 5.06–5.19 (2H, m), 7.07 (1H, d, J=8 Hz), 7.12–7.31 (7H, m), 7.43 (1H, t, J=8 Hz), 7.51 (1H, s), 7.58 (1H, d, J=8 Hz), 7.68 (1H, d, J=8 Hz), 7.78 (1×¼H, d, J=8 Hz), 7.80 (1×¾H, d, J=8 Hz), 8.20 (1×¼H, s), 8.28 (1×¾H, s), 8.32 (1H, d, J=8 Hz)

(9) MASS: 623 (M+1); NMR (CDCl$_3$, δ): 2.22 (3H, s), 2.26 (3H, s), 2.25–2.42 (4H, m), 2.61 (3×⅔H, s), 2.68–2.78 (1H, m), 2.82 (3×⅓H, s), 2.95–3.10 (2H, m), 3.19–3.30 (1H, m), 3.35–3.50 (2H, m), 3.55–3.70 (2H, m), 4.18 (2×⅙H, d, J=16 Hz), 4.20 (2×⅓H, d, J=15 Hz), 4.32 (2×⅙H, d, J=16 Hz), 4.68 (2×⅓H, d, J=15 Hz), 5.12–5.30 (2H, m), 6.76–7.18 (11H, m), 7.23 (1H, t, J=8 Hz), 7.44 (1H, d, J=8 Hz), 7.65 (1H, d, J=8 Hz), 7.99–8.10 (2H, m)

(10) MASS: 624 (M+1); NMR (CDCl$_3$, δ): 2.29 (3H, s), 2.31 (3H, s), 2.34–2.53 (4H, m), 2.59 (3×⅔H, s), 2.63–2.72 (1H, m), 2.81 (3×⅓H, s), 3.00–3.10 (2H, m), 3.28–3.39 (1H, m), 3.42–3.58 (2H, m), 3.63–3.72 (2H, m), 4.09 (2×⅙H, d, J=16 Hz), 4.32 (2×⅙H, d, J=16 Hz), 4.27 (2×⅓H, d, J=15

Hz), 4.60 (2×⅓H, d, J=15 Hz), 5.02–5.16 (2H, m), 6.74–7.06 (3H, m), 7.11–7.22 (6H, m), 7.29 (1H, t, J=8 Hz), 7.43 (1H, t, J=8 Hz), 7.50 (1H, s), 7.58 (1H, d, J=8 Hz), 7.68 (2×⅔H, d, J=8 Hz), 7.72 (2×⅓H, d, J=8 Hz), 8.22 (1H, d, J=8 Hz)

(11) MASS: 623 (M+1); NMR (CDCl₃, δ): 2.13 (3×⅓H, s), 2.16 (3×⅔H, s), 2.23 (3H, s), 2.28–2.42 (4H, m), 2.61 (3×⅔H, s), 2.59–2.74 (1H, m), 2.82 (3×⅓H, s), 2.99–3.09 (2H, m), 3.21 (1H, t, J=15 Hz), 3.36–3.48 (2H, m), 3.52–3.71 (2H, m), 4.12 (2×⅙H, d, J=16 Hz), 4.21 (2×⅙H, d, J=16 Hz), 4.40 (2×⅓H, d, J=15 Hz), 4.58 (2×⅓H, d, J=15 Hz), 4.98–5.28 (2H, m), 6.75 (1H, t, J=8 Hz), 6.98 (1H, d, J=8 Hz), 7.02–7.20 (9H, m), 7.23 (1H, t, J=8 Hz), 7.41 (1H, d, J=8 Hz), 7.64 (1H, d, J=8 Hz), 7.96–8.09 (2H, m)

(12) MASS: 640 (M+1); NMR (CDCl₃, δ): 2.13 (3×⅓H, s), 2.14 (3×⅔H, s), 2.23 (3H, s), 2.31–2.50 (4H, m), 2.59 (1H, dd, J=17, 8 Hz), 2.63 (3×⅔H, s), 2.85 (3×⅓H, s), 3.01–3.15 (2H, m), 3.21–3.35 (1H, m), 3.40–3.58 (2H, m), 3.60–3.74 (2H, m), 4.10 (2×⅙H, d, J=16 Hz), 4.24 (2×⅙H, d, J=16 Hz), 4.47 (2×⅓H, d, J=15 Hz), 4.53 (2×⅓H, d, J=15 Hz), 4.89–5.20 (2H, m), 6.80 (1H, t, J=8 Hz), 7.07–7.30 (8H, m), 7.38–7.47 (2H, m), 7.63–7.90 (4H, m), 8.11 (1H, t, J=8 Hz)

(13) MASS: 623 (M+1); NMR (CDCl₃, δ): 2.13 (3×⅓H, s), 2.15 (3×⅔H, s), 2.29 (3H, s), 2.33–2.49 (4H, m), 2.52–2.70 (1H, m), 2.62 (3×⅔H, s), 2.83 (3×⅓H, s), 2.99–3.17 (2H, m), 3.30 (1H, t, J=15 Hz), 3.41–3.58 (2H, m), 3.60–3.72 (2H, m), 4.06 (2×⅙H, d, J=16 Hz), 4.22 (2×⅙H, d, J=16 Hz), 4.48 (2×⅓H, d, J=15 Hz), 4.52 (2×⅓H, d, J=15 Hz), 4.93–5.22 (2H, m), 6.73 (1×⅓H, d, J=8 Hz), 6.79 (1×⅔H, d, J=8 Hz), 7.07–7.31 (9H, m), 7.42 (1H, s), 7.49 (1H, s), 7.57 (1H, d, J=8 Hz), 7.61–7.73 (2H, m), 8.20 (1H, d, J=8 Hz)

(14) MASS: 598 (M+1); NMR (CDCl₃, δ): 2.60–2.73 (1H, m), 2.82 (3×¾H, s), 2.88 (3×¼H, s), 2.92–3.12 (2H, m), 3.14–3.26 (1H, m), 3.30–3.45 (2H, m), 3.50–3.70 (6H, m), 4.30 (2×⅙H, d, J=17 Hz), 4.42 (2×⅓H, d, J=15 Hz), 4.50 (2×⅙H, d, J=17 Hz), 4.60 (2×⅓H, d, J=15 Hz), 4.98–5.08 (2×⅙H, m), 5.14–5.26 (2×⅚H, m), 6.82 (1×¼H, d, J=5 Hz), 6.86 (1×¾H, d, J=5 Hz), 6.98 (1H, s), 7.05–7.18 (6H, m), 7.27 (1H, t, J=8 Hz), 7.40 (1H, d, J=8 Hz), 7.63 (1H, d, J=5 Hz), 8.00–8.10 (2H, m), 8.53 (1H, d, J=5 Hz), 9.09 (1×¾H, s), 9.10 (1×¼H, s)

(15) MASS: 599 (M+1); NMR (CDCl₃, δ): 2.60–2.70 (1H, m), 2.82 (3×¾H, s), 2.87 (3×¼H, s), 2.98–3.18 (2H, m), 3.27–3.33 (1H, m), 3.40–3.57 (2H, m), 3.62–3.78 (6H, m), 4.32 (2×⅙H, d, J=17 Hz), 4.45 (2×⅙H, d, J=17 Hz), 4.48 (2×⅓H, d, J=15 Hz), 4.60 (2×⅓H, d, J=15 Hz), 4.93–5.22 (2H, m), 6.86 (1×¼H, d, J=5 Hz), 6.93 (1×¾H, d, J=5 Hz), 7.15–7.23 (5H, m), 7.30 (1H, t, J=8 Hz), 7.43 (1H, t, J=8 Hz), 7.50 (1H, d, J=8 Hz), 7.58 (1H, d, J=8 Hz), 7.62–7.71 (2H, m), 8.18–8.22 (1H, m), 8.57–8.62 (1H, m), 9.10 (1H, s)

(16) MASS: 648 (M+1); NMR (CDCl₃, δ): 2.60–2.78 (1H, m), 2.81 (3×⅘H, s), 2.92 (3×⅕H, s), 2.97–3.22 (3H, m), 3.28–3.42 (2H, m), 3.48–3.65 (6H, m), 4.67 (2×½H, d, J=15 Hz), 4.89 (2×½H, d, J=15 Hz), 5.11–5.32 (2H, m), 6.91–7.12 (7H, m), 7.20 (1H, t, J=8 Hz), 7.41 (1H, d, J=8 Hz), 7.61 (1H, d, J=8 Hz), 7.70–7.78 (2H, m), 7.94–8.02 (1H, m), 8.03–8.27 (3H, m), 8.70 (1×⅕H, s), 8.73 (1×⅘H, s)

(17) MASS: 649 (M+1); NMR (CDCl₃, δ): 2.58–2.73 (1H, m), 2.82 (3×¾H, s), 2.93 (3×¼H, s), 3.02–3.32 (3H, m), 3.40–3.55 (2H, m), 3.58–3.77 (6H, m), 4.59 (2×⅙H, d, J=16 Hz), 4.68 (2×⅙H, d, J=16 Hz), 4.70 (2×⅓H, d, J=15 Hz), 4.90 (2×⅓H, d, J=15 Hz), 5.03–5.28 (2H, m), 7.02–7.22 (5H, m), 7.29 (1H, t, J=8 Hz), 7.41 (1H, t, J=8 Hz), 7.48 (1H, s), 7.56 (1H, d, J=8 Hz), 7.68 (1H, d, J=8 Hz), 7.70–7.82 (3H, m), 7.98–8.03 (1H, m), 8.07–8.14 (1H, m), 8.19 (1H, d, J=8 Hz), 8.70 (1×¼H, s), 8.75 (1×¾H, s)

(18) MASS: 647 (M+1); NMR (CDCl₃, δ): 2.60–2.77 (1H, m), 2.82 (3×¾H, s), 2.93 (3×¼H, s), 3.00–3.25 (3H, m), 3.30–3.45 (2H, m), 3.50–3.70 (6H, m), 4.62 (2×⅓H, s), 4.67 (2×⅓H, d, J=15 Hz), 4.92 (2×⅓H, d, J=15 Hz), 5.19–5.31 (2H, m), 6.95–7.30 (9H, m), 7.41 (1H, d, J=8 Hz), 7.52 (1H, t, J=8 Hz), 7.61–7.71 (2H, m), 7.79 (1H, d, J=8 Hz), 7.98–8.18 (4H, m)

(19) MASS: 648 (M+1); NMR (CDCl₃, δ): 2.59–2.71 (1H, m), 2.74 (3×¾H, s), 2.89 (3×¼H, s), 3.01–3.20 (2H, m), 3.21–3.33 (1H, m), 3.40–3.55 (2H, m), 3.60–3.80 (6H, m), 4.60 (2×⅙H, d, J=16 Hz), 4.63 (2×⅙H, d, J=16 Hz), 4.68 (2×⅓H, d, J=15 Hz), 4.89 (2×⅓H, d, J=15 Hz), 5.05–5.25 (2H, m), 7.11–7.32 (7H, m), 7.41–7.59 (4H, m), 7.67–7.82 (4H, m), 8.00–8.12 (2H, m), 8.23 (1H, d, J=8 Hz)

(20) MASS: 647 (M+1); NMR (CDCl₃, δ): 2.63–2.80 (1H, m), 2.71 (3×¾H, s), 2.89 (3×¼H, s), 2.99–3.30 (3H, m), 3.31–3.49 (2H, m), 3.50–3.70 (6H, m), 4.30 (2×⅙H, d, J=16 Hz), 4.58 (2×⅙H, d, J=16 Hz), 4.69 (2×⅔H, s), 5.12–5.30 (2H, m), 6.95–7.20 (7H, m), 7.21–7.30 (2H, m), 7.33–7.49 (2H, m), 7.60–7.77 (2H, m), 7.80 (1×¼H, s), 7.88 (1×¾H, s), 8.05–8.20 (3H, m), 8.90 (1H, d, J=2 Hz)

(21) MASS: 648 (M+1); NMR (CDCl₃, δ): 2.61–2.75 (1H, m), 2.70 (3×¾H, s), 2.86 (3×¼H, s), 3.00–3.18 (2H, m), 3.22–3.33 (1H, m), 3.40–3.58 (2H, m), 3.60–3.80 (6H, m), 4.19 (2×⅙H, d, J=16 Hz), 4.58 (2×⅙H, d, J=16 Hz), 4.70 (2×⅓H, d, J=15 Hz), 4.81 (2×⅓H, d, J=15 Hz), 5.03–5.22 (2H, m), 7.10–7.60 (11H, m), 7.68 (1H, d, J=8 Hz), 7.71–7.82 (2H, m), 7.83 (1H, s), 8.12 (1H, d, J=8 Hz), 8.21 (1H, t, J=8 Hz), 8.89 (1H, d, J=2 Hz)

(22) MASS: 598 (M+1); NMR (CDCl₃, δ): 2.63–2.75 (1H, m), 2.80 (3×¾H, s), 2.88 (3×¼H, s), 2.94–3.20 (3H, m), 3.30–3.45 (2H, m), 3.50–3.67 (6H, m), 4.39 (2×⅙H, d, J=17 Hz), 4.48 (2×⅙H, d, J=17 Hz), 4.49 (2×⅓H, d, J=15 Hz), 4.70 (2×⅓H, d, J=15 Hz), 5.10–5.23 (2H, m), 6.93–6.98 (1H, m), 7.03–7.13 (6H, m), 7.22–7.28 (1H, m), 7.42 (1H, d, J=8 Hz), 7.62 (1H, d, J=8 Hz), 8.02–8.17 (2H, m), 8.33–8.49 (3H, m)

(23) MASS: 599 (M+1); NMR (CDCl₃, δ): 2.58–2.70 (1H, m), 2.81 (3×⅝H, s), 2.86 (3×⅜H, s), 3.00–3.18 (2H, m), 3.20–3.31 (1H, m), 3.39–3.54 (2H, m), 3.60–3.75 (6H, m), 4.41 (2×⅓H, s), 4.48 (2×⅓H, d, J=15 Hz), 4.70 (2×⅓H, d, J=15 Hz), 5.02–5.19 (2H, m), 7.10–7.22 (6H, m), 7.29 (1H, t, J=8 Hz), 7.42 (1H, t, J=8 Hz), 7.50 (1H, s), 7.56 (1H, d, J=8 Hz), 7.63–7.78 (2H, m), 8.13–8.22 (1H, m), 8.33–8.50 (2H, m)

(24) MASS: 675 (M+1); NMR (CDCl₃, δ): 2.61–2.74 (1H, m), 2.71 (3×¾H, s), 2.81 (3×¼H, s), 3.00–3.20 (2H, m), 3.28–3.38 (1H, m), 3.41–3.58 (2H, m), 3.62–3.80 (6H, m), 4.15 (2×⅙H, d, J=16 Hz), 4.41 (2×⅙H, d, J=16 Hz), 4.42 (2×⅓H, d, J=15 Hz), 4.60 (2×⅓H, d, J=15 Hz), 5.09–5.20 (2H, m), 7.12–7.80 (14H, m), 8.22 (1H, d, J=8 Hz), 8.30 (1H, d, J=8 Hz), 8.41 (1×¼H, s), 8.50 (1×¾H, s), 8.60–8.70 (1H, m), 9.12–9.22 (1H, m)

(25) MASS: 674 (M+1); NMR (CDCl₃, δ): 2.64–2.78 (1H, m), 2.65 (3×¾H, s), 2.79 (3×¼H, s), 2.98–3.27 (3H, m), 3.29–3.45 (2H, m), 3.48–3.70 (6H, m), 4.16 (2×⅙H, d, J=16 Hz), 4.33 (2×⅓H, d, J=15 Hz), 4.37 (2×⅙H, d, J=16 Hz), 4.57 (2×⅓H, d, J=15 Hz), 5.09–5.30 (2H, m), 6.99 (1H, s), 7.06–7.19 (6H, m), 7.20–7.30 (1H, m), 7.33–7.48 (3H, m), 7.53–7.68 (2H, m), 8.09–8.28 (3H, m), 8.40 (1×¼H, s), 8.48 (1×¾H, s), 8.63 (1H, s), 9.17 (1H, s)

(26) MASS: 674 (M+1); NMR (CDCl₃, δ): 2.61–2.78 (1H, m), 2.64 (3×¾H, s), 2.80 (3×¼H, s), 2.98–3.12 (2H, m), 3.13–3.25 (1H, m), 3.30–3.48 (2H, m), 3.52–3.68 (6H, m), 4.18 (2×⅙H, d, J=16 Hz), 4.33 (2×⅓H, d, J=15 Hz), 4.40 (2×⅙H, d, J=16 Hz), 4.65 (2×⅓H, d, J=15 Hz), 5.11–5.30 (2H, m), 6.98–7.02 (1H, m), 7.08–7.20 (6H, m), 7.22–7.32 (2H, m), 7.43 (2H, t, J=8 Hz), 7.63 (1H, d, J=8 Hz), 7.80 (1H, t, J=8 Hz), 8.02–8.20 (2H, m), 8.30 (1H, t, J=8 Hz), 8.38 (1H, d, J=8 Hz), 8.47 (1H, s), 8.68 (1H, d, J=5 Hz)

(27) MASS: 675 (M+1); NMR (CDCl$_3$, δ): 2.61–2.72 (1H, m), 2.69 (3×¾H, s), 2.81 (3×¼H, s), 3.01–3.18 (2H, m), 3.25–3.35 (1H, m), 3.40–3.58 (2H, m), 3.62–3.79 (6H, m), 4.19 (2×⅙H, d, J=16 Hz), 4.38 (2×⅓H, d, J=15 Hz), 4.42 (2×⅙H, d, J=16 Hz), 4.69 (2×⅓H, d, J=15 Hz), 5.10–5.22 (2H, m), 7.12–7.27 (6H, m), 7.31 (2H, t, J=8 Hz), 7.43 (1H, t, J=8 Hz), 7.50–7.60 (2H, m), 7.67–7.85 (3H, m), 8.21 (1H, d, J=8 Hz), 8.27–8.40 (2H, m), 8.48 (1H, s), 8.68 (1H, d, J=5 Hz)

(28) MASS (m/z): 548 (M$^+$+1); NMR (CDCl$_3$, δ): 0.88–0.98 (6H, m), 2.10 (1H, m), 2.71 (1H, dd, J=6, 15 Hz), 2.91 (3H×¼, s), 3.03 (3H×¾, s), 3.22 (1H, dd, J=4, 15 Hz), 3.38 (2H, m), 3.60 (6H, m), 4.33 (1H×¾, d, J=15 Hz), 4.64 (2H×¼, s), 4.87 (1H×¾, d, J=15 Hz), 4.87 (1H, m), 5.33 (1H, m), 7.02 (1H, s), 7.12 (1H, t, J=8 Hz), 7.22–7.37 (6H, m), 7.43 (1H, d, J=8 Hz), 7.64 (1H, d, J=8 Hz), 7.97 (1H×¼, d, J=7 Hz), 8.07 (1H×¾, d, J=7 Hz), 8.18 (1H, d, J=7 Hz)

(29) MASS (m/z): 549 (M$^+$+1); NMR (CDCl$_3$, δ): 0.91–0.99 (6H, m), 2.08 (1H, m), 2.66 (1H, m), 2.88 (3H×¼, s), 3.02 (3H×¾, s), 3.32 (1H, dd, J=3, 16 Hz), 3.47 (2H, m), 3.67 (6H, m), 4.35 (1H×¾, d, J=15 Hz), 4.56 (1H×¼, d, J=16 Hz), 4.69 (1H×¼, d, J=16 Hz), 4.79 (1H×¾, d, J=15 Hz), 4.81 (1H, m), 5.15 (1H, m), 7.18–7.37 (6H, m), 7.42 (1H, t, J=8 Hz), 7.50 (1H, s), 7.54 (1H, d, J=8 Hz), 7.65 (2H, d, J=8 Hz), 8.31 (1H, m)

(30) MASS (m/z): 602 (M$^+$+1); NMR (CDCl$_3$, δ): 0.62–1.21 (5H, m), 1.37–1.89 (8H, m), 2.62–2.71 (1H, m), 2.88 (3H×⅓, s), 2.89 (3H×⅔, s), 3.27 (1H, dd, J=4, 15 Hz), 3.41 (2H, m), 3.62 (6H, m), 4.14 (1H×⅔, d, J=15 Hz), 4.54 (1H×⅓, d, J=16 Hz), 4.64 (1H×⅓, d, J=16 Hz), 4.80 (1H×⅔, d, J=15 Hz), 5.02 (1H, m), 5.19 (1H×⅓, m), 5.27 (1H×⅔, m), 6.90 (1H, s), 7.10–7.38 (7H, m), 7.45 (1H, d, J=8 Hz), 7.65 (1H, d, J=8 Hz), 7.77 (1H×⅓, d, J=7 Hz), 7.95 (1H×⅔, d, J=7 Hz), 8.08 (1H, t, J=7 Hz)

(31) MASS (m/z): 603 (M$^+$+1); NMR (CDCl$_3$, δ): 0.62–1.25 (5H, m), 1.35–1.76 (8H, m), 2.62–2.72 (1H, m), 2.91 (3H×⅓, s), 2.99 (3H×⅔, s), 3.28 (1H, dd, J=3.15 Hz), 3.48 (2H, m), 3.68 (6H, m), 4.37 (1H×⅔, d, J=15 Hz), 4.62 (2H×⅓, s), 4.77 (1H×⅔, d, J=15 Hz), 5.02 (1H, m), 5.15 (1H, m), 7.18–7.38 (5H, m), 7.43 (1H t, J=8 Hz), 7.52 (1H, m), 7.55 (1H, d, J=8 Hz), 7.67 (2H, d, J=8 Hz), 8.23 (1H, m)

(32) MASS (m/z): 695 (M$^+$+1); NMR (CDCl$_3$, δ): 2.34 (3H, s), 2.57 (4H, m), 2.58 (3H×⅔, s), 2.65 (1H, dd, J=7, 16 Hz), 2.78 (3H×⅓, s), 3.03 (2H, m), 3.20 (4H, m), 3.30 (1H, m), 3.47 (2H, m), 3.68 (6H, m), 4.01 (1H×⅓, d, J=16 Hz), 4.21 (1H×⅔, d, J=15 Hz), 4.30 (1H×⅓, d, J=16 Hz), 4.54 (1H×⅔, d, J=15 Hz), 5.10 (2H, m), 6.83–7.02 (4H, m), 7.17 (5H, m), 7.32 (1H, d, J=8 Hz), 7.44 (1H, t, J=8 Hz), 7.51 (1H, s), 7.57 (1H, d, J=8 Hz), 7.64–7.71 (2H, m), 8.21 (1H, d, J=8 Hz)

(33) MASS (m/z): 694 (M$^{30}$ +1); NMR (CDCl$_3$, δ): 2.34 (3H, s), 2.57 (4H, m), 2.60 (3H×⅔, s), 2.72 (1H, m), 2.82 (3H×⅓, s), 3.02 (2H, d, J=7 Hz), 3.17 (5H, m), 3.37 (2H, m), 3.58 (6H, m), 4.07 (1H×⅓, d, J=16 Hz), 4.17 (1H×⅔, d, J=15 Hz), 4.30 (1H×⅓, d, J=16 Hz), 4.63 (1H×⅔, d, J=15 Hz), 5.14 (1H, q, J=7 Hz), 5.22–5.33 (1H, m), 6.81 (2H, d, J=8 Hz), 6.90 (1H, d, J=8 Hz), 6.98 (2H, d, J=8 Hz), 7.07 (6H, m), 7.22–7.27 (1H, m), 7.44 (1H, t, J=8 Hz), 7.64 (1H, d, J=8 Hz), 8.05 (1H, d, J=7 Hz), 8.14–8.21 (1H, m)

(34) MASS (m/z): 597 (M$^+$+1); NMR (CDCl$_3$, δ): 2.59–2.72 (1H, m), 2.73 (3H×⅔, s), 2.88 (3H×⅓, s), 2.91–3.06 (2H, m), 3.16 (1H, dt, J=4, 16 Hz), 3.35 (2H, m), 3.58 (6H, m), 4.12 (1H×⅔, d, J=15 Hz), 4.37 (1H×⅓, d, J=16 Hz), 4.53 (1H×⅓, d, J=16 Hz), 4.73 (1H×⅔, d, J=15 Hz), 5.14–5.27 (2H, m), 6.94–7.15 (8H, m), 7.27–7.29 (3H, m), 7.44 (1H, d, J=8 Hz), 7.65 (1H, d, J=8 Hz), 8.05–8.14 (2H, m), 8.32 (1H, d, J=5 Hz)

(35) MASS (m/z): 598 (M $^+$+1); NMR (CDCl$_3$, δ): 2.54–2.69 (1H, m), 2.77 (3H×⅔, s), 2.89 (3H×⅓, s), 2.91–3.12 (2H, m), 3.27 (1H, dt, J=4, 16 Hz), 3.47 (2H, m), 3.67 (6H, m), 4.24 (1H×⅔, d, J=15 Hz), 4.42 (1H×⅓, d, J=16 Hz), 4.49 (1H×⅓, d, J=16 Hz), 4.71 (1H×⅔, d, J=15 Hz), 5.03 (1H×⅓, m), 5.11 (1H×⅔, m), 5.15 (1H, m), 7.00–7.13 (5H, m), 7.27–7.32 (3H, m), 7.45 (1H, t, J=8 Hz), 7.52 (1H, s), 7.58 (1H, d, J=8 Hz), 7.64–7.72 (2H, m), 8.21 (1H, d, J=8 Hz), 8.39 (2H, d, J=5 Hz)

(36) MASS (m/z): 664 (M$^+$+1); NMR (CDCl$_3$, δ): 2.61–2.70 (1H, m), 2.67 (3H×¾,s), 2.81 (3H×¼, s), 3.07 (2H, m), 3.27–3.37 (1H, m), 3.48 (2H, m), 3.68 (6H, m), 4.18 (1H×¼, d, J=16 Hz), 4.38 (1H×¼, d, J=16 Hz), 4.39 (1H×¾, d, J=15 Hz), 4.62 (1H×¾, d, J=15 Hz), 5.13 (2H, m), 7.06–7.22 (7H, m), 7.31 (1H, t, J=8 Hz), 7.44 (1H, t, J=8 Hz), 7.52 (1H, s), 7.55–7.59 (3H, m), 7.70 (2H, t, J=8 Hz), 8.11 (1H, s), 8.21 (1H, m), 8.53 (1H×¾, s), 8.55 (1H×¼, s)

(37) MASS (m/z): 663 (M$^+$+1); NMR (CDCl$_3$, δ): 2.67 (3H×¾, s), 2.73 (1H, dd, J=7, 16 Hz), 2.80 (3H×¼, s), 3.04 (2H, m), 3.22 (1H, dd, J=3, 16 Hz), 3.37 (2H, m), 3.60 (6H, m), 4.18 (1H×¼, d, J=16 Hz), 4.33 (1H×¾, d, J=15 Hz), 4.35 (1H×¼, d, J=15 Hz), 4.61 (1H×¾, d, J=16 Hz), 5.18 (1H, q, J=7 Hz), 5.27 (1H, m), 6.99–7.15 (10H, m), 7.23 (1H, d, J=8 Hz), 7.44 (1H, d, J=8 Hz), 7.51 (2H, m), 7.63 (1H, d, J=8 Hz), 8.10 (1H, s), 8.13 (2H, m), 8.50 (1H×¾, s), 8.53 (1H×¼, s)

(38) MASS (m/z): 648 (M+H)$^+$; NMR (CDCl$_3$, δ): 2.55–2.72 (1H, m), 2.68 (¾×3H, s), 2.85 (¼×3H, s), 2.98–3.21 (2H, m), 3.21–3.38 (1H, m), 3.38–3.79 (8H, m), 4.29 (¼×1H, d, J=17 Hz), 4.56 (¼×1H, d, J=17 Hz), 4.65 (¾×2H, ABq, Δ=0.22, J=15 Hz), 5.02–5.25 (2H, m), 7.00–8.28 (17H, m), 8.65 (¼×1H, d, J=2 Hz), 8.73 (¾×1H, d, J=2 Hz)

(39) MASS (m/z): 647 (M+H)$^+$; NMR (CDCl$_3$, δ): 2.55–2.76 (1H, m), 2.71 (¾×3H, s), 2.85 (¼×3H, s), 2.95–3.30 (3H, m), 3.35–3.75 (8H, m), 4.30 (¼×1H, d, J=17 Hz), 4.57 (¼×1H, d, J=17 Hz), 4.63 (¾×2H, ABq, Δ=0.12, J=15 Hz), 5.05–5.28 (2H, m), 6.95–8.15 (17H, m), 8.65 (¼×1H, d, J=2 Hz), 8.73 (¾×1H, d, J=2 Hz), 9.75 (¼×1H, s), 9.95 (¾×1H, s)

(40) MASS (m/z): 648 (M+H)$^+$; NMR (CDCl$_3$, δ): 2.54–2.73 (1H, m), 2.70 (⅔×3H, s), 2.87 (⅓×3H, s), 2.95–3.18 (2H, m), 3.20–3.78 (9H, m), 4.43 (⅓×2H, ABq, Δ=0.16, J=17 Hz), 4.51 (⅔×1H, d, J=15 Hz), 4.80 (⅔×1H, d, J=15 Hz), 5.00–5.22 (2H, m), 7.08–7.80 (14H, m), 7.95–8.30 (3H, m), 8.90 (1H, d, J=2 Hz)

(41) MASS (m/z): 647 (M+H)$^+$; NMR (CDCl$_3$, δ): 2.55–2.75 (1H, m), 2.70 (⅔×3H, s), 2.87 (⅓×3H, s), 2.95–3.14 (2H, m), 3.14–3.33 (1H, m), 3.33–3.75 (8H, m), 4.46 (⅓×2H, ABq, Δ=0.15, J=17 Hz), 4.48 (⅔×1H, d, J=15 Hz), 4.82 (⅔×1H, d, J=15 Hz), 5.08–5.25 (2H, m), 6.94–7.72 (13H, m), 7.82–8.14 (4H, m), 8.89 (1H, d, J=2 Hz), 9.70 (⅓×1H, s), 9.72 (⅔×1H, s)

(42) MASS (m/z): 655 (M+H)$^+$; NMR (CDCl$_3$, δ): 2.20 (3H, s), 2.58–2.70 (1H, m), 2.61 (¾×3H, s), 2.72 (¼×3H, s), 2.93–3.18 (2H, m), 3.22–3.37 (1H, m), 3.37–3.80 (8H, m), 3.95 (¼×1H, d, J=17 Hz), 4.24 (¾×1H, d, J=15 Hz), 4.29 (¼×1H, d, J=17 Hz), 4.56 (¾×1H, d, J=15 Hz), 5.00–5.20 (2H, m), 7.06–7.80 (14H, m), 7.92–8.28 (2H, m)

(43) MASS (m/z): 654 (M+H)⁺; NMR (CDCl₃, δ): 2.20 (3H, s), 2.58–2.72 (1H, m), 2.59 (¾×3H, s), 2.71 (¼×3H, s), 2.88–3.12 (2H, m), 3.14–3.30 (1H, m), 3.33–3.78 (8H, m), 3.88 (¼×1H, d, J=17 Hz), 4.29 (¼×1H, d, J=17 Hz), 4.39 (¾×2H, ABq, Δ=0.10, J=15 Hz), 5.00–5.18 (2H, m), 6.90–8.50 (16H, m), 9.84 (¼×1H, s), 9.95 (¾×1H, s)

(44) MASS: 624 (M+1); NMR (CDCl₃, δ): 2.05–2.20 (1H, m), 2.23–2.43 (4H, m), 2.25 (3H, s), 2.45–2.60 (2H, m), 2.70 (3×⅔H, s), 2.71–2.80 (1H, m), 2.87 (3×⅓H, s), 2.97–3.14 (2H, m), 3.40–3.53 (2H, m), 3.60–3.75 (2H, m), 4.30 (2×¼H, d, J=16 Hz), 4.35 (2×¼H, d, J=15 Hz), 4.41 (2×¼H, d, J=16 Hz), 4.69 (2×¼H, d, J=15 Hz), 4.61–4.72 (1H, m), 5.10–5.20 (1H, m), 7.03–7.20 (8H, m), 7.23–7.34 (3H, m), 7.40–7.56 (3H, m), 7.67 (1H, d, J=8 Hz), 7.87–7.93 (1H, m), 8.17 (1H, t, J=8 Hz)

(45) MASS (m/z): 580 (M⁺+1); NMR (CDCl₃, δ): 2.64–2.75 (1H, m), 2.86 (1H, t, J=15 Hz), 3.23–3.43 (4H, m), 3.68 (6H, m), 4.59–4.74 (1H, m), 4.80–4.87 (1H, m), 5.21–5.37 (2H, m), 6.84 (1H, m), 6.94–7.27 (11H, m), 7.37–7.62 (2H, m), 8.05–8.31 (2H, m)

(46) MASS (m/z): 581 (M⁺+1); NMR (CDCl₃, δ): 2.64–2.78 (1H, m), 2.85–3.00 (1H, m), 3.31–3.59 (4H, m), 3.67 (6H, m), 4.57–4.75 (1H, m), 4.84–4.92 (1H, m), 5.21 (1H, m), 5.39 (1H, d, J=16 Hz), 6.89 (1H, d, J=8 Hz), 7.01 (1H, t, J=8 Hz), 7.12–7.31 (8H, m), 7.38–7.45 (1H, m), 7.52–7.56 (2H, m), 7.67 (1H, d, J=8 Hz), 7.92–8.12 (1H, m), 8.24–8.41 (1H, m)

(47) MASS (m/z): 603 (M+1)⁺; NMR (CDCl₃, δ): 2.61 (1H×⅓, dd, J=16.0, 6.0 Hz), 2.67 (1H×⅔, dd, J=16.0, 6.0 Hz), 2.79 (3H×⅓, s), 2.87 (3H×⅔, s), 3.16–3.57 (5H, m), 3.61–3.80 (6H, m), 4.37 (1H, d, J=14.5 Hz), 4.49 (1H×⅓, d, J=14.5 Hz), 4.66 (1H×⅔, d, J=14.5 Hz), 5.03–5.21 (2H, m), 6.81–6.90 (2H, m), 7.01–7.13 (3H, m), 7.23–7.36 (4H, m), 7.44 (1H, t, J=7.5 Hz), 7.51 (1H, d, J=1.5 Hz), 7.55–7.74 (3H, m), 8.22 (1H, d, J=7.5 Hz)

(48) MASS (m/z): 602 (M+1)⁺; NMR (CDCl₃, δ): 2.60 (1H×⅓, dd, J=16.0, 7.0 Hz), 2.67 (1H×⅔, dd, J=16.0, 7.0 Hz), 2.80 (3H×⅔, s), 2.88 (3H×⅓, s), 3.12–3.38 (3H, m), 3.40–3.55 (2H, m), 3.59–3.74 (6H, m), 4.35 (1H×⅔, d, J=14.5 Hz), 4.39 (1H×⅓, d, J=14.5 Hz), 4.49 (1H×⅓, d, J=14.5 Hz), 4.70 (1H×⅔, d, J=14.5 Hz), 5.04–5.21 (2H, m), 6.76–6.84 (2H, m), 6.98–7.19 (5H, m), 7.23–7.34 (4H, m), 7.43 (1H, d, J=7.5 Hz), 7.67 (1H, d, J=7.5 Hz), 7.81 (1H×⅓, d, J=7.5 Hz), 7.89 (1H×⅔, d, J=7.5 Hz), 8.07 (1H, d, J=7.5 Hz), 9.49 (1H×⅓, br s), 9.55 (1H×⅔, br s)

(49) MASS (m/z): 676 (M+H)⁺; NMR (CDCl₃, δ): 2.57–2.78 (1H, m), 2.62 (⅔×3H, s), 2.83 (⅓×3H, s), 2.93–3.11 (2H, m), 3.11–3.29 (1H, m), 3.29–3.72 (8H, m), 3.93 (3H, s), 4.27 (⅔×1H, d, J=15 Hz), 4.30 (⅓×2H, ABq, Δ=0.20, J=17 Hz), 4.72 (⅔×1H, d, J=15 Hz), 5.09–5.32 (2H, m), 6.50 (1H, m), 6.93–8.14 (17H, m), 10.00 (1H, br s)

(50) MASS (m/z): 677 (M+H)⁺; NMR (CDCl₃, δ): 2.53–2.72 (1H, m), 2.62 (⅔×3H, s), 2.82 (⅓×3H, s), 2.95–3.13 (2H, m), 3.21–3.38 (1H, m), 3.38–3.88 (8H, m), 3.94 (3H, s), 4.28 (⅓×2H, ABq, Δ=0.21, J=17 Hz), 4.29 (⅔×1H, d, J=15 Hz), 4.69 (⅔×1H, d, J=15 Hz), 5.02–5.22 (2H, m), 6.51 (1H, d, J=2 Hz), 6.97–7.78 (17H, m), 8.15–8.27 (1H, m)

(51) MASS (m/z): 640 (M+H)⁺; NMR (CDCl₃, δ): 2.58 (⅔×3H, s), 2.62–2.78 (1H, m), 2.73 (⅓×3H, s), 2.92–3.04 (2H, m), 3.05 (⅓×6H, s), 3.07 (⅔×6H, s), 3.13–3.30 (1H, m), 3.32–3.72 (8H, m), 3.82 (⅓×1H, d, J=17 Hz), 4.28 (⅓×1H, d, J=17 Hz), 4.32 (⅔×2H, ABq, Δ=0.24, J=15 Hz), 5.02–5.33 (2H, m), 6.41 (1H, d, J=9 Hz), 6.95–8.15 (14H, m), 10.00 (1H, br s)

(52) MASS (m/z): 641 (M+H)⁺; NMR (CDCl₃, δ): 2.55–2.81 (1H, m), 2.56 (⅔×3H, s), 2.72 (⅓×3H, s), 2.97–3.07 (2H, m), 3.08 (6H, s), 3.22–3.38 (1H, m), 3.38–3.78 (8H, m), 3.80 (⅓×1H, d, J=17 Hz), 4.27 (⅓×1H, d, J=17 Hz), 4.32 (⅔×2H, ABq, Δ=0.24, J=15 Hz), 4.98–5.30 (2H, m), 6.42 (⅓×1H, d, J=9 Hz), 6.45 (⅔×1H, d, J=9 Hz), 7.04–8.25 (14H, m)

(53) MASS (m/z): 662 (M+H)⁺; NMR (CDCl₃, δ): 2.55–2.71 (1H, m), 2.68 (¾×3H, s), 2.82 (¼×3H, s), 2.92–3.14 (2H, m), 3.20–3.35 (1H, m), 3.35–3.76 (8H, m), 4.27 (¼×2H, ABq, Δ=0.20, J=17 Hz), 4.49 (¾×2H, ABq, Δ=0.20, J=15 Hz), 5.05–5.21 (2H, m), 6.95–8.13 (19H, m), 9.55 (1H, br s)

(54) MASS (m/z): 663 (M+H)⁺; NMR (CDCl₃, δ): 2.57–2.72 (1H, m), 2.68 (¾×3H, s), 2.81 (¼×3H, s), 2.97–3.18 (2H, m), 3.25–3.40 (1H, m), 3.40–3.82 (8H, m), 4.26 (¼×2H, ABq, Δ=0.20, J=17 Hz), 4.49 (¾×2H, ABq, Δ=0.17, J=15 Hz), 5.03–5.20 (2H, m), 7.00–7.88 (18H, m), 8.14–8.27 (1H, m)

(55) MASS (m/z): 664 (M+H)⁺; NMR (CDCl₃, δ): 2.58 (⅖×3H, s), 2.60–2.73 (1H, m), 2.62 (⅗×3H, s), 2.65 (⅗×3H, s), 2.80 (⅖×3H, s), 2.92–3.12 (2H, m), 3.17–3.30 (1H, m), 3.36–3.74 (8H, m), 3.70 (3H, s), 4.12 (⅖×1H, d, J=17 Hz), 4.43 (⅗×1H, d, J=15 Hz), 4.57 (⅖×1H, d, J=17 Hz), 4.75 (⅗×1H, d, J=15 Hz), 5.02–5.32 (2H, m), 6.88–8.13 (15H, m), 9.78 (⅖×1H, s), 10.52 (⅗×1H, s)

(56) MASS (m/z): 665 (M+H)⁺; NMR (CDCl₃, δ): 2.58–2.72 (1H, m), 2.58 (3H, s), 2.60 (⅔×3H, s), 2.78 (⅓×3H, s), 2.92–3.14 (2H, m), 3.22–3.38 (1H, m), 3.40–3.80 (8H, m), 3.70 (3H, s), 4.13 (⅓×1H, d, J=17 Hz), 4.48 (⅔×1H, d, J=15 Hz), 4.53 (⅓×1H, d, J=17 Hz), 4.69 (⅔×1H, d, J=15 Hz), 5.02–5.30 (2H, m), 6.85–7.80 (14H, m), 8.15–8.28 (1H, m)

(57) MASS (m/z): 586 (M+H)⁺; NMR (CDCl₃, δ): 2.53–3.00 (3H, m), 2.87 (⅔×3H, s), 2.89 (⅓×3H, s), 3.16–3.33 (1H, m), 3.33–3.76 (8H, m), 4.32 (⅔×1H, d, J=15 Hz) 4.51 (⅓×2H, ABq, Δ=0.05, J=17 Hz), 4.72 (⅔×1H, d, J=15 Hz), 5.01–5.22 (2H, m), 6.18 (⅓×1H, s), 6.22 (⅔×1H, s), 6.92–8.14 (14H, m), 9.66 (⅓×1H, br s), 9.70 (⅔×1H, br s)

(58) MASS (m/z): 587 (M+H)⁺; NMR (CDCl₃, δ): 2.53–3.05 (3H, m), 2.88 (3H, s), 3.22–3.80 (9H, m), 4.35 (⅔×1H, d, J=15 Hz), 4.51 (⅓×2H, ABq, Δ=0.06, J=17 Hz), 4.70 (⅔×1H, d, J=15 Hz), 4.98–5.18 (2H, m), 6.21 (⅓×1H, s), 6.27 (⅔×1H, s), 7.03–7.74 (13H, m), 8.22 (1H, d, J=8 Hz)

(59) MASS (m/z): 600 (M+H)⁺; NMR (CDCl₃, δ): 2.59–2.73 (1H, m), 2.63 (⅔×3H, s), 2.81 (⅓×3H, s), 2.92–3.14 (2H, m), 3.18–3.32 (1H, m), 3.37–3.75 (8H, m), 3.81 (⅓×3H, s), 3.84 (⅔×3H, s), 4.08 (⅓×2H, ABq, Δ=0.18, J=17 Hz), 4.12 (⅔×1H, d, J=15 Hz), 4.42 (⅔×1H, d, J=15 Hz), 5.00–5.28 (2H, m), 6.95–8.10 (14H, m), 9.68 (1H, br s)

(60) MASS (m/z): 601 (M+H)⁺; NMR (CDCl₃, δ): 2.56–2.72 (1H, m), 2.62 (⅔×3H, s), 2.80 (⅓×3H, s), 2.90–3.18 (2H, m), 3.24–3.38 (1H, m), 3.38–3.80 (8H, m), 3.82 (⅓×3H, s), 3.85 (⅔×3H, s), 4.06 (⅓×2H, ABq, Δ=0.20, J=17 Hz), 4.13 (⅔×1H, d, J=15 Hz), 4.42 (⅔×1H, d, J=15 Hz), 4.98–5.25 (2H, m), 6.98–7.72 (13H, m), 8.13–8.25 (1H, m)

(61) MASS (m/z): 630 (M+H)⁺; NMR (CDCl₃, δ): 2.52–2.92 (1H, m), 2.72 (⅔×3H, s), 2.85–3.08 (2H, m), 2.87 (⅓×3H, s), 3.13–3.30 (1H, m), 3.33–3.75 (8H, m), 4.21 (⅔×1H, d, J=15 Hz), 4.41 (⅓×2H, ABq, Δ=0.07, J=17 Hz), 4.74 (⅔×1H, d, J=15 Hz), 5.04–5.25 (2H, m), 6.90–8.12 (16H, m), 9.77 (⅓×1H, s), 9.82 (⅔×1H, s)

(62) MASS (m/z): 631 (M+H)⁺; NMR (CDCl₃, δ): 2.51–2.78 (1H, m), 2.72 (⅔×3H, s), 2.84 (⅓×3H, s), 2.85–3.11 (2H, m), 3.20–3.37 (1H, m), 3.37–3.82 (8H, m), 4.25 (⅔×1H, d, J=15 Hz), 4.40 (⅓×2H, s), 4.71 (⅔×1H, d, J=15 Hz), 4.98–5.18 (2H, m), 6.90–7.74 (15H, m), 8.20 (1H, d, J=9 Hz)

(63) MASS (m/z): 586 (M+H)⁺; NMR (CDCl₃, δ): 2.53–2.75 (1H, m), 2.80 (⅔×3H, s), 2.87 (⅓×3H, s), 2.95–3.31 (3H, m), 3.31–3.78 (8H, m), 4.24 (⅔×1H, d, J=15 Hz), 4.45 (⅓×2H, ABq, Δ=0.13, J=17 Hz), 4.81 (⅔×1H, d, J=15 Hz), 5.08–5.32 (2H, m), 5.97–6.21 (2H, m), 6.92–8.15 (13H, m), 9.82 (⅓×1H, br s), 9.88 (⅔×1H, br s)

(64) MASS (m/z): 587 (M+H)⁺; NMR (CDCl₃, δ): 2.52–2.72 (1H, m), 2.79 (⅔×3H, s), 2.85 (⅓×3H, s), 2.96–3.19 (2H, m), 3.21–3.38 (1H, m), 3.38–3.82 (8H, m), 4.29 (⅔×1H, d, J=15 Hz), 4.43 (⅓×2H, ABq, Δ=0.17, J=17 Hz), 4.77 (⅔×1H, d, J=15 Hz), 5.01–5.28 (2H, m), 6.03–6.27 (2H, m), 7.07–7.80 (12H, m), 8.15–8.30 (1H, m)

(65) MASS (m/z): 603 (M+H)⁺; NMR (CDCl₃, δ): 2.51–2.70 (1H, m), 2.81 (⅔×3H, s), 2.86 (⅓×3H, s), 2.96–3.18 (2H, m), 3.18–3.38 (1H, m), 3.38–3.82 (8H, m), 4.30 (⅔×1H, d, J=15 Hz), 4.45 (⅓×2H, ABq, Δ=0.18, J=17 Hz), 4.77 (⅔×1H, d, J=15 Hz), 4.96–5.25 (2H, m), 6.05–6.25 (2H, m), 7.05–8.22 (13H, m)

(66) MASS: 648 (M+1); NMR (CDCl₃, δ): 2.60–2.78 (1H, m), 2.70 (3×⅔H, s), 2.85 (3×⅓H, s), 2.95–3.12 (2H, m), 3.13–3.30 (1H, m), 3.31–3.50 (2H, m), 3.51–3.90 (6H, m), 4.36 (2×⅙H, d, J=16 Hz), 4.55 (2×⅙H, d, J=16 Hz), 4.61 (2×⅓H, d, J=15 Hz), 4.73 (2×⅓H, d, J=15 Hz), 5.10–5.33 (2H, m), 6.95–7.35 (8H, m), 7.36–7.50 (2H, m), 7.62 (1H, d, J=8 Hz), 7.78 (1×⅓H, s), 7.83 (1×⅔H, s), 7.93–8.20 (3H, m), 8.81 (2H, s)

(67) MASS: 649 (M+1); NMR (CDCl₃, δ): 2.61–2.70 (1H, m), 2.71 (3×⅔H, s), 2.88 (3×⅓H, s), 3.00–3.18 (2H, m), 3.29 (1H, t, J=15 Hz), 3.40–3.59 (2H, m), 3.60–3.80 (6H, m), 4.38 (2×⅙H, d, J=16 Hz), 4.58 (2×⅙H, d, J=16 Hz), 4.62 (2×⅓H, d, J=15 Hz), 4.79 (2×⅓H, d, J=15 Hz), 5.08–5.22 (2H, m), 7.11–7.25 (5H, m), 7.26–7.37 (1H, m), 7.40–7.50 (2H, m), 7.51 (1H, s), 7.56 (1H, d, J=8 Hz), 7.68 (1H, d, J=8 Hz), 7.75–7.90 (2H, m), 8.02 (1H, d, J=8 Hz), 8.20 (1×⅓H, d, J=8 Hz), 8.23 (1×⅔H, d, J=8 Hz), 8.80 (2H, s)

(68) MASS: 646 (M+1); NMR (CDCl₃, δ): 2.02 (3×⅔H, s), 2.68 (3×⅓H, s), 2.71–2.90 (1H, m), 3.17–3.50 (5H, m), 3.51–3.70 (6H, m), 3.67 (2×⅙H, d, J=16 Hz), 3.96 (2×⅙H, d, J=16 Hz), 4.18 (2×⅓H, d, J=15 Hz), 4.50 (2×⅓H, d, J=15 Hz), 5.27–5.50 (2H, m), 6.71–6.80 (2×⅓H, m), 6.90–7.00 (2×⅔H, m), 7.01–7.32 (8H, m), 7.33–7.57 (3H, m), 7.60–7.70 (2H, m), 7.74 (1H, d, J=8 Hz), 7.93–8.12 (1H, m), 8.24 (2×⅓H, d, J=8 Hz), 8.31 (2×⅔H, d, J=8 Hz)

(69) MASS: 647 (M+1); NMR (CDCl₃, δ): 1.99 (3×⅔H, s), 2.61 (3×⅓H, s), 2.58–2.74 (1H, m), 3.28–3.60 (5H, m), 3.60–3.80 (6H, m), 3.72 (2×⅙H, d, J=16 Hz), 3.89 (2×⅙H, d, J=16 Hz), 4.19 (2×⅓H, d, J=15 Hz), 4.40 (2×⅓H, d, J=15 Hz), 5.08–5.22 (1H, m), 5.27–5.40 (1H, m), 6.68–6.78 (2×⅓H, m), 6.90–6.99 (2×⅔H, m), 7.10–7.37 (6H, m), 7.38–7.62 (5H, m), 7.62–7.90 (4H, m), 8.10–8.40 (2H, m)

(70) MASS: 598 (M+1); NMR (CDCl₃, δ): 2.53–2.70 (1H, m), 2.71 (3×⅔H, s), 2.85 (3×⅓H, s), 2.90–3.15 (2H, m), 3.22–3.35 (1H, m), 3.37–3.58 (2H, m), 3.60–3.80 (6H, m), 4.37 (2×⅓H, d, J=15 Hz), 4.38 (2×⅙H, d, J=16 Hz), 4.43 (2×⅙H, d, J=16 Hz), 4.60 (2×⅓H, d, J=15 Hz), 5.00–5.20 (2H, m), 7.98–8.18 (3H, m), 7.22–7.38 (4H, m), 7.40–7.73 (6H, m), 8.20 (1H, d, J=8 Hz), 8.33 (1×⅓H, s), 8.44 (1H, d, J=2 Hz), 8.49 (1×⅔H, s)

(71) MASS: 597 (M+1); NMR (CDCl₃, δ): 2.58–2.75 (1H, m), 2.78 (3×⅔H, s), 2.88 (3×⅓H, s), 2.91–3.30 (3H, m), 3.31–3.50 (2H, m), 3.51–3.70 (6H, m), 4.31 (2×⅓H, d, J=15 Hz), 4.42 (2×⅙H, d, J=16 Hz), 4.51 (2×⅙H, d, J=16 Hz), 4.67 (2×⅓H, d, J=15 Hz), 5.10–5.30 (2H, m), 6.90–7.18 (5H, m), 7.20–7.33 (4H, m), 7.34–7.50 (2H, m), 7.64 (1H, d, J=8 Hz), 7.95–8.10 (2H, m), 8.32 (1×⅓H, s), 8.43 (1×⅔H, s), 8.45 (1H, s)

(72) MASS: 658 (M+1); NMR (CDCl₃, δ): 2.27 (3H, s), 2.31–2.48 (4H, m), 2.52 (3×⅔H, s), 2.64–2.80 (1H, m), 2.70 (3×⅓H, s), 2.93–3.15 (2H, m), 3.29 (1H, d, J=15 Hz), 3.39–3.57 (2H, m), 3.58–3.73 (2H, m), 3.88 (3H, s), 4.18 (2×⅙H, d, J=16 Hz), 4.19 (2×⅓H, d, J=15 Hz), 4.23 (2×⅙H, d, J=16 Hz), 4.49 (2×⅓H, d, J=15 Hz), 4.98–5.22 (2H, m), 6.61 (1×⅓H, d, J=8 Hz), 6.63 (1×⅔H, d, J=8 Hz), 7.00–7.37 (6H, m), 7.40–7.60 (2H, m), 7.68 (1×⅓H, d, J=8 Hz), 7.70 (1×⅔H, d, J=8 Hz), 7.81 (1×⅓H, s), 7.90 (1×⅔H, s), 7.93 (1H, d, J=8 Hz), 8.11 (1H, d, J=8 Hz), 8.80 (1H, d, J=8 Hz)

(73) MASS: 563 (M+1); NMR (CDCl₃, δ): 0.70–0.95 (3H, m), 1.15–1.45 (4H, m), 1.55–1.85 (2H, m), 2.60–2.72 (1H, m), 2.90 (3×⅓H, s), 3.00 (3×⅔H, s), 3.30 (1H, d, J=15 Hz), 3.38–3.58 (2H, m), 3.58–3.77 (6H, m), 4.38 (2×⅓H, d, J=15 Hz), 4.62 (2×⅓H, s), 4.76 (2×⅓H, d, J=15 Hz), 4.83–4.99 (1H, m), 5.05–5.20 (1H, m), 7.10–7.37 (5H, m), 7.37–7.46 (2H, m), 7.49–7.60 (2H, m), 7.61–7.78 (2H, m), 8.27 (1H, d, J=8 Hz)

(74) MASS: 562 (M+1); NMR (CDCl₃, δ): 0.60–0.90 (3H, m), 1.03–1.38 (4H, m), 1.50–1.80 (2H, m), 2.60–2.75 (1H, m), 2.88 (3×⅓H, s), 2.91 (3×⅔H, s), 3.10–3.28 (1H, m), 3.29–3.43 (2H, m), 3.44–3.68 (6H, m), 4.22 (2×⅓H, d, J=15 Hz), 4.52 (2×⅙H, d, J=16 Hz), 4.61 (2×⅙H, d, J=16 Hz), 4.80 (2×⅓H, d, J=15 Hz), 4.86–5.00 (1H, m), 5.12–5.35 (1H, m), 7.01 (1H, s), 7.03–7.38 (7H, m), 7.42 (1H, d, J=8 Hz), 7.62 (1H, d, J=8 Hz), 7.97 (1×⅓H, d, J=8 Hz) 8.07 (1×⅔H, d, J=8 Hz), 8.11 (1H, d, J=8 Hz)

(75) MASS: 644 (M+1); NMR (CDCl₃, δ): 2.58–2.70 (1H, m), 2.61 (3×⅔H, s), 2.73 (3×⅓H, s), 2.97–3.12 (2H, m), 3.22–3.34 (1H, m), 3.40–3.58 (2H, m), 3.60–3.78 (6H, m), 3.87 (3H, s), 4.22 (2×⅓H, d, J=15 Hz), 4.23 (2×⅙H, d, J=16 Hz), 4.31 (2×⅙H, d, J=16 Hz), 4.51 (2×⅓H, d, J=15 Hz), 5.02–5.21 (2H, m), 6.61–6.70 (1H, m), 7.08–7.23 (5H, m), 7.30–7.50 (3H, m), 7.72–7.98 (5H, m), 8.13 (1H, d, J=8 Hz)

EXAMPLE 38

The following compound was obtained according to a similar manner to that of Example 8.

MASS (m/z): 610 (M+H)⁺; NMR (CDCl₃, δ): 2.2–2.3 (2H, m), 2.4–2.6 (2H, m), 2.73 (⅔×3H, s), 2.93 (⅓×3H, s), 3.0–3.1 (2H, m), 3.3–3.6 (8H, m), 4.2–4.8 (2H, m), 5.0–5.1 (1H, m), 5.2–5.3 (1H, m), 7.0–7.7 (15H, m), 7.72 (1H, br s), 8.05 (1H, br s), 8.50 (1H, br s) (1H, m), 5.2–5.3 (1H, m), 7.0–7.7 (15H, m), 7.72 (1H, br s), 8.05 (1H, br s), 8.50 (1H, br s)

EXAMPLE 39

To a mixture of Starting Compound (112 mg) and triethylamine (70 μl) in dichloromethane (1.2 ml) was added (benzofuran-2-yl)sulfonyl chloride (68 mg) with ice-cooling. The mixture was stirred at room temperature for 12 hours then subjected to column chromatography (silica gel, chloroform/methanol=50/1) to give Object Compound (130 mg) as a white powder.

MASS (m/z): 633 (M+H)⁺; NMR (CDCl₃, δ): 2.38–2.59 (1H, m), 2.52 (⅔×3H, s), 2.73 (⅓×3H, s), 2.81–3.04 (2H, m), 3.04–3.72 (9H, m), 3.98 (⅓×1H, d, J=17 Hz), 4.24 (⅓×1H, d, J=17 Hz), 4.25 (⅔×1H, d, J=15 Hz), 4.28–4.44 (1H, m), 4.57 (⅔×1H, d, J=15 Hz), 4.88–5.05 (1H, m), 6.78–6.90 (17H, m)

EXAMPLE 40

The following object compounds were obtained according to a similar manner to that of Example 39.

(1) MASS (m/z): 571 (M+H)$^+$; NMR (CDCl$_3$, δ): 2.61 (¾×3H, s), 2.74 (¼×3H, s), 2.78–3.05 (2H, m), 3.50–3.78 (2H, m), 3.87–4.04 (1H, m), 3.88 (¼×1H, d, J=17 Hz), 4.12 (1H, br s), 4.30 (¼×1H, d, J=17 Hz), 4.42 (¾×2H, ABq, Δ=0.14, J=15 Hz), 4.90–5.05 (1H, m), 6.45 (1H, br s), 6.96–7.72 (13H, m), 8.00–8.22 (1H, m)

(2) MASS (m/z): 598 (M+H)$^+$; NMR (CDCl$_3$, δ): 2.51 (¾×3H, s), 2.58–2.95 (2H, m), 2.72 (¼×3H, s), 2.95–3.34 (2H, m), 4.08 (¼×2H, ABq, Δ=0.21, J=17 Hz), 4.24 (¾×1H, d, J=15 Hz), 4.31–4.44 (1H, m), 4.55 (¾×1H, d, J=15 Hz), 4.90–5.06 (1H, m), 6.90–7.85 (17H, m), 8.14–8.55 (3H, m)

(3) MASS (m/z): 646 (M+H)$^+$; NMR (CDCl$_3$, δ): 2.11–2.40 (4H, m), 2.25 (3H, s), 2.40–2.58 (1H, m), 2.50 (⅔×3H, s), 2.73 (⅓×3H, s), 2.82–3.05 (2H, m), 3.13–3.70 (5H, m), 4.11 (⅓×2H, ABq, Δ=0.25, J=17 Hz), 4.22 (⅔×1H, d, J=15 Hz), 4.25–4.41 (1H, m), 4.58 (⅔×1H, d, J=15 Hz), 4.89–5.05 (1H, m), 6.78–7.90 (17H, m)

EXAMPLE 41

The following object compounds were obtained according to a similar manner to that of Example 1.

(1) MASS: 573 (M+1); NMR (CDCl$_3$, δ): 2.00 (3×⅓H, s), 2.01 (3×⅔H, s), 2.70 (3×⅔H, s), 2.91 (3×⅓H, s), 2.93–3.07 (2H, m), 3.07–3.23 (2H, m), 4.22 (2×⅓H, s), 4.27 (2×⅓H, d, J=15 Hz), 4.97 (2×⅓H, d, J=15 Hz), 5.10–5.40 (1H, m), 5.60–5.80 (1H, m), 6.78 (1H, d, J=8 Hz), 6.82 (1H, d, J=8 Hz), 6.89–7.18 (11H, m), 7.18–7.40 (5H, m), 7.48 (1H, d, J=8 Hz), 7.67 (1H, d, J=8 Hz), 8.99 (1H, t, J=8 Hz)

(2) MASS: 574 (M+1); NMR (CDCl$_3$, δ): 2.22 (3H, s), 2.60 (3×⅔H, s), 2.83 (3×⅓H, s), 2.90–3.03 (2H, m), 3.08–3.20 (2H, m), 4.11 (2×⅙H, d, J=16 Hz), 4.27 (2×⅙H, d, J=16 Hz), 4.32 (2×⅓H, d, J=15 Hz), 4.62 (2×⅓H, d, J=15 Hz), 4.95–5.08 (1H, m), 5.10–5.21 (1H, m), 6.90–7.33 (17H, m), 7.40 (1H, t, J=8 Hz), 7.43–7.56 (2H, m), 7.68 (1H, d, J=8 Hz)

(3) MASS: 571 (M+1); NMR (CDCl$_3$, δ): 2.78 (3×¼H, s), 3.00 (3×¾H, s), 2.90–3.30 (2H, m), 3.30–3.48 (1H, m), 4.40–4.53 (1H, m), 4.54–4.77 (2H, m), 4.78–4.98 (2H, m), 5.10–5.20 (1H, m), 5.50–5.68 (1H, m), 6.70–7.50 (19H, m), 7.58 (1×¾H, d, J=8 Hz), 7.72 (1×¼H, d, J=8 Hz), 9.73 (1×¼H, s), 9.82 (1×¾H, s)

(4) MASS: 517 (M+1); NMR (CDCl$_3$, δ): 0.75 (3×⅖H, t, J=8 Hz), 0.81 (3×⅗H, t, J=8 Hz), 1.08–1.48 (4H, m), 1.62–1.90 (2H, m), 2.99 (3×⅖H, s), 3.11 (3×⅗H, s), 3.70–3.90 (1H, m), 4.01–4.22 (1H, m), 4.73 (2×½H, d, J=15 Hz), 4.82 (2×½H, d, J=15 Hz), 4.83–5.10 (3H, m), 7.27 (1H, t, J=7 Hz), 7.38 (1H, t, J=8 Hz), 7.42–7.53 (3H, m), 7.54–7.90 (5H, m), 7.98–8.18 (2H, m), 8.80 (1×⅖H, d, J=2 Hz), 8.90 (1×⅗H, d, J=2 Hz)

(5) MASS: 516 (M+1); NMR (CDCl$_3$, δ): 0.69 (3×⅖H, t, J=8 Hz), 0.79 (3×⅗H, t, J=8 Hz), 1.08–1.45 (4H, m), 1.60–2.01 (2H, m), 3.10 (3×⅖H, s), 3.22 (3×⅗H, s), 3.90–4.16 (2H, m), 4.60 (2×⅖H, d, J=15 Hz), 4.71 (2×⅖H, s), 5.01 (2×⅖H, d, J=15 Hz), 4.82–5.15 (1H, m), 5.50–5.70 (1H, m), 6.58 (1×⅖H, s), 6.71 (1×⅖H, s), 6.92–7.20 (3H, m), 7.30–7.42 (3H, m), 7.50 (1H, d, J=8 Hz), 7.51–7.78 (2H, m), 71.81 (1H, s), 7.93 (1H, d, J=8 Hz), 8.71 (1×⅖H, s), 8.82 (1×⅖H, s), 8.90 (1×⅖H, d, J=8 Hz), 9.00 (1×⅖H, d, J=8 Hz)

(6) MASS: 578 (M+1); NMR (CDCl$_3$, δ): 0.72 (3×¼H, t, J=8 Hz), 0.78 (3×¾H, t, J=8 Hz), 1.16–1.36 (4H, m), 1.49–1.80 (2H, m), 2.92 (3×¼H, s), 3.00 (3×¾H, s), 3.28–3.52 (2H, m), 4.58 (2×⅜H, d, J=15 Hz), 4.79 (2×⅛H, d, J=16 Hz), 4.85 (2×⅛H, d, J=16 Hz), 4.90 (2×⅜H, d, J=15 Hz), 4.83–5.01 (1H, m), 5.02–5.18 (1H, m), 7.18 (1H, t, J=8 Hz), 7.21–7.35 (2H, m), 7.41 (1H, t, J=8 Hz), 7.48–7.89 (7H, m), 7.95–8.23 (3H, m), 8.59 (1H, d, J=4 Hz), 8.73 (1H, d, J=2 Hz), 8.79 (1H, d, J=8 Hz)

(7) MASS: 577 (M+1); NMR (CDCl$_3$, δ): 0.62 (3×¼H, t, J=8 Hz), 0.68 (3×¾H, t, J=8 Hz), 0.95–1.30 (4H, m), 1.38–1.57 (1H, m), 1.58–1.72 (1H, m), 2.92 (3×¼H, s), 2.98 (3×¾H, s), 2.98–3.50 (2H, m), 4.63 (2×⅜H, d, J=15 Hz), 4.64 (2×⅛H, d, J=16 Hz), 4.78 (2×⅜H, d, J=15 Hz), 4.81 (2×⅛H, d, J=16 Hz), 4.82–5.05 (1H, m), 5.17–5.38 (1H, m), 6.97–7.12 (3H, m), 7.13–7.22 (2H, m), 7.32–7.59 (3H, m), 7.60–7.80 (3H, m), 7.94 (1H, s), 8.06–8.18 (2H, m), 8.41 (1×¼H, d, J=8 Hz), 8.48 (1×¼H, d, J=4 Hz), 8.51 (1×¾H, d, J=4 Hz), 8.69 (1×¾H, d, J=8 Hz), 8.73 (1×¾H, d, J=2 Hz), 8.78 (1×¼H, d, J=2 Hz)

(8) MASS: 575 (M+1); NMR (CDCl$_3$, δ): 2.06–2.28 (2H, m), 2.10 (3H, s), 2.50–2.70 (2H, m), 2.61 (3×⅔H, s), 2.81 (3×⅓H, s), 2.92–3.12 (2H, m), 3.91 (3H, s), 3.99 (2×⅙H, d, J=16 Hz), 4.31 (2×⅓H, d, J=15 Hz), 4.32 (2×⅙H, d, J=16 Hz), 4.52 (2×⅓H, d, J=15 Hz), 4.97 (1H, q, J=8 Hz), 5.12 (1×⅔H, q, J=8 Hz), 5.27 (1×⅓H, q, J=8 Hz), 6.67 (1×⅓H, d, J=8 Hz), 6.69 (1×⅔H, d, J=8 Hz), 7.05–7.21 (5H, m), 7.22–7.48 (5H, m), 7.51 (1H, d, J=8 Hz), 7.54 (1H, s), 7.69 (1H, d, J=8 Hz), 7.89 (1×⅓H, d, J=2 Hz), 7.99 (1×⅔H, d, J=2 Hz)

(9) MASS: 591 (M+1); NMR (CDCl$_3$, δ): 2.07–2.23 (2H, m), 2.09 (3H, s), 2.50–2.72 (2H, m), 2.65 (3×⅔H, s), 2.79 (3×⅓H, s), 2.92–3.12 (2H, m), 3.89 (3H, s), 3.94 (2×⅙H, d, J=16 Hz), 4.29 (2×⅓H, d, J=15 Hz), 4.33 (2×⅙H, d, J=16 Hz), 4.51 (2×⅓H, d, J=15 Hz), 4.91 (1H, q, J=8 Hz), 5.11 (1×⅔H, q, J=8 Hz), 5.25 (1×⅓H, q, J=8 Hz), 6.63 (1×⅓H, d, J=8 Hz), 6.67 (1×⅔H, d, J=8 Hz), 7.02–7.21 (5H, m), 7.30–7.60 (5H, m), 7.73–7.90 (3H, m), 7.87 (1×⅓H, d, J=2 Hz), 7.98 (1×⅔H, d, J=2 Hz)

(10) MASS: 574 (M+1); NMR (CDCl$_3$, δ): 2.07 (3×⅔H, s), 2.08 (3×⅓H, s), 2.10–2.41 (2H, m), 2.53–2.68 (2H, m), 2.70 (3×⅔H, s), 2.93–3.12 (2H, m), 2.97 (3×⅓H, s), 3.91 (3×⅓H, s), 3.92 (3×⅔H, s), 4.02 (2×⅙H, d, J=16 Hz), 4.32 (2×⅙H, d, J=16 Hz), 4.42 (2×⅓H, d, J=15 Hz), 4.70 (2×⅓H, d, J=15 Hz), 5.30–5.50 (1H, m), 5.51–5.62 (1H, m), 6.63 (1×⅓H, d, J=8 Hz), 6.69 (1×⅔H, d, J=8 Hz), 6.93–7.18 (7H, m), 7.19–7.40 (3H, m), 7.50 (1H, d, J=8 Hz), 7.69 (1H, d, J=8 Hz), 7.89 (1×⅓H, d, J=2 Hz), 8.02 (1×⅔H, d, J=2 Hz), 9.03 (1×⅔H, d, J=8 Hz), 9.11 (1×⅓H, d, J=8 Hz)

(11) MASS: 561 (M+1); NMR (CDCl$_3$, δ): 0.72 (3×¼H, t, J=8 Hz), 0.80 (3×¾H, t, J=8 Hz), 1.10–1.40 (4H, m), 1.60–1.90 (2H, m), 2.08 (3H, s), 2.12–2.28 (2H, m), 2.53–2.73 (2H, m), 3.01 (3×¼H, s), 3.11 (3×¾H, s), 4.70 (2×⅜H, d, J=15 Hz), 4.89 (2×¼H, s), 4.91 (2×⅜H, d, J=15 Hz), 4.93–5.11 (2H, m), 7.20–7.33 (1H, m), 7.34–7.60 (6H, m), 7.60–7.89 (3H, m), 8.01 (1H, s), 8.10 (1×¾H, d, J=8 Hz), 8.12 (1×¼H, d, J=8 Hz), 8.81 (1×¾H, s), 8.88 (1×¼H, s)

(12) MASS: 560 (M+1); NMR (CDCl$_3$, δ): 0.59 (3×¼H, t, J=8 Hz), 0.65 (3×¾H, t, J=8 Hz), 0.98–1.50 (4H, m), 1.58–1.90 (2H, m), 2.00 (3×¾H, s), 2.02 (3×¼H, s), 2.10–2.33 (2H, m), 2.52–2.80 (2H, m), 3.13 (3H, s), 4.79 (2×⅜H, d, J=15 Hz), 4.91 (2×¼H, s), 5.10 (2×⅜H, d, J=15 Hz), 5.12–5.31 (1H, m), 5.43–5.60 (1H, m), 6.96–7.18 (3H, m), 7.27–7.47 (2H, m), 7.50–7.68 (2H, m), 7.69–7.90 (2H, m), 8.00 (1×¼H, s), 8.06 (1×¾H, s), 8.11 (1H, d, J=8 Hz), 8.72–9.00 (2H, m)

(13) MASS: 566 (M+1); NMR (CDCl$_3$, δ): 0.58 (3×¼H, t, J=8 Hz), 0.63 (3×¾H, t, J=8 Hz), 0.93–1.37 (4H, m), 1.50–1.80 (2H, m), 3.00 (3×¼H, s), 3.07 (3×¾H, s), 3.12–3.28 (2H, m), 4.61 (2×⅜H, d, J=15 Hz), 4.71 (2×⅛H, d, J=16 Hz), 4.87 (2×⅜H, d, J=15 Hz), 4.99 (2×⅛H, d, J=16 Hz), 4.90–5.10 (1H, m), 5.30–5.50 (1H, m), 6.69 (1×¾H, s), 6.73 (1×¼H, s), 6.94–7.20 (3H, m), 7.32 (1×¾H, s), 7.36 (1×¼H, s), 7.40 (1H, s), 7.48–7.61 (2H, m), 7.62–7.90 (3H, m), 7.99 (1H, s), 8.09 (1H, d, J=8 Hz), 8.53–8.70 (1H, m), 8.75 (1H, s)

(14) MASS: 567 (M+1); NMR (CDCl$_3$, δ): 0.70 (3×¼H, t, J=8 Hz), 0.78 (3×¾H, t, J=8 Hz), 1.00–1.40 (4H, m), 1.57–1.85 (2H, m), 3.01 (3×¼H, s), 3.11 (3×¾H, s), 3.03–3.33 (2H, m), 4.65–4.97 (3H, m), 4.98–5.10 (1H, m), 6.81 (1H, s), 7.18–7.30 (2H, m), 7.40 (1H, t, J=8 Hz), 7.42–7.90 (6H, m), 8.01 (1H, s), 8.10 (2H, d, J=8 Hz), 8.2–8.40 (1H, m), 8.80 (1×¾H, s), 8.87 (1×¼H, s)

(15) MASS: 530 (M+1); NMR (CDCl$_3$, δ): 2.70 (3×⅘H, s), 2.88 (3×⅕H, s), 3.00–3.20 (2H, m), 3.88 (3H, s), 3.91–4.08 (2H, m), 4.16 (2×¹⁄₁₀H, d, J=16 Hz), 4.30 (2×¹⁄₁₀H, d, J=16 Hz), 4.47 (2×⅘H, s), 4.81 (1H, br s), 5.30 (1×⅘H, q, J=8 Hz), 5.39 (1×⅕H, q, J=8 Hz), 5.59 (1H, q, J=8 Hz), 6.49 (1×⅘H, d, J=8 Hz), 6.61 (1×⅕H, d, J=8 Hz), 6.97–7.41 (10H, m), 7.48 (1H, d, J=8 Hz), 7.68 (1×⅕H, d, J=8 Hz), 7.86 (1×⅘H, d, J=2 Hz), 7.90 (1H, d, J=2 Hz), 9.01 (1×⅕H, d, J=8 Hz), 9.05 (1×⅘H, d, J=8 Hz)

(16) MASS: 531 (M+1); NMR (CDCl$_3$, δ): 2.68 (3×¾H, s), 2.81 (3×¼H, s), 2.92–3.17 (2H, m), 3.69–3.80 (1H, m), 3.90 (3H, s), 4.00 (2×⅛H, d, J=16 Hz), 4.03–4.18 (1H, m), 4.30 (2×⅜H, d, J=15 Hz), 4.41 (2×⅛H, d, J=16 Hz), 4.52 (2×⅜H, d, J=15 Hz), 4.73–4.88 (1H, m), 5.12 (1×¾H, q, J=8 Hz), 5.23 (1×¼H, q, J=8 Hz), 6.69 (1×¾H, d, J=8 Hz), 6.70 (1×¼H, d, J=8 Hz), 7.00–7.21 (6H, m), 7.28 (1H, t, J=8 Hz), 7.32–7.48 (2H, m), 7.48–7.72 (4H, m), 7.92 (1×¼H, d, J=2 Hz), 7.98 (1×¾H, d, J=2 Hz)

(17) MASS: 531 (M+1); NMR (CDCl$_3$, δ): 2.49 (3H, s), 2.62 (3×¾H, s), 2.74 (3×¼H, s), 2.92–3.15 (2H, m), 3.73–3.88 (1H, m), 3.97 (2×⅛H, d, J=16 Hz), 4.01–4.18 (1H, m), 4.36 (2×⅜H, d, J=15 Hz), 4.48 (2×⅛H, d, J=16 Hz), 4.49 (2×⅜H, d, J=15 Hz), 4.70–4.97 (2H, m), 5.11 (1×¾H, q, J=8 Hz), 5.21 (1×¼H, q, J=8 Hz), 6.98–7.20 (6H, m), 7.20–7.42 (3H, m), 7.49 (1×¾H, s), 7.51 (1×¼H, s), 7.70–7.87 (3H, m), 7.91 (1×¾H, d, J=8 Hz), 7.95 (1×¼H, d, J=8 Hz), 8.27 (1H, s)

(18) MASS: 671 (M+1); NMR (CDCl$_3$, δ): 1.38 (3H, t, J=8 Hz), 2.30 (3H, s), 2.32–2.51 (4H, m), 2.52–2.70 (1H, m), 2.53 (3×¾H, s), 2.73 (3×¼H, s), 2.93–3.13 (2H, m), 3.32 (1H, dd, J=17, 2 Hz), 3.40–3.59 (2H, m), 3.60–3.75 (2H, m), 3.93 (2×⅛H, d, J=16 Hz), 4.18 (2×⅜H, d, J=15 Hz), 4.26 (2×⅛H, d, J=16 Hz), 4.31 (2H, q, J=8 Hz), 4.51 (2×⅜H, d, J=15 Hz), 4.98–5.20 (2H, m), 6.60 (1×¼H, d, J=8 Hz), 6.62 (1×¾H, d, J=8 Hz), 7.00–7.22 (5H, m), 7.29 (1H, dd, J=12, 2 Hz), 7.32–7.48 (2H, m), 7.68–7.96 (5H, m), 8.14 (1H, d, J=8 Hz)

(19) MASS: 610 (M+1); NMR (CDCl$_3$, δ): 2.10 (3H, s), 2.55–2.80 (1H, m), 2.68 (3×¾H, s), 2.82 (3×¼H, s), 2.88–3.08 (2H, m), 3.09–3.21 (1H, m), 3.22–3.41 (2H, m), 3.42–3.70 (6H, m), 4.23 (2×⅜H, d, J=15 Hz), 4.30 (2×⅛H, d, J=16 Hz), 4.39 (2×⅛H, d, J=16 Hz), 4.73 (2×⅜H, d, J=15 Hz), 5.10–5.22 (1H, m), 5.23–5.40 (1H, m), 6.73–7.13 (9H, m), 7.14–7.30 (3H, m), 7.41 (1H, d, J=8 Hz), 7.61 (1H, d, J=8 Hz), 8.00 (1×⅓H, d, J=8 Hz), 8.07 (1×⅔H, d, J=8 Hz), 8.20 (1×⅓H, d, J=8 Hz), 8.27 (1×⅔H, d, J=8 Hz)

(20) MASS: 611 (M+1); NMR (CDCl$_3$, δ): 2.22 (3H, s), 2.53–2.73 (1H, m), 2.62 (3×¾H, s), 2.80 (3×¼H, s), 2.90–3.10 (2H, m), 3.20–3.37 (1H, m), 3.38–3.58 (2H, m), 3.58–3.80 (6H, m), 4.22 (2×⅛H, d, J=16 Hz), 4.30 (2×⅜H, d, J=15 Hz), 4.39 (2×⅛H, d, J=16 Hz), 4.63 (2×⅜H, d, J=15 Hz), 5.02–5.20 (2H, m), 6.87–7.13 (6H, m), 7.18–7.35 (4H, m), 7.42 (1H, t, J=8 Hz), 7.51 (1H, s), 7.57 (1H, d, J=8 Hz), 7.60–7.72 (2H, m), 8.21 (1H, d, J=8 Hz)

(21) MASS: 549 (M+1); NMR (CDCl$_3$, δ): 0.83 (3×⅓H, t, J=8 Hz), 0.92 (3×⅔H, t, J=8 Hz), 1.20–1.51 (2H, m), 1.57–1.81 (2H, m), 2.58–2.72 (1H, m), 2.88 (3×⅓H, s), 2.94 (3×⅔H, s), 3.30 (1H, d, J=16 Hz), 3.38–3.57 (2H, m), 3.58–3.80 (6H, m), 4.39 (2×⅓H, d, J=15 Hz), 4.60 (2×⅓H, s), 4.73 (2×⅓H, d, J=15 Hz), 4.82–5.01 (1H, m), 5.06–5.20 (1H, m), 7.10–7.47 (7H, m), 7.48–7.60 (2H, m), 7.68 (2×⅔H, d, J=8 Hz), 7.71 (2×⅓H, d, J=8 Hz), 8.27 (1H, d, J=8 Hz)

(22) MASS: 548 (M+1); NMR (CDCl$_3$, δ): 0.73 (3×⅓H, t, J=8 Hz), 0.81 (3×⅔H, t, J=8 Hz), 1.20–1.50 (2H, m), 1.50–1.78 (2H, m), 2.60–2.73 (1H, m), 2.85 (3×⅓H, s), 2.89 (3×⅔H, s), 3.19 (1H, d, J=15 Hz), 3.26–3.40 (2H, m), 3.41–3.68 (6H, m), 4.21 (2×⅓H, d, J=15 Hz), 4.52 (2×⅙H, d, J=16 Hz), 4.61 (2×⅙H, d, J=16 Hz), 4.80 (2×⅓H, d, J=15 Hz), 4.90–5.02 (1H, m), 5.20–5.33 (1H, m), 6.84 (1×⅓H, s), 7.01 (1×⅔H, s), 7.03–7.39 (7H, m), 7.43 (1H, d, J=8 Hz), 7.62 (1H, d, J=8 Hz), 7.98–8.20 (2H, m)

(23) MASS: 673 (M+1); NMR (CDl$_3$, δ): 2.27 (3H, s), 2.32–2.47 (4H, m), 2.52 (3H, s), 2.58 (3×¾H, s), 2.58–2.70 (1H, m), 2.73 (3×¼H, s), 2.92–3.13 (2H, m), 3.23–3.40 (1H, m), 3.40–3.60 (2H, m), 3.60–3.80 (2H, m), 4.01 (2×⅛H, d, J=16 Hz), 4.21 (2×⅜H, d, J=15 Hz), 4.30 (2×⅛H, d, J=16 Hz), 4.51 (2×⅜H, d, J=15 Hz), 4.98–5.18 (2H, m), 6.98–7.23 (7H, m), 7.32–7.50 (2H, m), 7.76 (1H, d, J=8 Hz), 7.79–7.93 (3H, m), 8.09–8.19 (1H, m), 8.21 (1H, s)

(24) MASS: 614 (M+1); NMR (CDCl$_3$, δ): 0.80 (3×⅕H, t, J=8 Hz), 0.88 (3×⅘H, t, J=8 Hz), 1.15–1.43 (4H, m), 1.60–1.88 (2H, m), 2.68 (1H, dd, J=17, 7 Hz), 2.98 (3×⅕H, s), 3.09 (3×⅘H, s), 3.29 (1H, dd, J=17, 2 Hz), 3.38–3.56 (2H, m), 3.57–3.80 (6H, m), 4.61 (2×½H, d, J=15 Hz), 4.89 (2×½H, d, J=15 Hz), 4.78–5.03 (1H, m), 5.04–5.20 (1H, m), 7.21–7.33 (1H, m), 7.41 (1H, t, J=8 Hz), 7.48–7.60 (3H, m), 7.61–7.73 (2H, m), 7.74–7.89 (2H, m), 8.01 (1H, s), 8.02–8.16 (1H, m), 8.28 (1H, d, J=8 Hz), 8.78 (1×⅘H, s), 8.84 (1×⅕H, s)

(25) MASS: 613 (M+1); NMR (CDCl$_3$, δ): 0.71 (3×⅕H, t, J=8 Hz), 0.78 (3×⅘H, t, J=8 Hz), 1.03–1.40 (4H, m), 1.53–1.82 (2H, m), 2.68 (1H, dd, J=17, 7 Hz), 2.90 (3×⅕H, s), 2.93 (3×⅘H, s), 3.23 (1H, d, J=15 Hz), 3.30–3.48 (2H, m), 3.48–3.71 (6H, m), 4.51 (2×½H, d, J=15 Hz), 4.81 (2×½H, d, J=15 Hz), 4.70–5.04 (1H, m), 5.15–5.30 (1H, m), 6.99 (1H, s), 7.09 (1H, t, J=8 Hz), 7.16–7.30 (1H, m), 7.39–7.57 (2H, m), 7.58–7.85 (3H, m), 7.92 (1H, s), 7.98 (1H, d, J=8 Hz), 8.10 (2H, t, J=8 Hz), 8.73 (1×⅘H, s), 8.81 (1×⅕H, s)

(26) MASS: 685 (M+1); NMR (CDCl$_3$, δ): 0.91 (3H, t, J=8 Hz), 1.63–1.82 (2H, m), 2.28 (3H, s), 2.32–2.53 (4H, m), 2.58–2.70 (1H, m), 2.58 (3×⅔H, s), 2.73 (3×⅓H, s), 2.93–3.13 (2H, m), 3.33 (1H, dd, J=15, 2 Hz), 3.41–3.60 (2H, m), 3.61–3.71 (2H, m), 3.72–3.90 (2H, m), 3.88 (2×⅙H, d, J=16 Hz), 3.99 (2×⅓H, d, J=15 Hz), 4.10 (2×⅙H, d, J=16 Hz), 4.31 (2×⅓H, d, J=15 Hz), 4.98–5.12 (2H, m), 6.88 (1×⅓H, dd, J=10, 2 Hz), 7.18 (1×⅔H, dd, J=10, 2 Hz), 7.06 (1H, dd, J=10, 2 Hz), 7.10–7.30 (6H, m), 7.37–7.49 (2H, m), 7.70 (1×⅔H, d, J=8 Hz), 7.78 (1×⅓H, d, J=8 Hz), 7.80–7.90 (3H, m), 8.11 (1×⅓H, d, J=8 Hz), 8.13 (1×⅔H, d, J=8 Hz)

(27) MASS: 628 (M+1); NMR (CDCl$_3$, δ): 2.59 (3×¾H, s), 2.65 (1H, dd, J=16, 8 Hz), 2.72 (3×¼H, s), 2.96–3.13 (2H, m), 3.30 (1H, dd, J=15, 2 Hz), 3.40–3.58 (2H, m), 3.60–3.80 (6H, m), 3.88 (3H, s), 4.20 (2×⅛H, d, J=16 Hz), 4.21 (2×⅜H, d, J=15 Hz), 4.29 (2×⅛H, d, J=16 Hz), 4.51 (2×⅜H, d, J=15 Hz), 5.01–5.22 (2H, m), 6.64 (1×¼H, d, J=8

Hz), 6.68 (1×¾H, d, J=8 Hz), 7.07–7.37 (7H, m), 7.42 (1H, t, J=8 Hz), 7.50 (1H, s), 7.57 (1H, d, J=8 Hz), 7.68 (1H, d, J=8 Hz), 7.70 (1H, d, J=8 Hz), 7.84 (1×¼H, d, J=2 Hz), 7.93 (1×¾H, d, J=2 Hz), 8.21 (1H, d, J=8 Hz)

(28) MASS: 627 (M+1); NMR (CDCl$_3$, δ): 2.53 (3×¾H, s), 2.61–2.78 (1H, m), 2.73 (3×¼H, s), 2.90–3.10 (2H, m), 3.18 (1H, d, J=16 Hz), 3.28–3.43 (2H, m), 3.44–3.68 (6H, m), 3.87 (3H, s), 3.94 (2×⅛H, d, J=16 Hz), 4.13 (2×⅜H, d, J=15 Hz), 4.24 (2×⅛H, d, J=16 Hz), 4.52 (2×⅜H, d, J=15 Hz), 5.02–5.18 (1H, m), 5.19–5.30 (1H, m), 6.60 (1H, d, J=8 Hz), 6.93–7.48 (9H, m), 7.43 (1H, d, J=8 Hz), 7.63 (1H, d, J=8 Hz), 7.81 (1×¼H, s), 7.91 (1×¾H, s), 8.01–8.22 (2H, m)

(29) MASS (m/z): 597 (M+H)$^+$; NMR (CDCl$_3$, δ): 2.51–2.67 (1H, m), 2.63 (3H×⅔, s), 2.82 (3H×⅓, s), 2.97–3.07 (2H, m), 3.23–3.38 (1H, m), 3.40–3.59 (2H, m), 3.60–3.80 (6H, m), 4.15 (1H×⅓, d, J=16.5 Hz), 4.31 (1H×⅔, d, J=16.5 Hz), 4.40 (1H×⅓, d, J=16.5 Hz), 4.63 (1H×⅔, d, J=16.5 Hz), 5.01–5.16 (2H, m), 6.84 (1H, d, J=2.5 Hz), 6.93–7.21 (7H, m), 7.23–7.33 (3H, m), 7.54 (1H, d, J=7.5 Hz), 7.63–7.83 (3H, m), 8.05–8.15 (2H, m)

(30) MASS (m/z): 623 (M+H)$^+$; NMR (CDCl$_3$, δ): 2.54–2.70 (1H, m), 2.63 (3H×⅔, s), 2.82 (3H×⅓, s), 2.99–3.12 (2H, m), 3.25 (1H×⅓, dd, J=16.0, 3.0 Hz), 3.29 (1H×⅔, dd, J=16.0, 3.0 Hz), 3.41–3.57 (2H, m), 3.61–3.77 (6H, m), 4.17 (1H×⅓, d, J=15.0 Hz), 4.31 (1H×⅔, d, J=15.0 Hz), 4.39 (1H×⅓, d, J=15.0 Hz), 4.64 (1H×⅔, d, J=15.0 Hz), 4.99–5.18 (2H, m), 6.77 (1H, d, J=2.5 Hz), 6.97–7.30 (11H, m), 7.36 (1H, d, J=7.5 Hz), 7.44 (2H, t, J=7.5 Hz), 7.60–7.73 (1H, m), 7.75 (2H, t, J=7.5 Hz), 8.01 (1H, d, J=7.5 Hz)

(31) MASS (m/z): 597 (M+H)$^+$; NMR (CDCl$_3$, δ): 2.42–2.60 (1H, m), 2.63 (3H×⅔, s), 2.82 (3H×⅓, s), 2.98–3.77 (13H, m), 4.06–4.69 (3H, m), 4.83–5.15 (2H, m), 6.75–7.02 (2H, m), 7.06–7.33 (11H, m), 7.41–7.74 (2H, m), 8.07 (1H×⅓, d, J=8.5 Hz), 8.32 (1H×⅔, d, J=8.5 Hz), 9.23 (1H, br s)

EXAMPLE 42

The following object compounds were obtained according to a similar manner to that of Example 1.

(1) MASS: 641 (M+1); NMR (CDCl$_3$, δ): 0.83 (3×¼H, t, J=8 Hz), 0.87 (3×¾H, t, J=8 Hz), 1.17–1.43 (4H, m), 1.58–1.84 (2H, m), 2.69 (1H, dd, J=16, 7 Hz), 2.91 (3×¼H, s), 3.02 (3×¾H, s), 3.30 (1H, dd, J=16, 2 Hz), 3.38–3.58 (2H, m), 3.58–3.78 (6H, m), 4.51 (2×⅜H, d, J=15 Hz), 4.62 (2×⅛H, d, J=16 Hz), 4.70 (2×⅜H, d, J=15 Hz), 4.78 (2×⅛H, d, J=16 Hz), 4.82–5.00 (1H, m), 5.08–5.20 (1H, m), 7.21–7.33 (1H, m), 7.34–7.48 (2H, m), 7.49 (1H, s), 7.55 (1H, d, J=8 Hz), 7.60–7.83 (4H, m), 8.18–8.38 (2H, m), 8.58 (1×¾H, s), 8.61 (1×¼H, s), 8.68 (1H, br s), 9.21 (1H, br s)

(2) MAS: 640 (M+1); NMR (CDCl$_3$, δ): 0.78 (3×¼H, t, J=8 Hz), 0.80 (3×¾H, t, J=8 Hz), 1.08–1.40 (4H, m), 1.51–1.81 (2H, m), 2.69 (1H, dd, J=16, 4 Hz), 2.89 (3×¼H, s), 2.93 (3×¾H, s), 3.30 (1H, dd, J=16, 2 Hz), 3.31–3.50 (2H, m), 3.50–3.72 (6H, m), 4.40 (2×⅜H, d, J=15 Hz), 4.61 (2×⅛H, d, J=16 Hz), 4.66 (2×⅜H, d, J=15 Hz), 4.69 (2×⅛H, d, J=16 Hz), 4.81–5.01 (1H, m), 5.18–5.30 (1H, m), 6.99 (1H, s), 7.10 (1H, t, J=8 Hz), 7.22 (1H, t, J=8 Hz), 7.30–7.49 (2H, m), 7.56–7.80 (3H, m), 7.96 (1H, d, J=8 Hz), 8.11 (1H, d, J=8 Hz), 8.28 (1×¾H, s), 8.30 (1×¼H, s), 8.51 (1×¾H, s), 8.59 (1×¼H, s), 8.63 (1H, s), 9.19 (1H, s)

(3) MASS: 605 (M+1); NMR (CDCl$_3$, δ): 0.79 (3×¼H, t, J=8 Hz), 0.80 (3×¾H, t, J=8 Hz), 1.03–1.40 (4H, m), 1.47–1.78 (2H, m), 2.90 (3×¼H, s), 3.00 (3×¾H, s), 3.31 (1×¼H, d, J=6 Hz), 3.39 (1×¾H, d, J=6 Hz), 3.43 (1×¼H, d, J=4 Hz), 3.50 (1×¾H, d, J=4 Hz), 4.51 (2×⅜H, d, J=15 Hz), 4.63 (2×⅛H, d, J=16 Hz), 4.68 (2×⅛H, d, J=16 Hz), 4.72 (2×⅜H, d, J=15 Hz), 4.81–5.00 (1H, m), 5.03–5.17 (1H, m), 7.19 (1H, t, J=8 Hz), 7.22–7.33 (2H, m), 7.33–7.43 (2H, m), 7.48 (1H, s), 7.51 (1×¾H, s), 7.55 (1×¼H, s), 7.58–7.81 (4H, m), 8.11 (1H, d, J=8 Hz), 8.28 (1×¾H, d, J=8 Hz), 8.31 (1×¼H, d, J=8 Hz), 8.50–8.70 (3H, m), 8.78 (1×¼H, d, J=8 Hz), 8.80 (1×¾H, d, J=8 Hz), 9.18 (1×¾H, s), 9.21 (1×¼H, s)

(4) MASS: 604 (M+1); NMR (CDCl$_3$, δ): 0.70 (3×⅕H, t, J=8 Hz), 0.72 (3×⅘H, t, J=8 Hz), 0.97–1.30 (4H, m), 1.38–1.53 (1H, m), 1.54–1.70 (1H, m), 2.90 (3×⅕H, s), 2.97 (3×⅘H, s), 3.30–3.50 (2H, m), 4.58 (2×⅘H, s), 4.61 (2×⅕H, s), 4.89 (1×⅕H, q, J=8 Hz), 4.95 (1×⅕H, q, J=8 Hz), 5.22 (1×⅕H, q, J=8 Hz), 5.31 (1×⅕H, q, J=8 Hz), 7.00–7.74 (11H, m), 8.09 (1×⅘H, d, J=8 Hz), 8.30 (1×⅕H, d, J=8 Hz), 8.25 (1×⅘H, d, J=8 Hz), 8.36 (1×⅕H, d, J=8 Hz), 8.47–8.60 (2H, m), 8.62 (1H, ,d, J=2 Hz), 8.71 (1H, d, J=2 Hz), 9.13 (1×⅕H, s), 9.19 (1×⅕H, s)

(5) MASS: 588 (M+1); NMR (CDCl$_3$, δ): 0.78 (3×⅕H, t, J=8 Hz), 0.81 (3×⅘H, t, J=8 Hz), 1.20–1.43 (4H, m), 1.57–1.90 (2H, m), 2.08 (3H, s), 2.13–2.27 (2H, m), 2.64 (2H, t, J=8 Hz), 3.00 (3×⅕H, s), 3.04 (3×⅘H, s), 4.60–4.82 (2H, m), 4.92–5.07 (2H, m), 7.20–7.84 (10H, m), 8.32 (1H, d, J=8 Hz), 8.62 (1H, s), 8.63–8.78 (1H, m), 9.24 (1H, s)

(6) MASS: 587 (M+1); NMR (CDCl$_3$, δ): 0.61 (3×⅕H, t, J=8 Hz), 0.65 (3×⅘H, t, J=8 Hz), 1.03–1.40 (4H, m), 1.56–1.90 (2H, m), 2.03 (3H, s), 2.14–2.40 (2H, m), 2.63 (2H, t, J=8 Hz), 3.14 (3×⅕H, s), 3.17 (3×⅘H, s), 4.64–4.96 (2H, m), 5.18 (1H, q, J=8 Hz), 5.52 (1H, q, J=8 Hz), 7.00–7.50 (7H, m), 7.64 (1H, d, J=8 Hz), 7.68–7.85 (2H, m), 8.34 (1H, d, J=8 Hz), 8.64 (1H, d, J=8 Hz), 8.82 (1×⅘H, d, J=8 Hz), 8.97 (1×⅕H, d, J=8 Hz), 9.22 (1H, s)

(7) MASS (m/z): 578 (M$^+$+1); NMR (CDCl$_3$, δ): 0.81 (3H, t, J=7 Hz), 1.26 (4H, m), 1.63 (2H, m), 2.50 (3H, s), 2.57–2.65 (1H, m), 2.81 (3H×¼, s), 2.93 (3H×¾, s), 3.22–3.27 (1H, m), 3.42 (2H, m), 3.60 (6H, m), 4.32 (1H×¾, d, J=15 Hz), 4.50 (1H×¼, d, J=16 Hz), 4.61 (1H×¼, d, J=16 Hz), 4.63 (1H×¾, d, J=15 Hz), 4.83 (1H, m), 5.06 (1H, m), 7.05–7.26 (2H, m), 7.35–7.51 (4H, m), 7.61–7.69 (2H, m), 8.20 (1H, m), 8.29–8.34 (1H, m)

(8) MASS (m/z): 577 (M$^+$+1); NMR (CDCl$_3$, δ): 0.77 (3H, t, J=7 Hz), 1.27 (4H, m), 1.64 (2H, m), 2.51 (3H, s), 2.67 (1H, m), 2.82 (3H×¼, s), 2.90 (3H×¾, s), 3.22–3.28 (1H, m), 3.37 (2H, m), 3.58 (6H, m), 4.27 (1H×¾, d, J=15 Hz), 4.53 (2H×¼, s), 4.62 (1H×¾, d, J=15 Hz), 4.86 (1H, m), 5.18 (1H, m), 6.98 (1H, m), 7.04–7.13 (2H, m), 7.25 (1H, m), 7.40–7.45 (2H, m), 7.62 (1H, m), 7.90 (1H, m), 8.10 (1H, m), 8.30–8.37 (1H, m)

(9) MASS (m/z): 542 (M$^+$+1); NMR (CDCl$_3$, δ): 0.75 (3H, t, J=7 Hz), 1.11 (4H, m); 1.48 (1H, m), 1.60 (1H, m), 2.45 (3H, s), 2.80 (3H×⅓, s), 2.92 (3H×⅔, s), 3.28–3.46 (2H, m), 4.31 (1H×⅔, d, J=15 Hz), 4.54 (2H×⅓, s), 4.62 (1H×⅔, d, J=15 Hz), 4.83 (1H, m), 5.07 (1H, m), 7.03–7.27 (4H, m), 7.37–7.62 (6H, m), 8.06 (1H, m), 8.29 (1H, m), 8.53 (1H, m), 8.73 (1H, m)

(10) MASS (m/z): 541 (M$^+$+1); NMR (CDCl$_3$, δ): 0.74 (3H, t, J=7 Hz), 1.09 (4H, m), 1.42 (1H, m), 1.60 (1H, m), 2.53 (3H, s), 2.92 (3H, s), 3.38 (2H, m), 4.49 (2H, s), 4.87 (1H, m), 5.19 (1H, m), 7.08–7.37 (7H, m), 7.39–7.53 (3H, m), 7.65 (1H, m), 7.97 (1H, m), 8.32 (1H, m), 8.52 (1H, m), 8.65 (1H, m)

(11) MASS (m/z): 525 (M$^+$+1); NMR (CDCl$_3$, δ): 0.80 (3H, t, J=7 Hz), 1.29 (4H, m), 1.62 (1H, m), 1.72 (1H, m), 2.10 (3H, s), 2.14–2.20 (2H, m), 2.52 (3H, s), 2.60 (2H, m), 2.91 (3H×¼, s), 3.01 (3H×¾, s), 4.47 (1H×¾, d, J=15 Hz), 4.56 (1H×¼, d, J=16 Hz), 4.66 (1H×¾, d, J=15 Hz), 4.66 (1H×¼, d, J=16 Hz), 4.93 (2H, m), 7.11 (1H, m), 7.21–7.47 (7H, m), 7.63–7.65 (1H, m), 8.35–8.40 (1H, m)

(12) MASS (m/z): 524 (M$^+$+1); NMR (CDCl$_3$, δ): 0.66 (3H, t, J=7 Hz), 1.22 (4H, m), 1.63 (1H, m), 1.74 (1H, m), 2.05 (3H, s), 2.17 (2H, m), 2.55 (3H, s), 2.62 (2H, m), 3.10 (3H, s), 4.64 (1H, d, J=15 Hz), 4.83 (1H, d, J=15 Hz), 5.13 (1H, m), 5.50 (1H, m), 7.02–7.33 (6H, m), 7.45–7.64 (2H, m), 8.43 (1H, m), 8.79 (1H, m) (13) MASS (m/z): 481 (M$^{30}$+1); NMR (CDCl$_3$, δ): 0.83 (3H, t, J=7 Hz), 1.33 (4H, m), 1.72 (2H, m), 2.49 (3H×⅝, s), 2.55 (3H×⅛, s), 2.89 (3H×¼, s), 3.03 (3H×¾, s), 3.77 (1H, m), 4.09 (1H, m), 4.54 (2H, m), 4.95 (3H, m), 7.04–7.49 (5H, m), 7.61–7.77 (3H, m), 8.30–8.42 (1H, m)

(14) MASS (m/z): 480 (M$^+$+1); NMR (CDCl$_3$, δ): 0.81 (3H, t, J=7 Hz), 1.31 (4H, m), 1.73 (1H, m), 1.93 (1H, m), 2.38 (3H, s), 3.03 (3H×⅙, s), 3.15 (3H×⅚, s), 3.97 (2H, m), 4.38 (1H, d, J=15 Hz), 4.87 (1H, d, J=15 Hz), 5.08 (1H, m), 5.62 (1H, m), 6.72 (1H, m), 6.95 (1H, m), 7.07–7.36 (6H, m), 7.61 (1H, m), 8.27 (1H×⅚, m), 8.38 (1H×⅙, m), 9.09 (1H, m)

(15) MASS (m/z): 641 (M$^+$+1); NMR (CDCl$_3$, δ): 2.30 (3H, s), 2.33–2.58(4H, m), 2.60 (3×¾H, s), 2.68 (1H, dd, J=17 and 8 Hz), 2.79 (3×¼H, s), 2.98–3.12 (2H, m), 3.23–3.40 (1H, m), 3.40–3.60 (2H, m), 3.62–3.75 (2H, m), 3.82 (3H, s), 3.90 (2×⅛H, d, J=16 Hz), 4.38 (2×⅛H, d, J=16 Hz), 4.41 (2×⅜H, d, J=15 Hz), 4.49 (2×⅜H, d, J=15 Hz), 5.01–5.20 (2H, m), 7.07 (1H, s), 7.11–7.38 (6H, m), 7.43 (1H, t, J=8 Hz), 7.50 (1H, s), 7.58 (1H, d, J=8 Hz), 7.69 (1H, d, J=8 Hz), 7.80 (1×¾H, d, J=8 Hz), 7.84 (1×¼H, d, J=8 Hz), 7.90 (1×¼H, s), 8.00 (1×¾H, s), 8.13–8.30 (2H, m)

(16) MASS (m/z): 640 (M$^+$+1); NMR (CDCl$_3$, δ): 2.21 (3H, s), 2.27–2.40 (4H, m), 2.56 (3×¾H, s), 2.69 (1H, dd, J=17 and 6 Hz), 2.73 (3×¼H, s), 2.92–3.10 (2H, m), 3.11–3.27 (1H, m), 3.30–3.48 (2H, m), 3.50–3.70 (2H, m), 3.72 (3×¾H, s), 3.78 (3×¼H, s), 3.93 (2×⅛H, d, J=16 Hz), 4.30 (2×⅛H, d, J=16 Hz), 4.31 (2×⅜H, d, J=15 Hz), 4.47 (2×⅜H, d, J=15 Hz), 5.08 (1H, q, J=8 Hz), 5.17–5.26 (1H, m), 6.90–7.20 (8H, m), 7.21 (1Hi d, J=8 Hz), 7.42 (1H, d, J=8 Hz), 7.62 (1H, d, J=8 Hz), 7.87 (1×¼H, s), 7.97 (1×¾H, s), 8.02–8.17 (2H, m), 8.20 (1H, s)

(17) NMR (CDCl$_3$, δ): 2.29 (3H, s), 2.32–2.55 (4H, m), 2.62–2.74 (1H, m), 2.68 (3×⅔H, s), 2.70 (3×⅓H, s), 2.98–3.18 (2H, m), 3.27–3.42 (1H, m), 3.43–3.60 (2H, m), 3.61–3.72 (2H, m), 3.82 (3H, s), 3.56 (2×⅙H, d, J=16 Hz), 4.33 (2×⅓H, d, J=15 Hz), 4.38 (2×⅙H, d, J=16 Hz), 4.60 (2×⅓H, d, J=15 Hz), 5.04–5.14 (1H, m), 5.10 (1×⅔H, q, J=8 Hz), 5.39 (1×⅓H, q, J=8 Hz), 6.72 (1H, d, J=7 Hz), 7.10–7.32 (6H, m), 7.41 (1H, t, J=8 Hz), 7.49 (1H, s), 7.53–7.82 (3H, m), 8.03 (1×⅓H, s), 8.20 (1×⅔H, s), 8.18–8.30 (1H, m), 8.41 (1H, dd, J=7, 2 Hz)

(18) NMR (CDCl$_3$, δ): 2.22 (3H, s), 2.29–2.48 (4H, m), 2.61–2.80 (1H, m), 2.69 (3×⅔H, s), 2.71 (3×⅓H, s), 2.90–3.12 (2H, m), 3.13–3.33 (1H, m), 3.35–3.50 (2H, m), 3.51–3.71 (2H, m), 3.73 (3×⅓H, s), 3.76 (3×⅔H, s), 3.70 (2×⅙H, d, J=16 Hz), 4.37 (2×⅙H, d, J=16 Hz), 4.42 (2×⅓H, d, J=15 Hz), 4.52 (2×⅓H, d, J=15 Hz), 5.08–5.25 (1H, m), 5.18 (1×⅔H, q, J=8 Hz), 5.41 (1×⅓H, q, J=8 Hz), 6.65–6.78 (1H, m), 6.99 (1H, s), 7.00–7.20 (5H, m), 7.21 (1H, d, J=8 Hz), 7.27 (1H, s), 7.42 (1H, d, J=8 Hz), 7.62 (1H, d, J=8 Hz), 7.91–8.09 (2H, m), 8.10 (1×⅓H, s), 8.20 (1×⅔H, s), 8.37–8.50 (1H, m)

(19) MASS: 705 (M+1); NMR (CDCl$_3$, δ): 2.28 (3H, s), 2.32–2.52 (4H, m), 2.58–2.72 (1H, m), 2.60 (3×¾H, s), 2.77 (3×¼H, s), 2.96–3.12 (2H, m), 3.31 (1H, dd, J=16, 2 Hz), 3.40–3.60 (2H, m), 3.61–3.80 (2H, m), 4.02 (2×⅛H, d, J=16 Hz), 4.30 (2×⅜H, d, J=15 Hz), 4.33 (2×⅜H, d, J=15 Hz), 4.54 (2×⅛H, d, J=16 Hz), 4.97–5.11 (2H, m), 7.10–7.23 (5H, m), 7.35–7.49 (2H, m), 7.51 (1×¼H, s), 7.68 (1×¾H, s), 7.78–7.90 (4H, m), 8.11 (1×¾H, d, J=8 Hz), 8.18 (1×¼H, d, J=8 Hz), 8.30 (1H, s), 8.59 (1H, s)

EXAMPLE 43

A mixture of Starting Compound (209 mg) and O-methyl benzo[b]furan-2-carbothioate (104 mg) in methanol (2.5 ml) was stirred at room temperature for 3 hours. The solvent was evaporated, and the residue was purified by column chromatography (silica gel, chloroform/methanol=70/1) to give Object Compound (121 mg) as yellow powder.

MASS (m/z): 578 (M+H)$^+$; NMR (CDCl$_3$, δ): 2.63 (⅕×3H, s), 2.77 (⅕×3H, s), 2.85–3.08 (2H, m), 3.25–3.42 (1H, m), 3.50–3.66 (1H, m), 4.23 (⅕×2H, ABq, Δ=0.20, J=17 Hz), 4.45 (⅘×2H, ABq, Δ=0.19, J=15 Hz), 5.05–5.21 (1H, m), 5.41–5.58 (1H, m), 7.05–7.80 (16H, m), 8.23–8.82 (4H, m)

EXAMPLE 44

The following compounds were obtained according to a similar manner to that of Example 1.

(1) MASS (m/z): 559 (M+H)$^+$; NMR (CDCl$_3$, δ): 1.60–2.05 (2H, m), 1.88 (¼×3H, s), 1.94 (¾×3H, s), 2.12–2.40 (2H, m), 2.54 (¼×3H, s), 2.58 (¾×3H, s), 2.87 (¼×3H, s), 2.99 (¾×3H, s), 3.25–3.52 (2H, m), 4.52 (¾×2H, ABq, Δ=0.26, J=15 Hz), 4.60 (¼×2H, ABq, Δ=0.08, J=17 Hz), 4.96–5.24 (2H, m), 7.00–7.80 (11H, m), 8.27–8.80 (3H, m), 10.50 (1H, br s)

(2) MASS (m/z): 560 (M+H)$^+$; NMR (CDCl$_3$, δ): 1.70–2.05 (2H, m), 1.93 (¼×3H, s), 1.98 (¾×3H, s), 2.20–2.40 (2H, m), 2.51 (¾×3H, s), 2.55 (¼×3H, s), 2.83 (¼×3H, s), 2.98 (¾×3H, s), 3.23–3.56 (2H, m), 4.51 (¾×2H, ABq, Δ=0.27, J=15 Hz), 4.60 (¼×2H, ABq, Δ=0.13, J=17 Hz), 4.95–5.18 (2H, m), 7.02–7.72 (10H, m), 8.02–8.83 (4H, m)

(3) MASS (m/z): 498 (M+H)$^+$; NMR (CDCl$_3$, δ): 1.92–2.32 (2H, m), 1.97 (⅕×3H, s), 2.06 (⅘×3H, s), 2.39 (3H, m), 2.42–2.70 (2H, s), 3.08 (⅕×3H, s), 3.25 (⅘×3H, s), 3.85–4.08 (2H, m), 4.30 (⅕×1H, d, J=15 Hz), 4.52 (⅕×1H, d, J=17 Hz), 4.91 (⅕×1H, d, J=17 Hz), 4.97 (⅘×1H, d, J=15 Hz), 5.23–5.67 (2H, m), 6.62–7.68 (8H, m), 8.25 (⅘×1H, s), 8.43 (⅕×1H, s), 9.02 (⅕×1H, d, J=9 Hz), 9.16 (⅘×1H, d, J=9 Hz), 10.50 (1H, br s)

(4) MASS (m/z): 4 99 (M+H)$^+$; NMR (CDCl$_3$, δ): 1.80–2.15 (2H, m), 1.98 (¼×3H, s), 2.06 (¾×3H, s), 2.45–2.67 (2H, m), 2.50 (3H, s), 2.92 (¼×3H, s), 3.08 (¾×3H, s), 3.68–3.88 (1H, m), 4.02–4.22 (1H, m), 4.48 (¼×1H, d, J=17 Hz), 4.56 (¾×2H, ABq, Δ=0.06, J=15 Hz), 4.68 (1H, br s), 4.80–5.28 (2H, m), 4.83 (¼×1H, d, J=17 Hz), 7.00–7.78 (9H, m), 8.32 (¾×1H, s), 8.43 (¼×1H, s)

(5) MASS (m/z): 595 (M+H)$^+$; NMR (CDCl$_3$, δ): 1.80–2.07 (2H, m), 1.99 (3H×⅕, s), 2.04 (3H×⅘, s), 2.47–2.59 (2H, m), 2.56 (3H, s), 2.63 (1H, dd, J=16.0, 6.0 Hz), 2.85 (3H×⅕, s), 2.99 (3H×⅘, s), 3.35 (1H, dd, J=16.0, 3.0 Hz), 3.41–3.52 (2H, m), 3.58–3.77 (6H, m), 4.41 (1H×⅘, d, J=15 Hz), 4.51 (1H×⅕, d, J=16.0 Hz), 4.56 (1H×⅕, d, J=15.0 Hz), 4.70 (1H×⅘, d, J=16.0 Hz), 5.04–5.22 (2H, m), 7.00 (1H, d, J=1.0 Hz), 7.09–7.21 (2H, m), 7.30 (1H, t, J=7.5 Hz), 7.40–7.52 (2H, m), 7.69 (2H, t, J=7.5 Hz), 8.04 (1H, d, J=7.5 Hz), 8.31 (1H×⅘, d, J=1.0 Hz), 8.39 (1H×⅕, d, J=1.0 Hz), 9.34 (1H×⅕, br s), 9.70 (1H×⅘, br s)

(6) MASS (m/z): 596 (M+H)$^+$; NMR (CDCl$_3$, δ): 1.82–2.07 (2H, m), 2.02 (3H×¼, s), 2.10 (3H×¾, s), 2.50–2.70 (3H, m), 2.53 (3H, s), 2.87 (3H×¼, s), 3.04 (3H×¾, s), 3.29–3.57 (3H, m), 3.60–3.78 (6H, m), 4.40 (1H×¾, d, J=15.0 Hz), 4.53 (1H×¼, d, J=16.0 Hz), 4.67

(1H×¾, d, J=15.0 Hz), 4.75 (1H×¼, d, J=16.0 Hz), 5.06–5.26 (2H, m), 7.12 (1H×¾, d, J=7.5 Hz), 7.21 (1H×¼, d, J=7.5 Hz), 7.31 (1H, t, J=7.5 Hz), 7.44 (2H, t, J=7.5 Hz), 7.51 (1H, s), 7.58 (1H, d, J=7.5 Hz), 7.66–7.74 (2H, m), 8.21 (1H, d, J=7.5 Hz), 8.35 (1H×¾, d, J=1.0 Hz), 8.40 (1H×¼, d, J=1.0 Hz)

(7) MASS (m/z): 542 (M+H)⁺; NMR (CDCl₃, δ): 1.72–2.31 (4H, m), 1.88 (3H×¼, s), 1.91 (3H×¾, s), 2.09 (3H, s), 2.39–2.54 (2H, m), 2.57–2.69 (2H, m), 2.58 (3H, s), 3.08 (3H×¼, s), 3.15 (3H×¾, s), 4.62 (1H×¼, d, J=16.0 Hz), 4.69 (1H×¾, d, J=15.0 Hz), 4.73 (1H×¾, d, J=15.0 Hz), 4.88 (1H×¼, d, J=16.0 Hz), 5.23–5.42 (2H, m), 6.99 (1H, s), 7.09–7.25 (4H, m), 7.40 (1H, d, J=7.5 Hz), 7.52 (1H, m), 7.67 (1H, d, J=7.5 Hz), 8.44 (1H, s), 8.47 (1H×¾, d, J=7.5 Hz), 8.61 (1H×¼, d, J=7.5 Hz), 10.10 (1H, br s)

(8) MASS (m/z): 543 (M+H)⁺; NMR (CDCl₃, δ): 1.83–2.27 (4H, m), 1.99 (3H×¼, s), 2.04 (3H×¾, s), 2.17 (3H, s), 2.43–2.76 (4H, m), 2.55 (3H, s), 2.91 (3H×¼, s), 3.07 (3H×¾, s), 4.49 (1H×¾, d, J=15.0 Hz), 4.60 (1H×¼, d, J=16.0 Hz), 4.65 (1H×¾, d, J=15.0 Hz), 4.79 (1H×¼, d, J=16.0 Hz), 4.83–4.96 (1H, m), 5.06–5.27 (1H, m), 7.05–7.23 (2H, m), 7.24–7.36 (1H, m), 7.37–7.57 (5H, m), 7.68 (1H, d, J=7.5 Hz), 8.37 (1H×¾, s), 8.40 (1H×¼, s)

We claim:

1. A compound of the formula:

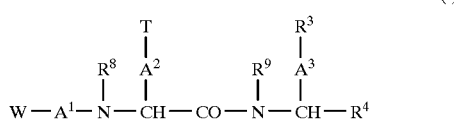

(I)

wherein:

W is benzofuryl or benzothienyl;

A¹ is >C=V, wherein V is O or S;

T is pyridyl;

A² is lower alkylene;

R⁸ is hydrogen or lower alkyl;

R³ is aryl, which is optionally substituted;

A³ is a direct bond or lower alkylene;

R⁹ is hydrogen or lower alkyl;

R⁴ has the formula

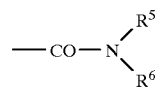

wherein R⁵ is hydrogen or lower alkyl; and R⁶ is pyridyl lower alkyl; or a pharmaceutically acceptable salt thereof.

2. The compound of claim 1, wherein W is benzofuryl.

3. The compound of claim 1, wherein W is benzothienyl.

4. The compound of claim 1, wherein A² is C₁- or C₂-alkylene.

5. The compound of claim 1, wherein R⁸ is hydrogen.

6. The compound of claim 1, wherein R⁹ is hydrogen.

7. The compound of claim 1, wherein R⁵ of group R⁴ is hydrogen.

8. The compound of claim 1, wherein R³ is phenyl or naphthyl each of which are optionally substituted by lower alkyl, lower alkoxy, lower alkenyl, lower alkynyl, mono-, di-, tri-halo (lower) alkyl, cyclo(lower)alkyl, cyclo(lower) alkenyl, halogen, carboxy, protected carboxy, hydroxy, protected hydroxy, phenyl, napthyl, ar(lower)alkyl, carboxy (lower) alkyl, protected carboxy(lower) alkyl, nitro, amino, protected amino, di(lower) alkylamino, amino (lower)alkyl, protected amino(lower)alkyl, cyano, sulfo, oxo, sulfamoyl, carbamoyloxy, mercapto, lower alkylthio and methylenedioxy.

9. The compound of claim 1, which is in the form of a salt, said salt being a salt of an inorganic base.

10. The compound of claim 1, which is in a form of a salt, said salt being a salt of an organic amine.

11. The compound of claim 1, which is in a form of a salt, said salt being a salt of an inorganic acid.

12. The compound of claim 1, which is in a form of a salt, said salt being a salt of a basic or acidic amino acid.

13. A method of inhibiting production of nitric oxide (NO) in a mammal, which comprises administrating to said mammal an effective amount of the compound of claim 1 or a pharmaceutically acceptable salt thereof.

14. The method of claim 13, wherein said mammal is a human.

* * * * *